US012076388B2

(12) United States Patent
Lavoie et al.

(10) Patent No.: US 12,076,388 B2
(45) Date of Patent: Sep. 3, 2024

(54) MODIFIED NOROVIRUS VP1 PROTEINS AND VLPS COMPRISING MODIFIED NOROVIRUS VP1 PROTEINS

(71) Applicant: ARAMIS BIOTECHNOLOGIES INC., Quebec City (CA)

(72) Inventors: Pierre-Olivier Lavoie, Quebec (CA); Marc-Andre D'Aoust, Québec (CA)

(73) Assignee: ARAMIS BIOTECHNOLOGIES INC., Québec City (CA)

( * ) Notice: Subject to any disclaimer, the term of this patent is extended or adjusted under 35 U.S.C. 154(b) by 0 days.

(21) Appl. No.: 18/165,804

(22) Filed: Feb. 7, 2023

(65) Prior Publication Data

US 2023/0293663 A1 Sep. 21, 2023

Related U.S. Application Data

(63) Continuation of application No. 16/768,524, filed as application No. PCT/CA2018/051530 on Nov. 30, 2018, now Pat. No. 11,602,558.

(60) Provisional application No. 62/712,744, filed on Jul. 31, 2018, provisional application No. 62/593,006, filed on Nov. 30, 2017.

(51) Int. Cl.

| | |
|---|---|
| ***A61K 39/00*** | (2006.01) |
| ***A61K 39/12*** | (2006.01) |
| ***A61K 39/42*** | (2006.01) |
| ***A61P 31/14*** | (2006.01) |
| ***C07K 14/005*** | (2006.01) |
| ***C07K 16/10*** | (2006.01) |
| ***C12N 7/00*** | (2006.01) |
| ***C12N 15/82*** | (2006.01) |

(52) U.S. Cl.

CPC .............. *A61K 39/12* (2013.01); *A61P 31/14* (2018.01); *C07K 14/005* (2013.01); *C12N 7/00* (2013.01); *C12N 15/8258* (2013.01); *A61K 2039/5258* (2013.01); *C12N 2770/16022* (2013.01); *C12N 2770/16023* (2013.01); *C12N 2770/16034* (2013.01)

(58) Field of Classification Search

CPC .......... A61P 31/14; A61P 31/12; C07K 16/10; C07K 14/005; C07K 14/08

See application file for complete search history.

(56) References Cited

U.S. PATENT DOCUMENTS

| | | | |
|---|---|---|---|
| 8,841,120 | B2 | 9/2014 | Richardson et al. |
| 9,518,096 | B2 | 12/2016 | Richardson et al. |
| 2013/0171185 | A1 | 7/2013 | Settembre et al. |
| 2013/0273105 | A1 | 10/2013 | Richardson et al. |
| 2014/0271712 | A1 | 9/2014 | Baric et al. |
| 2015/0023995 | A1 | 1/2015 | Richardson et al. |

FOREIGN PATENT DOCUMENTS

| | | | |
|---|---|---|---|
| WO | 2005/032457 | A3 | 4/2005 |
| WO | 2011/035422 | A1 | 3/2011 |
| WO | 2016/009788 | A1 | 1/2016 |
| WO | 2016/102136 | A1 | 6/2016 |
| WO | 2016/200951 | A1 | 12/2016 |
| WO | 2017/191264 | A1 | 11/2017 |
| WO | 2018/170603 | A1 | 9/2018 |

OTHER PUBLICATIONS

Souza et al., "Expression and assembly of Norwalk virus-like particles in plants using a viral RNA silencing suppressor gene", Appl. Microbiol. Biotechnol, 2013, vol. 97, pp. 9021-9027 (7 pages total).

Vongpunsawad et al., "Norwalk virus minor capsid protein VP2 associates within the VP1 shell domain", Journal of Virology, 2013, vol. 87, No. 9, pp. 4818-4825 (8 pages total).

Zhu et al., "Regulation of Norovirus Virulence by the VP1 Protruding Domain Correlates with B Cell Infection Efficiency", Journal of Virology, 2016, vol. 90, No. 6, pp. 2858-2867 (10 pages total).

GenBank Accession AWR17495, Identical Proteins, VP1 [Norovirus GII], 2018 (2 pages total).

Ausar et al., "Conformational Stability and Disassembly of Norwalk Virus-like Particles", Journal of Biological Chemistry, Jul. 14, 2006, vol. 281, No. 28, pp. 19478-19488 (11 pages).

Bertolotti-Ciarlet et al., "The 3' End of Norwalk Virus mRNA Contains Determinants That Regulate the Expression and Stability of the Viral Capsid Protein VP1: a Novel Function for the VP2 Protein", American Society for Microbiology, Journal of Virology, Nov. 2003, vol. 77, Issue 21, pp. 11603-11615 (27 pages).

GENBANK Accession APY24054.1, capsid protein, partial [*Norovirus* sp.], 2017, 1 page.

Hansman et al., "Genetic and antigenic diversity among noroviruses", Journal of General Virology, 2006, vol. 87, pp. 909-919 (11 pages).

Huang et al., "A DNA Replicon System for Rapid High-Level Production of Virus-Like Particles in Plants", Biotechnology and Bioengineering, Jul. 1, 2009, vol. 103, No. 4, pp. 706-714 (9 pages).

Huo et al., "Chimeric VLPs with GII.3 P2 domain in a backbone of GII.4 VP1 confers novel HBGA binding ability", Virus Research, 2016, vol. 224, pp. 1-5 (5 pages).

Mason et al., "Expression of Norwalk virus capsid protein in transgenic tobacco and potato and its oral immunogenicity in mice", Proc. Natl. Acad. Sci. USA, May 1996, vol. 93, pp. 5335-5340 (6 pages).

(Continued)

*Primary Examiner* — Barry A Chestnut

(74) *Attorney, Agent, or Firm* — Sughrue Mion, PLLC

(57) ABSTRACT

Nucleic acids encoding modified norovirus VP1 proteins, and virus-like particles (VLPs) containing one or more of the modified norovirus VP1 proteins, and compositions containing the nucleic acids, VP1 proteins, or the VLPs are provided. Methods for producing modified norovirus VP1 protein, and norovirus VLP, production in plants, portions of the plant or a plant cell, are also provided.

25 Claims, 142 Drawing Sheets

Specification includes a Sequence Listing.

(56) References Cited

OTHER PUBLICATIONS

Parra et al., "Identification of a Broadly Cross-Reactive Epitope in the Inner Shell of the Norovirus Capsid", PLOS ONE, Jun. 2013, vol. 8, Issue 6, e67592, pp. 1-7 (7 pages).
Tacket et al., "Human Immune Responses to a Novel Norwalk Virus Vaccine Delivered in Transgenic Potatoes", The Journal of Infectious Diseases, 2000, vol. 182, pp. 302-305 (4 pages).
Vongpunsawad et al., "Norwalk Virus Minor Capsid Protein VP2 Associates within the VP1 Shell Domain", Journal of Virology, May 2013, vol. 87, No. 9, pp. 4818-4825 (8 pages).

Figure 2A

| Norovirus VP1 Major Capsid Amino Acid Sequences | | |
|---|---|---|
| **Access (Uniprot)** | **Access (NCBI)** | **Strain Name** |
| Q83884 | NP_056821 | Hu/GI.1/United States/Norwalk/1968 |
| D2DEL3 | ACU56258 | Hu/GI.2/Leuven/2003/BEL |
| H2DG70 | AEY77318 | Hu/GI.3/S29/2008/Lilla Edet/Sweden |
| A0A023NFH0 | AHW99832 | Hu/GI.5/Siklos/HUN5407/2013/HUN |
| A0A1I9WIM4 | APA31979 | Hu/GI.7/GA5043/USA/2014 |
| H6V703 | AFA55174 | Hu/GII.1/Ascension208/2010/USA |
| S5ZGB5 | AGT39206 | Hu/GII.2/CGMH47/2011/TW |
| U3RI89 | AGX01095 | Hu/GII.3/Jingzhou/2013402/CHN |
| K4LM89 | AFV08795 | Hu/GII.4/Sydney/NSW0514/2012/AU |
| A0A1I9WIL4 | APA31970 | Hu/USA/2015/GII.P16_GII.4_Sydney/CA3477 |
| A0A0U3E729 | ALT54485 | Hu/GII.5/AlbertaEI390/2013/CA |
| M9T020 | AGI96397 | Hu/GII.6/Ohio/490/2012/USA |
| F8SRB4 | AEI29586 | Hu/GII.12/HS206/2010/USA |
| H9AWU4 | AFC89656 | Hu/GII.17/Kawasaki323/2014/JP |
| H9AWV4 | AFC89665 | Hu/GII.21/Salisbury150/2011/USA |
| **Norovirus VP2 Minor Capsid Amino Acid Sequence** | | |
| **Access (Uniprot)** | **Access (NCBI)** | **Strain Name** |
| W6APL0 | AHI59155 | Hu/GII.6/HS245/2010/USA |

Figure 2B

| Norovirus VP1 Major Capsid Nucleotide Sequences | |
|---|---|
| **Genome Access (NCBI)** | **Strain Name** |
| M87661 | Hu/GI.1/United States/Norwalk/1968 |
| FJ515294 | Hu/GI.2/Leuven/2003/BEL |
| JN603244 | Hu/GI.3/S29/2008/Lilla Edet/Sweden |
| KJ402295 | Hu/GI.5/Siklos/HUN5407/2013/HUN |
| KX907730 | Hu/GI.7/GA5043/USA/2014 |
| JN797508 | Hu/GII.1/Ascension208/2010/USA |
| KC464505 | Hu/GII.2/CGMH47/2011/TW |
| KF306213 | Hu/GII.3/Jingzhou/2013402/CHN |
| JX459908 | Hu/GII.4/Sydney/NSW0514/2012/AU |
| KU311160 | Hu/GII.5/AlbertaEI390/2013/CA |
| KC464321 | Hu/GII.6/Ohio/490/2012/USA |
| HQ664990 | Hu/GII.12/HS206/2010/USA |
| JN899242 | Hu/GII.17/Kawasaki323/2014/JP |
| JN899245 | Hu/GII.21/Salisbury150/2011/USA |
| **Norovirus VP2 Minor Capsid Nucleotide Sequence** | |
| **Access (NCBI)** | **Strain Name** |
| KJ407072 | Hu/GII.6/HS245/2010/USA |

GI.3/S29/2008/Lila Edet/Sweden

Mag. 15 K, 563-041-1
VP1 (GI.3)

Mag. 15 K, 563-041-3
VP1 (GI.3 S94L)

Mag. 15 K, 563-041-5
VP1 (GI.3 Q84S + S94L)

GI.3/S29/2008/Lila Edet/Sweden

VP1 (GI.3_M57I+S94L)

GI.5/Siklos/HUN54107/2013/HUN

VP1 GI.7/GA5043/USA/2014

GII.3/Jingzhou/2013402/CHN

Mag. 25 K, 563-041-7
VP1 (GII.3)

Mag. 15 K, 563-041-8
VP1 (GII.3 E80S)

GII.4/Sydney/SW0514/2012/AU

GII.4/Sydney/SW0514/2012/AU

Figure 9G
GII.4/Sydney/SW0514/2012/AU
GII.4_A39V+R53I+P80S
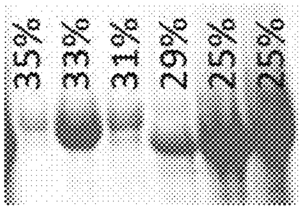
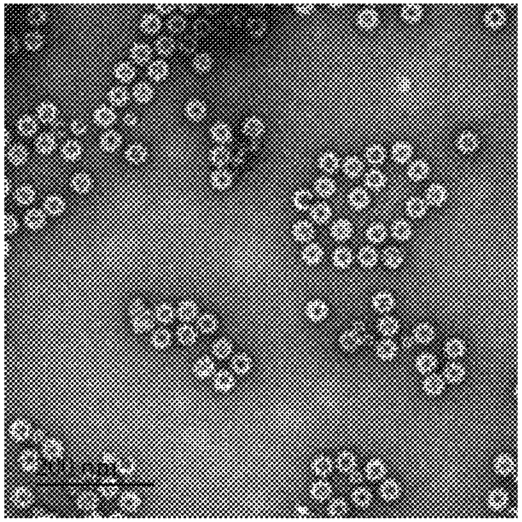

GII.12/HS206/2010/USA

GII.12/HS206/2010/USA

Figure 12A

Amino acid sequence of VP1 G1.1 (SEQ ID NO: 1)

MMMASKDATSSVDGASGAGQLVPEVNASDPLAMDPVAGSSTAVATAGQVNPIDPWIINNFVQAPQGEFTISPNNTP
GDVLFDLSLGPHLNPFLLHLSQMYNGWVGNMRVRIMLAGNAFTAGKIIVSCIPPGFGSHNLTIAQATLFPHVIADVRTLD
PIEVPLEDVRNVLFHNNDRNQQTMRLVCMLYTPLRTGGGTGDSFVVAGRVMTCPSPDFNFLFLVPPTVEQKTRPFTLPN
LPLSSLSNSRAPLPISSMGISPDNVQSVQFQNGRCTLDGRLVGTTPVSLSHVAKIRGTSNGTVINLTELDGTPFHPFEGPAPI
GFPDLGGCDWHINMTQFGHSSQTQYDVDTTPDTFVPHLGSIQANGIGSGNYVGVLSWISPPSHPSGSQVDLWKIPNYG
SSITEATHLAPSVYPPGFGEVLVFFMSKMPGPGAYNLPCLLPQEYISHLASEQAPTVGEAALLHYVDPDTGRNLGEFKAYP
DGFLTCVPNGASSGPQQLPINGVFVFVSWVSRFYQLKPVGTASSARGRLGLRR

Figure 12B

Nucleic acid sequence of wild-type VP1 G1.1 (SEQ ID NO: 2)

ATGATGATGGCGTCTAAGGACGCTACATCAAGCGTGGATGGCGCTAGTGGCGCTGGTCAGTTGGTACCGGAGGTTA
ATGCTTCTGACCCTCTTGCAATGGATCCTGTAGCAGGTTCTTCGACAGCAGTCGCGACTGCTGGACAAGTTAATCCTA
TTGATCCCTGGATAATTAATAATTTTGTGCAAGCCCCCCAAGGTGAATTTACTATTTCCCCAAATAATACCCCCGGTG
ATGTTTTGTTTGATTTGAGTTTGGGTCCCCATCTTAATCCTTTCTTGCTCCATCTATCACAAATGTATAATGGTTGGGTT
GGTAACATGAGAGTCAGGATTATGCTAGCTGGTAATGCCTTTACTGCGGGGAAGATAATAGTTTCCTGCATACCCCC
TGGTTTTGGTTCACATAATCTTACTATAGCACAAGCAACTCTCTTTCCACATGTGATTGCTGATGTTAGGACTCTAGAC
CCCATTGAGGTGCCTTTGGAAGATGTTAGGAATGTTCTCTTTCATAATAATGATAGAAATCAACAAACCATGCGCCTT
GTGTGCATGCTGTACACCCCCCTCCGCACTGGTGGTGGTACTGGTGATTCTTTTGTAGTTGCAGGGCGAGTTATGAC
TTGCCCCAGTCCTGATTTTAATTTCTTGTTTTTAGTCCCTCCTACGGTGGAGCAGAAAACCAGGCCCTTCACACTCCCA
AATCTGCCATTGAGTTCTCTGTCTAACTCACGTGCCCCTCTCCCAATCAGTAGTATGGGCATTTCCCCAGACAATGTCC
AGAGTGTGCAGTTCCAAAATGGTCGGTGTACTCTGGATGGCCGCCTGGTTGGCACCACCCCAGTTTCATTGTCACAT
GTTGCCAAGATAAGAGGGACCTCCAATGGCACTGTAATCAACCTTACTGAATTGGATGGCACACCCTTTCACCCTTTT
GAGGGCCCTGCCCCCATTGGGTTTCCAGACCTCGGTGGTTGTGATTGGCATATCAATATGACACAGTTTGGCCATTC
TAGCCAGACCCAGTATGATGTAGACACCACCCCTGACACTTTTGTCCCCCATCTTGGTTCAATTCAGGCAAATGGCAT
TGGCAGTGGTAATTATGTTGGTGTTCTTAGCTGGATTTCCCCCCCATCACACCCGTCTGGCTCCCAAGTTGACCTTTG
GAAGATCCCCAATTATGGGTCAAGTATTACGGAGGCAACACATCTAGCCCCTTCTGTATACCCCCCTGGTTTCGGAG
AGGTATTGGTCTTTTTCATGTCAAAAATGCCAGGTCCTGGTGCTTATAATTTGCCCTGTCTATTACCACAAGAGTACA
TTTCACATCTTGCTAGTGAACAAGCCCCTACTGTAGGTGAGGCTGCCCTGCTCCACTATGTTGACCCTGATACCGGTC
GGAATCTTGGGGAATTCAAAGCATACCCTGATGGTTTCCTCACTTGTGTCCCCAATGGGGCTAGCTCGGGTCCACAA
CAGCTGCCGATCAATGGGGTCTTTGTCTTTGTTTCATGGGTGTCCAGATTTTATCAATTAAAGCCTGTGGGAACTGCC
AGCTCGGCAAGAGGTAGGCTTGGTCTGCGCCGATAA

Figure 12C

Nucleic acid sequence of human codon-optimized VP1 G1.1 (SEQ ID NO: 3)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGCAGAAGACGCGGCCCTTTA
CACTGCCCAATCTCCCGCTTTCAAGTCTGAGTAATTCACGGGCCCCATTGCCGATCTCCTCAATGGGAATCTCCCCCG
ACAACGTCCAGTCTGTCCAATTCCAAAATGGGAGATGCACACTGGACGGTCGCCTGGTGGGAACAACTCCGGTGTC
CCTCTCACATGTCGCCAAAATCCGCGGCACATCAAATGGTACCGTAATCAATCTGACAGAACTTGATGGCACGCCCTT
CCATCCCTTTGAAGGACCAGCCCCTATTGGATTTCCTGATCTGGGAGGTTGCGACTGGCACATAAACATGACACAGT
TTGGCCACTCCAGCCAGACACAGTATGATGTCGATACAACCCCAGATACCTTCGTGCCACACCTGGGATCTATTCAA
GCTAACGGTATTGGATCCGGCAACTACGTGGGAGTCTTATCTTGGATCTCACCACCATCCCACCCCTCAGGATCCCAG
GTTGACTTGTGGAAGATACCGAATTATGGATCCTCGATCACTGAAGCCACGCACCTCGCACCTTCCGTCTACCCACCA
GGTTTTGGAGAAGTCTTGGTGTTTTTCATGAGCAAAATGCCCGGCCCTGGAGCCTACAATCTCCCTTGCCTACTCCCT
CAAGAGTATATTAGTCACCTCGCATCTGAGCAGGCCCCGACCGTTGGCGAGGCAGCCCTGCTGCATTATGTGGATCC
GGACACCGGCAGGAACCTGGGTGAGTTCAAAGCTTATCCTGACGGTTTTCTAACATGTGTACCAAATGGCGCTTCCA
GCGGCCCTCAACAGCTCCCAATCAATGGCGTGTTCGTTTTTGTCAGCTGGGTAAGCCGCTTCTACCAGCTGAAGCCC
GTGGGGACAGCTTCTTCTGCCCGCGGACGCCTCGGTCTGCGGAGATAA

Figure 13A

Amino acid sequence of VP1 G1.2_Leuven_2003_D2DEL3 (SEQ ID NO: 4)

MMMASKDAPQSADGASGAGQLVPEVNTADPLPMEPVAGPTTAVATAGQVNMIDPWIVNNFVQSPQGEFTISPNNT
PGDILFDLQLGPHLNPFLSHLSQMYNGWVGNMRVRILLAGNAFSAGKIIVCCVPPGFTSSSLTIAQATLFPHVIADVRTLEP
IEMPLEDVRNVLYHTNDNQPTMRLVCMLYTPLRTGGGSGNSDSFVVAGRVLTAPSSDFSFLFLVPPTIEQKTRAFTVPNIP
LQTLSNSRFPSLIQGMILSPDASQVVQFQNGRCLIDGQLLGTTPATSGQLFRVRGKINQGARTLNLTEVDGKPFMAFDSP
APVGFPDFGKCDWHMRISKTPNNTSSGDPMRSVDVQTDVQGFVPHLGSIQFDEVFNHPTGDYIGTIEWISQPSTPPGT
DINLWEIPDYGSSLSQAANLAPPVFPPGFGEALVYFVSAFPGPNNRSAPNDVPCLLPQEYVTHFVSEQAPTMGDAALLHY
VDPDTNRNLGEFKLYPGGYLTCVPNGVGAGPQQLPLNGVFLFVSWVSRFYQLKPVGTASTARGRLGVRRI

Figure 13B

Nucleic acid sequence of human codon-optimized VP1 G1.2_Leuven_2003_D2DEL3 (SEQ ID NO: 5)

ATGATGATGGCTTCAAAGGATGCTCCCCAAAGCGCGGACGGAGCTAGCGGCGCCGGACAGTTGGTTCCGGAAGTC
AACACTGCCGATCCACTGCCCATGGAACCCGTAGCTGGTCCAACAACCGCTGTTGCCACCGCCGGCCAGGTTAACAT
GATCGATCCATGGATTGTTAATAACTTTGTACAGAGCCCCCAGGGGGAGTTCACAATTTCTCCGAACAATACCCCTG
GGGACATTCTGTTCGATCTGCAACTGGGCCCACACTTGAATCCTTTCCTGAGCCATCTTTCACAGATGTACAACGGAT
GGGTTGGGAACATGCGTGTTCGGATCCTCCTTGCTGGCAACGCCTTCAGTGCTGGCAAGATTATCGTGTGCTGCGTA
CCACCAGGGTTTACCTCGAGTTCATTAACCATTGCTCAGGCCACCCTTTTCCCTCACGTGATCGCAGACGTGCGTACC
TTAGAACCAATCGAAATGCCCCTGGAAGATGTACGGAACGTGCTGTACCATACTAATGATAACCAGCCAACGATGA
GATTAGTGTGCATGCTGTACACCCCCCTGAGAACTGGAGGAGGTTCTGGAAATTCCGACAGTTTTGTGGTGGCTGG
CAGGGTCCTGACCGCTCCCAGTAGCGACTTCAGCTTTTTGTTCCTCGTTCCTCCTACAATCGAACAAAAAACAAGAGC
ATTCACAGTGCCCAACATTCCACTGCAGACTTTAAGCAATTCCAGGTTTCCCAGCTTGATCCAGGGTATGATCCTTTCT
CCCGACGCCTCCCAAGTTGTGCAGTTCCAGAATGGGAGATGTCTTATCGACGGTCAGCTTCTGGGAACAACCCCTGC
CACCTCCGGGCAACTCTTCCGGGTGAGAGGCAAAATCAATCAGGGCGCCAGAACACTGAATCTGACAGAAGTGGAC
GGGAAACCCTTTATGGCGTTCGATAGCCCCGCGCCCGTTGGATTCCCTGACTTCGGCAAGTGTGATTGGCACATGCG
CATCAGTAAGACTCCCAACAACACTTCATCTGGAGACCCCATGAGGAGCGTGGATGTCCAGACCGACGTGCAGGGC
TTCGTGCCGCACTTGGGATCTATCCAGTTCGATGAGGTGTTCAATCACCCTACTGGCGACTACATAGGCACAATTGA
GTGGATAAGTCAACCATCTACACCTCCAGGGACCGACATAAACCTGTGGGAAATTCCTGATTACGGGTCATCCCTGA
GTCAAGCTGCCAATCTTGCACCCCCTGTCTTTCCCCCCGGCTTTGGTGAGGCTCTTGTTTACTTCGTCTCTGCATTTCCT
GGTCCTAACAACCGCTCCGCCCCTAACGATGTTCCGTGTTTGTTACCCCAGGAATATGTGACTCATTTCGTTTCCGAA
CAGGCACCCACCATGGGGGACGCTGCCCTGCTACACTATGTGGACCCCGACACCAATAGAAACCTCGGCGAGTTCA
AACTCTACCCCGGGGGATACCTGACCTGTGTTCCAAATGGAGTGGGAGCAGGCCCACAACAGCTGCCCCTGAATGG
GGTCTTCCTGTTCGTTTCTTGGGTGTCACGCTTTTACCAGCTGAAGCCCGTTGGCACAGCTTCTACGGCACGCGGCAG
GCTAGGGGTCCGCCGAATCTGA

Figure 14A

Amino acid sequence of VP1 GI.3_LillaEdet_2008_H2DG70 (SEQ ID NO: 6)

MMMASKDAPTNMDGTSGAGQLVPEVSTAEPISMEPVAGAATAAATAGQVNMIDPWIMSNYVQAPQGEFTISPNNT
PGDILFDLQLGPHLNPFLSHLAQMYNGWVGNMKVRVLLAGNAFTAGKIIISCVPPGFAAQNVSIAQATMFPHVIADVRV
LEPIEVPLEDVRNVLFHNNDSTPTMRLICMLYTPLRASGSSSGTDPFVIAGRVLTCPSPDFNFLFLVPPNVEQKTKPFSVPNL
PLNVLSNSRVPSLIKSMMVSQDHGQMVQFQNGRVTLDGQLQGTTPTSASQLCKIRGTVYHATGGQGLNLTEIDGTPYH
AFESPAPIGFPDLGECDWHINASPANAFTDGSIIHRIDVAQDSTFAPHLGTIHYTNADYNANVGLICSLEWLSPPSGGAPK
VNPWAIPRYGSTLTEAAQLAPPIYPPGFGEAIVFFMSDFPIANGSDGLSVPCTIPQEFVTHFVNEQAPTRGEAALLHYVDP
DTHRNLGEFKLYPEGFMTCVPNSSGSGPQTLPINGVFTFISWVSRFYQLKPVGTTGPVRRLGIRRS

Figure 14B

Nucleic acid sequence of human codon-optimized VP1 GI.3_LillaEdet_2008_H2DG70 (SEQ ID NO: 7)

ATGATGATGGCTTCCAAGGATGCTCCCACAAACATGGATGGAACAAGCGGCGCGGGGCAACTTGTGCCGGAGGTG
TCCACGGCGGAACCCATTTCCATGGAACCTGTGGCCGGCGCAGCCACTGCTGCCGCCACCGCAGGACAGGTAAACA
TGATCGACCCCTGGATCATGTCAAATTACGTTCAGGCTCCACAGGGGGAGTTTACCATAAGCCCAAACAACACCCCG
GGTGACATCTTGTTTGACCTGCAGCTAGGACCACACTTGAATCCGTTTCTGAGTCACTTGGCTCAGATGTATAATGGA
TGGGTTGGAAACATGAAGGTGCGCGTGCTCCTGGCGGGCAATGCATTCACAGCCGGGAAGATTATTATCTCTTGCG
TGCCACCTGGATTTGCAGCCCAGAACGTGTCTATCGCACAGGCAACCATGTTTCCGCATGTCATCGCAGATGTGCGC
GTGCTAGAGCCCATCGAGGTGCCCCTTGAGGACGTGCGCAACGTCCTATTCCATAACAATGATAGCACCCCCACCAT
GCGCTTGATATGTATGTTATATACTCCCCTCCGCGCCAGTGGGTCCAGCTCCGGGACCGATCCTTTTGTGATTGCTGG
GCGGGTGTTGACTTGTCCTAGCCCTGACTTCAACTTCCTTTTTCTGGTGCCTCCAAATGTAGAACAGAAAACAAAGCC
ATTCAGCGTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCACAACCCC
AACCAGTGCCAGTCAGCTGTGTAAGATCAGAGGCACCGTCTACCACGCAACTGGCGGACAGGGGCTGAATCTTACT
GAGATCGATGGTACCCCCTACCATGCATTCGAGTCACCTGCACCTATTGGATTTCCCGATCTTGGGGAGTGTGATTG
GCATATCAATGCTTCACCTGCCAACGCTTTCACAGACGGGTCTATTATTCATCGCATTGACGTAGCACAGGATAGCAC
ATTTGCCCCGCACCTGGGTACCATCCACTATACGAACGCAGATTACAACGCAAACGTGGGTCTTATCTGTAGCCTAG
AGTGGCTATCTCCGCCAAGCGGTGGGGCCCCTAAAGTTAACCCATGGGCTATTCCTCGGTACGGGTCTACGCTGACT
GAGGCCGCTCAGCTGGCACCCCCCATATATCCACCAGGATTCGGGGAAGCCATTGTTTTCTTTATGTCCGATTTTCCG
ATAGCCAACGGTTCAGATGGCCTTAGTGTCCCTTGCACGATTCCACAGGAATTTGTGACACACTTCGTAAACGAGCA
GGCTCCTACTCGGGGCGAGGCTGCCTTGTTGCATTACGTAGACCCCGATACCCATAGAAACCTGGGCGAATTCAAAC
TCTACCCTGAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAGGCTCGGG
ATCAGACGGAGCTAG

Figure 15A

Amino acid sequence of VP1 GI.5_Siklos_HUN5407_2013_HUN_AHW99832 (SEQ ID NO: 12)

MMMASKDAPSSADGANGAGQLVPEVNNAEPLPLDPVAGASTALATAGQVNMIDPWIFNNFVQAPQGEFTISPNNTP
GDILFDLQLGPHLNPFLAHLSQMYNGWVGNMRVRVILAGNAFTAGKVIICCVPPGFQSRTLSIAQATLFPHIIADVRTLEPI
EIPLEDVRNTLYHTNDNQPTMRLLCMLYTPLRTGGGSGGTDAFVVAGRVLTCPSSDFNFLFLVPPTVEQKTRPFSVPNIPL
QLLSNSRVPNLIQSMVLSPDQAQNVQFQNGRCTTDGQLLGTTPVSVSQILKFRGKVSAGSKVINLTELDGSPFLAFEAPAP
TGFPDLGTSDWHVEMSLNSNSQSSGNPILLRDIHPNSSEFVPHLGSVCVTAAIEVAGDYTGTIQWTSQPSNVTPVPDVNF
WTIPHYGSNLAEASQLAPVVYPPGFGEAIVYFMSPIPGPNTAHKPNLVPCLLPQEFVTHFVSEQAPSMGEAALVHYVDPD
TNRNLGEFKLYPEGFITCVPNGTGPQQLPLNGVFVFASWVSRFYQLKPVGTASSARGRLGVRR

Figure 15B

Nucleic acid sequence of human codon-optimized VP1 GI.5_Siklos_HUN5407_2013_HUN AHW99832 (SEQ ID NO: 33)

ATGATGATGGCCTCCAAAGACGCTCCTAGCAGTGCTGATGGCGCTAACGGTGCCGGCCAGCTGGTCCCCGAGGTGA
ATAACGCCGAGCCTCTCCCCTTGGACCCAGTAGCCGGAGCTTCAACGGCCCTAGCTACTGCCGGACAGGTTAATATG
ATTGACCCCTGGATTTTCAATAATTTCGTGCAGGCCCCTCAAGGCGAGTTTACTATAAGCCCTAACAACACACCAGGG
GATATTCTGTTCGACCTGCAGTTAGGCCCTCATCTCAACCCCTTCTTGGCCCACCTGAGCCAGATGTACAATGGCTGG
GTGGGCAACATGCGAGTGAGAGTTATCCTCGCAGGGAACGCCTTTACCGCTGGTAAGGTGATCATTTGTTGCGTAC
CACCTGGATTCCAGTCTAGGACATTAAGTATTGCGCAAGCTACCCTCTTTCCTCATATCATCGCCGACGTGCGGACAC
TAGAGCCCATCGAGATCCCACTGGAGGATGTCCGGAATACCCTGTACCATACCAACGATAATCAGCCCACTATGAGG
TTACTGTGCATGCTGTACACGCCACTCCGGACTGGTGGGGGCAGTGGGGGGACCGATGCTTTCGTCGTTGCCGGTA
GGGTGCTCACTTGCCCGTCATCTGACTTTAACTTCCTATTCCTTGTGCCCCCAACGGTGGAACAGAAAACGAGACCTT
TTTCCGTACCTAACATCCCTTTACAGCTCCTAAGCAATAGCAGAGTACCTAACCTGATCCAATCCATGGTTCTTAGCCC
TGATCAAGCGCAGAACGTACAGTTTCAGAACGGGCGGTGCACCACAGATGGCCAGCTGCTTGGTACAACTCCCGTC
TCCGTGTCTCAGATACTTAAGTTTCGCGGCAAGGTCTCCGCTGGATCCAAAGTAATCAACCTCACTGAGCTTGATGG
CTCTCCCTTTCTGGCGTTCGAGGCGCCCGCCCCAACAGGCTTTCCAGACCTGGGAACATCCGATTGGCATGTCGAGA
TGAGTCTGAATAGCAACTCCCAGTCTTCTGGCAATCCAATACTGCTCCGCGATATCCATCCTAATTCTAGCGAGTTCG
TTCCACACCTGGGTTCTGTGTGCGTGACGGCTGCAATAGAGGTGGCTGGCGACTACACGGGTACCATTCAGTGGAC
CTCTCAGCCAAGTAACGTGACCCCTGTGCCAGACGTTAACTTTTGGACAATTCCACACTACGGCTCTAACTTGGCCGA
AGCATCCCAGCTTGCCCCCGTTGTATATCCCCCAGGCTTTGGCGAAGCAATAGTTTATTTTATGTCCCCAATCCCTGG
ACCTAACACAGCACACAAGCCAAACCTCGTCCCATGCCTGCTGCCCCAGGAGTTCGTGACTCATTTCGTTTCGGAACA
AGCCCCATCAATGGGGGAGGCCGCCCTGGTCCACTACGTGGATCCAGATACCAATCGGAATCTGGGAGAATTCAAA
CTCTACCCTGAAGGATTCATTACATGTGTGCCCAATGGAACAGGACCGCAGCAGCTCCCACTGAACGGTGTCTTTGT
ATTCGCATCATGGGTTAGCCGGTTCTATCAACTTAAACCCGTGGGGACAGCTTCATCTGCCCGGGGGCGCCTTGGCG
TGCGGCGCTGA

Figure 16A

Amino acid sequence of VP1_GI.7 (SEQ ID NO:101)

MMMASKDAPSNMDGTSGAGQLVPEVNAAEPLPLEPVVGAATAVATAGQVNMIDPWIMNNFVQAPEGEFTISPNNT
PGDILFDLRLGPHLNPFLLHLSQMYNGWVGNMRVRVMLAGNAFSAGKIIICCVPPGFESQNISIGQATMFPHVIADVRVL
EPIEVPLDDVRNVLFHTNENRPTMRLLCMLYTPLRAGGASSGTDPFVIAGRVLTCPAPDFNFLFLVPPSVEQKTRQLTIPNI
PLNNLANSRVPAMINKMTVSADQNQVVQFQNGRCTLEGQLLGTTPVSANQVARIRGKVFSTNSGTGLNLTEVDGTPYH
AFESPAPLGFPDIGNCDWHVYAFKVNQNTGDPMYRLDITQGNSFAPHLGSIEFSSENHPSGDQLGTLTWISPLNNASRV
DPWKIPTYGSTLTESTNLAPPIFPPGFGEAIVYFMSDFPIVSGNTAQIPCTLPQEFVSSFVEQQAPIRGEAALLHYVDPDTHR
NLGEFKLYPDGFITCVPNTGGGPQNLPSNGVFVFSSWVSRYYQLKPVGTTGPVRRLGVRRV

Figure 16B

Nucleic acid sequence of human codon-optimized VP1 GI.7/GA5043/USA/2014 VP1 (SEQ ID NO:175)

ATGATGATGGCCAGCAAGGACGCTCCGAGTAACATGGACGGCACTTCGGGCGCGGGGCAGCTGGTGCC
CGAGGTCAATGCCGCAGAACCACTTCCTCTTGAGCCCGTCGTTGGCGCCGCCACAGCTGTCGCAACTGCA
GGCCAAGTCAATATGATCGACCCGTGGATAATGAACAATTTCGTTCAGGCACCAGAAGGAGAATTCACC
ATCTCCCCCAATAACACCCCAGGGGATATTCTGTTTGACCTCAGGTTAGGACCCCACTTGAACCCCTTTCT
GCTTCATCTCTCACAAATGTATAATGGCTGGGTCGGGAATATGCGCGTGCGGGTGATGCTAGCCGGCAA
TGCTTTTTCTGCAGGCAAGATTATCATTTGCTGCGTTCCTCCTGGATTCGAATCTCAAAATATCAGCATTG
GTCAAGCAACCATGTTTCCACATGTGATCGCTGATGTTCGCGTCCTGGAACCCATTGAAGTTCCTCTCGAC
GACGTGAGAAATGTTCTCTTCCACACCAACGAGAATAGGCCGACTATGAGACTTCTGTGTATGCTCTACA
CCCCATTAAGAGCCGGGGGAGCATCCTCAGGTACTGACCCATTTGTGATTGCCGGGCGGGTGCTCACAT
GCCCGGCTCCAGACTTTAACTTCCTTTTCTTGGTGCCACCCAGTGTTGAACAGAAAACCAGACAGCTCACC
ATCCCAAATATCCCATTGAACAATCTCGCCAACAGCAGGGTGCCAGCAATGATAAACAAAATGACAGTCA
GTGCTGACCAGAACCAGGTAGTCCAGTTTCAGAACGGCAGATGCACGCTTGAGGGCCAACTGCTTGGGA
CGACCCCAGTCTCCGCGAACCAGGTGGCCCGAATCCGGGGTAAAGTCTTCAGTACAAACTCCGGCACTG
GCCTTAACCTCACAGAGGTTGACGGCACTCCCTATCATGCTTTTGAGTCTCCAGCCCCTCTTGGCTTTCCC
GATATAGGCAACTGTGACTGGCACGTTTATGCGTTTAAAGTAAACCAGAACACCGGCGATCCTATGTATA
GGTTGGATATAACACAAGGTAATTCATTCGCCCCACACTTGGGTAGCATCGAGTTCAGTTCAGAGAACCA
TCCGAGTGGTGATCAGCTAGGCACATTGACGTGGATCAGCCCTCTGAATAACGCATCAAGAGTGGATCC
CTGGAAGATCCCTACCTATGGGTCCACTCTGACAGAGAGCACAAATTTGGCTCCGCCCATTTTCCCACCCG
GATTCGGCGAGGCCATAGTGTACTTTATGTCTGACTTTCCTATCGTCAGCGGGAATACAGCCCAGATTCCT
TGCACACTGCCACAAGAATTCGTCTCATCCTTTGTAGAGCAGCAGGCACCTATTCGAGGTGAGGCCGCCC
TCTTGCACTACGTGGACCCTGACACCCACCGCAATCTTGGCGAGTTTAAGCTGTACCCTGACGGGTTTATT
ACCTGTGTACCCAACACCGGCGGCGGCCCACAAAATTTGCCCAGCAATGGCGTGTTTGTCTTTTCCTCTTG
GGTGTCTCGATACTACCAGCTTAAACCTGTCGGAACTACGGGCCCCGTGCGACGACTCGGCGTGAGGCG
GGTGTGA

Figure 16C

Amino acid sequence of GII.1_Ascension208_2010_USA_AFA55174 native VP1 (SEQ ID NO: 13)

MKMASNDAAPSNDGAAGLVPEVNNETMALEPVAGASIAAPLTGQNNVIDPWIRMNFVQAPNGEFTVSPRNSPGEVLL
NLELGPELNPFLAHLSRMYNGYAGGVEVQVLLAGNAFTAGKLVFAAIPPHFPLENLSPGQITMFPHVIIDVRTLEPVLLPLP
DVRNNFFHYNQQPEPRMRLVAMLYTPLRSNGSGDDVFTVSCRVLTRPSPDFDFNYLVPPTVESKTKPFTLPILTIGELSNS
RFPVPIDELYTSPNEGVVVQPQNGRSTLDGELLGTTQLVPSNICALRGRINAQVPDDHHQWNLQVTNANGTSFDPTEDV
PAPLGTPDFLANIYGVTSQRNPDNTCRAHDGVLATWSPKFTPKLGSVVLGTWEESDLDLNQPTRFTPVGLYDTGHFDQ
WVLPNYSGRLTLNMNLAPSVAPLFPGEQILFFRSHIPLKGGTSNGAIDCLLPQEWIQHFYQESAPSPTDVALIRYTNPDTG
RVLFEAKLHRQGFITVANSGSRPIVVPPNGYFRFDSWVNQFYSLAPMGTGNGRRRVQ

Figure 17A

Amino acid sequence of VP1 GII.2_CGMH47_2011_TW_AGT39206 (SEQ ID NO: 14)

MKMASNDAAPSTDGAAGLVPESNNEVMALEPVAGAALAAPVTGQTNIIDPWIRANFVQAPNGEFTVSPRNSPGEVLL
NLELGPELNPYLAHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVVVPANGYFRFDSWVNQFYSLAPMGTGNGRRRIQ

Figure 17B

Nucleic acid sequence of human codon-optimized VP1 GII.2 CGMH47 2011 TW AGT39206 (SEQ ID NO: 40)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGCTCCTGTGACCGGGCAGACAAATATCATCGATCCTTG
GATTAGAGCTAATTTCGTGCAAGCCCCAAATGGGGAGTTTACGGTCAGCCCTAGAAATAGCCCTGGGGAAGTGCTC
CTCAATCTCGAGCTGGGACCAGAACTTAATCCGTACCTGGCTCACCTGGCCCGGATGTACAATGGATATGCAGGAG
GGATGGAGGTGCAGGTTATGCTGGCTGGCAATGCCTTTACAGCAGGCAAACTCGTTTTCGCAGCCGTCCCTCCCCAC
TTCCCAGTTGAAAATCTTTCCCCTCAGCAGATTACCATGTTTCCCCATGTCATCATCGATGTGCGTACCCTGGAACCTG
TGCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

Figure 18A

Amino acid sequence of VP1 GII.3_Jingzhou_2013402_CHN_AGX01095 (SEQ ID NO: 15)

MKMASNDAAPSNDGAAGLVPEISSEAMALEPVAGAAIAAPLTGQQNIIDPWIMNNFVQAPGGEFTVSPRNSPGEVLLN
LELGPEINPYLAHLARMYNGYAGGFEVQVVLAGNAFTAGKIIFAAIPPNFPIDNLSAAQITMCPHVIVDVRQLEPVNLPMP
DVRNNFFHYNQGSDSRLRLIAMLYTPLRANNSGDDVFTVSCRVLTRPSPDFSFNFLVPPTVESKTKPFSLPILTISEMSNSRF
PVPIDSLHTSPTENIVVQCQNGRVTLDGELMGTTQLLPSQICAFRGTLTRSTSRASDQADTATPRLFNYYWHIQLDNLNG
TPYDPAEDIPAPLGTPDFRGKVFGVASQRNPDATTRAHEAKIDTTSGRFTPKLGSLEISTESGDFDQNQPTRFTPVGIGVD
HEPDFQQWALPDYAGQFTHNMNLAPAVAPNFPGEQLLFFRSQLPSSGGRSNGILDCLVPQEWVQHFYQESAPSQTQV
ALVRYVNPDTGRVLFEAKLHKLRFMTIAKSGDSPITVPPNGYFRFESWVNPFYTLAPMGTGNGRRRIQ

Figure 18B

Nucleic acid sequence of human codon-optimized VP1 GII.3_Jingzhou_2013402_CHN AGX01095 (SEQ ID NO: 45)

ATGAAAATGGCTTCCAACGATGCAGCACCCTCTAATGATGGCGCTGCCGGACTTGTGCCGGAGATTAGCTCTGAGG
CTATGGCCCTAGAACCAGTAGCCGGGGCAGCCATAGCTGCCCCACTGACTGGCCAGCAGAATATCATTGACCCCTG
GATAATGAACAATTTCGTGCAGGCACCGGGGGGAGAATTCACGGTCTCTCCTCGAAACTCCCCCGGGGAGGTTCTCT
TGAATTTGGAACTGGGCCCTGAAATTAATCCTTATCTGGCCCATCTAGCCCGAATGTACAACGGCTACGCCGGAGGT
TTCGAGGTCCAGGTGGTGCTCGCTGGTAACGCCTTCACAGCTGGCAAGATCATTTTTGCAGCAATCCCTCCAAACTTC
CCTATCGATAATCTTAGTGCCGCCCAGATCACAATGTGCCCTCACGTTATCGTAGATGTGAGGCAGCTGGAACCTGT
CAATCTCCCAATGCCCGACGTGCGCAACAACTTCTTTCACTATAACCAGGGATCTGACTCCCGCCTTCGCCTTATCGCT
ATGCTGTACACCCCTCTGAGGGCTAACAATTCCGGAGATGACGTTTTCACTGTGAGTTGTCGAGTCCTGACACGTCC
ATCTCCTGACTTTAGCTTTAATTTCCTCGTGCCCCCCACAGTGGAATCCAAAACTAAGCCATTCTCTCTGCCAATTCTT
ACCATTAGCGAAATGTCGAATAGTAGGTTCCCGGTGCCCATAGATTCACTGCATACCAGTCCAACAGAAAACATCGT
CGTACAGTGTCAGAACGGACGCGTGACTCTCGACGGGGAGCTTATGGGCACTACCCAGCTGCTGCCCAGCCAGATA
TGCGCCTTCCGCGGCACACTGACTAGAAGCACTTCGCGTGCTTCTGACCAGGCAGATACAGCTACACCAAGGCTGTT
CAATTATTATTGGCATATACAACTCGATAATCTGAATGGCACTCCTTATGACCCAGCCGAGGACATCCCCGCCCCACT
TGGCACCCCGGACTTTAGAGGGAAGGTCTTTGGAGTGGCTTCTCAAAGAAATCCCGACGCAACCACCCGGGCCCAC
GAGGCCAAAATCGATACTACATCAGGGCGTTTCACCCCTAAGTTAGGCAGTCTGGAGATATCTACCGAAAGTGGAG
ATTTCGATCAGAACCAGCCAACCCGGTTTACCCCCGTGGGAATCGGGGTTGACCACGAACCGGATTTCCAGCAGTG
GGCTCTGCCTGATTACGCAGGCCAGTTCACACATAACATGAATCTTGCCCCCGCTGTGGCCCCCAACTTCCCGGGAG
AACAACTTCTGTTTTTCAGGAGCCAACTGCCTTCCAGCGGCGGCCGATCTAACGGGATTTTGGACTGTCTCGTGCCCC
AGGAATGGGTGCAGCATTTTTACCAGGAGTCCGCGCCCTCCCAGACGCAGGTGGCTCTGGTTAGATATGTCAATCCC
GACACCGGCAGGGTGCTATTTGAGGCAAAGCTGCACAAGCTTCGCTTTATGACTATCGCTAAGAGCGGTGATTCGCC
TATTACAGTGCCCCCCAACGGATACTTCAGATTTGAGAGTTGGGTGAACCCATTCTATACCCTGGCCCCCATGGGTAC
AGGCAATGGCAGACGGCGGATCCAGTAA

Figure 19A

Amino acid sequence of VP1 GII.4_Sydney_2012_K4LM89 (SEQ ID NO: 16)

MKMASSDANPSDGSAANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 19B

Nucleic acid sequence of human codon-optimized VP1 GII.4_Sydney_2012_K4LM89 (SEQ ID NO:52)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATACGCAACAATTTTGTCCAAGCCCCTGGTGGGGAGTTCACCGTTAGCCCGAGAAATGCGCCAGGAGAAATCCT
GTGGTCGGCCCCATTGGGACCCGATCTGAACCCCTATTTGTCACATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 19C

Amino acid sequence of VP1 US96: GII.4/Dresden174/1997/DE_AY741811 (SEQ ID NO: 27)

MKMASNDANPSDGSTANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIIVDVRQLEPVLIP
LPDVRNNFYHYNQSNDSTIKLIAMLYTPLKANNAGDDVFTVSCRVLTRPSPDFDFIFLVPPTVESRTKPFTVPILTVEEMSN
SRFPIPLEKLYTGPSSAFVVQPQNGRCTTDGVLLGTTQLSAVNICTFRGDVTHIAGSHDYTMNLASQNWNNYDPTEEIPA
PLGTPDFVGKIQGMLTQTTREDGSTRAHKATVSTGSVHFTPKLGSVQYTTDTNNDFQTGQNTKFTPVGVIQDGNNHQN
EPQQWVLPNYSGRTGHNVHLAPAVAPTFPGEQLLFFRSTMPGCSGYPNMNLDCLLPQEWVQHFYQEAAPAQSDVALL
RFVNPDTGRVLFECKLHKSGYVTVAHTGPHDLVIPPNGYFRFDSWVNQFYTLAPMGNGAGRRRAL

Figure 19D

Amino acid sequence of VP1 FH02: GII.4/FarmingtonHills/2002/US_AY502023 (SEQ ID NO: 28)

MKMASNDANPSDGSTANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKIIFAAVPPNFPTEGLSPSQVTMFPHIIVDVRQLEPVLIP
LPDVRNNFYHYNQLNDPTIKLIAMLYTPLRANNAGEDVFTVSCRVLTRPSPDFDFIFLVPPTVESRTKPFTVPILTVEEMTN
SRFPIPLEKLFTGPSGAFVVQPQNGRCTTDGVLLGTTQLSPVNICTFRGDVTHIAGTHNYTMNLASQNWNNYDPTEEIPA
PLGTPDFVGRIQGMLTQTTRGDGSTRGHKATVSTGDVHFTPKLGSIQFNTDTNNDFETGQNTKFTPVGVVQDGNGTH
QNEPQQWVLPSYSGRTGHNVHLAPAVAPTFPGEQLLFFRSTMPGCSGYPNMNLDCLLPQEWVQHFYQEAAPAQSDV
ALLRFVNPDTGRVLFECKLHKSGYVTVAHTGQHDLVIPPNGYFRFDSWVNQFYTLAPMGNGTGRRRAL

Figure 19E

Amino acid sequence of VP1 Hnt04:GII.4/Hunter-NSW504D/2004/AU_DQ078814 (SEQ ID NO: 29)

MKMASNDATPSDGSTANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKIIFAAVPPNFPTEVLSPSQVTMFPHIIVDVRQLEPVLIP
LPDVRNNLYHYNQSNDPTIRLIAMLYTPLRANNAGDDVFTVSCRVLTRPSPDFDFIFLVPPTVESRTKPFSVPILTVEEMTN
SRFPIPLEKLFTGPSSAFVVQPQNGRCTTDGVLLGTTQLSPVNICTFRGDVTHIAGTQNYTMNLASQNWNNYDPTEEIPA
PLGTPDFVGRIQGVLTQTTRRDGSTRGHKATVSTGSVHFTPKLGSVQFSTDTSNDFETGQNTRFTPVGVVQDGSTTHQN
EPQQWVLPDYSGRDSHNVHLAPAVAPTFPGEQLLFFRSTMPGCSGYPNMNLDCLLPQEWVQHFYQESAPAQSDVALL
RFVNPDTGRVLFECKLHKSGYVTVAHTGQHDLVIPPNGYFRFDSWVNQFYTLAPMGNGAGRRRAL

Figure 19F

Amino acid sequence of VP1 2006b: GII.4/Shellharbour-NSW696T/2006/AU_EF684915 (SEQ ID NO: 30)

MKMASNDANPSDGSAANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKIIFAAVPPNFPTEGLSPSQVTMFPHIIVDVRQLEPVLIP
LPDVRNNFYHYNQSNDSTIKLIAMLYTPLRANNAGEDVFTVSCRVLTRPSPDFDFIFLVPPTVESRTKPFTVPILTVEEMTNS
RFPIPLEKLFTGPSGAFVVQPQNGRCTTDGVLLGTTQLSPVNICTFRGDVTHIAGSRNYTMNLASLKWNKYDPTEEIPAPL
GTPDFVGKIQGVLTQTTKGDGSTRGHKATIYTGSAPFTPKLGSVQFSTDTENDFETHQNTKFTPVGVTQDGSTTHRNEPQ
QWVLPSYSGRNVHNVHLAPAVAPTFPGEQLLFFRSTMPGCSGYPNMDLDCLLPQEWVQHFYQEAAPAQSDVALLRFV
NPDTGRVLFECKLHKSGYVTVAHTGQHDLVIPPNGYFRFDSWVNQFYTLAPMGNGTGRRRAL

Figure 19G

Amino acid sequence of VP1 NO09: GII.4/Orange-NSW001P/2008/AU_GQ845367 (SEQ ID NO: 31)

MKMASSDANPSDGSTANLVPEVNNEVMALEPVVGAAIAAPVAGQQNVIDPWIRNNFVQAPGGEFTVSPRNAPGEIL
WSAPLGPDMNPYLSHLARMYNGYAGGFEVQVILAGNAFTAGKIIFAAVPPNFPTEGLSPSQVTMFPHIIVDVRQLEPVLI
PLPDVRNNFYHYNQSNDPTIKLIAMLYTPLRANNAGDDVFTVSCRVLTRPSPDFDFIFLVPPTVESRTKPFSVPILTVEEMT
NSRFPIPLEKLFTGPSSAFVVQPQNGRCTTDGVLLGTTQLSPVNICTFRGDVTHIAGSRNYTMNLASQNWNSYDPTEEIPA
PLGTPDFVGKIQGVLTQTTRTDGSTRGHKATVYTGSADFSPKLGRVQFATDTDNDFDANQNTKFTPVGVIQDGNTAHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAL

Figure 20

Amino acid sequence of VP1 GII.5_Alberta_2013_CA_ALT54485 (SEQ ID NO: 17)

MKMASNDATPSNDGAAGLVPESNNEAMALEPVVGASLAAPVTGQTNIIDPWIRTNFVQAPNGEFTVSPRNSPGEILVN
LELGPELNPYLAHLARMYNGYAGGMEVQVLLAGNAFTAGKIIFAAVPPYFPVENLSPSQITMFPHVIIDVRTLEPVLLPMP
DVRSTLFHFNQKDEPKMRLVAMLYTPLRSNGSGDDVFTVSCRILTRPSPEFDFTYLVPPTVESKTKPFTLPVLTLGELSNSRF
PLSIDEMVTSPNESIVVQPQNGRVTLDGELLGTTQLQACNICSIRGKVTGQVPNEQHMWNLEITNLNGTQFDPTDDVPA
PLGVPDFAGEVFGVLSQRNRGESNPANRAHDAVVATYSDKYTPKLGLVQIGTWNTNDVENQPTKFTPIGLNEVANGHR
FEQWTLPRYSGALTLNMNLAPAVAPLFPGERLLFFRSYVPLKGGFGNPAIDCLVPQEWVQHFYQESAPSLGDVALVRYV
NPDTGRVLFEAKLHKGGFLTVSSTSTGPVVVPANGYFRFDSWVNQFYSLAPMGTGNGRRRFQ

Figure 21A

Amino acid sequence of VP1 GII.6_Ohio_2012_M9T020 (SEQ ID NO: 20)

MKMASNDAAPSNDGAANLVPEANNEVMALEPVVGASIAAPVVGQQNIIDPWIRENFVQAPQGEFTVSPRNSPGEMLL
NLELGPELNPYLSHLSRMYNGYAGGMQVQVVLAGNAFTAGKIIFAAVPPHFPVENINAAQITMCPHVIVDVRQLEPVLLP
LPDIRNRFFHYNQENTSRMRLVAMLYTPLRANSGEDVFTVSCRVLTRPAPDFEFTFLVPPTVESKTKPFSLPILTLGELSNSR
FPAPIDMLYTDPNEGIVVQPQNGRCTLDGTLQGTTQLVPTQICAFRGTLIGQTSRSPDSTDSAPRRRDHPLHVQLKNLDG
TQYDPTDEVPAVLGAIDFKGTVFGVASQRDVSGQQVGATRAHEVHINTTDPRYTPKLGSILMYSESDDFVTGQPVRFTPI
GMGDNDWHQWELPDYPGHLTLNMNLAPAVAPAFPGERILFFRSIVPSAGGYGSGQIDCLIPQEWVQHFYQEAAPSQS
AVALIRYVNPDTGRNIFEAKLHREGFITVANSGNNPIVVPPNGYFRFEAWVNQFYTLTPMGTGQGRRRDQ

Figure 21B

Nucleic acid sequence of human codon-optimized VP1 GII.6_Ohio_2012_M9T020 (SEQ ID NO: 21)

ATGAAGATGGCAAGCAACGACGCAGCTCCCTCCAATGATGGTGCCGCCAACCTGGTCCCCGAAGCTAATAATGAGG
TGATGGCGTTAGAGCCGGTGGTTGGCGCATCTATTGCAGCGCCTGTGGTCGGACAGCAGAACATCATTGATCCCTG
GATTCGCGAGAACTTCGTACAAGCTCCACAGGGGGAGTTCACAGTCTCCCCCCGGAACTCCCCGGGCGAGATGCTG
CTCAATCTGGAACTCGGCCCTGAACTAAACCCTTATCTGTCACACCTTTCACGGATGTACAATGGCTACGCAGGAGG
AATGCAAGTTCAGGTGGTCCTGGCCGGCAATGCTTTCACCGCGGGCAAAATCATCTTTGCGGCCGTTCCTCCACACT
TCCCTGTCGAAAATATCAACGCCGCCCAGATTACTATGTGCCCCCACGTGATTGTGGATGTGCGACAGTTAGAGCCA
GTTCTGCTGCCCCTGCCCGACATCAGAAACCGGTTCTTCCATTACAATCAAGAGAATACTTCACGGATGAGACTTGTT
GCGATGCTGTACACCCCTCTTCGTGCAAATTCCGGCGAAGACGTGTTCACTGTGTCTTGTCGAGTACTTACCCGACCC
GCCCCCGATTTCGAATTCACCTTCCTGGTTCCCCCTACTGTGGAGAGCAAGACAAAACCCTTCAGCCTCCCAATCTTA
ACACTCGGGGAGCTGTCTAATTCACGCTTCCCCGCACCTATTGATATGCTGTATACTGACCCCAACGAGGGGATAGT
GGTGCAGCCCCAAAATGGACGGTGTACTCTCGACGGCACGCTCCAGGGCACAACCCAACTGGTGCCAACCCAGATT
TGTGCATTCAGGGGCACTTTGATTGGGCAGACATCGAGATCTCCAGATTCTACTGATTCCGCGCCAAGGAGGAGGG
ACCACCCACTCCACGTTCAGTTAAAAAACCTGGACGGAACCCAGTACGACCCTACAGACGAGGTCCCCGCTGTCCTC
GGAGCCATCGACTTTAAAGGAACTGTATTTGGAGTGGCATCCCAAAGGGATGTCTCGGGGCAGCAGGTGGGAGCT
ACGAGAGCACATGAAGTCCACATTAACACCACAGACCCAAGATATACCCCAAAACTAGGGTCAATTTTAATGTATTC
GGAATCAGACGATTTTGTTACAGGTCAGCCCGTGCGGTTTACCCCGATCGGAATGGGGGACAACGATTGGCACCAG
TGGGAATTGCCCGATTACCCTGGACACCTCACCTTGAATATGAATCTGGCCCCAGCCGTCGCGCCCGCCTTCCCCGGT
GAGCGGATCCTCTTTTTTAGAAGCATAGTGCCCTCCGCAGGTGGGTATGGATCAGGGCAGATTGATTGCCTGATCCC
CCAAGAATGGGTACAGCATTTCTACCAGGAAGCAGCCCCTAGCCAGTCCGCAGTAGCACTGATCAGATATGTTAATC
CTGATACGGGAAGGAACATCTTCGAAGCAAAACTGCACCGTGAGGGCTTCATTACCGTCGCCAACAGTGGTAATAA
CCCTATTGTGGTGCCTCCTAATGGATACTTCAGGTTTGAGGCATGGGTGAATCAGTTTTATACTCTGACTCCCATGGG
GACAGGCCAGGGGCGACGCCGGGATCAGTGA

Figure 22

Amino acid sequence of VP1 GII.7_Musa_2010_AII73774 (SEQ ID NO: 18)

MKMASNDAAPSNDGAAGLVPEINNEVMPLEPVAGASLATPVVGQQNIIDPWIRNNFVQAPAGEFTVSPRNSPGEILLD
LELGPELNPYLAHLARMYNGHAGGMEVQIVLAGNAFTAGKIIFAAIPPGFPYENLSPSQITMCPHVIIDVRQLEPVLLPMP
DIRNNFFHYNQGNDPKLRLIAMLYTPLRANNSGDDVFTVSCRVLTKPSPDFEFTFLVPPTVESKTKQFTLPILKISEMTNSRF
PVPVEMMYTARNENQVVQPQNGRVTLDGELLGTTPLLAVNICKFKGEVIAKNGDVRSYRMDMEITNTDGTPIDPTEDT
PGPIGSPDFQGILFGVASQRNKNEQNPATRAHEANINTGGDQYAPKLAQVKFFSESQDFEVHQPTVFTPVGVAGDTSHP
FRQWVLPRYGGHLTNNTHLAPAVAPLFPGEQILFFRSQIPSSGGHELGYMDCLVPQEWVQHFYQEAATAQSEVALIRFIN
PDTGRVLFEAKLHKQGFITVAHTGDNPIVMPPNGYFRFEAWVNQFYSLAPVGTGNGRRRIQ

Figure 23A

Amino acid sequence of VP1 GII.12_HS206_2010_USA_AEI29586 (SEQ ID NO: 19)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELTNS
RFPVPIDELYTSPNESLVVQPQNGRCALDGELQGTTQLLPTAICSFRGRINQKVSGENHVWNMQVTNIDGTPFDPTEDV
PAPLGTPDFSGKLFGVLSQRDHDNACRSHDAVIATNSAKFTPKLGAIQIGTWEQDDVHINQPTKFTPVGLFESEGFNQW
TLPNYSGALTLNMGLAPPVAPTFPGEQILFFRSHIPLKGGVADPVIDCLLPQEWIQHLYQESAPSQTDVALIRFTNPDTGRV
LFEAKLHRSGYITVANTGSRPIVVPANGYFRFDSWVNQFYSLAPMGTGNGRRRVQ

Figure 23B

Human codon-optimized VP1 GII.12_HS206_2010_USA_AEI29586 (SEQ ID NO: 87)

ATGAAGATGGCGTCTAATGATGCTGCTCCTTCCAATGATGGCGCAGCCGGCCTGGTCCCTGAAGTGAATAACGAGA
CTATGGCTCTCGAACCCGTGGCCGGAGCCTCAATTGCCGCCCCCCTCACTGGCCAGAACAACGTGATTGATCCCTGG
ATCAGACTGAACTTCGTTCAGGCTCCTAATGGGGAGTTCACCGTGTCCCCGAGAAACTCCCCCGGCGAAGTGTTATT
GAATTTGGAATTAGGACCAGAACTCAACCCCTATCTGGCACATCTGTCTCGGATGTACAACGGCTATGCGGGCGGA
GTGGAGGTGCAAGTTCTTCTCGCTGGTAATGCATTCACAGCAGGAAAATTAGTATTTGCAGCGGTTCCACCCCATTTT
CCACTTGAAAACATAAGCCCAGGCCAGATCACCATGTTCCCTCACGTGATAATCGACGTGCGGACATTAGAGCCCGT
GCTGCTACCCCTGCCCGACGTGAGGAACAATTTCTTTCACTACAATCAGCAAAATGAACCAAGAATGCGCCTGGTCG
CCATGCTCTATACTCCTTTAAGAAGTAATGGCAGTGGGGATGACGTGTTTACTGTTAGCTGTCGGGTGCTCACCCGA
CCTTCCCCAGATTTCGACTTCAATTATCTGGTCCCCCCCACGGTAGAGTCCAAAACAAAGCCTTTCACTCTTCCAATCC
TTACAATTGGCGAACTGACCAACTCACGCTTTCCAGTGCCTATTGATGAGCTGTACACAAGTCCAAATGAATCCCTTG
TCGTTCAGCCACAGAATGGGCGCTGCGCGCTTGACGGTGAGCTCCAGGGCACAACACAACTGTTGCCAACCGCTAT
ATGCTCTTTCAGGGGGCGTATTAATCAGAAGGTCTCCGGGGAGAACCACGTGTGGAACATGCAAGTGACGAATATC
GACGGGACACCTTTCGATCCAACAGAGGATGTCCCAGCGCCTCTAGGTACCCCTGACTTCTCAGGCAAGTTGTTCGG
CGTCCTTTCCCAGCGCGACCATGATAATGCTTGCCGGAGCCACGATGCCGTCATTGCCACCAACTCAGCCAAATTCAC
CCCAAAACTTGGAGCGATACAGATCGGAACTTGGGAACAAGACGACGTCCATATCAACCAACCAACAAAGTTTACCC
CTGTTGGCCTTTTCGAAAGCGAAGGCTTTAACCAGTGGACACTTCCCAATTACAGCGGGGCTCTCACTCTTAATATGG
GACTCGCACCACCCGTCGCTCCAACGTTTCCTGGTGAGCAGATTTTGTTTTTCCGCAGTCATATTCCACTGAAGGGTG
GAGTTGCTGATCCCGTGATAGACTGCCTCCTCCCTCAGGAATGGATTCAGCACTTGTATCAGGAGTCCGCTCCCTCGC
AGACCGATGTGGCCCTGATACGCTTCACAAACCCCGATACCGGAAGAGTGTTGTTTGAAGCTAAACTTCATCGCTCC

Figure 23B (cont)

GGTTACATCACAGTAGCCAACACGGGTTCCAGGCCAATCGTAGTTCCGGCAAACGGATACTTTCGATTCGACAGTTG
GGTCAATCAGTTCTACAGCCTGGCTCCAATGGGAACAGGAAATGGGAGGAGGCGTGTGCAGTAA

Figure 24A

Amino acid sequence of VP1 GII.13_VA173_2010_H9AWU4 (SEQ ID NO: 22)

MKMASNDAAPSNDGAASLVPEAINETMPLEPVAGASIAAPVAGQTNIIDPWIRTNFVQAPNGEFTVSPRNS
PGEILLNLELGPDLNPYLAHLSRMYNGYAGGVEVQVLLAGNAFTAGKILFAAIPPNFPVDMISPAQITMLPHLI
VDVRTLEPIMIPLPDVRNVFYHFNNQPQPRMRLVAMLYTPLRSNGSGDDVFTVSCRVLTRPTPDFEFIYLVPP
SVESKTKPFTLPILTISELTNSRFPISIEQLYTAPNENNVVQCQNGRCTLDGELQGTTQLLSSAVCSYRGRTVANS
GDNWDQNVLQLTYPSGASYDPTDEVPAPLGTQDFSGILYGVLTQDNVRENTGEAKNAKGVYISTTSGKFTPK
IGSIGLHSITEDVRPNQQSRFTPVGVAQNENTPFQQWVLPHYAGALALNTNLAPAVAPTFPGEQLLFFRSRVP
CVQGLQGQDAFIDCLLPQEWVNHFYQEAAPSQADVALIRYVNPDTGRTLFEAKLHRSGFITVSHTGAYPLVV
PPNGHFRFDSWVNQFYSLAPMGTGNGRRRVQ

Figure 24B

Nucleic acid sequence of human codon-optimized VP1 GII.13_VA173_2010_H9AWU4 (SEQ ID NO: 23)

ATGAAAATGGCTTCTAATGATGCCGCGCCCAGCAATGATGGTGCCGCCAGCCTTGTGCCCGAAGCAATTAACGAGA
CAATGCCCTTGGAGCCAGTCGCCGGGGCTTCTATTGCGGCCCCAGTTGCTGGACAGACGAATATCATCGATCCTTGG
ATACGGACTAATTTTGTTCAAGCTCCTAACGGAGAGTTCACTGTCTCCCCCCGTAATAGTCCTGGCGAGATCCTGTTG
AACCTCGAGTTGGGGCCAGATCTCAATCCTTACCTGGCTCATCTGTCGAGAATGTACAACGGGTACGCGGGGGGGG
TTGAGGTGCAGGTCTTACTGGCAGGTAACGCATTCACAGCAGGCAAGATTCTGTTTGCGGCCATCCCTCCTAATTTTC
CAGTGGATATGATATCTCCAGCACAGATTACAATGCTGCCCCATTTGATAGTGGATGTGCGGACACTTGAACCTATC
ATGATCCCTTTGCCCGATGTCCGAAATGTGTTTTATCATTTCAACAACCAGCCGCAGCCAAGAATGCGTCTCGTCGCG
ATGCTGTACACCCCGTTGCGGTCCAACGGCTCTGGCGATGATGTTTTCACAGTGTCGTGTCGAGTGTTAACCCGCCCT
ACCCCAGATTTTGAGTTTATATATCTAGTTCCCCCTTCTGTGGAAAGCAAGACTAAACCCTTTACTCTTCCCATTCTGA
CTATATCCGAGCTTACCAACTCCCGGTTCCCCATCTCAATCGAGCAACTGTACACTGCACCCAACGAGAACAACGTAG
TCCAGTGCCAGAACGGGAGATGTACCCTGGACGGGGAGCTCCAAGGGACCACGCAACTGTTAAGTTCAGCCGTTTG
CAGTTACAGAGGCAGGACTGTGGCGAACTCTGGTGATAACTGGGATCAAAATGTGTTGCAGCTGACTTACCCATCC
GGCGCAAGCTACGATCCAACAGATGAGGTGCCAGCGCCCCTTGGCACACAGGATTTCTCAGGAATTCTATACGGGG
TGCTTACTCAGGATAATGTGCGAGAAAATACTGGCGAGGCCAAGAATGCTAAAGGAGTGTATATAAGCACGACAAG
CGGTAAGTTTACCCCCAAAATTGGCAGTATTGGGCTCCACAGCATTACTGAGGACGTCCGCCCAAACCAGCAGTCTC
GTTTCACTCCCGTGGGGGTGGCACAGAACGAGAACACACCTTTCCAGCAGTGGGTCTTGCCCCATTATGCAGGTGCT
TTGGCGCTCAATACAAATCTGGCACCCGCCGTAGCGCCGACATTTCCTGGGGAGCAATTGCTGTTCTTTAGAAGCCG
CGTCCCGTGTGTTCAGGGCTTGCAGGGCCAGGACGCGTTCATTGATTGCCTCTTGCCCCAGGAATGGGTCAACCACT
TTTATCAGGAGGCAGCGCCCTCTCAAGCAGATGTGGCCCTGATAAGATATGTGAATCCCGACACAGGACGGACTTT
GTTTGAGGCAAAACTCCACCGGTCAGGATTCATTACTGTGAGTCACACAGGAGCCTATCCCCTTGTGGTTCCACCTAA
TGGCCACTTCAGGTTCGACTCTTGGGTCAATCAGTTTTATTCGCTGGCACCAATGGGTACCGGGAATGGTCGCCGTC
GGGTGCAATGA

Figure 25

Amino acid sequence of VP1 GII.14_Saga_2008_JPN_ADE28701 (SEQ ID NO: 32)

MKMASNDATPSDDGAAGLVPEINNEVMALEPVAGASIAAPVVGQQNIIDPWIRNNFVQAPAGEFTVSPRNSPGELLLD
LELGPELNPYLAHLARMYNGHAGGMEVQIVLAGNAFTAGKILFAAIPPSFPYENLSPAQLTMCPHVIVDVRQLEPVLLPM
PDIRNVFYHYNQNNSPKLRLVAMLYTPLRANNSGDDVFTVSCRVLTRPSPDFQFTFLVPPTVESKTKNFTLPVLRVSEMTN
SRFPVVLDQMYTSRNENIIVQPQNGRCTTDGELLGTTILQSVSICNFKGTMQAKLNEEPRYQLQLTNLDGSPIDPTDDMP
APLGTPDFQAMLYGVASQRSSIDNATRAHDAQIDTAGDTFAPKIGQVRFKSSSNDFDLHDPTKFTPIGVNVDDQHPFRQ
WSLPNYGGHLALNNHLAPAVTPLFPGEQILFFRSYIPSAGGHTDGAMDCLLPQEWVEHFYQEAAPSQSDIALVRFINPDT
GRVLFEAKLHKQGFLTIAASGDHPIVMPTNGYFRFEAWVNPFYTLAPVGTGSGRRRIQ

Figure 26A

Amino acid sequence of VP1 GII.17_Kawa_2014_A0A077KVU6 (SEQ ID NO: 24)

MKMASNDAAPSNDGAAGLVPEGNNETLPLEPVAGAAIAAPVTGQNNIIDPWIRTNFVQAPNGEFTVSPRNS
PGEILLNLELGPDLNPYLAHLSRMYNGYAGGVEVQVLLAGNAFTAGKILFAAVPPNFPVEFLSPAQITMLPHLI
VDVRTLEPIMIPLPDVRNTFFHYNNQPNSRMRLVAMLYTPLRSNGSGDDVFTVSCRVLTRPTPDFEFTYLVPP
SVESKTKPFSLPILTLSELTNSRFPVPIDSLFTAQNNVLQVQCQNGRCTLDGELQGTTQLLPSGICAFRGRVTAE
TDHRDKWHMQLQNLNGTTYDPTDDVPAPLGTPDFKGVVFGVASQRNVGNDAPGSTRAHEAVISTYSPQFV
PKLGSVNFRSNDNDFQLQPTKFTPVGINDDGDHPFRQWELPDYSGLLTLNMNLAPPVAPNFPGEQLLFFRSF
VPCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

Figure 26B

Human codon-optimized VP1 GII.17_Kawa_2014_A0A077KVU6 (SEQ ID NO: 25)

ATGAAAATGGCATCTAACGACGCAGCCCCCTCAAACGATGGCGCTGCTGGACTCGTGCCGGAGGGGAATAATGAG
ACACTTCCACTAGAGCCGGTTGCAGGCGCCGCTATAGCTGCCCCAGTGACAGGGCAGAATAATATTATAGACCCTTG
GATTCGGACAAACTTCGTGCAGGCACCCAACGGCGAGTTTACAGTATCCCCCCGGAACTCCCCAGGTGAGATACTCC
TGAATCTTGAGCTCGGCCCTGACCTCAATCCATATCTGGCTCATCTGAGCCGCATGTACAATGGTTACGCTGGGGGG
GTCGAAGTGCAGGTCCTCCTGGCCGGAAACGCCTTTACCGCTGGCAAAATTCTGTTTGCCGCCGTTCCACCAAACTTT
CCAGTCGAATTCCTCTCTCCCGCGCAAATAACCATGCTGCCACATTTGATCGTTGACGTGCGGACCCTGGAGCCAATA
ATGATTCCCCTGCCGGATGTGCGTAACACCTTTTTCCATTATAACAATCAGCCAAACTCTCGGATGAGACTTGTTGCT
ATGCTGTACACCCCCCTGCGGAGCAACGGCAGTGGCGATGATGTGTTTACCGTGAGTTGCAGAGTCCTGACGCGCC
CAACCCCGGACTTCGAGTTCACCTACCTGGTGCCCCCTTCTGTGGAATCTAAGACCAAACCGTTTTCACTGCCAATCT
TAACTCTCTCCGAACTGACTAACAGCCGGTTTCCAGTACCCATAGATTCTCTTTTTACCGCTCAAAACAACGTACTCCA
AGTCCAGTGCCAGAACGGCCGCTGTACGCTTGATGGTGAGTTGCAGGGGACAACACAGCTACTCCCCAGTGGCATC
TGTGCATTCCGGGGCCGCGTGACCGCTGAGACAGACCATCGTGACAAATGGCACATGCAACTCCAAAACTTAAACG
GGACCACCTACGACCCAACCGACGACGTCCCTGCTCCGCTAGGGACTCCTGACTTTAAGGGGGTGGTGTTCGGAGT
GGCCTCTCAGCGGAATGTTGGGAATGACGCCCCCGGCTCTACCCGAGCTCACGAGGCCGTTATCTCAACATATAGCC
CCCAATTTGTGCCCAAGCTCGGATCCGTTAATTTTCGTAGTAACGACAACGACTTCCAACTGCAACCAACGAAGTTTA
CGCCAGTGGGGATTAATGATGATGGAGACCATCCTTTCCGCCAATGGGAACTACCAGATTATTCTGGGCTGCTCACC
CTCAATATGAACCTCGCCCCACCCGTGGCCCCTAATTTCCCCGGTGAGCAGCTGCTGTTTTTTCGGAGCTTTGTGCCA
TGCAGTGGCGGATATAATCAAGGCATCGTAGACTGCTTGATTCCCCAAGAGTGGATACAACATTTTTACCAGGAAAG

Figure 26B (cont)

TGCGCCCTCCCAGTCCGATGTGGCCCTGATACGGTACGTTAACCCCGATACCGGAAGAACATTATTCGAAGCGAAAT
TGCACAGATCAGGGTACATTACCGTTGCACATTCCGGCGATTATCCCCTGGTGGTTCCCGCCAACGGTTACTTTAGGT
TCGATAGTTGGGTCAACCAGTTCTATTCACTAGCCCCAATGGGCACCGGTAACGGCAGACGCCGGGCTCAGTAG

Figure 27

Amino acid sequence of VP1 GII.21_Sali_2011_USA_AFC89665 (SEQ ID NO: 26)

MKMASNDAAPSNDGATGLVPEINTETLPLEPVAGAAIAAPVTGQNNIIDPWIRNNFVQAPNGEFTVSPRNSPGEILMNL
ELGPDLNPYLAHLSRMYNGYAGGVEVQVLLAGNAFTAGKILFAAVPPNFPVDMLSPAQITMLPHLIVDVRTLEPIMIPLP
DVRNVFYHFNNQPAPRMRLVAMLYTPLRSNGSGDDVFTVSCRVLTRPTPDFEFTYLVPPSVESKTKPFTLPILTIGELTNSR
FPAPIDQLYTSPNADVVVQPQNGRCTLDGELQGTTQLLTTAICSYRGMTSNPTSDYWDDHLLHLVHPNGATYDPTEDVP
APFGTQDFRGILYGMLTQNPRTSGDEAANSHGIYISSTSEKFTPKLGTIGLHQVQGDIASNQQSKFTPVGIAVNGNTPFRQ
WELPNYSGALTLNTNLAPAVGPNFPGEQILFFRSNVPSVQGGQPIEIDCLIPQEWVSHFYQESAPSQSDVALVRYVNPDT
GRTIFEAKLHRQGFITIAATGSNPVVVPPNGYFRFDSWVNQFYALAPMGTGNGRRRVQ

Figure 28A

Amino acid sequence of VP1_GI.3_Lil08_Q84S (SEQ ID NO:98)

MMMASKDAPTNMDGTSGAGQLVPEVSTAEPISMEPVAGAATAAATAGQVNMIDPWIMSNYVQAPQGEFTISPNNT
PGDILFDLSLGPHLNPFLSHLAQMYNGWVGNMKVRVLLAGNAFTAGKIIISCVPPGFAAQNVSIAQATMFPHVIADVRV
LEPIEVPLEDVRNVLFHNNDSTPTMRLICMLYTPLRASGSSSGTDPFVIAGRVLTCPSPDFNFLFLVPPNVEQKTKPFSVPNL
PLNVLSNSRVPSLIKSMMVSQDHGQMVQFQNGRVTLDGQLQGTTPTSASQLCKIRGTVYHATGGQGLNLTEIDGTPYH
AFESPAPIGFPDLGECDWHINASPANAFTDGSIIHRIDVAQDSTFAPHLGTIHYTNADYNANVGLICSLEWLSPPSGGAPK
VNPWAIPRYGSTLTEAAQLAPPIYPPGFGEAIVFFMSDFPIANGSDGLSVPCTIPQEFVTHFVNEQAPTRGEAALLHYVDP
DTHRNLGEFKLYPEGFMTCVPNSSGSGPQTLPINGVFTFISWVSRFYQLKPVGTTGPVRRLGIRRS

Figure 28B

Nucleic acid sequence of human codon optimized VP1_GI.3_Lil08_Q84S (SEQ ID NO:167)

ATGATGATGGCTTCCAAGGATGCTCCCACAAACATGGATGGAACAAGCGGCGCGGGGCAACTTGTGCCGGAGGTG
TCCACGGCGGAACCCATTTCCATGGAACCTGTGGCCGGCGCAGCCACTGCTGCCGCCACCGCAGGACAGGTAAACA
TGATCGACCCCTGGATCATGTCAAATTACGTTCAGGCTCCACAGGGGGAGTTTACCATAAGCCCAAACAACACCCCG
GGTGACATCTTGTTTGACCTGAGCCTAGGACCACACTTGAATCCGTTTCTGAGTCACTTGGCTCAGATGTATAATGGA
TGGGTTGGAAACATGAAGGTGCGCGTGCTCCTGGCGGGCAATGCATTCACAGCCGGGAAGATTATTATCTCTTGCG
TGCCACCTGGATTTGCAGCCCAGAACGTGTCTATCGCACAGGCAACCATGTTTCCGCATGTCATCGCAGATGTGCGC
GTGCTAGAGCCCATCGAGGTGCCCCTTGAGGACGTGCGCAACGTCCTATTCCATAACAATGATAGCACCCCCACCAT
GCGCTTGATATGTATGTTATATACTCCCCTCCGCGCCAGTGGGTCCAGCTCCGGGACCGATCCTTTTGTGATTGCTGG
GCGGGTGTTGACTTGTCCTAGCCCTGACTTCAACTTCCTTTTTCTGGTGCCTCCAAATGTAGAACAGAAAACAAAGCC
ATTCAGCGTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCACAACCCC
AACCAGTGCCAGTCAGCTGTGTAAGATCAGAGGCACCGTCTACCACGCAACTGGCGGACAGGGGCTGAATCTTACT
GAGATCGATGGTACCCCCTACCATGCATTCGAGTCACCTGCACCTATTGGATTTCCCGATCTTGGGGAGTGTGATTG
GCATATCAATGCTTCACCTGCCAACGCTTTCACAGACGGGTCTATTATTCATCGCATTGACGTAGCACAGGATAGCAC

Figure 28B (cont)

ATTTGCCCCGCACCTGGGTACCATCCACTATACGAACGCAGATTACAACGCAAACGTGGGTCTTATCTGTAGCCTAG
AGTGGCTATCTCCGCCAAGCGGTGGGGCCCCTAAAGTTAACCCATGGGCTATTCCTCGGTACGGGTCTACGCTGACT
GAGGCCGCTCAGCTGGCACCCCCCATATATCCACCAGGATTCGGGGAAGCCATTGTTTTCTTTATGTCCGATTTTCCG
ATAGCCAACGGTTCAGATGGCCTTAGTGTCCCTTGCACGATTCCACAGGAATTTGTGACACACTTCGTAAACGAGCA
GGCTCCTACTCGGGGCGAGGCTGCCTTGTTGCATTACGTAGACCCCGATACCCATAGAAACCTGGGCGAATTCAAAC
TCTACCCTGAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAGGCTCGGG
ATCAGACGGAGCTAG

Figure 28C

Amino acid sequence of VP1_GI.3_Lil08_S94L (SEQ ID NO:8)

MMMASKDAPTNMDGTSGAGQLVPEVSTAEPISMEPVAGAATAAATAGQVNMIDPWIMSNYVQAPQGEFTISPNNT
PGDILFDLQLGPHLNPFLLHLAQMYNGWVGNMKVRVLLAGNAFTAGKIIISCVPPGFAAQNVSIAQATMFPHVIADVRV
LEPIEVPLEDVRNVLFHNNDSTPTMRLICMLYTPLRASGSSSGTDPFVIAGRVLTCPSPDFNFLFLVPPNVEQKTKPFSVPNL
PLNVLSNSRVPSLIKSMMVSQDHGQMVQFQNGRVTLDGQLQGTTPTSASQLCKIRGTVYHATGGQGLNLTEIDGTPYH
AFESPAPIGFPDLGECDWHINASPANAFTDGSIIHRIDVAQDSTFAPHLGTIHYTNADYNANVGLICSLEWLSPPSGGAPK
VNPWAIPRYGSTLTEAAQLAPPIYPPGFGEAIVFFMSDFPIANGSDGLSVPCTIPQEFVTHFVNEQAPTRGEAALLHYVDP
DTHRNLGEFKLYPEGFMTCVPNSSGSGPQTLPINGVFTFISWVSRFYQLKPVGTTGPVRRLGIRRS

Figure 28D

Nucleic acid sequence of human codon optimized VP1_GI.3_Lil08_S94L (SEQ ID NO:9)

ATGATGATGGCTTCCAAGGATGCTCCCACAAACATGGATGGAACAAGCGGCGCGGGGCAACTTGTGCCGGAGGTG
TCCACGGCGGAACCCATTTCCATGGAACCTGTGGCCGGCGCAGCCACTGCTGCCGCCACCGCAGGACAGGTAAACA
TGATCGACCCCTGGATCATGTCAAATTACGTTCAGGCTCCACAGGGGGAGTTTACCATAAGCCCAAACAACACCCCG
GGTGACATCTTGTTTGACCTGCAGCTAGGACCACACTTGAATCCGTTTCTGCTCCACTTGGCTCAGATGTATAATGGA
TGGGTTGGAAACATGAAGGTGCGCGTGCTCCTGGCGGGCAATGCATTCACAGCCGGGAAGATTATTATCTCTTGCG
TGCCACCTGGATTTGCAGCCCAGAACGTGTCTATCGCACAGGCAACCATGTTTCCGCATGTCATCGCAGATGTGCGC
GTGCTAGAGCCCATCGAGGTGCCCCTTGAGGACGTGCGCAACGTCCTATTCCATAACAATGATAGCACCCCCACCAT
GCGCTTGATATGTATGTTATATACTCCCCTCCGCGCCAGTGGGTCCAGCTCCGGGACCGATCCTTTTGTGATTGCTGG
GCGGGTGTTGACTTGTCCTAGCCCTGACTTCAACTTCCTTTTTCTGGTGCCTCCAAATGTAGAACAGAAAACAAAGCC
ATTCAGCGTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCACAACCCC
AACCAGTGCCAGTCAGCTGTGTAAGATCAGAGGCACCGTCTACCACGCAACTGGCGGACAGGGGCTGAATCTTACT
GAGATCGATGGTACCCCCTACCATGCATTCGAGTCACCTGCACCTATTGGATTTCCCGATCTTGGGGAGTGTGATTG
GCATATCAATGCTTCACCTGCCAACGCTTTCACAGACGGGTCTATTATTCATCGCATTGACGTAGCACAGGATAGCAC
ATTTGCCCCGCACCTGGGTACCATCCACTATACGAACGCAGATTACAACGCAAACGTGGGTCTTATCTGTAGCCTAG
AGTGGCTATCTCCGCCAAGCGGTGGGGCCCCTAAAGTTAACCCATGGGCTATTCCTCGGTACGGGTCTACGCTGACT
GAGGCCGCTCAGCTGGCACCCCCCATATATCCACCAGGATTCGGGGAAGCCATTGTTTTCTTTATGTCCGATTTTCCG
ATAGCCAACGGTTCAGATGGCCTTAGTGTCCCTTGCACGATTCCACAGGAATTTGTGACACACTTCGTAAACGAGCA
GGCTCCTACTCGGGGCGAGGCTGCCTTGTTGCATTACGTAGACCCCGATACCCATAGAAACCTGGGCGAATTCAAAC
TCTACCCTGAAGGTTTCATGACCTGCGTACCTAACTCCTCCGGCAGTGGCCCTCAAACCTTGCCGATCAACGGCGTGT

Figure 28D (cont)

TCACGTTTATCAGCTGGGTTTCACGGTTTTACCAACTCAAGCCCGTCGGAACAACTGGGCCAGTTCGGAGGCTCGGG
ATCAGACGGAGCTAG

Figure 28E

Amino acid sequence of VP1_GI.3_Lil08_Q84S+S94L (SEQ ID NO:10)

MMMASKDAPTNMDGTSGAGQLVPEVSTAEPISMEPVAGAATAAATAGQVNMIDPWIMSNYVQAPQGEFTISPNNT
PGDILFDLSLGPHLNPFLLHLAQMYNGWVGNMKVRVLLAGNAFTAGKIIISCVPPGFAAQNVSIAQATMFPHVIADVRVL
EPIEVPLEDVRNVLFHNNDSTPTMRLICMLYTPLRASGSSSGTDPFVIAGRVLTCPSPDFNFLFLVPPNVEQKTKPFSVPNL
PLNVLSNSRVPSLIKSMMVSQDHGQMVQFQNGRVTLDGQLQGTTPTSASQLCKIRGTVYHATGGQGLNLTEIDGTPYH
AFESPAPIGFPDLGECDWHINASPANAFTDGSIIHRIDVAQDSTFAPHLGTIHYTNADYNANVGLICSLEWLSPPSGGAPK
VNPWAIPRYGSTLTEAAQLAPPIYPPGFGEAIVFFMSDFPIANGSDGLSVPCTIPQEFVTHFVNEQAPTRGEAALLHYVDP
DTHRNLGEFKLYPEGFMTCVPNSSGSGPQTLPINGVFTFISWVSRFYQLKPVGTTGPVRRLGIRRS

Figure 28F

Nucleic acid sequence of human codon optimized VP1_GI.3_Lil08_Q84S+S94L (SEQ ID NO:11)

ATGATGATGGCTTCCAAGGATGCTCCCACAAACATGGATGGAACAAGCGGCGCGGGGCAACTTGTGCCGGAGGTG
TCCACGGCGGAACCCATTTCCATGGAACCTGTGGCCGGCGCAGCCACTGCTGCCGCCACCGCAGGACAGGTAAACA
TGATCGACCCCTGGATCATGTCAAATTACGTTCAGGCTCCACAGGGGGAGTTTACCATAAGCCCAAACAACACCCCG
GGTGACATCTTGTTTGACCTGAGCCTAGGACCACACTTGAATCCGTTTCTGCTCCACTTGGCTCAGATGTATAATGGA
TGGGTTGGAAACATGAAGGTGCGCGTGCTCCTGGCGGGCAATGCATTCACAGCCGGGAAGATTATTATCTCTTGCG
TGCCACCTGGATTTGCAGCCCAGAACGTGTCTATCGCACAGGCAACCATGTTTCCGCATGTCATCGCAGATGTGCGC
GTGCTAGAGCCCATCGAGGTGCCCCTTGAGGACGTGCGCAACGTCCTATTCCATAACAATGATAGCACCCCCACCAT
GCGCTTGATATGTATGTTATATACTCCCCTCCGCGCCAGTGGGTCCAGCTCCGGGACCGATCCTTTTGTGATTGCTGG
GCGGGTGTTGACTTGTCCTAGCCCTGACTTCAACTTCCTTTTTCTGGTGCCTCCAAATGTAGAACAGAAAACAAAGCC
ATTCAGCGTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCACAACCCC
AACCAGTGCCAGTCAGCTGTGTAAGATCAGAGGCACCGTCTACCACGCAACTGGCGGACAGGGGCTGAATCTTACT
GAGATCGATGGTACCCCCTACCATGCATTCGAGTCACCTGCACCTATTGGATTTCCCGATCTTGGGGAGTGTGATTG
GCATATCAATGCTTCACCTGCCAACGCTTTCACAGACGGGTCTATTATTCATCGCATTGACGTAGCACAGGATAGCAC
ATTTGCCCCGCACCTGGGTACCATCCACTATACGAACGCAGATTACAACGCAAACGTGGGTCTTATCTGTAGCCTAG
AGTGGCTATCTCCGCCAAGCGGTGGGGCCCCTAAAGTTAACCCATGGGCTATTCCTCGGTACGGGTCTACGCTGACT
GAGGCCGCTCAGCTGGCACCCCCCATATATCCACCAGGATTCGGGGAAGCCATTGTTTTCTTTATGTCCGATTTTCCG
ATAGCCAACGGTTCAGATGGCCTTAGTGTCCCTTGCACGATTCCACAGGAATTTGTGACACACTTCGTAAACGAGCA
GGCTCCTACTCGGGGCGAGGCTGCCTTGTTGCATTACGTAGACCCCGATACCCATAGAAACCTGGGCGAATTCAAAC
TCTACCCTGAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAGGCTCGGG
ATCAGACGGAGCTAG

Figure 28G

Amino acid sequence of VP1_GI.3_Lil08_A43V+S94L (SEQ ID NO:170)

MMMASKDAPTNMDGTSGAGQLVPEVSTAEPISMEPVAGAATAVATAGQVNMIDPWIMSNYVQAPQGE
FTISPNNTPGDILFDLQLGPHLNPFLLHLAQMYNGWVGNMKVRVLLAGNAFTAGKIIISCVPPGFAAQNVSIA
QATMFPHVIADVRVLEPIEVPLEDVRNVLFHNNDSTPTMRLICMLYTPLRASGSSSGTDPFVIAGRVLTCPSPD
FNFLFLVPPNVEQKTKPFSVPNLPLNVLSNSRVPSLIKSMMVSQDHGQMVQFQNGRVTLDGQLQGTTPTSA
SQLCKIRGTVYHATGGQGLNLTEIDGTPYHAFESPAPIGFPDLGECDWHINASPANAFTDGSIIHRIDVAQDST
FAPHLGTIHYTNADYNANVGLICSLEWLSPPSGGAPKVNPWAIPRYGSTLTEAAQLAPPIYPPGFGEAIVFFMS
DFPIANGSDGLSVPCTIPQEFVTHFVNEQAPTRGEAALLHYVDPDTHRNLGEFKLYPEGFMTCVPNSSGSGPQ
TLPINGVFTFISWVSRFYQLKPVGTTGPVRRLGIRRS

Figure 28H

Nucleic acid sequence of human codon optimized VP1_GI.3_Lil08_A43V+S94L (SEQ ID NO:169)

ATGATGATGGCTTCCAAGGATGCTCCCACAAACATGGATGGAACAAGCGGCGCGGGGCAACTTGTGCCG
GAGGTGTCCACGGCGGAACCCATTTCCATGGAACCTGTGGCCGGCGCAGCCACTGCTGTGGCCACCGCA
GGACAGGTAAACATGATCGACCCCTGGATCATGTCAAATTACGTTCAGGCTCCACAGGGGGAGTTTACC
ATAAGCCCAAACAACACCCCGGGTGACATCTTGTTTGACCTGCAGCTAGGACCACACTTGAATCCGTTTCT
GCTCCACTTGGCTCAGATGTATAATGGATGGGTTGGAAACATGAAGGTGCGCGTGCTCCTGGCGGGCAA
TGCATTCACAGCCGGGAAGATTATTATCTCTTGCGTGCCACCTGGATTTGCAGCCCAGAACGTGTCTATC
GCACAGGCAACCATGTTTCCGCATGTCATCGCAGATGTGCGCGTGCTAGAGCCCATCGAGGTGCCCCTTG
AGGACGTGCGCAACGTCCTATTCCATAACAATGATAGCACCCCCACCATGCGCTTGATATGTATGTTATAT
ACTCCCCTCCGCGCCAGTGGGTCCAGCTCCGGGACCGATCCTTTTGTGATTGCTGGGCGGGTGTTGACTT
GTCCTAGCCCTGACTTCAACTTCCTTTTTCTGGTGCCTCCAAATGTAGAACAGAAAACAAAGCCATTCAGC
GTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCA
CAACCCCAACCAGTGCCAGTCAGCTGTGTAAGATCAGAGGCACCGTCTACCACGCAACTGGCGGACAGG
GGCTGAATCTTACTGAGATCGATGGTACCCCCTACCATGCATTCGAGTCACCTGCACCTATTGGATTTCCC
GATCTTGGGGAGTGTGATTGGCATATCAATGCTTCACCTGCCAACGCTTTCACAGACGGGTCTATTATTCA
TCGCATTGACGTAGCACAGGATAGCACATTTGCCCCGCACCTGGGTACCATCCACTATACGAACGCAGAT
TACAACGCAAACGTGGGTCTTATCTGTAGCCTAGAGTGGCTATCTCCGCCAAGCGGTGGGGCCCCTAAA
GTTAACCCATGGGCTATTCCTCGGTACGGGTCTACGCTGACTGAGGCCGCTCAGCTGGCACCCCCCATAT
ATCCACCAGGATTCGGGGAAGCCATTGTTTTCTTTATGTCCGATTTTCCGATAGCCAACGGTTCAGATGGC
CTTAGTGTCCCTTGCACGATTCCACAGGAATTTGTGACACACTTCGTAAACGAGCAGGCTCCTACTCGGG
GCGAGGCTGCCTTGTTGCATTACGTAGACCCCGATACCCATAGAAACCTGGGCGAATTCAAACTCTACCC
TGAAGGTTTCATGACCTGCGTACCTAACTCCTCCGGCAGTGGCCCTCAAACCTTGCCGATCAACGGCGTG
TTCACGTTTATCAGCTGGGTTTCACGGTTTTACCAACTCAAGCCCGTCGGAACAACTGGGCCAGTTCGGA
GGCTCGGGATCAGACGGAGCTAG

Figure 28I

Amino acid sequence of VP1_GI.3_Lil08_M57I+S94L (SEQ ID NO:172)

MMMASKDAPTNMDGTSGAGQLVPEVSTAEPISMEPVAGAATAAATAGQVNMIDPWIISNYVQAPQGEFT
ISPNNTPGDILFDLQLGPHLNPFLLHLAQMYNGWVGNMKVRVLLAGNAFTAGKIIISCVPPGFAAQNVSIAQ
ATMFPHVIADVRVLEPIEVPLEDVRNVLFHNNDSTPTMRLICMLYTPLRASGSSSGTDPFVIAGRVLTCPSPDF
NFLFLVPPNVEQKTKPFSVPNLPLNVLSNSRVPSLIKSMMVSQDHGQMVQFQNGRVTLDGQLQGTTPTSAS
QLCKIRGTVYHATGGQGLNLTEIDGTPYHAFESPAPIGFPDLGECDWHINASPANAFTDGSIIHRIDVAQDSTF
APHLGTIHYTNADYNANVGLICSLEWLSPPSGGAPKVNPWAIPRYGSTLTEAAQLAPPIYPPGFGEAIVFFMS
DFPIANGSDGLSVPCTIPQEFVTHFVNEQAPTRGEAALLHYVDPDTHRNLGEFKLYPEGFMTCVPNSSGSGPQ
TLPINGVFTFISWVSRFYQLKPVGTTGPVRRLGIRRS

Figure 28J

Nucleic acid sequence of human codon optimized VP1_GI.3_Lil08_M57I+S94L (SEQ ID NO:171)

ATGATGATGGCTTCCAAGGATGCTCCCACAAACATGGATGGAACAAGCGGCGCGGGGCAACTTGTGCCG
GAGGTGTCCACGGCGGAACCCATTTCCATGGAACCTGTGGCCGGCGCAGCCACTGCTGCCGCCACCGCA
GGACAGGTAAACATGATCGACCCCTGGATCATCTCAAATTACGTTCAGGCTCCACAGGGGGAGTTTACCA
TAAGCCCAAACAACACCCCGGGTGACATCTTGTTTGACCTGCAGCTAGGACCACACTTGAATCCGTTTCTG
CTCCACTTGGCTCAGATGTATAATGGATGGGTTGGAAACATGAAGGTGCGCGTGCTCCTGGCGGGCAAT
GCATTCACAGCCGGGAAGATTATTATCTCTTGCGTGCCACCTGGATTTGCAGCCCAGAACGTGTCTATCG
CACAGGCAACCATGTTTCCGCATGTCATCGCAGATGTGCGCGTGCTAGAGCCCATCGAGGTGCCCCTTGA
GGACGTGCGCAACGTCCTATTCCATAACAATGATAGCACCCCCACCATGCGCTTGATATGTATGTTATATA
CTCCCCTCCGCGCCAGTGGGTCCAGCTCCGGGACCGATCCTTTTGTGATTGCTGGGCGGGTGTTGACTTG
TCCTAGCCCTGACTTCAACTTCCTTTTTCTGGTGCCTCCAAATGTAGAACAGAAAACAAAGCCATTCAGCG
TGCCAAACCTGCCCCTTAACGTGCTGTCGAATTCCCGAGTGCCTTCCCTTATTAAGTCCATGATGGTATCT
CAGGATCACGGTCAAATGGTGCAGTTTCAGAACGGCCGAGTGACGTTAGACGGGCAGCTGCAGGGCAC
AACCCCAACCAGTGCCAGTCAGCTGTGTAAGATCAGAGGCACCGTCTACCACGCAACTGGCGGACAGGG
GCTGAATCTTACTGAGATCGATGGTACCCCCTACCATGCATTCGAGTCACCTGCACCTATTGGATTTCCCG
ATCTTGGGGAGTGTGATTGGCATATCAATGCTTCACCTGCCAACGCTTTCACAGACGGGTCTATTATTCAT
CGCATTGACGTAGCACAGGATAGCACATTTGCCCCGCACCTGGGTACCATCCACTATACGAACGCAGATT
ACAACGCAAACGTGGGTCTTATCTGTAGCCTAGAGTGGCTATCTCCGCCAAGCGGTGGGGCCCCTAAAG
TTAACCCATGGGCTATTCCTCGGTACGGGTCTACGCTGACTGAGGCCGCTCAGCTGGCACCCCCCATATA
TCCACCAGGATTCGGGGAAGCCATTGTTTTCTTTATGTCCGATTTTCCGATAGCCAACGGTTCAGATGGCC
TTAGTGTCCCTTGCACGATTCCACAGGAATTTGTGACACACTTCGTAAACGAGCAGGCTCCTACTCGGGG
CGAGGCTGCCTTGTTGCATTACGTAGACCCCGATACCCATAGAAACCTGGGCGAATTCAAACTCTACCCT
GAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAG
GCTCGGGATCAGACGGAGCTAG

Figure 28K

Amino acid sequence of VP1_GI.3_Lil08_A43V+M57I+S94L (SEQ ID NO:174)

MMMASKDAPTNMDGTSGAGQLVPEVSTAEPISMEPVAGAATAVATAGQVNMIDPWIISNYVQAPQGEFT
ISPNNTPGDILFDLQLGPHLNPFLLHLAQMYNGWVGNMKVRVLLAGNAFTAGKIIISCVPPGFAAQNVSIAQ
ATMFPHVIADVRVLEPIEVPLEDVRNVLFHNNDSTPTMRLICMLYTPLRASGSSSGTDPFVIAGRVLTCPSPDF
NFLFLVPPNVEQKTKPFSVPNLPLNVLSNSRVPSLIKSMMVSQDHGQMVQFQNGRVTLDGQLQGTTPTSAS
QLCKIRGTVYHATGGQGLNLTEIDGTPYHAFESPAPIGFPDLGECDWHINASPANAFTDGSIIHRIDVAQDSTF
APHLGTIHYTNADYNANVGLICSLEWLSPPSGGAPKVNPWAIPRYGSTLTEAAQLAPPIYPPGFGEAIVFFMS
DFPIANGSDGLSVPCTIPQEFVTHFVNEQAPTRGEAALLHYVDPDTHRNLGEFKLYPEGFMTCVPNSSGSGPQ
TLPINGVFTFISWVSRFYQLKPVGTTGPVRRLGIRRS

Figure 28L

Nucleic acid sequence of human codon optimized VP1_GI.3_Lil08_A43V+M57I+S94L (SEQ ID NO:173)

ATGATGATGGCTTCCAAGGATGCTCCCACAAACATGGATGGAACAAGCGGCGCGGGGCAACTTGTGCCG
GAGGTGTCCACGGCGGAACCCATTTCCATGGAACCTGTGGCCGGCGCAGCCACTGCTGTGGCCACCGCA
GGACAGGTAAACATGATCGACCCCTGGATCATCTCAAATTACGTTCAGGCTCCACAGGGGGAGTTTACCA
TAAGCCCAAACAACACCCCGGGTGACATCTTGTTTGACCTGCAGCTAGGACCACACTTGAATCCGTTTCTG
CTCCACTTGGCTCAGATGTATAATGGATGGGTTGGAAACATGAAGGTGCGCGTGCTCCTGGCGGGCAAT
GCATTCACAGCCGGGAAGATTATTATCTCTTGCGTGCCACCTGGATTTGCAGCCCAGAACGTGTCTATCG
CACAGGCAACCATGTTTCCGCATGTCATCGCAGATGTGCGCGTGCTAGAGCCCATCGAGGTGCCCCTTGA
GGACGTGCGCAACGTCCTATTCCATAACAATGATAGCACCCCCACCATGCGCTTGATATGTATGTTATATA
CTCCCCTCCGCGCCAGTGGGTCCAGCTCCGGGACCGATCCTTTTGTGATTGCTGGGCGGGTGTTGACTTG
TCCTAGCCCTGACTTCAACTTCCTTTTTCTGGTGCCTCCAAATGTAGAACAGAAAACAAAGCCATTCAGCG
TGCCAAACCTGCCCCTTAACGTGCTGTCGAATTCCCGAGTGCCTTCCCTTATTAAGTCCATGATGGTATCT
CAGGATCACGGTCAAATGGTGCAGTTTCAGAACGGCCGAGTGACGTTAGACGGGCAGCTGCAGGGCAC
AACCCCAACCAGTGCCAGTCAGCTGTGTAAGATCAGAGGCACCGTCTACCACGCAACTGGCGGACAGGG
GCTGAATCTTACTGAGATCGATGGTACCCCCTACCATGCATTCGAGTCACCTGCACCTATTGGATTTCCCG
ATCTTGGGGAGTGTGATTGGCATATCAATGCTTCACCTGCCAACGCTTTCACAGACGGGTCTATTATTCAT
CGCATTGACGTAGCACAGGATAGCACATTTGCCCCGCACCTGGGTACCATCCACTATACGAACGCAGATT
ACAACGCAAACGTGGGTCTTATCTGTAGCCTAGAGTGGCTATCTCCGCCAAGCGGTGGGGCCCCTAAAG
TTAACCCATGGGCTATTCCTCGGTACGGGTCTACGCTGACTGAGGCCGCTCAGCTGGCACCCCCCATATA
TCCACCAGGATTCGGGGAAGCCATTGTTTTCTTTATGTCCGATTTTCCGATAGCCAACGGTTCAGATGGCC
TTAGTGTCCCTTGCACGATTCCACAGGAATTTGTGACACACTTCGTAAACGAGCAGGCTCCTACTCGGGG
CGAGGCTGCCTTGTTGCATTACGTAGACCCCGATACCCATAGAAACCTGGGCGAATTCAAACTCTACCCT
GAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAG
GCTCGGGATCAGACGGAGCTAG

Figure 28M (SEQ ID NO:292)

AA sequence of VP1_GI.3_Lil08_S94X; where X = V, I, M, T, E, D, N, Q, K, or H

MMMASKDAPTNMDGTSGAGQLVPEVSTAEPISMEPVAGAATAAATAGQVNMIDPWIMSNYVQAPQGE
FTISPNNTPGDILFDLQLGPHLNPFLXHLAQMYNGWVGNMKVRVLLAGNAFTAGKIIISCVPPGFAAQNVSIA
QATMFPHVIADVRVLEPIEVPLEDVRNVLFHNNDSTPTMRLICMLYTPLRASGSSSGTDPFVIAGRVLTCPSPD
FNFLFLVPPNVEQKTKPFSVPNLPLNVLSNSRVPSLIKSMMVSQDHGQMVQFQNGRVTLDGQLQGTTPTSA
SQLCKIRGTVYHATGGQGLNLTEIDGTPYHAFESPAPIGFPDLGECDWHINASPANAFTDGSIIHRIDVAQDST
FAPHLGTIHYTNADYNANVGLICSLEWLSPPSGGAPKVNPWAIPRYGSTLTEAAQLAPPIYPPGFGEAIVFFMS
DFPIANGSDGLSVPCTIPQEFVTHFVNEQAPTRGEAALLHYVDPDTHRNLGEFKLYPEGFMTCVPNSSGSGPQ
TLPINGVFTFISWVSRFYQLKPVGTTGPVRRLGIRRS*

Figure 28N (SEQ ID NO:293)

hCod optimized VP1_GI.3_Lil08_S94x; 'x' = V (XXX=GTG), I (XXX=ATC), M (XXX=ATG), T (XXX = ACC), E (XXX=GAG), D (XXX=GAC), N (XXX=AAC), Q (XXX=CAG), K (XXX=AAG), or H (XXX=CAC)

ATGATGATGGCTTCCAAGGATGCTCCCACAAACATGGATGGAACAAGCGGCGCGGGGCAACTTGTGCCG
GAGGTGTCCACGGCGGAACCCATTTCCATGGAACCTGTGGCCGGCGCAGCCACTGCTGCCGCCACCGCA
GGACAGGTAAACATGATCGACCCCTGGATCATGTCAAATTACGTTCAGGCTCCACAGGGGGAGTTTACC
ATAAGCCCAAACAACACCCCGGGTGACATCTTGTTTGACCTGCAGCTAGGACCACACTTGAATCCGTTTCT
GXXXCACTTGGCTCAGATGTATAATGGATGGGTTGGAAACATGAAGGTGCGCGTGCTCCTGGCGGGCAA
TGCATTCACAGCCGGGAAGATTATTATCTCTTGCGTGCCACCTGGATTTGCAGCCCAGAACGTGTCTATC
GCACAGGCAACCATGTTTCCGCATGTCATCGCAGATGTGCGCGTGCTAGAGCCCATCGAGGTGCCCCTTG
AGGACGTGCGCAACGTCCTATTCCATAACAATGATAGCACCCCCACCATGCGCTTGATATGTATGTTATAT
ACTCCCCTCCGCGCCAGTGGGTCCAGCTCCGGGACCGATCCTTTTGTGATTGCTGGGCGGGTGTTGACTT
GTCCTAGCCCTGACTTCAACTTCCTTTTTCTGGTGCCTCCAAATGTAGAACAGAAAACAAAGCCATTCAGC
GTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCA
CAACCCCAACCAGTGCCAGTCAGCTGTGTAAGATCAGAGGCACCGTCTACCACGCAACTGGCGGACAGG
GGCTGAATCTTACTGAGATCGATGGTACCCCCTACCATGCATTCGAGTCACCTGCACCTATTGGATTTCCC
GATCTTGGGGAGTGTGATTGGCATATCAATGCTTCACCTGCCAACGCTTTCACAGACGGGTCTATTATTCA
TCGCATTGACGTAGCACAGGATAGCACATTTGCCCCGCACCTGGGTACCATCCACTATACGAACGCAGAT
TACAACGCAAACGTGGGTCTTATCTGTAGCCTAGAGTGGCTATCTCCGCCAAGCGGTGGGGCCCCTAAA
GTTAACCCATGGGCTATTCCTCGGTACGGGTCTACGCTGACTGAGGCCGCTCAGCTGGCACCCCCCATAT
ATCCACCAGGATTCGGGGAAGCCATTGTTTTCTTTATGTCCGATTTTCCGATAGCCAACGGTTCAGATGGC
CTTAGTGTCCCTTGCACGATTCCACAGGAATTTGTGACACACTTCGTAAACGAGCAGGCTCCTACTCGGG
GCGAGGCTGCCTTGTTGCATTACGTAGACCCCGATACCCATAGAAACCTGGGCGAATTCAAACTCTACCC
TGAAGGTTTCATGACCTGCGTACCTAACTCCTCCGGCAGTGGCCCTCAAACCTTGCCGATCAACGGCGTG
TTCACGTTTATCAGCTGGGTTTCACGGTTTTACCAACTCAAGCCCGTCGGAACAACTGGGCCAGTTCGGA
GGCTCGGGATCAGACGGAGCTAG

Figure 29A

Amino acid sequence of VP1_GI.5_Siklos_Q84S (SEQ ID NO:34)

MMMASKDAPSSADGANGAGQLVPEVNNAEPLPLDPVAGASTALATAGQVNMIDPWIFNNFVQAPQGEFTISPNNTP
GDILFDLSLGPHLNPFLAHLSQMYNGWVGNMRVRVILAGNAFTAGKVIICCVPPGFQSRTLSIAQATLFPHIIADVRTLEPI
EIPLEDVRNTLYHTNDNQPTMRLLCMLYTPLRTGGGSGGTDAFVVAGRVLTCPSSDFNFLFLVPPTVEQKTRPFSVPNIPL
QLLSNSRVPNLIQSMVLSPDQAQNVQFQNGRCTTDGQLLGTTPVSVSQILKFRGKVSAGSKVINLTELDGSPFLAFEAPAP
TGFPDLGTSDWHVEMSLNSNSQSSGNPILLRDIHPNSSEFVPHLGSVCVTAAIEVAGDYTGTIQWTSQPSNVTPVPDVNF
WTIPHYGSNLAEASQLAPVVYPPGFGEAIVYFMSPIPGPNTAHKPNLVPCLLPQEFVTHFVSEQAPSMGEAALVHYVDPD
TNRNLGEFKLYPEGFITCVPNGTGPQQLPLNGVFVFASWVSRFYQLKPVGTASSARGRLGVRR

Figure 29B

Nucleic acid sequence of human codon optimized VP1_GI.5_Siklos_Q84S (SEQ ID NO:35)

ATGATGATGGCCTCCAAAGACGCTCCTAGCAGTGCTGATGGCGCTAACGGTGCCGGCCAGCTGGTCCCCGAGGTGA
ATAACGCCGAGCCTCTCCCCTTGGACCCAGTAGCCGGAGCTTCAACGGCCCTAGCTACTGCCGGACAGGTTAATATG
ATTGACCCCTGGATTTTCAATAATTTCGTGCAGGCCCCTCAAGGCGAGTTTACTATAAGCCCTAACAACACACCAGGG
GATATTCTGTTCGACCTGAGCTTAGGCCCTCATCTCAACCCCTTCTTGGCCCACCTGAGCCAGATGTACAATGGCTGG
GTGGGCAACATGCGAGTGAGAGTTATCCTCGCAGGGAACGCCTTTACCGCTGGTAAGGTGATCATTTGTTGCGTAC
CACCTGGATTCCAGTCTAGGACATTAAGTATTGCGCAAGCTACCCTCTTTCCTCATATCATCGCCGACGTGCGGACAC
TAGAGCCCATCGAGATCCCACTGGAGGATGTCCGGAATACCCTGTACCATACCAACGATAATCAGCCCACTATGAGG
TTACTGTGCATGCTGTACACGCCACTCCGGACTGGTGGGGGCAGTGGGGGGACCGATGCTTTCGTCGTTGCCGGTA
GGGTGCTCACTTGCCCGTCATCTGACTTTAACTTCCTATTCCTTGTGCCCCCAACGGTGGAACAGAAAACGAGACCTT
TTTCCGTACCTAACATCCCTTTACAGCTCCTAAGCAATAGCAGAGTACCTAACCTGATCCAATCCATGGTTCTTAGCCC
TGATCAAGCGCAGAACGTACAGTTTCAGAACGGGCGGTGCACCACAGATGGCCAGCTGCTTGGTACAACTCCCGTC
TCCGTGTCTCAGATACTTAAGTTTCGCGGCAAGGTCTCCGCTGGATCCAAAGTAATCAACCTCACTGAGCTTGATGG
CTCTCCCTTTCTGGCGTTCGAGGCGCCCGCCCCAACAGGCTTTCCAGACCTGGGAACATCCGATTGGCATGTCGAGA
TGAGTCTGAATAGCAACTCCCAGTCTTCTGGCAATCCAATACTGCTCCGCGATATCCATCCTAATTCTAGCGAGTTCG
TTCCACACCTGGGTTCTGTGTGCGTGACGGCTGCAATAGAGGTGGCTGGCGACTACACGGGTACCATTCAGTGGAC
CTCTCAGCCAAGTAACGTGACCCCTGTGCCAGACGTTAACTTTTGGACAATTCCACACTACGGCTCTAACTTGGCCGA
AGCATCCCAGCTTGCCCCCGTTGTATATCCCCCAGGCTTTGGCGAAGCAATAGTTTATTTTATGTCCCCAATCCCTGG
ACCTAACACAGCACACAAGCCAAACCTCGTCCCATGCCTGCTGCCCCAGGAGTTCGTGACTCATTTCGTTTCGGAACA
AGCCCCATCAATGGGGGAGGCCGCCCTGGTCCACTACGTGGATCCAGATACCAATCGGAATCTGGGAGAATTCAAA
CTCTACCCTGAAGGATTCATTACATGTGTGCCCAATGGAACAGGACCGCAGCAGCTCCCACTGAACGGTGTCTTTGT
ATTCGCATCATGGGTTAGCCGGTTCTATCAACTTAAACCCGTGGGGACAGCTTCATCTGCCCGGGGGCGCCTTGGCG
TGCGGCGCTGA

Figure 29C

Amino acid sequence of VP1_GI.5_Siklos_A94L (SEQ ID NO:36)

MMMASKDAPSSADGANGAGQLVPEVNNAEPLPLDPVAGASTALATAGQVNMIDPWIFNNFVQAPQGEFTISPNNTP
GDILFDLQLGPHLNPFLLHLSQMYNGWVGNMRVRVILAGNAFTAGKVIICCVPPGFQSRTLSIAQATLFPHIIADVRTLEPI
EIPLEDVRNTLYHTNDNQPTMRLLCMLYTPLRTGGGSGGTDAFVVAGRVLTCPSSDFNFLFLVPPTVEQKTRPFSVPNIPL
QLLSNSRVPNLIQSMVLSPDQAQNVQFQNGRCTTDGQLLGTTPVSVSQILKFRGKVSAGSKVINLTELDGSPFLAFEAPAP
TGFPDLGTSDWHVEMSLNSNSQSSGNPILLRDIHPNSSEFVPHLGSVCVTAAIEVAGDYTGTIQWTSQPSNVTPVPDVNF
WTIPHYGSNLAEASQLAPVVYPPGFGEAIVYFMSPIPGPNTAHKPNLVPCLLPQEFVTHFVSEQAPSMGEAALVHYVDPD
TNRNLGEFKLYPEGFITCVPNGTGPQQLPLNGVFVFASWVSRFYQLKPVGTASSARGRLGVRR

Figure 29D

Nucleic acid sequence of human codon optimized VP1_GI.5_siklos_A94L (SEQ ID NO:37)

ATGATGATGGCCTCCAAAGACGCTCCTAGCAGTGCTGATGGCGCTAACGGTGCCGGCCAGCTGGTCCCCGAGGTGA
ATAACGCCGAGCCTCTCCCCTTGGACCCAGTAGCCGGAGCTTCAACGGCCCTAGCTACTGCCGGACAGGTTAATATG
ATTGACCCCTGGATTTTCAATAATTTCGTGCAGGCCCCTCAAGGCGAGTTTACTATAAGCCCTAACAACACACCAGGG
GATATTCTGTTCGACCTGCAGTTAGGCCCTCATCTCAACCCCTTCTTGCTCCACCTGAGCCAGATGTACAATGGCTGG
GTGGGCAACATGCGAGTGAGAGTTATCCTCGCAGGGAACGCCTTTACCGCTGGTAAGGTGATCATTTGTTGCGTAC
CACCTGGATTCCAGTCTAGGACATTAAGTATTGCGCAAGCTACCCTCTTTCCTCATATCATCGCCGACGTGCGGACAC
TAGAGCCCATCGAGATCCCACTGGAGGATGTCCGGAATACCCTGTACCATACCAACGATAATCAGCCCACTATGAGG
TTACTGTGCATGCTGTACACGCCACTCCGGACTGGTGGGGGCAGTGGGGGGACCGATGCTTTCGTCGTTGCCGGTA
GGGTGCTCACTTGCCCGTCATCTGACTTTAACTTCCTATTCCTTGTGCCCCCAACGGTGGAACAGAAAACGAGACCTT
TTTCCGTACCTAACATCCCTTTACAGCTCCTAAGCAATAGCAGAGTACCTAACCTGATCCAATCCATGGTTCTTAGCCC
TGATCAAGCGCAGAACGTACAGTTTCAGAACGGGCGGTGCACCACAGATGGCCAGCTGCTTGGTACAACTCCCGTC
TCCGTGTCTCAGATACTTAAGTTTCGCGGCAAGGTCTCCGCTGGATCCAAAGTAATCAACCTCACTGAGCTTGATGG
CTCTCCCTTTCTGGCGTTCGAGGCGCCCGCCCCAACAGGCTTTCCAGACCTGGGAACATCCGATTGGCATGTCGAGA
TGAGTCTGAATAGCAACTCCCAGTCTTCTGGCAATCCAATACTGCTCCGCGATATCCATCCTAATTCTAGCGAGTTCG
TTCCACACCTGGGTTCTGTGTGCGTGACGGCTGCAATAGAGGTGGCTGGCGACTACACGGGTACCATTCAGTGGAC
CTCTCAGCCAAGTAACGTGACCCCTGTGCCAGACGTTAACTTTTGGACAATTCCACACTACGGCTCTAACTTGGCCGA
AGCATCCCAGCTTGCCCCCGTTGTATATCCCCCAGGCTTTGGCGAAGCAATAGTTTATTTTATGTCCCCAATCCCTGG
ACCTAACACAGCACACAAGCCAAACCTCGTCCCATGCCTGCTGCCCCAGGAGTTCGTGACTCATTTCGTTTCGGAACA
AGCCCCATCAATGGGGGAGGCCGCCCTGGTCCACTACGTGGATCCAGATACCAATCGGAATCTGGGAGAATTCAAA
CTCTACCCTGAAGGATTCATTACATGTGTGCCCAATGGAACAGGACCGCAGCAGCTCCCACTGAACGGTGTCTTTGT
ATTCGCATCATGGGTTAGCCGGTTCTATCAACTTAAACCCGTGGGGACAGCTTCATCTGCCCGGGGGCGCCTTGGCG
TGCGGCGCTGA

Figure 29E

Amino acid sequence of VP1_GI.5_siklos_Q84S+A94L (SEQ ID NO:38)

MMMASKDAPSSADGANGAGQLVPEVNNAEPLPLDPVAGASTALATAGQVNMIDPWIFNNFVQAPQGEFTISPNNTP
GDILFDLSLGPHLNPFLLHLSQMYNGWVGNMRVRVILAGNAFTAGKVIICCVPPGFQSRTLSIAQATLFPHIIADVRTLEPI
EIPLEDVRNTLYHTNDNQPTMRLLCMLYTPLRTGGGSGGTDAFVVAGRVLTCPSSDFNFLFLVPPTVEQKTRPFSVPNIPL
QLLSNSRVPNLIQSMVLSPDQAQNVQFQNGRCTTDGQLLGTTPVSVSQILKFRGKVSAGSKVINLTELDGSPFLAFEAPAP

Figure 29E (cont)

TGFPDLGTSDWHVEMSLNSNSQSSGNPILLRDIHPNSSEFVPHLGSVCVTAAIEVAGDYTGTIQWTSQPSNVTPVPDVNF
WTIPHYGSNLAEASQLAPVVYPPGFGEAIVYFMSPIPGPNTAHKPNLVPCLLPQEFVTHFVSEQAPSMGEAALVHYVDPD
TNRNLGEFKLYPEGFITCVPNGTGPQQLPLNGVFVFASWVSRFYQLKPVGTASSARGRLGVRR

Figure 29F

Nucleic acid sequence of human codon optimized VP1_GI.5_siklos_Q84S+A94L (SEQ ID NO:39)

ATGATGATGGCCTCCAAAGACGCTCCTAGCAGTGCTGATGGCGCTAACGGTGCCGGCCAGCTGGTCCCCGAGGTGA
ATAACGCCGAGCCTCTCCCCTTGGACCCAGTAGCCGGAGCTTCAACGGCCCTAGCTACTGCCGGACAGGTTAATATG
ATTGACCCCTGGATTTTCAATAATTTCGTGCAGGCCCCTCAAGGCGAGTTTACTATAAGCCCTAACAACACACCAGGG
GATATTCTGTTCGACCTGAGCTTAGGCCCTCATCTCAACCCCTTCTTGCTCCACCTGAGCCAGATGTACAATGGCTGG
GTGGGCAACATGCGAGTGAGAGTTATCCTCGCAGGGAACGCCTTTACCGCTGGTAAGGTGATCATTTGTTGCGTAC
CACCTGGATTCCAGTCTAGGACATTAAGTATTGCGCAAGCTACCCTCTTTCCTCATATCATCGCCGACGTGCGGACAC
TAGAGCCCATCGAGATCCCACTGGAGGATGTCCGGAATACCCTGTACCATACCAACGATAATCAGCCCACTATGAGG
TTACTGTGCATGCTGTACACGCCACTCCGGACTGGTGGGGGCAGTGGGGGGACCGATGCTTTCGTCGTTGCCGGTA
GGGTGCTCACTTGCCCGTCATCTGACTTTAACTTCCTATTCCTTGTGCCCCCAACGGTGGAACAGAAAACGAGACCTT
TTTCCGTACCTAACATCCCTTTACAGCTCCTAAGCAATAGCAGAGTACCTAACCTGATCCAATCCATGGTTCTTAGCCC
TGATCAAGCGCAGAACGTACAGTTTCAGAACGGGCGGTGCACCACAGATGGCCAGCTGCTTGGTACAACTCCCGTC
TCCGTGTCTCAGATACTTAAGTTTCGCGGCAAGGTCTCCGCTGGATCCAAAGTAATCAACCTCACTGAGCTTGATGG
CTCTCCCTTTCTGGCGTTCGAGGCGCCCGCCCCAACAGGCTTTCCAGACCTGGGAACATCCGATTGGCATGTCGAGA
TGAGTCTGAATAGCAACTCCCAGTCTTCTGGCAATCCAATACTGCTCCGCGATATCCATCCTAATTCTAGCGAGTTCG
TTCCACACCTGGGTTCTGTGTGCGTGACGGCTGCAATAGAGGTGGCTGGCGACTACACGGGTACCATTCAGTGGAC
CTCTCAGCCAAGTAACGTGACCCCTGTGCCAGACGTTAACTTTTGGACAATTCCACACTACGGCTCTAACTTGGCCGA
AGCATCCCAGCTTGCCCCCGTTGTATATCCCCCAGGCTTTGGCGAAGCAATAGTTTATTTTATGTCCCCAATCCCTGG
ACCTAACACAGCACACAAGCCAAACCTCGTCCCATGCCTGCTGCCCCAGGAGTTCGTGACTCATTTCGTTTCGGAACA
AGCCCCATCAATGGGGGAGGCCGCCCTGGTCCACTACGTGGATCCAGATACCAATCGGAATCTGGGAGAATTCAAA
CTCTACCCTGAAGGATTCATTACATGTGTGCCCAATGGAACAGGACCGCAGCAGCTCCCACTGAACGGTGTCTTTGT
ATTCGCATCATGGGTTAGCCGGTTCTATCAACTTAAACCCGTGGGGACAGCTTCATCTGCCCGGGGGCGCCTTGGCG
TGCGGCGCTGA

Figure 29G

Amino acid sequence of VP1_ GI.7/GA5043/USA/2014_R84S (SEQ ID NO:177)

MMMASKDAPSNMDGTSGAGQLVPEVNAAEPLPLEPVVGAATAVATAGQVNMIDPWIMNNFVQAPEGE
FTISPNNTPGDILFDLSLGPHLNPFLLHLSQMYNGWVGNMRVRVMLAGNAFSAGKIIICCVPPGFESQNISIG
QATMFPHVIADVRVLEPIEVPLDDVRNVLFHTNENRPTMRLLCMLYTPLRAGGASSGTDPFVIAGRVLTCPAP
DFNFLFLVPPSVEQKTRQLTIPNIPLNNLANSRVPAMINKMTVSADQNQVVQFQNGRCTLEGQLLGTTPVSA
NQVARIRGKVFSTNSGTGLNLTEVDGTPYHAFESPAPLGFPDIGNCDWHVYAFKVNQNTGDPMYRLDITQG
NSFAPHLGSIEFSSENHPSGDQLGTLTWISPLNNASRVDPWKIPTYGSTLTESTNLAPPIFPPGFGEAIVYFMSD
FPIVSGNTAQIPCTLPQEFVSSFVEQQAPIRGEAALLHYVDPDTHRNLGEFKLYPDGFITCVPNTGGGPQNLPS
NGVFVFSSWVSRYYQLKPVGTTGPVRRLGVRRV

Figure 29H

Nucleic acid sequence of human codon optimized VP1_ GI.7/GA5043/USA/2014_R84S (SEQ ID NO:176)

ATGATGATGGCCAGCAAGGACGCTCCGAGTAACATGGACGGCACTTCGGGCGCGGGGCAGCTGGTGCC
CGAGGTCAATGCCGCAGAACCACTTCCTCTTGAGCCCGTCGTTGGCGCCGCCACAGCTGTCGCAACTGCA
GGCCAAGTCAATATGATCGACCCGTGGATAATGAACAATTTCGTTCAGGCACCAGAAGGAGAATTCACC
ATCTCCCCCAATAACACCCCAGGGGATATTCTGTTTGACCTCAGCTTAGGACCCCACTTGAACCCCTTTCT
GCTTCATCTCTCACAAATGTATAATGGCTGGGTCGGGAATATGCGCGTGCGGGTGATGCTAGCCGGCAA
TGCTTTTTCTGCAGGCAAGATTATCATTTGCTGCGTTCCTCCTGGATTCGAATCTCAAAATATCAGCATTG
GTCAAGCAACCATGTTTCCACATGTGATCGCTGATGTTCGCGTCCTGGAACCCATTGAAGTTCCTCTCGAC
GACGTGAGAAATGTTCTCTTCCACACCAACGAGAATAGGCCGACTATGAGACTTCTGTGTATGCTCTACA
CCCCATTAAGAGCCGGGGGAGCATCCTCAGGTACTGACCCATTTGTGATTGCCGGGCGGGTGCTCACAT
GCCCGGCTCCAGACTTTAACTTCCTTTTCTTGGTGCCACCCAGTGTTGAACAGAAAACCAGACAGCTCACC
ATCCCAAATATCCCATTGAACAATCTCGCCAACAGCAGGGTGCCAGCAATGATAAACAAAATGACAGTCA
GTGCTGACCAGAACCAGGTAGTCCAGTTTCAGAACGGCAGATGCACGCTTGAGGGCCAACTGCTTGGGA
CGACCCCAGTCTCCGCGAACCAGGTGGCCCGAATCCGGGGTAAAGTCTTCAGTACAAACTCCGGCACTG
GCCTTAACCTCACAGAGGTTGACGGCACTCCCTATCATGCTTTTGAGTCTCCAGCCCCTCTTGGCTTTCCC
GATATAGGCAACTGTGACTGGCACGTTTATGCGTTTAAAGTAAACCAGAACACCGGCGATCCTATGTATA
GGTTGGATATAACACAAGGTAATTCATTCGCCCCACACTTGGGTAGCATCGAGTTCAGTTCAGAGAACCA
TCCGAGTGGTGATCAGCTAGGCACATTGACGTGGATCAGCCCTCTGAATAACGCATCAAGAGTGGATCC
CTGGAAGATCCCTACCTATGGGTCCACTCTGACAGAGAGCACAAATTTGGCTCCGCCCATTTTCCCACCCG
GATTCGGCGAGGCCATAGTGTACTTTATGTCTGACTTTCCTATCGTCAGCGGGAATACAGCCCAGATTCCT
TGCACACTGCCACAAGAATTCGTCTCATCCTTTGTAGAGCAGCAGGCACCTATTCGAGGTGAGGCCGCCC
TCTTGCACTACGTGGACCCTGACACCCACCGCAATCTTGGCGAGTTTAAGCTGTACCCTGACGGGTTTATT
ACCTGTGTACCCAACACCGGCGGCGGCCCACAAAATTTGCCCAGCAATGGCGTGTTTGTCTTTTCCTCTTG
GGTGTCTCGATACTACCAGCTTAAACCTGTCGGAACTACGGGCCCCGTGCGACGACTCGGCGTGAGGCG
GGTGTGA

Figure 29I

Amino acid sequence of VP1_ GI.7/GA5043/USA/2014_M57I (SEQ ID NO:179)

MMMASKDAPSNMDGTSGAGQLVPEVNAAEPLPLEPVVGAATAVATAGQVNMIDPWIINNFVQAPEGEFT
ISPNNTPGDILFDLRLGPHLNPFLLHLSQMYNGWVGNMRVRVMLAGNAFSAGKIIICCVPPGFESQNISIGQA
TMFPHVIADVRVLEPIEVPLDDVRNVLFHTNENRPTMRLLCMLYTPLRAGGASSGTDPFVIAGRVLTCPAPDF
NFLFLVPPSVEQKTRQLTIPNIPLNNLANSRVPAMINKMTVSADQNQVVQFQNGRCTLEGQLLGTTPVSANQ
VARIRGKVFSTNSGTGLNLTEVDGTPYHAFESPAPLGFPDIGNCDWHVYAFKVNQNTGDPMYRLDITQGNSF
APHLGSIEFSSENHPSGDQLGTLTWISPLNNASRVDPWKIPTYGSTLTESTNLAPPIFPPGFGEAIVYFMSDFPI
VSGNTAQIPCTLPQEFVSSFVEQQAPIRGEAALLHYVDPDTHRNLGEFKLYPDGFITCVPNTGGGPQNLPSNG
VFVFSSWVSRYYQLKPVGTTGPVRRLGVRRV

Figure 29J human codon optimized VP1_ GI.7/GA5043/USA/2014_M57I (SEQ ID NO:178)

ATGATGATGGCCAGCAAGGACGCTCCGAGTAACATGGACGGCACTTCGGGCGCGGGGCAGCTGGTGCC
CGAGGTCAATGCCGCAGAACCACTTCCTCTTGAGCCCGTCGTTGGCGCCGCCACAGCTGTCGCAACTGCA
GGCCAAGTCAATATGATCGACCCGTGGATAATCAACAATTTCGTTCAGGCACCAGAAGGAGAATTCACCA
TCTCCCCCAATAACACCCCAGGGGATATTCTGTTTGACCTCAGGTTAGGACCCCACTTGAACCCCTTTCTG
CTTCATCTCTCACAAATGTATAATGGCTGGGTCGGGAATATGCGCGTGCGGGTGATGCTAGCCGGCAAT
GCTTTTTCTGCAGGCAAGATTATCATTTGCTGCGTTCCTCCTGGATTCGAATCTCAAAATATCAGCATTGG
TCAAGCAACCATGTTTCCACATGTGATCGCTGATGTTCGCGTCCTGGAACCCATTGAAGTTCCTCTCGACG
ACGTGAGAAATGTTCTCTTCCACACCAACGAGAATAGGCCGACTATGAGACTTCTGTGTATGCTCTACAC
CCCATTAAGAGCCGGGGGAGCATCCTCAGGTACTGACCCATTTGTGATTGCCGGGCGGGTGCTCACATG
CCCGGCTCCAGACTTTAACTTCCTTTTCTTGGTGCCACCCAGTGTTGAACAGAAAACCAGACAGCTCACCA
TCCCAAATATCCCATTGAACAATCTCGCCAACAGCAGGGTGCCAGCAATGATAAACAAAATGACAGTCAG
TGCTGACCAGAACCAGGTAGTCCAGTTTCAGAACGGCAGATGCACGCTTGAGGGCCAACTGCTTGGGAC
GACCCCAGTCTCCGCGAACCAGGTGGCCCGAATCCGGGGTAAAGTCTTCAGTACAAACTCCGGCACTGG
CCTTAACCTCACAGAGGTTGACGGCACTCCCTATCATGCTTTTGAGTCTCCAGCCCCTCTTGGCTTTCCCGA
TATAGGCAACTGTGACTGGCACGTTTATGCGTTTAAAGTAAACCAGAACACCGGCGATCCTATGTATAGG
TTGGATATAACACAAGGTAATTCATTCGCCCCACACTTGGGTAGCATCGAGTTCAGTTCAGAGAACCATC
CGAGTGGTGATCAGCTAGGCACATTGACGTGGATCAGCCCTCTGAATAACGCATCAAGAGTGGATCCCT
GGAAGATCCCTACCTATGGGTCCACTCTGACAGAGAGCACAAATTTGGCTCCGCCCATTTTCCCACCCGG
ATTCGGCGAGGCCATAGTGTACTTTATGTCTGACTTTCCTATCGTCAGCGGGAATACAGCCCAGATTCCTT
GCACACTGCCACAAGAATTCGTCTCATCCTTTGTAGAGCAGCAGGCACCTATTCGAGGTGAGGCCGCCCT
CTTGCACTACGTGGACCCTGACACCCACCGCAATCTTGGCGAGTTTAAGCTGTACCCTGACGGGTTTATTA
CCTGTGTACCCAACACCGGCGGCGGCCCACAAAATTTGCCCAGCAATGGCGTGTTTGTCTTTTCCTCTTGG
GTGTCTCGATACTACCAGCTTAAACCTGTCGGAACTACGGGCCCCGTGCGACGACTCGGCGTGAGGCGG
GTGTGA

Figure 29K

Amino acid sequence of VP1_ GI.7/GA5043/USA/2014_M57I+R84S (SEQ ID NO:181)

MMMASKDAPSNMDGTSGAGQLVPEVNAAEPLPLEPVVGAATAVATAGQVNMIDPWIINNFVQAPEGEFT
ISPNNTPGDILFDLSLGPHLNPFLLHLSQMYNGWVGNMRVRVMLAGNAFSAGKIIICCVPPGFESQNISIGQA
TMFPHVIADVRVLEPIEVPLDDVRNVLFHTNENRPTMRLLCMLYTPLRAGGASSGTDPFVIAGRVLTCPAPDF
NFLFLVPPSVEQKTRQLTIPNIPLNNLANSRVPAMINKMTVSADQNQVVQFQNGRCTLEGQLLGTTPVSANQ
VARIRGKVFSTNSGTGLNLTEVDGTPYHAFESPAPLGFPDIGNCDWHVYAFKVNQNTGDPMYRLDITQGNSF
APHLGSIEFSSENHPSGDQLGTLTWISPLNNASRVDPWKIPTYGSTLTESTNLAPPIFPPGFGEAIVYFMSDFPI
VSGNTAQIPCTLPQEFVSSFVEQQAPIRGEAALLHYVDPDTHRNLGEFKLYPDGFITCVPNTGGGPQNLPSNG
VFVFSSWVSRYYQLKPVGTTGPVRRLGVRRV

Figure 29L

Human codon optimized VP1_ GI.7/GA5043/USA/2014_M57I+R84S (SEQ ID NO:180)

ATGATGATGGCCAGCAAGGACGCTCCGAGTAACATGGACGGCACTTCGGGCGCGGGGCAGCTGGTGCCCGAGGTC
AATGCCGCAGAACCACTTCCTCTTGAGCCCGTCGTTGGCGCCGCCACAGCTGTCGCAACTGCAGGCCAAGTCAATAT
GATCGACCCGTGGATAATCAACAATTTCGTTCAGGCACCAGAAGGAGAATTCACCATCTCCCCCAATAACACCCCAG
GGGATATTCTGTTTGACCTCAGCTTAGGACCCCACTTGAACCCCTTTCTGCTTCATCTCTCACAAATGTATAATGGCTG
GGTCGGGAATATGCGCGTGCGGGTGATGCTAGCCGGCAATGCTTTTTCTGCAGGCAAGATTATCATTTGCTGCGTTC
CTCCTGGATTCGAATCTCAAAATATCAGCATTGGTCAAGCAACCATGTTTCCACATGTGATCGCTGATGTTCGCGTCC
TGGAACCCATTGAAGTTCCTCTCGACGACGTGAGAAATGTTCTCTTCCACACCAACGAGAATAGGCCGACTATGAGA
CTTCTGTGTATGCTCTACACCCCATTAAGAGCCGGGGGAGCATCCTCAGGTACTGACCCATTTGTGATTGCCGGGCG
GGTGCTCACATGCCCGGCTCCAGACTTTAACTTCCTTTTCTTGGTGCCACCCAGTGTTGAACAGAAAACCAGACAGCT
CACCATCCCAAATATCCCATTGAACAATCTCGCCAACAGCAGGGTGCCAGCAATGATAAACAAAATGACAGTCAGTG
CTGACCAGAACCAGGTAGTCCAGTTTCAGAACGGCAGATGCACGCTTGAGGGCCAACTGCTTGGGACGACCCCAGT
CTCCGCGAACCAGGTGGCCCGAATCCGGGGTAAAGTCTTCAGTACAAACTCCGGCACTGGCCTTAACCTCACAGAG
GTTGACGGCACTCCCTATCATGCTTTTGAGTCTCCAGCCCCTCTTGGCTTTCCCGATATAGGCAACTGTGACTGGCAC
GTTTATGCGTTTAAAGTAAACCAGAACACCGGCGATCCTATGTATAGGTTGGATATAACACAAGGTAATTCATTCGC
CCCACACTTGGGTAGCATCGAGTTCAGTTCAGAGAACCATCCGAGTGGTGATCAGCTAGGCACATTGACGTGGATC
AGCCCTCTGAATAACGCATCAAGAGTGGATCCCTGGAAGATCCCTACCTATGGGTCCACTCTGACAGAGAGCACAAA
TTTGGCTCCGCCCATTTTCCCACCCGGATTCGGCGAGGCCATAGTGTACTTTATGTCTGACTTTCCTATCGTCAGCGG
GAATACAGCCCAGATTCCTTGCACACTGCCACAAGAATTCGTCTCATCCTTTGTAGAGCAGCAGGCACCTATTCGAG
GTGAGGCCGCCCTCTTGCACTACGTGGACCCTGACACCCACCGCAATCTTGGCGAGTTTAAGCTGTACCCTGACGGG
TTTATTACCTGTGTACCCAACACCGGCGGCGGCCCACAAAATTTGCCCAGCAATGGCGTGTTTGTCTTTTCCTCTTGG
GTGTCTCGATACTACCAGCTTAAACCTGTCGGAACTACGGGCCCCGTGCGACGACTCGGCGTGAGGCGGGTGTGA

Figure 29M (SEQ ID NO:290)

AA sequence of VP1_GI.7/GA5043/USA/2014_M57X; where X = L, G, S, T, N, Q, K, or H MMMASKDAPSNMDGTSGAGQLVPEVNAAEPLPLEPVVGAATAVATAGQVNMIDPWIXNNFVQAPEGEF
TISPNNTPGDILFDLRLGPHLNPFLLHLSQMYNGWVGNMRVRVMLAGNAFSAGKIIICCVPPGFESQNISIGQ
ATMFPHVIADVRVLEPIEVPLDDVRNVLFHTNENRPTMRLLCMLYTPLRAGGASSGTDPFVIAGRVLTCPAPD
FNFLFLVPPSVEQKTRQLTIPNIPLNNLANSRVPAMINKMTVSADQNQVVQFQNGRCTLEGQLLGTTPVSAN
QVARIRGKVFSTNSGTGLNLTEVDGTPYHAFESPAPLGFPDIGNCDWHVYAFKVNQNTGDPMYRLDITQGN
SFAPHLGSIEFSSENHPSGDQLGTLTWISPLNNASRVDPWKIPTYGSTLTESTNLAPPIFPPGFGEAIVYFMSDF
PIVSGNTAQIPCTLPQEFVSSFVEQQAPIRGEAALLHYVDPDTHRNLGEFKLYPDGFITCVPNTGGGPQNLPSN
GVFVFSSWVSRYYQLKPVGTTGPVRRLGVRRV*

Figure 29N (SEQ ID NO:291)

Human codon optimized VP1_GI.7/GA5043/USA/2014_M57x; 'x' = L (XXX=CTG), G (XXX=GGC), S (XXX=AGC), T (XXX=ACC), N (XXX=AAC), Q (XXX=CAG), K (XXX=AAG), or H (XXX=CAC)

ATGATGATGGCCAGCAAGGACGCTCCGAGTAACATGGACGGCACTTCGGGCGCGGGGCAGCTGGTGCC
CGAGGTCAATGCCGCAGAACCACTTCCTCTTGAGCCCGTCGTTGGCGCCGCCACAGCTGTCGCAACTGCA
GGCCAAGTCAATATGATCGACCCGTGGATAXXXAACAATTTCGTTCAGGCACCAGAAGGAGAATTCACC
ATCTCCCCCAATAACACCCCAGGGGATATTCTGTTTGACCTCAGGTTAGGACCCCACTTGAACCCCTTTCT
GCTTCATCTCTCACAAATGTATAATGGCTGGGTCGGGAATATGCGCGTGCGGGTGATGCTAGCCGGCAA
TGCTTTTTCTGCAGGCAAGATTATCATTTGCTGCGTTCCTCCTGGATTCGAATCTCAAAATATCAGCATTG
GTCAAGCAACCATGTTTCCACATGTGATCGCTGATGTTCGCGTCCTGGAACCCATTGAAGTTCCTCTCGAC
GACGTGAGAAATGTTCTCTTCCACACCAACGAGAATAGGCCGACTATGAGACTTCTGTGTATGCTCTACA
CCCCATTAAGAGCCGGGGGAGCATCCTCAGGTACTGACCCATTTGTGATTGCCGGGCGGGTGCTCACAT
GCCCGGCTCCAGACTTTAACTTCCTTTTCTTGGTGCCACCCAGTGTTGAACAGAAAACCAGACAGCTCACC
ATCCCAAATATCCCATTGAACAATCTCGCCAACAGCAGGGTGCCAGCAATGATAAACAAAATGACAGTCA
GTGCTGACCAGAACCAGGTAGTCCAGTTTCAGAACGGCAGATGCACGCTTGAGGGCCAACTGCTTGGGA
CGACCCCAGTCTCCGCGAACCAGGTGGCCCGAATCCGGGGTAAAGTCTTCAGTACAAACTCCGGCACTG
GCCTTAACCTCACAGAGGTTGACGGCACTCCCTATCATGCTTTTGAGTCTCCAGCCCCTCTTGGCTTTCCC
GATATAGGCAACTGTGACTGGCACGTTTATGCGTTTAAAGTAAACCAGAACACCGGCGATCCTATGTATA
GGTTGGATATAACACAAGGTAATTCATTCGCCCCACACTTGGGTAGCATCGAGTTCAGTTCAGAGAACCA
TCCGAGTGGTGATCAGCTAGGCACATTGACGTGGATCAGCCCTCTGAATAACGCATCAAGAGTGGATCC
CTGGAAGATCCCTACCTATGGGTCCACTCTGACAGAGAGCACAAATTTGGCTCCGCCCATTTTCCCACCCG
GATTCGGCGAGGCCATAGTGTACTTTATGTCTGACTTTCCTATCGTCAGCGGGAATACAGCCCAGATTCCT
TGCACACTGCCACAAGAATTCGTCTCATCCTTTGTAGAGCAGCAGGCACCTATTCGAGGTGAGGCCGCCC
TCTTGCACTACGTGGACCCTGACACCCACCGCAATCTTGGCGAGTTTAAGCTGTACCCTGACGGGTTTATT
ACCTGTGTACCCAACACCGGCGGCGGCCCACAAAATTTGCCCAGCAATGGCGTGTTTGTCTTTTCCTCTTG
GGTGTCTCGATACTACCAGCTTAAACCTGTCGGAACTACGGGCCCCGTGCGACGACTCGGCGTGAGGCG
GGTGTGA

Figure 30A

Amino acid sequence of VP1_GII.2_CGMH47_E80S (SEQ ID NO:85)

MKMASNDAAPSTDGAAGLVPESNNEVMALEPVAGAALAAPVTGQTNIIDPWIRANFVQAPNGEFTVSPRNSPGEVLL
NLSLGPELNPYLAHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVVVPANGYFRFDSWVNQFYSLAPMGTGNGRRRIQ

Figure 30B

Nucleic acid sequence of human codon optimized VP1_GII.2_CGMH47_E80S_ (SEQ ID NO:86)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGCTCCTGTGACCGGGCAGACAAATATCATCGATCCTTG
GATTAGAGCTAATTTCGTGCAAGCCCCAAATGGGGAGTTTACGGTCAGCCCTAGAAATAGCCCTGGGGAAGTGCTC
CTCAATCTCAGCCTGGGACCAGAACTTAATCCGTACCTGGCTCACCTGGCCCGGATGTACAATGGATATGCAGGAGG
GATGGAGGTGCAGGTTATGCTGGCTGGCAATGCCTTTACAGCAGGCAAACTCGTTTTCGCAGCCGTCCCTCCCCACT
TCCCAGTTGAAAATCTTTCCCCTCAGCAGATTACCATGTTTCCCCATGTCATCATCGATGTGCGTACCCTGGAACCTGT
GCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

Figure 30C

Amino acid sequence of VP1_GII.2_CGMH47_A90L (SEQ ID NO:41)

MKMASNDAAPSTDGAAGLVPESNNEVMALEPVAGAALAAPVTGQTNIIDPWIRANFVQAPNGEFTVSPRNSPGEVLL
NLELGPELNPYLLHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVVVPANGYFRFDSWVNQFYSLAPMGTGNGRRRIQ

Figure 30D

Nucleic acid sequence of human codon optimized VP1_GII.2_CGMH47_A90L (SEQ ID NO:42)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGCTCCTGTGACCGGGCAGACAAATATCATCGATCCTTG
GATTAGAGCTAATTTCGTGCAAGCCCCAAATGGGGAGTTTACGGTCAGCCCTAGAAATAGCCCTGGGGAAGTGCTC
CTCAATCTCGAGCTGGGACCAGAACTTAATCCGTACCTGCTCCACCTGGCCCGGATGTACAATGGATATGCAGGAGG

Figure 30D (cont)

GATGGAGGTGCAGGTTATGCTGGCTGGCAATGCCTTTACAGCAGGCAAACTCGTTTTCGCAGCCGTCCCTCCCCACT
TCCCAGTTGAAAATCTTTCCCCTCAGCAGATTACCATGTTTCCCCATGTCATCATCGATGTGCGTACCCTGGAACCTGT
GCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

Figure 30E

Amino acid sequence of VP1_GII.2_CGMH47_E80S+A90L (SEQ ID NO:43)

MKMASNDAAPSTDGAAGLVPESNNEVMALEPVAGAALAAPVTGQTNIIDPWIRANFVQAPNGEFTVSPRNSPGEVLL
NLSLGPELNPYLLHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVVVPANGYFRFDSWVNQFYSLAPMGTGNGRRRIQ

Figure 30F

Nucleic acid sequence of human codon optimized VP1_GII.2_CGMH47_E80S+A90L (SEQ ID NO:44)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGCTCCTGTGACCGGGCAGACAAATATCATCGATCCTTG
GATTAGAGCTAATTTCGTGCAAGCCCCAAATGGGGAGTTTACGGTCAGCCCTAGAAATAGCCCTGGGGAAGTGCTC
CTCAATCTCAGCCTGGGACCAGAACTTAATCCGTACCTGCTCCACCTGGCCCGGATGTACAATGGATATGCAGGAGG
GATGGAGGTGCAGGTTATGCTGGCTGGCAATGCCTTTACAGCAGGCAAACTCGTTTTCGCAGCCGTCCCTCCCCACT
TCCCAGTTGAAAATCTTTCCCCTCAGCAGATTACCATGTTTCCCCATGTCATCATCGATGTGCGTACCCTGGAACCTGT
GCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC

Figure 30F (cont)

TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

FIGURE 30G

Amino acid sequence of VP1_GII.2_CGMH47_A39V+E80S+A90L (SEQ ID NO:182)

MKMASNDAAPSTDGAAGLVPESNNEVMALEPVAGAALAVPVTGQTNIIDPWIRANFVQAPNGEFTVSPRNSPGEVLL
NLSLGPELNPYLLHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVVVPANGYFRFDSWVNQFYSLAPMGTGNGRRRIQ

FIGURE 30H

Nucleic acid sequence of human codon optimized VP1_GII.2_CGMH47_A39V+E80S+A90L (SEQ ID NO:183)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGTGCCTGTGACCGGGCAGACAAATATCATCGATCCTT
GGATTAGAGCTAATTTCGTGCAAGCCCCAAATGGGGAGTTTACGGTCAGCCCTAGAAATAGCCCTGGGGAAGTGCT
CCTCAATCTCAGCCTGGGACCAGAACTTAATCCGTACCTGCTCCACCTGGCCCGGATGTACAATGGATATGCAGGAG
GGATGGAGGTGCAGGTTATGCTGGCTGGCAATGCCTTTACAGCAGGCAAACTCGTTTTCGCAGCCGTCCCTCCCCAC
TTCCCAGTTGAAAATCTTTCCCCTCAGCAGATTACCATGTTTCCCCATGTCATCATCGATGTGCGTACCCTGGAACCTG
TGCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC

Figure 30H (cont)

CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

FIGURE 30I

Amino acid sequence of VP1_GII.2_CGMH47_ R53I+E80S+A90L (SEQ ID NO:184)

MKMASNDAAPSTDGAAGLVPESNNEVMALEPVAGAALAAPVTGQTNIIDPWIIANFVQAPNGEFTVSPRNSPGEVLLN
LSLGPELNPYLLHLARMYNGYAGGMEVQVMLAGNAFTAGKLVFAAVPPHFPVENLSPQQITMFPHVIIDVRTLEPVLLPL
PDVRNNFFHYNQKDDPKMRIVAMLYTPLRSNGSGDDVFTVSCRVLTRPSPDFDFTYLVPPTVESKTKPFTLPILTLGELSNS
RFPVSIDQMYTSPNEVISVQCQNGRCTLDGELQGTTQLQVSGICAFKGEVTAHLHDNDHLYNVTITNLNGSPFDPSEDIP
APLGVPDFQGRVFGVISQRDKHNTPGHNEPANRAHDAVVPTYTAQYTPKLGQIQIGTWQTDDLTVNQPVKFTPVGLND
TDHFNQWVVPRYAGALNLNTNLAPSVAPVFPGERLLFFRSYIPLKGGYGTPAIDCLLPQEWVQHFYQEAAPSMSEVALV
RYINPDTGRALFEAKLHRAGFMTVSSNTSAPVVVPANGYFRFDSWVNQFYSLAPMGTGNGRRRIQ

FIGURE 30J

Nucleic acid sequence of human codon optimized VP1_GII.2_CGMH47_ R53I+E80S+A90L (SEQ ID NO:185)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGCTCCTGTGACCGGGCAGACAAATATCATCGATCCTTG
GATTATCGCTAATTTCGTGCAAGCCCCAAATGGGGAGTTTACGGTCAGCCCTAGAAATAGCCCTGGGGAAGTGCTCC
TCAATCTCAGCCTGGGACCAGAACTTAATCCGTACCTGCTCCACCTGGCCCGGATGTACAATGGATATGCAGGAGGG
ATGGAGGTGCAGGTTATGCTGGCTGGCAATGCCTTTACAGCAGGCAAACTCGTTTTCGCAGCCGTCCCTCCCCACTT
CCCAGTTGAAAATCTTTCCCCTCAGCAGATTACCATGTTTCCCCATGTCATCATCGATGTGCGTACCCTGGAACCTGT
GCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

FIGURE 30K

Amino acid sequence of VP1_GII.2_CGMH47_A39V+ R53I+E80S+A90L (SEQ ID NO:186)

MKMASNDAAPSTDGAAGLVPESNNEVMALEPVAGAALAVPVTGQTNIIDPWIIANFVQAPNGEFTVSPRNSPGEVLLN
LSLGPELNPYLLHLARMYNGYAGGMEVQVMLAGNAFTAGKLVFAAVPPHFPVENLSPQQITMFPHVIIDVRTLEPVLLPL
PDVRNNFFHYNQKDDPKMRIVAMLYTPLRSNGSGDDVFTVSCRVLTRPSPDFDFTYLVPPTVESKTKPFTLPILTLGELSNS
RFPVSIDQMYTSPNEVISVQCQNGRCTLDGELQGTTQLQVSGICAFKGEVTAHLHDNDHLYNVTITNLNGSPFDPSEDIP
APLGVPDFQGRVFGVISQRDKHNTPGHNEPANRAHDAVVPTYTAQYTPKLGQIQIGTWQTDDLTVNQPVKFTPVGLND
TDHFNQWVVPRYAGALNLNTNLAPSVAPVFPGERLLFFRSYIPLKGGYGTPAIDCLLPQEWVQHFYQEAAPSMSEVALV
RYINPDTGRALFEAKLHRAGFMTVSSNTSAPVVVPANGYFRFDSWVNQFYSLAPMGTGNGRRRIQ

FIGURE 30L (SEQ ID NO:187)

Nucleic acid sequence of human codon optimized VP1_GII.2_CGMH47_A39V+ R53I+E80S+A90L ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGTGCCTGTGACCGGGCAGACAAATATCATCGATCCTT
GGATTATCGCTAATTTCGTGCAAGCCCCAAATGGGGAGTTTACGGTCAGCCCTAGAAATAGCCCTGGGGAAGTGCT
CCTCAATCTCAGCCTGGGACCAGAACTTAATCCGTACCTGCTCCACCTGGCCCGGATGTACAATGGATATGCAGGAG
GGATGGAGGTGCAGGTTATGCTGGCTGGCAATGCCTTTACAGCAGGCAAACTCGTTTTCGCAGCCGTCCCTCCCCAC
TTCCCAGTTGAAAATCTTTCCCCTCAGCAGATTACCATGTTTCCCCATGTCATCATCGATGTGCGTACCCTGGAACCTG
TGCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

Figure 31A

Amino acid sequence of VP1_GII.3_Jing_E80S (SEQ ID NO:46)

MKMASNDAAPSNDGAAGLVPEISSEAMALEPVAGAAIAAPLTGQQNIIDPWIMNNFVQAPGGEFTVSPRNSPGEVLLN
LSLGPEINPYLAHLARMYNGYAGGFEVQVVLAGNAFTAGKIIFAAIPPNFPIDNLSAAQITMCPHVIVDVRQLEPVNLPMP
DVRNNFFHYNQGSDSRLRLIAMLYTPLRANNSGDDVFTVSCRVLTRPSPDFSFNFLVPPTVESKTKPFSLPILTISEMSNSRF
PVPIDSLHTSPTENIVVQCQNGRVTLDGELMGTTQLLPSQICAFRGTLTRSTSRASDQADTATPRLFNYYWHIQLDNLNG
TPYDPAEDIPAPLGTPDFRGKVFGVASQRNPDATTRAHEAKIDTTSGRFTPKLGSLEISTESGDFDQNQPTRFTPVGIGVD

Figure 31A (cont)

HEPDFQQWALPDYAGQFTHNMNLAPAVAPNFPGEQLLFFRSQLPSSGGRSNGILDCLVPQEWVQHFYQESAPSQTQV
ALVRYVNPDTGRVLFEAKLHKLRFMTIAKSGDSPITVPPNGYFRFESWVNPFYTLAPMGTGNGRRRIQ

Figure 31B

Nucleic acid sequence of human codon optimized VP1_GII.3_Jing_E80S (SEQ ID NO:47)

ATGAAAATGGCTTCCAACGATGCAGCACCCTCTAATGATGGCGCTGCCGGACTTGTGCCGGAGATTAGCTCTGAGG
CTATGGCCCTAGAACCAGTAGCCGGGGCAGCCATAGCTGCCCCACTGACTGGCCAGCAGAATATCATTGACCCCTG
GATAATGAACAATTTCGTGCAGGCACCGGGGGGAGAATTCACGGTCTCTCCTCGAAACTCCCCCGGGGAGGTTCTCT
TGAATTTGAGCCTGGGCCCTGAAATTAATCCTTATCTGGCCCATCTAGCCCGAATGTACAACGGCTACGCCGGAGGT
TTCGAGGTCCAGGTGGTGCTCGCTGGTAACGCCTTCACAGCTGGCAAGATCATTTTTGCAGCAATCCCTCCAAACTTC
CCTATCGATAATCTTAGTGCCGCCCAGATCACAATGTGCCCTCACGTTATCGTAGATGTGAGGCAGCTGGAACCTGT
CAATCTCCCAATGCCCGACGTGCGCAACAACTTCTTTCACTATAACCAGGGATCTGACTCCCGCCTTCGCCTTATCGCT
ATGCTGTACACCCCTCTGAGGGCTAACAATTCCGGAGATGACGTTTTCACTGTGAGTTGTCGAGTCCTGACACGTCC
ATCTCCTGACTTTAGCTTTAATTTCCTCGTGCCCCCCACAGTGGAATCCAAAACTAAGCCATTCTCTCTGCCAATTCTT
ACCATTAGCGAAATGTCGAATAGTAGGTTCCCGGTGCCCATAGATTCACTGCATACCAGTCCAACAGAAAACATCGT
CGTACAGTGTCAGAACGGACGCGTGACTCTCGACGGGGAGCTTATGGGCACTACCCAGCTGCTGCCCAGCCAGATA
TGCGCCTTCCGCGGCACACTGACTAGAAGCACTTCGCGTGCTTCTGACCAGGCAGATACAGCTACACCAAGGCTGTT
CAATTATTATTGGCATATACAACTCGATAATCTGAATGGCACTCCTTATGACCCAGCCGAGGACATCCCCGCCCCACT
TGGCACCCCGGACTTTAGAGGGAAGGTCTTTGGAGTGGCTTCTCAAAGAAATCCCGACGCAACCACCCGGGCCCAC
GAGGCCAAAATCGATACTACATCAGGGCGTTTCACCCCTAAGTTAGGCAGTCTGGAGATATCTACCGAAAGTGGAG
ATTTCGATCAGAACCAGCCAACCCGGTTTACCCCCGTGGGAATCGGGGTTGACCACGAACCGGATTTCCAGCAGTG
GGCTCTGCCTGATTACGCAGGCCAGTTCACACATAACATGAATCTTGCCCCCGCTGTGGCCCCCAACTTCCCGGGAG
AACAACTTCTGTTTTTCAGGAGCCAACTGCCTTCCAGCGGCGGCCGATCTAACGGGATTTTGGACTGTCTCGTGCCCC
AGGAATGGGTGCAGCATTTTTACCAGGAGTCCGCGCCCTCCCAGACGCAGGTGGCTCTGGTTAGATATGTCAATCCC
GACACCGGCAGGGTGCTATTTGAGGCAAAGCTGCACAAGCTTCGCTTTATGACTATCGCTAAGAGCGGTGATTCGCC
TATTACAGTGCCCCCCAACGGATACTTCAGATTTGAGAGTTGGGTGAACCCATTCTATACCCTGGCCCCCATGGGTAC
AGGCAATGGCAGACGGCGGATCCAGTAA

Figure 31C

Amino acid sequence of VP1_GII.3_Jing_A90L (SEQ ID NO:48)

MKMASNDAAPSNDGAAGLVPEISSEAMALEPVAGAAIAAPLTGQQNIIDPWIMNNFVQAPGGEFTVSPRNSPGEVLLN
LELGPEINPYLLHLARMYNGYAGGFEVQVVLAGNAFTAGKIIFAAIPPNFPIDNLSAAQITMCPHVIVDVRQLEPVNLPMP
DVRNNFFHYNQGSDSRLRLIAMLYTPLRANNSGDDVFTVSCRVLTRPSPDFSFNFLVPPTVESKTKPFSLPILTISEMSNSRF
PVPIDSLHTSPTENIVVQCQNGRVTLDGELMGTTQLLPSQICAFRGTLTRSTSRASDQADTATPRLFNYYWHIQLDNLNG
TPYDPAEDIPAPLGTPDFRGKVFGVASQRNPDATTRAHEAKIDTTSGRFTPKLGSLEISTESGDFDQNQPTRFTPVGIGVD
HEPDFQQWALPDYAGQFTHNMNLAPAVAPNFPGEQLLFFRSQLPSSGGRSNGILDCLVPQEWVQHFYQESAPSQTQV
ALVRYVNPDTGRVLFEAKLHKLRFMTIAKSGDSPITVPPNGYFRFESWVNPFYTLAPMGTGNGRRRIQ

Figure 31D

Nucleic acid sequence of human codon optimized VP1_GII.3_Jing_A90L (SEQ ID NO:49)

ATGAAAATGGCTTCCAACGATGCAGCACCCTCTAATGATGGCGCTGCCGGACTTGTGCCGGAGATTAGCTCTGAGG
CTATGGCCCTAGAACCAGTAGCCGGGGCAGCCATAGCTGCCCCACTGACTGGCCAGCAGAATATCATTGACCCCTG
GATAATGAACAATTTCGTGCAGGCACCGGGGGGAGAATTCACGGTCTCTCCTCGAAACTCCCCCGGGGAGGTTCTCT
TGAATTTGGAACTGGGCCCTGAAATTAATCCTTATCTGCTCCATCTAGCCCGAATGTACAACGGCTACGCCGGAGGT
TTCGAGGTCCAGGTGGTGCTCGCTGGTAACGCCTTCACAGCTGGCAAGATCATTTTTGCAGCAATCCCTCCAAACTTC
CCTATCGATAATCTTAGTGCCGCCCAGATCACAATGTGCCCTCACGTTATCGTAGATGTGAGGCAGCTGGAACCTGT
CAATCTCCCAATGCCCGACGTGCGCAACAACTTCTTTCACTATAACCAGGGATCTGACTCCCGCCTTCGCCTTATCGCT
ATGCTGTACACCCCTCTGAGGGCTAACAATTCCGGAGATGACGTTTTCACTGTGAGTTGTCGAGTCCTGACACGTCC
ATCTCCTGACTTTAGCTTTAATTTCCTCGTGCCCCCCACAGTGGAATCCAAAACTAAGCCATTCTCTCTGCCAATTCTT
ACCATTAGCGAAATGTCGAATAGTAGGTTCCCGGTGCCCATAGATTCACTGCATACCAGTCCAACAGAAAACATCGT
CGTACAGTGTCAGAACGGACGCGTGACTCTCGACGGGGAGCTTATGGGCACTACCCAGCTGCTGCCCAGCCAGATA
TGCGCCTTCCGCGGCACACTGACTAGAAGCACTTCGCGTGCTTCTGACCAGGCAGATACAGCTACACCAAGGCTGTT
CAATTATTATTGGCATATACAACTCGATAATCTGAATGGCACTCCTTATGACCCAGCCGAGGACATCCCCGCCCCACT
TGGCACCCCGGACTTTAGAGGGAAGGTCTTTGGAGTGGCTTCTCAAAGAAATCCCGACGCAACCACCCGGGCCCAC
GAGGCCAAAATCGATACTACATCAGGGCGTTTCACCCCTAAGTTAGGCAGTCTGGAGATATCTACCGAAAGTGGAG
ATTTCGATCAGAACCAGCCAACCCGGTTTACCCCCGTGGGAATCGGGGTTGACCACGAACCGGATTTCCAGCAGTG
GGCTCTGCCTGATTACGCAGGCCAGTTCACACATAACATGAATCTTGCCCCCGCTGTGGCCCCCAACTTCCCGGGAG
AACAACTTCTGTTTTTCAGGAGCCAACTGCCTTCCAGCGGCGGCCGATCTAACGGGATTTTGGACTGTCTCGTGCCCC
AGGAATGGGTGCAGCATTTTTACCAGGAGTCCGCGCCCTCCCAGACGCAGGTGGCTCTGGTTAGATATGTCAATCCC
GACACCGGCAGGGTGCTATTTGAGGCAAAGCTGCACAAGCTTCGCTTTATGACTATCGCTAAGAGCGGTGATTCGCC
TATTACAGTGCCCCCCAACGGATACTTCAGATTTGAGAGTTGGGTGAACCCATTCTATACCCTGGCCCCCATGGGTAC
AGGCAATGGCAGACGGCGGATCCAGTAA

Figure 31E

Amino acid sequence of VP1_GII.3_Jing_E80S+A90L (SEQ ID NO:50)

MKMASNDAAPSNDGAAGLVPEISSEAMALEPVAGAAIAAPLTGQQNIIDPWIMNNFVQAPGGEFTVSPRNSPGEVLLN
LSLGPEINPYLLHLARMYNGYAGGFEVQVVLAGNAFTAGKIIFAAIPPNFPIDNLSAAQITMCPHVIVDVRQLEPVNLPMP
DVRNNFFHYNQGSDSRLRLIAMLYTPLRANNSGDDVFTVSCRVLTRPSPDFSFNFLVPPTVESKTKPFSLPILTISEMSNSRF
PVPIDSLHTSPTENIVVQCQNGRVTLDGELMGTTQLLPSQICAFRGTLTRSTSRASDQADTATPRLFNYYWHIQLDNLNG
TPYDPAEDIPAPLGTPDFRGKVFGVASQRNPDATTRAHEAKIDTTSGRFTPKLGSLEISTESGDFDQNQPTRFTPVGIGVD
HEPDFQQWALPDYAGQFTHNMNLAPAVAPNFPGEQLLFFRSQLPSSGGRSNGILDCLVPQEWVQHFYQESAPSQTQV
ALVRYVNPDTGRVLFEAKLHKLRFMTIAKSGDSPITVPPNGYFRFESWVNPFYTLAPMGTGNGRRRIQ

Figure 31F

Nucleic acid sequence of human codon optimized VP1_GII.3_Jing_E80S+A90L (SEQ ID NO:51)

ATGAAAATGGCTTCCAACGATGCAGCACCCTCTAATGATGGCGCTGCCGGACTTGTGCCGGAGATTAGCTCTGAGG
CTATGGCCCTAGAACCAGTAGCCGGGGCAGCCATAGCTGCCCCACTGACTGGCCAGCAGAATATCATTGACCCCTG
GATAATGAACAATTTCGTGCAGGCACCGGGGGGAGAATTCACGGTCTCTCCTCGAAACTCCCCCGGGGAGGTTCTCT
TGAATTTGAGCCTGGGCCCTGAAATTAATCCTTATCTGCTCCATCTAGCCCGAATGTACAACGGCTACGCCGGAGGT

Figure 31F (cont)

TTCGAGGTCCAGGTGGTGCTCGCTGGTAACGCCTTCACAGCTGGCAAGATCATTTTTGCAGCAATCCCTCCAAACTTC
CCTATCGATAATCTTAGTGCCGCCCAGATCACAATGTGCCCTCACGTTATCGTAGATGTGAGGCAGCTGGAACCTGT
CAATCTCCCAATGCCCGACGTGCGCAACAACTTCTTTCACTATAACCAGGGATCTGACTCCCGCCTTCGCCTTATCGCT
ATGCTGTACACCCCTCTGAGGGCTAACAATTCCGGAGATGACGTTTTCACTGTGAGTTGTCGAGTCCTGACACGTCC
ATCTCCTGACTTTAGCTTTAATTTCCTCGTGCCCCCCACAGTGGAATCCAAAACTAAGCCATTCTCTCTGCCAATTCTT
ACCATTAGCGAAATGTCGAATAGTAGGTTCCCGGTGCCCATAGATTCACTGCATACCAGTCCAACAGAAAACATCGT
CGTACAGTGTCAGAACGGACGCGTGACTCTCGACGGGGAGCTTATGGGCACTACCCAGCTGCTGCCCAGCCAGATA
TGCGCCTTCCGCGGCACACTGACTAGAAGCACTTCGCGTGCTTCTGACCAGGCAGATACAGCTACACCAAGGCTGTT
CAATTATTATTGGCATATACAACTCGATAATCTGAATGGCACTCCTTATGACCCAGCCGAGGACATCCCCGCCCCACT
TGGCACCCCGGACTTTAGAGGGAAGGTCTTTGGAGTGGCTTCTCAAAGAAATCCCGACGCAACCACCCGGGCCCAC
GAGGCCAAAATCGATACTACATCAGGGCGTTTCACCCCTAAGTTAGGCAGTCTGGAGATATCTACCGAAAGTGGAG
ATTTCGATCAGAACCAGCCAACCCGGTTTACCCCCGTGGGAATCGGGGTTGACCACGAACCGGATTTCCAGCAGTG
GGCTCTGCCTGATTACGCAGGCCAGTTCACACATAACATGAATCTTGCCCCCGCTGTGGCCCCCAACTTCCCGGGAG
AACAACTTCTGTTTTTCAGGAGCCAACTGCCTTCCAGCGGCGGCCGATCTAACGGGATTTTGGACTGTCTCGTGCCCC
AGGAATGGGTGCAGCATTTTTACCAGGAGTCCGCGCCCTCCCAGACGCAGGTGGCTCTGGTTAGATATGTCAATCCC
GACACCGGCAGGGTGCTATTTGAGGCAAAGCTGCACAAGCTTCGCTTTATGACTATCGCTAAGAGCGGTGATTCGCC
TATTACAGTGCCCCCCAACGGATACTTCAGATTTGAGAGTTGGGTGAACCCATTCTATACCCTGGCCCCCATGGGTAC
AGGCAATGGCAGACGGCGGATCCAGTAA

Figure 32A

Amino acid sequence of VP1_GII.4_Syd12_A39V (SEQ ID NO:53)

MKMASSDANPSDGSAANLVPEVNNEVMALEPVVGAAIAVPVAGQQNVIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32B

Nucleic acid sequence of human codon optimized VP1_GII.4_Syd12_A39V (SEQ ID NO:54)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGTCCCCGTGGCCGGTCAGCAGAATGTGATTGACCCGTG
GATACGCAACAATTTTGTCCAAGCCCCTGGTGGGGAGTTCACCGTTAGCCCGAGAAATGCGCCAGGAGAAATCCTG
TGGTCGGCCCCATTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT
TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC

Figure 32B (cont)

GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32C

Amino acid sequence of VP1_GII.4_Syd12_V47P (SEQ ID NO:55)

MKMASSDANPSDGSAANLVPEVNNEVMALEPVVGAAIAAPVAGQQNPIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32D

Nucleic acid sequence of human codon optimized VP1_GII.4_Syd12_V47P (SEQ ID NO:56)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATCCCATTGACCCGTG
GATACGCAACAATTTTGTCCAAGCCCCTGGTGGGGAGTTCACCGTTAGCCCGAGAAATGCGCCAGGAGAAATCCTG
TGGTCGGCCCCATTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT
TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG

Figure 32D (cont)

AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32E

Amino acid sequence of VP1_GII.4_Syd12_R53I (SEQ ID NO:57)

MKMASSDANPSDGSAANLVPEVNNEVMALEPVVGAAIAAPVAGQQNVIDPWIINNFVQAPGGEFTVSPRNAPGEILW
SAPLGPDLNPYLSHLARMYNGYAGGFEVQVILAGNAFTAGKVIFAAVPPNFPTEGLSPSQVTMFPHIVVDVRQLEPVLIPL
PDVRNNFYHYNQSNDPTIKLIAMLYTPLRANNAGDDVFTVSCRVLTRPSPDFDFIFLVPPTVESRTKPFSVPVLTVEEMTN
SRFPIPLEKLFTGPSSAFVVQPQNGRCTTDGVLLGTTQLSPVNICTFRGDVTHITGSRNYTMNLASQNWNDYDPTEEIPAP
LGTPDFVGKIQGVLTQTTRTDGSTRGHKATVYTGSADFAPKLGRVQFETDTDRDFEANQNTKFTPVGVIQDGGTTHRNE
PQQWVLPSYSGRNTHNVHLAPAVAPTFPGEQLLFFRSTMPGCSGYPNMDLDCLLPQEWVQYFYQEAAPAQSDVALLR
FVNPDTGRVLFECKLHKSGYVTVAHTGQHDLVIPPNGYFRFDSWVNQFYTLAPMGNGTGRRRAV

Figure 32F

Nucleic acid sequence of human codon optimized VP1_GII.4_Syd12_R53I (SEQ ID NO:58)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATAATCAACAATTTTGTCCAAGCCCCTGGTGGGGAGTTCACCGTTAGCCCGAGAAATGCGCCAGGAGAAATCCT
GTGGTCGGCCCCATTGGGACCCGATCTGAACCCCTATTTGTCACATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32G

Amino acid sequence of VP1_GII.4_Syd12_P80S (SEQ ID NO:59)

MKMASSDANPSDGSAANLVPEVNNEVMALEPVVGAAIAAPVAGQQNVIDPWIRNNFVQAPGGEFTVSPRNAPGEIL
WSASLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32H

Nucleic acid sequence of human codon optimized VP1_GII.4_Syd12_P80S (SEQ IDNO:60)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATACGCAACAATTTTGTCCAAGCCCCTGGTGGGGAGTTCACCGTTAGCCCGAGAAATGCGCCAGGAGAAATCCT
GTGGTCGGCCAGCTTGGGACCCGATCTGAACCCCTATTTGTCACATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32I

Amino acid sequence of VP1_GII.4_Syd12_S90L (SEQ ID NO:61)

MKMASSDANPSDGSAANLVPEVNNEVMALEPVVGAAIAAPVAGQQNVIDPWIRNNFVQAPGGEFTVSPRNAPGEIL
WSAPLGPDLNPYLLHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP

Figure 32I (cont)

APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32J

Nucleic acid sequence of human codon optimized VP1_GII.4_Syd12_S90L (SEQ IDNO:62)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATACGCAACAATTTTGTCCAAGCCCCTGGTGGGGAGTTCACCGTTAGCCCGAGAAATGCGCCAGGAGAAATCCT
GTGGTCGGCCCCATTGGGACCCGATCTGAACCCCTATTTGCTGCATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32K

Amino acid sequence of VP1_GII.4_Syd12_Δ35-42 (SEQ ID NO:63)

MKMASSDANPSDGSAANLVPEVNNEVMALEPVVGGQQNVIDPWIRNNFVQAPGGEFTVSPRNAPGEILWSAPLGPD
LNPYLSHLARMYNGYAGGFEVQVILAGNAFTAGKVIFAAVPPNFPTEGLSPSQVTMFPHIVVDVRQLEPVLIPLPDVRNN
FYHYNQSNDPTIKLIAMLYTPLRANNAGDDVFTVSCRVLTRPSPDFDFIFLVPPTVESRTKPFSVPVLTVEEMTNSRFPIPLE
KLFTGPSSAFVVQPQNGRCTTDGVLLGTTQLSPVNICTFRGDVTHITGSRNYTMNLASQNWNDYDPTEEIPAPLGTPDFV
GKIQGVLTQTTRTDGSTRGHKATVYTGSADFAPKLGRVQFETDTDRDFEANQNTKFTPVGVIQDGGTTHRNEPQQWVL
PSYSGRNTHNVHLAPAVAPTFPGEQLLFFRSTMPGCSGYPNMDLDCLLPQEWVQYFYQEAAPAQSDVALLRFVNPDTG
RVLFECKLHKSGYVTVAHTGQHDLVIPPNGYFRFDSWVNQFYTLAPMGNGTGRRRAV

Figure 32L

Nucleic acid sequence of human codon optimized VP1_GII.4_Syd12_Δ35-42 (SEQ IDNO:64)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGGTCAGCAGAATGTGATTGACCCGTGGATACGCAACAATTTTGTCCAAGC
CCCTGGTGGGGAGTTCACCGTTAGCCCGAGAAATGCGCCAGGAGAAATCCTGTGGTCGGCCCCATTGGGACCCGAT
CTGAACCCCTATTTGTCACATCTCGCTCGGATGTACAACGGGTATGCCGGCGGATTTGAAGTGCAGGTGATTCTGGC
TGGGAACGCGTTCACTGCTGGCAAAGTGATCTTTGCAGCGGTGCCTCCCAACTTCCCCACTGAAGGACTGTCTCCAA
GCCAGGTCACAATGTTTCCACACATCGTGGTGGACGTACGGCAGCTAGAGCCTGTCCTGATTCCCCTCCCTGATGTA
CGCAATAATTTCTACCACTACAATCAATCCAATGATCCGACCATTAAACTCATCGCGATGTTGTACACCCCTCTGCGC
GCTAACAATGCTGGAGACGACGTATTCACCGTGTCATGCAGAGTGCTCACCAGACCTTCACCAGACTTTGACTTTATC
TTCTTAGTGCCCCCCACTGTTGAGAGCCGAACCAAGCCCTTTAGTGTCCCCGTACTCACAGTCGAGGAGATGACAAA
TAGCCGCTTTCCAATCCCCCTTGAGAAACTGTTCACAGGACCTTCCTCGGCATTCGTGGTTCAGCCACAGAACGGACG
CTGCACAACTGACGGCGTGCTGCTCGGAACCACCCAGCTTAGCCCTGTTAATATCTGTACGTTTAGAGGCGACGTAA
CTCACATAACTGGCTCACGGAACTATACCATGAATCTGGCATCACAGAATTGGAATGACTACGACCCAACCGAAGAG
ATTCCCGCACCTCTTGGAACCCCCGACTTTGTGGGAAAAATACAGGGCGTCCTGACACAAACCACCAGAACCGATGG
CTCCACACGGGGACACAAGGCAACCGTCTACACTGGCTCTGCCGATTTTGCCCCGAAACTGGGTAGAGTGCAGTTTG
AGACCGACACTGACCGGGACTTTGAAGCCAATCAGAATACTAAGTTCACACCTGTAGGAGTGATTCAGGACGGGGG
CACCACTCACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTTCGTTCAACCATGCCTGGATGCTCCGGATATC
CCAATATGGATCTCGATTGCCTGCTCCCACAGGAATGGGTGCAGTATTTTTATCAAGAGGCCGCACCAGCCCAATCC
GACGTCGCACTTCTGCGGTTCGTGAATCCAGACACAGGCCGCGTGTTGTTTGAGTGCAAATTGCACAAATCAGGATA
CGTTACAGTGGCTCATACTGGACAGCATGACCTGGTGATCCCACCCAACGGATATTTTAGGTTCGACTCCTGGGTGA
ATCAGTTTTATACATTAGCCCCCATGGGGAATGGGACTGGCAGACGCAGGGCTGTCTGA

Figure 32M

Amino acid sequence of VP1_GII.4_Syd12_SSTAVATA (SEQ ID NO:65)

MKMASSDANPSDGSAANLVPEVNNEVMALEPVVGSSTAVATAGQQNVIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32N

Nucleic acid sequence of human codon optimized VP1_GII.4_Syd12_SSTAVATA (SEQ ID NO:66)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCAGCTCCACCGCCGTCGCTACAGCCGGTCAGCAGAATGTGATTGACCCGTG
GATACGCAACAATTTTGTCCAAGCCCCTGGTGGGGAGTTCACCGTTAGCCCGAGAAATGCGCCAGGAGAAATCCTG
TGGTCGGCCCCATTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT

Figure 32N (cont)

TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32O

Amino acid sequence of VP1_GII.4_Syd12_P80S+A39V (SEQ ID NO:67)

MKMASSDANPSDGSAANLVPEVNNEVMALEPVVGAAIAVPVAGQQNVIDPWIRNNFVQAPGGEFTVSPRNAPGEIL
WSASLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32P

Nucleic acid sequence of human codon optimized VP1_GII.4_Syd12_P80S+A39V (SEQ ID NO:68)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGTCCCCGTGGCCGGTCAGCAGAATGTGATTGACCCGTG
GATACGCAACAATTTTGTCCAAGCCCCTGGTGGGGAGTTCACCGTTAGCCCGAGAAATGCGCCAGGAGAAATCCTG
TGGTCGGCCAGCTTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT
TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT

Figure 32P (cont)

CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32Q

Amino acid sequence of VP1_GII.4_Syd12_P80S+V47P (SEQ ID NO:69)

MKMASSDANPSDGSAANLVPEVNNEVMALEPVVGAAIAAPVAGQQNPIDPWIRNNFVQAPGGEFTVSPRNAPGEIL
WSASLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32R

Nucleic acid sequence of human codon optimized VP1_GII.4_Syd12_P80S+V47P (SEQ ID NO:70)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATCCCATTGACCCGTG
GATACGCAACAATTTTGTCCAAGCCCCTGGTGGGGAGTTCACCGTTAGCCCGAGAAATGCGCCAGGAGAAATCCTG
TGGTCGGCCAGCTTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT
TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA

Figure 32R (cont)

ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32S

Amino acid sequence of VP1_GII.4_Syd12_P80S+R53I (SEQID NO:71)

MKMASSDANPSDGSAANLVPEVNNEVMALEPVVGAAIAAPVAGQQNVIDPWIINNFVQAPGGEFTVSPR
NAPGEILWSASLGPDLNPYLSHLARMYNGYAGGFEVQVILAGNAFTAGKVIFAAVPPNFPTEGLSPSQVTMF
PHIVVDVRQLEPVLIPLPDVRNNFYHYNQSNDPTIKLIAMLYTPLRANNAGDDVFTVSCRVLTRPSPDFDFIFLV
PPTVESRTKPFSVPVLTVEEMTNSRFPIPLEKLFTGPSSAFVVQPQNGRCTTDGVLLGTTQLSPVNICTFRGDVT
HITGSRNYTMNLASQNWNDYDPTEEIPAPLGTPDFVGKIQGVLTQTTRTDGSTRGHKATVYTGSADFAPKLG
RVQFETDTDRDFEANQNTKFTPVGVIQDGGTTHRNEPQQWVLPSYSGRNTHNVHLAPAVAPTFPGEQLLFF
RSTMPGCSGYPNMDLDCLLPQEWVQYFYQEAAPAQSDVALLRFVNPDTGRVLFECKLHKSGYVTVAHTGQ
HDLVIPPNGYFRFDSWVNQFYTLAPMGNGTGRRRAV

Figure 32T

Nucleic acid sequence of human codon optimized VP1_GII.4_Syd12_P80S+R53I (SEQ ID NO:72)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATAATCAACAATTTTGTCCAAGCCCCTGGTGGGGAGTTCACCGTTAGCCCGAGAAATGCGCCAGGAGAAATCCT
GTGGTCGGCCAGCTTGGGACCCGATCTGAACCCCTATTTGTCACATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32U

Amino acid sequence of VP1_GII.4_Syd12_P80S+S90L (SEQ ID NO:73)

MKMASSDANPSDGSAANLVPEVNNEVMALEPVVGAAIAAPVAGQQNVIDPWIRNNFVQAPGGEFTVSPRNAPGEIL
WSASLGPDLNPYLLHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32V

Nucleic acid sequence of human codon optimized VP1_GII.4_Syd12_P80S+S90L (SEQ ID NO:74)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATACGCAACAATTTTGTCCAAGCCCCTGGTGGGGAGTTCACCGTTAGCCCGAGAAATGCGCCAGGAGAAATCCT
GTGGTCGGCCAGCTTGGGACCCGATCTGAACCCCTATTTGCTGCATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32W

Amino acid sequence of VP1_GII.4_Syd12_P80S+Δ35-42 (SEQ ID NO:75)

MKMASSDANPSDGSAANLVPEVNNEVMALEPVVGGQQNVIDPWIRNNFVQAPGGEFTVSPRNAPGEILWSASLGPD
LNPYLSHLARMYNGYAGGFEVQVILAGNAFTAGKVIFAAVPPNFPTEGLSPSQVTMFPHIVVDVRQLEPVLIPLPDVRNN
FYHYNQSNDPTIKLIAMLYTPLRANNAGDDVFTVSCRVLTRPSPDFDFIFLVPPTVESRTKPFSVPVLTVEEMTNSRFPIPLE
KLFTGPSSAFVVQPQNGRCTTDGVLLGTTQLSPVNICTFRGDVTHITGSRNYTMNLASQNWNDYDPTEEIPAPLGTPDFV

Figure 32W (cont)

GKIQGVLTQTTRTDGSTRGHKATVYTGSADFAPKLGRVQFETDTDRDFEANQNTKFTPVGVIQDGGTTHRNEPQQWVL
PSYSGRNTHNVHLAPAVAPTFPGEQLLFFRSTMPGCSGYPNMDLDCLLPQEWVQYFYQEAAPAQSDVALLRFVNPDTG
RVLFECKLHKSGYVTVAHTGQHDLVIPPNGYFRFDSWVNQFYTLAPMGNGTGRRRAV

Figure 32X

Nucleic acid sequence of human codon optimized VP1_GII.4_Syd12_P80S+Δ35-42 (SEQ ID NO:76)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGGTCAGCAGAATGTGATTGACCCGTGGATACGCAACAATTTTGTCCAAGC
CCCTGGTGGGGAGTTCACCGTTAGCCCGAGAAATGCGCCAGGAGAAATCCTGTGGTCGGCCAGCTTGGGACCCGAT
CTGAACCCCTATTTGTCACATCTCGCTCGGATGTACAACGGGTATGCCGGCGGATTTGAAGTGCAGGTGATTCTGGC
TGGGAACGCGTTCACTGCTGGCAAAGTGATCTTTGCAGCGGTGCCTCCCAACTTCCCCACTGAAGGACTGTCTCCAA
GCCAGGTCACAATGTTTCCACACATCGTGGTGGACGTACGGCAGCTAGAGCCTGTCCTGATTCCCCTCCCTGATGTA
CGCAATAATTTCTACCACTACAATCAATCCAATGATCCGACCATTAAACTCATCGCGATGTTGTACACCCCTCTGCGC
GCTAACAATGCTGGAGACGACGTATTCACCGTGTCATGCAGAGTGCTCACCAGACCTTCACCAGACTTTGACTTTATC
TTCTTAGTGCCCCCCACTGTTGAGAGCCGAACCAAGCCCTTTAGTGTCCCCGTACTCACAGTCGAGGAGATGACAAA
TAGCCGCTTTCCAATCCCCCTTGAGAAACTGTTCACAGGACCTTCCTCGGCATTCGTGGTTCAGCCACAGAACGGACG
CTGCACAACTGACGGCGTGCTGCTCGGAACCACCCAGCTTAGCCCTGTTAATATCTGTACGTTTAGAGGCGACGTAA
CTCACATAACTGGCTCACGGAACTATACCATGAATCTGGCATCACAGAATTGGAATGACTACGACCCAACCGAAGAG
ATTCCCGCACCTCTTGGAACCCCCGACTTTGTGGGAAAAATACAGGGCGTCCTGACACAAACCACCAGAACCGATGG
CTCCACACGGGGACACAAGGCAACCGTCTACACTGGCTCTGCCGATTTTGCCCCGAAACTGGGTAGAGTGCAGTTTG
AGACCGACACTGACCGGGACTTTGAAGCCAATCAGAATACTAAGTTCACACCTGTAGGAGTGATTCAGGACGGGGG
CACCACTCACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTTCGTTCAACCATGCCTGGATGCTCCGGATATC
CCAATATGGATCTCGATTGCCTGCTCCCACAGGAATGGGTGCAGTATTTTTATCAAGAGGCCGCACCAGCCCAATCC
GACGTCGCACTTCTGCGGTTCGTGAATCCAGACACAGGCCGCGTGTTGTTTGAGTGCAAATTGCACAAATCAGGATA
CGTTACAGTGGCTCATACTGGACAGCATGACCTGGTGATCCCACCCAACGGATATTTTAGGTTCGACTCCTGGGTGA
ATCAGTTTTATACATTAGCCCCCATGGGGAATGGGACTGGCAGACGCAGGGCTGTCTGA

Figure 32Y

Amino acid sequence of VP1_GII.4_Syd12_P80S+SSTAVATA (SEQ ID NO:77)

MKMASSDANPSDGSAANLVPEVNNEVMALEPVVGSSTAVATAGQQNVIDPWIRNNFVQAPGGEFTVSPRNAPGEIL
WSASLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32Z

Nucleic acid sequence of human codon optimized VP1_GII.4_Syd12_P80S+SSTAVATA (SEQ ID NO:78)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCAGCTCCACCGCCGTCGCTACAGCCGGTCAGCAGAATGTGATTGACCCGTG
GATACGCAACAATTTTGTCCAAGCCCCTGGTGGGGAGTTCACCGTTAGCCCGAGAAATGCGCCAGGAGAAATCCTG
TGGTCGGCCAGCTTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT
TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

FIGURE 32AA

Amino acid sequence of VP1 GII.4 Syd12 A39V+R53I (SEQ ID NO:188)

MKMASSDANPSDGSAANLVPEVNNEVMALEPVVGAAIAVPVAGQQNVIDPWIINNFVQAPGGEFTVSPR
NAPGEILWSAPLGPDLNPYLSHLARMYNGYAGGFEVQVILAGNAFTAGKVIFAAVPPNFPTEGLSPSQVTMF
PHIVVDVRQLEPVLIPLPDVRNNFYHYNQSNDPTIKLIAMLYTPLRANNAGDDVFTVSCRVLTRPSPDFDFIFLV
PPTVESRTKPFSVPVLTVEEMTNSRFPIPLEKLFTGPSSAFVVQPQNGRCTTDGVLLGTTQLSPVNICTFRGDVT
HITGSRNYTMNLASQNWNDYDPTEEIPAPLGTPDFVGKIQGVLTQTTRTDGSTRGHKATVYTGSADFAPKLG
RVQFETDTDRDFEANQNTKFTPVGVIQDGGTTHRNEPQQWVLPSYSGRNTHNVHLAPAVAPTFPGEQLLFF
RSTMPGCSGYPNMDLDCLLPQEWVQYFYQEAAPAQSDVALLRFVNPDTGRVLFECKLHKSGYVTVAHTGQ
HDLVIPPNGYFRFDSWVNQFYTLAPMGNGTGRRRAV

FIGURE 32BB

Nucleic acid sequence of human codon optimized VP1 GII.4_Syd12_A39V+R53I (SEQ ID NO:189)

ATGAAAATGGCCTCGAGTGACGCTAACCCTAGTGACGGCAGCGCCGCCAATCTTGTGCCTGAGGTTAAT
AATGAGGTGATGGCCCTGGAGCCTGTGGTGGGCGCAGCCATAGCAGTCCCCGTGGCCGGTCAGCAGAA
TGTGATTGACCCGTGGATAATCAACAATTTTGTCCAAGCCCCTGGTGGGGAGTTCACCGTTAGCCCGAGA
AATGCGCCAGGAGAAATCCTGTGGTCGGCCCCATTGGGACCCGATCTGAACCCCTATTTGTCACATCTCG
CTCGGATGTACAACGGGTATGCCGGCGGATTTGAAGTGCAGGTGATTCTGGCTGGGAACGCGTTCACTG
CTGGCAAAGTGATCTTTGCAGCGGTGCCTCCCAACTTCCCCACTGAAGGACTGTCTCCAAGCCAGGTCAC
AATGTTTCCACACATCGTGGTGGACGTACGGCAGCTAGAGCCTGTCCTGATTCCCCTCCCTGATGTACGC
AATAATTTCTACCACTACAATCAATCCAATGATCCGACCATTAAACTCATCGCGATGTTGTACACCCCTCTG
CGCGCTAACAATGCTGGAGACGACGTATTCACCGTGTCATGCAGAGTGCTCACCAGACCTTCACCAGACT
TTGACTTTATCTTCTTAGTGCCCCCCACTGTTGAGAGCCGAACCAAGCCCTTTAGTGTCCCCGTACTCACA
GTCGAGGAGATGACAAATAGCCGCTTTCCAATCCCCCTTGAGAAACTGTTCACAGGACCTTCCTCGGCAT
TCGTGGTTCAGCCACAGAACGGACGCTGCACAACTGACGGCGTGCTGCTCGGAACCACCCAGCTTAGCC
CTGTTAATATCTGTACGTTTAGAGGCGACGTAACTCACATAACTGGCTCACGGAACTATACCATGAATCTG
GCATCACAGAATTGGAATGACTACGACCCAACCGAAGAGATTCCCGCACCTCTTGGAACCCCCGACTTTG
TGGGAAAAATACAGGGCGTCCTGACACAAACCACCAGAACCGATGGCTCCACACGGGGACACAAGGCA
ACCGTCTACACTGGCTCTGCCGATTTTGCCCCGAAACTGGGTAGAGTGCAGTTTGAGACCGACACTGACC
GGGACTTTGAAGCCAATCAGAATACTAAGTTCACACCTGTAGGAGTGATTCAGGACGGGGGCACCACTC
ACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTTCGTTCAACCATGCCTGGATGCTCC
GGATATCCCAATATGGATCTCGATTGCCTGCTCCCACAGGAATGGGTGCAGTATTTTTATCAAGAGGCCG
CACCAGCCCAATCCGACGTCGCACTTCTGCGGTTCGTGAATCCAGACACAGGCCGCGTGTTGTTTGAGTG
CAAATTGCACAAATCAGGATACGTTACAGTGGCTCATACTGGACAGCATGACCTGGTGATCCCACCCAAC
GGATATTTTAGGTTCGACTCCTGGGTGAATCAGTTTTATACATTAGCCCCCATGGGGAATGGGACTGGCA
GACGCAGGGCTGTCTGA

FIGURE 32CC

Amino acid sequence of VP1 GII.4 Syd12 A39V+R53I+P80S (SEQ ID NO:190)

MKMASSDANPSDGSAANLVPEVNNEVMALEPVVGAAIAVPVAGQQNVIDPWIINNFVQAPGGEFTVSPR
NAPGEILWSASLGPDLNPYLSHLARMYNGYAGGFEVQVILAGNAFTAGKVIFAAVPPNFPTEGLSPSQVTMF
PHIVVDVRQLEPVLIPLPDVRNNFYHYNQSNDPTIKLIAMLYTPLRANNAGDDVFTVSCRVLTRPSPDFDFIFLV
PPTVESRTKPFSVPVLTVEEMTNSRFPIPLEKLFTGPSSAFVVQPQNGRCTTDGVLLGTTQLSPVNICTFRGDVT
HITGSRNYTMNLASQNWNDYDPTEEIPAPLGTPDFVGKIQGVLTQTTRTDGSTRGHKATVYTGSADFAPKLG
RVQFETDTDRDFEANQNTKFTPVGVIQDGGTTHRNEPQQWVLPSYSGRNTHNVHLAPAVAPTFPGEQLLFF
RSTMPGCSGYPNMDLDCLLPQEWVQYFYQEAAPAQSDVALLRFVNPDTGRVLFECKLHKSGYVTVAHTGQ
HDLVIPPNGYFRFDSWVNQFYTLAPMGNGTGRRRAV

FIGURE 32DD

Nucleic acid sequence of human codon optimized VP1 GII.4_Syd12_A39V+R53I+P80S (SEQ ID NO:191)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGTCCCCGTGGCCGGTCAGCAGAATGTGATTGACCCGTG
GATAATCAACAATTTTGTCCAAGCCCCTGGTGGGGAGTTCACCGTTAGCCCGAGAAATGCGCCAGGAGAAATCCTGT
GGTCGGCCAGCTTGGGACCCGATCTGAACCCCTATTTGTCACATCTCGCTCGGATGTACAACGGGTATGCCGGCGGA
TTTGAAGTGCAGGTGATTCTGGCTGGGAACGCGTTCACTGCTGGCAAAGTGATCTTTGCAGCGGTGCCTCCCAACTT
CCCCACTGAAGGACTGTCTCCAAGCCAGGTCACAATGTTTCCACACATCGTGGTGGACGTACGGCAGCTAGAGCCTG
TCCTGATTCCCCTCCCTGATGTACGCAATAATTTCTACCACTACAATCAATCCAATGATCCGACCATTAAACTCATCGC
GATGTTGTACACCCCTCTGCGCGCTAACAATGCTGGAGACGACGTATTCACCGTGTCATGCAGAGTGCTCACCAGAC
CTTCACCAGACTTTGACTTTATCTTCTTAGTGCCCCCCACTGTTGAGAGCCGAACCAAGCCCTTTAGTGTCCCCGTACT
CACAGTCGAGGAGATGACAAATAGCCGCTTTCCAATCCCCCTTGAGAAACTGTTCACAGGACCTTCCTCGGCATTCG
TGGTTCAGCCACAGAACGGACGCTGCACAACTGACGGCGTGCTGCTCGGAACCACCCAGCTTAGCCCTGTTAATATC
TGTACGTTTAGAGGCGACGTAACTCACATAACTGGCTCACGGAACTATACCATGAATCTGGCATCACAGAATTGGAA
TGACTACGACCCAACCGAAGAGATTCCCGCACCTCTTGGAACCCCCGACTTTGTGGGAAAAATACAGGGCGTCCTGA
CACAAACCACCAGAACCGATGGCTCCACACGGGGACACAAGGCAACCGTCTACACTGGCTCTGCCGATTTTGCCCCG
AAACTGGGTAGAGTGCAGTTTGAGACCGACACTGACCGGGACTTTGAAGCCAATCAGAATACTAAGTTCACACCTG
TAGGAGTGATTCAGGACGGGGGCACCACTCACCGGAACGAGCCGCAACAATGGGTCCTGCCCTCTTATAGCGGGA
GGAATACTCATAATGTGCATTTGGCTCCTGCAGTGGCTCCCACGTTTCCCGGGGAACAACTGCTCTTTTTTCGTTCAA
CCATGCCTGGATGCTCCGGATATCCCAATATGGATCTCGATTGCCTGCTCCCACAGGAATGGGTGCAGTATTTTTATC
AAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

FIGURE 32EE

Nucleic acid sequence of human codon optimized VP1 GII.4_Syd12_P80X; where X = A (XXX=GCC), N (XXX=AAC), K(XXX=AAG), or H(XXX=CAC) (SEQ ID NO:287)

ATGAAAATGGCCTCGAGTGACGCTAACCCTAGTGACGGCAGCGCCGCCAATCTTGTGCCTGAGGTTAAT
AATGAGGTGATGGCCCTGGAGCCTGTGGTGGGCGCAGCCATAGCAGCGCCCGTGGCCGGTCAGCAGAA
TGTGATTGACCCGTGGATACGCAACAATTTTGTCCAAGCCCCTGGTGGGGAGTTCACCGTTAGCCCGAGA
AATGCGCCAGGAGAAATCCTGTGGTCGGCCXXXTTGGGACCCGATCTGAACCCCTATTTGTCACATCTCG
CTCGGATGTACAACGGGTATGCCGGCGGATTTGAAGTGCAGGTGATTCTGGCTGGGAACGCGTTCACTG
CTGGCAAAGTGATCTTTGCAGCGGTGCCTCCCAACTTCCCCACTGAAGGACTGTCTCCAAGCCAGGTCAC
AATGTTTCCACACATCGTGGTGGACGTACGGCAGCTAGAGCCTGTCCTGATTCCCCTCCCTGATGTACGC
AATAATTTCTACCACTACAATCAATCCAATGATCCGACCATTAAACTCATCGCGATGTTGTACACCCCTCTG
CGCGCTAACAATGCTGGAGACGACGTATTCACCGTGTCATGCAGAGTGCTCACCAGACCTTCACCAGACT
TTGACTTTATCTTCTTAGTGCCCCCCACTGTTGAGAGCCGAACCAAGCCCTTTAGTGTCCCCGTACTCACA
GTCGAGGAGATGACAAATAGCCGCTTTCCAATCCCCCTTGAGAAACTGTTCACAGGACCTTCCTCGGCAT
TCGTGGTTCAGCCACAGAACGGACGCTGCACAACTGACGGCGTGCTGCTCGGAACCACCCAGCTTAGCC

FIGURE 32EE (cont)

CTGTTAATATCTGTACGTTTAGAGGCGACGTAACTCACATAACTGGCTCACGGAACTATACCATGAATCTG
GCATCACAGAATTGGAATGACTACGACCCAACCGAAGAGATTCCCGCACCTCTTGGAACCCCCGACTTTG
TGGGAAAAATACAGGGCGTCCTGACACAAACCACCAGAACCGATGGCTCCACACGGGGACACAAGGCA
ACCGTCTACACTGGCTCTGCCGATTTTGCCCCGAAACTGGGTAGAGTGCAGTTTGAGACCGACACTGACC
GGGACTTTGAAGCCAATCAGAATACTAAGTTCACACCTGTAGGAGTGATTCAGGACGGGGGCACCACTC
ACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTCGTTCAACCATGCCTGGATGCTCC
GGATATCCCAATATGGATCTCGATTGCCTGCTCCCACAGGAATGGGTGCAGTATTTTTATCAAGAGGCCG
CACCAGCCCAATCCGACGTCGCACTTCTGCGGTTCGTGAATCCAGACACAGGCCGCGTGTTGTTTGAGTG
CAAATTGCACAAATCAGGATACGTTACAGTGGCTCATACTGGACAGCATGACCTGGTGATCCCACCCAAC
GGATATTTTAGGTTCGACTCCTGGGTGAATCAGTTTTATACATTAGCCCCCATGGGGAATGGGACTGGCA
GACGCAGGGCTGTCTGA

FIGURE 32FF

Amino acid sequence of VP1_GII.4_Syd12_P80X; where X = A, N, K, or H (SEQ ID NO:286)

MKMASSDANPSDGSAANLVPEVNNEVMALEPVVGAAIAAPVAGQQNVIDPWIRNNFVQAPGGEFTVSPR
NAPGEILWSAXLGPDLNPYLSHLARMYNGYAGGFEVQVILAGNAFTAGKVIFAAVPPNFPTEGLSPSQVTMF
PHIVVDVRQLEPVLIPLPDVRNNFYHYNQSNDPTIKLIAMLYTPLRANNAGDDVFTVSCRVLTRPSPDFDFIFLV
PPTVESRTKPFSVPVLTVEEMTNSRFPIPLEKLFTGPSSAFVVQPQNGRCTTDGVLLGTTQLSPVNICTFRGDVT
HITGSRNYTMNLASQNWNDYDPTEEIPAPLGTPDFVGKIQGVLTQTTRTDGSTRGHKATVYTGSADFAPKLG
RVQFETDTDRDFEANQNTKFTPVGVIQDGGTTHRNEPQQWVLPSYSGRNTHNVHLAPAVAPTFPGEQLLFF
RSTMPGCSGYPNMDLDCLLPQEWVQYFYQEAAPAQSDVALLRFVNPDTGRVLFECKLHKSGYVTVAHTGQ
HDLVIPPNGYFRFDSWVNQFYTLAPMGNGTGRRRAV

FIGURE 32GG (SEQ ID NO:289)

hCod optimize sequence of VP1 GII.4_Syd12_P80S+A39X; X = I(XXX=ATC), M(XXX=ATG), G(XXX=GGC), S(XXX=AGC), E(XXX=GAG), D(XXX=GAC), N(XXX=AAC), Q(XXX=CAG), K(XXX=AAG), or H(XXX=CAC)

ATGAAAATGGCCTCGAGTGACGCTAACCCTAGTGACGGCAGCGCCGCCAATCTTGTGCCTGAGGTTAAT
AATGAGGTGATGGCCCTGGAGCCTGTGGTGGGCGCAGCCATAGCAXXXCCCGTGGCCGGTCAGCAGAA
TGTGATTGACCCGTGGATACGCAACAATTTTGTCCAAGCCCCTGGTGGGGAGTTCACCGTTAGCCCGAGA
AATGCGCCAGGAGAAATCCTGTGGTCGGCCAGCTTGGGACCCGATCTGAACCCCTATTTGTCACATCTCG
CTCGGATGTACAACGGGTATGCCGGCGGATTTGAAGTGCAGGTGATTCTGGCTGGGAACGCGTTCACTG
CTGGCAAAGTGATCTTTGCAGCGGTGCCTCCCAACTTCCCCACTGAAGGACTGTCTCCAAGCCAGGTCAC
AATGTTTCCACACATCGTGGTGGACGTACGGCAGCTAGAGCCTGTCCTGATTCCCCTCCCTGATGTACGC
AATAATTTCTACCACTACAATCAATCCAATGATCCGACCATTAAACTCATCGCGATGTTGTACACCCCTCTG
CGCGCTAACAATGCTGGAGACGACGTATTCACCGTGTCATGCAGAGTGCTCACCAGACCTTCACCAGACT
TTGACTTTATCTTCTTAGTGCCCCCCACTGTTGAGAGCCGAACCAAGCCCTTTAGTGTCCCCGTACTCACA

FIGURE 32GG (cont)

GTCGAGGAGATGACAAATAGCCGCTTTCCAATCCCCCTTGAGAAACTGTTCACAGGACCTTCCTCGGCAT
TCGTGGTTCAGCCACAGAACGGACGCTGCACAACTGACGGCGTGCTGCTCGGAACCACCCAGCTTAGCC
CTGTTAATATCTGTACGTTTAGAGGCGACGTAACTCACATAACTGGCTCACGGAACTATACCATGAATCTG
GCATCACAGAATTGGAATGACTACGACCCAACCGAAGAGATTCCCGCACCTCTTGGAACCCCCGACTTTG
TGGGAAAAATACAGGGCGTCCTGACACAAACCACCAGAACCGATGGCTCCACACGGGGACACAAGGCA
ACCGTCTACACTGGCTCTGCCGATTTTGCCCCGAAACTGGGTAGAGTGCAGTTTGAGACCGACACTGACC
GGGACTTTGAAGCCAATCAGAATACTAAGTTCACACCTGTAGGAGTGATTCAGGACGGGGGCACCACTC
ACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTTCGTTCAACCATGCCTGGATGCTCC
GGATATCCCAATATGGATCTCGATTGCCTGCTCCCACAGGAATGGGTGCAGTATTTTTATCAAGAGGCCG
CACCAGCCCAATCCGACGTCGCACTTCTGCGGTTCGTGAATCCAGACACAGGCCGCGTGTTGTTTGAGTG
CAAATTGCACAAATCAGGATACGTTACAGTGGCTCATACTGGACAGCATGACCTGGTGATCCCACCCAAC
GGATATTTTAGGTTCGACTCCTGGGTGAATCAGTTTTATACATTAGCCCCCATGGGGAATGGGACTGGCA
GACGCAGGGCTGTCTGA

FIGURE 32HH (SEQ ID NO:288)

Amino acid sequence of VP1_GII.4_Syd12_P80S+A39X; where X = I, M, G, S, E, D, N, Q, K, or H MKMASSDANPSDGSAANLVPEVNNEVMALEPVVGAAIAXPVAGQQNVIDPWIRNNFVQAPGGEFTVSPR
NAPGEILWSASLGPDLNPYLSHLARMYNGYAGGFEVQVILAGNAFTAGKVIFAAVPPNFPTEGLSPSQVTMF
PHIVVDVRQLEPVLIPLPDVRNNFYHYNQSNDPTIKLIAMLYTPLRANNAGDDVFTVSCRVLTRPSPDFDFIFLV
PPTVESRTKPFSVPVLTVEEMTNSRFPIPLEKLFTGPSSAFVVQPQNGRCTTDGVLLGTTQLSPVNICTFRGDVT
HITGSRNYTMNLASQNWNDYDPTEEIPAPLGTPDFVGKIQGVLTQTTRTDGSTRGHKATVYTGSADFAPKLG
RVQFETDTDRDFEANQNTKFTPVGVIQDGGTTHRNEPQQWVLPSYSGRNTHNVHLAPAVAPTFPGEQLLFF
RSTMPGCSGYPNMDLDCLLPQEWVQYFYQEAAPAQSDVALLRFVNPDTGRVLFECKLHKSGYVTVAHTGQ
HDLVIPPNGYFRFDSWVNQFYTLAPMGNGTGRRRAV

Figure 33A

Amino acid sequence of VP1_GII.6_Ohio_E80S (SEQ ID NO:79)

MKMASNDAAPSNDGAANLVPEANNEVMALEPVVGASIAAPVVGQQNIIDPWIRENFVQAPQGEFTVSPRNSPGEMLL
NLSLGPELNPYLSHLSRMYNGYAGGMQVQVVLAGNAFTAGKIIFAAVPPHFPVENINAAQITMCPHVIVDVRQLEPVLLP
LPDIRNRFFHYNQENTSRMRLVAMLYTPLRANSGEDVFTVSCRVLTRPAPDFEFTFLVPPTVESKTKPFSLPILTLGELSNSR
FPAPIDMLYTDPNEGIVVQPQNGRCTLDGTLQGTTQLVPTQICAFRGTLIGQTSRSPDSTDSAPRRRDHPLHVQLKNLDG
TQYDPTDEVPAVLGAIDFKGTVFGVASQRDVSGQQVGATRAHEVHINTTDPRYTPKLGSILMYSESDDFVTGQPVRFTPI
GMGDNDWHQWELPDYPGHLTLNMNLAPAVAPAFPGERILFFRSIVPSAGGYGSGQIDCLIPQEWVQHFYQEAAPSQS
AVALIRYVNPDTGRNIFEAKLHREGFITVANSGNNPIVVPPNGYFRFEAWVNQFYTLTPMGTGQGRRRDQ

Figure 33B

Nucleic acid sequence of human codon optimized VP1_GII.6_Ohio_E80S (SEQ ID NO:80)

ATGAAGATGGCAAGCAACGACGCAGCTCCCTCCAATGATGGTGCCGCCAACCTGGTCCCCGAAGCTAATAATGAGG
TGATGGCGTTAGAGCCGGTGGTTGGCGCATCTATTGCAGCGCCTGTGGTCGGACAGCAGAACATCATTGATCCCTG
GATTCGCGAGAACTTCGTACAAGCTCCACAGGGGGAGTTCACAGTCTCCCCCCGGAACTCCCCGGGCGAGATGCTG
CTCAATCTGAGCCTCGGCCCTGAACTAAACCCTTATCTGTCACACCTTTCACGGATGTACAATGGCTACGCAGGAGG
AATGCAAGTTCAGGTGGTCCTGGCCGGCAATGCTTTCACCGCGGGCAAAATCATCTTTGCGGCCGTTCCTCCACACT
TCCCTGTCGAAAATATCAACGCCGCCCAGATTACTATGTGCCCCCACGTGATTGTGGATGTGCGACAGTTAGAGCCA
GTTCTGCTGCCCCTGCCCGACATCAGAAACCGGTTCTTCCATTACAATCAAGAGAATACTTCACGGATGAGACTTGTT
GCGATGCTGTACACCCCTCTTCGTGCAAATTCCGGCGAAGACGTGTTCACTGTGTCTTGTCGAGTACTTACCCGACCC
GCCCCCGATTTCGAATTCACCTTCCTGGTTCCCCCTACTGTGGAGAGCAAGACAAAACCCTTCAGCCTCCCAATCTTA
ACACTCGGGGAGCTGTCTAATTCACGCTTCCCCGCACCTATTGATATGCTGTATACTGACCCCAACGAGGGGATAGT
GGTGCAGCCCCAAAATGGACGGTGTACTCTCGACGGCACGCTCCAGGGCACAACCCAACTGGTGCCAACCCAGATT
TGTGCATTCAGGGGCACTTTGATTGGGCAGACATCGAGATCTCCAGATTCTACTGATTCCGCGCCAAGGAGGAGGG
ACCACCCACTCCACGTTCAGTTAAAAAACCTGGACGGAACCCAGTACGACCCTACAGACGAGGTCCCCGCTGTCCTC
GGAGCCATCGACTTTAAAGGAACTGTATTTGGAGTGGCATCCCAAAGGGATGTCTCGGGGCAGCAGGTGGGAGCT
ACGAGAGCACATGAAGTCCACATTAACACCACAGACCCAAGATATACCCCAAAACTAGGGTCAATTTTAATGTATTC
GGAATCAGACGATTTTGTTACAGGTCAGCCCGTGCGGTTTACCCCGATCGGAATGGGGGACAACGATTGGCACCAG
TGGGAATTGCCCGATTACCCTGGACACCTCACCTTGAATATGAATCTGGCCCCAGCCGTCGCGCCCGCCTTCCCCGGT
GAGCGGATCCTCTTTTTTAGAAGCATAGTGCCCTCCGCAGGTGGGTATGGATCAGGGCAGATTGATTGCCTGATCCC
CCAAGAATGGGTACAGCATTTCTACCAGGAAGCAGCCCCTAGCCAGTCCGCAGTAGCACTGATCAGATATGTTAATC
CTGATACGGGAAGGAACATCTTCGAAGCAAAACTGCACCGTGAGGGCTTCATTACCGTCGCCAACAGTGGTAATAA
CCCTATTGTGGTGCCTCCTAATGGATACTTCAGGTTTGAGGCATGGGTGAATCAGTTTTATACTCTGACTCCCATGGG
GACAGGCCAGGGGCGACGCCGGGATCAGTGA

Figure 33C

Amino acid sequence of VP1_GII.6_Ohio_S90L (SEQ ID NO:81)

MKMASNDAAPSNDGAANLVPEANNEVMALEPVVGASIAAPVVGQQNIIDPWIRENFVQAPQGEFTVSPRNSPGEMLL
NLELGPELNPYLLHLSRMYNGYAGGMQVQVVLAGNAFTAGKIIFAAVPPHFPVENINAAQITMCPHVIVDVRQLEPVLLP
LPDIRNRFFHYNQENTSRMRLVAMLYTPLRANSGEDVFTVSCRVLTRPAPDFEFTFLVPPTVESKTKPFSLPILTLGELSNSR
FPAPIDMLYTDPNEGIVVQPQNGRCTLDGTLQGTTQLVPTQICAFRGTLIGQTSRSPDSTDSAPRRRDHPLHVQLKNLDG
TQYDPTDEVPAVLGAIDFKGTVFGVASQRDVSGQQVGATRAHEVHINTTDPRYTPKLGSILMYSESDDFVTGQPVRFTPI
GMGDNDWHQWELPDYPGHLTLNMNLAPAVAPAFPGERILFFRSIVPSAGGYGSGQIDCLIPQEWVQHFYQEAAPSQS
AVALIRYVNPDTGRNIFEAKLHREGFITVANSGNNPIVVPPNGYFRFEAWVNQFYTLTPMGTGQGRRRDQ

Figure 33D

Nucleic acid sequence of human codon optimized VP1_GII.6_Ohio_S90L (SEQ ID NO:82)

ATGAAGATGGCAAGCAACGACGCAGCTCCCTCCAATGATGGTGCCGCCAACCTGGTCCCCGAAGCTAATAATGAGG
TGATGGCGTTAGAGCCGGTGGTTGGCGCATCTATTGCAGCGCCTGTGGTCGGACAGCAGAACATCATTGATCCCTG
GATTCGCGAGAACTTCGTACAAGCTCCACAGGGGGAGTTCACAGTCTCCCCCCGGAACTCCCCGGGCGAGATGCTG
CTCAATCTGGAACTCGGCCCTGAACTAAACCCTTATCTGCTCCACCTTTCACGGATGTACAATGGCTACGCAGGAGG

FIGURE 33D (cont)

AATGCAAGTTCAGGTGGTCCTGGCCGGCAATGCTTTCACCGCGGGCAAAATCATCTTTGCGGCCGTTCCTCCACACT
TCCCTGTCGAAAATATCAACGCCGCCCAGATTACTATGTGCCCCCACGTGATTGTGGATGTGCGACAGTTAGAGCCA
GTTCTGCTGCCCCTGCCCGACATCAGAAACCGGTTCTTCCATTACAATCAAGAGAATACTTCACGGATGAGACTTGTT
GCGATGCTGTACACCCCTCTTCGTGCAAATTCCGGCGAAGACGTGTTCACTGTGTCTTGTCGAGTACTTACCCGACCC
GCCCCCGATTTCGAATTCACCTTCCTGGTTCCCCCTACTGTGGAGAGCAAGACAAAACCCTTCAGCCTCCCAATCTTA
ACACTCGGGGAGCTGTCTAATTCACGCTTCCCCGCACCTATTGATATGCTGTATACTGACCCCAACGAGGGGATAGT
GGTGCAGCCCCAAAATGGACGGTGTACTCTCGACGGCACGCTCCAGGGCACAACCCAACTGGTGCCAACCCAGATT
TGTGCATTCAGGGGCACTTTGATTGGGCAGACATCGAGATCTCCAGATTCTACTGATTCCGCGCCAAGGAGGAGGG
ACCACCCACTCCACGTTCAGTTAAAAAACCTGGACGGAACCCAGTACGACCCTACAGACGAGGTCCCCGCTGTCCTC
GGAGCCATCGACTTTAAAGGAACTGTATTTGGAGTGGCATCCCAAAGGGATGTCTCGGGGCAGCAGGTGGGAGCT
ACGAGAGCACATGAAGTCCACATTAACACCACAGACCCAAGATATACCCCAAAACTAGGGTCAATTTTAATGTATTC
GGAATCAGACGATTTTGTTACAGGTCAGCCCGTGCGGTTTACCCCGATCGGAATGGGGGACAACGATTGGCACCAG
TGGGAATTGCCCGATTACCCTGGACACCTCACCTTGAATATGAATCTGGCCCCAGCCGTCGCGCCCGCCTTCCCCGGT
GAGCGGATCCTCTTTTTTAGAAGCATAGTGCCCTCCGCAGGTGGGTATGGATCAGGGCAGATTGATTGCCTGATCCC
CCAAGAATGGGTACAGCATTTCTACCAGGAAGCAGCCCCTAGCCAGTCCGCAGTAGCACTGATCAGATATGTTAATC
CTGATACGGGAAGGAACATCTTCGAAGCAAAACTGCACCGTGAGGGCTTCATTACCGTCGCCAACAGTGGTAATAA
CCCTATTGTGGTGCCTCCTAATGGATACTTCAGGTTTGAGGCATGGGTGAATCAGTTTTATACTCTGACTCCCATGGG
GACAGGCCAGGGGCGACGCCGGGATCAGTGA

Figure 33E

Amino acid sequence of VP1_GII.6_Ohio_E80S+S90L (SEQ ID NO:83)

MKMASNDAAPSNDGAANLVPEANNEVMALEPVVGASIAAPVVGQQNIIDPWIRENFVQAPQGEFTVSPRNSPGEMLL
NLSLGPELNPYLLHLSRMYNGYAGGMQVQVVLAGNAFTAGKIIFAAVPPHFPVENINAAQITMCPHVIVDVRQLEPVLLP
LPDIRNRFFHYNQENTSRMRLVAMLYTPLRANSGEDVFTVSCRVLTRPAPDFEFTFLVPPTVESKTKPFSLPILTLGELSNSR
FPAPIDMLYTDPNEGIVVQPQNGRCTLDGTLQGTTQLVPTQICAFRGTLIGQTSRSPDSTDSAPRRRDHPLHVQLKNLDG
TQYDPTDEVPAVLGAIDFKGTVFGVASQRDVSGQQVGATRAHEVHINTTDPRYTPKLGSILMYSESDDFVTGQPVRFTPI
GMGDNDWHQWELPDYPGHLTLNMNLAPAVAPAFPGERILFFRSIVPSAGGYGSGQIDCLIPQEWVQHFYQEAAPSQS
AVALIRYVNPDTGRNIFEAKLHREGFITVANSGNNPIVVPPNGYFRFEAWVNQFYTLTPMGTGQGRRRDQ

Figure 33F

Nucleic acid sequence of human codon optimized VP1_GII.6_Ohio_E80S+S90L (SEQ IDNO:84)

ATGAAGATGGCAAGCAACGACGCAGCTCCCTCCAATGATGGTGCCGCCAACCTGGTCCCCGAAGCTAATAATGAGG
TGATGGCGTTAGAGCCGGTGGTTGGCGCATCTATTGCAGCGCCTGTGGTCGGACAGCAGAACATCATTGATCCCTG
GATTCGCGAGAACTTCGTACAAGCTCCACAGGGGGAGTTCACAGTCTCCCCCCGGAACTCCCCGGGCGAGATGCTG
CTCAATCTGAGCCTCGGCCCTGAACTAAACCCTTATCTGCTCCACCTTTCACGGATGTACAATGGCTACGCAGGAGGA
ATGCAAGTTCAGGTGGTCCTGGCCGGCAATGCTTTCACCGCGGGCAAAATCATCTTTGCGGCCGTTCCTCCACACTTC
CCTGTCGAAAATATCAACGCCGCCCAGATTACTATGTGCCCCCACGTGATTGTGGATGTGCGACAGTTAGAGCCAGT
TCTGCTGCCCCTGCCCGACATCAGAAACCGGTTCTTCCATTACAATCAAGAGAATACTTCACGGATGAGACTTGTTGC
GATGCTGTACACCCCTCTTCGTGCAAATTCCGGCGAAGACGTGTTCACTGTGTCTTGTCGAGTACTTACCCGACCCGC
CCCCGATTTCGAATTCACCTTCCTGGTTCCCCCTACTGTGGAGAGCAAGACAAAACCCTTCAGCCTCCCAATCTTAAC
ACTCGGGGAGCTGTCTAATTCACGCTTCCCCGCACCTATTGATATGCTGTATACTGACCCCAACGAGGGGATAGTGG

FIGURE 33F (cont)

TGCAGCCCCAAAATGGACGGTGTACTCTCGACGGCACGCTCCAGGGCACAACCCAACTGGTGCCAACCCAGATTTGT
GCATTCAGGGGCACTTTGATTGGGCAGACATCGAGATCTCCAGATTCTACTGATTCCGCGCCAAGGAGGAGGGACC
ACCCACTCCACGTTCAGTTAAAAAACCTGGACGGAACCCAGTACGACCCTACAGACGAGGTCCCCGCTGTCCTCGGA
GCCATCGACTTTAAAGGAACTGTATTTGGAGTGGCATCCCAAAGGGATGTCTCGGGGCAGCAGGTGGGAGCTACGA
GAGCACATGAAGTCCACATTAACACCACAGACCCAAGATATACCCCAAAACTAGGGTCAATTTTAATGTATTCGGAA
TCAGACGATTTTGTTACAGGTCAGCCCGTGCGGTTTACCCCGATCGGAATGGGGGACAACGATTGGCACCAGTGGG
AATTGCCCGATTACCCTGGACACCTCACCTTGAATATGAATCTGGCCCCAGCCGTCGCGCCCGCCTTCCCCGGTGAGC
GGATCCTCTTTTTTAGAAGCATAGTGCCCTCCGCAGGTGGGTATGGATCAGGGCAGATTGATTGCCTGATCCCCCAA
GAATGGGTACAGCATTTCTACCAGGAAGCAGCCCCTAGCCAGTCCGCAGTAGCACTGATCAGATATGTTAATCCTGA
TACGGGAAGGAACATCTTCGAAGCAAAACTGCACCGTGAGGGCTTCATTACCGTCGCCAACAGTGGTAATAACCCT
ATTGTGGTGCCTCCTAATGGATACTTCAGGTTTGAGGCATGGGTGAATCAGTTTTATACTCTGACTCCCATGGGGAC
AGGCCAGGGGCGACGCCGGGATCAGTGA

Figure 34A

Amino acid sequence of VP1_GII.12_HS10_E80S (SEQ ID NO:88)

MKMASNDAAPSNDGAAGLVPEVNNETMALEPVAGASIAAPLTGQNNVIDPWIRLNFVQAPNGEFTVSPRNSPGEVLL
NLSLGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELTNS
RFPVPIDELYTSPNESLVVQPQNGRCALDGELQGTTQLLPTAICSFRGRINQKVSGENHVWNMQVTNIDGTPFDPTEDV
PAPLGTPDFSGKLFGVLSQRDHDNACRSHDAVIATNSAKFTPKLGAIQIGTWEQDDVHINQPTKFTPVGLFESEGFNQW
TLPNYSGALTLNMGLAPPVAPTFPGEQILFFRSHIPLKGGVADPVIDCLLPQEWIQHLYQESAPSQTDVALIRFTNPDTGRV
LFEAKLHRSGYITVANTGSRPIVVPANGYFRFDSWVNQFYSLAPMGTGNGRRRVQ

Figure 34B

Nucleic acid sequence of human codon optimized VP1_GII.12_HS10_E80S (SEQ ID NO:89)

ATGAAGATGGCGTCTAATGATGCTGCTCCTTCCAATGATGGCGCAGCCGGCCTGGTCCCTGAAGTGAATAACGAGA
CTATGGCTCTCGAACCCGTGGCCGGAGCCTCAATTGCCGCCCCCCTCACTGGCCAGAACAACGTGATTGATCCCTGG
ATCAGACTGAACTTCGTTCAGGCTCCTAATGGGGAGTTCACCGTGTCCCCGAGAAACTCCCCCGGCGAAGTGTTATT
GAATTTGAGCTTAGGACCAGAACTCAACCCCTATCTGGCACATCTGTCTCGGATGTACAACGGCTATGCGGGCGGAG
TGGAGGTGCAAGTTCTTCTCGCTGGTAATGCATTCACAGCAGGAAAATTAGTATTTGCAGCGGTTCCACCCCATTTTC
CACTTGAAAACATAAGCCCAGGCCAGATCACCATGTTCCCTCACGTGATAATCGACGTGCGGACATTAGAGCCCGTG
CTGCTACCCCTGCCCGACGTGAGGAACAATTTCTTTCACTACAATCAGCAAAATGAACCAAGAATGCGCCTGGTCGC
CATGCTCTATACTCCTTTAAGAAGTAATGGCAGTGGGGATGACGTGTTTACTGTTAGCTGTCGGGTGCTCACCCGAC
CTTCCCCAGATTTCGACTTCAATTATCTGGTCCCCCCCACGGTAGAGTCCAAAACAAAGCCTTTCACTCTTCCAATCCT
TACAATTGGCGAACTGACCAACTCACGCTTTCCAGTGCCTATTGATGAGCTGTACACAAGTCCAAATGAATCCCTTGT
CGTTCAGCCACAGAATGGGCGCTGCGCGCTTGACGGTGAGCTCCAGGGCACAACACAACTGTTGCCAACCGCTATA
TGCTCTTTCAGGGGGCGTATTAATCAGAAGGTCTCCGGGGAGAACCACGTGTGGAACATGCAAGTGACGAATATCG
ACGGGACACCTTTCGATCCAACAGAGGATGTCCCAGCGCCTCTAGGTACCCCTGACTTCTCAGGCAAGTTGTTCGGC
GTCCTTTCCCAGCGCGACCATGATAATGCTTGCCGGAGCCACGATGCCGTCATTGCCACCAACTCAGCCAAATTCACC
CCAAAACTTGGAGCGATACAGATCGGAACTTGGGAACAAGACGACGTCCATATCAACCAACCAACAAAGTTTACCCC
TGTTGGCCTTTTCGAAAGCGAAGGCTTTAACCAGTGGACACTTCCCAATTACAGCGGGGCTCTCACTCTTAATATGG

FIGURE 34B (cont)

GACTCGCACCACCCGTCGCTCCAACGTTTCCTGGTGAGCAGATTTTGTTTTTCCGCAGTCATATTCCACTGAAGGGTG
GAGTTGCTGATCCCGTGATAGACTGCCTCCTCCCTCAGGAATGGATTCAGCACTTGTATCAGGAGTCCGCTCCCTCGC
AGACCGATGTGGCCCTGATACGCTTCACAAACCCCGATACCGGAAGAGTGTTGTTTGAAGCTAAACTTCATCGCTCC
GGTTACATCACAGTAGCCAACACGGGTTCCAGGCCAATCGTAGTTCCGGCAAACGGATACTTTCGATTCGACAGTTG
GGTCAATCAGTTCTACAGCCTGGCTCCAATGGGAACAGGAAATGGGAGGAGGCGTGTGCAGTAA

Figure 34C

Amino acid sequence of VP1_GII.12_HS10_A90L (SEQ ID NO:90)

MKMASNDAAPSNDGAAGLVPEVNNETMALEPVAGASIAAPLTGQNNVIDPWIRLNFVQAPNGEFTVSPRNSPGEVLL
NLELGPELNPYLLHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELTNS
RFPVPIDELYTSPNESLVVQPQNGRCALDGELQGTTQLLPTAICSFRGRINQKVSGENHVWNMQVTNIDGTPFDPTEDV
PAPLGTPDFSGKLFGVLSQRDHDNACRSHDAVIATNSAKFTPKLGAIQIGTWEQDDVHINQPTKFTPVGLFESEGFNQW
TLPNYSGALTLNMGLAPPVAPTFPGEQILFFRSHIPLKGGVADPVIDCLLPQEWIQHLYQESAPSQTDVALIRFTNPDTGRV
LFEAKLHRSGYITVANTGSRPIVVPANGYFRFDSWVNQFYSLAPMGTGNGRRRVQ

Figure 34D

Nucleic acid sequence of human codon optimized VP1_GII.12_HS10_A90L (SEQ ID NO:91)

ATGAAGATGGCGTCTAATGATGCTGCTCCTTCCAATGATGGCGCAGCCGGCCTGGTCCCTGAAGTGAATAACGAGA
CTATGGCTCTCGAACCCGTGGCCGGAGCCTCAATTGCCGCCCCCCTCACTGGCCAGAACAACGTGATTGATCCCTGG
ATCAGACTGAACTTCGTTCAGGCTCCTAATGGGGAGTTCACCGTGTCCCCGAGAAACTCCCCCGGCGAAGTGTTATT
GAATTTGGAATTAGGACCAGAACTCAACCCCTATCTGCTCCATCTGTCTCGGATGTACAACGGCTATGCGGGCGGAG
TGGAGGTGCAAGTTCTTCTCGCTGGTAATGCATTCACAGCAGGAAAATTAGTATTTGCAGCGGTTCCACCCCATTTTC
CACTTGAAAACATAAGCCCAGGCCAGATCACCATGTTCCCTCACGTGATAATCGACGTGCGGACATTAGAGCCCGTG
CTGCTACCCCTGCCCGACGTGAGGAACAATTTCTTTCACTACAATCAGCAAAATGAACCAAGAATGCGCCTGGTCGC
CATGCTCTATACTCCTTTAAGAAGTAATGGCAGTGGGGATGACGTGTTTACTGTTAGCTGTCGGGTGCTCACCCGAC
CTTCCCCAGATTTCGACTTCAATTATCTGGTCCCCCCCACGGTAGAGTCCAAAACAAAGCCTTTCACTCTTCCAATCCT
TACAATTGGCGAACTGACCAACTCACGCTTTCCAGTGCCTATTGATGAGCTGTACACAAGTCCAAATGAATCCCTTGT
CGTTCAGCCACAGAATGGGCGCTGCGCGCTTGACGGTGAGCTCCAGGGCACAACACAACTGTTGCCAACCGCTATA
TGCTCTTTCAGGGGGCGTATTAATCAGAAGGTCTCCGGGGAGAACCACGTGTGGAACATGCAAGTGACGAATATCG
ACGGGACACCTTTCGATCCAACAGAGGATGTCCCAGCGCCTCTAGGTACCCCTGACTTCTCAGGCAAGTTGTTCGGC
GTCCTTTCCCAGCGCGACCATGATAATGCTTGCCGGAGCCACGATGCCGTCATTGCCACCAACTCAGCCAAATTCACC
CCAAAACTTGGAGCGATACAGATCGGAACTTGGGAACAAGACGACGTCCATATCAACCAACCAACAAAGTTTACCCC
TGTTGGCCTTTTCGAAAGCGAAGGCTTTAACCAGTGGACACTTCCCAATTACAGCGGGGCTCTCACTCTTAATATGG
GACTCGCACCACCCGTCGCTCCAACGTTTCCTGGTGAGCAGATTTTGTTTTTCCGCAGTCATATTCCACTGAAGGGTG
GAGTTGCTGATCCCGTGATAGACTGCCTCCTCCCTCAGGAATGGATTCAGCACTTGTATCAGGAGTCCGCTCCCTCGC
AGACCGATGTGGCCCTGATACGCTTCACAAACCCCGATACCGGAAGAGTGTTGTTTGAAGCTAAACTTCATCGCTCC
GGTTACATCACAGTAGCCAACACGGGTTCCAGGCCAATCGTAGTTCCGGCAAACGGATACTTTCGATTCGACAGTTG
GGTCAATCAGTTCTACAGCCTGGCTCCAATGGGAACAGGAAATGGGAGGAGGCGTGTGCAGTAA

Figure 34E

Amino acid sequence of VP1_GII.12_HS10_E80S+A90L (SEQ ID NO:92)

MKMASNDAAPSNDGAAGLVPEVNNETMALEPVAGASIAAPLTGQNNVIDPWIRLNFVQAPNGEFTVSPRNSPGEVLL
NLSLGPELNPYLLHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELTNS
RFPVPIDELYTSPNESLVVQPQNGRCALDGELQGTTQLLPTAICSFRGRINQKVSGENHVWNMQVTNIDGTPFDPTEDV
PAPLGTPDFSGKLFGVLSQRDHDNACRSHDAVIATNSAKFTPKLGAIQIGTWEQDDVHINQPTKFTPVGLFESEGFNQW
TLPNYSGALTLNMGLAPPVAPTFPGEQILFFRSHIPLKGGVADPVIDCLLPQEWIQHLYQESAPSQTDVALIRFTNPDTGRV
LFEAKLHRSGYITVANTGSRPIVVPANGYFRFDSWVNQFYSLAPMGTGNGRRRVQ

Figure 34F

Nucleic acid sequence of human codon optimized VP1_GII.12_HS10_E80S+A90L (SEQ ID NO:93)

ATGAAGATGGCGTCTAATGATGCTGCTCCTTCCAATGATGGCGCAGCCGGCCTGGTCCCTGAAGTGAATAACGAGA
CTATGGCTCTCGAACCCGTGGCCGGAGCCTCAATTGCCGCCCCCCTCACTGGCCAGAACAACGTGATTGATCCCTGG
ATCAGACTGAACTTCGTTCAGGCTCCTAATGGGGAGTTCACCGTGTCCCCGAGAAACTCCCCCGGCGAAGTGTTATT
GAATTTGAGCTTAGGACCAGAACTCAACCCCTATCTGCTCCATCTGTCTCGGATGTACAACGGCTATGCGGGCGGAG
TGGAGGTGCAAGTTCTTCTCGCTGGTAATGCATTCACAGCAGGAAAATTAGTATTTGCAGCGGTTCCACCCCATTTTC
CACTTGAAAACATAAGCCCAGGCCAGATCACCATGTTCCCTCACGTGATAATCGACGTGCGGACATTAGAGCCCGTG
CTGCTACCCCTGCCCGACGTGAGGAACAATTTCTTTCACTACAATCAGCAAAATGAACCAAGAATGCGCCTGGTCGC
CATGCTCTATACTCCTTTAAGAAGTAATGGCAGTGGGGATGACGTGTTTACTGTTAGCTGTCGGGTGCTCACCCGAC
CTTCCCCAGATTTCGACTTCAATTATCTGGTCCCCCCCACGGTAGAGTCCAAAACAAAGCCTTTCACTCTTCCAATCCT
TACAATTGGCGAACTGACCAACTCACGCTTTCCAGTGCCTATTGATGAGCTGTACACAAGTCCAAATGAATCCCTTGT
CGTTCAGCCACAGAATGGGCGCTGCGCGCTTGACGGTGAGCTCCAGGGCACAACACAACTGTTGCCAACCGCTATA
TGCTCTTTCAGGGGGCGTATTAATCAGAAGGTCTCCGGGGAGAACCACGTGTGGAACATGCAAGTGACGAATATCG
ACGGGACACCTTTCGATCCAACAGAGGATGTCCCAGCGCCTCTAGGTACCCCTGACTTCTCAGGCAAGTTGTTCGGC
GTCCTTTCCCAGCGCGACCATGATAATGCTTGCCGGAGCCACGATGCCGTCATTGCCACCAACTCAGCCAAATTCACC
CCAAAACTTGGAGCGATACAGATCGGAACTTGGGAACAAGACGACGTCCATATCAACCAACCAACAAAGTTTACCCC
TGTTGGCCTTTTCGAAAGCGAAGGCTTTAACCAGTGGACACTTCCCAATTACAGCGGGGCTCTCACTCTTAATATGG
GACTCGCACCACCCGTCGCTCCAACGTTTCCTGGTGAGCAGATTTTGTTTTTCCGCAGTCATATTCCACTGAAGGGTG
GAGTTGCTGATCCCGTGATAGACTGCCTCCTCCCTCAGGAATGGATTCAGCACTTGTATCAGGAGTCCGCTCCCTCGC
AGACCGATGTGGCCCTGATACGCTTCACAAACCCCGATACCGGAAGAGTGTTGTTTGAAGCTAAACTTCATCGCTCC
GGTTACATCACAGTAGCCAACACGGGTTCCAGGCCAATCGTAGTTCCGGCAAACGGATACTTTCGATTCGACAGTTG
GGTCAATCAGTTCTACAGCCTGGCTCCAATGGGAACAGGAAATGGGAGGAGGCGTGTGCAGTAA

FIGURE 34G

Amino acid sequence of VP1 GII.17 Kawa 2014 A0A077KVU6_A39V (SEQ ID NO:192)

MKMASNDAAPSNDGAAGLVPEGNNETLPLEPVAGAAIAVPVTGQNNIIDPWIRTNFVQAPNGEFTVSPRNS
PGEILLNLELGPDLNPYLAHLSRMYNGYAGGVEVQVLLAGNAFTAGKILFAAVPPNFPVEFLSPAQITMLPHLI
VDVRTLEPIMIPLPDVRNTFFHYNNQPNSRMRLVAMLYTPLRSNGSGDDVFTVSCRVLTRPTPDFEFTYLVPP
SVESKTKPFSLPILTLSELTNSRFPVPIDSLFTAQNNVLQVQCQNGRCTLDGELQGTTQLLPSGICAFRGRVTAE
TDHRDKWHMQLQNLNGTTYDPTDDVPAPLGTPDFKGVVFGVASQRNVGNDAPGSTRAHEAVISTYSPQFV

FIGURE 34G (cont)

PKLGSVNFRSNDNDFQLQPTKFTPVGINDDGDHPFRQWELPDYSGLLTLNMNLAPPVAPNFPGEQLLFFRSF
VPCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

FIGURE 34H

Nucleic acid sequence of VP1 hCod GII.17 Kawa 2014 A0A077KVU6_A39V (SEQ ID NO:193)

ATGAAAATGGCATCTAACGACGCAGCCCCCTCAAACGATGGCGCTGCTGGACTCGTGCCGGAGGGGAAT
AATGAGACACTTCCACTAGAGCCGGTTGCAGGCGCCGCTATAGCTGTGCCAGTGACAGGGCAGAATAAT
ATTATAGACCCTTGGATTCGGACAAACTTCGTGCAGGCACCCAACGGCGAGTTTACAGTATCCCCCCGGA
ACTCCCCAGGTGAGATACTCCTGAATCTTGAGCTCGGCCCTGACCTCAATCCATATCTGGCTCATCTGAGC
CGCATGTACAATGGTTACGCTGGGGGGGTCGAAGTGCAGGTCCTCCTGGCCGGAAACGCCTTTACCGCT
GGCAAAATTCTGTTTGCCGCCGTTCCACCAAACTTTCCAGTCGAATTCCTCTCTCCCGCGCAAATAACCAT
GCTGCCACATTTGATCGTTGACGTGCGGACCCTGGAGCCAATAATGATTCCCCTGCCGGATGTGCGTAAC
ACCTTTTTCCATTATAACAATCAGCCAAACTCTCGGATGAGACTTGTTGCTATGCTGTACACCCCCCTGCG
GAGCAACGGCAGTGGCGATGATGTGTTTACCGTGAGTTGCAGAGTCCTGACGCGCCCAACCCCGGACTT
CGAGTTCACCTACCTGGTGCCCCCTTCTGTGGAATCTAAGACCAAACCGTTTTCACTGCCAATCTTAACTCT
CTCCGAACTGACTAACAGCCGGTTTCCAGTACCCATAGATTCTCTTTTTACCGCTCAAAACAACGTACTCC
AAGTCCAGTGCCAGAACGGCCGCTGTACGCTTGATGGTGAGTTGCAGGGGACAACACAGCTACTCCCCA
GTGGCATCTGTGCATTCCGGGGCCGCGTGACCGCTGAGACAGACCATCGTGACAAATGGCACATGCAAC
TCCAAAACTTAAACGGGACCACCTACGACCCAACCGACGACGTCCCTGCTCCGCTAGGGACTCCTGACTT
TAAGGGGGTGGTGTTCGGAGTGGCCTCTCAGCGGAATGTTGGGAATGACGCCCCCGGCTCTACCCGAGC
TCACGAGGCCGTTATCTCAACATATAGCCCCCAATTTGTGCCCAAGCTCGGATCCGTTAATTTTCGTAGTA
ACGACAACGACTTCCAACTGCAACCAACGAAGTTTACGCCAGTGGGGATTAATGATGATGGAGACCATC
CTTTCCGCCAATGGGAACTACCAGATTATTCTGGGCTGCTCACCCTCAATATGAACCTCGCCCCACCCGTG
GCCCCTAATTTCCCCGGTGAGCAGCTGCTGTTTTTTCGGAGCTTTGTGCCATGCAGTGGCGGATATAATCA
AGGCATCGTAGACTGCTTGATTCCCCAAGAGTGGATACAACATTTTTACCAGGAAAGTGCGCCCTCCCAG
TCCGATGTGGCCCTGATACGGTACGTTAACCCCGATACCGGAAGAACATTATTCGAAGCGAAATTGCACA
GATCAGGGTACATTACCGTTGCACATTCCGGCGATTATCCCCTGGTGGTTCCCGCCAACGGTTACTTTAG
GTTCGATAGTTGGGTCAACCAGTTCTATTCACTAGCCCCAATGGGCACCGGTAACGGCAGACGCCGGGCT
CAGTAG

FIGURE 34I

Amino acid sequence of VP1GII.17 Kawa 2014 A0A077KVU6_R53I (SEQ ID NO:194)

MKMASNDAAPSNDGAAGLVPEGNNETLPLEPVAGAAIAAPVTGQNNIIDPWIITNFVQAPNGEFTVSPRNS
PGEILLNLELGPDLNPYLAHLSRMYNGYAGGVEVQVLLAGNAFTAGKILFAAVPPNFPVEFLSPAQITMLPHLI
VDVRTLEPIMIPLPDVRNTFFHYNNQPNSRMRLVAMLYTPLRSNGSGDDVFTVSCRVLTRPTPDFEFTYLVPP
SVESKTKPFSLPILTLSELTNSRFPVPIDSLFTAQNNVLQVQCQNGRCTLDGELQGTTQLLPSGICAFRGRVTAE
TDHRDKWHMQLQNLNGTTYDPTDDVPAPLGTPDFKGVVFGVASQRNVGNDAPGSTRAHEAVISTYSPQFV

FIGURE 34I (cont)

PKLGSVNFRSNDNDFQLQPTKFTPVGINDDGDHPFRQWELPDYSGLLTLNMNLAPPVAPNFPGEQLLFFRSF
VPCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

FIGURE 34J

Nucleic acid sequence of VP1 hCod GII.17 Kawa 2014 A0A077KVU6_R53I (SEQ ID NO:195)

ATGAAAATGGCATCTAACGACGCAGCCCCCTCAAACGATGGCGCTGCTGGACTCGTGCCGGAGGGGAAT
AATGAGACACTTCCACTAGAGCCGGTTGCAGGCGCCGCTATAGCTGCCCCAGTGACAGGGCAGAATAAT
ATTATAGACCCTTGGATTATCACAAACTTCGTGCAGGCACCCAACGGCGAGTTTACAGTATCCCCCCGGA
ACTCCCCAGGTGAGATACTCCTGAATCTTGAGCTCGGCCCTGACCTCAATCCATATCTGGCTCATCTGAGC
CGCATGTACAATGGTTACGCTGGGGGGGTCGAAGTGCAGGTCCTCCTGGCCGGAAACGCCTTTACCGCT
GGCAAAATTCTGTTTGCCGCCGTTCCACCAAACTTTCCAGTCGAATTCCTCTCTCCCGCGCAAATAACCAT
GCTGCCACATTTGATCGTTGACGTGCGGACCCTGGAGCCAATAATGATTCCCCTGCCGGATGTGCGTAAC
ACCTTTTTCCATTATAACAATCAGCCAAACTCTCGGATGAGACTTGTTGCTATGCTGTACACCCCCCTGCG
GAGCAACGGCAGTGGCGATGATGTGTTTACCGTGAGTTGCAGAGTCCTGACGCGCCCAACCCCGGACTT
CGAGTTCACCTACCTGGTGCCCCCTTCTGTGGAATCTAAGACCAAACCGTTTTCACTGCCAATCTTAACTCT
CTCCGAACTGACTAACAGCCGGTTTCCAGTACCCATAGATTCTCTTTTTACCGCTCAAAACAACGTACTCC
AAGTCCAGTGCCAGAACGGCCGCTGTACGCTTGATGGTGAGTTGCAGGGGACAACACAGCTACTCCCCA
GTGGCATCTGTGCATTCCGGGGCCGCGTGACCGCTGAGACAGACCATCGTGACAAATGGCACATGCAAC
TCCAAAACTTAAACGGGACCACCTACGACCCAACCGACGACGTCCCTGCTCCGCTAGGGACTCCTGACTT
TAAGGGGGTGGTGTTCGGAGTGGCCTCTCAGCGGAATGTTGGGAATGACGCCCCCGGCTCTACCCGAGC
TCACGAGGCCGTTATCTCAACATATAGCCCCCAATTTGTGCCCAAGCTCGGATCCGTTAATTTTCGTAGTA
ACGACAACGACTTCCAACTGCAACCAACGAAGTTTACGCCAGTGGGGATTAATGATGATGGAGACCATC
CTTTCCGCCAATGGGAACTACCAGATTATTCTGGGCTGCTCACCCTCAATATGAACCTCGCCCCACCCGTG
GCCCCTAATTTCCCCGGTGAGCAGCTGCTGTTTTTTCGGAGCTTTGTGCCATGCAGTGGCGGATATAATCA
AGGCATCGTAGACTGCTTGATTCCCCAAGAGTGGATACAACATTTTTACCAGGAAAGTGCGCCCTCCCAG
TCCGATGTGGCCCTGATACGGTACGTTAACCCCGATACCGGAAGAACATTATTCGAAGCGAAATTGCACA
GATCAGGGTACATTACCGTTGCACATTCCGGCGATTATCCCCTGGTGGTTCCCGCCAACGGTTACTTTAG
GTTCGATAGTTGGGTCAACCAGTTCTATTCACTAGCCCCAATGGGCACCGGTAACGGCAGACGCCGGGCT
CAGTAG

FIGURE 34K

Amino acid sequence of VP1GII.17 Kawa 2014 A0A077KVU6_A90L (SEQ ID NO:196)

MKMASNDAAPSNDGAAGLVPEGNNETLPLEPVAGAAIAAPVTGQNNIIDPWIRTNFVQAPNGEFTVSPRNS
PGEILLNLELGPDLNPYLLHLSRMYNGYAGGVEVQVLLAGNAFTAGKILFAAVPPNFPVEFLSPAQITMLPHLIV
DVRTLEPIMIPLPDVRNTFFHYNNQPNSRMRLVAMLYTPLRSNGSGDDVFTVSCRVLTRPTPDFEFTYLVPPS
VESKTKPFSLPILTLSELTNSRFPVPIDSLFTAQNNVLQVQCQNGRCTLDGELQGTTQLLPSGICAFRGRVTAET
DHRDKWHMQLQNLNGTTYDPTDDVPAPLGTPDFKGVVFGVASQRNVGNDAPGSTRAHEAVISTYSPQFVP

FIGURE 34K (cont)

KLGSVNFRSNDNDFQLQPTKFTPVGINDDGDHPFRQWELPDYSGLLTLNMNLAPPVAPNFPGEQLLFFRSFV
PCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

FIGURE 34L

Nucleic acid sequence of VP1 hCod GII.17 Kawa 2014 A0A077KVU6_A90L (SEQ ID NO:197)

ATGAAAATGGCATCTAACGACGCAGCCCCCTCAAACGATGGCGCTGCTGGACTCGTGCCGGAGGGGAAT
AATGAGACACTTCCACTAGAGCCGGTTGCAGGCGCCGCTATAGCTGCCCCAGTGACAGGGCAGAATAAT
ATTATAGACCCTTGGATTCGGACAAACTTCGTGCAGGCACCCAACGGCGAGTTTACAGTATCCCCCCGGA
ACTCCCCAGGTGAGATACTCCTGAATCTTGAGCTCGGCCCTGACCTCAATCCATATCTGCTGCATCTGAGC
CGCATGTACAATGGTTACGCTGGGGGGGTCGAAGTGCAGGTCCTCCTGGCCGGAAACGCCTTTACCGCT
GGCAAAATTCTGTTTGCCGCCGTTCCACCAAACTTTCCAGTCGAATTCCTCTCTCCCGCGCAAATAACCAT
GCTGCCACATTTGATCGTTGACGTGCGGACCCTGGAGCCAATAATGATTCCCCTGCCGGATGTGCGTAAC
ACCTTTTTCCATTATAACAATCAGCCAAACTCTCGGATGAGACTTGTTGCTATGCTGTACACCCCCCTGCG
GAGCAACGGCAGTGGCGATGATGTGTTTACCGTGAGTTGCAGAGTCCTGACGCGCCCAACCCCGGACTT
CGAGTTCACCTACCTGGTGCCCCCTTCTGTGGAATCTAAGACCAAACCGTTTTCACTGCCAATCTTAACTCT
CTCCGAACTGACTAACAGCCGGTTTCCAGTACCCATAGATTCTCTTTTTACCGCTCAAAACAACGTACTCC
AAGTCCAGTGCCAGAACGGCCGCTGTACGCTTGATGGTGAGTTGCAGGGGACAACACAGCTACTCCCCA
GTGGCATCTGTGCATTCCGGGGCCGCGTGACCGCTGAGACAGACCATCGTGACAAATGGCACATGCAAC
TCCAAAACTTAAACGGGACCACCTACGACCCAACCGACGACGTCCCTGCTCCGCTAGGGACTCCTGACTT
TAAGGGGGTGGTGTTCGGAGTGGCCTCTCAGCGGAATGTTGGGAATGACGCCCCCGGCTCTACCCGAGC
TCACGAGGCCGTTATCTCAACATATAGCCCCCAATTTGTGCCCAAGCTCGGATCCGTTAATTTTCGTAGTA
ACGACAACGACTTCCAACTGCAACCAACGAAGTTTACGCCAGTGGGGATTAATGATGATGGAGACCATC
CTTTCCGCCAATGGGAACTACCAGATTATTCTGGGCTGCTCACCCTCAATATGAACCTCGCCCCACCCGTG
GCCCCTAATTTCCCCGGTGAGCAGCTGCTGTTTTTTCGGAGCTTTGTGCCATGCAGTGGCGGATATAATCA
AGGCATCGTAGACTGCTTGATTCCCCAAGAGTGGATACAACATTTTTACCAGGAAAGTGCGCCCTCCCAG
TCCGATGTGGCCCTGATACGGTACGTTAACCCCGATACCGGAAGAACATTATTCGAAGCGAAATTGCACA
GATCAGGGTACATTACCGTTGCACATTCCGGCGATTATCCCCTGGTGGTTCCCGCCAACGGTTACTTTAG
GTTCGATAGTTGGGTCAACCAGTTCTATTCACTAGCCCCAATGGGCACCGGTAACGGCAGACGCCGGGCT
CAGTAG

FIGURE 34M

Amino acid sequence of VP1GII.17 Kawa 2014 A0A077KVU6_A39V+M53I (SEQ ID NO:198)

MKMASNDAAPSNDGAAGLVPEGNNETLPLEPVAGAAIAVPVTGQNNIIDPWIITNFVQAPNGEFTVSPRNS
PGEILLNLELGPDLNPYLAHLSRMYNGYAGGVEVQVLLAGNAFTAGKILFAAVPPNFPVEFLSPAQITMLPHLI
VDVRTLEPIMIPLPDVRNTFFHYNNQPNSRMRLVAMLYTPLRSNGSGDDVFTVSCRVLTRPTPDFEFTYLVPP
SVESKTKPFSLPILTLSELTNSRFPVPIDSLFTAQNNVLQVQCQNGRCTLDGELQGTTQLLPSGICAFRGRVTAE
TDHRDKWHMQLQNLNGTTYDPTDDVPAPLGTPDFKGVVFGVASQRNVGNDAPGSTRAHEAVISTYSPQFV

FIGURE 34M (cont)

PKLGSVNFRSNDNDFQLQPTKFTPVGINDDGDHPFRQWELPDYSGLLTLNMNLAPPVAPNFPGEQLLFFRSF
VPCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

FIGURE 34N

Nucleic acid sequence of VP1 hCod GII.17 Kawa 2014 A0A077KVU6_A39V+M53I (SEQ ID NO:199)

ATGAAAATGGCATCTAACGACGCAGCCCCCTCAAACGATGGCGCTGCTGGACTCGTGCCGGAGGGGAAT
AATGAGACACTTCCACTAGAGCCGGTTGCAGGCGCCGCTATAGCTGTGCCAGTGACAGGGCAGAATAAT
ATTATAGACCCTTGGATTATCACAAACTTCGTGCAGGCACCCAACGGCGAGTTTACAGTATCCCCCCGGA
ACTCCCCAGGTGAGATACTCCTGAATCTTGAGCTCGGCCCTGACCTCAATCCATATCTGGCTCATCTGAGC
CGCATGTACAATGGTTACGCTGGGGGGGTCGAAGTGCAGGTCCTCCTGGCCGGAAACGCCTTTACCGCT
GGCAAAATTCTGTTTGCCGCCGTTCCACCAAACTTTCCAGTCGAATTCCTCTCTCCCGCGCAAATAACCAT
GCTGCCACATTTGATCGTTGACGTGCGGACCCTGGAGCCAATAATGATTCCCCTGCCGGATGTGCGTAAC
ACCTTTTTCCATTATAACAATCAGCCAAACTCTCGGATGAGACTTGTTGCTATGCTGTACACCCCCCTGCG
GAGCAACGGCAGTGGCGATGATGTGTTTACCGTGAGTTGCAGAGTCCTGACGCGCCCAACCCCGGACTT
CGAGTTCACCTACCTGGTGCCCCCTTCTGTGGAATCTAAGACCAAACCGTTTTCACTGCCAATCTTAACTCT
CTCCGAACTGACTAACAGCCGGTTTCCAGTACCCATAGATTCTCTTTTTACCGCTCAAAACAACGTACTCC
AAGTCCAGTGCCAGAACGGCCGCTGTACGCTTGATGGTGAGTTGCAGGGGACAACACAGCTACTCCCCA
GTGGCATCTGTGCATTCCGGGGCCGCGTGACCGCTGAGACAGACCATCGTGACAAATGGCACATGCAAC
TCCAAAACTTAAACGGGACCACCTACGACCCAACCGACGACGTCCCTGCTCCGCTAGGGACTCCTGACTT
TAAGGGGGTGGTGTTCGGAGTGGCCTCTCAGCGGAATGTTGGGAATGACGCCCCCGGCTCTACCCGAGC
TCACGAGGCCGTTATCTCAACATATAGCCCCCAATTTGTGCCCAAGCTCGGATCCGTTAATTTTCGTAGTA
ACGACAACGACTTCCAACTGCAACCAACGAAGTTTACGCCAGTGGGGATTAATGATGATGGAGACCATC
CTTTCCGCCAATGGGAACTACCAGATTATTCTGGGCTGCTCACCCTCAATATGAACCTCGCCCCACCCGTG
GCCCCTAATTTCCCCGGTGAGCAGCTGCTGTTTTTTCGGAGCTTTGTGCCATGCAGTGGCGGATATAATCA
AGGCATCGTAGACTGCTTGATTCCCCAAGAGTGGATACAACATTTTTACCAGGAAAGTGCGCCCTCCCAG
TCCGATGTGGCCCTGATACGGTACGTTAACCCCGATACCGGAAGAACATTATTCGAAGCGAAATTGCACA
GATCAGGGTACATTACCGTTGCACATTCCGGCGATTATCCCCTGGTGGTTCCCGCCAACGGTTACTTTAG
GTTCGATAGTTGGGTCAACCAGTTCTATTCACTAGCCCCAATGGGCACCGGTAACGGCAGACGCCGGGCT
CAGTAG

FIGURE 34O

Amino acid sequence of VP1GII.17 Kawa 2014 A0A077KVU6_E80S+A90L (SEQ ID NO:200)

MKMASNDAAPSNDGAAGLVPEGNNETLPLEPVAGAAIAAPVTGQNNIIDPWIRTNFVQAPNGEFTVSPRNS
PGEILLNLSLGPDLNPYLLHLSRMYNGYAGGVEVQVLLAGNAFTAGKILFAAVPPNFPVEFLSPAQITMLPHLIV
DVRTLEPIMIPLPDVRNTFFHYNNQPNSRMRLVAMLYTPLRSNGSGDDVFTVSCRVLTRPTPDFEFTYLVPPS
VESKTKPFSLPILTLSELTNSRFPVPIDSLFTAQNNVLQVQCQNGRCTLDGELQGTTQLLPSGICAFRGRVTAET
DHRDKWHMQLQNLNGTTYDPTDDVPAPLGTPDFKGVVFGVASQRNVGNDAPGSTRAHEAVISTYSPQFVP

FIGURE 34O (cont)

KLGSVNFRSNDNDFQLQPTKFTPVGINDDGDHPFRQWELPDYSGLLTLNMNLAPPVAPNFPGEQLLFFRSFV
PCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

FIGURE 34P

Nucleic acid sequence of VP1 hCod GII.17 Kawa 2014 A0A077KVU6_E80S+A90L (SEQ ID NO:201)

ATGAAAATGGCATCTAACGACGCAGCCCCCTCAAACGATGGCGCTGCTGGACTCGTGCCGGAGGGGAAT
AATGAGACACTTCCACTAGAGCCGGTTGCAGGCGCCGCTATAGCTGCCCCAGTGACAGGGCAGAATAAT
ATTATAGACCCTTGGATTCGGACAAACTTCGTGCAGGCACCCAACGGCGAGTTTACAGTATCCCCCCGGA
ACTCCCCAGGTGAGATACTCCTGAATCTTAGCCTCGGCCCTGACCTCAATCCATATCTGCTGCATCTGAGC
CGCATGTACAATGGTTACGCTGGGGGGGTCGAAGTGCAGGTCCTCCTGGCCGGAAACGCCTTTACCGCT
GGCAAAATTCTGTTTGCCGCCGTTCCACCAAACTTTCCAGTCGAATTCCTCTCTCCCGCGCAAATAACCAT
GCTGCCACATTTGATCGTTGACGTGCGGACCCTGGAGCCAATAATGATTCCCCTGCCGGATGTGCGTAAC
ACCTTTTTCCATTATAACAATCAGCCAAACTCTCGGATGAGACTTGTTGCTATGCTGTACACCCCCCTGCG
GAGCAACGGCAGTGGCGATGATGTGTTTACCGTGAGTTGCAGAGTCCTGACGCGCCCAACCCCGGACTT
CGAGTTCACCTACCTGGTGCCCCCTTCTGTGGAATCTAAGACCAAACCGTTTTCACTGCCAATCTTAACTCT
CTCCGAACTGACTAACAGCCGGTTTCCAGTACCCATAGATTCTCTTTTTACCGCTCAAAACAACGTACTCC
AAGTCCAGTGCCAGAACGGCCGCTGTACGCTTGATGGTGAGTTGCAGGGGACAACACAGCTACTCCCCA
GTGGCATCTGTGCATTCCGGGGCCGCGTGACCGCTGAGACAGACCATCGTGACAAATGGCACATGCAAC
TCCAAAACTTAAACGGGACCACCTACGACCCAACCGACGACGTCCCTGCTCCGCTAGGGACTCCTGACTT
TAAGGGGGTGGTGTTCGGAGTGGCCTCTCAGCGGAATGTTGGGAATGACGCCCCCGGCTCTACCCGAGC
TCACGAGGCCGTTATCTCAACATATAGCCCCCAATTTGTGCCCAAGCTCGGATCCGTTAATTTTCGTAGTA
ACGACAACGACTTCCAACTGCAACCAACGAAGTTTACGCCAGTGGGGATTAATGATGATGGAGACCATC
CTTTCCGCCAATGGGAACTACCAGATTATTCTGGGCTGCTCACCCTCAATATGAACCTCGCCCCACCCGTG
GCCCCTAATTTCCCCGGTGAGCAGCTGCTGTTTTTTCGGAGCTTTGTGCCATGCAGTGGCGGATATAATCA
AGGCATCGTAGACTGCTTGATTCCCCAAGAGTGGATACAACATTTTTACCAGGAAAGTGCGCCCTCCCAG
TCCGATGTGGCCCTGATACGGTACGTTAACCCCGATACCGGAAGAACATTATTCGAAGCGAAATTGCACA
GATCAGGGTACATTACCGTTGCACATTCCGGCGATTATCCCCTGGTGGTTCCCGCCAACGGTTACTTTAG
GTTCGATAGTTGGGTCAACCAGTTCTATTCACTAGCCCCAATGGGCACCGGTAACGGCAGACGCCGGGCT
CAGTAG

Figure 35A

Amino acid sequence of VP2_GI.1_Norwalk (SEQ ID NO:99)

MAQAIIGAIAASTAGSALGAGIQVGGEAALQSQRYQQNLQLQENSFKHDREMIGYQVEASNQLLAKNLATRYSLLRAGG
LTSADAARSVAGAPVTRIVDWNGVRVSAPESSATTLRSGGFMSVPIPFASKQKQVQSSGISNPNYSPSSISRTTSWVESQ
NSSRFGNLSPYHAEALNTVWLTPPGSTASSTLSSVPRGYFNTDRLPLFANNRR

Figure 35B

Nucleic acid sequence of human codon optimized VP.2_GI1_Norwalk (SEQ ID NO:100)

ATGGCTCAGGCCATTATTGGCGCCATCGCTGCAAGTACAGCCGGGAGTGCATTGGGGGCCGGAATACAGGTGGGC
GGGGAAGCTGCATTGCAGAGCCAGCGGTACCAGCAAAACCTGCAGTTACAGGAGAATAGCTTTAAACACGACAGG
GAGATGATTGGATATCAGGTGGAGGCCAGCAATCAGCTGCTCGCCAAAAACTTGGCTACTCGATACTCATTACTGCG
CGCCGGGGGGTTGACTAGCGCCGACGCCGCACGATCTGTCGCAGGCGCCCCCGTGACTCGGATCGTAGACTGGAA
CGGGGTACGAGTCTCGGCTCCCGAGTCGTCTGCAACCACCCTGAGGTCGGGAGGGTTTATGTCCGTGCCCATCCCAT
TCGCTAGCAAACAGAAACAGGTCCAGAGCTCCGGAATCTCCAATCCCAATTACTCCCCTAGCTCTATCTCTCGTACCA
CTTCCTGGGTCGAGAGTCAGAACAGCAGTAGATTTGGCAACCTGAGCCCCTACCATGCTGAAGCCCTGAACACTGTG
TGGTTGACTCCACCTGGTAGCACGGCCTCCTCAACCCTGAGTTCCGTGCCTCGCGGGTACTTCAATACCGACAGACTT
CCTCTGTTCGCTAACAACCGCCGCTGA

Figure 36A

Amino acid sequence of VP2_GI.3_Lil08 (SEQ ID NO:94)

MAQAIFGAIAATAAGSAVGAGIQAGTEAALQHQRFQQDLTLQSNTFKHDKEMLGLQVGASTALLQNSLNTRYNMLTD
AGLSSSDAARMVVGAPATRVVDWNGTRISAPRSTATTLRSGGFMTIPTLYKGKQQQKAPTEIGLSNPNYGSSVSSRVAD
WVSSQNSSHSSLGPYHPSALQTTWVTPPGSSSTSTISSVSTVPRYFNTDRLPLFANMRK

Figure 36B

Nucleic acid sequence of human codon optimized VP2_GI.3_Lil08 (SEQ ID NO:95)

ATGGCTCAGGCAATCTTCGGCGCAATCGCTGCCACTGCTGCCGGATCCGCTGTGGGAGCCGGCATACAGGCCGGAA
CTGAGGCGGCCCTTCAGCATCAGCGGTTCCAGCAGGATCTGACATTACAGAGTAACACATTCAAACATGACAAGGA
GATGCTGGGTCTGCAGGTGGGTGCCAGTACTGCCCTGCTCCAAAACTCTCTGAATACCAGATATAACATGTTAACTG
ATGCGGGACTGTCTAGTAGCGACGCAGCTCGCATGGTCGTGGGCGCCCCAGCTACGAGAGTTGTGGACTGGAATG
GCACCCGAATCAGTGCACCAAGGTCTACAGCCACTACCCTCAGAAGTGGCGGCTTTATGACCATCCCGACTTTATAC
AAGGGCAAACAACAGCAGAAGGCACCTACTGAAATCGGTCTCTCCAATCCCAACTACGGCAGCAGTGTGTCTTCTCG
CGTGGCCGATTGGGTCTCAAGCCAGAACTCCAGTCATAGTTCTCTTGGGCCTTATCATCCATCAGCCTTGCAGACAAC
TTGGGTCACCCCACCCGGGTCCAGTAGCACGTCAACCATCAGTTCCGTCTCCACAGTCCCTCGCTATTTTAATACTGA
TAGGCTTCCCCTGTTCGCAAACATGAGGAAGTGA

Figure 37A

Amino acid sequence of VP2_GII6_HS10 (SEQ ID NO:96)

MASAFLAGLAGDVITNGVGSLINAGANAVNQKVEYDFNKQLQMASFKHDKEMLQSQVLATKQLQQEMMNIRQGVLT
AGGFSPADAARGAVNAPMTKILDWNGTRYWAPNSMKTTSYSGQFSSSPVHKSPAPSQHTALPKSRLQNDFASVYSFPS
SVSSQSTHSTALSAGTGSSRSISPSTATPTLSRTSDWVRGQNERLSPFMDGALQTAFVTPPSSKASSNGTVSTVPKAVLDS
WTPMFNTHRQPLFAHPRRRGESQV

Figure 37B

Nucleic acid sequence of human codon optimized VP2_GII6_HS10 (SEQ ID NO:97)

ATGGCCTCCGCATTTCTAGCTGGATTGGCCGGGGACGTGATCACCAACGGCGTAGGATCGCTGATTAATGCAGGCG
CCAATGCTGTTAATCAGAAGGTTGAATACGACTTCAACAAACAACTGCAGATGGCTTCATTCAAGCACGACAAAGAA
ATGTTGCAGTCACAGGTTCTCGCCACCAAGCAGCTACAACAGGAGATGATGAACATTCGGCAGGGCGTACTGACCG
CTGGAGGATTCAGCCCTGCTGACGCAGCACGGGGGGCCGTGAACGCGCCGATGACCAAGATCCTGGATTGGAACG
GAACTCGGTATTGGGCTCCCAACTCTATGAAAACCACTTCTTACTCTGGTCAGTTCTCCAGCTCGCCAGTCCACAAAA
GTCCGGCCCCTTCACAGCACACAGCACTCCCTAAGTCCAGGCTGCAAAACGACTTTGCCTCCGTGTACTCCTTCCCAT
CCAGCGTGTCATCTCAGAGCACTCATTCAACCGCCCTGTCCGCCGGAACTGGGTCTAGCCGCAGCATTTCCCCAAGC
ACAGCTACTCCAACTCTGAGCAGGACTAGCGATTGGGTCAGAGGACAAAACGAACGACTGTCCCCTTTCATGGACG
GAGCTCTGCAAACCGCCTTCGTCACTCCACCTAGCAGCAAGGCCTCGAGCAACGGTACGGTTAGTACCGTGCCAAAG
GCTGTTCTTGACAGCTGGACCCCCATGTTTAACACACACAGGCAGCCATTGTTTGCACACCCCAGGCGACGGGGAGA
ATCACAAGTTTAG

Figure 38A

Cloning vector 1190 from left to right T-DNA (SEQ ID NO:162)

TGGCAGGATATATTGTGGTGTAAACAAATTGACGCTTAGACAACTTAATAACACATTGCGGACGTTTTTAATGTACT
GAATTAACGCCGAATCCCGGGCTGGTATATTTATATGTTGTCAAATAACTCAAAAACCATAAAAGTTTAAGTTAGCA
AGTGTGTACATTTTTACTTGAACAAAAATATTCACCTACTACTGTTATAAATCATTATTAAACATTAGAGTAAAGAAAT
ATGGATGATAAGAACAAGAGTAGTGATATTTTGACAACAATTTTGTTGCAACATTTGAGAAAATTTTGTTGTTCTCTC
TTTTCATTGGTCAAAAACAATAGAGAGAGAAAAAGGAAGAGGGAGAATAAAAACATAATGTGAGTATGAGAGAGA
AAGTTGTACAAAAGTTGTACCAAAATAGTTGTACAAATATCATTGAGGAATTTGACAAAAGCTACACAAATAAGGGT
TAATTGCTGTAAATAAATAAGGATGACGCATTAGAGAGATGTACCATTAGAGAATTTTTGGCAAGTCATTAAAAAGA
AAGAATAAATTATTTTTAAAATTAAAAGTTGAGTCATTTGATTAAACATGTGATTATTTAATGAATTGATGAAAGAGT
TGGATTAAAGTTGTATTAGTAATTAGAATTTGGTGTCAAATTTAATTTGACATTTGATCTTTTCCTATATATTGCCCCA
TAGAGTCAGTTAACTCATTTTTATATTTCATAGATCAAATAAGAGAAATAACGGTATATTAATCCCTCCAAAAAAAAA
AAACGGTATATTTACTAAAAAATCTAAGCCACGTAGGAGGATAACAGGATCCCCGTAGGAGGATAACATCCAATCC
AACCAATCACAACAATCCTGATGAGATAACCCACTTTAAGCCCACGCATCTGTGGCACATCTACATTATCTAAATCAC
ACATTCTTCCACACATCTGAGCCACACAAAAACCAATCCACATCTTTATCACCCATTCTATAAAAAATCACACTTTGTG
AGTCTACACTTTGATTCCCTTCAAACACATACAAAGAGAAGAGACTAATTAATTAATTAATCATCTTGAGAGAAAATG
GAACGAGCTATACAAGGAAACGACGCTAGGGAACAAGCTAACAGTGAACGTTGGGATGGAGGATCAGGAGGTACC
ACTTCTCCCTTCAAACTTCCTGACGAAAGTCCGAGTTGGACTGAGTGGCGGCTACATAACGATGAGACGAATTCGAA
TCAAGATAATCCCCTTGGTTTCAAGGAAAGCTGGGGTTTCGGGAAAGTTGTATTTAAGAGATATCTCAGATACGACA
GGACGGAAGCTTCACTGCACAGAGTCCTTGGATCTTGGACGGGAGATTCGGTTAACTATGCAGCATCTCGATTTTTC
GGTTTCGACCAGATCGGATGTACCTATAGTATTCGGTTTCGAGGAGTTAGTATCACCGTTTCTGGAGGGTCGCGAAC
TCTTCAGCATCTCTGTGAGATGGCAATTCGGTCTAAGCAAGAACTGCTACAGCTTGCCCCAATCGAAGTGGAAAGTA
ATGTATCAAGAGGATGCCCTGAAGGTACTCAAACCTTCGAAAAAGAAAGCGAGTAAGTTAAAATGCTTCTTCGTCTC
CTATTTATAATATGGTTTGTTATTGTTAATTTTGTTCTTGTAGAAGAGCTTAATTAATCGTTGTTGTTATGAAATACTAT
TTGTATGAGATGAACTGGTGTAATGTAATTCATTTACATAAGTGGAGTCAGAATCAGAATGTTTCCTCCATAACTAAC
TAGACATGAAGACCTGCCGCGTACAATTGTCTTATATTTGAACAACTAAAATTGAACATCTTTTGCCACAACTTTATA
AGTGGTTAATATAGCTCAAATATATGGTCAAGTTCAATAGATTAATAATGGAAATATCAGTTATCGAAATTCATTAAC
AATCAACTTAACGTTATTAACTACTAATTTTATATCATCCCCTTTGATAAATGATAGTACACCAATTAGGAAGGAGCAT
GCTCGCCTAGGAGATTGTCGTTTCCCGCCTTCAGTTTGCAAGCTGCTCTAGCCGTGTAGCCAATACGCAAACCGCCTC

FIGURE 38A (cont)

TCCCCGCGCGTTGGGAATTACTAGCGCGTGTCGACAAGCTTGCATGCCGGTCAACATGGTGGAGCACGACACACTT
GTCTACTCCAAAAATATCAAAGATACAGTCTCAGAAGACCAAAGGGCAATTGAGACTTTTCAACAAAGGGTAATATC
CGGAAACCTCCTCGGATTCCATTGCCCAGCTATCTGTCACTTTATTGTGAAGATAGTGGAAAAGGAAGGTGGCTCCT
ACAAATGCCATCATTGCGATAAAGGAAAGGCCATCGTTGAAGATGCCTCTGCCGACAGTGGTCCCAAAGATGGACC
CCCACCCACGAGGAGCATCGTGGAAAAAGAAGACGTTCCAACCACGTCTTCAAAGCAAGTGGATTGATGTGATAAC
ATGGTGGAGCACGACACACTTGTCTACTCCAAAAATATCAAAGATACAGTCTCAGAAGACCAAAGGGCAATTGAGA
CTTTTCAACAAAGGGTAATATCCGGAAACCTCCTCGGATTCCATTGCCCAGCTATCTGTCACTTTATTGTGAAGATAG
TGGAAAAGGAAGGTGGCTCCTACAAATGCCATCATTGCGATAAAGGAAAGGCCATCGTTGAAGATGCCTCTGCCGA
CAGTGGTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCCTTCCTCT
ATATAAGGAAGTTCATTTCATTTGGAGAGGTATTAAAATCTTAATAGGTTTTGATAAAAGCGAACGTGGGGAAACCC
GAACCAAACCTTCTTCTAAACTCTCTCTCATCTCTCTTAAAGCAAACTTCTCTCTTGTCTTTCTTGCGTGAGCGATCTTC
AACGTTGTCAGATCGTGCTTCGGCACCGCGGATGGCGAAAAACGTTGCGATTTTCGGCTTATTGTTTTCTCTTCTTGT
GTTGGTTCCTTCTCAGATCTTCGCCTGCAGGCTCCTCAGCCAAAACGACACCCCCATCTGTCTATCCACTGGCCCCTG
GATCTGCTGCCCAAACTAACTCCATGGTGACCCTGGGATGCCTGGTCAAGGGCTATTTCCCTGAGCCAGTGACAGTG
ACCTGGAACTCTGGATCCCTGTCCAGCGGTGTGCACACCTTCCCAGCTGTCCTGCAGTCTGACCTCTACACTCTGAGC
AGCTCAGTGACTGTCCCCTCCAGCACCTGGCCCAGCGAGACCGTCACCTGCAACGTTGCCCACCCGGCCAGCAGCAC
CAAGGTGGACAAGAAAATTGTGCCCAGGGATTGTGGTTGTAAGCCTTGCATATGTACAGTCCCAGAAGTATCATCTG
TCTTCATCTTCCCCCCAAAGCCCAAGGATGTGCTCACCATTACTCTGACTCCTAAGGTCACGTGTGTTGTGGTAGACA
TCAGCAAGGATGATCCCGAGGTCCAGTTCAGCTGGTTTGTAGATGATGTGGAGGTGCACACAGCTCAGACGCAACC
CCGGGAGGAGCAGTTCAACAGCACTTTCCGCTCAGTCAGTGAACTTCCCATCATGCACCAGGACTGGCTCAATGGCA
AGGAGCGATCGCTCACCATCACCATCACCATCACCATCACCATTAAAGGCCTATTTTCTTTAGTTTGAATTTACTGTTA
TTCGGTGTGCATTTCTATGTTTGGTGAGCGGTTTTCTGTGCTCAGAGTGTGTTTATTTTATGTAATTTAATTTCTTTGT
GAGCTCCTGTTTAGCAGGTCGTCCCTTCAGCAAGGACACAAAAAGATTTTAATTTTATTAAAAAAAAAAAAAAAAAA
GACCGGGAATTCGATATCAAGCTTATCGACCTGCAGATCGTTCAAACATTTGGCAATAAAGTTTCTTAAGATTGAATC
CTGTTGCCGGTCTTGCGATGATTATCATATAATTTCTGTTGAATTACGTTAAGCATGTAATAATTAACATGTAATGCAT
GACGTTATTTATGAGATGGGTTTTTATGATTAGAGTCCCGCAATTATACATTTAATACGCGATAGAAAACAAAATATA
GCGCGCAAACTAGGATAAATTATCGCGCGCGGTGTCATCTATGTTACTAGATCTCTAGAGTCTCAAGCTTGGCGCGC
CCACGTGACTAGTGGCACTGGCCGTCGTTTTACAACGTCGTGACTGGGAAAACCCTGGCGTTACCCAACTTAATCGC
CTTGCAGCACATCCCCCTTTCGCCAGCTGGCGTAATAGCGAAGAGGCCCGCACCGATCGCCCTTCCCAACAGTTGCG
CAGCCTGAATGGCGAATGCTAGAGCAGCTTGAGCTTGGATCAGATTGTCGTTTCCCGCCTTCAGTTTAAACTATCAG
TGTTTGACAGGATATATTGGCGGGTAAACCTAAGAGAAAAGAGCGTTTA

Figure 38B

Construct 2724 from 2X35S promoter to NOS terminator (SEQ ID NO:163)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC

FIGURE 38B (cont)

CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGATGATGGCTAGTAAA
GATGCGACCTCCTCTGTGGATGGTGCGTCAGGGGCAGGACAACTCGTACCCGAGGTAAACGCCAGCGACCCACTTG
CCATGGACCCCGTTGCCGGAAGTTCCACAGCAGTGGCCACAGCCGGTCAAGTGAATCCAATTGATCCGTGGATTATC
AACAATTTCGTCCAGGCACCCCAGGGCGAGTTCACAATTTCACCAAACAATACACCGGGCGATGTGCTATTCGATCT
TTCCTTGGGTCCTCACCTTAACCCTTTTCTACTCCATCTCTCACAGATGTACAATGGTTGGGTAGGAAACATGAGAGT
CCGGATCATGCTGGCTGGCAATGCCTTTACCGCTGGCAAGATCATCGTCAGTTGTATTCCTCCCGGATTTGGATCTCA
TAATCTGACCATTGCTCAAGCGACTCTCTTTCCCCATGTCATCGCCGACGTTAGGACCCTGGACCCCATCGAGGTGCC
CCTGGAGGACGTCCGGAATGTTTTGTTCCACAACAACGACAGAAACCAGCAGACGATGAGACTTGTCTGTATGCTCT
ATACCCCACTGCGGACTGGAGGCGGGACTGGAGACTCCTTCGTTGTGGCAGGAAGAGTGATGACATGCCCCTCCCC
CGACTTCAACTTTCTTTTTCTGGTCCCACCAACCGTTGAGCAGAAGACGCGGCCCTTTACACTGCCCAATCTCCCGCTT
TCAAGTCTGAGTAATTCACGGGCCCCATTGCCGATCTCCTCAATGGGAATCTCCCCCGACAACGTCCAGTCTGTCCAA
TTCCAAAATGGGAGATGCACACTGGACGGTCGCCTGGTGGGAACAACTCCGGTGTCCCTCTCACATGTCGCCAAAAT
CCGCGGCACATCAAATGGTACCGTAATCAATCTGACAGAACTTGATGGCACGCCCTTCCATCCCTTTGAAGGACCAG
CCCCTATTGGATTTCCTGATCTGGGAGGTTGCGACTGGCACATAAACATGACACAGTTTGGCCACTCCAGCCAGACA
CAGTATGATGTCGATACAACCCCAGATACCTTCGTGCCACACCTGGGATCTATTCAAGCTAACGGTATTGGATCCGG
CAACTACGTGGGAGTCTTATCTTGGATCTCACCACCATCCCACCCCTCAGGATCCCAGGTTGACTTGTGGAAGATACC
GAATTATGGATCCTCGATCACTGAAGCCACGCACCTCGCACCTTCCGTCTACCCACCAGGTTTTGGAGAAGTCTTGGT
GTTTTTCATGAGCAAAATGCCCGGCCCTGGAGCCTACAATCTCCCTTGCCTACTCCCTCAAGAGTATATTAGTCACCT
CGCATCTGAGCAGGCCCCGACCGTTGGCGAGGCAGCCCTGCTGCATTATGTGGATCCGGACACCGGCAGGAACCTG
GGTGAGTTCAAAGCTTATCCTGACGGTTTTCTAACATGTGTACCAAATGGCGCTTCCAGCGGCCCTCAACAGCTCCCA
ATCAATGGCGTGTTCGTTTTTGTCAGCTGGGTAAGCCGCTTCTACCAGCTGAAGCCCGTGGGGACAGCTTCTTCTGC
CCGCGGACGCCTCGGTCTGCGGAGATAAAGGCCTATTTTCTTTAGTTTGAATTTACTGTTATTCGGTGTGCATTTCTA
TGTTTGGTGAGCGGTTTTCTGTGCTCAGAGTGTGTTTATTTTATGTAATTTAATTTCTTTGTGAGCTCCTGTTTAGCAG
GTCGTCCCTTCAGCAAGGACACAAAAAGATTTTAATTTTATTAAAAAAAAAAAAAAAAAAAGACCGGGAATTCGATAT
CAAGCTTATCGACCTGCAGATCGTTCAAACATTTGGCAATAAAGTTTCTTAAGATTGAATCCTGTTGCCGGTCTTGCG
ATGATTATCATATAATTTCTGTTGAATTACGTTAAGCATGTAATAATTAACATGTAATGCATGACGTTATTTATGAGAT
GGGTTTTTATGATTAGAGTCCCGCAATTATACATTTAATACGCGATAGAAAACAAAATATAGCGCGCAAACTAGGAT
AAATTATCGCGCGCGGTGTCATCTATGTTACTAGAT

Figure 38C

Cloning vector 3677 from left to right T-DNA (SEQ ID NO:164)

TGGCAGGATATATTGTGGTGTAAACAAATTGACGCTTAGACAACTTAATAACACATTGCGGACGTTTTTAATGTACT
GAATTAACGCCGAATCCCGGGCTGGTATATTTATATGTTGTCAAATAACTCAAAAACCATAAAAGTTTAAGTTAGCA
AGTGTGTACATTTTTACTTGAACAAAAATATTCACCTACTACTGTTATAAATCATTATTAAACATTAGAGTAAAGAAAT
ATGGATGATAAGAACAAGAGTAGTGATATTTTGACAACAATTTTGTTGCAACATTTGAGAAAATTTTGTTGTTCTCTC
TTTTCATTGGTCAAAAACAATAGAGAGAGAAAAAGGAAGAGGGAGAATAAAAACATAATGTGAGTATGAGAGAGA
AAGTTGTACAAAAGTTGTACCAAAATAGTTGTACAAATATCATTGAGGAATTTGACAAAAGCTACACAAATAAGGGT
TAATTGCTGTAAATAAATAAGGATGACGCATTAGAGAGATGTACCATTAGAGAATTTTTGGCAAGTCATTAAAAAGA
AAGAATAAATTATTTTTAAAATTAAAAGTTGAGTCATTTGATTAAACATGTGATTATTTAATGAATTGATGAAAGAGT
TGGATTAAAGTTGTATTAGTAATTAGAATTTGGTGTCAAATTTAATTTGACATTTGATCTTTTCCTATATATTGCCCCA
TAGAGTCAGTTAACTCATTTTTATATTTCATAGATCAAATAAGAGAAATAACGGTATATTAATCCCTCCAAAAAAAAA
AAACGGTATATTTACTAAAAAATCTAAGCCACGTAGGAGGATAACAGGATCCCCGTAGGAGGATAACATCCAATCC
AACCAATCACAACAATCCTGATGAGATAACCCACTTTAAGCCCACGCATCTGTGGCACATCTACATTATCTAAATCAC
ACATTCTTCCACACATCTGAGCCACACAAAAACCAATCCACATCTTTATCACCCATTCTATAAAAAATCACACTTTGTG
AGTCTACACTTTGATTCCCTTCAAACACATACAAAGAGAAGAGACTAATTAATTAATTAATCATCTTGAGAGAAAATG
GAACGAGCTATACAAGGAAACGACGCTAGGGAACAAGCTAACAGTGAACGTTGGGATGGAGGATCAGGAGGTACC

FIGURE 38C (cont)

ACTTCTCCCTTCAAACTTCCTGACGAAAGTCCGAGTTGGACTGAGTGGCGGCTACATAACGATGAGACGAATTCGAA
TCAAGATAATCCCCTTGGTTTCAAGGAAAGCTGGGGTTTCGGGAAAGTTGTATTTAAGAGATATCTCAGATACGACA
GGACGGAAGCTTCACTGCACAGAGTCCTTGGATCTTGGACGGGAGATTCGGTTAACTATGCAGCATCTCGATTTTTC
GGTTTCGACCAGATCGGATGTACCTATAGTATTCGGTTTCGAGGAGTTAGTATCACCGTTTCTGGAGGGTCGCGAAC
TCTTCAGCATCTCTGTGAGATGGCAATTCGGTCTAAGCAAGAACTGCTACAGCTTGCCCCAATCGAAGTGGAAAGTA
ATGTATCAAGAGGATGCCCTGAAGGTACTCAAACCTTCGAAAAAGAAAGCGAGTAAGTTAAAATGCTTCTTCGTCTC
CTATTTATAATATGGTTTGTTATTGTTAATTTTGTTCTTGTAGAAGAGCTTAATTAATCGTTGTTGTTATGAAATACTAT
TTGTATGAGATGAACTGGTGTAATGTAATTCATTTACATAAGTGGAGTCAGAATCAGAATGTTTCCTCCATAACTAAC
TAGACATGAAGACCTGCCGCGTACAATTGTCTTATATTTGAACAACTAAAATTGAACATCTTTTGCCACAACTTTATA
AGTGGTTAATATAGCTCAAATATATGGTCAAGTTCAATAGATTAATAATGGAAATATCAGTTATCGAAATTCATTAAC
AATCAACTTAACGTTATTAACTACTAATTTTATATCATCCCCTTTGATAAATGATAGTACACCAATTAGGAAGGAGCAT
GCTCGCCTAGGAGATTGTCGTTTCCCGCCTTCAGTTTGCAAGCTGCTCTAGCCGTGTAGCCAATACGCAAACCGCCTC
TCCCCGCGCGTTGGGAATTACTAGCGCGTGTCGACAAGCTTGCATGCCGGTCAACATGGTGGAGCACGACACACTT
GTCTACTCCAAAAATATCAAAGATACAGTCTCAGAAGACCAAAGGGCAATTGAGACTTTTCAACAAAGGGTAATATC
CGGAAACCTCCTCGGATTCCATTGCCCAGCTATCTGTCACTTTATTGTGAAGATAGTGGAAAAGGAAGGTGGCTCCT
ACAAATGCCATCATTGCGATAAAGGAAAGGCCATCGTTGAAGATGCCTCTGCCGACAGTGGTCCCAAAGATGGACC
CCCACCCACGAGGAGCATCGTGGAAAAAGAAGACGTTCCAACCACGTCTTCAAAGCAAGTGGATTGATGTGATAAC
ATGGTGGAGCACGACACACTTGTCTACTCCAAAAATATCAAAGATACAGTCTCAGAAGACCAAAGGGCAATTGAGA
CTTTTCAACAAAGGGTAATATCCGGAAACCTCCTCGGATTCCATTGCCCAGCTATCTGTCACTTTATTGTGAAGATAG
TGGAAAAGGAAGGTGGCTCCTACAAATGCCATCATTGCGATAAAGGAAAGGCCATCGTTGAAGATGCCTCTGCCGA
CAGTGGTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCCTTCCTCT
ATATAAGGAAGTTCATTTCATTTGGAGAGGTATTAAAATCTTAATAGGTTTTGATAAAAGCGAACGTGGGGAAACCC
GAACCAAACCTTCTTCTAAACTCTCTCTCATCTCTCTTAAAGCAAACTTCTCTCTTGTCTTTCTTGCGTGAGCGATCTTC
AACGTTGTCAGATCGTGCTTCGGCACCGCGGATGGCGAAAAACGTTGCGATTTTCGGCTTATTGTTTTCTCTTCTTGT
GTTGGTTCCTTCTCAGATCTTCGCCTGCAGGCTCCTCAGCCAAAACGACACCCCCATCTGTCTATCCACTGGCCCCTG
GATCTGCTGCCCAAACTAACTCCATGGTGACCCTGGGATGCCTGGTCAAGGGCTATTTCCCTGAGCCAGTGACAGTG
ACCTGGAACTCTGGATCCCTGTCCAGCGGTGTGCACACCTTCCCAGCTGTCCTGCAGTCTGACCTCTACACTCTGAGC
AGCTCAGTGACTGTCCCCTCCAGCACCTGGCCCAGCGAGACCGTCACCTGCAACGTTGCCCACCCGGCCAGCAGCAC
CAAGGTGGACAAGAAAATTGTGCCCAGGGATTGTGGTTGTAAGCCTTGCATATGTACAGTCCCAGAAGTATCATCTG
TCTTCATCTTCCCCCCAAAGCCCAAGGATGTGCTCACCATTACTCTGACTCCTAAGGTCACGTGTGTTGTGGTAGACA
TCAGCAAGGATGATCCCGAGGTCCAGTTCAGCTGGTTTGTAGATGATGTGGAGGTGCACACAGCTCAGACGCAACC
CCGGGAGGAGCAGTTCAACAGCACTTTCCGCTCAGTCAGTGAACTTCCCATCATGCACCAGGACTGGCTCAATGGCA
AGGAGCGATCGCTCACCATCACCATCACCATCACCATCACCATTAAAGGCCTATTTTCTTTAGTTTGAATTTACTGTTA
TTCGGTGTGCATTTCTATGTTTGGTGAGCGGTTTTCTGTGCTCAGAGTGTGTTTATTTTATGTAATTTAATTTCTTTGT
GAGCTCCTGTTTAGCAGGTCGTCCCTTCAGCAAGGACACAAAAAGATTTTAATTTTATTATCGTTCAAACATTTGGCA
ATAAAGTTTCTTAAGATTGAATCCTGTTGCCGGTCTTGCGATGATTATCATATAATTTCTGTTGAATTACGTTAAGCAT
GTAATAATTAACATGTAATGCATGACGTTATTTATGAGATGGGTTTTTATGATTAGAGTCCCGCAATTATACATTTAA
TACGCGATAGAAAACAAAATATAGCGCGCAAACTAGGATAAATTATCGCGCGCGGTGTCATCTATGTTACTAGATCT
CTAGGTAAAAATCCCAATTATATTTGGTCTAATTTAGTTTGGTATTGAGTAAAACAAATTCGAACCAAACCAAAATAT
AAATATATAGTTTTTATATATATGCCTTTAAGACTTTTTATAGAATTTTCTTTAAAAAATATCTAGAAATATTTGCGACT
CTTCTGGCATGTAATATTTCGTTAAATATGAAGTGCTCCATTTTTATTAACTTTAAATAATTGGTTGTACGATCACTTTC
TTATCAAGTGTTACTAAAATGCGTCAATCTCTTTGTTCTTCCATATTCATATGTCAAAATCTATCAAAATTCTTATATAT
CTTTTTCGAATTTGAAGTGAAATTTCGATAATTTAAAATTAAATAGAACATATCATTATTTAGGTATCATATTGATTTTT
ATACTTAATTACTAAATTTGGTTAACTTTGAAAGTGTACATCAACGAAAAATTAGTCAAACGACTAAAATAAATAAAT
ATCATGTGTTATTAAGAAAATTCTCCTATAAGAATATTTTAATAGATCATATGTTTGTAAAAAAAAATTAATTTTTACTA
ACACATATATTTACTTATCAAAAATTTGACAAAGTAAGATTAAAATAATATTCATCTAACAAAAAAAAAACCAGAAAA
TGCTGAAAACCCGGCAAAACCGAACCAATCCAAACCGATATAGTTGGTTTGGTTTGATTTTGATATAAACCGAACCA
ACTCGGTCCATTTGCACCCCTAATCATAATAGCTTTAATATTTCAAGATATTATTAAGTTAACGTTGTCAATATCCTGG
AAATTTTGCAAAATGAATCAAGCCTATATGGCTGTAATATGAATTTAAAAGCAGCTCGATGTGGTGGTAATATGTAA

FIGURE 38C (cont)

TTTACTTGATTCTAAAAAAATATCCCAAGTATTAATAATTTCTGCTAGGAAGAAGGTTAGCTACGATTTACAGCAAAG
CCAGAATACAAAGAACCATAAAGTGATTGAAGCTCGAAATATACGAAGGAACAAATATTTTTAAAAAAATACGCAAT
GACTTGGAACAAAAGAAAGTGATATATTTTTTGTTCTTAAACAAGCATCCCCTCTAAAGAATGGCAGTTTTCCTTTGC
ATGTAACTATTATGCTCCCTTCGTTACAAAAATTTTGGACTACTATTGGGAACTTCTTCTGAAAATTCTAGAGTCTCAA
GCTTGGCGCGCCCACGTGACTAGTGGCACTGGCCGTCGTTTTACAACGTCGTGACTGGGAAAACCCTGGCGTTACCC
AACTTAATCGCCTTGCAGCACATCCCCCTTTCGCCAGCTGGCGTAATAGCGAAGAGGCCCGCACCGATCGCCCTTCCC
AACAGTTGCGCAGCCTGAATGGCGAATGCTAGAGCAGCTTGAGCTTGGATCAGATTGTCGTTTCCCGCCTTCAGTTT
AAACTATCAGTGTTTGACAGGATATATTGGCGGGTAAACCTAAGAGAAAAGAGCGTTTA

Figure 38D

Construct 4133 from 2X35S promoter to NOS terminator (SEQ ID NO:165)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGAAAATGGCCTCGAGT
GACGCTAACCCTAGTGACGGCAGCGCCGCCAATCTTGTGCCTGAGGTTAATAATGAGGTGATGGCCCTGGAGCCTG
TGGTGGGCGCAGCCATAGCAGCGCCCGTGGCCGGTCAGCAGAATGTGATTGACCCGTGGATACGCAACAATTTTGT
CCAAGCCCCTGGTGGGGAGTTCACCGTTAGCCCGAGAAATGCGCCAGGAGAAATCCTGTGGTCGGCCAGCTTGGGA
CCCGATCTGAACCCCTATTTGTCACATCTCGCTCGGATGTACAACGGGTATGCCGGCGGATTTGAAGTGCAGGTGAT
TCTGGCTGGGAACGCGTTCACTGCTGGCAAAGTGATCTTTGCAGCGGTGCCTCCCAACTTCCCCACTGAAGGACTGT
CTCCAAGCCAGGTCACAATGTTTCCACACATCGTGGTGGACGTACGGCAGCTAGAGCCTGTCCTGATTCCCCTCCCT
GATGTACGCAATAATTTCTACCACTACAATCAATCCAATGATCCGACCATTAAACTCATCGCGATGTTGTACACCCCTC
TGCGCGCTAACAATGCTGGAGACGACGTATTCACCGTGTCATGCAGAGTGCTCACCAGACCTTCACCAGACTTTGAC
TTTATCTTCTTAGTGCCCCCCACTGTTGAGAGCCGAACCAAGCCCTTTAGTGTCCCCGTACTCACAGTCGAGGAGATG
ACAAATAGCCGCTTTCCAATCCCCCTTGAGAAACTGTTCACAGGACCTTCCTCGGCATTCGTGGTTCAGCCACAGAAC
GGACGCTGCACAACTGACGGCGTGCTGCTCGGAACCACCCAGCTTAGCCCTGTTAATATCTGTACGTTTAGAGGCGA
CGTAACTCACATAACTGGCTCACGGAACTATACCATGAATCTGGCATCACAGAATTGGAATGACTACGACCCAACCG
AAGAGATTCCCGCACCTCTTGGAACCCCCGACTTTGTGGGAAAAATACAGGGCGTCCTGACACAAACCACCAGAACC
GATGGCTCCACACGGGGACACAAGGCAACCGTCTACACTGGCTCTGCCGATTTTGCCCCGAAACTGGGTAGAGTGC
AGTTTGAGACCGACACTGACCGGGACTTTGAAGCCAATCAGAATACTAAGTTCACACCTGTAGGAGTGATTCAGGA
CGGGGGCACCACTCACCGGAACGAGCCGCAACAATGGGTCCTGCCCTCTTATAGCGGGAGGAATACTCATAATGTG
CATTTGGCTCCTGCAGTGGCTCCCACGTTTCCCGGGGAACAACTGCTCTTTTTTCGTTCAACCATGCCTGGATGCTCC
GGATATCCCAATATGGATCTCGATTGCCTGCTCCCACAGGAATGGGTGCAGTATTTTTATCAAGAGGCCGCACCAGC
CCAATCCGACGTCGCACTTCTGCGGTTCGTGAATCCAGACACAGGCCGCGTGTTGTTTGAGTGCAAATTGCACAAAT
CAGGATACGTTACAGTGGCTCATACTGGACAGCATGACCTGGTGATCCCACCCAACGGATATTTTAGGTTCGACTCC
TGGGTGAATCAGTTTTATACATTAGCCCCCATGGGGAATGGGACTGGCAGACGCAGGGCTGTCTGAAGGCCTATTT
TCTTTAGTTTGAATTTACTGTTATTCGGTGTGCATTTCTATGTTTGGTGAGCGGTTTTCTGTGCTCAGAGTGTGTTTAT
TTTATGTAATTTAATTTCTTTGTGAGCTCCTGTTTAGCAGGTCGTCCCTTCAGCAAGGACACAAAAAGATTTTAATTTT
ATTATCGTTCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTATGATTAG

FIGURE 38D (cont)

AGTCCCGCAATTATACATTTAATACGCGATAGAAAACAAAATATAGCGCGCAAACTAGGATAAATTATCGCGCGCGG
TGTCATCTATGTTACTAGAT

Figure 38E

Construct 4135 from 2X35S promoter to NOS terminator (SEQ ID NO:166)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGAAAATGGCCTCGAGT
GACGCTAACCCTAGTGACGGCAGCGCCGCCAATCTTGTGCCTGAGGTTAATAATGAGGTGATGGCCCTGGAGCCTG
TGGTGGGCGCAGCCATAGCAGCGCCCGTGGCCGGTCAGCAGAATGTGATTGACCCGTGGATACGCAACAATTTTGT
CCAAGCCCCTGGTGGGGAGTTCACCGTTAGCCCGAGAAATGCGCCAGGAGAAATCCTGTGGTCGGCCAGCTTGGGA
CCCGATCTGAACCCCTATTTGCTGCATCTCGCTCGGATGTACAACGGGTATGCCGGCGGATTTGAAGTGCAGGTGAT
TCTGGCTGGGAACGCGTTCACTGCTGGCAAAGTGATCTTTGCAGCGGTGCCTCCCAACTTCCCCACTGAAGGACTGT
CTCCAAGCCAGGTCACAATGTTTCCACACATCGTGGTGGACGTACGGCAGCTAGAGCCTGTCCTGATTCCCCTCCCT
GATGTACGCAATAATTTCTACCACTACAATCAATCCAATGATCCGACCATTAAACTCATCGCGATGTTGTACACCCCTC
TGCGCGCTAACAATGCTGGAGACGACGTATTCACCGTGTCATGCAGAGTGCTCACCAGACCTTCACCAGACTTTGAC
TTTATCTTCTTAGTGCCCCCCACTGTTGAGAGCCGAACCAAGCCCTTTAGTGTCCCCGTACTCACAGTCGAGGAGATG
ACAAATAGCCGCTTTCCAATCCCCCTTGAGAAACTGTTCACAGGACCTTCCTCGGCATTCGTGGTTCAGCCACAGAAC
GGACGCTGCACAACTGACGGCGTGCTGCTCGGAACCACCCAGCTTAGCCCTGTTAATATCTGTACGTTTAGAGGCGA
CGTAACTCACATAACTGGCTCACGGAACTATACCATGAATCTGGCATCACAGAATTGGAATGACTACGACCCAACCG
AAGAGATTCCCGCACCTCTTGGAACCCCCGACTTTGTGGGAAAAATACAGGGCGTCCTGACACAAACCACCAGAACC
GATGGCTCCACACGGGGACACAAGGCAACCGTCTACACTGGCTCTGCCGATTTTGCCCCGAAACTGGGTAGAGTGC
AGTTTGAGACCGACACTGACCGGGACTTTGAAGCCAATCAGAATACTAAGTTCACACCTGTAGGAGTGATTCAGGA
CGGGGGCACCACTCACCGGAACGAGCCGCAACAATGGGTCCTGCCCTCTTATAGCGGGAGGAATACTCATAATGTG
CATTTGGCTCCTGCAGTGGCTCCCACGTTTCCCGGGGAACAACTGCTCTTTTTTCGTTCAACCATGCCTGGATGCTCC
GGATATCCCAATATGGATCTCGATTGCCTGCTCCCACAGGAATGGGTGCAGTATTTTTATCAAGAGGCCGCACCAGC
CCAATCCGACGTCGCACTTCTGCGGTTCGTGAATCCAGACACAGGCCGCGTGTTGTTTGAGTGCAAATTGCACAAAT
CAGGATACGTTACAGTGGCTCATACTGGACAGCATGACCTGGTGATCCCACCCAACGGATATTTTAGGTTCGACTCC
TGGGTGAATCAGTTTTATACATTAGCCCCCATGGGGAATGGGACTGGCAGACGCAGGGCTGTCTGAAGGCCTATTT
TCTTTAGTTTGAATTTACTGTTATTCGGTGTGCATTTCTATGTTTGGTGAGCGGTTTTCTGTGCTCAGAGTGTGTTTAT
TTTATGTAATTTAATTTCTTTGTGAGCTCCTGTTTAGCAGGTCGTCCCTTCAGCAAGGACACAAAAAGATTTTAATTTT
ATTATCGTTCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTATGATTAG
AGTCCCGCAATTATACATTTAATACGCGATAGAAAACAAAATATAGCGCGCAAACTAGGATAAATTATCGCGCGCGG
TGTCATCTATGTTACTAGAT

Construct 2724 (VP1 Wt GI.1 hCod)

Construct 3300 (Wt GI.2 hCod)

Construct 3979 (Wt GI.3 hCod)

Construct 4140 (VP1 GI.3_Q84S hCod)

Construct 4141 (VP1 GI.3_S94L hCod)

Construct 4142 (VP1 GI.3_Q84S+S94L hCod)

Construct 4179 (VP1 GI.3_A43V+S94L hCod)

Construct 4180 (VP1 GI.3_M57I+S94L hCod)

Construct 4181 (VP1 GI.3_A43V+M57I+S94L hCod)

Construct 3980 (VP1 Wt GI.5 hCod)

Construct 4130 (VP1 GI.5_Q84S)

Construct 4131 (VP1 GI.5_A94L hCod)

Construct 4132 (VP1 GI.5_Q84S+A94L hCod)

Construct 4210 (VP1 GI.7_R84S hCod)

Construct 4217 (VP1 GI.7_M57I hCod)

Construct 4218 (VP1 GI.7_M57I+R84S hCod)

Construct 3982 (Wt VP1 GII.2 hCod)

Construct 4143 (VP1 GII.2_E80S)

Construct 4144 (VP1 GII.2_A90L hCod)

Construct 4145 (VP1 GII.2_E80S+A90L hCod)

Construct 4182 (VP1 GII.2_A39V+E80S+A90L hCod)

Construct 4183Y (VP1 GII.2_R53I+E80S+A90L hCod)

Construct 4184 (VP1 GII.2_A39V+R53I+E80S+A90L hCod).

Construct 3983 (Wt VP1 GII.3 hCod)

Construct 4146 (VP1 GII.3_E80S hCod)

Construct 4147 (VP1 GII.3_A90L hCod)

Construct 4148 (VP1 GII.3_E80S+A90L)

Construct 3760 (Wt VP1 GII.4 hCod)

Construct 4155 (VP1 GII.4_A39V hCod)

Construct 4156 (VP1 GII.4_V47P hCod)

Construct 4157 (VP1 GII.4_R53I hCod)

Construct 4133 (VP1 GII.4_P80S hCod)

Construct 4134 (VP1 GII.4_S90L hCod)

Construct 4158 (VP1 GII.4_ Δ35-42 hCod)

Construct 4159 (VP1 GII.4_SSTAVATA hCod)

Construct 4165 (VP1 GII.4_A39V+P80S hCod)

Construct 4166 (VP1 GII.4_V47P+P80S hCod)

Construct 4167 (VP1 GII.4_R53I+P80S hCod)

Construct 4135 (VP1 GII.4_P80S+S90L hCod)

Construct 4168 (GII.4_ P80S+Δ35-42 hCod)

Construct 4169 (VP1 GII.4_P80S+SSTAVATA hCod)

Construct 4185 (VP1 GII.4_A39V+R53I hCod);

Construct 4186Y (VP1 GII.4_A39V+R53I+P80S hCod)

Construct 3993 (Wt VP1 GII.6 hCod)

Construct 4149 (VP1 GII.6_E80S hCod)

Construct 4150 (VP1 GII.6_S90L hCod)

Construct 4151 (VP1 GII.6_E80S+S90L)

Construct 3995 (Wt VP1 GII.12 hCod)

Construct 4136 (VP1 GII.12_E80S hCod)

Construct 4137 (VP1 GII.12_A90L hCod)

Construct 4138 (VP1 GII.12_E80S+A90L)

Construct 4234 (VP1 GII.17_A39V hCod)

Construct 4235 (VP1 GII.17_R53I hCod)

Construct 4232 (VP1 GII.17_ A90L hCod)

Construct 4236 (VP1 GII.17_A39V+R53I hCod)

Construct 4233 (VP1 GII.17_E80S+A90L hCod)

Construct 2725 (Wt VP2 GI.1)

Construct 3303 (Wt VP2 GI.3 hCod)

Construct 3307 (Wt VP2 GII.6)

Construct 1190 (Cloning vector 1190)

Construct 3677 (Cloning vector 3677)

GII.4 P80X constructs (cloning vectors), wherein X=A (4281); X=N (4285); X=K (4286); X=H (4287)

GII.4 P80s+A39X constructs (cloning vectors), wherein X=I (4256); X=M (4257); X=G (4258); X=S (4259); X=E (4260); X=D (4261); X=N (4262); X=Q (4263); X=K (4264); X=H (4265)

GI.7 M57X constructs (cloning vectors), wherein X= L 4266); G (4268); S (4269); T (4270; N (4273); Q (4274); K (4275); or H (4276).

GI.3 S94X constructs (cloning vectors), wherein X=V (4288); I (4289); M (4290); T (4292); E (4293); D (4294); N (4295); Q (4296); K (4297); or H (4298).

SEQUENCE LISTING

```
Sequence total quantity: 293
SEQ ID NO: 1            moltype = AA  length = 530
FEATURE                 Location/Qualifiers
source                  1..530
                        mol_type = protein
                        note = Norovirus
                        organism = unidentified
SEQUENCE: 1
MMMASKDATS SVDGASGAGQ LVPEVNASDP LAMDPVAGSS TAVATAGQVN PIDPWIINNF  60
VQAPQGEFTI SPNNTPGDVL FDLSLGPHLN PFLLHLSQMY NGWVGNMRVR IMLAGNAFTA  120
GKIIVSCIPP GFGSHNLTIA QATLFPHVIA DVRTLDPIEV PLEDVRNVLF HNNDRNQQTM  180
RLVCMLYTPL RTGGGTGDSF VVAGRVMTCP SPDFNFLFLV PPTVEQKTRP FTLPNLPLSS  240
LSNSRAPLPI SSMGISPDNV QSVQFQNGRC TLDGRLVGTT PVSLSHVAKI RGTSNGTVIN  300
LTELDGTPFH PFEGPAPIGF PDLGGCDWHI NMTQFGHSSQ TQYDVDTTPD TFVPHLGSIQ  360
ANGIGSGNYV GVLSWISPPS HPSGSQVDLW KIPNYGSSIT EATHLAPSVY PPGFGEVLVF  420
FMSKMPGPGA YNLPCLLPQE YISHLASEQA PTVGEAALLH YVDPDTGRNL GEFKAYPDGF  480
LTCVPNGASS GPQQLPINGV FVFVSWVSRF YQLKPVGTAS SARGRLGLRR             530

SEQ ID NO: 2            moltype = DNA  length = 1593
FEATURE                 Location/Qualifiers
source                  1..1593
                        mol_type = genomic DNA
                        note = Norovirus
                        organism = unidentified
SEQUENCE: 2
atgatgatgg cgtctaagga cgctacatca agcgtggatg gcgctagtgg cgctggtcag  60
ttggtaccgg aggttaatgc ttctgaccct cttgcaatgg atcctgtagc aggttcttcg  120
acagcagtcg cgactgctgg acaagttaat cctattgatc cctggataat taataatttt  180
gtgcaagccc cccaaggtga atttactatt tccccaaata atacccccgg tgatgttttg  240
tttgatttga gtttgggtcc ccatcttaat cctttcttgc tccatctatc acaaatgtat  300
aatggttggg ttggtaacat gagagtcagg attatgctag ctggtaatgc ctttactgcg  360
gggaagataa tagtttcctg catacccct ggttttggtt cacataatct tactatagca  420
caagcaactc tctttccaca tgtgattgct gatgttagga ctctagaccc cattgaggtg  480
cctttggaag atgttaggaa tgttctcttt cataataatg atagaaatca acaaaccatg  540
cgccttgtgt gcatgctgta cacccccctc cgcactggtg gtggtactgg tgattctttt  600
gtagttgcag ggcgagttat gacttgcccc agtcctgatt ttaatttctt gtttttagtc  660
cctcctacgg tggagcagaa aaccaggccc ttcacactcc caaatctgcc attgagttct  720
ctgtctaact cacgtgcccc tctcccaatc agtagtatgg gcatttcccc agacaatgtc  780
cagagtgtgc agttccaaaa tggtcggtgt actctggatg gccgcctggt tggcaccacc  840
ccagtttcat tgtcacatgt tgccaagata agagggacct ccaatggcac tgtaatcaac  900
cttactgaat tggatggcac accctttcac ccttttgagg gccctgcccc cattgggttt  960
ccagacctcg gtggttgtga ttggcatatc aatatgacac agtttggcca ttctagccag  1020
acccagtatg atgtagacac cacccctgac actttttgtcc cccatcttgg ttcaattcag  1080
gcaaatggca ttggcagtgg taattatgtt ggtgttctta gctggatttc cccccccatca  1140
cacccgtctg gctcccaagt tgacctttgg aagatcccca attatgggtc aagtattacg  1200
```

-continued

```
gaggcaacac atctagcccc ttctgtatac ccccctggtt tcggagaggt attggtcttt  1260
ttcatgtcaa aaatgccagg tcctggtgct tataatttgc cctgtctatt accacaagag  1320
tacatttcac atcttgctag tgaacaagcc cctactgtag gtgaggctgc cctgctccac  1380
tatgttgacc ctgataccgg tcggaatctt ggggaattca aagcataccc tgatggtttc  1440
ctcacttgtg tccccaatgg ggctagctcg ggtccacaac agctgccgat caatggggtc  1500
tttgtctttg tttcatgggt gtccagattt tatcaattaa agcctgtggg aactgccagc  1560
tcggcaagag gtaggcttgg tctgcgccga taa                                1593

SEQ ID NO: 3            moltype = DNA  length = 1593
FEATURE                 Location/Qualifiers
misc_feature            1..1593
                        note = Nucleic acid sequence of human codon-optimized VP1
                         G1.1
source                  1..1593
                        mol_type = other DNA
                        organism = synthetic construct
SEQUENCE: 3
atgatgatgg ctagtaaaga tgcgacctcc tctgtggatg gtgcgtcagg ggcaggacaa  60
ctcgtacccg aggtaaacgc cagcgaccca cttgccatgg accccgttgc cggaagttcc  120
acagcagtgg ccacagccgg tcaagtgaat ccaattgatc cgtggattat caacaatttc  180
gtccaggcac cccagggcga gttcacaatt tcaccaaaca atacaccggg cgatgtgcta  240
ttcgatcttt ccttgggtcc tcaccttaac ccttttctac tccatctctc acagatgtac  300
aatggttggg taggaaacat gagagtccgg atcatgctgg ctggcaatgc ctttaccgct  360
ggcaagatca tcgtcagttg tattcctccc ggatttggat ctcataatct gaccattgct  420
caagcgactc tctttcccca tgtcatcgcc gacgttagga ccctggaccc catcgaggtg  480
cccctggagg acgtccggaa tgttttgttc cacaacaacg acagaaacca gcagacgatg  540
agacttgtct gtatgctcta taccccactg cggactggag gcgggactgg agactccttc  600
gttgtggcag gaagagtgat gacatgcccc tcccccgact tcaactttct ttttctggtc  660
ccaccaaccg ttgagcagaa gacgcggccc tttacactgc ccaatctccc gctttcaagt  720
ctgagtaatt cacgggcccc attgccgatc tcctcaatgg gaatctcccc cgacaacgtc  780
cagtctgtcc aattccaaaa tgggagatgc acactggacg gtcgcctggt gggaacaact  840
ccggtgtccc tctcacatgt cgccaaaatc cgcggcacat caaatggtac cgtaatcaat  900
ctgacagaac ttgatggcac gcccttccat ccctttgaag gaccagcccc tattggattt  960
cctgatctgg gaggttgcga ctggcacata aacatgacac agtttggcca ctccagccag  1020
acacagtatg atgtcgatac aaccccagat accttcgtgc cacacctggg atctattcaa  1080
gctaacggta ttggatccgg caactacgtg ggagtcttat cttggatctc accaccatcc  1140
cacccctcag gatcccaggt tgacttgtgg aagataccga attatggatc ctcgatcact  1200
gaagccacgc acctcgcacc ttccgtctac ccaccaggtt ttggagaagt cttggtgttt  1260
ttcatgagca aaatgcccgg ccctggagcc tacaatctcc cttgcctact ccctcaagag  1320
tatattagtc acctcgcatc tgagcaggcc ccgaccgttg gcgaggcagc cctgctgcat  1380
tatgtggatc cggacaccgg caggaacctg ggtgagttca aagcttatcc tgacggtttt  1440
ctaacatgtg taccaaatgg cgcttccagc ggccctcaac agctcccaat caatggcgtg  1500
ttcgtttttg tcagctgggt aagccgcttc taccagctga agcccgtggg gacagcttct  1560
tctgcccgcg gacgcctcgg tctgcggaga taa                                1593

SEQ ID NO: 4            moltype = AA  length = 546
FEATURE                 Location/Qualifiers
source                  1..546
                        mol_type = protein
                        note = Norovirus
                        organism = unidentified
SEQUENCE: 4
MMMASKDAPQ SADGASGAGQ LVPEVNTADP LPMEPVAGPT TAVATAGQVN MIDPWIVNNF  60
VQSPQGEFTI SPNNTPGDIL FDLQLGPHLN PFLSHLSQMY NGWVGNMRVR ILLAGNAFSA  120
GKIIVCCVPP GFTSSSLTIA QATLFPHVIA DVRTLEPIEM PLEDVRNVLY HTNDNQPTMR  180
LVCMLYTPLR TGGGSGNSDS FVVAGRVLTA PSSDFSFLFL VPPTIEQKTR AFTVPNIPLQ  240
TLSNSRFPSL IQGMILSPDA SQVVQFQNGR CLIDGQLLGT TPATSGQLFR VRGKINQGAR  300
TLNLTEVDGK PFMAFDSPAP VGFPDFGKCD WHMRISKTPN NTSSGDPMRS VDVQTDVQGF  360
VPHLGSIQFD EVFNHPTGDY IGTIEWISQP STPPGTDINL WEIPDYGSSL SQAANLAPPV  420
FPPGFGEALV YFVSAFPGPN NRSAPNDVPC LLPQEYVTHF VSEQAPTMGD AALLHYVDPD  480
TNRNLGEFKL YPGGYLTCVP NGVGAGPQQL PLNGVFLFVS WVSRFYQLKP VGTASTARGR  540
LGVRRI                                                              546

SEQ ID NO: 5            moltype = DNA  length = 1641
FEATURE                 Location/Qualifiers
misc_feature            1..1641
                        note = Nucleic acid sequence of human codon-optimized VP1
                         G1.2 Leuven 2003 D2DEL3
source                  1..1641
                        mol_type = other DNA
                        organism = synthetic construct
SEQUENCE: 5
atgatgatgg cttcaaagga tgctccccaa agcgcggacg gagctagcgg cgccggacag  60
ttggttccgg aagtcaacac tgccgatcca ctgcccatgg aacccgtagc tggtccaaca  120
accgctgttg ccaccgccgg ccaggttaac atgatcgatc catggattgt taataacttt  180
gtacagagcc cccaggggga gttcacaatt tctccgaaca atacccctgg ggacattctg  240
ttcgatctgc aactgggccc acacttgaat cctttcctga gccatctttc acagatgtac  300
aacggatggg ttgggaacat gcgtgttcgg atcctccttg ctggcaacgc cttcagtgct  360
ggcaagatta tcgtgtgctg cgtaccacca gggtttacct cgagttcatt aaccattgct  420
```

-continued

```
caggccaccc ttttccctca cgtgatcgca gacgtgcgta ccttagaacc aatcgaaatg  480
cccctggaag atgtacggaa cgtgctgtac catactaatg ataaccagcc aacgatgaga  540
ttagtgtgca tgctgtacac ccccctgaga actggaggag gttctggaaa ttccgacagt  600
tttgtggtgg ctggcagggt cctgaccgct cccagtagcg acttcagctt tttgttcctc  660
gttcctccta caatcgaaca aaaaacaaga gcattcacag tgcccaacat tccactgcag  720
actttaagca attccaggtt tcccagcttg atccagggta tgatcctttc tcccgacgcc  780
tcccaagttg tgcagttcca gaatgggaga tgtcttatcg acggtcagct tctgggaaca  840
acccctgcca cctccgggca actcttccgg gtgagaggca aaatcaatca gggcgccaga  900
acactgaatc tgacagaagt ggacgggaaa ccctttatgg cgttcgatag ccccgcgccc  960
gttggattcc ctgacttcgg caagtgtgat tggcacatgc gcatcagtaa gactcccaac  1020
aacacttcat ctggagaccc catgaggagc gtggatgtcc agaccgacgt gcagggcttc  1080
gtgccgcact tgggatctat ccagttcgat gaggtgttca atcaccctac tggcgactac  1140
ataggcacaa ttgagtggat aagtcaacca tctacacctc cagggaccga cataaacctg  1200
tgggaaattc ctgattacgg gtcatccctg agtcaagctg ccaatcttgc acccccctgtc  1260
tttccccccg gctttggtga ggctcttgtt tacttcgtct ctgcatttcc tggtcctaac  1320
aaccgctccg cccctaacga tgttccgtgt ttgttacccc aggaatatgt gactcatttc  1380
gtttccgaac aggcacccac catgggggac gctgccctgc tacactatgt ggaccccgac  1440
accaatagaa acctcggcga gttcaaactc taccccgggg gatacctgac ctgtgttcca  1500
aatggagtgg gagcaggccc acaacagctg cccctgaatg ggtcttcct gttcgtttct  1560
tgggtgtcac gcttttacca gctgaagccc gttggcacag cttctacggc acgcggcagg  1620
ctaggggtcc gccgaatctg a                                            1641
```

```
SEQ ID NO: 6            moltype = AA  length = 543
FEATURE                 Location/Qualifiers
REGION                  1..543
                        note = Amino acid sequence of VP1 GI.3 LillaEdet 2008 H2DG70
source                  1..543
                        mol_type = protein
                        organism = synthetic construct
SEQUENCE: 6
MMMASKDAPT NMDGTSGAGQ LVPEVSTAEP ISMEPVAGAA TAAATAGQVN MIDPWIMSNY  60
VQAPQGEFTI SPNNTPGDIL FDLQLGPHLN PFLSHLAQMY NGWVGNMKVR VLLAGNAFTA  120
GKIIISCVPP GFAAQNVSIA QATMFPHVIA DVRVLEPIEV PLEDVRNVLF HNNDSTPTMR  180
LICMLYTPLR ASGSSSGTDP FVIAGRVLTC PSPDFNFLFL VPPNVEQKTK PFSVPNLPLN  240
VLSNSRVPSL IKSMMVSQDH GQMVQFQNGR VTLDGQLQGT TPTSASQLCK IRGTVYHATG  300
GQGLNLTEID GTPYHAFESP APIGFPDLGE CDWHINASPA NAFTDGSIIH RIDVAQDSTF  360
APHLGTIHYT NADYNANVGL ICSLEWLSPP SGGAPKVNPW AIPRYGSTLT EAAQLAPPIY  420
PPGFGEAIVF FMSDFPIANG SDGLSVPCTI PQEFVTHFVN EQAPTRGEAA LLHYVDPDTH  480
RNLGEFKLYP EGFMTCVPNS SGSGPQTLPI NGVFTFISWV SRFYQLKPVG TTGPVRRLGI  540
RRS                                                                543
```

```
SEQ ID NO: 7            moltype = DNA  length = 1632
FEATURE                 Location/Qualifiers
misc_feature            1..1632
                        note = Nucleic acid sequence of human codon-optimized VP1
                         GI.3 LillaEdet 2008 H2DG70
source                  1..1632
                        mol_type = other DNA
                        organism = synthetic construct
SEQUENCE: 7
atgatgatgg cttccaagga tgctcccaca aacatggatg gaacaagcgg cgcggggcaa  60
cttgtgccgg aggtgtccac ggcggaaccc atttccatgg aacctgtggc cggcgcagcc  120
actgctgccg ccaccgcagg acaggtaaac atgatcgacc cctggatcat gtcaaattac  180
gttcaggctc cacaggggga gtttaccata agcccaaaca acaccccggg tgacatcttg  240
tttgacctgc agctaggacc acacttgaat ccgtttctga gtcacttggc tcagatgtat  300
aatggatggg ttggaaacat gaaggtgcgc gtgctcctgg cgggcaatgc attcacagcc  360
gggaagatta ttatctcttg cgtgccacct ggatttgcag cccagaacgt gtctatcgca  420
caggcaacca tgtttccgca tgtcatcgca gatgtgcgcg tgctagagcc catcgaggtg  480
ccccttgagg acgtgcgcaa cgtcctattc cataacaatg atagcacccc caccatgcgc  540
ttgatatgta tgttatatac tcccctccgc gccagtgggt ccagctccgg gaccgatcct  600
tttgtgattg ctgggcgggt gttgacttgt cctagccctg acttcaactt cctttttctg  660
gtgcctccaa atgtagaaca gaaaacaaag ccattcagcg tgccaaacct gccccttaac  720
gtgctgtcga attcccgagt gccttccctt attaagtcca tgatggtatc tcaggatcac  780
ggtcaaatgg tgcagtttca gaacggccga gtgacgttag acgggcagct gcagggcaca  840
accccaacca gtgccagtca gctgtgtaag atcagaggca ccgtctacca cgcaactggc  900
ggacaggggc tgaatcttac tgagatcgat ggtacccccct accatgcatt cgagtcacct  960
gcacctattg gatttcccga tcttggggag tgtgattggc atatcaatgc ttcacctgcc  1020
aacgctttca cagacgggtc tattattcat cgcattgacg tagcacagga tagcacattt  1080
gccccgcacc tgggtaccat ccactatacg aacgcagatt acaacgcaaa cgtgggtctt  1140
atctgtagcc tagagtggct atctccgcca agcggtgggg cccctaaagt taacccatgg  1200
gctattcctc ggtacgggtc tacgctgact gaggccgctc agctggcacc ccccatatat  1260
ccaccaggat tcggggaagc cattgttttc tttatgtccg attttccgat agccaacggt  1320
tcagatggcc ttagtgtccc ttgcacgatt ccacaggaat ttgtgacaca cttcgtaaac  1380
gagcaggctc ctactcgggg cgaggctgcc ttgttgcatt acgtagaccc cgatacccat  1440
agaaacctgg gcgaattcaa actctaccct gaaggtttca tgacctgcgt acctaactcc  1500
tccggcagtg gccctcaaac cttgccgatc aacggcgtgt tcacgtttat cagctgggtt  1560
tcacggtttt accaactcaa gcccgtcgga acaactgggc cagttcggag gctcgggatc  1620
agacggagct ag                                                      1632
```

-continued

```
SEQ ID NO: 8           moltype = AA  length = 543
FEATURE                Location/Qualifiers
source                 1..543
                       mol_type = protein
                       note = Norovirus
                       organism = unidentified
SEQUENCE: 8
MMMASKDAPT NMDGTSGAGQ LVPEVSTAEP ISMEPVAGAA TAAATAGQVN MIDPWIMSNY  60
VQAPQGEFTI SPNNTPGDIL FDLQLGPHLN PFLLHLAQMY NGWVGNMKVR VLLAGNAFTA  120
GKIIISCVPP GFAAQNVSIA QATMFPHVIA DVRVLEPIEV PLEDVRNVLF HNNDSTPTMR  180
LICMLYTPLR ASGSSSGTDP FVIAGRVLTC PSPDFNFLFL VPPNVEQKTK PFSVPNLPLN  240
VLSNSRVPSL IKSMMVSQDH GQMVQFQNGR VTLDGQLQGT TPTSASQLCK IRGTVYHATG  300
GQGLNLTEID GTPYHAFESP APIGFPDLGE CDWHINASPA NAFTDGSIIH RIDVAQDSTF  360
APHLGTIHYT NADYNANVGL ICSLEWLSPP SGGAPKVNPW AIPRYGSTLT EAAQLAPPIY  420
PPGFGEAIVF FMSDFPIANG SDGLSVPCTI PQEFVTHFVN EQAPTRGEAA LLHYVDPDTH  480
RNLGEFKLYP EGFMTCVPNS SGSGPQTLPI NGVFTFISWV SRFYQLKPVG TTGPVRRLGI  540
RRS                                                               543

SEQ ID NO: 9           moltype = DNA  length = 1632
FEATURE                Location/Qualifiers
misc_feature           1..1632
                       note = Nucleic acid sequence of human codon optimized VP1
                        GI.3 Lil08 S94L
source                 1..1632
                       mol_type = other DNA
                       organism = synthetic construct
SEQUENCE: 9
atgatgatgg cttccaagga tgctcccaca aacatggatg gaacaagcgg cgcggggcaa  60
cttgtgccgg aggtgtccac ggcggaaccc atttccatgg aacctgtggc cggcgcagcc  120
actgctgccg ccaccgcagg acaggtaaac atgatcgacc cctggatcat gtcaaattac  180
gttcaggctc cacaggggga gtttaccata agcccaaaca acacccgggg tgacatcttg  240
tttgacctgc agctaggacc acacttgaat ccgtttctgc tccacttggc tcagatgtat  300
aatggatggg ttggaaacat gaaggtgcgc gtgctcctgg cgggcaatgc attcacagcc  360
gggaagatta ttatctcttg cgtgccacct ggatttgcag cccagaacgt gtctatcgca  420
caggcaacca tgtttccgca tgtcatcgca gatgtgcgcg tgctagagcc catcgaggtg  480
ccccttgagg acgtgcgcaa cgtcctattc cataacaatg atagcacccc caccatgcgc  540
ttgatatgta tgttatatac tcccctccgc gccagtgggt ccagctccgg gaccgatcct  600
tttgtgattg ctgggcgggt gttgacttgt cctagccctg acttcaactt cctttttctg  660
gtgcctccaa atgtagaaca gaaaacaaag ccattcagcg tgccaaacct gccccttaac  720
gtgctgtcga attcccgagt gccttccctt attaagtcca tgatggtatc tcaggatcac  780
ggtcaaatgg tgcagtttca gaacggccga gtgacgttag acgggcagct gcagggcaca  840
accccaacca gtgccagtca gctgtgtaag atcagaggca ccgtctacca cgcaactggc  900
ggacaggggc tgaatcttac tgagatcgat ggtaccccct accatgcatt cgagtcacct  960
gcacctattg gatttcccga tcttggggag tgtgattggc atatcaatgc ttcacctgcc  1020
aacgctttca cagacgggtc tattattcat cgcattgacg tagcacagga tagcacattt  1080
gccccgcacc tgggtaccat ccactatacg aacgcagatt acaacgcaaa cgtgggtctt  1140
atctgtagcc tagagtggct atctccgcca agcggtgggg cccctaaagt taacccatgg  1200
gctattcctc ggtacgggtc tacgctgact gaggccgctc agctggcacc ccccatatat  1260
ccaccaggat tcggggaagc cattgttttc tttatgtccg attttccgat agccaacggt  1320
tcagatggcc ttagtgtccc ttgcacgatt ccacaggaat ttgtgacaca cttcgtaaac  1380
gagcaggctc ctactcgggg cgaggctgcc ttgttgcatt acgtagaccc cgatacccat  1440
agaaacctgg gcgaattcaa actctaccct gaaggtttca tgacctgcgt acctaactcc  1500
tccggcagtg gccctcaaac cttgccgatc aacggcgtgt tcacgtttat cagctgggtt  1560
tcacggtttt accaactcaa gcccgtcgga acaactgggc cagttcggag gctcgggatc  1620
agacggagct ag                                                     1632

SEQ ID NO: 10          moltype = AA  length = 543
FEATURE                Location/Qualifiers
source                 1..543
                       mol_type = protein
                       note = Norovirus
                       organism = unidentified
SEQUENCE: 10
MMMASKDAPT NMDGTSGAGQ LVPEVSTAEP ISMEPVAGAA TAAATAGQVN MIDPWIMSNY  60
VQAPQGEFTI SPNNTPGDIL FDLSLGPHLN PFLLHLAQMY NGWVGNMKVR VLLAGNAFTA  120
GKIIISCVPP GFAAQNVSIA QATMFPHVIA DVRVLEPIEV PLEDVRNVLF HNNDSTPTMR  180
LICMLYTPLR ASGSSSGTDP FVIAGRVLTC PSPDFNFLFL VPPNVEQKTK PFSVPNLPLN  240
VLSNSRVPSL IKSMMVSQDH GQMVQFQNGR VTLDGQLQGT TPTSASQLCK IRGTVYHATG  300
GQGLNLTEID GTPYHAFESP APIGFPDLGE CDWHINASPA NAFTDGSIIH RIDVAQDSTF  360
APHLGTIHYT NADYNANVGL ICSLEWLSPP SGGAPKVNPW AIPRYGSTLT EAAQLAPPIY  420
PPGFGEAIVF FMSDFPIANG SDGLSVPCTI PQEFVTHFVN EQAPTRGEAA LLHYVDPDTH  480
RNLGEFKLYP EGFMTCVPNS SGSGPQTLPI NGVFTFISWV SRFYQLKPVG TTGPVRRLGI  540
RRS                                                               543

SEQ ID NO: 11          moltype = DNA  length = 1632
FEATURE                Location/Qualifiers
misc_feature           1..1632
                       note = Nucleic acid sequence of human codon optimized VP1
                        GI.3 Lil08 Q84S plus sign S94L
```

```
source                  1..1632
                        mol_type = other DNA
                        organism = synthetic construct
SEQUENCE: 11
atgatgatgg cttccaagga tgctcccaca aacatggatg gaacaagcgg cgcggggcaa  60
cttgtgccgg aggtgtccac ggcggaaccc atttccatgg aacctgtggc cggcgcagcc  120
actgctgccg ccaccgcagg acaggtaaac atgatcgacc cctggatcat gtcaaattac  180
gttcaggctc cacaggggga gtttaccata agcccaaaca acaccccggg tgacatcttg  240
tttgacctga gcctaggacc acacttgaat ccgtttctgc tccacttggc tcagatgtat  300
aatggatggg ttggaaacat gaaggtgcgc gtgctcctgg cgggcaatgc attcacagcc  360
gggaagatta ttatctcttg cgtgccacct ggatttgcag cccagaacgt gtctatcgca  420
caggcaacca tgtttccgca tgtcatcgca gatgtgcgcg tgctagagcc catcgaggtg  480
ccccttgagg acgtgcgcaa cgtcctattc cataacaatg atagcacccc caccatgcgc  540
ttgatatgta tgttatatac tcccctccgc gccagtgggt ccagctccgg gaccgatcct  600
tttgtgattg ctgggcgggt gttgacttgt cctagccctg acttcaactt cctttttctg  660
gtgcctccaa atgtagaaca gaaaacaaag ccattcagcg tgccaaacct gccccttaac  720
gtgctgtcga attcccgagt gccttccctt attaagtcca tgatggtatc tcaggatcac  780
ggtcaaatgg tgcagtttca gaacggccga gtgacgttag acgggcagct gcagggcaca  840
accccaacca gtgccagtca gctgtgtaag atcagaggca ccgtctacca cgcaactggc  900
ggacaggggc tgaatcttac tgagatcgat ggtacccct accatgcatt cgagtcacct  960
gcacctattg gatttcccga tcttggggag tgtgattggc atatcaatgc ttcacctgcc  1020
aacgctttca cagacgggtc tattattcat cgcattgacg tagcacagga tagcacattt  1080
gccccgcacc tgggtaccat ccactatacg aacgcagatt acaacgcaaa cgtgggtctt  1140
atctgtagcc tagagtggct atctccgcca agcggtgggg cccctaaagt taacccatgg  1200
gctattcctc ggtacgggtc tacgctgact gaggccgctc agctggcacc ccccatatat  1260
ccaccaggat tcggggaagc cattgtttc ttatgtccg atttccgat agccaacggt  1320
tcagatggcc ttagtgtccc ttgcacgatt ccacaggaat ttgtgacaca cttcgtaaac  1380
gagcaggctc ctactcgggg cgaggctgcc ttgttgcatt acgtagaccc cgatacccat  1440
agaaacctgg gcgaattcaa actctaccct gaaggtttca tgacctgcgt acctaactcc  1500
tccggcagtg gccctcaaac cttgccgatc aacggcgtgt tcacgtttat cagctgggtt  1560
tcacggtttt accaactcaa gcccgtcgga acaactgggc cagttcggag gctcgggatc  1620
agacggagct ag                                                     1632

SEQ ID NO: 12           moltype = AA  length = 543
FEATURE                 Location/Qualifiers
source                  1..543
                        mol_type = protein
                        note = Norovirus
                        organism = unidentified
SEQUENCE: 12
MMMASKDAPS SADGANGAGQ LVPEVNNAEP LPLDPVAGAS TALATAGQVN MIDPWIFNNF  60
VQAPQGEFTI SPNNTPGDIL FDLQLGPHLN PFLAHLSQMY NGWVGNMRVR VILAGNAFTA  120
GKVIICCVPP GFQSRTLSIA QATLFPHIIA DVRTLEPIEI PLEDVRNTLY HTNDNQPTMR  180
LLCMLYTPLR TGGGSGGTDA FVVAGRVLTC PSSDFNFLFL VPPTVEQKTR PFSVPNIPLQ  240
LLSNSRVPNL IQSMVLSPDQ AQNVQFQNGR CTTDGQLLGT TPVSVSQILK FRGKVSAGSK  300
VINLTELDGS PFLAFEAPAP TGFPDLGTSD WHVEMSLNSN SQSSGNPILL RDIHPNSSEF  360
VPHLGSVCVT AAIEVAGDYT GTIQWTSQPS NVTPVPDVNF WTIPHYGSNL AEASQLAPVV  420
YPPGFGEAIV YFMSPIPGPN TAHKPNLVPC LLPQEFVTHF VSEQAPSMGE AALVHYVDPD  480
TNRNLGEFKL YPEGFITCVP NGTGPQQLPL NGVFVFASWV SRFYQLKPVG TASSARGRLG  540
VRR                                                               543

SEQ ID NO: 13           moltype = AA  length = 535
FEATURE                 Location/Qualifiers
source                  1..535
                        mol_type = protein
                        note = Norovirus
                        organism = unidentified
SEQUENCE: 13
MKMASNDAAP SNDGAAGLVP EVNNETMALE PVAGASIAAP LTGQNNVIDP WIRMNFVQAP  60
NGEFTVSPRN SPGEVLLNLE LGPELNPFLA HLSRMYNGYA GGVEVQVLLA GNAFTAGKLV  120
FAAIPPHFPL ENLSPGQITM FPHVIIDVRT LEPVLLPLPD VRNNFFHYNQ QPEPRMRLVA  180
MLYTPLRSNG SGDDVFTVSC RVLTRPSPDF DFNYLVPPTV ESKTKPFTLP ILTIGELSNS  240
RFPVPIDELY TSPNEGVVVQ PQNGRSTLDG ELLGTTQLVP SNICALRGRI NAQVPDDHHQ  300
WNLQVTNANG TSFDPTEDVP APLGTPDFLA NIYGVTSQRN PDNTCRAHDG VLATWSPKFT  360
PKLGSVVLGT WEESDLDLNQ PTRFTPVGLY DTGHFDQWVL PNYSGRLTLN MNLAPSVAPL  420
FPGEQILFFR SHIPLKGGTS NGAIDCLLPQ EWIQHFYQES APSPTDVALI RYTNPDTGRV  480
LFEAKLHRQG FITVANSGSR PIVVPPNGYF RFDSWVNQFY SLAPMGTGNG RRRVQ       535

SEQ ID NO: 14           moltype = AA  length = 542
FEATURE                 Location/Qualifiers
source                  1..542
                        mol_type = protein
                        note = Norovirus
                        organism = unidentified
SEQUENCE: 14
MKMASNDAAP STDGAAGLVP ESNNEVMALE PVAGAALAAP VTGQTNIIDP WIRANFVQAP  60
NGEFTVSPRN SPGEVLLNLE LGPELNPYLA HLARMYNGYA GGMEVQVMLA GNAFTAGKLV  120
FAAVPPHFPV ENLSPQQITM FPHVIIDVRT LEPVLLPLPD VRNNFFHYNQ KDDPKMRIVA  180
MLYTPLRSNG SGDDVFTVSC RVLTRPSPDF DFTYLVPPTV ESKTKPFTLP ILTLGELSNS  240
```

-continued

```
RFPVSIDQMY TSPNEVISVQ CQNGRCTLDG ELQGTTQLQV SGICAFKGEV TAHLHDNDHL  300
YNVTITNLNG SPFDPSEDIP APLGVPDFQG RVFGVISQRD KHNTPGHNEP ANRAHDAVVP  360
TYTAQYTPKL GQIQIGTWQT DDLTVNQPVK FTPVGLNDTD HFNQWVVPRY AGALNLNTNL  420
APSVAPVFPG ERLLFFRSYI PLKGGYGTPA IDCLLPQEWV QHFYQEAAPS MSEVALVRYI  480
NPDTGRALFE AKLHRAGFMT VSSNTSAPVV VPANGYFRFD SWVNQFYSLA PMGTGNGRRR  540
IQ                                                                542

SEQ ID NO: 15          moltype = AA  length = 548
FEATURE                Location/Qualifiers
source                 1..548
                       mol_type = protein
                       note = Norovirus
                       organism = unidentified
SEQUENCE: 15
MKMASNDAAP SNDGAAGLVP EISSEAMALE PVAGAAIAAP LTGQQNIIDP WIMNNFVQAP  60
GGEFTVSPRN SPGEVLLNLE LGPEINPYLA HLARMYNGYA GGFEVQVVLA GNAFTAGKII  120
FAAIPPNFPI DNLSAAQITM CPHVIVDVRQ LEPVNLPMPD VRNNFFHYNQ GSDSRLRLIA  180
MLYTPLRANN SGDDVFTVSC RVLTRPSPDF SFNFLVPPTV ESKTKPFSLP ILTISEMSNS  240
RFPVPIDSLH TSPTENIVVQ CQNGRVTLDG ELMGTTQLLP SQICAFRGTL TRSTSRASDQ  300
ADTATPRLFN YYWHIQLDNL NGTPYDPAED IPAPLGTPDF RGKVFGVASQ RNPDATTRAH  360
EAKIDTTSGR FTPKLGSLEI STESGDFDQN QPTRFTPVGI GVDHEPDFQQ WALPDYAGQF  420
THNMNLAPAV APNFPGEQLL FFRSQLPSSG GRSNGILDCL VPQEWVQHFY QESAPSQTQV  480
ALVRYVNPDT GRVLFEAKLH KLRFMTIAKS GDSPITVPPN GYFRFESWVN PFYTLAPMGT  540
GNGRRRIQ                                                          548

SEQ ID NO: 16          moltype = AA  length = 540
FEATURE                Location/Qualifiers
source                 1..540
                       mol_type = protein
                       note = Norovirus
                       organism = unidentified
SEQUENCE: 16
MKMASSDANP SDGSAANLVP EVNNEVMALE PVVGAAIAAP VAGQQNVIDP WIRNNFVQAP  60
GGEFTVSPRN APGEILWSAP LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 17          moltype = AA  length = 540
FEATURE                Location/Qualifiers
source                 1..540
                       mol_type = protein
                       note = Norovirus
                       organism = unidentified
SEQUENCE: 17
MKMASNDATP SNDGAAGLVP ESNNEAMALE PVVGASLAAP VTGQTNIIDP WIRTNFVQAP  60
NGEFTVSPRN SPGEILVNLE LGPELNPYLA HLARMYNGYA GGMEVQVLLA GNAFTAGKII  120
FAAVPPYFPV ENLSPSQITM FPHVIIDVRT LEPVLLPMPD VRSTLFHFNQ KDEPKMRLVA  180
MLYTPLRSNG SGDDVFTVSC RILTRPSPEF DFTYLVPPTV ESKTKPFTLP VLTLGELSNS  240
RFPLSIDEMV TSPNESIVVQ PQNGRVTLDG ELLGTTQLQA CNICSIRGKV TGQVPNEQHM  300
WNLEITNLNG TQFDPTDDVP APLGVPDFAG EVFGVLSQRN RGESNPANRA HDAVVATYSD  360
KYTPKLGLVQ IGTWNTNDVE NQPTKFTPIG LNEVANGHRF EQWTLPRYSG ALTLNMNLAP  420
AVAPLFPGER LLFFRSYVPL KGGFGNPAID CLVPQEWVQH FYQESAPSLG DVALVRYVNP  480
DTGRVLFEAK LHKGGFLTVS STSTGPVVVP ANGYFRFDSW VNQFYSLAPM GTGNGRRRFQ  540

SEQ ID NO: 18          moltype = AA  length = 540
FEATURE                Location/Qualifiers
source                 1..540
                       mol_type = protein
                       note = Norovirus
                       organism = unidentified
SEQUENCE: 18
MKMASNDAAP SNDGAAGLVP EINNEVMPLE PVAGASLATP VVGQQNIIDP WIRNNFVQAP  60
AGEFTVSPRN SPGEILLDLE LGPELNPYLA HLARMYNGHA GGMEVQIVLA GNAFTAGKII  120
FAAIPPGFPY ENLSPSQITM CPHVIIDVRQ LEPVLLPMPD IRNNFFHYNQ GNDPKLRLIA  180
MLYTPLRANN SGDDVFTVSC RVLTKPSPDF EFTFLVPPTV ESKTKQFTLP ILKISEMTNS  240
RFPVPVEMMY TARNENQVVQ PQNGRVTLDG ELLGTTPLLA VNICKFKGEV IAKNGDVRSY  300
RMDMEITNTD GTPIDPTEDT PGPIGSPDFQ GILFGVASQR NKNEQNPATR AHEANINTGG  360
DQYAPKLAQV KFFSESQDFE VHQPTVFTPV GVAGDTSHPF RQWVLPRYGG HLTNNTHLAP  420
AVAPLFPGEQ ILFFRSQIPS SGGHELGYMD CLVPQEWVQH FYQEAATAQS EVALIRFINP  480
DTGRVLFEAK LHKQGFITVA HTGDNPIVMP PNGYFRFEAW VNQFYSLAPV GTGNGRRRIQ  540

SEQ ID NO: 19          moltype = AA  length = 535
FEATURE                Location/Qualifiers
source                 1..535
```

```
                        mol_type = protein
                        note = Norovirus
                        organism = unidentified
SEQUENCE: 19
MKMASNDAAP SNDGAAGLVP EVNNETMALE PVAGASIAAP LTGQNNVIDP WIRLNFVQAP  60
NGEFTVSPRN SPGEVLLNLE LGPELNPYLA HLSRMYNGYA GGVEVQVLLA GNAFTAGKLV  120
FAAVPPHFPL ENISPGQITM FPHVIIDVRT LEPVLLPLPD VRNNFFHYNQ QNEPRMRLVA  180
MLYTPLRSNG SGDDVFTVSC RVLTRPSPDF DFNYLVPPTV ESKTKPFTLP ILTIGELTNS  240
RFPVPIDELY TSPNESLVVQ PQNGRCALDG ELQGTTQLLP TAICSFRGRI NQKVSGENHV  300
WNMQVTNIDG TPFDPTEDVP APLGTPDFSG KLFGVLSQRD HDNACRSHDA VIATNSAKFT  360
PKLGAIQIGT WEQDDVHINQ PTKFTPVGLF ESEGFNQWTL PNYSGALTLN MGLAPPVAPT  420
FPGEQILFFR SHIPLKGGVA DPVIDCLLPQ EWIQHLYQES APSQTDVALI RFTNPDTGRV  480
LFEAKLHRSG YITVANTGSR PIVVPANGYF RFDSWVNQFY SLAPMGTGNG RRRVQ       535

SEQ ID NO: 20           moltype = AA  length = 547
FEATURE                 Location/Qualifiers
source                  1..547
                        mol_type = protein
                        note = Norovirus
                        organism = unidentified
SEQUENCE: 20
MKMASNDAAP SNDGAANLVP EANNEVMALE PVVGASIAAP VVGQQNIIDP WIRENFVQAP  60
QGEFTVSPRN SPGEMLLNLE LGPELNPYLS HLSRMYNGYA GGMQVQVVLA GNAFTAGKII  120
FAAVPPHFPV ENINAAQITM CPHVIVDVRQ LEPVLLPLPD IRNRFFHYNQ ENTSRMRLVA  180
MLYTPLRANS GEDVFTVSCR VLTRPAPDFE FTFLVPPTVE SKTKPFSLPI LTLGELSNSR  240
FPAPIDMLYT DPNEGIVVQP QNGRCTLDGT LQGTTQLVPT QICAFRGTLI GQTSRSPDST  300
DSAPRRRDHP LHVQLKNLDG TQYDPTDEVP AVLGAIDFKG TVFGVASQRD VSGQQVGATR  360
AHEVHINTTD PRYTPKLGSI LMYSESDDFV TGQPVRFTPI GMGDNDWHQW ELPDYPGHLT  420
LNMNLAPAVA PAFPGERILF FRSIVPSAGG YGSGQIDCLI PQEWVQHFYQ EAAPSQSAVA  480
LIRYVNPDTG RNIFEAKLHR EGFITVANSG NNPIVVPPNG YFRFEAWVNQ FYTLTPMGTG  540
QGRRRDQ                                                           547

SEQ ID NO: 21           moltype = DNA  length = 1644
FEATURE                 Location/Qualifiers
misc_feature            1..1644
                        note = Nucleic acid sequence of human codon-optimized VP1
                         GII.6 Ohio 2012 M9T020
source                  1..1644
                        mol_type = other DNA
                        organism = synthetic construct
SEQUENCE: 21
atgaagatgg caagcaacga cgcagctccc tccaatgatg gtgccgccaa cctggtcccc  60
gaagctaata atgaggtgat ggcgttagag ccggtggttg gcgcatctat tgcagcgcct  120
gtggtcggac agcagaacat cattgatccc tggattcgcg agaacttcgt acaagctcca  180
cagggggagt tcacagtctc cccccggaac tccccgggcg agatgctgct caatctggaa  240
ctcggccctg aactaaaccc ttatctgtca cacctttcac ggatgtacaa tggctacgca  300
ggaggaatgc aagttcaggt ggtcctggcc ggcaatgctt tcaccgcggg caaaatcatc  360
tttgcggccg ttcctccaca cttccctgtc gaaaatatca acgccgccca gattactatg  420
tgcccccacg tgattgtgga tgtgcgacag ttagagccag ttctgctgcc cctgcccgac  480
atcagaaacc ggttcttcca ttacaatcaa gagaatactt cacggatgag acttgttgcg  540
atgctgtaca cccctcttcg tgcaaattcc ggcgaagacg tgttcactgt gtcttgtcga  600
gtacttaccc gacccgcccc cgatttcgaa ttcaccttcc tggttccccc tactgtggag  660
agcaagacaa aacccttcag cctcccaatc ttaacactcg gggagctgtc taattcacgc  720
ttccccgcac ctattgatat gctgtatact gaccccaacg aggggatagt ggtgcagccc  780
caaaatggac ggtgtactct cgacggcacg ctccagggca caacccaact ggtgccaacc  840
cagatttgtg cattcagggg cactttgatt gggcagacat cgagatctcc agattctact  900
gattccgcgc caaggaggag ggaccaccca ctccacgttc agttaaaaaa cctggacgga  960
acccagtacg accctacaga cgaggtcccc gctgtcctcg gagccatcga ctttaaagga  1020
actgtatttg gagtggcatc ccaaagggat gtctcggggc agcaggtggg agctacgaga  1080
gcacatgaag tccacattaa caccacagac ccaagatata ccccaaaact agggtcaatt  1140
ttaatgtatt cggaatcaga cgattttgtt acaggtcagc ccgtgcggtt taccccgatc  1200
ggaatggggg acaacgattg gcaccagtgg gaattgcccg attaccctgg acacctcacc  1260
ttgaatatga atctggcccc agccgtcgcg cccgccttcc ccggtgagcg gatcctcttt  1320
tttagaagca tagtgccctc cgcaggtggg tatggatcag ggcagattga ttgcctgatc  1380
ccccaagaat gggtacagca tttctaccag gaagcagccc ctagccagtc cgcagtagca  1440
ctgatcagat atgttaatcc tgatacggga aggaacatct tcgaagcaaa actgcaccgt  1500
gagggcttca ttaccgtcgc caacagtggt aataacccta ttgtggtgcc tcctaatgga  1560
tacttcaggt ttgaggcatg ggtgaatcag ttttatactc tgactcccat ggggacaggc  1620
caggggcgac gccgggatca gtga                                        1644

SEQ ID NO: 22           moltype = AA  length = 542
FEATURE                 Location/Qualifiers
source                  1..542
                        mol_type = protein
                        note = Norovirus
                        organism = unidentified
SEQUENCE: 22
MKMASNDAAP SNDGAASLVP EAINETMPLE PVAGASIAAP VAGQTNIIDP WIRTNFVQAP  60
NGEFTVSPRN SPGEILLNLE LGPDLNPYLA HLSRMYNGYA GGVEVQVLLA GNAFTAGKIL  120
```

-continued

```
FAAIPPNFPV DMISPAQITM LPHLIVDVRT LEPIMIPLPD VRNVFYHFNN QPQPRMRLVA  180
MLYTPLRSNG SGDDVFTVSC RVLTRPTPDF EFIYLVPPSV ESKTKPFTLP ILTISELTNS  240
RFPISIEQLY TAPNENNVVQ CQNGRCTLDG ELQGTTQLLS SAVCSYRGRT VANSGDNWDQ  300
NVLQLTYPSG ASYDPTDEVP APLGTQDFSG ILYGVLTQDN VRENTGEAKN AKGVYISTTS  360
GKFTPKIGSI GLHSITEDVR PNQQSRFTPV GVAQNENTPF QQWVLPHYAG ALALNTNLAP  420
AVAPTFPGEQ LLFFRSRVPC VQGLQGQDAF IDCLLPQEWV NHFYQEAAPS QADVALIRYV  480
NPDTGRTLFE AKLHRSGFIT VSHTGAYPLV VPPNGHFRFD SWVNQFYSLA PMGTGNGRRR  540
VQ                                                                 542

SEQ ID NO: 23          moltype = DNA  length = 1629
FEATURE                Location/Qualifiers
misc_feature           1..1629
                       note = Nucleic acid sequence of human codon-optimized VP1
                        GII.17_Kawa_2014_A0A077KVU6
source                 1..1629
                       mol_type = other DNA
                       organism = synthetic construct
SEQUENCE: 23
atgaaaatgg cttctaatga tgccgcgccc agcaatgatg gtgccgccag ccttgtgccc  60
gaagcaatta acgagacaat gcccttggag ccagtcgccg gggcttctat tgcggcccca  120
gttgctggac agacgaatat catcgatcct tggatacgga ctaattttgt tcaagctcct  180
aacggagagt tcactgtctc cccccgtaat agtcctggcg agatcctgtt gaacctcgag  240
ttggggccag atctcaatcc ttacctggct catctgtcga gaatgtacaa cgggtacgcg  300
ggggggggttg aggtgcaggt cttactggca ggtaacgcat tcacagcagg caagattctg  360
tttgcggcca tccctcctaa ttttccagtg gatatgatat ctccagcaca gattacaatg  420
ctgccccatt tgatagtgga tgtgcggaca cttgaaccta tcatgatccc tttgcccgat  480
gtccgaaatg tgttttatca tttcaacaac cagccgcagc caagaatgcg tctcgtcgcg  540
atgctgtaca ccccgttgcg gtccaacggc tctggcgatg atgttttcac agtgtcgtgt  600
cgagtgttaa cccgccctac cccagatttt gagtttatat atctagttcc cccttctgtg  660
gaaagcaaga ctaaaccctt tactcttccc attctgacta tatccgagct taccaactcc  720
cggttcccca tctcaatcga gcaactgtac actgcaccca acgagaacaa cgtagtccag  780
tgccagaacg ggagatgtac cctggacggg gagctccaag ggaccacgca actgttaagt  840
tcagccgttt gcagttacag aggcaggact gtggcgaact ctggtgataa ctgggatcaa  900
aatgtgttgc agctgactta cccatccggc gcaagctacg atccaacaga tgaggtgcca  960
gcgccccttg gcacacagga tttctcagga attctatacg gggtgcttac tcaggataat  1020
gtgcgagaaa atactggcga ggccaagaat gctaaaggag tgtatataag cacgacaagc  1080
ggtaagttta cccccaaaat tggcagtatt gggctccaca gcattactga ggacgtccgc  1140
ccaaaccagc agtctcgttt cactcccgtg ggggtggcac agaacgagaa cacacctttc  1200
cagcagtggg tcttgcccca ttatgcaggt gctttggcgc tcaatacaaa tctggcaccc  1260
gccgtagcgc cgacatttcc tggggagcaa ttgctgttct ttagaagccg cgtcccgtgt  1320
gttcagggct tgcagggcca ggacgcgttc attgattgcc tcttgcccca ggaatgggtc  1380
aaccactttt atcaggaggc agcgccctct caagcagatg tggccctgat aagatatgtg  1440
aatcccgaca caggacggac tttgtttgag gcaaaactcc accggtcagg attcattact  1500
gtgagtcaca caggagccta tccccttgtg gttccaccta atggccactt caggttcgac  1560
tcttgggtca atcagtttta ttcgctggca ccaatgggta ccgggaatgg tcgccgtcgg  1620
gtgcaatga                                                          1629

SEQ ID NO: 24          moltype = AA  length = 538
FEATURE                Location/Qualifiers
source                 1..538
                       mol_type = protein
                       note = Norovirus
                       organism = unidentified
SEQUENCE: 24
MKMASNDAAP SNDGAAGLVP EGNNETLPLE PVAGAAIAAP VTGQNNIIDP WIRTNFVQAP  60
NGEFTVSPRN SPGEILLNLE LGPDLNPYLA HLSRMYNGYA GGVEVQVLLA GNAFTAGKIL  120
FAAVPPNFPV EFLSPAQITM LPHLIVDVRT LEPIMIPLPD VRNTFFHYNN QPNSRMRLVA  180
MLYTPLRSNG SGDDVFTVSC RVLTRPTPDF EFTYLVPPSV ESKTKPFSLP ILTLSELTNS  240
RFPVPIDSLF TAQNNVLQVQ CQNGRCTLDG ELQGTTQLLP SGICAFRGRV TAETDHRDKW  300
HMQLQNLNGT TYDPTDDVPA PLGTPDFKGV VFGVASQRNV GNDAPGSTRA HEAVISTYSP  360
QFVPKLGSVN FRSNDNDFQL QPTKFTPVGI NDDGDHPFRQ WELPDYSGLL TLNMNLAPPV  420
APNFPGEQLL FFRSFVPCSG GYNQGIVDCL IPQEWIQHFY QESAPSQSDV ALIRYVNPDT  480
GRTLFEAKLH RSGYITVAHS GDYPLVVPAN GYFRFDSWVN QFYSLAPMGT GNGRRRAQ    538

SEQ ID NO: 25          moltype = DNA  length = 1617
FEATURE                Location/Qualifiers
misc_feature           1..1617
                       note = Nucleic acid sequence of human codon-optimized VP1
                        GII.17_Kawa_2014_A0A077KVU6
source                 1..1617
                       mol_type = other DNA
                       organism = synthetic construct
SEQUENCE: 25
atgaaaatgg catctaacga cgcagccccc tcaaacgatg gcgctgctgg actcgtgccg  60
gaggggaata atgagacact tccactagag ccggttgcag gcgccgctat agctgcccca  120
gtgacagggc agaataatat tatagaccct tggattcgga caaacttcgt gcaggcaccc  180
aacggcgagt ttacagtatc cccccggaac tccccaggtg agatactcct gaatcttgag  240
ctcggccctg acctcaatcc atatctggct catctgagcc gcatgtacaa tggttacgct  300
ggggggtcg aagtgcaggt cctcctggcc ggaaacgcct ttaccgctgg caaaattctg  360
```

-continued

```
tttgccgccg ttccaccaaa ctttccagtc gaattcctct ctcccgcgca aataaccatg  420
ctgccacatt tgatcgttga cgtgcggacc ctggagccaa taatgattcc cctgccggat  480
gtgcgtaaca ccttttttcca ttataacaat cagccaaact ctcggatgag acttgttgct  540
atgctgtaca cccccctgcg gagcaacggc agtggcgatg atgtgtttac cgtgagttgc  600
agagtcctga cgcgcccaac cccggacttc gagttcacct acctggtgcc cccttctgtg  660
gaatctaaga ccaaaccgtt ttcactgcca atcttaactc tctccgaact gactaacagc  720
cggtttccag tacccataga ttctcttttt accgctcaaa acaacgtact ccaagtccag  780
tgccagaacg gccgctgtac gcttgatggt gagttgcagg ggacaacaca gctactcccc  840
agtggcatct gtgcattccg gggccgcgtg accgctgaga cagaccatcg tgacaaatgg  900
cacatgcaac tccaaaactt aaacgggacc acctacgacc caaccgacga cgtccctgct  960
ccgctaggga ctcctgactt taagggggtg gtgttcggag tggcctctca gcggaatgtt  1020
gggaatgacg cccccggctc tacccgagct cacgaggccg ttatctcaac atatagcccc  1080
caatttgtgc ccaagctcgg atccgttaat tttcgtagta acgacaacga cttccaactg  1140
caaccaacga agtttacgcc agtggggatt aatgatgatg gagaccatcc tttccgccaa  1200
tgggaactac cagattattc tgggctgctc accctcaata tgaacctcgc cccacccgtg  1260
gcccctaatt tccccggtga gcagctgctg ttttttcgga gctttgtgcc atgcagtggc  1320
ggatataatc aaggcatcgt agactgcttg attccccaag agtggataca acatttttac  1380
caggaaagtg cgccctccca gtccgatgtg gccctgatac ggtacgttaa ccccgatacc  1440
ggaagaacat tattcgaagc gaaattgcac agatcagggt acattaccgt tgcacattcc  1500
ggcgattatc ccctggtggt tcccgccaac ggttacttta ggttcgatag ttgggtcaac  1560
cagttctatt cactagcccc aatgggcacc ggtaacggca gacgccgggc tcagtag     1617

SEQ ID NO: 26          moltype = AA  length = 539
FEATURE                Location/Qualifiers
source                 1..539
                       mol_type = protein
                       note = Norovirus
                       organism = unidentified
SEQUENCE: 26
MKMASNDAAP SNDGATGLVP EINTETLPLE PVAGAAIAAP VTGQNNIIDP WIRNNFVQAP  60
NGEFTVSPRN SPGEILMNLE LGPDLNPYLA HLSRMYNGYA GGVEVQVLLA GNAFTAGKIL  120
FAAVPPNFPV DMLSPAQITM LPHLIVDVRT LEPIMIPLPD VRNVFYHFNN QPAPRMRLVA  180
MLYTPLRSNG SGDDVFTVSC RVLTRPTPDF EFTYLVPPSV ESKTKPFTLP ILTIGELTNS  240
RFPAPIDQLY TSPNADVVVQ PQNGRCTLDG ELQGTTQLLT TAICSYRGMT SNPTSDYWDD  300
HLLHLVHPNG ATYDPTEDVP APFGTQDFRG ILYGMLTQNP RTSGDEAANS HGIYISSTSE  360
KFTPKLGTIG LHQVQGDIAS NQQSKFTPVG IAVNGNTPFR QWELPNYSGA LTLNTNLAPA  420
VGPNFPGEQI LFFRSNVPSV QGGQPIEIDC LIPQEWVSHF YQESAPSQSD VALVRYVNPD  480
TGRTIFEAKL HRQGFITIAA TGSNPVVVPP NGYFRFDSWV NQFYALAPMG TGNGRRRVQ   539

SEQ ID NO: 27          moltype = AA  length = 539
FEATURE                Location/Qualifiers
source                 1..539
                       mol_type = protein
                       note = Norovirus
                       organism = unidentified
SEQUENCE: 27
MKMASNDANP SDGSTANLVP EVNNEVMALE PVVGAAIAAP VAGQQNVIDP WIRNNFVQAP  60
GGEFTVSPRN APGEILWSAP LGPDLNPYLS HLARMYNGYA GGFEVQVILA GNAFTAGKVI  120
FAAVPPNFPT EGLSPSQVTM FPHIIVDVRQ LEPVLIPLPD VRNNFYHYNQ SNDSTIKLIA  180
MLYTPLKANN AGDDVFTVSC RVLTRPSPDF DFIFLVPPTV ESRTKPFTVP ILTVEEMSNS  240
RFPIPLEKLY TGPSSAFVVQ PQNGRCTTDG VLLGTTQLSA VNICTFRGDV THIAGSHDYT  300
MNLASQNWNN YDPTEEIPAP LGTPDFVGKI QGMLTQTTRE DGSTRAHKAT VSTGSVHFTP  360
KLGSVQYTTD TNNDFQTGQN TKFTPVGVIQ DGNNHQNEPQ QWVLPNYSGR TGHNVHLAPA  420
VAPTFPGEQL LFFRSTMPGC SGYPNMNLDC LLPQEWVQHF YQEAAPAQSD VALLRFVNPD  480
TGRVLFECKL HKSGYVTVAH TGPHDLVIPP NGYFRFDSWV NQFYTLAPMG NGAGRRRAL   539

SEQ ID NO: 28          moltype = AA  length = 540
FEATURE                Location/Qualifiers
source                 1..540
                       mol_type = protein
                       note = Norovirus
                       organism = unidentified
SEQUENCE: 28
MKMASNDANP SDGSTANLVP EVNNEVMALE PVVGAAIAAP VAGQQNVIDP WIRNNFVQAP  60
GGEFTVSPRN APGEILWSAP LGPDLNPYLS HLARMYNGYA GGFEVQVILA GNAFTAGKII  120
FAAVPPNFPT EGLSPSQVTM FPHIIVDVRQ LEPVLIPLPD VRNNFYHYNQ LNDPTIKLIA  180
MLYTPLRANN AGEDVFTVSC RVLTRPSPDF DFIFLVPPTV ESRTKPFTVP ILTVEEMTNS  240
RFPIPLEKLF TGPSGAFVVQ PQNGRCTTDG VLLGTTQLSP VNICTFRGDV THIAGTHNYT  300
MNLASQNWNN YDPTEEIPAP LGTPDFVGRI QGMLTQTTRG DGSTRGHKAT VSTGDVHFTP  360
KLGSIQFNTD TNNDFETGQN TKFTPVGVVQ DGNGTHQNEP QQWVLPSYSG RTGHNVHLAP  420
AVAPTFPGEQ LLFFRSTMPG CSGYPNMNLD CLLPQEWVQH FYQEAAPAQS DVALLRFVNP  480
DTGRVLFECK LHKSGYVTVA HTGQHDLVIP PNGYFRFDSW VNQFYTLAPM GNGTGRRRAL  540

SEQ ID NO: 29          moltype = AA  length = 540
FEATURE                Location/Qualifiers
source                 1..540
                       mol_type = protein
                       note = Norovirus
                       organism = unidentified
```

```
SEQUENCE: 29
MKMASNDATP SDGSTANLVP EVNNEVMALE PVVGAAIAAP VAGQQNVIDP WIRNNFVQAP  60
GGEFTVSPRN APGEILWSAP LGPDLNPYLS HLARMYNGYA GGFEVQVILA GNAFTAGKII  120
FAAVPPNFPT EVLSPSQVTM FPHIIVDVRQ LEPVLIPLPD VRNNLYHYNQ SNDPTIRLIA  180
MLYTPLRANN AGDDVFTVSC RVLTRPSPDF DFIFLVPPTV ESRTKPFSVP ILTVEEMTNS  240
RFPIPLEKLF TGPSSAFVVQ PQNGRCTTDG VLLGTTQLSP VNICTFRGDV THIAGTQNYT  300
MNLASQNWNN YDPTEEIPAP LGTPDFVGRI QGVLTQTTRR DGSTRGHKAT VSTGSVHFTP  360
KLGSVQFSTD TSNDFETGQN TRFTPVGVVQ DGSTTHQNEP QQWVLPDYSG RDSHNVHLAP  420
AVAPTFPGEQ LLFFRSTMPG CSGYPNMNLD CLLPQEWVQH FYQESAPAQS DVALLRFVNP  480
DTGRVLFECK LHKSGYVTVA HTGQHDLVIP PNGYFRFDSW VNQFYTLAPM GNGAGRRRAL  540

SEQ ID NO: 30          moltype = AA  length = 540
FEATURE                Location/Qualifiers
source                 1..540
                       mol_type = protein
                       note = Norovirus
                       organism = unidentified
SEQUENCE: 30
MKMASNDANP SDGSAANLVP EVNNEVMALE PVVGAAIAAP VAGQQNVIDP WIRNNFVQAP  60
GGEFTVSPRN APGEILWSAP LGPDLNPYLS HLARMYNGYA GGFEVQVILA GNAFTAGKII  120
FAAVPPNFPT EGLSPSQVTM FPHIIVDVRQ LEPVLIPLPD VRNNFYHYNQ SNDSTIKLIA  180
MLYTPLRANN AGEDVFTVSC RVLTRPSPDF DFIFLVPPTV ESRTKPFTVP ILTVEEMTNS  240
RFPIPLEKLF TGPSGAFVVQ PQNGRCTTDG VLLGTTQLSP VNICTFRGDV THIAGSRNYT  300
MNLASLKWNK YDPTEEIPAP LGTPDFVGKI QGVLTQTTKG DGSTRGHKAT IYTGSAPFTP  360
KLGSVQFSTD TENDFETHQN TKFTPVGVTQ DGSTTHRNEP QQWVLPSYSG RNVHNVHLAP  420
AVAPTFPGEQ LLFFRSTMPG CSGYPNMDLD CLLPQEWVQH FYQEAAPAQS DVALLRFVNP  480
DTGRVLFECK LHKSGYVTVA HTGQHDLVIP PNGYFRFDSW VNQFYTLAPM GNGTGRRRAL  540

SEQ ID NO: 31          moltype = AA  length = 540
FEATURE                Location/Qualifiers
source                 1..540
                       mol_type = protein
                       note = Norovirus
                       organism = unidentified
SEQUENCE: 31
MKMASSDANP SDGSTANLVP EVNNEVMALE PVVGAAIAAP VAGQQNVIDP WIRNNFVQAP  60
GGEFTVSPRN APGEILWSAP LGPDMNPYLS HLARMYNGYA GGFEVQVILA GNAFTAGKII  120
FAAVPPNFPT EGLSPSQVTM FPHIIVDVRQ LEPVLIPLPD VRNNFYHYNQ SNDPTIKLIA  180
MLYTPLRANN AGDDVFTVSC RVLTRPSPDF DFIFLVPPTV ESRTKPFSVP ILTVEEMTNS  240
RFPIPLEKLF TGPSSAFVVQ PQNGRCTTDG VLLGTTQLSP VNICTFRGDV THIAGSRNYT  300
MNLASQNWNS YDPTEEIPAP LGTPDFVGKI QGVLTQTTRT DGSTRGHKAT VYTGSADFSP  360
KLGRVQFATD TDNDFDANQN TKFTPVGVIQ DGNTAHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAL  540

SEQ ID NO: 32          moltype = AA  length = 536
FEATURE                Location/Qualifiers
source                 1..536
                       mol_type = protein
                       note = Norovirus
                       organism = unidentified
SEQUENCE: 32
MKMASNDATP SDDGAAGLVP EINNEVMALE PVAGASIAAP VVGQQNIIDP WIRNNFVQAP  60
AGEFTVSPRN SPGELLLDLE LGPELNPYLA HLARMYNGHA GGMEVQIVLA GNAFTAGKIL  120
FAAIPPSFPY ENLSPAQLTM CPHVIVDVRQ LEPVLLPMPD IRNVFYHYNQ NNSPKLRLVA  180
MLYTPLRANN SGDDVFTVSC RVLTRPSPDF QFTFLVPPTV ESKTKNFTLP VLRVSEMTNS  240
RFPVVLDQMY TSRNENIIVQ PQNGRCTTDG ELLGTTILQS VSICNFKGTM QAKLNEEPRY  300
QLQLTNLDGS PIDPTDDMPA PLGTPDFQAM LYGVASQRSS IDNATRAHDA QIDTAGDTFA  360
PKIGQVRFKS SSNDFDLHDP TKFTPIGVNV DDQHPFRQWS LPNYGGHLAL NNHLAPAVTP  420
LFPGEQILFF RSYIPSAGGH TDGAMDCLLP QEWVEHFYQE AAPSQSDIAL VRFINPDTGR  480
VLFEAKLHKQ GFLTIAASGD HPIVMPTNGY FRFEAWVNPF YTLAPVGTGS GRRRIQ      536

SEQ ID NO: 33          moltype = DNA  length = 1632
FEATURE                Location/Qualifiers
misc_feature           1..1632
                       note = Nucleic acid sequence of human codon-optimized VP1
                        GI.5 Siklos HUN5407 2013 HUN AHW99832
source                 1..1632
                       mol_type = other DNA
                       organism = synthetic construct
SEQUENCE: 33
atgatgatgg cctccaaaga cgctcctagc agtgctgatg gcgctaacgg tgccggccag  60
ctggtccccg aggtgaataa cgccgagcct ctccccttgg acccagtagc cggagcttca  120
acggccctag ctactgccgg acaggttaat atgattgacc cctggatttt caataatttc  180
gtgcaggccc ctcaaggcga gtttactata agccctaaca acacaccagg ggatattctg  240
ttcgacctgc agttaggccc tcatctcaac cccttcttgg cccacctgag ccagatgtac  300
aatggctggg tgggcaacat gcgagtgaga gttatcctcg cagggaacgc ctttaccgct  360
ggtaaggtga tcatttgttg cgtaccacct ggattccagt ctaggacatt aagtattgcg  420
caagctaccc tctttcctca tatcatcgcc gacgtgcgga cactagagcc catcgagatc  480
```

-continued

```
ccactggagg atgtccggaa taccctgtac cataccaacg ataatcagcc cactatgagg  540
ttactgtgca tgctgtacac gccactccgg actggtgggg gcagtggggg gaccgatgct  600
ttcgtcgttg ccggtagggt gctcacttgc ccgtcatctg actttaactt cctattcctt  660
gtgcccccaa cggtggaaca gaaaacgaga cctttttccg tacctaacat ccctttacag  720
ctcctaagca atagcagagt acctaacctg atccaatcca tggttcttag ccctgatcaa  780
gcgcagaacg tacagtttca gaacgggcgg tgcaccacag atggccagct gcttggtaca  840
actcccgtct ccgtgtctca gatacttaag tttcgcggca aggtctccgc tggatccaaa  900
gtaatcaacc tcactgagct tgatggctct ccctttctgg cgttcgaggc gcccgcccca  960
acaggctttc cagacctggg aacatccgat tggcatgtcg agatgagtct gaatagcaac  1020
tcccagtctt ctggcaatcc aatactgctc cgcgatatcc atcctaattc tagcgagttc  1080
gttccacacc tgggttctgt gtgcgtgacg gctgcaatag aggtggctgg cgactacacg  1140
ggtaccattc agtggacctc tcagccaagt aacgtgaccc ctgtgccaga cgttaacttt  1200
tggacaattc cacactacgg ctctaacttg gccgaagcat cccagcttgc ccccgttgta  1260
tatcccccag gctttggcga agcaatagtt tattttatgt ccccaatccc tggacctaac  1320
acagcacaca agccaaacct cgtcccatgc ctgctgcccc aggagttcgt gactcatttc  1380
gtttcggaac aagccccatc aatgggggag gccgccctgg tccactacgt ggatccagat  1440
accaatcgga atctgggaga attcaaactc taccctgaag gattcattac atgtgtgccc  1500
aatggaacag gaccgcagca gctcccactg aacggtgtct ttgtattcgc atcatgggtt  1560
agccggttct atcaacttaa acccgtgggg acagcttcat ctgcccgggg gcgccttggc  1620
gtgcggcgct ga                                                      1632

SEQ ID NO: 34           moltype = AA  length = 543
FEATURE                 Location/Qualifiers
source                  1..543
                        mol_type = protein
                        note = Norovirus
                        organism = unidentified
SEQUENCE: 34
MMMASKDAPS SADGANGAGQ LVPEVNNAEP LPLDPVAGAS TALATAGQVN MIDPWIFNNF  60
VQAPQGEFTI SPNNTPGDIL FDLSLGPHLN PFLAHLSQMY NGWVGNMRVR VILAGNAFTA  120
GKVIICCVPP GFQSRTLSIA QATLFPHIIA DVRTLEPIEI PLEDVRNTLY HTNDNQPTMR  180
LLCMLYTPLR TGGGSGGTDA FVVAGRVLTC PSSDFNFLFL VPPTVEQKTR PFSVPNIPLQ  240
LLSNSRVPNL IQSMVLSPDQ AQNVQFQNGR CTTDGQLLGT TPVSVSQILK FRGKVSAGSK  300
VINLTELDGS PFLAFEAPAP TGFPDLGTSD WHVEMSLNSN SQSSGNPILL RDIHPNSSEF  360
VPHLGSVCVT AAIEVAGDYT GTIQWTSQPS NVTPVPDVNF WTIPHYGSNL AEASQLAPVV  420
YPPGFGEAIV YFMSPIPGPN TAHKPNLVPC LLPQEFVTHF VSEQAPSMGE AALVHYVDPD  480
TNRNLGEFKL YPEGFITCVP NGTGPQQLPL NGVFVFASWV SRFYQLKPVG TASSARGRLG  540
VRR                                                                543

SEQ ID NO: 35           moltype = DNA  length = 1632
FEATURE                 Location/Qualifiers
misc_feature            1..1632
                        note = Nucleic acid sequence of human codon optimized VP1
                         GI.5 Siklos Q84S
source                  1..1632
                        mol_type = other DNA
                        organism = synthetic construct
SEQUENCE: 35
atgatgatgg cctccaaaga cgctcctagc agtgctgatg gcgctaacgg tgccggccag  60
ctggtccccg aggtgaataa cgccgagcct ctccccttgg acccagtagc cggagcttca  120
acggccctag ctactgccgg acaggttaat atgattgacc cctggatttt caataatttc  180
gtgcaggccc ctcaaggcga gtttactata agccctaaca acacaccagg ggatattctg  240
ttcgacctga gcttaggccc tcatctcaac cccttcttgg cccacctgag ccagatgtac  300
aatggctggg tgggcaacat gcgagtgaga gttatcctcg cagggaacgc ctttaccgct  360
ggtaaggtga tcatttgttg cgtaccacct ggattccagt ctaggacatt aagtattgcg  420
caagctaccc tctttcctca tatcatcgcc gacgtgcgga cactagagcc catcgagatc  480
ccactggagg atgtccggaa taccctgtac cataccaacg ataatcagcc cactatgagg  540
ttactgtgca tgctgtacac gccactccgg actggtgggg gcagtggggg gaccgatgct  600
ttcgtcgttg ccggtagggt gctcacttgc ccgtcatctg actttaactt cctattcctt  660
gtgcccccaa cggtggaaca gaaaacgaga cctttttccg tacctaacat ccctttacag  720
ctcctaagca atagcagagt acctaacctg atccaatcca tggttcttag ccctgatcaa  780
gcgcagaacg tacagtttca gaacgggcgg tgcaccacag atggccagct gcttggtaca  840
actcccgtct ccgtgtctca gatacttaag tttcgcggca aggtctccgc tggatccaaa  900
gtaatcaacc tcactgagct tgatggctct ccctttctgg cgttcgaggc gcccgcccca  960
acaggctttc cagacctggg aacatccgat tggcatgtcg agatgagtct gaatagcaac  1020
tcccagtctt ctggcaatcc aatactgctc cgcgatatcc atcctaattc tagcgagttc  1080
gttccacacc tgggttctgt gtgcgtgacg gctgcaatag aggtggctgg cgactacacg  1140
ggtaccattc agtggacctc tcagccaagt aacgtgaccc ctgtgccaga cgttaacttt  1200
tggacaattc cacactacgg ctctaacttg gccgaagcat cccagcttgc ccccgttgta  1260
tatcccccag gctttggcga agcaatagtt tattttatgt ccccaatccc tggacctaac  1320
acagcacaca agccaaacct cgtcccatgc ctgctgcccc aggagttcgt gactcatttc  1380
gtttcggaac aagccccatc aatgggggag gccgccctgg tccactacgt ggatccagat  1440
accaatcgga atctgggaga attcaaactc taccctgaag gattcattac atgtgtgccc  1500
aatggaacag gaccgcagca gctcccactg aacggtgtct ttgtattcgc atcatgggtt  1560
agccggttct atcaacttaa acccgtgggg acagcttcat ctgcccgggg gcgccttggc  1620
gtgcggcgct ga                                                      1632

SEQ ID NO: 36           moltype = AA  length = 543
FEATURE                 Location/Qualifiers
```

```
source                  1..543
                        mol_type = protein
                        note = Norovirus
                        organism = unidentified
SEQUENCE: 36
MMMASKDAPS SADGANGAGQ LVPEVNNAEP LPLDPVAGAS TALATAGQVN MIDPWIFNNF  60
VQAPQGEFTI SPNNTPGDIL FDLQLGPHLN PFLLHLSQMY NGWVGNMRVR VILAGNAFTA  120
GKVIICCVPP GFQSRTLSIA QATLFPHIIA DVRTLEPIEI PLEDVRNTLY HTNDNQPTMR  180
LLCMLYTPLR TGGGSGGTDA FVVAGRVLTC PSSDFNFLFL VPPTVEQKTR PFSVPNIPLQ  240
LLSNSRVPNL IQSMVLSPDQ AQNVQFQNGR CTTDGQLLGT TPVSVSQILK FRGKVSAGSK  300
VINLTELDGS PFLAFEAPAP TGFPDLGTSD WHVEMSLNSN SQSSGNPILL RDIHPNSSEF  360
VPHLGSVCVT AAIEVAGDYT GTIQWTSQPS NVTPVPDVNF WTIPHYGSNL AEASQLAPVV  420
YPPGFGEAIV YFMSPIPGPN TAHKPNLVPC LLPQEFVTHF VSEQAPSMGE AALVHYVDPD  480
TNRNLGEFKL YPEGFITCVP NGTGPQQLPL NGVFVFASWV SRFYQLKPVG TASSARGRLG  540
VRR                                                               543

SEQ ID NO: 37           moltype = DNA  length = 1632
FEATURE                 Location/Qualifiers
misc_feature            1..1632
                        note = Nucleic acid sequence of human codon optimized VP1
                         GI.5 siklos A94L
source                  1..1632
                        mol_type = other DNA
                        organism = synthetic construct
SEQUENCE: 37
atgatgatgg cctccaaaga cgctcctagc agtgctgatg gcgctaacgg tgccggccag  60
ctggtccccg aggtgaataa cgccgagcct ctccccttgg acccagtagc cggagcttca  120
acggccctag ctactgccgg acaggttaat atgattgacc cctggatttt caataatttc  180
gtgcaggccc ctcaaggcga gtttactata agccctaaca acacaccagg ggatattctg  240
ttcgacctgc agttaggccc tcatctcaac cccttcttgc tccacctgag ccagatgtac  300
aatggctggg tgggcaacat gcgagtgaga gttatcctcg cagggaacgc ctttaccgct  360
ggtaaggtga tcatttgttg cgtaccacct ggattccagt ctaggacatt aagtattgcg  420
caagctaccc tctttcctca tatcatcgcc gacgtgcgga cactagagcc catcgagatc  480
ccactggagg atgtccggaa taccctgtac cataccaacg ataatcagcc cactatgagg  540
ttactgtgca tgctgtacac gccactccgg actggtgggg gcagtggggg gaccgatgct  600
ttcgtcgttg ccggtagggt gctcacttgc ccgtcatctg actttaactt cctattcctt  660
gtgcccccaa cggtggaaca gaaaacgaga cctttttccg tacctaacat ccctttacag  720
ctcctaagca atagcagagt acctaacctg atccaatcca tggttcttag ccctgatcaa  780
gcgcagaacg tacagtttca gaacgggcgg tgcaccacag atggccagct gcttggtaca  840
actcccgtct ccgtgtctca gatacttaag tttcgcggca aggtctccgc tggatccaaa  900
gtaatcaacc tcactgagct tgatggctct ccctttctgg cgttcgaggc gcccgcccca  960
acaggctttc cagacctggg aacatccgat tggcatgtcg agatgagtct gaatagcaac  1020
tcccagtctt ctggcaatcc aatactgctc cgcgatatcc atcctaattc tagcgagttc  1080
gttccacacc tgggttctgt gtgcgtgacg gctgcaatag aggtggctgg cgactacacg  1140
ggtaccattc agtggacctc tcagccaagt aacgtgaccc ctgtgccaga cgttaacttt  1200
tggacaattc cacactacgg ctctaacttg gccgaagcat cccagcttgc ccccgttgta  1260
tatcccccag gctttggcga agcaatagtt tattttatgt ccccaatccc tggacctaac  1320
acagcacaca agccaaacct cgtcccatgc ctgctgcccc aggagttcgt gactcatttc  1380
gtttcggaac aagccccatc aatgggggag gccgccctgg tccactacgt ggatccagat  1440
accaatcgga atctgggaga attcaaactc taccctgaag gattcattac atgtgtgccc  1500
aatggaacag gaccgcagca gctcccactg aacggtgtct ttgtattcgc atcatgggtt  1560
agccggttct atcaacttaa acccgtgggg acagcttcat ctgcccgggg gcgccttggc  1620
gtgcggcgct ga                                                     1632

SEQ ID NO: 38           moltype = AA  length = 543
FEATURE                 Location/Qualifiers
source                  1..543
                        mol_type = protein
                        note = Norovirus
                        organism = unidentified
SEQUENCE: 38
MMMASKDAPS SADGANGAGQ LVPEVNNAEP LPLDPVAGAS TALATAGQVN MIDPWIFNNF  60
VQAPQGEFTI SPNNTPGDIL FDLSLGPHLN PFLLHLSQMY NGWVGNMRVR VILAGNAFTA  120
GKVIICCVPP GFQSRTLSIA QATLFPHIIA DVRTLEPIEI PLEDVRNTLY HTNDNQPTMR  180
LLCMLYTPLR TGGGSGGTDA FVVAGRVLTC PSSDFNFLFL VPPTVEQKTR PFSVPNIPLQ  240
LLSNSRVPNL IQSMVLSPDQ AQNVQFQNGR CTTDGQLLGT TPVSVSQILK FRGKVSAGSK  300
VINLTELDGS PFLAFEAPAP TGFPDLGTSD WHVEMSLNSN SQSSGNPILL RDIHPNSSEF  360
VPHLGSVCVT AAIEVAGDYT GTIQWTSQPS NVTPVPDVNF WTIPHYGSNL AEASQLAPVV  420
YPPGFGEAIV YFMSPIPGPN TAHKPNLVPC LLPQEFVTHF VSEQAPSMGE AALVHYVDPD  480
TNRNLGEFKL YPEGFITCVP NGTGPQQLPL NGVFVFASWV SRFYQLKPVG TASSARGRLG  540
VRR                                                               543

SEQ ID NO: 39           moltype = DNA  length = 1632
FEATURE                 Location/Qualifiers
misc_feature            1..1632
                        note = Nucleic acid sequence of human codon optimized VP1
                         GI.5 siklos Q84S plus sign A94L
source                  1..1632
                        mol_type = other DNA
```

```
                        organism = synthetic construct
SEQUENCE: 39
atgatgatgg cctccaaaga cgctcctagc agtgctgatg gcgctaacgg tgccggccag  60
ctggtccccg aggtgaataa cgccgagcct ctccccttgg acccagtagc cggagcttca  120
acggccctag ctactgccgg acaggttaat atgattgacc cctggatttt caataatttc  180
gtgcaggccc ctcaaggcga gtttactata agccctaaca acacaccagg ggatattctg  240
ttcgacctga gcttaggccc tcatctcaac cccttcttgc tccacctgag ccagatgtac  300
aatggctggg tgggcaacat gcgagtgaga gttatcctcg cagggaacgc ctttaccgct  360
ggtaaggtga tcatttgttg cgtaccacct ggattccagt ctaggacatt aagtattgcg  420
caagctaccc tctttcctca tatcatcgcc gacgtgcgga cactagagcc catcgagatc  480
ccactggagg atgtccggaa taccctgtac cataccaacg ataatcagcc cactatgagg  540
ttactgtgca tgctgtacac gccactccgg actggtgggg gcagtggggg gaccgatgct  600
ttcgtcgttg ccggtagggt gctcacttgc ccgtcatctg actttaactt cctattcctt  660
gtgcccccaa cggtggaaca gaaaacgaga cctttttccg tacctaacat ccctttacag  720
ctcctaagca atagcagagt acctaacctg atccaatcca tggttcttag ccctgatcaa  780
gcgcagaacg tacagtttca gaacgggcgg tgcaccacag atggccagct gcttggtaca  840
actcccgtct ccgtgtctca gatacttaag tttcgcggca aggtctccgc tggatccaaa  900
gtaatcaacc tcactgagct tgatggctct ccctttctgg cgttcgaggc gcccgcccca  960
acaggctttc cagacctggg aacatccgat tggcatgtcg agatgagtct gaatagcaac  1020
tcccagtctt ctggcaatcc aatactgctc cgcgatatcc atcctaattc tagcgagttc  1080
gttccacacc tgggttctgt gtgcgtgacg gctgcaatag aggtggctgg cgactacacg  1140
ggtaccattc agtggacctc tcagccaagt aacgtgaccc ctgtgccaga cgttaacttt  1200
tggacaattc cacactacgg ctctaacttg gccgaagcat cccagcttgc ccccgttgta  1260
tatcccccag gctttggcga agcaatagtt tattttatgt ccccaatccc tggacctaac  1320
acagcacaca agccaaacct cgtcccatgc ctgctgcccc aggagttcgt gactcatttc  1380
gtttcggaac aagccccatc aatgggggag gccgccctgg tccactacgt ggatccagat  1440
accaatcgga atctgggaga attcaaactc taccctgaag gattcattac atgtgtgccc  1500
aatggaacag gaccgcagca gctcccactg aacggtgtct ttgtattcgc atcatgggtt  1560
agccggttct atcaacttaa acccgtgggg acagcttcat ctgcccgggg gcgccttggc  1620
gtgcggcgct ga                                                     1632

SEQ ID NO: 40           moltype = DNA  length = 1629
FEATURE                 Location/Qualifiers
misc_feature            1..1629
                        note = Nucleic acid sequence of human codon-optimized VP1
                         GII.2 CGMH47 2011 TW AGT39206
source                  1..1629
                        mol_type = other DNA
                        organism = synthetic construct
SEQUENCE: 40
atgaagatgg catccaacga cgccgcaccc agcacagacg gagctgccgg attggtaccc  60
gagtctaata acgaggtgat ggccttggag cctgttgcag gggctgccct cgcagctcct  120
gtgaccgggc agacaaatat catcgatcct tggattagag ctaatttcgt gcaagcccca  180
aatggggagt ttacggtcag ccctagaaat agccctgggg aagtgctcct caatctcgag  240
ctgggaccag aacttaatcc gtacctggct cacctggccc ggatgtacaa tggatatgca  300
ggagggatgg aggtgcaggt tatgctggct ggcaatgcct ttacagcagg caaactcgtt  360
ttcgcagccg tccctcccca cttcccagtt gaaaatcttt cccctcagca gattaccatg  420
tttccccatg tcatcatcga tgtgcgtacc ctggaacctg tgctgttgcc tttaccagac  480
gtgcggaata atttctttca ctataatcag aaggatgacc caaaaatgcg gatcgttgcg  540
atgctttata ctcccctgcg tagcaatggt agtggggatg acgtttttac agtgagttgt  600
cgggtactaa ctcgcccttc accagacttc gactttacgt acttggtgcc tcccactgtc  660
gaaagcaaaa ctaagccatt cacacttccc atcctcaccc tcggagaact ctcgaactcc  720
cgcttccctg tttcaattga tcagatgtac acgtctccaa atgaagtcat ttctgtgcag  780
tgtcagaacg gcaggtgcac cttagacggt gaactgcagg ggacaacgca gttgcaggtc  840
agtggaattt gcgcctttaa gggcgaagtg acagctcacc tccacgacaa cgatcatctc  900
tacaatgtta ctattactaa tctcaatgga agtcctttcg acccctcgga agatattccc  960
gctccactcg gagtacctga ctttcaggga cgcgtcttcg gcgtgatatc acaacgagat  1020
aagcataaca cacccggaca taatgagcca gccaatagag cccacgacgc agtcgttccg  1080
acctatacgg ctcagtacac cccaaagctc ggccagatac aaatcgggac ttggcagacc  1140
gatgacctca ctgtgaatca acctgtgaaa ttcactccag taggtctgaa tgatacagac  1200
cactttaacc agtgggtggt ccctagatac gccggagcct tgaacctaaa cactaacctt  1260
gccccttccg ttgcacctgt gtttccgggg gagcggttgc tcttctttag aagctatatt  1320
cctctgaagg gcgggtatgg tactccagca atcgactgcc tgctacctca ggagtgggtt  1380
caacatttct atcaagaggc cgcacctagt atgagcgagg tggctttggt cagatacatc  1440
aatccagaca caggaagagc actgttcgag gccaagctgc acagagccgg cttcatgacc  1500
gtctcatcca atacatccgc acccgtagta gtccccgcca acgggtactt cagattcgac  1560
agttgggtga atcagtttta ctcgttggcc cccatgggca cagggaacgg tcgccgacgg  1620
atccagtaa                                                         1629

SEQ ID NO: 41           moltype = AA  length = 542
FEATURE                 Location/Qualifiers
source                  1..542
                        mol_type = protein
                        note = Norovirus
                        organism = unidentified
SEQUENCE: 41
MKMASNDAAP STDGAAGLVP ESNNEVMALE PVAGAALAAP VTGQTNIIDP WIRANFVQAP  60
NGEFTVSPRN SPGEVLLNLE LGPELNPYLL HLARMYNGYA GGMEVQVMLA GNAFTAGKLV  120
FAAVPPHFPV ENLSPQQITM FPHVIIDVRT LEPVLLPLPD VRNNFFHYNQ KDDPKMRIVA  180
```

-continued

```
MLYTPLRSNG SGDDVFTVSC RVLTRPSPDF DFTYLVPPTV ESKTKPFTLP ILTLGELSNS  240
RFPVSIDQMY TSPNEVISVQ CQNGRCTLDG ELQGTTQLQV SGICAFKGEV TAHLHDNDHL  300
YNVTITNLNG SPFDPSEDIP APLGVPDFQG RVFGVISQRD KHNTPGHNEP ANRAHDAVVP  360
TYTAQYTPKL GQIQIGTWQT DDLTVNQPVK FTPVGLNDTD HFNQWVVPRY AGALNLNTNL  420
APSVAPVFPG ERLLFFRSYI PLKGGYGTPA IDCLLPQEWV QHFYQEAAPS MSEVALVRYI  480
NPDTGRALFE AKLHRAGFMT VSSNTSAPVV VPANGYFRFD SWVNQFYSLA PMGTGNGRRR  540
IQ                                                                542

SEQ ID NO: 42          moltype = DNA  length = 1629
FEATURE                Location/Qualifiers
misc_feature           1..1629
                       note = Nucleic acid sequence of human codon optimized VP1
                        GII.2 CGMH47 A90L
source                 1..1629
                       mol_type = other DNA
                       organism = synthetic construct
SEQUENCE: 42
atgaagatgg catccaacga cgccgcaccc agcacagacg gagctgccgg attggtaccc  60
gagtctaata acgaggtgat ggccttggag cctgttgcag gggctgccct cgcagctcct  120
gtgaccgggc agacaaatat catcgatcct tggattagag ctaatttcgt gcaagcccca  180
aatggggagt ttacggtcag ccctagaaat agccctgggg aagtgctcct caatctcgag  240
ctgggaccag aacttaatcc gtacctgctc cacctggccc ggatgtacaa tggatatgca  300
ggagggatgg aggtgcaggt tatgctggct ggcaatgcct ttacagcagg caaactcgtt  360
ttcgcagccg tccctcccca cttcccagtt gaaaatcttt cccctcagca gattaccatg  420
tttccccatg tcatcatcga tgtgcgtacc ctggaacctg tgctgttgcc tttaccagac  480
gtgcggaata atttctttca ctataatcag aaggatgacc caaaaatgcg gatcgttgcg  540
atgctttata ctcccctgcg tagcaatggt agtggggatg acgtttttac agtgagttgt  600
cgggtactaa ctcgcccttc accagacttc gactttacgt acttggtgcc tcccactgtc  660
gaaagcaaaa ctaagccatt cacacttccc atcctcaccc tcggagaact ctcgaactcc  720
cgcttccctg tttcaattga tcagatgtac acgtctccaa atgaagtcat ttctgtgcag  780
tgtcagaacg gcaggtgcac cttagacggt gaactgcagg ggacaacgca gttgcaggtc  840
agtggaattt gcgcctttaa gggcgaagtg acagctcacc tccacgacaa cgatcatctc  900
tacaatgtta ctattactaa tctcaatgga agtcctttcg acccctcgga agatattccc  960
gctccactcg gagtacctga ctttcaggga cgcgtcttcg gcgtgatatc acaacgagat  1020
aagcataaca cacccggaca taatgagcca gccaatagag cccacgacgc agtcgttccg  1080
acctatacgg ctcagtacac cccaaagctc ggccagatac aaatcgggac ttggcagacc  1140
gatgacctca ctgtgaatca acctgtgaaa ttcactccag taggtctgaa tgatacagac  1200
cactttaacc agtgggtggt ccctagatac gccggagcct tgaacctaaa cactaacctt  1260
gcccccttccg ttgcacctgt gtttccgggg gagcggttgc tcttctttag aagctatatt  1320
cctctgaagg gcgggtatgg tactccagca atcgactgcc tgctacctca ggagtgggtt  1380
caacatttct atcaagaggc cgcacctagt atgagcgagg tggctttggt cagatacatc  1440
aatccagaca caggaagagc actgttcgag gccaagctgc acagagccgg cttcatgacc  1500
gtctcatcca atacatccgc acccgtagta gtccccgcca acgggtactt cagattcgac  1560
agttgggtga atcagtttta ctcgttggcc cccatgggca cagggaacgg tcgccgacgg  1620
atccagtaa                                                         1629

SEQ ID NO: 43          moltype = AA  length = 542
FEATURE                Location/Qualifiers
source                 1..542
                       mol_type = protein
                       note = Norovirus
                       organism = unidentified
SEQUENCE: 43
MKMASNDAAP STDGAAGLVP ESNNEVMALE PVAGAALAAP VTGQTNIIDP WIRANFVQAP  60
NGEFTVSPRN SPGEVLLNLS LGPELNPYLL HLARMYNGYA GGMEVQVMLA GNAFTAGKLV  120
FAAVPPHFPV ENLSPQQITM FPHVIIDVRT LEPVLLPLPD VRNNFFHYNQ KDDPKMRIVA  180
MLYTPLRSNG SGDDVFTVSC RVLTRPSPDF DFTYLVPPTV ESKTKPFTLP ILTLGELSNS  240
RFPVSIDQMY TSPNEVISVQ CQNGRCTLDG ELQGTTQLQV SGICAFKGEV TAHLHDNDHL  300
YNVTITNLNG SPFDPSEDIP APLGVPDFQG RVFGVISQRD KHNTPGHNEP ANRAHDAVVP  360
TYTAQYTPKL GQIQIGTWQT DDLTVNQPVK FTPVGLNDTD HFNQWVVPRY AGALNLNTNL  420
APSVAPVFPG ERLLFFRSYI PLKGGYGTPA IDCLLPQEWV QHFYQEAAPS MSEVALVRYI  480
NPDTGRALFE AKLHRAGFMT VSSNTSAPVV VPANGYFRFD SWVNQFYSLA PMGTGNGRRR  540
IQ                                                                542

SEQ ID NO: 44          moltype = DNA  length = 1629
FEATURE                Location/Qualifiers
misc_feature           1..1629
                       note = Nucleic acid sequence of human codon optimized VP1
                        GII.2 CGMH47 E80S plus sign A90L
source                 1..1629
                       mol_type = other DNA
                       organism = synthetic construct
SEQUENCE: 44
atgaagatgg catccaacga cgccgcaccc agcacagacg gagctgccgg attggtaccc  60
gagtctaata acgaggtgat ggccttggag cctgttgcag gggctgccct cgcagctcct  120
gtgaccgggc agacaaatat catcgatcct tggattagag ctaatttcgt gcaagcccca  180
aatggggagt ttacggtcag ccctagaaat agccctgggg aagtgctcct caatctcagc  240
ctgggaccag aacttaatcc gtacctgctc cacctggccc ggatgtacaa tggatatgca  300
ggagggatgg aggtgcaggt tatgctggct ggcaatgcct ttacagcagg caaactcgtt  360
```

```
ttcgcagccg tccctcccca cttcccagtt gaaaatcttt cccctcagca gattaccatg  420
tttccccatg tcatcatcga tgtgcgtacc ctggaacctg tgctgttgcc tttaccagac  480
gtgcggaata atttctttca ctataatcag aaggatgacc caaaaatgcg gatcgttgcg  540
atgctttata ctcccctgcg tagcaatggt agtggggatg acgtttttac agtgagttgt  600
cgggtactaa ctcgcccttc accagacttc gactttacgt acttggtgcc tcccactgtc  660
gaaagcaaaa ctaagccatt cacacttccc atcctcaccc tcggagaact ctcgaactcc  720
cgcttccctg tttcaattga tcagatgtac acgtctccaa atgaagtcat ttctgtgcag  780
tgtcagaacg gcaggtgcac cttagacggt gaactgcagg ggacaacgca gttgcaggtc  840
agtggaattt gcgcctttaa gggcgaagtg acagctcacc tccacgacaa cgatcatctc  900
tacaatgtta ctattactaa tctcaatgga agtcctttcg acccctcgga agatattccc  960
gctccactcg gagtacctga ctttcaggga cgcgtcttcg gcgtgatatc acaacgagat  1020
aagcataaca cacccggaca taatgagcca gccaatagag cccacgacgc agtcgttccg  1080
acctatacgg ctcagtacac cccaaagctc ggccagatac aaatcgggac ttggcagacc  1140
gatgacctca ctgtgaatca acctgtgaaa ttcactccag taggtctgaa tgatacagac  1200
cactttaacc agtgggtggt ccctagatac gccggagcct tgaacctaaa cactaacctt  1260
gccccttccg ttgcacctgt gtttccgggg gagcggttgc tcttctttag aagctatatt  1320
cctctgaagg gcgggtatgg tactccagca atcgactgcc tgctacctca ggagtgggtt  1380
caacatttct atcaagaggc cgcacctagt atgagcgagg tggctttggt cagatacatc  1440
aatccagaca caggaagagc actgttcgag gccaagctgc acagagccgg cttcatgacc  1500
gtctcatcca atacatccgc acccgtagta gtccccgcca acgggtactt cagattcgac  1560
agttgggtga atcagtttta ctcgttggcc cccatgggca cagggaacgg tcgccgacgg  1620
atccagtaa                                                         1629
```

```
SEQ ID NO: 45          moltype = DNA  length = 1647
FEATURE                Location/Qualifiers
misc_feature           1..1647
                       note = Nucleic acid sequence of human codon-optimized VP1
                        GII.3_Jingzhou_2013402_CHN AGX01095
source                 1..1647
                       mol_type = other DNA
                       organism = synthetic construct
SEQUENCE: 45
atgaaaatgg cttccaacga tgcagcaccc tctaatgatg gcgctgccgg acttgtgccg  60
gagattagct ctgaggctat ggccctagaa ccagtagccg gggcagccat agctgcccca  120
ctgactggcc agcagaatat cattgacccc tggataatga acaatttcgt gcaggcaccg  180
gggggagaat tcacggtctc tcctcgaaac tcccccgggg aggttctctt gaatttggaa  240
ctgggccctg aaattaatcc ttatctggcc catctagccc gaatgtacaa cggctacgcc  300
ggaggtttcg aggtccaggt ggtgctcgct ggtaacgcct tcacagctgg caagatcatt  360
tttgcagcaa tccctccaaa cttccctatc gataatctta gtgccgccca gatcacaatg  420
tgccctcacg ttatcgtaga tgtgaggcag ctggaacctg tcaatctccc aatgcccgac  480
gtgcgcaaca acttctttca ctataaccag ggatctgact cccgccttcg ccttatcgct  540
atgctgtaca cccctctgag ggctaacaat tccggagatg acgttttcac tgtgagttgt  600
cgagtcctga cacgtccatc tcctgacttt agctttaatt tcctcgtgcc ccccacagtg  660
gaatccaaaa ctaagccatt ctctctgcca attcttacca ttagcgaaat gtcgaatagt  720
aggttccccgg tgcccataga ttcactgcat accagtccaa cagaaaacat cgtcgtacag  780
tgtcagaacg gacgcgtgac tctcgacggg gagcttatgg gcactaccca gctgctgccc  840
agccagatat gcgccttccg cggcacactg actagaagca cttcgcgtgc ttctgaccag  900
gcagatacag ctacaccaag gctgttcaat tattattggc atatacaact cgataatctg  960
aatggcactc cttatgaccc agccgaggac atccccgccc cacttggcac cccggacttt  1020
agagggaagg tctttggagt ggcttctcaa agaaatcccg acgcaaccac ccgggcccac  1080
gaggccaaaa tcgatactac atcagggcgt ttcaccccta agttaggcag tctggagata  1140
tctaccgaaa gtggagattt cgatcagaac cagccaaccc ggtttacccc cgtgggaatc  1200
ggggttgacc acgaaccgga tttccagcag tgggctctgc ctgattacgc aggccagttc  1260
acacataaca tgaatcttgc ccccgctgtg gcccccaact tcccgggaga acaacttctg  1320
tttttcagga gccaactgcc ttccagcggc ggccgatcta acgggatttt ggactgtctc  1380
gtgccccagg aatgggtgca gcatttttac caggagtccg cgccctccca gacgcaggtg  1440
gctctggtta gatatgtcaa tcccgacacc ggcagggtgc tatttgaggc aaagctgcac  1500
aagcttcgct ttatgactat cgctaagagc ggtgattcgc ctattacagt gccccccaac  1560
ggatacttca gatttgagag ttgggtgaac ccattctata ccctggcccc catgggtaca  1620
ggcaatggca gacggcggat ccagtaa                                     1647
```

```
SEQ ID NO: 46          moltype = AA  length = 548
FEATURE                Location/Qualifiers
source                 1..548
                       mol_type = protein
                       note = Norovirus
                       organism = unidentified
SEQUENCE: 46
MKMASNDAAP SNDGAAGLVP EISSEAMALE PVAGAAIAAP LTGQQNIIDP WIMNNFVQAP  60
GGEFTVSPRN SPGEVLLNLS LGPEINPYLA HLARMYNGYA GGFEVQVVLA GNAFTAGKII  120
FAAIPPNFPI DNLSAAQITM CPHVIVDVRQ LEPVNLPMPD VRNNFFHYNQ GSDSRLRLIA  180
MLYTPLRANN SGDDVFTVSC RVLTRPSPDF SFNFLVPPTV ESKTKPFSLP ILTISEMSNS  240
RFPVPIDSLH TSPTENIVVQ CQNGRVTLDG ELMGTTQLLP SQICAFRGTL TRSTSRASDQ  300
ADTATPRLFN YYWHIQLDNL NGTPYDPAED IPAPLGTPDF RGKVFGVASQ RNPDATTRAH  360
EAKIDTTSGR FTPKLGSLEI STESGDFDQN QPTRFTPVGI GVDHEPDFQQ WALPDYAGQF  420
THNMNLAPAV APNFPGEQLL FFRSQLPSSG GRSNGILDCL VPQEWVQHFY QESAPSQTQV  480
ALVRYVNPDT GRVLFEAKLH KLRFMTIAKS GDSPITVPPN GYFRFESWVN PFYTLAPMGT  540
GNGRRRIQ                                                          548
```

```
SEQ ID NO: 47           moltype = DNA  length = 1647
FEATURE                 Location/Qualifiers
misc_feature            1..1647
                        note = Nucleic acid sequence of human codon optimized
                         VP1_GII.3_Jing_E80S
source                  1..1647
                        mol_type = other DNA
                        organism = synthetic construct
SEQUENCE: 47
atgaaaatgg cttccaacga tgcagcaccc tctaatgatg gcgctgccgg acttgtgccg  60
gagattagct ctgaggctat ggccctagaa ccagtagccg gggcagccat agctgcccca  120
ctgactggcc agcagaatat cattgacccc tggataatga acaatttcgt gcaggcaccg  180
gggggagaat tcacggtctc tcctcgaaac tcccccgggg aggttctctt gaatttgagc  240
ctgggccctg aaattaatcc ttatctggcc catctagccc gaatgtacaa cggctacgcc  300
ggaggtttcg aggtccaggt ggtgctcgct ggtaacgcct tcacagctgg caagatcatt  360
tttgcagcaa tccctccaaa cttccctatc gataatctta gtgccgccca gatcacaatg  420
tgccctcacg ttatcgtaga tgtgaggcag ctggaacctg tcaatctccc aatgcccgac  480
gtgcgcaaca acttctttca ctataaccag ggatctgact cccgccttcg ccttatcgct  540
atgctgtaca cccctctgag ggctaacaat tccggagatg acgttttcac tgtgagttgt  600
cgagtcctga cacgtccatc tcctgacttt agctttaatt tcctcgtgcc ccccacagtg  660
gaatccaaaa ctaagccatt ctctctgcca attcttacca ttagcgaaat gtcgaatagt  720
aggttcccgg tgcccataga ttcactgcat accagtccaa cagaaaacat cgtcgtacag  780
tgtcagaacg gacgcgtgac tctcgacggg gagcttatgg gcactaccca gctgctgccc  840
agccagatat gcgccttccg cggcacactg actagaagca cttcgcgtgc ttctgaccag  900
gcagatacag ctacaccaag gctgttcaat tattattggc atatacaact cgataatctg  960
aatggcactc cttatgaccc agccgaggac atccccgccc cacttggcac cccggacttt  1020
agagggaagg tctttggagt ggcttctcaa agaaatcccg acgcaaccac ccgggcccac  1080
gaggccaaaa tcgatactac atcagggcgt ttcaccccta agttaggcag tctggagata  1140
tctaccgaaa gtggagattt cgatcagaac cagccaaccc ggtttacccc cgtgggaatc  1200
ggggttgacc acgaaccgga tttccagcag tgggctctgc ctgattacgc aggccagttc  1260
acacataaca tgaatcttgc ccccgctgtg gcccccaact tcccgggaga acaacttctg  1320
tttttcagga gccaactgcc ttccagcggc ggccgatcta acgggatttt ggactgtctc  1380
gtgccccagg aatgggtgca gcatttttac caggagtccg cgccctccca gacgcaggtg  1440
gctctggtta gatatgtcaa tcccgacacc ggcagggtgc tatttgaggc aaagctgcac  1500
aagcttcgct ttatgactat cgctaagagc ggtgattcgc ctattacagt gccccccaac  1560
ggatacttca gatttgagag ttgggtgaac ccattctata ccctggcccc catgggtaca  1620
ggcaatggca gacggcggat ccagtaa                                     1647

SEQ ID NO: 48           moltype = AA  length = 548
FEATURE                 Location/Qualifiers
source                  1..548
                        mol_type = protein
                        note = Norovirus
                        organism = unidentified
SEQUENCE: 48
MKMASNDAAP SNDGAAGLVP EISSEAMALE PVAGAAIAAP LTGQQNIIDP WIMNNFVQAP  60
GGEFTVSPRN SPGEVLLNLE LGPEINPYLL HLARMYNGYA GGFEVQVVLA GNAFTAGKII  120
FAAIPPNFPI DNLSAAQITM CPHVIVDVRQ LEPVNLPMPD VRNNFFHYNQ GSDSRLRLIA  180
MLYTPLRANN SGDDVFTVSC RVLTRPSPDF SFNFLVPPTV ESKTKPFSLP ILTISEMSNS  240
RFPVPIDSLH TSPTENIVVQ CQNGRVTLDG ELMGTTQLLP SQICAFRGTL TRSTSRASDQ  300
ADTATPRLFN YYWHIQLDNL NGTPYDPAED IPAPLGTPDF RGKVFGVASQ RNPDATTRAH  360
EAKIDTTSGR FTPKLGSLEI STESGDFDQN QPTRFTPVGI GVDHEPDFQQ WALPDYAGQF  420
THNMNLAPAV APNFPGEQLL FFRSQLPSSG GRSNGILDCL VPQEWVQHFY QESAPSQTQV  480
ALVRYVNPDT GRVLFEAKLH KLRFMTIAKS GDSPITVPPN GYFRFESWVN PFYTLAPMGT  540
GNGRRRIQ                                                          548

SEQ ID NO: 49           moltype = DNA  length = 1647
FEATURE                 Location/Qualifiers
misc_feature            1..1647
                        note = Nucleic acid sequence of human codon optimized
                         VP1_GII.3_Jing_A90L
source                  1..1647
                        mol_type = other DNA
                        organism = synthetic construct
SEQUENCE: 49
atgaaaatgg cttccaacga tgcagcaccc tctaatgatg gcgctgccgg acttgtgccg  60
gagattagct ctgaggctat ggccctagaa ccagtagccg gggcagccat agctgcccca  120
ctgactggcc agcagaatat cattgacccc tggataatga acaatttcgt gcaggcaccg  180
gggggagaat tcacggtctc tcctcgaaac tcccccgggg aggttctctt gaatttggaa  240
ctgggccctg aaattaatcc ttatctgctc catctagccc gaatgtacaa cggctacgcc  300
ggaggtttcg aggtccaggt ggtgctcgct ggtaacgcct tcacagctgg caagatcatt  360
tttgcagcaa tccctccaaa cttccctatc gataatctta gtgccgccca gatcacaatg  420
tgccctcacg ttatcgtaga tgtgaggcag ctggaacctg tcaatctccc aatgcccgac  480
gtgcgcaaca acttctttca ctataaccag ggatctgact cccgccttcg ccttatcgct  540
atgctgtaca cccctctgag ggctaacaat tccggagatg acgttttcac tgtgagttgt  600
cgagtcctga cacgtccatc tcctgacttt agctttaatt tcctcgtgcc ccccacagtg  660
gaatccaaaa ctaagccatt ctctctgcca attcttacca ttagcgaaat gtcgaatagt  720
aggttcccgg tgcccataga ttcactgcat accagtccaa cagaaaacat cgtcgtacag  780
tgtcagaacg gacgcgtgac tctcgacggg gagcttatgg gcactaccca gctgctgccc  840
```

-continued

```
agccagatat gcgccttccg cggcacactg actagaagca cttcgcgtgc ttctgaccag  900
gcagatacag ctacaccaag gctgttcaat tattattggc atatacaact cgataatctg  960
aatggcactc cttatgaccc agccgaggac atccccgccc cacttggcac cccggacttt  1020
agagggaagg tctttggagt ggcttctcaa agaaatcccg acgcaaccac ccgggcccac  1080
gaggccaaaa tcgatactac atcagggcgt ttcaccccta agttaggcag tctggagata  1140
tctaccgaaa gtggagattt cgatcagaac cagccaaccc ggtttacccc cgtgggaatc  1200
ggggttgacc acgaaccgga tttccagcag tgggctctgc ctgattacgc aggccagttc  1260
acacataaca tgaatcttgc ccccgctgtg gcccccaact tcccgggaga acaacttctg  1320
tttttcagga gccaactgcc ttccagcggc ggccgatcta acgggatttt ggactgtctc  1380
gtgccccagg aatgggtgca gcatttttac caggagtccg cgccctccca gacgcaggtg  1440
gctctggtta gatatgtcaa tcccgacacc ggcagggtgc tatttgaggc aaagctgcac  1500
aagcttcgct ttatgactat cgctaagagc ggtgattcgc ctattacagt gccccccaac  1560
ggatacttca gatttgagag ttgggtgaac ccattctata ccctggcccc catgggtaca  1620
ggcaatggca gacggcggat ccagtaa                                      1647

SEQ ID NO: 50          moltype = AA  length = 548
FEATURE                Location/Qualifiers
source                 1..548
                       mol_type = protein
                       note = Norovirus
                       organism = unidentified
SEQUENCE: 50
MKMASNDAAP SNDGAAGLVP EISSEAMALE PVAGAAIAAP LTGQQNIIDP WIMNNFVQAP  60
GGEFTVSPRN SPGEVLLNLS LGPEINPYLL HLARMYNGYA GGFEVQVVLA GNAFTAGKII  120
FAAIPPNFPI DNLSAAQITM CPHVIVDVRQ LEPVNLPMPD VRNNFFHYNQ GSDSRLRLIA  180
MLYTPLRANN SGDDVFTVSC RVLTRPSPDF SFNFLVPPTV ESKTKPFSLP ILTISEMSNS  240
RFPVPIDSLH TSPTENIVVQ CQNGRVTLDG ELMGTTQLLP SQICAFRGTL TRSTSRASDQ  300
ADTATPRLFN YYWHIQLDNL NGTPYDPAED IPAPLGTPDF RGKVFGVASQ RNPDATTRAH  360
EAKIDTTSGR FTPKLGSLEI STESGDFDQN QPTRFTPVGI GVDHEPDFQQ WALPDYAGQF  420
THNMNLAPAV APNFPGEQLL FFRSQLPSSG GRSNGILDCL VPQEWVQHFY QESAPSQTQV  480
ALVRYVNPDT GRVLFEAKLH KLRFMTIAKS GDSPITVPPN GYFRFESWVN PFYTLAPMGT  540
GNGRRRIQ                                                           548

SEQ ID NO: 51          moltype = DNA  length = 1647
FEATURE                Location/Qualifiers
misc_feature           1..1647
                       note = Nucleic acid sequence of human codon optimized
                        VP1_GII.3_Jing_E80S+A90L
source                 1..1647
                       mol_type = other DNA
                       organism = synthetic construct
SEQUENCE: 51
atgaaaatgg cttccaacga tgcagcaccc tctaatgatg gcgctgccgg acttgtgccg  60
gagattagct ctgaggctat ggccctagaa ccagtagccg gggcagccat agctgcccca  120
ctgactggcc agcagaatat cattgacccc tggataatga acaatttcgt gcaggcaccg  180
gggggagaat tcacggtctc tcctcgaaac tcccccgggg aggttctctt gaatttgagc  240
ctgggccctg aaattaatcc ttatctgctc catctagccc gaatgtacaa cggctacgcc  300
ggaggtttcg aggtccaggt ggtgctcgct ggtaacgcct tcacagctgg caagatcatt  360
tttgcagcaa tccctccaaa cttccctatc gataatctta gtgccgccca gatcacaatg  420
tgccctcacg ttatcgtaga tgtgaggcag ctggaacctg tcaatctccc aatgcccgac  480
gtgcgcaaca acttctttca ctataaccag ggatctgact cccgccttcg ccttatcgct  540
atgctgtaca cccctctgag ggctaacaat tccggagatg acgttttcac tgtgagttgt  600
cgagtcctga cacgtccatc tcctgacttt agctttaatt tcctcgtgcc ccccacagtg  660
gaatccaaaa ctaagccatt ctctctgcca attcttacca ttagcgaaat gtcgaatagt  720
aggttcccgg tgcccataga ttcactgcat accagtccaa cagaaaacat cgtcgtacag  780
tgtcagaacg gacgcgtgac tctcgacggg gagcttatgg gcactaccca gctgctgccc  840
agccagatat gcgccttccg cggcacactg actagaagca cttcgcgtgc ttctgaccag  900
gcagatacag ctacaccaag gctgttcaat tattattggc atatacaact cgataatctg  960
aatggcactc cttatgaccc agccgaggac atccccgccc cacttggcac cccggacttt  1020
agagggaagg tctttggagt ggcttctcaa agaaatcccg acgcaaccac ccgggcccac  1080
gaggccaaaa tcgatactac atcagggcgt ttcaccccta agttaggcag tctggagata  1140
tctaccgaaa gtggagattt cgatcagaac cagccaaccc ggtttacccc cgtgggaatc  1200
ggggttgacc acgaaccgga tttccagcag tgggctctgc ctgattacgc aggccagttc  1260
acacataaca tgaatcttgc ccccgctgtg gcccccaact tcccgggaga acaacttctg  1320
tttttcagga gccaactgcc ttccagcggc ggccgatcta acgggatttt ggactgtctc  1380
gtgccccagg aatgggtgca gcatttttac caggagtccg cgccctccca gacgcaggtg  1440
gctctggtta gatatgtcaa tcccgacacc ggcagggtgc tatttgaggc aaagctgcac  1500
aagcttcgct ttatgactat cgctaagagc ggtgattcgc ctattacagt gccccccaac  1560
ggatacttca gatttgagag ttgggtgaac ccattctata ccctggcccc catgggtaca  1620
ggcaatggca gacggcggat ccagtaa                                      1647

SEQ ID NO: 52          moltype = DNA  length = 1623
FEATURE                Location/Qualifiers
misc_feature           1..1623
                       note = Nucleic acid sequence of human codon-optimized VP1
                        GII.4_Sydney_2012_K4LM89
source                 1..1623
                       mol_type = other DNA
                       organism = synthetic construct
```

```
SEQUENCE: 52
atgaaaatgg cctcgagtga cgctaaccct agtgacggca gcgccgccaa tcttgtgcct  60
gaggttaata atgaggtgat ggccctggag cctgtggtgg gcgcagccat agcagcgccc  120
gtggccggtc agcagaatgt gattgacccg tggatacgca acaattttgt ccaagcccct  180
ggtggggagt tcaccgttag cccgagaaat gcgccaggag aaatcctgtg gtcggcccca  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agccccatg gggaatggga ctggcagacg cagggctgtc  1620
tga                                                               1623

SEQ ID NO: 53          moltype = AA  length = 540
FEATURE                Location/Qualifiers
source                 1..540
                       mol_type = protein
                       note = Norovirus
                       organism = unidentified
SEQUENCE: 53
MKMASSDANP SDGSAANLVP EVNNEVMALE PVVGAAIAVP VAGQQNVIDP WIRNNFVQAP  60
GGEFTVSPRN APGEILWSAP LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 54          moltype = DNA  length = 1623
FEATURE                Location/Qualifiers
misc_feature           1..1623
                       note = Nucleic acid sequence of human codon optimized
                        VP1_GII.4_Syd12_A39V
source                 1..1623
                       mol_type = other DNA
                       organism = synthetic construct
SEQUENCE: 54
atgaaaatgg cctcgagtga cgctaaccct agtgacggca gcgccgccaa tcttgtgcct  60
gaggttaata atgaggtgat ggccctggag cctgtggtgg gcgcagccat agcagtcccc  120
gtggccggtc agcagaatgt gattgacccg tggatacgca acaattttgt ccaagcccct  180
ggtggggagt tcaccgttag cccgagaaat gcgccaggag aaatcctgtg gtcggcccca  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
```

-continued

```
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg gggaatggga ctggcagacg cagggctgtc  1620
tga                                                                1623

SEQ ID NO: 55           moltype = AA  length = 540
FEATURE                 Location/Qualifiers
source                  1..540
                        mol_type = protein
                        note = Norovirus
                        organism = unidentified
SEQUENCE: 55
MKMASSDANP SDGSAANLVP EVNNEVMALE PVVGAAIAAP VAGQQNPIDP WIRNNFVQAP  60
GGEFTVSPRN APGEILWSAP LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 56           moltype = DNA  length = 1623
FEATURE                 Location/Qualifiers
misc_feature            1..1623
                        note = Nucleic acid sequence of human codon optimized
                         VP1_GII.4_Syd12_V47P
source                  1..1623
                        mol_type = other DNA
                        organism = synthetic construct
SEQUENCE: 56
atgaaaatgg cctcgagtga cgctaaccct agtgacggca gcgccgccaa tcttgtgcct  60
gaggttaata atgaggtgat ggccctggag cctgtggtgg gcgcagccat agcagcgccc  120
gtggccggtc agcagaatcc cattgacccg tggatacgca acaattttgt ccaagcccct  180
ggtggggagt tcaccgttag cccgagaaat gcgccaggag aaatcctgtg gtcggcccca  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tcccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg gggaatggga ctggcagacg cagggctgtc  1620
tga                                                                1623

SEQ ID NO: 57           moltype = AA  length = 540
FEATURE                 Location/Qualifiers
source                  1..540
                        mol_type = protein
                        note = Norovirus
                        organism = unidentified
SEQUENCE: 57
MKMASSDANP SDGSAANLVP EVNNEVMALE PVVGAAIAAP VAGQQNVIDP WIINNFVQAP  60
GGEFTVSPRN APGEILWSAP LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 58           moltype = DNA  length = 1623
```

```
FEATURE                Location/Qualifiers
misc_feature           1..1623
                       note = Nucleic acid sequence of human codon optimized
                        VP1_GII.4_Syd12_R53I
source                 1..1623
                       mol_type = other DNA
                       organism = synthetic construct
SEQUENCE: 58
atgaaaatgg cctcgagtga cgctaaccct agtgacggca gcgccgccaa tcttgtgcct  60
gaggttaata atgaggtgat ggccctggag cctgtggtgg gcgcagccat agcagcgccc  120
gtggccggtc agcagaatgt gattgacccg tggataatca acaattttgt ccaagcccct  180
ggtggggagt tcaccgttag cccgagaaat gcgccaggag aaatcctgtg gtcggcccca  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg ggaatggga ctggcagacg cagggctgtc  1620
tga                                                                1623

SEQ ID NO: 59          moltype = AA  length = 540
FEATURE                Location/Qualifiers
source                 1..540
                       mol_type = protein
                       note = Norovirus
                       organism = unidentified
SEQUENCE: 59
MKMASSDANP SDGSAANLVP EVNNEVMALE PVVGAAIAAP VAGQQNVIDP WIRNNFVQAP  60
GGEFTVSPRN APGEILWSAS LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 60          moltype = DNA  length = 1623
FEATURE                Location/Qualifiers
misc_feature           1..1623
                       note = Nucleic acid sequence of human codon optimized
                        VP1_GII.4_Syd12_P80S
source                 1..1623
                       mol_type = other DNA
                       organism = synthetic construct
SEQUENCE: 60
atgaaaatgg cctcgagtga cgctaaccct agtgacggca gcgccgccaa tcttgtgcct  60
gaggttaata atgaggtgat ggccctggag cctgtggtgg gcgcagccat agcagcgccc  120
gtggccggtc agcagaatgt gattgacccg tggatacgca acaattttgt ccaagcccct  180
ggtggggagt tcaccgttag cccgagaaat gcgccaggag aaatcctgtg gtcggccagc  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
```

-continued

```
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg gggaatggga ctggcagacg cagggctgtc  1620
tga                                                                1623

SEQ ID NO: 61          moltype = AA  length = 540
FEATURE                Location/Qualifiers
source                 1..540
                       mol_type = protein
                       note = Norovirus
                       organism = unidentified
SEQUENCE: 61
MKMASSDANP SDGSAANLVP EVNNEVMALE PVVGAAIAAP VAGQQNVIDP WIRNNFVQAP  60
GGEFTVSPRN APGEILWSAP LGPDLNPYLL HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 62          moltype = DNA  length = 1623
FEATURE                Location/Qualifiers
misc_feature           1..1623
                       note = Nucleic acid sequence of human codon optimized
                        VP1_GII.4_Syd12_S90L
source                 1..1623
                       mol_type = other DNA
                       organism = synthetic construct
SEQUENCE: 62
atgaaaatgg cctcgagtga cgctaaccct agtgacggca gcgccgccaa tcttgtgcct  60
gaggttaata atgaggtgat ggccctggag cctgtggtgg gcgcagccat agcagcgccc  120
gtggccggtc agcagaatgt gattgacccg tggatacgca acaattttgt ccaagcccct  180
ggtggggagt tcaccgttag cccgagaaat gcgccaggag aaatcctgtg gtcggcccca  240
ttgggacccg atctgaaccc ctatttgctg catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tcccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg gggaatggga ctggcagacg cagggctgtc  1620
tga                                                                1623

SEQ ID NO: 63          moltype = AA  length = 532
FEATURE                Location/Qualifiers
source                 1..532
                       mol_type = protein
                       note = Norovirus
                       organism = unidentified
SEQUENCE: 63
MKMASSDANP SDGSAANLVP EVNNEVMALE PVVGGQQNVI DPWIRNNFVQ APGGEFTVSP  60
RNAPGEILWS APLGPDLNPY LSHLARMYNG YAGGFEVQVI LAGNAFTAGK VIFAAVPPNF  120
PTEGLSPSQV TMFPHIVVDV RQLEPVLIPL PDVRNNFYHY NQSNDPTIKL IAMLYTPLRA  180
NNAGDDVFTV SCRVLTRPSP DFDFIFLVPP TVESRTKPFS VPVLTVEEMT NSRFPIPLEK  240
```

-continued

```
LFTGPSSAFV VQPQNGRCTT DGVLLGTTQL SPVNICTFRG DVTHITGSRN YTMNLASQNW  300
NDYDPTEEIP APLGTPDFVG KIQGVLTQTT RTDGSTRGHK ATVYTGSADF APKLGRVQFE  360
TDTDRDFEAN QNTKFTPVGV IQDGGTTHRN EPQQWVLPSY SGRNTHNVHL APAVAPTFPG  420
EQLLFFRSTM PGCSGYPNMD LDCLLPQEWV QYFYQEAAPA QSDVALLRFV NPDTGRVLFE  480
CKLHKSGYVT VAHTGQHDLV IPPNGYFRFD SWVNQFYTLA PMGNGTGRRR AV          532

SEQ ID NO: 64          moltype = DNA  length = 1599
FEATURE                Location/Qualifiers
misc_feature           1..1599
                       note = Nucleic acid sequence of human codon optimized
                        VP1_GII.4_Syd12_ delta 35-42
source                 1..1599
                       mol_type = other DNA
                       organism = synthetic construct
SEQUENCE: 64
atgaaaatgg cctcgagtga cgctaaccct agtgacggca gcgccgccaa tcttgtgcct  60
gaggttaata atgaggtgat ggccctggag cctgtggtgg gcggtcagca gaatgtgatt  120
gacccgtgga tacgcaacaa ttttgtccaa gcccctggtg gggagttcac cgttagcccg  180
agaaatgcgc caggagaaat cctgtggtcg gccccattgg gacccgatct gaacccctat  240
ttgtcacatc tcgctcggat gtacaacggg tatgccggcg gatttgaagt gcaggtgatt  300
ctggctggga acgcgttcac tgctggcaaa gtgatctttg cagcggtgcc tcccaacttc  360
cccactgaag gactgtctcc aagccaggtc acaatgtttc cacacatcgt ggtggacgta  420
cggcagctag agcctgtcct gattcccctc cctgatgtac gcaataattt ctaccactac  480
aatcaatcca atgatccgac cattaaactc atcgcgatgt tgtacacccc tctgcgcgct  540
aacaatgctg gagacgacgt attcaccgtg tcatgcagag tgctcaccag accttcacca  600
gactttgact ttatcttctt agtgcccccc actgttgaga gccgaaccaa gcccttttagt  660
gtccccgtac tcacagtcga ggagatgaca aatagccgct ttccaatccc ccttgagaaa  720
ctgttcacag gaccttcctc ggcattcgtg gttcagccac agaacggacg ctgcacaact  780
gacggcgtgc tgctcggaac cacccagctt agccctgtta atatctgtac gtttagaggc  840
gacgtaactc acataactgg ctcacggaac tataccatga atctggcatc acagaattgg  900
aatgactacg acccaaccga agagattccc gcacctcttg gaacccccga ctttgtggga  960
aaaatacagg gcgtcctgac acaaaccacc agaaccgatg gctccacacg gggacacaag  1020
gcaaccgtct acactggctc tgccgatttt gccccgaaac tgggtagagt gcagtttgag  1080
accgacactg accgggactt tgaagccaat cagaatacta agttcacacc tgtaggagtg  1140
attcaggacg gggggcaccac tcaccggaac gagccgcaac aatgggtcct gccctcttat  1200
agcgggagga atactcataa tgtgcatttg gctcctgcag tggctcccac gtttcccggg  1260
gaacaactgc tctttttttcg ttcaaccatg cctggatgct ccggatatcc caatatggat  1320
ctcgattgcc tgctcccaca ggaatgggtg cagtattttt atcaagaggc cgcaccagcc  1380
caatccgacg tcgcacttct gcggttcgtg aatccagaca caggccgcgt gttgtttgag  1440
tgcaaattgc acaaatcagg atacgttaca gtggctcata ctggacagca tgacctggtg  1500
atcccaccca acggatattt taggttcgac tcctgggtga atcagtttta tacattagcc  1560
cccatgggga atgggactgg cagacgcagg gctgtctga                         1599

SEQ ID NO: 65          moltype = AA  length = 540
FEATURE                Location/Qualifiers
source                 1..540
                       mol_type = protein
                       note = Norovirus
                       organism = unidentified
SEQUENCE: 65
MKMASSDANP SDGSAANLVP EVNNEVMALE PVVGSSTAVA TAGQQNVIDP WIRNNFVQAP  60
GGEFTVSPRN APGEILWSAP LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 66          moltype = DNA  length = 1623
FEATURE                Location/Qualifiers
misc_feature           1..1623
                       note = Nucleic acid sequence of human codon optimized
                        VP1_GII.4_Syd12_SSTAVATA
source                 1..1623
                       mol_type = other DNA
                       organism = synthetic construct
SEQUENCE: 66
atgaaaatgg cctcgagtga cgctaaccct agtgacggca gcgccgccaa tcttgtgcct  60
gaggttaata atgaggtgat ggccctggag cctgtggtgg gcagctccac cgccgtcgct  120
acagccggtc agcagaatgt gattgacccg tggatacgca acaattttgt ccaagcccct  180
ggtggggagt tcaccgttag cccgagaaat gcgccaggag aaatcctgtg gtcggcccca  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
```

```
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg gggaatggga ctggcagacg cagggctgtc  1620
tga                                                                1623

SEQ ID NO: 67          moltype = AA  length = 540
FEATURE                Location/Qualifiers
source                 1..540
                       mol_type = protein
                       note = Norovirus
                       organism = unidentified
SEQUENCE: 67
MKMASSDANP SDGSAANLVP EVNNEVMALE PVVGAAIAVP VAGQQNVIDP WIRNNFVQAP  60
GGEFTVSPRN APGEILWSAS LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 68          moltype = DNA  length = 1623
FEATURE                Location/Qualifiers
misc_feature           1..1623
                       note = Nucleic acid sequence of human codon optimized
                        VP1_GII.4_Syd12_P80S plus sign A39V
source                 1..1623
                       mol_type = other DNA
                       organism = synthetic construct
SEQUENCE: 68
atgaaaatgg cctcgagtga cgctaaccct agtgacggca gcgccgccaa tcttgtgcct  60
gaggttaata atgaggtgat ggccctggag cctgtggtgg gcgcagccat agcagtcccc  120
gtggccggtc agcagaatgt gattgacccg tggatacgca acaattttgt ccaagcccct  180
ggtggggagt tcaccgttag cccgagaaat gcgccaggag aaatcctgtg gtcggccagc  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg gggaatggga ctggcagacg cagggctgtc  1620
tga                                                                1623

SEQ ID NO: 69          moltype = AA  length = 540
FEATURE                Location/Qualifiers
source                 1..540
                       mol_type = protein
                       note = Norovirus
```

```
                        organism = unidentified
SEQUENCE: 69
MKMASSDANP SDGSAANLVP EVNNEVMALE PVVGAAIAAP VAGQQNPIDP WIRNNFVQAP  60
GGEFTVSPRN APGEILWSAS LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 70           moltype = DNA  length = 1623
FEATURE                 Location/Qualifiers
misc_feature            1..1623
                        note = Nucleic acid sequence of human codon optimized
                         VP1_GII.4_Syd12_P80S plus sign V47P
source                  1..1623
                        mol_type = other DNA
                        organism = synthetic construct
SEQUENCE: 70
atgaaaatgg cctcgagtga cgctaaccct agtgacggca gcgccgccaa tcttgtgcct  60
gaggttaata atgaggtgat ggccctggag cctgtggtgg gcgcagccat agcagcgccc  120
gtggccggtc agcagaatcc cattgacccg tggatacgca acaattttgt ccaagcccct  180
ggtggggagt tcaccgttag cccgagaaat gcgccaggag aaatcctgtg gtcggccagc  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg ggaatggga ctggcagacg cagggctgtc  1620
tga                                                               1623

SEQ ID NO: 71           moltype = AA  length = 540
FEATURE                 Location/Qualifiers
source                  1..540
                        mol_type = protein
                        note = Norovirus
                        organism = unidentified
SEQUENCE: 71
MKMASSDANP SDGSAANLVP EVNNEVMALE PVVGAAIAAP VAGQQNVIDP WIINNFVQAP  60
GGEFTVSPRN APGEILWSAS LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 72           moltype = DNA  length = 1623
FEATURE                 Location/Qualifiers
misc_feature            1..1623
                        note = Nucleic acid sequence of human codon optimized
                         VP1_GII.4_Syd12_P80S plus sign R53I
source                  1..1623
                        mol_type = other DNA
                        organism = synthetic construct
SEQUENCE: 72
atgaaaatgg cctcgagtga cgctaaccct agtgacggca gcgccgccaa tcttgtgcct  60
gaggttaata atgaggtgat ggccctggag cctgtggtgg gcgcagccat agcagcgccc  120
gtggccggtc agcagaatgt gattgacccg tggataatca acaattttgt ccaagcccct  180
```

```
ggtggggagt tcaccgttag cccgagaaat gcgccaggag aaatcctgtg gtcggccagc  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg ggaatggga ctggcagacg cagggctgtc  1620
tga                                                                1623
```

```
SEQ ID NO: 73          moltype = AA  length = 540
FEATURE                Location/Qualifiers
source                 1..540
                       mol_type = protein
                       note = Norovirus
                       organism = unidentified
SEQUENCE: 73
MKMASSDANP SDGSAANLVP EVNNEVMALE PVVGAAIAAP VAGQQNVIDP WIRNNFVQAP  60
GGEFTVSPRN APGEILWSAS LGPDLNPYLL HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540
```

```
SEQ ID NO: 74          moltype = DNA  length = 1623
FEATURE                Location/Qualifiers
misc_feature           1..1623
                       note = Nucleic acid sequence of human codon optimized
                        VP1_GII.4_Syd12_P80S plus sign S90L
source                 1..1623
                       mol_type = other DNA
                       organism = synthetic construct
SEQUENCE: 74
atgaaaatgg cctcgagtga cgctaaccct agtgacggca gcgccgccaa tcttgtgcct  60
gaggttaata atgaggtgat ggccctggag cctgtggtgg gcgcagccat agcagcgccc  120
gtggccggtc agcagaatgt gattgacccg tggatacgca acaattttgt ccaagcccct  180
ggtggggagt tcaccgttag cccgagaaat gcgccaggag aaatcctgtg gtcggccagc  240
ttgggacccg atctgaaccc ctatttgctg catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg ggaatggga ctggcagacg cagggctgtc  1620
```

```
tga                                                                 1623

SEQ ID NO: 75           moltype = AA  length = 532
FEATURE                 Location/Qualifiers
source                  1..532
                        mol_type = protein
                        note = Norovirus
                        organism = unidentified
SEQUENCE: 75
MKMASSDANP SDGSAANLVP EVNNEVMALE PVVGGQQNVI DPWIRNNFVQ APGGEFTVSP  60
RNAPGEILWS ASLGPDLNPY LSHLARMYNG YAGGFEVQVI LAGNAFTAGK VIFAAVPPNF  120
PTEGLSPSQV TMFPHIVVDV RQLEPVLIPL PDVRNNFYHY NQSNDPTIKL IAMLYTPLRA  180
NNAGDDVFTV SCRVLTRPSP DFDFIFLVPP TVESRTKPFS VPVLTVEEMT NSRFPIPLEK  240
LFTGPSSAFV VQPQNGRCTT DGVLLGTTQL SPVNICTFRG DVTHITGSRN YTMNLASQNW  300
NDYDPTEEIP APLGTPDFVG KIQGVLTQTT RTDGSTRGHK ATVYTGSADF APKLGRVQFE  360
TDTDRDFEAN QNTKFTPVGV IQDGGTTHRN EPQQWVLPSY SGRNTHNVHL APAVAPTFPG  420
EQLLFFRSTM PGCSGYPNMD LDCLLPQEWV QYFYQEAAPA QSDVALLRFV NPDTGRVLFE  480
CKLHKSGYVT VAHTGQHDLV IPPNGYFRFD SWVNQFYTLA PMGNGTGRRR AV          532

SEQ ID NO: 76           moltype = DNA  length = 1599
FEATURE                 Location/Qualifiers
misc_feature            1..1599
                        note = Nucleic acid sequence of human codon optimized
                         VP1_GII.4_Syd12_P80Splus sign delta 35-42
source                  1..1599
                        mol_type = other DNA
                        organism = synthetic construct
SEQUENCE: 76
atgaaaatgg cctcgagtga cgctaaccct agtgacggca gcgccgccaa tcttgtgcct  60
gaggttaata atgaggtgat ggccctggag cctgtggtgg gcggtcagca gaatgtgatt  120
gacccgtgga tacgcaacaa ttttgtccaa gcccctggtg gggagttcac cgttagcccg  180
agaaatgcgc caggagaaat cctgtggtcg gccagcttgg gacccgatct gaacccctat  240
ttgtcacatc tcgctcggat gtacaacggg tatgccggcg gatttgaagt gcaggtgatt  300
ctggctggga acgcgttcac tgctggcaaa gtgatctttg cagcggtgcc tcccaacttc  360
cccactgaag gactgtctcc aagccaggtc acaatgtttc cacacatcgt ggtggacgta  420
cggcagctag agcctgtcct gattcccctc cctgatgtac gcaataattt ctaccactac  480
aatcaatcca atgatccgac cattaaactc atcgcgatgt tgtacacccc tctgcgcgct  540
aacaatgctg gagacgacgt attcaccgtg tcatgcagag tgctcaccag accttcacca  600
gactttgact ttatcttctt agtgcccccc actgttgaga gccgaaccaa gccctttagt  660
gtccccgtac tcacagtcga ggagatgaca aatagccgct ttccaatccc ccttgagaaa  720
ctgttcacag gaccttcctc ggcattcgtg gttcagccac agaacggacg ctgcacaact  780
gacggcgtgc tgctcggaac cacccagctt agccctgtta atatctgtac gtttagaggc  840
gacgtaactc acataactgg ctcacggaac tataccatga atctggcatc acagaattgg  900
aatgactacg acccaaccga agagattccc gcacctcttg gaacccccga ctttgtggga  960
aaaatacagg gcgtcctgac acaaaccacc agaaccgatg gctccacacg gggacacaag  1020
gcaaccgtct acactggctc tgccgatttt gccccgaaac tgggtagagt gcagtttgag  1080
accgacactg accgggactt tgaagccaat cagaatacta agttcacacc tgtaggagtg  1140
attcaggacg ggggcaccac tcaccggaac gagccgcaac aatgggtcct gccctcttat  1200
agcgggagga atactcataa tgtgcatttg gctcctgcag tggctcccac gtttcccggg  1260
gaacaactgc tctttttttcg ttcaaccatg cctggatgct ccggatatcc caatatggat  1320
ctcgattgcc tgctcccaca ggaatgggtg cagtattttt atcaagaggc cgcaccagcc  1380
caatccgacg tcgcacttct gcggttcgtg aatccagaca caggccgcgt gttgtttgag  1440
tgcaaattgc acaaatcagg atacgttaca gtggctcata ctggacagca tgacctggtg  1500
atcccaccca acggatattt taggttcgac tcctgggtga atcagtttta tacattagcc  1560
cccatgggga atgggactgg cagacgcagg gctgtctga                          1599

SEQ ID NO: 77           moltype = AA  length = 540
FEATURE                 Location/Qualifiers
source                  1..540
                        mol_type = protein
                        note = Norovirus
                        organism = unidentified
SEQUENCE: 77
MKMASSDANP SDGSAANLVP EVNNEVMALE PVVGSSTAVA TAGQQNVIDP WIRNNFVQAP  60
GGEFTVSPRN APGEILWSAS LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 78           moltype = DNA  length = 1623
FEATURE                 Location/Qualifiers
misc_feature            1..1623
                        note = Nucleic acid sequence of human codon optimized
                         VP1_GII.4_Syd12_P80S plus sign SSTAVATA
source                  1..1623
```

```
                        mol_type = other DNA
                        organism = synthetic construct
SEQUENCE: 78
atgaaaatgg cctcgagtga cgctaaccct agtgacggca gcgccgccaa tcttgtgcct  60
gaggttaata atgaggtgat ggccctggag cctgtggtgg gcagctccac cgccgtcgct  120
acagccggtc agcagaatgt gattgacccg tggatacgca acaattttgt ccaagcccct  180
ggtggggagt tcaccgttag cccgagaaat gcgccaggag aaatcctgtg gtcggccagc  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tcccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg ggaatggga ctggcagacg cagggctgtc  1620
tga                                                               1623

SEQ ID NO: 79           moltype = AA  length = 547
FEATURE                 Location/Qualifiers
source                  1..547
                        mol_type = protein
                        note = Norovirus
                        organism = unidentified
SEQUENCE: 79
MKMASNDAAP SNDGAANLVP EANNEVMALE PVVGASIAAP VVGQQNIIDP WIRENFVQAP  60
QGEFTVSPRN SPGEMLLNLS LGPELNPYLS HLSRMYNGYA GGMQVQVVLA GNAFTAGKII  120
FAAVPPHFPV ENINAAQITM CPHVIVDVRQ LEPVLLPLPD IRNRFFHYNQ ENTSRMRLVA  180
MLYTPLRANS GEDVFTVSCR VLTRPAPDFE FTFLVPPTVE SKTKPFSLPI LTLGELSNSR  240
FPAPIDMLYT DPNEGIVVQP QNGRCTLDGT LQGTTQLVPT QICAFRGTLI GQTSRSPDST  300
DSAPRRRDHP LHVQLKNLDG TQYDPTDEVP AVLGAIDFKG TVFGVASQRD VSGQQVGATR  360
AHEVHINTTD PRYTPKLGSI LMYSESDDFV TGQPVRFTPI GMGDNDWHQW ELPDYPGHLT  420
LNMNLAPAVA PAFPGERILF FRSIVPSAGG YGSGQIDCLI PQEWVQHFYQ EAAPSQSAVA  480
LIRYVNPDTG RNIFEAKLHR EGFITVANSG NNPIVVPPNG YFRFEAWVNQ FYTLTPMGTG  540
QGRRRDQ                                                           547

SEQ ID NO: 80           moltype = DNA  length = 1644
FEATURE                 Location/Qualifiers
misc_feature            1..1644
                        note = Nucleic acid sequence of human codon optimized
                         VP1_GII.6_Ohio_E80S
source                  1..1644
                        mol_type = other DNA
                        organism = synthetic construct
SEQUENCE: 80
atgaagatgg caagcaacga cgcagctccc tccaatgatg gtgccgccaa cctggtcccc  60
gaagctaata atgaggtgat ggcgttagag ccggtggttg gcgcatctat tgcagcgcct  120
gtggtcggac agcagaacat cattgatccc tggattcgcg agaacttcgt acaagctcca  180
caggggggagt tcacagtctc cccccggaac tccccgggcg agatgctgct caatctgagc  240
ctcggccctg aactaaaccc ttatctgtca cacctttcac ggatgtacaa tggctacgca  300
ggaggaatgc aagttcaggt ggtcctggcc ggcaatgctt tcaccgcggg caaaatcatc  360
tttgcggccg ttcctccaca cttccctgtc gaaaatatca acgccgccca gattactatg  420
tgcccccacg tgattgtgga tgtgcgacag ttagagccag ttctgctgcc cctgcccgac  480
atcagaaacc ggttcttcca ttacaatcaa gagaatactt cacggatgag acttgttgcg  540
atgctgtaca cccctcttcg tgcaaattcc ggcgaagacg tgttcactgt gtcttgtcga  600
gtacttaccc gacccgcccc cgatttcgaa ttcaccttcc tggttccccc tactgtggag  660
agcaagacaa aacccttcag cctcccaatc ttaacactcg gggagctgtc taattcacgc  720
ttccccgcac ctattgatat gctgtatact gaccccaacg aggggatagt ggtgcagccc  780
caaaatggac ggtgtactct cgacggcacg ctccagggca caacccaact ggtgccaacc  840
cagatttgtg cattcagggg cactttgatt gggcagacat cgagatctcc agattctact  900
gattccgcgc caaggaggag ggaccaccca ctccacgttc agttaaaaaa cctggacgga  960
acccagtacg accctacaga cgaggtcccc gctgtcctcg gagccatcga ctttaaagga  1020
actgtatttg gagtggcatc ccaaagggat gtctcggggc agcaggtggg agctacgaga  1080
gcacatgaag tccacattaa caccacagac ccaagatata ccccaaaact agggtcaatt  1140
ttaatgtatt cggaatcaga cgattttgtt acaggtcagc ccgtgcggtt taccccgatc  1200
```

```
ggaatggggg acaacgattg gcaccagtgg gaattgcccg attaccctgg acacctcacc  1260
ttgaatatga atctggcccc agccgtcgcg cccgccttcc ccggtgagcg gatcctcttt  1320
tttagaagca tagtgccctc cgcaggtggg tatggatcag ggcagattga ttgcctgatc  1380
ccccaagaat gggtacagca tttctaccag gaagcagccc ctagccagtc cgcagtagca  1440
ctgatcagat atgttaatcc tgatacggga aggaacatct tcgaagcaaa actgcaccgt  1500
gagggcttca ttaccgtcgc caacagtggt aataacccta ttgtggtgcc tcctaatgga  1560
tacttcaggt ttgaggcatg ggtgaatcag ttttatactc tgactcccat ggggacaggc  1620
caggggcgac gccgggatca gtga                                         1644

SEQ ID NO: 81          moltype = AA  length = 547
FEATURE                Location/Qualifiers
source                 1..547
                       mol_type = protein
                       note = Norovirus
                       organism = unidentified
SEQUENCE: 81
MKMASNDAAP SNDGAANLVP EANNEVMALE PVVGASIAAP VVGQQNIIDP WIRENFVQAP  60
QGEFTVSPRN SPGEMLLNLE LGPELNPYLL HLSRMYNGYA GGMQVQVVLA GNAFTAGKII  120
FAAVPPHFPV ENINAAQITM CPHVIVDVRQ LEPVLLPLPD IRNRFFHYNQ ENTSRMRLVA  180
MLYTPLRANS GEDVFTVSCR VLTRPAPDFE FTFLVPPTVE SKTKPFSLPI LTLGELSNSR  240
FPAPIDMLYT DPNEGIVVQP QNGRCTLDGT LQGTTQLVPT QICAFRGTLI GQTSRSPDST  300
DSAPRRRDHP LHVQLKNLDG TQYDPTDEVP AVLGAIDFKG TVFGVASQRD VSGQQVGATR  360
AHEVHINTTD PRYTPKLGSI LMYSESDDFV TGQPVRFTPI GMGDNDWHQW ELPDYPGHLT  420
LNMNLAPAVA PAFPGERILF FRSIVPSAGG YGSGQIDCLI PQEWVQHFYQ EAAPSQSAVA  480
LIRYVNPDTG RNIFEAKLHR EGFITVANSG NNPIVVPPNG YFRFEAWVNQ FYTLTPMGTG  540
QGRRRDQ                                                            547

SEQ ID NO: 82          moltype = DNA  length = 1644
FEATURE                Location/Qualifiers
misc_feature           1..1644
                       note = Nucleic acid sequence of human codon optimized
                        VP1_GII.6_Ohio_S90L
source                 1..1644
                       mol_type = other DNA
                       organism = synthetic construct
SEQUENCE: 82
atgaagatgg caagcaacga cgcagctccc tccaatgatg gtgccgccaa cctggtcccc  60
gaagctaata atgaggtgat ggcgttagag ccggtggttg gcgcatctat tgcagcgcct  120
gtggtcggac agcagaacat cattgatccc tggattcgcg agaacttcgt acaagctcca  180
cagggggagt tcacagtctc cccccggaac tccccgggcg agatgctgct caatctggaa  240
ctcggccctg aactaaaccc ttatctgctc cacctttcac ggatgtacaa tggctacgca  300
ggaggaatgc aagttcaggt ggtcctggcc ggcaatgctt tcaccgcggg caaaatcatc  360
tttgcggccg ttcctccaca cttccctgtc gaaaatatca acgccgccca gattactatg  420
tgcccccacg tgattgtgga tgtgcgacag ttagagccag ttctgctgcc cctgcccgac  480
atcagaaacc ggttcttcca ttacaatcaa gagaatactt cacggatgag acttgttgcg  540
atgctgtaca cccctcttcg tgcaaattcc ggcgaagacg tgttcactgt gtcttgtcga  600
gtacttaccc gacccgcccc cgatttcgaa ttcaccttcc tggttccccc tactgtggag  660
agcaagacaa aacccttcag cctcccaatc ttaacactcg gggagctgtc taattcacgc  720
ttccccgcac ctattgatat gctgtatact gaccccaacg aggggatagt ggtgcagccc  780
caaaatggac ggtgtactct cgacggcacg ctccagggca caacccaact ggtgccaacc  840
cagatttgtg cattcagggg cactttgatt gggcagacat cgagatctcc agattctact  900
gattccgcgc caaggaggag ggaccaccca ctccacgttc agttaaaaaa cctggacgga  960
acccagtacg accctacaga cgaggtcccc gctgtcctcg gagccatcga ctttaaagga  1020
actgtatttg gagtggcatc ccaaagggat gtctcggggc agcaggtggg agctacgaga  1080
gcacatgaag tccacattaa caccacagac ccaagatata ccccaaaact agggtcaatt  1140
ttaatgtatt cggaatcaga cgattttgtt acaggtcagc ccgtgcggtt taccccgatc  1200
ggaatggggg acaacgattg gcaccagtgg gaattgcccg attaccctgg acacctcacc  1260
ttgaatatga atctggcccc agccgtcgcg cccgccttcc ccggtgagcg gatcctcttt  1320
tttagaagca tagtgccctc cgcaggtggg tatggatcag ggcagattga ttgcctgatc  1380
ccccaagaat gggtacagca tttctaccag gaagcagccc ctagccagtc cgcagtagca  1440
ctgatcagat atgttaatcc tgatacggga aggaacatct tcgaagcaaa actgcaccgt  1500
gagggcttca ttaccgtcgc caacagtggt aataacccta ttgtggtgcc tcctaatgga  1560
tacttcaggt ttgaggcatg ggtgaatcag ttttatactc tgactcccat ggggacaggc  1620
caggggcgac gccgggatca gtga                                         1644

SEQ ID NO: 83          moltype = AA  length = 547
FEATURE                Location/Qualifiers
source                 1..547
                       mol_type = protein
                       note = Norovirus
                       organism = unidentified
SEQUENCE: 83
MKMASNDAAP SNDGAANLVP EANNEVMALE PVVGASIAAP VVGQQNIIDP WIRENFVQAP  60
QGEFTVSPRN SPGEMLLNLS LGPELNPYLL HLSRMYNGYA GGMQVQVVLA GNAFTAGKII  120
FAAVPPHFPV ENINAAQITM CPHVIVDVRQ LEPVLLPLPD IRNRFFHYNQ ENTSRMRLVA  180
MLYTPLRANS GEDVFTVSCR VLTRPAPDFE FTFLVPPTVE SKTKPFSLPI LTLGELSNSR  240
FPAPIDMLYT DPNEGIVVQP QNGRCTLDGT LQGTTQLVPT QICAFRGTLI GQTSRSPDST  300
DSAPRRRDHP LHVQLKNLDG TQYDPTDEVP AVLGAIDFKG TVFGVASQRD VSGQQVGATR  360
AHEVHINTTD PRYTPKLGSI LMYSESDDFV TGQPVRFTPI GMGDNDWHQW ELPDYPGHLT  420
```

-continued

```
LNMNLAPAVA PAFPGERILF FRSIVPSAGG YGSGQIDCLI PQEWVQHFYQ EAAPSQSAVA  480
LIRYVNPDTG RNIFEAKLHR EGFITVANSG NNPIVVPPNG YFRFEAWVNQ FYTLTPMGTG  540
QGRRRDQ                                                            547

SEQ ID NO: 84          moltype = DNA  length = 1644
FEATURE                Location/Qualifiers
misc_feature           1..1644
                       note = Nucleic acid sequence of human codon optimized
                        VP1_GII.6_Ohio_E80S plus sign S90L
source                 1..1644
                       mol_type = other DNA
                       organism = synthetic construct
SEQUENCE: 84
atgaagatgg caagcaacga cgcagctccc tccaatgatg gtgccgccaa cctggtcccc  60
gaagctaata atgaggtgat ggcgttagag ccggtggttg gcgcatctat tgcagcgcct  120
gtggtcggac agcagaacat cattgatccc tggattcgcg agaacttcgt acaagctcca  180
caggggggagt tcacagtctc cccccggaac tccccgggcg agatgctgct caatctgagc  240
ctcggccctg aactaaaccc ttatctgctc cacctttcac ggatgtacaa tggctacgca  300
ggaggaatgc aagttcaggt ggtcctggcc ggcaatgctt tcaccgcggg caaaatcatc  360
tttgcggccg ttcctccaca cttccctgtc gaaaatatca acgccgccca gattactatg  420
tgcccccacg tgattgtgga tgtgcgacag ttagagccag ttctgctgcc cctgcccgac  480
atcagaaacc ggttcttcca ttacaatcaa gagaatactt cacggatgag acttgttgcg  540
atgctgtaca cccctcttcg tgcaaattcc ggcgaagacg tgttcactgt gtcttgtcga  600
gtacttaccc gacccgcccc cgatttcgaa ttcaccttcc tggttccccc tactgtggag  660
agcaagacaa aacccttcag cctcccaatc ttaacactcg gggagctgtc taattcacgc  720
ttccccgcac ctattgatat gctgtatact gaccccaacg aggggatagt ggtgcagccc  780
caaaatggac ggtgtactct cgacggcacg ctccagggca caacccaact ggtgccaacc  840
cagatttgtg cattcagggg cactttgatt gggcagacat cgagatctcc agattctact  900
gattccgcgc caaggaggag ggaccaccca ctccacgttc agttaaaaaa cctggacgga  960
acccagtacg accctacaga cgaggtcccc gctgtcctcg gagccatcga ctttaaagga  1020
actgtatttg gagtggcatc ccaaagggat gtctcggggc agcaggtggg agctacgaga  1080
gcacatgaag tccacattaa caccacagac ccaagatata ccccaaaact agggtcaatt  1140
ttaatgtatt cggaatcaga cgattttgtt acaggtcagc ccgtgcggtt taccccgatc  1200
ggaatggggg acaacgattg gcaccagtgg gaattgcccg attaccctgg acacctcacc  1260
ttgaatatga atctggcccc agccgtcgcg cccgccttcc ccggtgagcg gatcctcttt  1320
tttagaagca tagtgccctc cgcaggtggg tatggatcag ggcagattga ttgcctgatc  1380
ccccaagaat gggtacagca tttctaccag gaagcagccc ctagccagtc cgcagtagca  1440
ctgatcagat atgttaatcc tgatacggga aggaacatct tcgaagcaaa actgcaccgt  1500
gagggcttca ttaccgtcgc caacagtggt aataacccta ttgtggtgcc tcctaatgga  1560
tacttcaggt ttgaggcatg ggtgaatcag ttttatactc tgactcccat ggggacaggc  1620
caggggcgac gccgggatca gtga                                         1644

SEQ ID NO: 85          moltype = AA  length = 542
FEATURE                Location/Qualifiers
source                 1..542
                       mol_type = protein
                       note = Norovirus
                       organism = unidentified
SEQUENCE: 85
MKMASNDAAP STDGAAGLVP ESNNEVMALE PVAGAALAAP VTGQTNIIDP WIRANFVQAP  60
NGEFTVSPRN SPGEVLLNLS LGPELNPYLA HLARMYNGYA GGMEVQVMLA GNAFTAGKLV  120
FAAVPPHFPV ENLSPQQITM FPHVIIDVRT LEPVLLPLPD VRNNFFHYNQ KDDPKMRIVA  180
MLYTPLRSNG SGDDVFTVSC RVLTRPSPDF DFTYLVPPTV ESKTKPFTLP ILTLGELSNS  240
RFPVSIDQMY TSPNEVISVQ CQNGRCTLDG ELQGTTQLQV SGICAFKGEV TAHLHDNDHL  300
YNVTITNLNG SPFDPSEDIP APLGVPDFQG RVFGVISQRD KHNTPGHNEP ANRAHDAVVP  360
TYTAQYTPKL GQIQIGTWQT DDLTVNQPVK FTPVGLNDTD HFNQWVVPRY AGALNLNTNL  420
APSVAPVFPG ERLLFFRSYI PLKGGYGTPA IDCLLPQEWV QHFYQEAAPS MSEVALVRYI  480
NPDTGRALFE AKLHRAGFMT VSSNTSAPVV VPANGYFRFD SWVNQFYSLA PMGTGNGRRR  540
IQ                                                                 542

SEQ ID NO: 86          moltype = DNA  length = 1629
FEATURE                Location/Qualifiers
misc_feature           1..1629
                       note = Nucleic acid sequence of human codon optimized
                        VP1_GII.2_CGMH47_E80S_
source                 1..1629
                       mol_type = other DNA
                       organism = synthetic construct
SEQUENCE: 86
atgaagatgg catccaacga cgccgcaccc agcacagacg gagctgccgg attggtaccc  60
gagtctaata acgaggtgat ggccttggag cctgttgcag ggctgccct cgcagctcct  120
gtgaccgggc agacaaatat catcgatcct tggattagag ctaatttcgt gcaagcccca  180
aatggggagt ttacggtcag ccctagaaat agccctgggg aagtgctcct caatctcagc  240
ctgggaccag aacttaatcc gtacctggct cacctggccc ggatgtacaa tggatatgca  300
ggagggatgg aggtgcaggt tatgctggct ggcaatgcct ttacagcagg caaactcgtt  360
ttcgcagccg tccctcccca cttcccagtt gaaaatcttt cccctcagca gattaccatg  420
tttccccatg tcatcatcga tgtgcgtacc ctggaacctg tgctgttgcc tttaccagac  480
gtgcggaata atttctttca ctataatcag aaggatgacc caaaaatgcg gatcgttgcg  540
atgctttata ctcccctgcg tagcaatggt agtggggatg acgtttttac agtgagttgt  600
```

```
cgggtactaa ctcgcccttc accagacttc gactttacgt acttggtgcc tcccactgtc  660
gaaagcaaaa ctaagccatt cacacttccc atcctcaccc tcggagaact ctcgaactcc  720
cgcttccctg tttcaattga tcagatgtac acgtctccaa atgaagtcat ttctgtgcag  780
tgtcagaacg gcaggtgcac cttagacggt gaactgcagg ggacaacgca gttgcaggtc  840
agtggaattt gcgcctttaa gggcgaagtg acagctcacc tccacgacaa cgatcatctc  900
tacaatgtta ctattactaa tctcaatgga agtcctttcg acccctcgga agatattccc  960
gctccactcg gagtacctga ctttcaggga cgcgtcttcg gcgtgatatc acaacgagat  1020
aagcataaca cacccggaca taatgagcca gccaatagag cccacgacgc agtcgttccg  1080
acctatacgg ctcagtacac cccaaagctc ggccagatac aaatcgggac ttggcagacc  1140
gatgacctca ctgtgaatca acctgtgaaa ttcactccag taggtctgaa tgatacagac  1200
cactttaacc agtgggtggt ccctagatac gccggagcct tgaacctaaa cactaacctt  1260
gccccttccg ttgcacctgt gtttccgggg gagcggttgc tcttctttag aagctatatt  1320
cctctgaagg gcgggtatgg tactccagca atcgactgcc tgctacctca ggagtgggtt  1380
caacatttct atcaagaggc cgcacctagt atgagcgagg tggctttggt cagatacatc  1440
aatccagaca caggaagagc actgttcgag gccaagctgc acagagccgg cttcatgacc  1500
gtctcatcca atacatccgc acccgtagta gtccccgcca acgggtactt cagattcgac  1560
agttgggtga atcagtttta ctcgttggcc cccatgggca cagggaacgg tcgccgacgg  1620
atccagtaa                                                           1629
```

```
SEQ ID NO: 87          moltype = DNA  length = 1608
FEATURE                Location/Qualifiers
misc_feature           1..1608
                       note = Nucleic acid sequence of human codon-optimized VP1
                        GII.12_HS206_2010_USA_
source                 1..1608
                       mol_type = other DNA
                       organism = synthetic construct
SEQUENCE: 87
atgaagatgg cgtctaatga tgctgctcct tccaatgatg gcgcagccgg cctggtccct  60
gaagtgaata acgagactat ggctctcgaa cccgtggccg gagcctcaat tgccgccccc  120
ctcactggcc agaacaacgt gattgatccc tggatcagac tgaacttcgt tcaggctcct  180
aatggggagt tcaccgtgtc cccgagaaac tcccccggcg aagtgttatt gaatttggaa  240
ttaggaccag aactcaaccc ctatctggca catctgtctc ggatgtacaa cggctatgcg  300
ggcggagtgg aggtgcaagt tcttctcgct ggtaatgcat tcacagcagg aaaattagta  360
tttgcagcgg ttccacccca ttttccactt gaaaacataa gcccaggcca gatcaccatg  420
ttccctcacg tgataatcga cgtgcggaca ttagagcccg tgctgctacc cctgcccgac  480
gtgaggaaca atttctttca ctacaatcag caaaatgaac caagaatgcg cctggtcgcc  540
atgctctata ctcctttaag aagtaatggc agtggggatg acgtgtttac tgttagctgt  600
cgggtgctca cccgaccttc cccagatttc gacttcaatt atctggtccc ccccacggta  660
gagtccaaaa caaagccttt cactcttcca atccttacaa ttggcgaact gaccaactca  720
cgctttccag tgcctattga tgagctgtac acaagtccaa atgaatccct tgtcgttcag  780
ccacagaatg ggcgctgcgc gcttgacggt gagctccagg gcacaacaca actgttgcca  840
accgctatat gctctttcag gggcgtatt aatcagaagg tctccgggga gaaccacgtg  900
tggaacatgc aagtgacgaa tatcgacggg acacctttcg atccaacaga ggatgtccca  960
gcgcctctag gtacccctga cttctcaggc aagttgttcg gcgtcctttc ccagcgcgac  1020
catgataatg cttgccggag ccacgatgcc gtcattgcca ccaactcagc caaattcacc  1080
ccaaaacttg gagcgataca gatcggaact tgggaacaag acgacgtcca tatcaaccaa  1140
ccaacaaagt ttacccctgt tggccttttc gaaagcgaag gctttaacca gtggacactt  1200
cccaattaca gcggggctct cactcttaat atgggactcg caccacccgt cgctccaacg  1260
tttcctggtg agcagatttt gtttttccgc agtcatattc cactgaaggg tggagttgct  1320
gatcccgtga tagactgcct cctccctcag gaatggattc agcacttgta tcaggagtcc  1380
gctccctcgc agaccgatgt ggccctgata cgcttcacaa accccgatac cggaagagtg  1440
ttgtttgaag ctaaacttca tcgctccggt tacatcacag tagccaacac gggttccagg  1500
ccaatcgtag ttccggcaaa cggatacttt cgattcgaca gttgggtcaa tcagttctac  1560
agcctggctc caatgggaac aggaaatggg aggaggcgtg tgcagtaa                1608
```

```
SEQ ID NO: 88          moltype = AA  length = 535
FEATURE                Location/Qualifiers
source                 1..535
                       mol_type = protein
                       note = Norovirus
                       organism = unidentified
SEQUENCE: 88
MKMASNDAAP SNDGAAGLVP EVNNETMALE PVAGASIAAP LTGQNNVIDP WIRLNFVQAP  60
NGEFTVSPRN SPGEVLLNLS LGPELNPYLA HLSRMYNGYA GGVEVQVLLA GNAFTAGKLV  120
FAAVPPHFPL ENISPGQITM FPHVIIDVRT LEPVLLPLPD VRNNFFHYNQ QNEPRMRLVA  180
MLYTPLRSNG SGDDVFTVSC RVLTRPSPDF DFNYLVPPTV ESKTKPFTLP ILTIGELTNS  240
RFPVPIDELY TSPNESLVVQ PQNGRCALDG ELQGTTQLLP TAICSFRGRI NQKVSGENHV  300
WNMQVTNIDG TPFDPTEDVP APLGTPDFSG KLFGVLSQRD HDNACRSHDA VIATNSAKFT  360
PKLGAIQIGT WEQDDVHINQ PTKFTPVGLF ESEGFNQWTL PNYSGALTLN MGLAPPVAPT  420
FPGEQILFFR SHIPLKGGVA DPVIDCLLPQ EWIQHLYQES APSQTDVALI RFTNPDTGRV  480
LFEAKLHRSG YITVANTGSR PIVVPANGYF RFDSWVNQFY SLAPMGTGNG RRRVQ       535
```

```
SEQ ID NO: 89          moltype = DNA  length = 1608
FEATURE                Location/Qualifiers
misc_feature           1..1608
                       note = Nucleic acid sequence of human codon optimized
                        VP1_GII.12_HS10_E80S
source                 1..1608
```

```
                        mol_type = other DNA
                        organism = synthetic construct
SEQUENCE: 89
atgaagatgg cgtctaatga tgctgctcct tccaatgatg gcgcagccgg cctggtccct  60
gaagtgaata acgagactat ggctctcgaa cccgtggccg gagcctcaat tgccgccccc  120
ctcactggcc agaacaacgt gattgatccc tggatcagac tgaacttcgt tcaggctcct  180
aatggggagt tcaccgtgtc cccgagaaac tcccccggcg aagtgttatt gaatttgagc  240
ttaggaccag aactcaaccc ctatctggca catctgtctc ggatgtacaa cggctatgcg  300
ggcggagtgg aggtgcaagt tcttctcgct ggtaatgcat tcacagcagg aaaattagta  360
tttgcagcgg ttccacccca ttttccactt gaaaacataa gcccaggcca gatcaccatg  420
ttccctcacg tgataatcga cgtgcggaca ttagagcccg tgctgctacc cctgcccgac  480
gtgaggaaca atttctttca ctacaatcag caaaatgaac caagaatgcg cctggtcgcc  540
atgctctata ctcctttaag aagtaatggc agtggggatg acgtgtttac tgttagctgt  600
cgggtgctca cccgaccttc cccagatttc gacttcaatt atctggtccc ccccacggta  660
gagtccaaaa caaagccttt cactcttcca atccttacaa ttggcgaact gaccaactca  720
cgctttccag tgcctattga tgagctgtac acaagtccaa atgaatccct tgtcgttcag  780
ccacagaatg ggcgctgcgc gcttgacggt gagctccagg gcacaacaca actgttgcca  840
accgctatat gctctttcag gggcgtatt aatcagaagg tctccgggga gaaccacgtg  900
tggaacatgc aagtgacgaa tatcgacggg acacctttcg atccaacaga ggatgtccca  960
gcgcctctag gtacccctga cttctcaggc aagttgttcg gcgtcctttc ccagcgcgac  1020
catgataatg cttgccggag ccacgatgcc gtcattgcca ccaactcagc caaattcacc  1080
ccaaaacttg gagcgataca gatcggaact tgggaacaag acgacgtcca tatcaaccaa  1140
ccaacaaagt ttacccctgt tggccttttc gaaagcgaag gctttaacca gtggacactt  1200
cccaattaca gcggggctct cactcttaat atggactcg caccacccgt cgctccaacg  1260
tttcctggtg agcagatttt gtttttccgc agtcatattc cactgaaggg tggagttgct  1320
gatcccgtga tagactgcct cctccctcag gaatggattc agcacttgta tcaggagtcc  1380
gctccctcgc agaccgatgt ggccctgata cgcttcacaa accccgatac cggaagagtg  1440
ttgtttgaag ctaaacttca tcgctccggt tacatcacag tagccaacac gggttccagg  1500
ccaatcgtag ttccggcaaa cggatacttt cgattcgaca gttgggtcaa tcagttctac  1560
agcctggctc caatgggaac aggaaatggg aggaggcgtg tgcagtaa             1608

SEQ ID NO: 90           moltype = AA  length = 535
FEATURE                 Location/Qualifiers
source                  1..535
                        mol_type = protein
                        note = Norovirus
                        organism = unidentified
SEQUENCE: 90
MKMASNDAAP SNDGAAGLVP EVNNETMALE PVAGASIAAP LTGQNNVIDP WIRLNFVQAP  60
NGEFTVSPRN SPGEVLLNLE LGPELNPYLL HLSRMYNGYA GGVEVQVLLA GNAFTAGKLV  120
FAAVPPHFPL ENISPGQITM FPHVIIDVRT LEPVLLPLPD VRNNFFHYNQ QNEPRMRLVA  180
MLYTPLRSNG SGDDVFTVSC RVLTRPSPDF DFNYLVPPTV ESKTKPFTLP ILTIGELTNS  240
RFPVPIDELY TSPNESLVVQ PQNGRCALDG ELQGTTQLLP TAICSFRGRI NQKVSGENHV  300
WNMQVTNIDG TPFDPTEDVP APLGTPDFSG KLFGVLSQRD HDNACRSHDA VIATNSAKFT  360
PKLGAIQIGT WEQDDVHINQ PTKFTPVGLF ESEGFNQWTL PNYSGALTLN MGLAPPVAPT  420
FPGEQILFFR SHIPLKGGVA DPVIDCLLPQ EWIQHLYQES APSQTDVALI RFTNPDTGRV  480
LFEAKLHRSG YITVANTGSR PIVVPANGYF RFDSWVNQFY SLAPMGTGNG RRRVQ       535

SEQ ID NO: 91           moltype = DNA  length = 1608
FEATURE                 Location/Qualifiers
misc_feature            1..1608
                        note = Nucleic acid sequence of human codon optimized
                         VP1_GII.12_HS10_A90L
source                  1..1608
                        mol_type = other DNA
                        organism = synthetic construct
SEQUENCE: 91
atgaagatgg cgtctaatga tgctgctcct tccaatgatg gcgcagccgg cctggtccct  60
gaagtgaata acgagactat ggctctcgaa cccgtggccg gagcctcaat tgccgccccc  120
ctcactggcc agaacaacgt gattgatccc tggatcagac tgaacttcgt tcaggctcct  180
aatggggagt tcaccgtgtc cccgagaaac tcccccggcg aagtgttatt gaatttggaa  240
ttaggaccag aactcaaccc ctatctgctc catctgtctc ggatgtacaa cggctatgcg  300
ggcggagtgg aggtgcaagt tcttctcgct ggtaatgcat tcacagcagg aaaattagta  360
tttgcagcgg ttccacccca ttttccactt gaaaacataa gcccaggcca gatcaccatg  420
ttccctcacg tgataatcga cgtgcggaca ttagagcccg tgctgctacc cctgcccgac  480
gtgaggaaca atttctttca ctacaatcag caaaatgaac caagaatgcg cctggtcgcc  540
atgctctata ctcctttaag aagtaatggc agtggggatg acgtgtttac tgttagctgt  600
cgggtgctca cccgaccttc cccagatttc gacttcaatt atctggtccc ccccacggta  660
gagtccaaaa caaagccttt cactcttcca atccttacaa ttggcgaact gaccaactca  720
cgctttccag tgcctattga tgagctgtac acaagtccaa atgaatccct tgtcgttcag  780
ccacagaatg ggcgctgcgc gcttgacggt gagctccagg gcacaacaca actgttgcca  840
accgctatat gctctttcag gggcgtatt aatcagaagg tctccgggga gaaccacgtg  900
tggaacatgc aagtgacgaa tatcgacggg acacctttcg atccaacaga ggatgtccca  960
gcgcctctag gtacccctga cttctcaggc aagttgttcg gcgtcctttc ccagcgcgac  1020
catgataatg cttgccggag ccacgatgcc gtcattgcca ccaactcagc caaattcacc  1080
ccaaaacttg gagcgataca gatcggaact tgggaacaag acgacgtcca tatcaaccaa  1140
ccaacaaagt ttacccctgt tggccttttc gaaagcgaag gctttaacca gtggacactt  1200
cccaattaca gcggggctct cactcttaat atggactcg caccacccgt cgctccaacg  1260
tttcctggtg agcagatttt gtttttccgc agtcatattc cactgaaggg tggagttgct  1320
```

```
gatcccgtga tagactgcct cctccctcag gaatggattc agcacttgta tcaggagtcc  1380
gctccctcgc agaccgatgt ggccctgata cgcttcacaa accccgatac cggaagagtg  1440
ttgtttgaag ctaaacttca tcgctccggt tacatcacag tagccaacac gggttccagg  1500
ccaatcgtag ttccggcaaa cggatacttt cgattcgaca gttgggtcaa tcagttctac  1560
agcctggctc caatgggaac aggaaatggg aggaggcgtg tgcagtaa              1608

SEQ ID NO: 92          moltype = AA  length = 535
FEATURE                Location/Qualifiers
source                 1..535
                       mol_type = protein
                       note = Norovirus
                       organism = unidentified
SEQUENCE: 92
MKMASNDAAP SNDGAAGLVP EVNNETMALE PVAGASIAAP LTGQNNVIDP WIRLNFVQAP  60
NGEFTVSPRN SPGEVLLNLS LGPELNPYLL HLSRMYNGYA GGVEVQVLLA GNAFTAGKLV  120
FAAVPPHFPL ENISPGQITM FPHVIIDVRT LEPVLLPLPD VRNNFFHYNQ QNEPRMRLVA  180
MLYTPLRSNG SGDDVFTVSC RVLTRPSPDF DFNYLVPPTV ESKTKPFTLP ILTIGELTNS  240
RFPVPIDELY TSPNESLVVQ PQNGRCALDG ELQGTTQLLP TAICSFRGRI NQKVSGENHV  300
WNMQVTNIDG TPFDPTEDVP APLGTPDFSG KLFGVLSQRD HDNACRSHDA VIATNSAKFT  360
PKLGAIQIGT WEQDDVHINQ PTKFTPVGLF ESEGFNQWTL PNYSGALTLN MGLAPPVAPT  420
FPGEQILFFR SHIPLKGGVA DPVIDCLLPQ EWIQHLYQES APSQTDVALI RFTNPDTGRV  480
LFEAKLHRSG YITVANTGSR PIVVPANGYF RFDSWVNQFY SLAPMGTGNG RRRVQ       535

SEQ ID NO: 93          moltype = DNA  length = 1608
FEATURE                Location/Qualifiers
misc_feature           1..1608
                       note = Nucleic acid sequence of human codon optimized
                        VP1_GII.12_HS10_E80S plus sign A90L
source                 1..1608
                       mol_type = other DNA
                       organism = synthetic construct
SEQUENCE: 93
atgaagatgg cgtctaatga tgctgctcct tccaatgatg gcgcagccgg cctggtccct  60
gaagtgaata acgagactat ggctctcgaa cccgtggccg gagcctcaat tgccgccccc  120
ctcactggcc agaacaacgt gattgatccc tggatcagac tgaacttcgt tcaggctcct  180
aatggggagt tcaccgtgtc cccgagaaac tcccccggcg aagtgttatt gaatttgagc  240
ttaggaccag aactcaaccc ctatctgctc catctgtctc ggatgtacaa cggctatgcg  300
ggcggagtgg aggtgcaagt tcttctcgct ggtaatgcat tcacagcagg aaaattagta  360
tttgcagcgg ttccacccca ttttccactt gaaaacataa gcccaggcca gatcaccatg  420
ttccctcacg tgataatcga cgtgcggaca ttagagcccg tgctgctacc cctgcccgac  480
gtgaggaaca atttctttca ctacaatcag caaaatgaac caagaatgcg cctggtcgcc  540
atgctctata ctcctttaag aagtaatggc agtggggatg acgtgtttac tgttagctgt  600
cgggtgctca cccgaccttc cccagatttc gacttcaatt atctggtccc ccccacggta  660
gagtccaaaa caaagccttt cactcttcca atccttacaa ttggcgaact gaccaactca  720
cgctttccag tgcctattga tgagctgtac acaagtccaa atgaatccct tgtcgttcag  780
ccacagaatg ggcgctgcgc gcttgacggt gagctccagg gcacaacaca actgttgcca  840
accgctatat gctctttcag ggggcgtatt aatcagaagg tctccgggga gaaccacgtg  900
tggaacatgc aagtgacgaa tatcgacggg acacctttcg atccaacaga ggatgtccca  960
gcgcctctag gtacccctga cttctcaggc aagttgttcg gcgtcctttc ccagcgcgac  1020
catgataatg cttgccggag ccacgatgcc gtcattgcca ccaactcagc caaattcacc  1080
ccaaaacttg gagcgataca gatcggaact tgggaacaag acgacgtcca tatcaaccaa  1140
ccaacaaagt ttacccctgt tggccttttc gaaagcgaag gctttaacca gtggacactt  1200
cccaattaca gcggggctct cactcttaat atgggactcg caccacccgt cgctccaacg  1260
tttcctggtg agcagatttt gtttttccgc agtcatattc cactgaaggg tggagttgct  1320
gatcccgtga tagactgcct cctccctcag gaatggattc agcacttgta tcaggagtcc  1380
gctccctcgc agaccgatgt ggccctgata cgcttcacaa accccgatac cggaagagtg  1440
ttgtttgaag ctaaacttca tcgctccggt tacatcacag tagccaacac gggttccagg  1500
ccaatcgtag ttccggcaaa cggatacttt cgattcgaca gttgggtcaa tcagttctac  1560
agcctggctc caatgggaac aggaaatggg aggaggcgtg tgcagtaa              1608

SEQ ID NO: 94          moltype = AA  length = 215
FEATURE                Location/Qualifiers
source                 1..215
                       mol_type = protein
                       note = Norovirus
                       organism = unidentified
SEQUENCE: 94
MAQAIFGAIA ATAAGSAVGA GIQAGTEAAL QHQRFQQDLT LQSNTFKHDK EMLGLQVGAS  60
TALLQNSLNT RYNMLTDAGL SSSDAARMVV GAPATRVVDW NGTRISAPRS TATTLRSGGF  120
MTIPTLYKGK QQQKAPTEIG LSNPNYGSSV SSRVADWVSS QNSSHSSLGP YHPSALQTTW  180
VTPPGSSSTS TISSVSTVPR YFNTDRLPLF ANMRK                             215

SEQ ID NO: 95          moltype = DNA  length = 648
FEATURE                Location/Qualifiers
misc_feature           1..648
                       note = Nucleic acid sequence of human codon optimized
                        VP2_GI.3_Lil08
source                 1..648
                       mol_type = other DNA
```

```
                         organism = synthetic construct
SEQUENCE: 95
atggctcagg caatcttcgg cgcaatcgct gccactgctg ccggatccgc tgtgggagcc  60
ggcatacagg ccggaactga ggcggccctt cagcatcagc ggttccagca ggatctgaca  120
ttacagagta acacattcaa acatgacaag gagatgctgg gtctgcaggt gggtgccagt  180
actgccctgc tccaaaactc tctgaatacc agatataaca tgttaactga tgcgggactg  240
tctagtagcg acgcagctcg catggtcgtg ggcgccccag ctacgagagt tgtggactgg  300
aatggcaccc gaatcagtgc accaaggtct acagccacta ccctcagaag tggcggcttt  360
atgaccatcc cgactttata caagggcaaa caacagcaga aggcacctac tgaaatcggt  420
ctctccaatc ccaactacgg cagcagtgtg tcttctcgcg tggccgattg ggtctcaagc  480
cagaactcca gtcatagttc tcttgggcct tatcatccat cagccttgca gacaacttgg  540
gtcaccccac ccgggtccag tagcacgtca accatcagtt ccgtctccac agtccctcgc  600
tattttaata ctgataggct tcccctgttc gcaaacatga ggaagtga              648

SEQ ID NO: 96            moltype = AA  length = 259
FEATURE                  Location/Qualifiers
source                   1..259
                         mol_type = protein
                         note = Norovirus
                         organism = unidentified
SEQUENCE: 96
MASAFLAGLA GDVITNGVGS LINAGANAVN QKVEYDFNKQ LQMASFKHDK EMLQSQVLAT  60
KQLQQEMMNI RQGVLTAGGF SPADAARGAV NAPMTKILDW NGTRYWAPNS MKTTSYSGQF  120
SSSPVHKSPA PSQHTALPKS RLQNDFASVY SFPSSVSSQS THSTALSAGT GSSRSISPST  180
ATPTLSRTSD WVRGQNERLS PFMDGALQTA FVTPPSSKAS SNGTVSTVPK AVLDSWTPMF  240
NTHRQPLFAH PRRRGESQV                                              259

SEQ ID NO: 97            moltype = DNA  length = 780
FEATURE                  Location/Qualifiers
misc_feature             1..780
                         note = Nucleic acid sequence of human codon optimized
                          VP2_GII6_HS10
source                   1..780
                         mol_type = other DNA
                         organism = synthetic construct
SEQUENCE: 97
atggcctccg catttctagc tggattggcc ggggacgtga tcaccaacgg cgtaggatcg  60
ctgattaatg caggcgccaa tgctgttaat cagaaggttg aatacgactt caacaaacaa  120
ctgcagatgg cttcattcaa gcacgacaaa gaaatgttgc agtcacaggt tctcgccacc  180
aagcagctac aacaggagat gatgaacatt cggcagggcg tactgaccgc tggaggattc  240
agccctgctg acgcagcacg gggggccgtg aacgcgccga tgaccaagat cctggattgg  300
aacggaactc ggtattgggc tcccaactct atgaaaacca cttcttactc tggtcagttc  360
tccagctcgc cagtccacaa aagtccggcc ccttcacagc acacagcact ccctaagtcc  420
aggctgcaaa acgactttgc ctccgtgtac tccttcccat ccagcgtgtc atctcagagc  480
actcattcaa ccgccctgtc cgccggaact gggtctagcc gcagcatttc cccaagcaca  540
gctactccaa ctctgagcag gactagcgat tgggtcagag gacaaaacga acgactgtcc  600
cctttcatgg acggagctct gcaaaccgcc ttcgtcactc cacctagcag caaggcctcg  660
agcaacggta cggttagtac cgtgccaaag gctgttcttg acagctggac ccccatgttt  720
aacacacaca ggcagccatt gtttgcacac cccaggcgac ggggagaatc acaagtttag  780

SEQ ID NO: 98            moltype = AA  length = 543
FEATURE                  Location/Qualifiers
source                   1..543
                         mol_type = protein
                         note = Norovirus
                         organism = unidentified
SEQUENCE: 98
MMMASKDAPT NMDGTSGAGQ LVPEVSTAEP ISMEPVAGAA TAAATAGQVN MIDPWIMSNY  60
VQAPQGEFTI SPNNTPGDIL FDLSLGPHLN PFLSHLAQMY NGWVGNMKVR VLLAGNAFTA  120
GKIIISCVPP GFAAQNVSIA QATMFPHVIA DVRVLEPIEV PLEDVRNVLF HNNDSTPTMR  180
LICMLYTPLR ASGSSSGTDP FVIAGRVLTC PSPDFNFLFL VPPNVEQKTK PFSVPNLPLN  240
VLSNSRVPSL IKSMMVSQDH GQMVQFQNGR VTLDGQLQGT TPTSASQLCK IRGTVYHATG  300
GQGLNLTEID GTPYHAFESP APIGFPDLGE CDWHINASPA NAFTDGSIIH RIDVAQDSTF  360
APHLGTIHYT NADYNANVGL ICSLEWLSPP SGGAPKVNPW AIPRYGSTLT EAAQLAPPIY  420
PPGFGEAIVF FMSDFPIANG SDGLSVPCTI PQEFVTHFVN EQAPTRGEAA LLHYVDPDTH  480
RNLGEFKLYP EGFMTCVPNS SGSGPQTLPI NGVFTFISWV SRFYQLKPVG TTGPVRRLGI  540
RRS                                                               543

SEQ ID NO: 99            moltype = AA  length = 212
FEATURE                  Location/Qualifiers
source                   1..212
                         mol_type = protein
                         note = Norovirus
                         organism = unidentified
SEQUENCE: 99
MAQAIIGAIA ASTAGSALGA GIQVGGEAAL QSQRYQQNLQ LQENSFKHDR EMIGYQVEAS  60
NQLLAKNLAT RYSLLRAGGL TSADAARSVA GAPVTRIVDW NGVRVSAPES SATTLRSGGF  120
MSVPIPFASK QKQVQSSGIS NPNYSPSSIS RTTSWVESQN SSRFGNLSPY HAEALNTVWL  180
TPPGSTASST LSSVPRGYFN TDRLPLFANN RR                               212
```

```
SEQ ID NO: 100         moltype = DNA  length = 639
FEATURE                Location/Qualifiers
misc_feature           1..639
                       note = Nucleic acid sequence of human codon optimized
                        VP.2_GI1_Norwalk
source                 1..639
                       mol_type = other DNA
                       organism = synthetic construct
SEQUENCE: 100
atggctcagg ccattattgg cgccatcgct gcaagtacag ccgggagtgc attgggggcc  60
ggaatacagg tgggcgggga agctgcattg cagagccagc ggtaccagca aaacctgcag  120
ttacaggaga atagctttaa acacgacagg gagatgattg gatatcaggt ggaggccagc  180
aatcagctgc tcgccaaaaa cttggctact cgatactcat tactgcgcgc cggggggttg  240
actagcgccg acgccgcacg atctgtcgca ggcgcccccg tgactcggat cgtagactgg  300
aacggggtac gagtctcggc tcccgagtcg tctgcaacca ccctgaggtc gggagggttt  360
atgtccgtgc ccatcccatt cgctagcaaa cagaaacagg tccagagctc cggaatctcc  420
aatcccaatt actcccctag ctctatctct cgtaccactt cctgggtcga gagtcagaac  480
agcagtagat ttggcaacct gagcccctac catgctgaag ccctgaacac tgtgtggttg  540
actccacctg gtagcacggc ctcctcaacc ctgagttccg tgcctcgcgg gtacttcaat  600
accgacagac ttcctctgtt cgctaacaac cgccgctga                         639

SEQ ID NO: 101         moltype = AA  length = 538
FEATURE                Location/Qualifiers
source                 1..538
                       mol_type = protein
                       note = Norovirus
                       organism = unidentified
SEQUENCE: 101
MMMASKDAPS NMDGTSGAGQ LVPEVNAAEP LPLEPVVGAA TAVATAGQVN MIDPWIMNNF  60
VQAPEGEFTI SPNNTPGDIL FDLRLGPHLN PFLLHLSQMY NGWVGNMRVR VMLAGNAFSA  120
GKIIICCVPP GFESQNISIG QATMFPHVIA DVRVLEPIEV PLDDVRNVLF HTNENRPTMR  180
LLCMLYTPLR AGGASSGTDP FVIAGRVLTC PAPDFNFLFL VPPSVEQKTR QLTIPNIPLN  240
NLANSRVPAM INKMTVSADQ NQVVQFQNGR CTLEGQLLGT TPVSANQVAR IRGKVFSTNS  300
GTGLNLTEVD GTPYHAFESP APLGFPDIGN CDWHVYAFKV NQNTGDPMYR LDITQGNSFA  360
PHLGSIEFSS ENHPSGDQLG TLTWISPLNN ASRVDPWKIP TYGSTLTEST NLAPPIFPPG  420
FGEAIVYFMS DFPIVSGNTA QIPCTLPQEF VSSFVEQQAP IRGEAALLHY VDPDTHRNLG  480
EFKLYPDGFI TCVPNTGGGP QNLPSNGVFV FSSWVSRYYQ LKPVGTTGPV RRLGVRRV    538

SEQ ID NO: 102         moltype = DNA  length = 49
FEATURE                Location/Qualifiers
misc_feature           1..49
                       note = Primer IF-NoV(US68)VP1(ORF1)(hCod).c
source                 1..49
                       mol_type = other DNA
                       organism = synthetic construct
SEQUENCE: 102
tcgtgcttcg gcaccagtac aatgatgatg gctagtaaag atgcgacct              49

SEQ ID NO: 103         moltype = DNA  length = 52
FEATURE                Location/Qualifiers
misc_feature           1..52
                       note = Primer IF-NoV(US68)VP1(ORF1)(hCod).r
source                 1..52
                       mol_type = other DNA
                       organism = synthetic construct
SEQUENCE: 103
actaaagaaa ataggccttt atctccgcag accgaggcgt ccgcgggcag aa          52

SEQ ID NO: 104         moltype = DNA  length = 49
FEATURE                Location/Qualifiers
misc_feature           1..49
                       note = Primer IF-GI3Lil08VP1.c
source                 1..49
                       mol_type = other DNA
                       organism = synthetic construct
SEQUENCE: 104
tcgtgcttcg gcaccagtac aatgatgatg gcttccaagg atgctccca              49

SEQ ID NO: 105         moltype = DNA  length = 49
FEATURE                Location/Qualifiers
misc_feature           1..49
                       note = Primer IF-GI3Lil08VP1.r
source                 1..49
                       mol_type = other DNA
                       organism = synthetic construct
SEQUENCE: 105
actaaagaaa ataggcctct agctccgtct gatcccgagc ctccgaact              49
```

```
SEQ ID NO: 106         moltype = DNA  length = 59
FEATURE                Location/Qualifiers
misc_feature           1..59
                       note = Primer VP1_GI.3Lil08(S94L).r
source                 1..59
                       mol_type = other DNA
                       organism = synthetic construct
SEQUENCE: 106
ctgagccaag tggagcagaa acggattcaa gtgtggtcct agctgcaggt caaacaaga   59

SEQ ID NO: 107         moltype = DNA  length = 56
FEATURE                Location/Qualifiers
misc_feature           1..56
                       note = Primer VP1_GI.3Lil08(S94L).c
source                 1..56
                       mol_type = other DNA
                       organism = synthetic construct
SEQUENCE: 107
aggaccacac ttgaatccgt ttctgctcca cttggctcag atgtataatg gatggg      56

SEQ ID NO: 108         moltype = DNA  length = 57
FEATURE                Location/Qualifiers
misc_feature           1..57
                       note = Primer VP1_GI.3Lil08(Q84S).r
source                 1..57
                       mol_type = other DNA
                       organism = synthetic construct
SEQUENCE: 108
gtgtggtcct aggctcaggt caaacaagat gtcacccggg gtgttgtttg ggcttat     57

SEQ ID NO: 109         moltype = DNA  length = 48
FEATURE                Location/Qualifiers
misc_feature           1..48
                       note = Primer VP1_GI.3Lil08(Q84S).c
source                 1..48
                       mol_type = other DNA
                       organism = synthetic construct
SEQUENCE: 109
ggtgacatct tgtttgacct gagcctagga ccacacttga atccgttt               48

SEQ ID NO: 110         moltype = DNA  length = 48
FEATURE                Location/Qualifiers
misc_feature           1..48
                       note = Primer IF-GI3Lil08VP2.c
source                 1..48
                       mol_type = other DNA
                       organism = synthetic construct
SEQUENCE: 110
tcgtgcttcg gcaccagtac aatggctcag gcaatcttcg gcgcaatc               48

SEQ ID NO: 111         moltype = DNA  length = 49
FEATURE                Location/Qualifiers
misc_feature           1..49
                       note = Primer IF-GI3Lil08VP2.r
source                 1..49
                       mol_type = other DNA
                       organism = synthetic construct
SEQUENCE: 111
actaaagaaa ataggccttc acttcctcat gtttgcgaac aggggaagc              49

SEQ ID NO: 112         moltype = DNA  length = 48
FEATURE                Location/Qualifiers
misc_feature           1..48
                       note = Primer IF-(160)GI.5_Sikl13_VP1.c
source                 1..48
                       mol_type = other DNA
                       organism = synthetic construct
SEQUENCE: 112
tcgtgcttcg gcaccagtac aatgatgatg gcctccaaag acgctcct               48

SEQ ID NO: 113         moltype = DNA  length = 53
FEATURE                Location/Qualifiers
misc_feature           1..53
                       note = Primer IF-GI.5_Sikl13_VP1.r
source                 1..53
                       mol_type = other DNA
                       organism = synthetic construct
SEQUENCE: 113
actaaagaaa ataggccttc agcgccgcac gccaaggcgc ccccgggcag atg         53
```

```
SEQ ID NO: 114          moltype = DNA  length = 51
FEATURE                 Location/Qualifiers
misc_feature            1..51
                        note = Primer GI.5(hCod)(Q84S).r
source                  1..51
                        mol_type = other DNA
                        organism = synthetic construct
SEQUENCE: 114
gatgagggcc taagctcagg tcgaacagaa tatcccctgg tgtgttgtta g           51

SEQ ID NO: 115          moltype = DNA  length = 51
FEATURE                 Location/Qualifiers
misc_feature            1..51
                        note = Primer GI.5(hCod)(Q84S).c
source                  1..51
                        mol_type = other DNA
                        organism = synthetic construct
SEQUENCE: 115
tattctgttc gacctgagct taggccctca tctcaacccc ttcttggccc a           51

SEQ ID NO: 116          moltype = DNA  length = 50
FEATURE                 Location/Qualifiers
misc_feature            1..50
                        note = Primer GI.5(hCod)(A94L).r
source                  1..50
                        mol_type = other DNA
                        organism = synthetic construct
SEQUENCE: 116
atctggctca ggtggagcaa gaaggggttg agatgagggc ctaactgcag             50

SEQ ID NO: 117          moltype = DNA  length = 51
FEATURE                 Location/Qualifiers
misc_feature            1..51
                        note = Primer GI.5(hCod)(A94L).c
source                  1..51
                        mol_type = other DNA
                        organism = synthetic construct
SEQUENCE: 117
tctcaacccc ttcttgctcc acctgagcca gatgtacaat ggctgggtgg g           51

SEQ ID NO: 118          moltype = DNA  length = 54
FEATURE                 Location/Qualifiers
misc_feature            1..54
                        note = Primer IF-(160)GII.2_CGMH11_VP1.c
source                  1..54
                        mol_type = other DNA
                        organism = synthetic construct
SEQUENCE: 118
tcgtgcttcg gcaccagtac aatgaagatg gcatccaacg acgccgcacc cagc        54

SEQ ID NO: 119          moltype = DNA  length = 53
FEATURE                 Location/Qualifiers
misc_feature            1..53
                        note = Primer IF-GII.2_CGMH11_VP1.r
source                  1..53
                        mol_type = other DNA
                        organism = synthetic construct
SEQUENCE: 119
actaaagaaa ataggccttt actggatccg tcggcgaccg ttccctgtgc cca         53

SEQ ID NO: 120          moltype = DNA  length = 59
FEATURE                 Location/Qualifiers
misc_feature            1..59
                        note = Primer VP1_GII.2CGMH11(E80S).r
source                  1..59
                        mol_type = other DNA
                        organism = synthetic construct
SEQUENCE: 120
ttctggtccc aggctgagat tgaggagcac ttccccaggg ctatttctag ggctgaccg   59

SEQ ID NO: 121          moltype = DNA  length = 48
FEATURE                 Location/Qualifiers
misc_feature            1..48
                        note = Primer VP1_GII.2CGMH11(E80S).c
source                  1..48
                        mol_type = other DNA
                        organism = synthetic construct
SEQUENCE: 121
```

-continued

```
ggaagtgctc ctcaatctca gcctgggacc agaacttaat ccgtacct             48

SEQ ID NO: 122          moltype = DNA  length = 59
FEATURE                 Location/Qualifiers
misc_feature            1..59
                        note = Primer VP1_GII.2CGMH11(A90L).r
source                  1..59
                        mol_type = other DNA
                        organism = synthetic construct
SEQUENCE: 122
tccgggccag gtggagcagg tacggattaa gttctggtcc cagctcgaga ttgaggagc   59

SEQ ID NO: 123          moltype = DNA  length = 59
FEATURE                 Location/Qualifiers
misc_feature            1..59
                        note = Primer VP1_GII.2CGMH11(A90L).c
source                  1..59
                        mol_type = other DNA
                        organism = synthetic construct
SEQUENCE: 123
gggaccagaa cttaatccgt acctgctcca cctggcccgg atgtacaatg gatatgcag   59

SEQ ID NO: 124          moltype = DNA  length = 52
FEATURE                 Location/Qualifiers
misc_feature            1..52
                        note = Primer IF-(160)GII.3_Jing13_VP1.c
source                  1..52
                        mol_type = other DNA
                        organism = synthetic construct
SEQUENCE: 124
tcgtgcttcg gcaccagtac aatgaaaatg gcttccaacg atgcagcacc ct          52

SEQ ID NO: 125          moltype = DNA  length = 50
FEATURE                 Location/Qualifiers
misc_feature            1..50
                        note = Primer IF-GII.3_Jing13_VP1.r
source                  1..50
                        mol_type = other DNA
                        organism = synthetic construct
SEQUENCE: 125
actaaagaaa ataggccttt actggatccg ccgtctgcca ttgcctgtac             50

SEQ ID NO: 126          moltype = DNA  length = 59
FEATURE                 Location/Qualifiers
misc_feature            1..59
                        note = Primer VP1_GII.3Jing13(E80S).r
source                  1..59
                        mol_type = other DNA
                        organism = synthetic construct
SEQUENCE: 126
atttcagggc ccaggctcaa attcaagaga acctccccgg gggagtttcg aggagagac   59

SEQ ID NO: 127          moltype = DNA  length = 48
FEATURE                 Location/Qualifiers
misc_feature            1..48
                        note = Primer VP1_GII.3Jing13(E80S).c
source                  1..48
                        mol_type = other DNA
                        organism = synthetic construct
SEQUENCE: 127
ggaggttctc ttgaatttga gcctgggccc tgaaattaat ccttatct             48

SEQ ID NO: 128          moltype = DNA  length = 59
FEATURE                 Location/Qualifiers
misc_feature            1..59
                        note = Primer VP1_GII.3Jing13(A90L).r
source                  1..59
                        mol_type = other DNA
                        organism = synthetic construct
SEQUENCE: 128
attcgggcta gatggagcag ataaggatta atttcagggc ccagttccaa attcaagag   59

SEQ ID NO: 129          moltype = DNA  length = 56
FEATURE                 Location/Qualifiers
misc_feature            1..56
                        note = Primer VP1_GII.3Jing13(A90L).c
source                  1..56
                        mol_type = other DNA
                        organism = synthetic construct
```

```
SEQUENCE: 129
gggccctgaa attaatcctt atctgctcca tctagcccga atgtacaacg gctacg      56

SEQ ID NO: 130         moltype = DNA  length = 49
FEATURE                Location/Qualifiers
misc_feature           1..49
                       note = Primer IF-GII.4Syd12VP1.c
source                 1..49
                       mol_type = other DNA
                       organism = synthetic construct
SEQUENCE: 130
tcgtgcttcg gcaccagtac aatgaaaatg gcctcgagtg acgctaacc              49

SEQ ID NO: 131         moltype = DNA  length = 48
FEATURE                Location/Qualifiers
misc_feature           1..48
                       note = Primer IF-GII.4Syd12VP1.r
source                 1..48
                       mol_type = other DNA
                       organism = synthetic construct
SEQUENCE: 131
actaaagaaa ataggccttc agacagccct gcgtctgcca gtcccatt               48

SEQ ID NO: 132         moltype = DNA  length = 54
FEATURE                Location/Qualifiers
misc_feature           1..54
                       note = Primer VP1_GII.4Syd12(A39V).r
source                 1..54
                       mol_type = other DNA
                       organism = synthetic construct
SEQUENCE: 132
gaccggccac ggggactgct atggctgcgc ccaccacagg ctccagggcc atca        54

SEQ ID NO: 133         moltype = DNA  length = 54
FEATURE                Location/Qualifiers
misc_feature           1..54
                       note = Primer VP1_GII.4Syd12(A39V).c
source                 1..54
                       mol_type = other DNA
                       organism = synthetic construct
SEQUENCE: 133
gggcgcagcc atagcagtcc ccgtggccgg tcagcagaat gtgattgacc cgtg        54

SEQ ID NO: 134         moltype = DNA  length = 51
FEATURE                Location/Qualifiers
misc_feature           1..51
                       note = Primer VP1_GII.4Syd12(V47P).r
source                 1..51
                       mol_type = other DNA
                       organism = synthetic construct
SEQUENCE: 134
cgtatccacg ggtcaatggg attctgctga ccggccacgg gcgctgctat g           51

SEQ ID NO: 135         moltype = DNA  length = 53
FEATURE                Location/Qualifiers
misc_feature           1..53
                       note = Primer VP1_GII.4Syd12(V47P).c
source                 1..53
                       mol_type = other DNA
                       organism = synthetic construct
SEQUENCE: 135
ggccggtcag cagaatccca ttgacccgtg gatacgcaac aattttgtcc aag         53

SEQ ID NO: 136         moltype = DNA  length = 48
FEATURE                Location/Qualifiers
misc_feature           1..48
                       note = Primer VP1_GII.4Syd12(R53I).r
source                 1..48
                       mol_type = other DNA
                       organism = synthetic construct
SEQUENCE: 136
tggacaaaat tgttgattat ccacgggtca atcacattct gctgaccg               48

SEQ ID NO: 137         moltype = DNA  length = 50
FEATURE                Location/Qualifiers
misc_feature           1..50
                       note = Primer VP1_GII.4Syd12(R53I).c
source                 1..50
                       mol_type = other DNA
```

```
                       organism = synthetic construct
SEQUENCE: 137
gattgacccg tggataatca acaattttgt ccaagcccct ggtggggagt             50

SEQ ID NO: 138         moltype = DNA  length = 50
FEATURE                Location/Qualifiers
misc_feature           1..50
                       note = Primer GII.4(P80S).r
source                 1..50
                       mol_type = other DNA
                       organism = synthetic construct
SEQUENCE: 138
gatcgggtcc caagctggcc gaccacagga tttctcctgg cgcatttctc             50

SEQ ID NO: 139         moltype = DNA  length = 50
FEATURE                Location/Qualifiers
misc_feature           1..50
                       note = Primer GII.4(P80S).c
source                 1..50
                       mol_type = other DNA
                       organism = synthetic construct
SEQUENCE: 139
aatcctgtgg tcggccagct tgggacccga tctgaacccc tatttgtcac             50

SEQ ID NO: 140         moltype = DNA  length = 56
FEATURE                Location/Qualifiers
misc_feature           1..56
                       note = Primer GII.4(S90L).r
source                 1..56
                       mol_type = other DNA
                       organism = synthetic construct
SEQUENCE: 140
atccgagcga gatgcagcaa ataggggttc agatcgggtc ccaatggggc cgacca      56

SEQ ID NO: 141         moltype = DNA  length = 48
FEATURE                Location/Qualifiers
misc_feature           1..48
                       note = Primer GII.4(S90L).c
source                 1..48
                       mol_type = other DNA
                       organism = synthetic construct
SEQUENCE: 141
tctgaacccc tatttgctgc atctcgctcg gatgtacaac gggtatgc               48

SEQ ID NO: 142         moltype = DNA  length = 50
FEATURE                Location/Qualifiers
misc_feature           1..50
                       note = Primer VP1_GII.4Syd12(Del(35-42)).r
source                 1..50
                       mol_type = other DNA
                       organism = synthetic construct
SEQUENCE: 142
cacattctgc tgaccgccca ccacaggctc cagggccatc acctcattat             50

SEQ ID NO: 143         moltype = DNA  length = 48
FEATURE                Location/Qualifiers
misc_feature           1..48
                       note = Primer VP1_GII.4Syd12(Del(35-42)).c
source                 1..48
                       mol_type = other DNA
                       organism = synthetic construct
SEQUENCE: 143
ggagcctgtg gtgggcggtc agcagaatgt gattgacccg tggatacg               48

SEQ ID NO: 144         moltype = DNA  length = 60
FEATURE                Location/Qualifiers
misc_feature           1..60
                       note = Primer VP1_GII.4Syd12(SSTAVATA).r
source                 1..60
                       mol_type = other DNA
                       organism = synthetic construct
SEQUENCE: 144
ctgaccggct gtagcgacgg cggtggagct gcccaccaca ggctccaggg ccatcacctc  60

SEQ ID NO: 145         moltype = DNA  length = 60
FEATURE                Location/Qualifiers
misc_feature           1..60
                       note = Primer VP1_GII.4Syd12(SSTAVATA).c
source                 1..60
```

```
                        mol_type = other DNA
                        organism = synthetic construct
SEQUENCE: 145
tgtggtgggc agctccaccg ccgtcgctac agccggtcag cagaatgtga ttgacccgtg  60

SEQ ID NO: 146          moltype = DNA  length = 49
FEATURE                 Location/Qualifiers
misc_feature            1..49
                        note = Primer IF-GII.6Ohi12VP1.c
source                  1..49
                        mol_type = other DNA
                        organism = synthetic construct
SEQUENCE: 146
tcgtgcttcg gcaccagtac aatgaagatg gcaagcaacg acgcagctc             49

SEQ ID NO: 147          moltype = DNA  length = 54
FEATURE                 Location/Qualifiers
misc_feature            1..54
                        note = Primer IF-GII.6Ohi12VP1.r
source                  1..54
                        mol_type = other DNA
                        organism = synthetic construct
SEQUENCE: 147
actaaagaaa ataggccttc actgatcccg gcgtcgcccc tggcctgtcc ccat       54

SEQ ID NO: 148          moltype = DNA  length = 51
FEATURE                 Location/Qualifiers
misc_feature            1..51
                        note = Primer IF-GII.6HS10VP2.c
source                  1..51
                        mol_type = other DNA
                        organism = synthetic construct
SEQUENCE: 148
tcgtgcttcg gcaccagtac aatggcctcc gcatttctag ctggattggc c          51

SEQ ID NO: 149          moltype = DNA  length = 53
FEATURE                 Location/Qualifiers
misc_feature            1..53
                        note = Primer IF-GII.6HS10VP2.r
source                  1..53
                        mol_type = other DNA
                        organism = synthetic construct
SEQUENCE: 149
actaaagaaa ataggcctct aaacttgtga ttctccccgt cgcctggggt gtg        53

SEQ ID NO: 150          moltype = DNA  length = 59
FEATURE                 Location/Qualifiers
misc_feature            1..59
                        note = Primer VP1_GII.6Ohi12(E80S).r
source                  1..59
                        mol_type = other DNA
                        organism = synthetic construct
SEQUENCE: 150
agttcagggc cgaggctcag attgagcagc atctcgcccg gggagttccg gggggagac   59

SEQ ID NO: 151          moltype = DNA  length = 48
FEATURE                 Location/Qualifiers
misc_feature            1..48
                        note = Primer VP1_GII.6Ohi12(E80S).c
source                  1..48
                        mol_type = other DNA
                        organism = synthetic construct
SEQUENCE: 151
cgagatgctg ctcaatctga gcctcggccc tgaactaaac ccttatct              48

SEQ ID NO: 152          moltype = DNA  length = 59
FEATURE                 Location/Qualifiers
misc_feature            1..59
                        note = Primer VP1_GII.6Ohi12(S90L).c
source                  1..59
                        mol_type = other DNA
                        organism = synthetic construct
SEQUENCE: 152
ccctgaacta aacccttatc tgctccacct ttcacggatg tacaatggct acgcaggag   59

SEQ ID NO: 153          moltype = DNA  length = 52
FEATURE                 Location/Qualifiers
misc_feature            1..52
                        note = Primer IF-(160)GII.12_HS10_VP1.c
```

```
source                  1..52
                        mol_type = other DNA
                        organism = synthetic construct
SEQUENCE: 153
tcgtgcttcg gcaccagtac aatgaagatg gcgtctaatg atgctgctcc tt          52

SEQ ID NO: 154          moltype = DNA  length = 54
FEATURE                 Location/Qualifiers
misc_feature            1..54
                        note = Primer IF-GII.12_HS10_VP1.r
source                  1..54
                        mol_type = other DNA
                        organism = synthetic construct
SEQUENCE: 154
actaaagaaa ataggccttt actgcacacg cctcctccca tttcctgttc ccat        54

SEQ ID NO: 155          moltype = DNA  length = 48
FEATURE                 Location/Qualifiers
misc_feature            1..48
                        note = Primer GII.12(E80S).r
source                  1..48
                        mol_type = other DNA
                        organism = synthetic construct
SEQUENCE: 155
agttctggtc ctaagctcaa attcaataac acttcgccgg gggagttt               48

SEQ ID NO: 156          moltype = DNA  length = 49
FEATURE                 Location/Qualifiers
misc_feature            1..49
                        note = Primer GII.12(E80S).c
source                  1..49
                        mol_type = other DNA
                        organism = synthetic construct
SEQUENCE: 156
agtgttattg aatttgagct taggaccaga actcaacccc tatctggca              49

SEQ ID NO: 157          moltype = DNA  length = 50
FEATURE                 Location/Qualifiers
misc_feature            1..50
                        note = Primer GII.12(A90L).r
source                  1..50
                        mol_type = other DNA
                        organism = synthetic construct
SEQUENCE: 157
atccgagaca gatggagcag ataggggttg agttctggtc ctaattccaa             50

SEQ ID NO: 158          moltype = DNA  length = 57
FEATURE                 Location/Qualifiers
misc_feature            1..57
                        note = Primer GII.12(A90L).c
source                  1..57
                        mol_type = other DNA
                        organism = synthetic construct
SEQUENCE: 158
actcaacccc tatctgctcc atctgtctcg gatgtacaac ggctatgcgg gcggagt     57

SEQ ID NO: 159          moltype = DNA  length = 47
FEATURE                 Location/Qualifiers
misc_feature            1..47
                        note = Primer IF-NoV(US68)VP2(ORF3)(hCod).c
source                  1..47
                        mol_type = other DNA
                        organism = synthetic construct
SEQUENCE: 159
tcgtgcttcg gcaccagtac aatggctcag gccattattg gcgccat                47

SEQ ID NO: 160          moltype = DNA  length = 47
FEATURE                 Location/Qualifiers
misc_feature            1..47
                        note = Primer IF-NoV(US68)VP2(ORF3)(hCod).c
source                  1..47
                        mol_type = other DNA
                        organism = synthetic construct
SEQUENCE: 160
tcgtgcttcg gcaccagtac aatggctcag gccattattg gcgccat                47

SEQ ID NO: 161          moltype = DNA  length = 50
FEATURE                 Location/Qualifiers
misc_feature            1..50
```

```
                         note = Primer IF-NoV(US68)VP2(ORF3)(hCod).r
source                   1..50
                         mol_type = other DNA
                         organism = synthetic construct
SEQUENCE: 161
actaaagaaa ataggccttc agcggcggtt gttagcgaac agaggaagtc            50

SEQ ID NO: 162           moltype = DNA  length = 4540
FEATURE                  Location/Qualifiers
misc_feature             1..4540
                         note = Cloning vector 1190 from left to right T-DNA
source                   1..4540
                         mol_type = other DNA
                         organism = synthetic construct
SEQUENCE: 162
tggcaggata tattgtggtg taaacaaatt gacgcttaga caacttaata acacattgcg  60
gacgttttta atgtactgaa ttaacgccga atcccgggct ggtatattta tatgttgtca  120
aataactcaa aaaccataaa agtttaagtt agcaagtgtg tacattttta cttgaacaaa  180
aatattcacc tactactgtt ataaatcatt attaaacatt agagtaaaga aatatggatg  240
ataagaacaa gagtagtgat attttgacaa caattttgtt gcaacatttg agaaaatttt  300
gttgttctct cttttcattg gtcaaaaaca atagagagag aaaaaggaag agggagaata  360
aaaacataat gtgagtatga gagagaaagt tgtacaaaag ttgtaccaaa atagttgtac  420
aaatatcatt gaggaatttg acaaaagcta cacaaataag ggttaattgc tgtaaataaa  480
taaggatgac gcattagaga gatgtaccat tagagaattt ttggcaagtc attaaaaaga  540
aagaataaat tatttttaaa attaaaagtt gagtcatttg attaaacatg tgattattta  600
atgaattgat gaaagagttg gattaaagtt gtattagtaa ttagaatttg gtgtcaaatt  660
taatttgaca tttgatcttt tcctatatat tgccccatag agtcagttaa ctcattttta  720
tatttcatag atcaaataag agaaataacg gtatattaat ccctccaaaa aaaaaaaacg  780
gtatatttac taaaaaatct aagccacgta ggaggataac aggatccccg taggaggata  840
acatccaatc caaccaatca caacaatcct gatgagataa cccactttaa gcccacgcat  900
ctgtggcaca tctacattat ctaaatcaca cattcttcca cacatctgag ccacacaaaa  960
accaatccac atctttatca cccattctat aaaaaatcac actttgtgag tctacacttt  1020
gattcccttc aaacacatac aaagagaaga gactaattaa ttaattaatc atcttgagag  1080
aaaatggaac gagctataca aggaaacgac gctagggaac aagctaacag tgaacgttgg  1140
gatggaggat caggaggtac cacttctccc ttcaaacttc ctgacgaaag tccgagttgg  1200
actgagtggc ggctacataa cgatgagacg aattcgaatc aagataatcc ccttggtttc  1260
aaggaaagct ggggtttcgg gaaagttgta tttaagagat atctcagata cgacaggacg  1320
gaagcttcac tgcacagagt ccttggatct tggacgggag attcggttaa ctatgcagca  1380
tctcgatttt tcggtttcga ccagatcgga tgtacctata gtattcggtt tcgaggagtt  1440
agtatcaccg tttctggagg gtcgcgaact cttcagcatc tctgtgagat ggcaattcgg  1500
tctaagcaag aactgctaca gcttgcccca atcgaagtgg aaagtaatgt atcaagagga  1560
tgccctgaag gtactcaaac cttcgaaaaa gaaagcgagt aagttaaaat gcttcttcgt  1620
ctcctattta taatatggtt tgttattgtt aattttgttc ttgtagaaga gcttaattaa  1680
tcgttgttgt tatgaaatac tatttgtatg agatgaactg gtgtaatgta attcatttac  1740
ataagtggag tcagaatcag aatgtttcct ccataactaa ctagacatga agacctgccg  1800
cgtacaattg tcttatattt gaacaactaa aattgaacat cttttgccac aactttataa  1860
gtggttaata tagctcaaat atatggtcaa gttcaataga ttaataatgg aaatatcagt  1920
tatcgaaatt cattaacaat caacttaacg ttattaacta ctaattttat atcatcccct  1980
ttgataaatg atagtacacc aattaggaag gagcatgctc gcctaggaga ttgtcgtttc  2040
ccgccttcag tttgcaagct gctctagccg tgtagccaat acgcaaaccg cctctccccg  2100
cgcgttggga attactagcg cgtgtcgaca agcttgcatg ccggtcaaca tggtggagca  2160
cgacacactt gtctactcca aaaatatcaa agatacagtc tcagaagacc aaagggcaat  2220
tgagactttt caacaaaggg taatatccgg aaacctcctc ggattccatt gcccagctat  2280
ctgtcacttt attgtgaaga tagtggaaaa ggaaggtggc tcctacaaat gccatcattg  2340
cgataaagga aaggccatcg ttgaagatgc ctctgccgac agtggtccca aagatggacc  2400
cccacccacg aggagcatcg tggaaaaaga agacgttcca accacgtctt caaagcaagt  2460
ggattgatgt gataacatgg tggagcacga cacacttgtc tactccaaaa atatcaaaga  2520
tacagtctca gaagaccaaa gggcaattga gacttttcaa caaagggtaa tatccggaaa  2580
cctcctcgga ttccattgcc cagctatctg tcactttatt gtgaagatag tggaaaagga  2640
aggtggctcc tacaaatgcc atcattgcga taaaggaaag gccatcgttg aagatgcctc  2700
tgccgacagt ggtcccaaag atggaccccc acccacgagg agcatcgtgg aaaaagaaga  2760
cgttccaacc acgtcttcaa agcaagtgga ttgatgtgat atctccactg acgtaaggga  2820
tgacgcacaa tcccactatc cttcgcaaga cccttcctct atataaggaa gttcatttca  2880
tttggagagg tattaaaatc ttaataggtt ttgataaaag cgaacgtggg gaaacccgaa  2940
ccaaaccttc ttctaaactc tctctcatct ctcttaaagc aaacttctct cttgtctttc  3000
ttgcgtgagc gatcttcaac gttgtcagat cgtgcttcgg caccgcggat ggcgaaaaac  3060
gttgcgattt tcggcttatt gttttctctt cttgtgttgg ttccttctca gatcttcgcc  3120
tgcaggctcc tcagccaaaa cgacaccccc atctgtctat ccactggccc ctggatctgc  3180
tgcccaaact aactccatgg tgaccctggg atgcctggtc aagggctatt tccctgagcc  3240
agtgacagtg acctggaact ctggatccct gtccagcggt gtgcacacct tcccagctgt  3300
cctgcagtct gacctctaca ctctgagcag ctcagtgact gtcccctcca gcacctggcc  3360
cagcgagacc gtcacctgca acgttgccca cccggccagc agcaccaagg tggacaagaa  3420
aattgtgccc agggattgtg gttgtaagcc ttgcatatgt acagtcccag aagtatcatc  3480
tgtcttcatc ttccccccaa agcccaagga tgtgctcacc attactctga ctcctaaggt  3540
cacgtgtgtt gtggtagaca tcagcaagga tgatcccgag gtccagttca gctggtttgt  3600
agatgatgtg gaggtgcaca cagctcagac gcaaccccgg gaggagcagt tcaacagcac  3660
tttccgctca gtcagtgaac ttcccatcat gcaccaggac tggctcaatg gcaaggagcg  3720
atcgctcacc atcaccatca ccatcaccat caccattaaa ggcctatttt ctttagtttg  3780
aatttactgt tattcggtgt gcatttctat gtttggtgag cggttttctg tgctcagagt  3840
```

```
gtgtttattt tatgtaattt aatttctttg tgagctcctg tttagcaggt cgtcccttca  3900
gcaaggacac aaaaagattt taattttatt aaaaaaaaaa aaaaaaaaga ccgggaattc  3960
gatatcaagc ttatcgacct gcagatcgtt caaacatttg gcaataaagt ttcttaagat  4020
tgaatcctgt tgccggtctt gcgatgatta tcatataatt tctgttgaat tacgttaagc  4080
atgtaataat taacatgtaa tgcatgacgt tatttatgag atgggttttt atgattagag  4140
tcccgcaatt atacatttaa tacgcgatag aaaacaaaat atagcgcgca aactaggata  4200
aattatcgcg cgcggtgtca tctatgttac tagatctcta gagtctcaag cttggcgcgc  4260
ccacgtgact agtggcactg gccgtcgttt tacaacgtcg tgactgggaa aaccctggcg  4320
ttacccaact taatcgcctt gcagcacatc ccccttttcgc cagctggcgt aatagcgaag  4380
aggcccgcac cgatcgccct tcccaacagt tgcgcagcct gaatggcgaa tgctagagca  4440
gcttgagctt ggatcagatt gtcgtttccc gccttcagtt taaactatca gtgtttgaca  4500
ggatatattg gcgggtaaac ctaagagaaa agagcgttta                        4540
```

```
SEQ ID NO: 163          moltype = DNA  length = 2976
FEATURE                 Location/Qualifiers
misc_feature            1..2976
                        note = Construct 2724 from 2X35S promoter to NOS terminator
source                  1..2976
                        mol_type = other DNA
                        organism = synthetic construct
SEQUENCE: 163
gtcaacatgg tggagcacga cacacttgtc tactccaaaa atatcaaaga tacagtctca  60
gaagaccaaa gggcaattga gacttttcaa caaagggtaa tatccggaaa cctcctcgga  120
ttccattgcc cagctatctg tcactttatt gtgaagatag tggaaaagga aggtggctcc  180
tacaaatgcc atcattgcga taaaggaaag gccatcgttg aagatgcctc tgccgacagt  240
ggtcccaaag atggaccccc acccacgagg agcatcgtgg aaaaagaaga cgttccaacc  300
acgtcttcaa agcaagtgga ttgatgtgat aacatggtgg agcacgacac acttgtctac  360
tccaaaaata tcaaagatac agtctcagaa gaccaaaggg caattgagac ttttcaacaa  420
agggtaatat ccggaaacct cctcggattc cattgcccag ctatctgtca ctttattgtg  480
aagatagtgg aaaaggaagg tggctcctac aaatgccatc attgcgataa aggaaaggcc  540
atcgttgaag atgcctctgc cgacagtggt cccaaagatg gacccccacc cacgaggagc  600
atcgtggaaa aagaagacgt tccaaccacg tcttcaaagc aagtggattg atgtgatatc  660
tccactgacg taagggatga cgcacaatcc cactatcctt cgcaagaccc ttcctctata  720
taaggaagtt catttcattt ggagaggtat taaaatctta ataggttttg ataaaagcga  780
acgtggggaa acccgaacca aaccttcttc taaactctct ctcatctctc ttaaagcaaa  840
cttctctctt gtctttcttg cgtgagcgat cttcaacgtt gtcagatcgt gcttcggcac  900
cagtacaatg atgatggcta gtaaagatgc gacctcctct gtggatggtg cgtcaggggc  960
aggacaactc gtacccgagg taaacgccag cgacccactt gccatggacc ccgttgccgg  1020
aagttccaca gcagtggcca cagccggtca agtgaatcca attgatccgt ggattatcaa  1080
caatttcgtc caggcacccc agggcgagtt cacaatttca ccaaacaata caccgggcga  1140
tgtgctattc gatctttcct tgggtcctca ccttaaccct tttctactcc atctctcaca  1200
gatgtacaat ggttgggtag gaaacatgag agtccggatc atgctggctg gcaatgcctt  1260
taccgctggc aagatcatcg tcagttgtat tcctcccgga tttggatctc ataatctgac  1320
cattgctcaa gcgactctct ttccccatgt catcgccgac gttaggaccc tggaccccat  1380
cgaggtgccc ctggaggacg tccggaatgt tttgttccac aacaacgaca gaaaccagca  1440
gacgatgaga cttgtctgta tgctctatac cccactgcgg actggaggcg ggactggaga  1500
ctccttcgtt gtggcaggaa gagtgatgac atgccccctcc cccgacttca actttctttt  1560
tctggtccca ccaaccgttg agcagaagac gcggcccttt acactgccca atctcccgct  1620
ttcaagtctg agtaattcac gggccccatt gccgatctcc tcaatgggaa tctcccccga  1680
caacgtccag tctgtccaat tccaaaatgg gagatgcaca ctggacggtc gcctggtggg  1740
aacaactccg gtgtccctct cacatgtcgc caaaatccgc ggcacatcaa atggtaccgt  1800
aatcaatctg acagaacttg atggcacgcc cttccatccc tttgaaggac cagcccctat  1860
tggatttcct gatctgggag gttgcgactg gcacataaac atgacacagt ttggccactc  1920
cagccagaca cagtatgatg tcgatacaac cccagatacc ttcgtgccac acctgggatc  1980
tattcaagct aacggtattg gatccggcaa ctacgtggga gtcttatctt ggatctcacc  2040
accatcccac ccctcaggat cccaggttga cttgtggaag ataccgaatt atggatcctc  2100
gatcactgaa gccacgcacc tcgcaccttc cgtctaccca ccaggttttg gagaagtctt  2160
ggtgtttttc atgagcaaaa tgcccggccc tggagcctac aatctccctt gcctactccc  2220
tcaagagtat attagtcacc tcgcatctga gcaggccccg accgttggcg aggcagccct  2280
gctgcattat gtggatccgg acaccggcag gaacctgggt gagttcaaag cttatcctga  2340
cggttttcta acatgtgtac caaatggcgc ttccagcggc cctcaacagc tcccaatcaa  2400
tggcgtgttc gtttttgtca gctgggtaag ccgcttctac cagctgaagc ccgtggggac  2460
agcttcttct gcccgcggac gcctcggtct gcggagataa aggcctattt tctttagttt  2520
gaatttactg ttattcggtg tgcatttcta tgtttggtga gcggttttct gtgctcagag  2580
tgtgtttatt ttatgtaatt taatttcttt gtgagctcct gtttagcagg tcgtcccttc  2640
agcaaggaca caaaaagatt ttaattttat taaaaaaaaa aaaaaaaaag accgggaatt  2700
cgatatcaag cttatcgacc tgcagatcgt tcaaacattt ggcaataaag tttcttaaga  2760
ttgaatcctg ttgccggtct tgcgatgatt atcatataat ttctgttgaa ttacgttaag  2820
catgtaataa ttaacatgta atgcatgacg ttatttatga gatgggtttt tatgattaga  2880
gtcccgcaat tatacattta atacgcgata gaaaacaaaa tatagcgcgc aaactaggat  2940
aaattatcgc gcgcggtgtc atctatgtta ctagat                            2976
```

```
SEQ ID NO: 164          moltype = DNA  length = 5652
FEATURE                 Location/Qualifiers
misc_feature            1..5652
                        note = Cloning vector 3677 from left to right T-DNA
source                  1..5652
                        mol_type = other DNA
                        organism = synthetic construct
```

SEQUENCE: 164
tggcaggata tattgtggtg taaacaaatt gacgcttaga caacttaata acacattgcg 60
gacgttttta atgtactgaa ttaacgccga atcccgggct ggtatattta tatgttgtca 120
aataactcaa aaaccataaa agtttaagtt agcaagtgtg tacattttta cttgaacaaa 180
aatattcacc tactactgtt ataaatcatt attaaacatt agagtaaaga aatatggatg 240
ataagaacaa gagtagtgat attttgacaa caattttgtt gcaacatttg agaaaatttt 300
gttgttctct cttttcattg gtcaaaaaca atagagagag aaaaaggaag agggagaata 360
aaaacataat gtgagtatga gagagaaagt tgtacaaaag ttgtaccaaa atagttgtac 420
aaatatcatt gaggaatttg acaaaagcta cacaaataag ggttaattgc tgtaaataaa 480
taaggatgac gcattagaga gatgtaccat tagagaattt ttggcaagtc attaaaaaga 540
aagaataaat tatttttaaa attaaaagtt gagtcatttg attaaacatg tgattattta 600
atgaattgat gaaagagttg gattaaagtt gtattagtaa ttagaatttg gtgtcaaatt 660
taatttgaca tttgatcttt tcctatatat tgccccatag agtcagttaa ctcattttta 720
tatttcatag atcaaataag agaaataacg gtatattaat ccctccaaaa aaaaaaaacg 780
gtatatttac taaaaaatct aagccacgta ggaggataac aggatccccg taggaggata 840
acatccaatc caaccaatca caacaatcct gatgagataa cccactttaa gcccacgcat 900
ctgtggcaca tctacattat ctaaatcaca cattcttcca cacatctgag ccacacaaaa 960
accaatccac atctttatca cccattctat aaaaaatcac actttgtgag tctacacttt 1020
gattcccttc aaacacatac aaagagaaga gactaattaa ttaattaatc atcttgagag 1080
aaaatggaac gagctataca aggaaacgac gctagggaac aagctaacag tgaacgttgg 1140
gatggaggat caggaggtac cacttctccc ttcaaacttc ctgacgaaag tccgagttgg 1200
actgagtggc ggctacataa cgatgagacg aattcgaatc aagataatcc ccttggtttc 1260
aaggaaagct ggggtttcgg gaaagttgta tttaagagat atctcagata cgacaggacg 1320
gaagcttcac tgcacagagt ccttggatct tggacgggag attcggttaa ctatgcagca 1380
tctcgatttt tcggtttcga ccagatcgga tgtacctata gtattcggtt tcgaggagtt 1440
agtatcaccg tttctggagg gtcgcgaact cttcagcatc tctgtgagat ggcaattcgg 1500
tctaagcaag aactgctaca gcttgcccca atcgaagtgg aaagtaatgt atcaagagga 1560
tgccctgaag gtactcaaac cttcgaaaaa gaaagcgagt aagttaaaat gcttcttcgt 1620
ctcctattta taatatggtt tgttattgtt aattttgttc ttgtagaaga gcttaattaa 1680
tcgttgttgt tatgaaatac tatttgtatg agatgaactg gtgtaatgta attcatttac 1740
ataagtggag tcagaatcag aatgtttcct ccataactaa ctagacatga agacctgccg 1800
cgtacaattg tcttatattt gaacaactaa aattgaacat cttttgccac aactttataa 1860
gtggttaata tagctcaaat atatggtcaa gttcaataga ttaataatgg aaatatcagt 1920
tatcgaaatt cattaacaat caacttaacg ttattaacta ctaattttat atcatcccct 1980
ttgataaatg atagtacacc aattaggaag gagcatgctc gcctaggaga ttgtcgtttc 2040
ccgccttcag tttgcaagct gctctagccg tgtagccaat acgcaaaccg cctctccccg 2100
cgcgttggga attactagcg cgtgtcgaca agcttgcatg ccggtcaaca tggtggagca 2160
cgacacactt gtctactcca aaaatatcaa agatacagtc tcagaagacc aaagggcaat 2220
tgagactttt caacaaaggg taatatccgg aaacctcctc ggattccatt gcccagctat 2280
ctgtcacttt attgtgaaga tagtggaaaa ggaaggtggc tcctacaaat gccatcattg 2340
cgataaagga aaggccatcg ttgaagatgc ctctgccgac agtggtccca aagatggacc 2400
cccacccacg aggagcatcg tggaaaaaga agacgttcca accacgtctt caaagcaagt 2460
ggattgatgt gataacatgg tggagcacga cacacttgtc tactccaaaa atatcaaaga 2520
tacagtctca gaagaccaaa gggcaattga gacttttcaa caaagggtaa tatccggaaa 2580
cctcctcgga ttccattgcc cagctatctg tcactttatt gtgaagatag tggaaaagga 2640
aggtggctcc tacaaatgcc atcattgcga taaaggaaag gccatcgttg aagatgcctc 2700
tgccgacagt ggtcccaaag atggaccccc acccacgagg agcatcgtgg aaaaagaaga 2760
cgttccaacc acgtcttcaa agcaagtgga ttgatgtgat atctccactg acgtaaggga 2820
tgacgcacaa tcccactatc cttcgcaaga cccttccctct atataaggaa gttcatttca 2880
tttggagagg tattaaaatc ttaataggtt ttgataaaag cgaacgtggg gaaacccgaa 2940
ccaaaccttc ttctaaactc tctctcatct ctcttaaagc aaacttctct cttgtctttc 3000
ttgcgtgagc gatcttcaac gttgtcagat cgtgcttcgg caccgcggat ggcgaaaaac 3060
gttgcgattt tcggcttatt gttttctctt cttgtgttgg ttccttctca gatcttcgcc 3120
tgcaggctcc tcagccaaaa cgacaccccc atctgtctat ccactggccc ctggatctgc 3180
tgcccaaact aactccatgg tgaccctggg atgcctggtc aagggctatt tccctgagcc 3240
agtgacagtg acctggaact ctggatccct gtccagcggt gtgcacacct tcccagctgt 3300
cctgcagtct gacctctaca ctctgagcag ctcagtgact gtcccctcca gcacctggcc 3360
cagcgagacc gtcacctgca acgttgccca cccggccagc agcaccaagg tggacaagaa 3420
aattgtgccc agggattgtg gttgtaagcc ttgcatatgt acagtcccag aagtatcatc 3480
tgtcttcatc ttccccccaa agcccaagga tgtgctcacc attactctga ctcctaaggt 3540
cacgtgtgtt gtggtagaca tcagcaagga tgatcccgag gtccagttca gctggtttgt 3600
agatgatgtg gaggtgcaca cagctcagac gcaaccccgg gaggagcagt tcaacagcac 3660
tttccgctca gtcagtgaac ttcccatcat gcaccaggac tggctcaatg gcaaggagcg 3720
atcgctcacc atcaccatca ccatcaccat caccattaaa ggcctatttt ctttagtttg 3780
aatttactgt tattcggtgt gcatttctat gtttggtgag cggttttctg tgctcagagt 3840
gtgtttattt tatgtaattt aatttctttg tgagctcctg tttagcaggt cgtcccttca 3900
gcaaggacac aaaaagattt taattttatt atcgttcaaa catttggcaa taaagtttct 3960
taagattgaa tcctgttgcc ggtcttgcga tgattatcat ataatttctg ttgaattacg 4020
ttaagcatgt aataattaac atgtaatgca tgacgttatt tatgagatgg gtttttatga 4080
ttagagtccc gcaattatac atttaatacg cgatagaaaa caaaatatag cgcgcaaact 4140
aggataaatt atcgcgcgcg gtgtcatcta tgttactaga tctctaggta aaaatcccaa 4200
ttatatttgg tctaatttag tttggtattg agtaaaacaa attcgaacca aaccaaaata 4260
taaatatata gtttttatat atatgccttt aagacttttt atagaatttt ctttaaaaaa 4320
tatctagaaa tatttgcgac tcttctggca tgtaatattt cgttaaatat gaagtgctcc 4380
atttttatta actttaaata attggttgta cgatcacttt cttatcaagt gttactaaaa 4440
tgcgtcaatc tctttgttct tccatattca tatgtcaaaa tctatcaaaa ttcttatata 4500
tctttttcga atttgaagtg aaatttcgat aatttaaaat taaatagaac atatcattat 4560
ttaggtatca tattgatttt tatacttaat tactaaattt ggttaacttt gaaagtgtac 4620
atcaacgaaa aattagtcaa acgactaaaa taaataaata tcatgtgtta ttaagaaaat 4680

```
tctcctataa gaatatttta atagatcata tgtttgtaaa aaaaattaat ttttactaac  4740
acatatattt acttatcaaa aatttgacaa agtaagatta aaataatatt catctaacaa  4800
aaaaaaaacc agaaaatgct gaaaacccgg caaaaccgaa ccaatccaaa ccgatatagt  4860
tggtttggtt tgattttgat ataaaccgaa ccaactcggt ccatttgcac ccctaatcat  4920
aatagcttta atatttcaag atattattaa gttaacgttg tcaatatcct ggaaattttg  4980
caaaatgaat caagcctata tggctgtaat atgaatttaa aagcagctcg atgtggtggt  5040
aatatgtaat ttacttgatt ctaaaaaaat atcccaagta ttaataattt ctgctaggaa  5100
gaaggttagc tacgatttac agcaaagcca gaatacaaag aaccataaag tgattgaagc  5160
tcgaaatata cgaaggaaca aatattttta aaaaaatacg caatgacttg gaacaaaaga  5220
aagtgatata tttttttgttc ttaaacaagc atcccctcta aagaatggca gttttccttt  5280
gcatgtaact attatgctcc cttcgttaca aaaattttgg actactattg ggaacttctt  5340
ctgaaaattc tagagtctca agcttggcgc gcccacgtga ctagtggcac tggccgtcgt  5400
tttacaacgt cgtgactggg aaaaccctgg cgttacccaa cttaatcgcc ttgcagcaca  5460
tccccctttc gccagctggc gtaatagcga agaggcccgc accgatcgcc cttcccaaca  5520
gttgcgcagc ctgaatggcg aatgctagag cagcttgagc ttggatcaga ttgtcgtttc  5580
ccgccttcag tttaaactat cagtgtttga caggatatat tggcgggtaa acctaagaga  5640
aaagagcgtt ta                                                       5652

SEQ ID NO: 165         moltype = DNA  length = 2952
FEATURE                Location/Qualifiers
misc_feature           1..2952
                       note = Construct 4133 from 2X35S promoter to NOS terminator
source                 1..2952
                       mol_type = other DNA
                       organism = synthetic construct
SEQUENCE: 165
gtcaacatgg tggagcacga cacacttgtc tactccaaaa atatcaaaga tacagtctca  60
gaagaccaaa gggcaattga gacttttcaa caaagggtaa tatccggaaa cctcctcgga  120
ttccattgcc cagctatctg tcactttatt gtgaagatag tggaaaagga aggtggctcc  180
tacaaatgcc atcattgcga taaaggaaag gccatcgttg aagatgcctc tgccgacagt  240
ggtcccaaag atggaccccc acccacgagg agcatcgtgg aaaaagaaga cgttccaacc  300
acgtcttcaa agcaagtgga ttgatgtgat aacatggtgg agcacgacac acttgtctac  360
tccaaaaata tcaaagatac agtctcagaa gaccaaaggg caattgagac ttttcaacaa  420
agggtaatat ccggaaacct cctcggattc cattgcccag ctatctgtca ctttattgtg  480
aagatagtgg aaaaggaagg tggctcctac aaatgccatc attgcgataa aggaaaggcc  540
atcgttgaag atgcctctgc cgacagtggt cccaaagatg gacccccacc cacgaggagc  600
atcgtggaaa aagaagacgt tccaaccacg tcttcaaagc aagtggattg atgtgatatc  660
tccactgacg taagggatga cgcacaatcc cactatcctt cgcaagaccc ttcctctata  720
taaggaagtt catttcattt ggagaggtat taaaatctta ataggttttg ataaaagcga  780
acgtggggaa acccgaacca aaccttcttc taaactctct ctcatctctc ttaaagcaaa  840
cttctctctt gtctttcttg cgtgagcgat cttcaacgtt gtcagatcgt gcttcggcac  900
cagtacaatg aaaatggcct cgagtgacgc taaccctagt gacggcagcg ccgccaatct  960
tgtgcctgag gttaataatg aggtgatggc cctggagcct gtggtgggcg cagccatagc  1020
agcgcccgtg gccggtcagc agaatgtgat tgacccgtgg atacgcaaca attttgtcca  1080
agcccctggt ggggagttca ccgttagccc gagaaatgcg ccaggagaaa tcctgtggtc  1140
ggccagcttg ggacccgatc tgaaccccta tttgtcacat ctcgctcgga tgtacaacgg  1200
gtatgccggc ggatttgaag tgcaggtgat tctggctggg aacgcgttca ctgctggcaa  1260
agtgatcttt gcagcggtgc ctcccaactt ccccactgaa ggactgtctc caagccaggt  1320
cacaatgttt ccacacatcg tggtggacgt acggcagcta gagcctgtcc tgattcccct  1380
ccctgatgta cgcaataatt tctaccacta caatcaatcc aatgatccga ccattaaact  1440
catcgcgatg ttgtacaccc ctctgcgcgc taacaatgct ggagacgacg tattcaccgt  1500
gtcatgcaga gtgctcacca gaccttcacc agactttgac tttatcttct tagtgccccc  1560
cactgttgag agccgaacca agccctttag tgtccccgta ctcacagtcg aggagatgac  1620
aaatagccgc tttccaatcc cccttgagaa actgttcaca ggaccttcct cggcattcgt  1680
ggttcagcca cagaacggac gctgcacaac tgacggcgtg ctgctcggaa ccacccagct  1740
tagccctgtt aatatctgta cgtttagagg cgacgtaact cacataactg gctcacggaa  1800
ctataccatg aatctggcat cacagaattg gaatgactac gacccaaccg aagagattcc  1860
cgcacctctt ggaacccccg actttgtggg aaaaatacag ggcgtcctga cacaaaccac  1920
cagaaccgat ggctccacac ggggacacaa ggcaaccgtc tacactggct ctgccgattt  1980
tgccccgaaa ctgggtagag tgcagtttga gaccgacact gaccgggact ttgaagccaa  2040
tcagaatact aagttcacac ctgtaggagt gattcaggac gggggcacca ctcaccggaa  2100
cgagccgcaa caatgggtcc tgccctctta tagcgggagg aatactcata atgtgcattt  2160
ggctcctgca gtggctccca cgtttcccgg ggaacaactg ctcttttttc gttcaaccat  2220
gcctggatgc tccggatatc ccaatatgga tctcgattgc ctgctcccac aggaatgggt  2280
gcagtatttt tatcaagagg ccgcaccagc ccaatccgac gtcgcacttc tgcggttcgt  2340
gaatccagac acaggccgcg tgttgtttga gtgcaaattg cacaaatcag gatacgttac  2400
agtggctcat actggacagc atgacctggt gatcccaccc aacggatatt ttaggttcga  2460
ctcctgggtg aatcagtttt atacattagc ccccatgggg aatgggactg gcagacgcag  2520
ggctgtctga aggcctattt tctttagttt gaatttactg ttattcggtg tgcatttcta  2580
tgtttggtga gcggttttct gtgctcagag tgtgtttatt ttatgtaatt taatttcttt  2640
gtgagctcct gtttagcagg tcgtcccttc agcaaggaca caaaaagatt ttaattttat  2700
tatcgttcaa acatttggca ataaagtttc ttaagattga atcctgttgc cggtcttgcg  2760
atgattatca tataatttct gttgaattac gttaagcatg taataattaa catgtaatgc  2820
atgacgttat ttatgagatg ggtttttatg attagagtcc cgcaattata catttaatac  2880
gcgatagaaa acaaaatata gcgcgcaaac taggataaat tatcgcgcgc ggtgtcatct  2940
atgttactag at                                                       2952

SEQ ID NO: 166         moltype = DNA  length = 2952
FEATURE                Location/Qualifiers
```

```
misc_feature          1..2952
                      note = Construct 4135 from 2X35S promoter to NOS terminator
source                1..2952
                      mol_type = other DNA
                      organism = synthetic construct
SEQUENCE: 166
gtcaacatgg tggagcacga cacacttgtc tactccaaaa atatcaaaga tacagtctca  60
gaagaccaaa gggcaattga gacttttcaa caaagggtaa tatccggaaa cctcctcgga  120
ttccattgcc cagctatctg tcactttatt gtgaagatag tggaaaagga aggtggctcc  180
tacaaatgcc atcattgcga taaaggaaag gccatcgttg aagatgcctc tgccgacagt  240
ggtcccaaag atggaccccc acccacgagg agcatcgtgg aaaaagaaga cgttccaacc  300
acgtcttcaa agcaagtgga ttgatgtgat aacatggtgg agcacgacac acttgtctac  360
tccaaaaata tcaaagatac agtctcagaa gaccaaaggg caattgagac ttttcaacaa  420
agggtaatat ccggaaacct cctcggattc cattgcccag ctatctgtca ctttattgtg  480
aagatagtgg aaaaggaagg tggctcctac aaatgccatc attgcgataa aggaaaggcc  540
atcgttgaag atgcctctgc cgacagtggt cccaaagatg gacccccacc cacgaggagc  600
atcgtggaaa aagaagacgt tccaaccacg tcttcaaagc aagtggattg atgtgatatc  660
tccactgacg taagggatga cgcacaatcc cactatcctt cgcaagaccc ttcctctata  720
taaggaagtt catttcattt ggagaggtat taaaatctta ataggttttg ataaaagcga  780
acgtggggaa acccgaacca aaccttcttc taaactctct ctcatctctc ttaaagcaaa  840
cttctctctt gtctttcttg cgtgagcgat cttcaacgtt gtcagatcgt gcttcggcac  900
cagtacaatg aaaatggcct cgagtgacgc taaccctagt gacggcagcg ccgccaatct  960
tgtgcctgag gttaataatg aggtgatggc cctggagcct gtggtgggcg cagccatagc  1020
agcgcccgtg gccggtcagc agaatgtgat tgacccgtgg atacgcaaca attttgtcca  1080
agcccctggt ggggagttca ccgttagccc gagaaatgcg ccaggagaaa tcctgtggtc  1140
ggccagcttg ggacccgatc tgaaccccta tttgctgcat ctcgctcgga tgtacaacgg  1200
gtatgccggc ggatttgaag tgcaggtgat tctggctggg aacgcgttca ctgctggcaa  1260
agtgatcttt gcagcggtgc ctcccaactt ccccactgaa ggactgtctc caagccaggt  1320
cacaatgttt ccacacatcg tggtggacgt acggcagcta gagcctgtcc tgattcccct  1380
ccctgatgta cgcaataatt tctaccacta caatcaatcc aatgatccga ccattaaact  1440
catcgcgatg ttgtacaccc ctctgcgcgc taacaatgct ggagacgacg tattcaccgt  1500
gtcatgcaga gtgctcacca gaccttcacc agactttgac tttatcttct tagtgccccc  1560
cactgttgag agccgaacca agccctttag tgtccccgta ctcacagtcg aggagatgac  1620
aaatagccgc tttccaatcc cccttgagaa actgttcaca ggaccttcct cggcattcgt  1680
ggttcagcca cagaacggac gctgcacaac tgacggcgtg ctgctcggaa ccacccagct  1740
tagccctgtt aatatctgta cgtttagagg cgacgtaact cacataactg gctcacggaa  1800
ctataccatg aatctggcat cacagaattg gaatgactac gacccaaccg aagagattcc  1860
cgcacctctt ggaacccccg actttgtggg aaaaatacag ggcgtcctga cacaaaccac  1920
cagaaccgat ggctccacac ggggacacaa ggcaaccgtc tacactggct ctgccgattt  1980
tgcccccgaaa ctgggtagag tgcagtttga gaccgacact gaccgggact ttgaagccaa  2040
tcagaatact aagttcacac ctgtaggagt gattcaggac gggggcacca ctcaccggaa  2100
cgagccgcaa caatgggtcc tgccctctta tagcgggagg aatactcata atgtgcattt  2160
ggctcctgca gtggctccca cgtttcccgg ggaacaactg ctcttttttc gttcaaccat  2220
gcctggatgc tccggatatc ccaatatgga tctcgattgc ctgctcccac aggaatgggt  2280
gcagtatttt tatcaagagg ccgcaccagc ccaatccgac gtcgcacttc tgcggttcgt  2340
gaatccagac acaggcgcgg tgttgtttga gtgcaaattg cacaaatcag gatacgttac  2400
agtggctcat actggacagc atgacctggt gatcccaccc aacggatatt ttaggttcga  2460
ctcctgggtg aatcagtttt atacattagc cccccatgggg aatgggactg gcagacgcag  2520
ggctgtctga aggcctattt tctttagttt gaatttactg ttattcggtg tgcatttcta  2580
tgtttggtga gcggttttct gtgctcagag tgtgtttatt ttatgtaatt taatttcttt  2640
gtgagctcct gtttagcagg tcgtcccttc agcaaggaca caaaaaagatt ttaattttat  2700
tatcgttcaa acatttggca ataaagtttc ttaagattga atcctgttgc cggtcttgcg  2760
atgattatca tataatttct gttgaattac gttaagcatg taataattaa catgtaatgc  2820
atgacgttat ttatgagatg ggtttttatg attagagtcc cgcaattata catttaatac  2880
gcgatagaaa acaaaatata gcgcgcaaac taggataaat tatcgcgcgc ggtgtcatct  2940
atgttactag at                                                      2952

SEQ ID NO: 167        moltype = DNA  length = 1632
FEATURE               Location/Qualifiers
misc_feature          1..1632
                      note = Nucleic acid sequence of human codon optimized
                       VP1_GI.3_Lil08_Q84S
source                1..1632
                      mol_type = other DNA
                      organism = synthetic construct
SEQUENCE: 167
atgatgatgg cttccaagga tgctcccaca aacatggatg gaacaagcgg cgcggggcaa  60
cttgtgccgg aggtgtccac ggcggaaccc atttccatgg aacctgtggc cggcgcagcc  120
actgctgccg ccaccgcagg acaggtaaac atgatcgacc cctggatcat gtcaaattac  180
gttcaggctc cacaggggga gtttaccata agcccaaaca acaccccggg tgacatcttg  240
tttgacctga gcctaggacc acacttgaat ccgtttctga gtcacttggc tcagatgtat  300
aatggatggg ttggaaacat gaaggtgcgc gtgctcctgg cgggcaatgc attcacagcc  360
gggaagatta ttatctcttg cgtgccacct ggatttgcag cccagaacgt gtctatcgca  420
caggcaacca tgtttccgca tgtcatcgca gatgtgcgcg tgctagagcc catcgaggtg  480
ccccttgagg acgtgcgcaa cgtcctattc cataacaatg atagcacccc caccatgcgc  540
ttgatatgta tgttatatac tcccctccgc gccagtgggt ccagctccgg gaccgatcct  600
tttgtgattg ctgggcgggt gttgacttgt cctagccctg acttcaactt cctttttctg  660
gtgcctccaa atgtagaaca gaaaacaaag ccattcagcg tgccaaacct gcccccttaac  720
gtgctgtcga attcccgagt gccttccctt attaagtcca tgatggtatc tcaggatcac  780
```

-continued

```
ggtcaaatgg tgcagtttca gaacggccga gtgacgttag acgggcagct gcagggcaca  840
accccaacca gtgccagtca gctgtgtaag atcagaggca ccgtctacca cgcaactggc  900
ggacaggggc tgaatcttac tgagatcgat ggtacccccct accatgcatt cgagtcacct  960
gcacctattg gatttcccga tcttggggag tgtgattggc atatcaatgc ttcacctgcc  1020
aacgctttca cagacgggtc tattattcat cgcattgacg tagcacagga tagcacattt  1080
gccccgcacc tgggtaccat ccactatacg aacgcagatt acaacgcaaa cgtgggtctt  1140
atctgtagcc tagagtggct atctccgcca agcggtgggg cccctaaagt taacccatgg  1200
gctattcctc ggtacgggtc tacgctgact gaggccgctc agctggcacc ccccatatat  1260
ccaccaggat tcggggaagc cattgttttc tttatgtccg attttccgat agccaacggt  1320
tcagatggcc ttagtgtccc ttgcacgatt ccacaggaat ttgtgacaca cttcgtaaac  1380
gagcaggctc ctactcgggg cgaggctgcc ttgttgcatt acgtagaccc cgatacccat  1440
agaaacctgg gcgaattcaa actctaccct gaaggtttca tgacctgcgt acctaactcc  1500
tccggcagtg gccctcaaac cttgccgatc aacggcgtgt tcacgtttat cagctgggtt  1560
tcacggtttt accaactcaa gcccgtcgga acaactgggc cagttcggag gctcgggatc  1620
agacggagct ag                                                      1632

SEQ ID NO: 168         moltype = AA  length = 8
FEATURE                Location/Qualifiers
REGION                 1..8
                       note = Mutation of SEQ ID NO;1 at positions 39-46
source                 1..8
                       mol_type = protein
                       organism = synthetic construct
SEQUENCE: 168
SSTAVATA                                                           8

SEQ ID NO: 169         moltype = DNA  length = 1632
FEATURE                Location/Qualifiers
misc_feature           1..1632
                       note = Nucleic acid sequence of human codon optimized
                        VP1_GI.3_Lil08_A43V plus sign
source                 1..1632
                       mol_type = other DNA
                       organism = synthetic construct
SEQUENCE: 169
atgatgatgg cttccaagga tgctcccaca aacatggatg gaacaagcgg cgcggggcaa  60
cttgtgccgg aggtgtccac ggcggaaccc atttccatgg aacctgtggc cggcgcagcc  120
actgctgtgg ccaccgcagg acaggtaaac atgatcgacc cctggatcat gtcaaattac  180
gttcaggctc cacaggggga gtttaccata agcccaaaca acaccccggg tgacatcttg  240
tttgacctgc agctaggacc acacttgaat ccgtttctgc tccacttggc tcagatgtat  300
aatggatggg ttggaaacat gaaggtgcgc gtgctcctgg cgggcaatgc attcacagcc  360
gggaagatta ttatctcttg cgtgccacct ggatttgcag cccagaacgt gtctatcgca  420
caggcaacca tgtttccgca tgtcatcgca gatgtgcgcg tgctagagcc catcgaggtg  480
ccccttgagg acgtgcgcaa cgtcctattc cataacaatg atagcacccc caccatgcgc  540
ttgatatgta tgttatatac tcccctccgc gccagtgggt ccagctccgg gaccgatcct  600
tttgtgattg ctgggcgggt gttgacttgt cctagccctg acttcaactt cctttttctg  660
gtgcctccaa atgtagaaca gaaaacaaag ccattcagcg tgccaaacct gccccttaac  720
gtgctgtcga attcccgagt gccttccctt attaagtcca tgatggtatc tcaggatcac  780
ggtcaaatgg tgcagtttca gaacggccga gtgacgttag acgggcagct gcagggcaca  840
accccaacca gtgccagtca gctgtgtaag atcagaggca ccgtctacca cgcaactggc  900
ggacaggggc tgaatcttac tgagatcgat ggtacccccct accatgcatt cgagtcacct  960
gcacctattg gatttcccga tcttggggag tgtgattggc atatcaatgc ttcacctgcc  1020
aacgctttca cagacgggtc tattattcat cgcattgacg tagcacagga tagcacattt  1080
gccccgcacc tgggtaccat ccactatacg aacgcagatt acaacgcaaa cgtgggtctt  1140
atctgtagcc tagagtggct atctccgcca agcggtgggg cccctaaagt taacccatgg  1200
gctattcctc ggtacgggtc tacgctgact gaggccgctc agctggcacc ccccatatat  1260
ccaccaggat tcggggaagc cattgttttc tttatgtccg attttccgat agccaacggt  1320
tcagatggcc ttagtgtccc ttgcacgatt ccacaggaat ttgtgacaca cttcgtaaac  1380
gagcaggctc ctactcgggg cgaggctgcc ttgttgcatt acgtagaccc cgatacccat  1440
agaaacctgg gcgaattcaa actctaccct gaaggtttca tgacctgcgt acctaactcc  1500
tccggcagtg gccctcaaac cttgccgatc aacggcgtgt tcacgtttat cagctgggtt  1560
tcacggtttt accaactcaa gcccgtcgga acaactgggc cagttcggag gctcgggatc  1620
agacggagct ag                                                      1632

SEQ ID NO: 170         moltype = AA  length = 543
FEATURE                Location/Qualifiers
source                 1..543
                       mol_type = protein
                       note = Norovirus
                       organism = unidentified
SEQUENCE: 170
MMMASKDAPT NMDGTSGAGQ LVPEVSTAEP ISMEPVAGAA TAVATAGQVN MIDPWIMSNY  60
VQAPQGEFTI SPNNTPGDIL FDLQLGPHLN PFLLHLAQMY NGWVGNMKVR VLLAGNAFTA  120
GKIIISCVPP GFAAQNVSIA QATMFPHVIA DVRVLEPIEV PLEDVRNVLF HNNDSTPTMR  180
LICMLYTPLR ASGSSSGTDP FVIAGRVLTC PSPDFNFLFL VPPNVEQKTK PFSVPNLPLN  240
VLSNSRVPSL IKSMMVSQDH GQMVQFQNGR VTLDGQLQGT TPTSASQLCK IRGTVYHATG  300
GQGLNLTEID GTPYHAFESP APIGFPDLGE CDWHINASPA NAFTDGSIIH RIDVAQDSTF  360
APHLGTIHYT NADYNANVGL ICSLEWLSPP SGGAPKVNPW AIPRYGSTLT EAAQLAPPIY  420
PPGFGEAIVF FMSDFPIANG SDGLSVPCTI PQEFVTHFVN EQAPTRGEAA LLHYVDPDTH  480
```

-continued

```
RNLGEFKLYP EGFMTCVPNS SGSGPQTLPI NGVFTFISWV SRFYQLKPVG TTGPVRRLGI  540
RRS                                                               543

SEQ ID NO: 171         moltype = DNA  length = 1632
FEATURE                Location/Qualifiers
misc_feature           1..1632
                       note = Nucleic acid sequence of human codon optimized
                        VP1_GI.3_Lil08_M57I plus sign S94L
source                 1..1632
                       mol_type = other DNA
                       organism = synthetic construct
SEQUENCE: 171
atgatgatgg cttccaagga tgctcccaca aacatggatg gaacaagcgg cgcggggcaa  60
cttgtgccgg aggtgtccac ggcggaaccc atttccatgg aacctgtggc cggcgcagcc  120
actgctgccg ccaccgcagg acaggtaaac atgatcgacc cctggatcat ctcaaattac  180
gttcaggctc cacaggggga gtttaccata agcccaaaca acaccccggg tgacatcttg  240
tttgacctgc agctaggacc acacttgaat ccgtttctgc tccacttggc tcagatgtat  300
aatggatggg ttggaaacat gaaggtgcgc gtgctcctgg cgggcaatgc attcacagcc  360
gggaagatta ttatctcttg cgtgccacct ggatttgcag cccagaacgt gtctatcgca  420
caggcaacca tgtttccgca tgtcatcgca gatgtgcgcg tgctagagcc catcgaggtg  480
ccccttgagg acgtgcgcaa cgtcctattc cataacaatg atagcacccc caccatgcgc  540
ttgatatgta tgttatatac tcccctccgc gccagtgggt ccagctccgg gaccgatcct  600
tttgtgattg ctgggcgggt gttgacttgt cctagccctg acttcaactt cctttttctg  660
gtgcctccaa atgtagaaca gaaaacaaag ccattcagcg tgccaaacct gccccttaac  720
gtgctgtcga attcccgagt gccttccctt attaagtcca tgatggtatc tcaggatcac  780
ggtcaaatgg tgcagtttca gaacggccga gtgacgttag acgggcagct gcagggcaca  840
accccaacca gtgccagtca gctgtgtaag atcagaggca ccgtctacca cgcaactggc  900
ggacaggggc tgaatcttac tgagatcgat ggtacccccct accatgcatt cgagtcacct  960
gcacctattg gatttcccga tcttggggag tgtgattggc atatcaatgc ttcacctgcc  1020
aacgctttca cagacgggtc tattattcat cgcattgacg tagcacagga tagcacattt  1080
gccccgcacc tgggtaccat ccactatacg aacgcagatt acaacgcaaa cgtgggtctt  1140
atctgtagcc tagagtggct atctccgcca agcggtgggg cccctaaagt taacccatgg  1200
gctattcctc ggtacgggtc tacgctgact gaggccgctc agctggcacc ccccatatat  1260
ccaccaggat tcggggaagc cattgttttc tttatgtccg attttccgat agccaacggt  1320
tcagatggcc ttagtgtccc ttgcacgatt ccacaggaat ttgtgacaca cttcgtaaac  1380
gagcaggctc ctactcgggg cgaggctgcc ttgttgcatt acgtagaccc cgatacccat  1440
agaaacctgg gcgaattcaa actctaccct gaaggtttca tgacctgcgt acctaactcc  1500
tccggcagtg gccctcaaac cttgccgatc aacggcgtgt tcacgtttat cagctgggtt  1560
tcacggtttt accaactcaa gcccgtcgga acaactgggc cagttcggag gctcgggatc  1620
agacggagct ag                                                     1632

SEQ ID NO: 172         moltype = AA  length = 543
FEATURE                Location/Qualifiers
source                 1..543
                       mol_type = protein
                       note = Norovirus
                       organism = unidentified
SEQUENCE: 172
MMMASKDAPT NMDGTSGAGQ LVPEVSTAEP ISMEPVAGAA TAAATAGQVN MIDPWIISNY  60
VQAPQGEFTI SPNNTPGDIL FDLQLGPHLN PFLLHLAQMY NGWVGNMKVR VLLAGNAFTA  120
GKIIISCVPP GFAAQNVSIA QATMFPHVIA DVRVLEPIEV PLEDVRNVLF HNNDSTPTMR  180
LICMLYTPLR ASGSSSGTDP FVIAGRVLTC PSPDFNFLFL VPPNVEQKTK PFSVPNLPLN  240
VLSNSRVPSL IKSMMVSQDH GQMVQFQNGR VTLDGQLQGT TPTSASQLCK IRGTVYHATG  300
GQGLNLTEID GTPYHAFESP APIGFPDLGE CDWHINASPA NAFTDGSIIH RIDVAQDSTF  360
APHLGTIHYT NADYNANVGL ICSLEWLSPP SGGAPKVNPW AIPRYGSTLT EAAQLAPPIY  420
PPGFGEAIVF FMSDFPIANG SDGLSVPCTI PQEFVTHFVN EQAPTRGEAA LLHYVDPDTH  480
RNLGEFKLYP EGFMTCVPNS SGSGPQTLPI NGVFTFISWV SRFYQLKPVG TTGPVRRLGI  540
RRS                                                               543

SEQ ID NO: 173         moltype = DNA  length = 1632
FEATURE                Location/Qualifiers
misc_feature           1..1632
                       note = Nucleic acid sequence of human codon optimized
                        VP1_GI.3_Lil08_A43Vplus sign M57Iplus sign S94L
source                 1..1632
                       mol_type = other DNA
                       organism = synthetic construct
SEQUENCE: 173
atgatgatgg cttccaagga tgctcccaca aacatggatg gaacaagcgg cgcggggcaa  60
cttgtgccgg aggtgtccac ggcggaaccc atttccatgg aacctgtggc cggcgcagcc  120
actgctgtgg ccaccgcagg acaggtaaac atgatcgacc cctggatcat ctcaaattac  180
gttcaggctc cacaggggga gtttaccata agcccaaaca acaccccggg tgacatcttg  240
tttgacctgc agctaggacc acacttgaat ccgtttctgc tccacttggc tcagatgtat  300
aatggatggg ttggaaacat gaaggtgcgc gtgctcctgg cgggcaatgc attcacagcc  360
gggaagatta ttatctcttg cgtgccacct ggatttgcag cccagaacgt gtctatcgca  420
caggcaacca tgtttccgca tgtcatcgca gatgtgcgcg tgctagagcc catcgaggtg  480
ccccttgagg acgtgcgcaa cgtcctattc cataacaatg atagcacccc caccatgcgc  540
ttgatatgta tgttatatac tcccctccgc gccagtgggt ccagctccgg gaccgatcct  600
tttgtgattg ctgggcgggt gttgacttgt cctagccctg acttcaactt cctttttctg  660
```

```
gtgcctccaa atgtagaaca gaaaacaaag ccattcagcg tgccaaacct gcccccttaac  720
gtgctgtcga attcccgagt gccttccctt attaagtcca tgatggtatc tcaggatcac  780
ggtcaaatgg tgcagtttca gaacggccga gtgacgttag acgggcagct gcagggcaca  840
accccaacca gtgccagtca gctgtgtaag atcagaggca ccgtctacca cgcaactggc  900
ggacaggggc tgaatcttac tgagatcgat ggtacccccct accatgcatt cgagtcacct  960
gcacctattg gatttcccga tcttggggag tgtgattggc atatcaatgc ttcacctgcc  1020
aacgctttca cagacgggtc tattattcat cgcattgacg tagcacagga tagcacattt  1080
gccccgcacc tgggtaccat ccactatacg aacgcagatt acaacgcaaa cgtgggtctt  1140
atctgtagcc tagagtggct atctccgcca agcggtgggg cccctaaagt taacccatgg  1200
gctattcctc ggtacgggtc tacgctgact gaggccgctc agctggcacc ccccatatat  1260
ccaccaggat tcggggaagc cattgttttc tttatgtccg attttccgat agccaacggt  1320
tcagatggcc ttagtgtccc ttgcacgatt ccacaggaat ttgtgacaca cttcgtaaac  1380
gagcaggctc ctactcgggg cgaggctgcc ttgttgcatt acgtagaccc cgatacccat  1440
agaaacctgg gcgaattcaa actctaccct gaaggtttca tgacctgcgt acctaactcc  1500
tccggcagtg gccctcaaac cttgccgatc aacggcgtgt tcacgtttat cagctgggtt  1560
tcacggtttt accaactcaa gcccgtcgga acaactgggc cagttcggag gctcgggatc  1620
agacggagct ag                                                       1632

SEQ ID NO: 174         moltype = AA  length = 543
FEATURE                Location/Qualifiers
source                 1..543
                       mol_type = protein
                       note = Norovirus
                       organism = unidentified
SEQUENCE: 174
MMMASKDAPT NMDGTSGAGQ LVPEVSTAEP ISMEPVAGAA TAVATAGQVN MIDPWIISNY  60
VQAPQGEFTI SPNNTPGDIL FDLQLGPHLN PFLLHLAQMY NGWVGNMKVR VLLAGNAFTA  120
GKIIISCVPP GFAAQNVSIA QATMFPHVIA DVRVLEPIEV PLEDVRNVLF HNNDSTPTMR  180
LICMLYTPLR ASGSSSGTDP FVIAGRVLTC PSPDFNFLFL VPPNVEQKTK PFSVPNLPLN  240
VLSNSRVPSL IKSMMVSQDH GQMVQFQNGR VTLDGQLQGT TPTSASQLCK IRGTVYHATG  300
GQGLNLTEID GTPYHAFESP APIGFPDLGE CDWHINASPA NAFTDGSIIH RIDVAQDSTF  360
APHLGTIHYT NADYNANVGL ICSLEWLSPP SGGAPKVNPW AIPRYGSTLT EAAQLAPPIY  420
PPGFGEAIVF FMSDFPIANG SDGLSVPCTI PQEFVTHFVN EQAPTRGEAA LLHYVDPDTH  480
RNLGEFKLYP EGFMTCVPNS SGSGPQTLPI NGVFTFISWV SRFYQLKPVG TTGPVRRLGI  540
RRS                                                                 543

SEQ ID NO: 175         moltype = DNA  length = 1617
FEATURE                Location/Qualifiers
source                 1..1617
                       mol_type = genomic DNA
                       note = Norovirus
                       organism = unidentified
SEQUENCE: 175
atgatgatgg ccagcaagga cgctccgagt aacatggacg gcacttcggg cgcggggcag  60
ctggtgcccg aggtcaatgc cgcagaacca cttcctcttg agcccgtcgt tggcgccgcc  120
acagctgtcg caactgcagg ccaagtcaat atgatcgacc cgtggataat gaacaatttc  180
gttcaggcac cagaaggaga attcaccatc tcccccaata acaccccagg ggatattctg  240
tttgacctca ggttaggacc ccacttgaac ccctttctgc ttcatctctc acaaatgtat  300
aatggctggg tcgggaatat gcgcgtgcgg gtgatgctag ccggcaatgc tttttctgca  360
ggcaagatta tcatttgctg cgttcctcct ggattcgaat ctcaaaatat cagcattggt  420
caagcaacca tgtttccaca tgtgatcgct gatgttcgcg tcctggaacc cattgaagtt  480
cctctcgacg acgtgagaaa tgttctcttc cacaccaacg agaataggcc gactatgaga  540
cttctgtgta tgctctacac ccccattaaga gccgggggag catcctcagg tactgaccca  600
tttgtgattg ccgggcgggt gctcacatgc ccggctccag actttaactt ccttttcttg  660
gtgccaccca gtgttgaaca gaaaaccaga cagctcacca tcccaaatat cccattgaac  720
aatctcgcca acagcagggt gccagcaatg ataaacaaaa tgacagtcag tgctgaccag  780
aaccaggtag tccagtttca gaacggcaga tgcacgcttg agggccaact gcttgggacg  840
accccagtct ccgcgaacca ggtggcccga atccggggta aagtcttcag tacaaactcc  900
ggcactggcc ttaacctcac agaggttgac ggcactccct atcatgcttt tgagtctcca  960
gcccctcttg gctttcccga tataggcaac tgtgactggc acgtttatgc gtttaaagta  1020
aaccagaaca ccggcgatcc tatgtatagg ttggatataa cacaaggtaa ttcattcgcc  1080
ccacacttgg gtagcatcga gttcagttca gagaaccatc cgagtggtga tcagctaggc  1140
acattgacgt ggatcagccc tctgaataac gcatcaagag tggatccctg gaagatccct  1200
acctatgggt ccactctgac agagagcaca aatttggctc cgcccatttt cccaccccgga  1260
ttcggcgagg ccatagtgta ctttatgtct gactttccta tcgtcagcgg gaatacagcc  1320
cagattcctt gcacactgcc acaagaattc gtctcatcct ttgtagagca gcaggcacct  1380
attcgaggtg aggccgccct cttgcactac gtggaccctg acacccaccg caatcttggc  1440
gagtttaagc tgtaccctga cgggtttatt acctgtgtac ccaacaccgg cggcggccca  1500
caaaatttgc ccagcaatgg cgtgtttgtc ttttcctctt gggtgtctcg atactaccag  1560
cttaaacctg tcggaactac gggccccgtg cgacgactcg gcgtgaggcg ggtgtga      1617

SEQ ID NO: 176         moltype = DNA  length = 1617
FEATURE                Location/Qualifiers
misc_feature           1..1617
                       note = Nucleic acid sequence of human codon optimized VP1_
                        GI.7/GA5043/USA/2014_R84S
source                 1..1617
                       mol_type = other DNA
                       organism = synthetic construct
```

```
SEQUENCE: 176
atgatgatgg ccagcaagga cgctccgagt aacatggacg gcacttcggg cgcggggcag  60
ctggtgcccg aggtcaatgc cgcagaacca cttcctcttg agcccgtcgt tggcgccgcc  120
acagctgtcg caactgcagg ccaagtcaat atgatcgacc cgtggataat gaacaatttc  180
gttcaggcac cagaaggaga attcaccatc tcccccaata acaccccagg ggatattctg  240
tttgacctca gcttaggacc ccacttgaac ccctttctgc ttcatctctc acaaatgtat  300
aatggctggg tcgggaatat gcgcgtgcgg gtgatgctag ccggcaatgc tttttctgca  360
ggcaagatta tcatttgctg cgttcctcct ggattcgaat ctcaaaatat cagcattggt  420
caagcaacca tgtttccaca tgtgatcgct gatgttcgcg tcctggaacc cattgaagtt  480
cctctcgacg acgtgagaaa tgttctcttc cacaccaacg agaataggcc gactatgaga  540
cttctgtgta tgctctacac ccccattaaga gccgggggag catcctcagg tactgaccca  600
tttgtgattg ccgggcgggt gctcacatgc ccggctccag actttaactt ccttttcttg  660
gtgccaccca gtgttgaaca gaaaaccaga cagctcacca tcccaaatat cccattgaac  720
aatctcgcca acagcagggt gccagcaatg ataaacaaaa tgacagtcag tgctgaccag  780
aaccaggtag tccagtttca gaacggcaga tgcacgcttg agggccaact gcttgggacg  840
accccagtct ccgcgaacca ggtggcccga atccggggta aagtcttcag tacaaactcc  900
ggcactggcc ttaacctcac agaggttgac ggcactccct atcatgcttt tgagtctcca  960
gcccctcttg gctttcccga tataggcaac tgtgactggc acgtttatgc gtttaaagta  1020
aaccagaaca ccggcgatcc tatgtatagg ttggatataa cacaaggtaa ttcattcgcc  1080
ccacacttgg gtagcatcga gttcagttca gagaaccatc cgagtggtga tcagctaggc  1140
acattgacgt ggatcagccc tctgaataac gcatcaagag tggatccctg gaagatccct  1200
acctatgggt ccactctgac agagagcaca aatttggctc cgcccatttt cccacccgga  1260
ttcggcgagg ccatagtgta ctttatgtct gactttccta tcgtcagcgg gaatacagcc  1320
cagattcctt gcacactgcc acaagaattc gtctcatcct ttgtagagca gcaggcacct  1380
attcgaggtg aggccgccct cttgcactac gtggaccctg acacccaccg caatcttggc  1440
gagtttaagc tgtaccctga cgggtttatt acctgtgtac ccaacaccgg cggcggccca  1500
caaaatttgc ccagcaatgg cgtgtttgtc ttttcctctt gggtgtctcg atactaccag  1560
cttaaacctg tcggaactac gggccccgtg cgacgactcg gcgtgaggcg ggtgtga     1617

SEQ ID NO: 177         moltype = AA  length = 538
FEATURE                Location/Qualifiers
source                 1..538
                       mol_type = protein
                       note = Norovirus
                       organism = unidentified
SEQUENCE: 177
MMMASKDAPS NMDGTSGAGQ LVPEVNAAEP LPLEPVVGAA TAVATAGQVN MIDPWIMNNF  60
VQAPEGEFTI SPNNTPGDIL FDLSLGPHLN PFLLHLSQMY NGWVGNMRVR VMLAGNAFSA  120
GKIIICCVPP GFESQNISIG QATMFPHVIA DVRVLEPIEV PLDDVRNVLF HTNENRPTMR  180
LLCMLYTPLR AGGASSGTDP FVIAGRVLTC PAPDFNFLFL VPPSVEQKTR QLTIPNIPLN  240
NLANSRVPAM INKMTVSADQ NQVVQFQNGR CTLEGQLLGT TPVSANQVAR IRGKVFSTNS  300
GTGLNLTEVD GTPYHAFESP APLGFPDIGN CDWHVYAFKV NQNTGDPMYR LDITQGNSFA  360
PHLGSIEFSS ENHPSGDQLG TLTWISPLNN ASRVDPWKIP TYGSTLTEST NLAPPIFPPG  420
FGEAIVYFMS DFPIVSGNTA QIPCTLPQEF VSSFVEQQAP IRGEAALLHY VDPDTHRNLG  480
EFKLYPDGFI TCVPNTGGGP QNLPSNGVFV FSSWVSRYYQ LKPVGTTGPV RRLGVRRV    538

SEQ ID NO: 178         moltype = DNA  length = 1617
FEATURE                Location/Qualifiers
misc_feature           1..1617
                       note = Nucleic acid sequence of human codon optimized VP1_
                        GI.7/GA5043/USA/2014_M57I
source                 1..1617
                       mol_type = other DNA
                       organism = synthetic construct
SEQUENCE: 178
atgatgatgg ccagcaagga cgctccgagt aacatggacg gcacttcggg cgcggggcag  60
ctggtgcccg aggtcaatgc cgcagaacca cttcctcttg agcccgtcgt tggcgccgcc  120
acagctgtcg caactgcagg ccaagtcaat atgatcgacc cgtggataat caacaatttc  180
gttcaggcac cagaaggaga attcaccatc tcccccaata acaccccagg ggatattctg  240
tttgacctca ggttaggacc ccacttgaac ccctttctgc ttcatctctc acaaatgtat  300
aatggctggg tcgggaatat gcgcgtgcgg gtgatgctag ccggcaatgc tttttctgca  360
ggcaagatta tcatttgctg cgttcctcct ggattcgaat ctcaaaatat cagcattggt  420
caagcaacca tgtttccaca tgtgatcgct gatgttcgcg tcctggaacc cattgaagtt  480
cctctcgacg acgtgagaaa tgttctcttc cacaccaacg agaataggcc gactatgaga  540
cttctgtgta tgctctacac ccccattaaga gccgggggag catcctcagg tactgaccca  600
tttgtgattg ccgggcgggt gctcacatgc ccggctccag actttaactt ccttttcttg  660
gtgccaccca gtgttgaaca gaaaaccaga cagctcacca tcccaaatat cccattgaac  720
aatctcgcca acagcagggt gccagcaatg ataaacaaaa tgacagtcag tgctgaccag  780
aaccaggtag tccagtttca gaacggcaga tgcacgcttg agggccaact gcttgggacg  840
accccagtct ccgcgaacca ggtggcccga atccggggta aagtcttcag tacaaactcc  900
ggcactggcc ttaacctcac agaggttgac ggcactccct atcatgcttt tgagtctcca  960
gcccctcttg gctttcccga tataggcaac tgtgactggc acgtttatgc gtttaaagta  1020
aaccagaaca ccggcgatcc tatgtatagg ttggatataa cacaaggtaa ttcattcgcc  1080
ccacacttgg gtagcatcga gttcagttca gagaaccatc cgagtggtga tcagctaggc  1140
acattgacgt ggatcagccc tctgaataac gcatcaagag tggatccctg gaagatccct  1200
acctatgggt ccactctgac agagagcaca aatttggctc cgcccatttt cccacccgga  1260
ttcggcgagg ccatagtgta ctttatgtct gactttccta tcgtcagcgg gaatacagcc  1320
cagattcctt gcacactgcc acaagaattc gtctcatcct ttgtagagca gcaggcacct  1380
attcgaggtg aggccgccct cttgcactac gtggaccctg acacccaccg caatcttggc  1440
```

-continued

```
gagtttaagc tgtaccctga cgggtttatt acctgtgtac ccaacaccgg cggcggccca  1500
caaaatttgc ccagcaatgg cgtgtttgtc ttttcctctt gggtgtctcg atactaccag  1560
cttaaacctg tcggaactac gggccccgtg cgacgactcg gcgtgaggcg ggtgtga     1617

SEQ ID NO: 179         moltype = AA  length = 538
FEATURE                Location/Qualifiers
source                 1..538
                       mol_type = protein
                       note = Norovirus
                       organism = unidentified
SEQUENCE: 179
MMMASKDAPS NMDGTSGAGQ LVPEVNAAEP LPLEPVVGAA TAVATAGQVN MIDPWIINNF  60
VQAPEGEFTI SPNNTPGDIL FDLRLGPHLN PFLLHLSQMY NGWVGNMRVR VMLAGNAFSA  120
GKIIICCVPP GFESQNISIG QATMFPHVIA DVRVLEPIEV PLDDVRNVLF HTNENRPTMR  180
LLCMLYTPLR AGGASSGTDP FVIAGRVLTC PAPDFNFLFL VPPSVEQKTR QLTIPNIPLN  240
NLANSRVPAM INKMTVSADQ NQVVQFQNGR CTLEGQLLGT TPVSANQVAR IRGKVFSTNS  300
GTGLNLTEVD GTPYHAFESP APLGFPDIGN CDWHVYAFKV NQNTGDPMYR LDITQGNSFA  360
PHLGSIEFSS ENHPSGDQLG TLTWISPLNN ASRVDPWKIP TYGSTLTEST NLAPPIFPPG  420
FGEAIVYFMS DFPIVSGNTA QIPCTLPQEF VSSFVEQQAP IRGEAALLHY VDPDTHRNLG  480
EFKLYPDGFI TCVPNTGGGP QNLPSNGVFV FSSWVSRYYQ LKPVGTTGPV RRLGVRRV    538

SEQ ID NO: 180         moltype = DNA  length = 1617
FEATURE                Location/Qualifiers
misc_feature           1..1617
                       note = Nucleic acid sequence of human codon optimized VP1_
                        GI.7/GA5043/USA/2014_M57I plus sign R84S
source                 1..1617
                       mol_type = other DNA
                       organism = synthetic construct
SEQUENCE: 180
atgatgatgg ccagcaagga cgctccgagt aacatggacg gcacttcggg cgcggggcag  60
ctggtgcccg aggtcaatgc cgcagaacca cttcctcttg agcccgtcgt tggcgccgcc  120
acagctgtcg caactgcagg ccaagtcaat atgatcgacc cgtggataat caacaatttc  180
gttcaggcac cagaaggaga attcaccatc tcccccaata acaccccagg ggatattctg  240
tttgacctca gcttaggacc ccacttgaac ccctttctgc ttcatctctc acaaatgtat  300
aatggctggg tcgggaatat gcgcgtgcgg gtgatgctag ccggcaatgc tttttctgca  360
ggcaagatta tcatttgctg cgttcctcct ggattcgaat ctcaaaatat cagcattggt  420
caagcaacca tgtttccaca tgtgatcgct gatgttcgcg tcctggaacc cattgaagtt  480
cctctcgacg acgtgagaaa tgttctcttc cacaccaacg agaataggcc gactatgaga  540
cttctgtgta tgctctacac cccattaaga gccgggggag catcctcagg tactgaccca  600
tttgtgattg ccgggcgggt gctcacatgc ccggctccag actttaactt ccttttcttg  660
gtgccaccca gtgttgaaca gaaaaccaga cagctcacca tcccaaatat cccattgaac  720
aatctcgcca acagcagggt gccagcaatg ataaacaaaa tgacagtcag tgctgaccag  780
aaccaggtag tccagtttca gaacggcaga tgcacgcttg agggccaact gcttgggacg  840
accccagtct ccgcgaacca ggtggcccga atccggggta aagtcttcag tacaaactcc  900
ggcactggcc ttaacctcac agaggttgac ggcactccct atcatgcttt tgagtctcca  960
gcccctcttg gctttcccga tataggcaac tgtgactggc acgtttatgc gtttaaagta  1020
aaccagaaca ccggcgatcc tatgtatagg ttggatataa cacaaggtaa ttcattcgcc  1080
ccacacttgg gtagcatcga gttcagttca gagaaccatc cgagtggtga tcagctaggc  1140
acattgacgt ggatcagccc tctgaataac gcatcaagag tggatccctg gaagatccct  1200
acctatgggt ccactctgac agagagcaca aatttggctc cgcccatttt cccacccgga  1260
ttcggcgagg ccatagtgta ctttatgtct gactttccta tcgtcagcgg gaatacagcc  1320
cagattcctt gcacactgcc acaagaattc gtctcatcct ttgtagagca gcaggcacct  1380
attcgaggtg aggccgccct cttgcactac gtggaccctg acacccaccg caatcttggc  1440
gagtttaagc tgtaccctga cgggtttatt acctgtgtac ccaacaccgg cggcggccca  1500
caaaatttgc ccagcaatgg cgtgtttgtc ttttcctctt gggtgtctcg atactaccag  1560
cttaaacctg tcggaactac gggccccgtg cgacgactcg gcgtgaggcg ggtgtga     1617

SEQ ID NO: 181         moltype = AA  length = 538
FEATURE                Location/Qualifiers
source                 1..538
                       mol_type = protein
                       note = Norovirus
                       organism = unidentified
SEQUENCE: 181
MMMASKDAPS NMDGTSGAGQ LVPEVNAAEP LPLEPVVGAA TAVATAGQVN MIDPWIINNF  60
VQAPEGEFTI SPNNTPGDIL FDLSLGPHLN PFLLHLSQMY NGWVGNMRVR VMLAGNAFSA  120
GKIIICCVPP GFESQNISIG QATMFPHVIA DVRVLEPIEV PLDDVRNVLF HTNENRPTMR  180
LLCMLYTPLR AGGASSGTDP FVIAGRVLTC PAPDFNFLFL VPPSVEQKTR QLTIPNIPLN  240
NLANSRVPAM INKMTVSADQ NQVVQFQNGR CTLEGQLLGT TPVSANQVAR IRGKVFSTNS  300
GTGLNLTEVD GTPYHAFESP APLGFPDIGN CDWHVYAFKV NQNTGDPMYR LDITQGNSFA  360
PHLGSIEFSS ENHPSGDQLG TLTWISPLNN ASRVDPWKIP TYGSTLTEST NLAPPIFPPG  420
FGEAIVYFMS DFPIVSGNTA QIPCTLPQEF VSSFVEQQAP IRGEAALLHY VDPDTHRNLG  480
EFKLYPDGFI TCVPNTGGGP QNLPSNGVFV FSSWVSRYYQ LKPVGTTGPV RRLGVRRV    538

SEQ ID NO: 182         moltype = AA  length = 542
FEATURE                Location/Qualifiers
source                 1..542
                       mol_type = protein
```

```
                        note = Norovirus
                        organism = unidentified
SEQUENCE: 182
MKMASNDAAP STDGAAGLVP ESNNEVMALE PVAGAALAVP VTGQTNIIDP WIRANFVQAP  60
NGEFTVSPRN SPGEVLLNLS LGPELNPYLL HLARMYNGYA GGMEVQVMLA GNAFTAGKLV  120
FAAVPPHFPV ENLSPQQITM FPHVIIDVRT LEPVLLPLPD VRNNFFHYNQ KDDPKMRIVA  180
MLYTPLRSNG SGDDVFTVSC RVLTRPSPDF DFTYLVPPTV ESKTKPFTLP ILTLGELSNS  240
RFPVSIDQMY TSPNEVISVQ CQNGRCTLDG ELQGTTQLQV SGICAFKGEV TAHLHDNDHL  300
YNVTITNLNG SPFDPSEDIP APLGVPDFQG RVFGVISQRD KHNTPGHNEP ANRAHDAVVP  360
TYTAQYTPKL GQIQIGTWQT DDLTVNQPVK FTPVGLNDTD HFNQWVVPRY AGALNLNTNL  420
APSVAPVFPG ERLLFFRSYI PLKGGYGTPA IDCLLPQEWV QHFYQEAAPS MSEVALVRYI  480
NPDTGRALFE AKLHRAGFMT VSSNTSAPVV VPANGYFRFD SWVNQFYSLA PMGTGNGRRR  540
IQ                                                                542

SEQ ID NO: 183          moltype = DNA  length = 1629
FEATURE                 Location/Qualifiers
misc_feature            1..1629
                        note = Nucleic acid sequence of human codon optimized
                         VP1_GII.2_CGMH47_A39V plus sign E80S plus sign A90L
source                  1..1629
                        mol_type = other DNA
                        organism = synthetic construct
SEQUENCE: 183
atgaagatgg catccaacga cgccgcaccc agcacagacg gagctgccgg attggtaccc  60
gagtctaata acgaggtgat ggccttggag cctgttgcag ggctgccct cgcagtgcct  120
gtgaccgggc agacaaatat catcgatcct tggattagag ctaatttcgt gcaagcccca  180
aatggggagt ttacggtcag ccctagaaat agccctgggg aagtgctcct caatctcagc  240
ctgggaccag aacttaatcc gtacctgctc cacctggccc ggatgtacaa tggatatgca  300
ggagggatgg aggtgcaggt tatgctggct ggcaatgcct ttacagcagg caaactcgtt  360
ttcgcagccg tccctcccca cttcccagtt gaaaatcttt cccctcagca gattaccatg  420
tttccccatg tcatcatcga tgtgcgtacc ctggaacctg tgctgttgcc tttaccagac  480
gtgcggaata atttctttca ctataatcag aaggatgacc caaaaatgcg gatcgttgcg  540
atgctttata ctcccctgcg tagcaatggt agtggggatg acgtttttac agtgagttgt  600
cgggtactaa ctcgcccttc accagacttc gactttacgt acttggtgcc tcccactgtc  660
gaaagcaaaa ctaagccatt cacacttccc atcctcaccc tcggagaact ctcgaactcc  720
cgcttccctg tttcaattga tcagatgtac acgtctccaa atgaagtcat ttctgtgcag  780
tgtcagaacg gcaggtgcac cttagacggt gaactgcagg ggacaacgca gttgcaggtc  840
agtggaattt gcgcctttaa gggcgaagtg acagctcacc tccacgacaa cgatcatctc  900
tacaatgtta ctattactaa tctcaatgga agtcctttcg acccctcgga agatattccc  960
gctccactcg gagtacctga ctttcaggga cgcgtcttcg gcgtgatatc acaacgagat  1020
aagcataaca cacccggaca taatgagcca gccaatagag cccacgacgc agtcgttccg  1080
acctatacgg ctcagtacac cccaaagctc ggccagatac aaatcgggac ttggcagacc  1140
gatgacctca ctgtgaatca acctgtgaaa ttcactccag taggtctgaa tgatacagac  1200
cactttaacc agtgggtggt ccctagatac gccggagcct tgaacctaaa cactaacctt  1260
gccccttccg ttgcacctgt gtttccgggg gagcggttgc tcttctttag aagctatatt  1320
cctctgaagg gcgggtatgg tactccagca atcgactgcc tgctacctca ggagtgggtt  1380
caacatttct atcaagaggc cgcacctagt atgagcgagg tggctttggt cagatacatc  1440
aatccagaca caggaagagc actgttcgag gccaagctgc acagagccgg cttcatgacc  1500
gtctcatcca atacatccgc acccgtagta gtccccgcca acgggtactt cagattcgac  1560
agttgggtga atcagtttta ctcgttggcc cccatgggca cagggaacgg tcgccgacgg  1620
atccagtaa                                                         1629

SEQ ID NO: 184          moltype = AA  length = 542
FEATURE                 Location/Qualifiers
source                  1..542
                        mol_type = protein
                        note = Norovirus
                        organism = unidentified
SEQUENCE: 184
MKMASNDAAP STDGAAGLVP ESNNEVMALE PVAGAALAAP VTGQTNIIDP WIIANFVQAP  60
NGEFTVSPRN SPGEVLLNLS LGPELNPYLL HLARMYNGYA GGMEVQVMLA GNAFTAGKLV  120
FAAVPPHFPV ENLSPQQITM FPHVIIDVRT LEPVLLPLPD VRNNFFHYNQ KDDPKMRIVA  180
MLYTPLRSNG SGDDVFTVSC RVLTRPSPDF DFTYLVPPTV ESKTKPFTLP ILTLGELSNS  240
RFPVSIDQMY TSPNEVISVQ CQNGRCTLDG ELQGTTQLQV SGICAFKGEV TAHLHDNDHL  300
YNVTITNLNG SPFDPSEDIP APLGVPDFQG RVFGVISQRD KHNTPGHNEP ANRAHDAVVP  360
TYTAQYTPKL GQIQIGTWQT DDLTVNQPVK FTPVGLNDTD HFNQWVVPRY AGALNLNTNL  420
APSVAPVFPG ERLLFFRSYI PLKGGYGTPA IDCLLPQEWV QHFYQEAAPS MSEVALVRYI  480
NPDTGRALFE AKLHRAGFMT VSSNTSAPVV VPANGYFRFD SWVNQFYSLA PMGTGNGRRR  540
IQ                                                                542

SEQ ID NO: 185          moltype = DNA  length = 1629
FEATURE                 Location/Qualifiers
misc_feature            1..1629
                        note = Nucleic acid sequence of human codon optimized
                         VP1_GII.2_CGMH47_ R53I plus sign E80S plus sign A90L
source                  1..1629
                        mol_type = other DNA
                        organism = synthetic construct
SEQUENCE: 185
```

-continued

```
atgaagatgg catccaacga cgccgcaccc agcacagacg gagctgccgg attggtaccc  60
gagtctaata acgaggtgat ggccttggag cctgttgcag gggctgccct cgcagctcct  120
gtgaccgggc agacaaatat catcgatcct tggattatcg ctaatttcgt gcaagcccca  180
aatggggagt ttacggtcag ccctagaaat agccctgggg aagtgctcct caatctcagc  240
ctgggaccag aacttaatcc gtacctgctc cacctggccc ggatgtacaa tggatatgca  300
ggagggatgg aggtgcaggt tatgctggct ggcaatgcct ttacagcagg caaactcgtt  360
ttcgcagccg tccctcccca cttcccagtt gaaaatcttt cccctcagca gattaccatg  420
tttccccatg tcatcatcga tgtgcgtacc ctggaacctg tgctgttgcc tttaccagac  480
gtgcggaata atttctttca ctataatcag aaggatgacc caaaaatgcg gatcgttgcg  540
atgctttata ctcccctgcg tagcaatggt agtggggatg acgtttttac agtgagttgt  600
cgggtactaa ctcgcccttc accagacttc gactttacgt acttggtgcc tcccactgtc  660
gaaagcaaaa ctaagccatt cacacttccc atcctcaccc tcggagaact ctcgaactcc  720
cgcttccctg tttcaattga tcagatgtac acgtctccaa atgaagtcat ttctgtgcag  780
tgtcagaacg gcaggtgcac cttagacggt gaactgcagg ggacaacgca gttgcaggtc  840
agtggaattt gcgcctttaa gggcgaagtg acagctcacc tccacgacaa cgatcatctc  900
tacaatgtta ctattactaa tctcaatgga agtcctttcg acccctcgga agatattccc  960
gctccactcg gagtacctga ctttcaggga cgcgtcttcg gcgtgatatc acaacgagat  1020
aagcataaca cacccggaca taatgagcca gccaatagag cccacgacgc agtcgttccg  1080
acctatacgg ctcagtacac cccaaagctc ggccagatac aaatcgggac ttggcagacc  1140
gatgacctca ctgtgaatca acctgtgaaa ttcactccag taggtctgaa tgatacagac  1200
cactttaacc agtgggtggt ccctagatac gccggagcct tgaacctaaa cactaacctt  1260
gccccttccg ttgcacctgt gtttccgggg gagcggttgc tcttctttag aagctatatt  1320
cctctgaagg gcgggtatgg tactccagca atcgactgcc tgctacctca ggagtgggtt  1380
caacatttct atcaagaggc cgcacctagt atgagcgagg tggctttggt cagatacatc  1440
aatccagaca caggaagagc actgttcgag gccaagctgc acagagccgg cttcatgacc  1500
gtctcatcca atacatccgc acccgtagta gtccccgcca acgggtactt cagattcgac  1560
agttgggtga atcagtttta ctcgttggcc cccatgggca cagggaacgg tcgccgacgg  1620
atccagtaa                                                         1629
```

```
SEQ ID NO: 186          moltype = AA  length = 542
FEATURE                 Location/Qualifiers
source                  1..542
                        mol_type = protein
                        note = Norovirus
                        organism = unidentified
SEQUENCE: 186
MKMASNDAAP STDGAAGLVP ESNNEVMALE PVAGAALAVP VTGQTNIIDP WIIANFVQAP  60
NGEFTVSPRN SPGEVLLNLS LGPELNPYLL HLARMYNGYA GGMEVQVMLA GNAFTAGKLV  120
FAAVPPHFPV ENLSPQQITM FPHVIIDVRT LEPVLLPLPD VRNNFFHYNQ KDDPKMRIVA  180
MLYTPLRSNG SGDDVFTVSC RVLTRPSPDF DFTYLVPPTV ESKTKPFTLP ILTLGELSNS  240
RFPVSIDQMY TSPNEVISVQ CQNGRCTLDG ELQGTTQLQV SGICAFKGEV TAHLHDNDHL  300
YNVTITNLNG SPFDPSEDIP APLGVPDFQG RVFGVISQRD KHNTPGHNEP ANRAHDAVVP  360
TYTAQYTPKL GQIQIGTWQT DDLTVNQPVK FTPVGLNDTD HFNQWVVPRY AGALNLNTNL  420
APSVAPVFPG ERLLFFRSYI PLKGGYGTPA IDCLLPQEWV QHFYQEAAPS MSEVALVRYI  480
NPDTGRALFE AKLHRAGFMT VSSNTSAPVV VPANGYFRFD SWVNQFYSLA PMGTGNGRRR  540
IQ                                                                542
```

```
SEQ ID NO: 187          moltype = DNA  length = 1629
FEATURE                 Location/Qualifiers
misc_feature            1..1629
                        note = Nucleic acid sequence of human codon optimized
                         VP1_GII.2_CGMH47_A39Vplus sign R53I plus sign E80S plus
                         sign A90L
source                  1..1629
                        mol_type = other DNA
                        organism = synthetic construct
SEQUENCE: 187
atgaagatgg catccaacga cgccgcaccc agcacagacg gagctgccgg attggtaccc  60
gagtctaata acgaggtgat ggccttggag cctgttgcag gggctgccct cgcagtgcct  120
gtgaccgggc agacaaatat catcgatcct tggattatcg ctaatttcgt gcaagcccca  180
aatggggagt ttacggtcag ccctagaaat agccctgggg aagtgctcct caatctcagc  240
ctgggaccag aacttaatcc gtacctgctc cacctggccc ggatgtacaa tggatatgca  300
ggagggatgg aggtgcaggt tatgctggct ggcaatgcct ttacagcagg caaactcgtt  360
ttcgcagccg tccctcccca cttcccagtt gaaaatcttt cccctcagca gattaccatg  420
tttccccatg tcatcatcga tgtgcgtacc ctggaacctg tgctgttgcc tttaccagac  480
gtgcggaata atttctttca ctataatcag aaggatgacc caaaaatgcg gatcgttgcg  540
atgctttata ctcccctgcg tagcaatggt agtggggatg acgtttttac agtgagttgt  600
cgggtactaa ctcgcccttc accagacttc gactttacgt acttggtgcc tcccactgtc  660
gaaagcaaaa ctaagccatt cacacttccc atcctcaccc tcggagaact ctcgaactcc  720
cgcttccctg tttcaattga tcagatgtac acgtctccaa atgaagtcat ttctgtgcag  780
tgtcagaacg gcaggtgcac cttagacggt gaactgcagg ggacaacgca gttgcaggtc  840
agtggaattt gcgcctttaa gggcgaagtg acagctcacc tccacgacaa cgatcatctc  900
tacaatgtta ctattactaa tctcaatgga agtcctttcg acccctcgga agatattccc  960
gctccactcg gagtacctga ctttcaggga cgcgtcttcg gcgtgatatc acaacgagat  1020
aagcataaca cacccggaca taatgagcca gccaatagag cccacgacgc agtcgttccg  1080
acctatacgg ctcagtacac cccaaagctc ggccagatac aaatcgggac ttggcagacc  1140
gatgacctca ctgtgaatca acctgtgaaa ttcactccag taggtctgaa tgatacagac  1200
cactttaacc agtgggtggt ccctagatac gccggagcct tgaacctaaa cactaacctt  1260
gccccttccg ttgcacctgt gtttccgggg gagcggttgc tcttctttag aagctatatt  1320
```

-continued

```
cctctgaagg gcgggtatgg tactccagca atcgactgcc tgctacctca ggagtgggtt  1380
caacatttct atcaagaggc cgcacctagt atgagcgagg tggctttggt cagatacatc  1440
aatccagaca caggaagagc actgttcgag gccaagctgc acagagccgg cttcatgacc  1500
gtctcatcca atacatccgc acccgtagta gtccccgcca acgggtactt cagattcgac  1560
agttgggtga atcagtttta ctcgttggcc cccatgggca cagggaacgg tcgccgacgg  1620
atccagtaa                                                          1629

SEQ ID NO: 188         moltype = AA  length = 540
FEATURE                Location/Qualifiers
source                 1..540
                       mol_type = protein
                       note = Norovirus
                       organism = unidentified
SEQUENCE: 188
MKMASSDANP SDGSAANLVP EVNNEVMALE PVVGAAIAVP VAGQQNVIDP WIINNFVQAP  60
GGEFTVSPRN APGEILWSAP LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 189         moltype = DNA  length = 1623
FEATURE                Location/Qualifiers
misc_feature           1..1623
                       note = Nucleic acid sequence of human codon optimized VP1
                        GII.4_Syd12_A39V plus sign R53I
source                 1..1623
                       mol_type = other DNA
                       organism = synthetic construct
SEQUENCE: 189
atgaaaatgg cctcgagtga cgctaaccct agtgacggca gcgccgccaa tcttgtgcct  60
gaggttaata atgaggtgat ggccctggag cctgtggtgg gcgcagccat agcagtcccc  120
gtggccggtc agcagaatgt gattgacccg tggataatca acaatttgt ccaagcccct  180
ggtggggagt tcaccgttag cccgagaaat gcgccaggag aaatcctgtg gtcggcccca  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg ggaatggga ctggcagacg cagggctgtc  1620
tga                                                                1623

SEQ ID NO: 190         moltype = AA  length = 540
FEATURE                Location/Qualifiers
source                 1..540
                       mol_type = protein
                       note = Norovirus
                       organism = unidentified
SEQUENCE: 190
MKMASSDANP SDGSAANLVP EVNNEVMALE PVVGAAIAVP VAGQQNVIDP WIINNFVQAP  60
GGEFTVSPRN APGEILWSAS LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540
```

-continued

```
SEQ ID NO: 191         moltype = DNA  length = 1623
FEATURE                Location/Qualifiers
misc_feature           1..1623
                       note = Nucleic acid sequence of human codon optimized VP1
                        GII.4_Syd12_A39V plus sign R53I plus sign P80S
source                 1..1623
                       mol_type = other DNA
                       organism = synthetic construct
SEQUENCE: 191
atgaaaatgg cctcgagtga cgctaaccct agtgacggca gcgccgccaa tcttgtgcct  60
gaggttaata atgaggtgat ggccctggag cctgtggtgg gcgcagccat agcagtcccc  120
gtggccggtc agcagaatgt gattgacccg tggataatca acaattttgt ccaagcccct  180
ggtggggagt tcaccgttag cccgagaaat gcgccaggag aaatcctgtg gtcggccagc  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agcccccatg ggaatggga ctggcagacg cagggctgtc  1620
tga                                                                1623

SEQ ID NO: 192         moltype = AA  length = 538
FEATURE                Location/Qualifiers
source                 1..538
                       mol_type = protein
                       note = Norovirus
                       organism = unidentified
SEQUENCE: 192
MKMASNDAAP SNDGAAGLVP EGNNETLPLE PVAGAAIAVP VTGQNNIIDP WIRTNFVQAP  60
NGEFTVSPRN SPGEILLNLE LGPDLNPYLA HLSRMYNGYA GGVEVQVLLA GNAFTAGKIL  120
FAAVPPNFPV EFLSPAQITM LPHLIVDVRT LEPIMIPLPD VRNTFFHYNN QPNSRMRLVA  180
MLYTPLRSNG SGDDVFTVSC RVLTRPTPDF EFTYLVPPSV ESKTKPFSLP ILTLSELTNS  240
RFPVPIDSLF TAQNNVLQVQ CQNGRCTLDG ELQGTTQLLP SGICAFRGRV TAETDHRDKW  300
HMQLQNLNGT TYDPTDDVPA PLGTPDFKGV VFGVASQRNV GNDAPGSTRA HEAVISTYSP  360
QFVPKLGSVN FRSNDNDFQL QPTKFTPVGI NDDGDHPFRQ WELPDYSGLL TLNMNLAPPV  420
APNFPGEQLL FFRSFVPCSG GYNQGIVDCL IPQEWIQHFY QESAPSQSDV ALIRYVNPDT  480
GRTLFEAKLH RSGYITVAHS GDYPLVVPAN GYFRFDSWVN QFYSLAPMGT GNGRRRAQ    538

SEQ ID NO: 193         moltype = DNA  length = 1617
FEATURE                Location/Qualifiers
misc_feature           1..1617
                       note = Nucleic acid sequence of VP1 hCod GII.17 Kawa 2014
                        A0A077KVU6_A39V
source                 1..1617
                       mol_type = other DNA
                       organism = synthetic construct
SEQUENCE: 193
atgaaaatgg catctaacga cgcagccccc tcaaacgatg gcgctgctgg actcgtgccg  60
gaggggaata atgagacact tccactagag ccggttgcag gcgccgctat agctgtgcca  120
gtgacagggc agaataatat tatagaccct tggattcgga caaacttcgt gcaggcaccc  180
aacggcgagt ttacagtatc cccccggaac tccccaggtg agatactcct gaatcttgag  240
ctcggccctg acctcaatcc atatctggct catctgagcc gcatgtacaa tggttacgct  300
ggggggggtcg aagtgcaggt cctcctggcc ggaaacgcct ttaccgctgg caaaattctg  360
tttgccgccg ttccaccaaa ctttccagtc gaattcctct ctcccgcgca aataaccatg  420
ctgccacatt tgatcgttga cgtgcggacc ctggagccaa taatgattcc cctgccggat  480
gtgcgtaaca ccttttttcca ttataacaat cagccaaact ctcggatgag acttgttgct  540
atgctgtaca cccccctgcg gagcaacggc agtggcgatg atgtgtttac cgtgagttgc  600
agagtcctga cgcgcccaac cccggacttc gagttcacct acctggtgcc cccttctgtg  660
gaatctaaga ccaaaccgtt ttcactgcca atcttaactc tctccgaact gactaacagc  720
cggtttccag tacccataga ttctcttttt accgctcaaa acaacgtact ccaagtccag  780
tgccagaacg gccgctgtac gcttgatggt gagttgcagg ggacaacaca gctactcccc  840
agtggcatct gtgcattccg gggccgcgtg accgctgaga cagaccatcg tgacaaatgg  900
```

```
cacatgcaac tccaaaactt aaacgggacc acctacgacc caaccgacga cgtccctgct  960
ccgctaggga ctcctgactt taagggggtg gtgttcggag tggcctctca gcggaatgtt  1020
gggaatgacg cccccggctc tacccgagct cacgaggccg ttatctcaac atatagcccc  1080
caatttgtgc ccaagctcgg atccgttaat tttcgtagta acgacaacga cttccaactg  1140
caaccaacga agtttacgcc agtggggatt aatgatgatg gagaccatcc tttccgccaa  1200
tgggaactac cagattattc tgggctgctc accctcaata tgaacctcgc cccacccgtg  1260
gcccctaatt tccccggtga gcagctgctg ttttttcgga gctttgtgcc atgcagtggc  1320
ggatataatc aaggcatcgt agactgcttg attccccaag agtggataca acatttttac  1380
caggaaagtg cgccctccca gtccgatgtg gccctgatac ggtacgttaa ccccgatacc  1440
ggaagaacat tattcgaagc gaaattgcac agatcagggt acattaccgt tgcacattcc  1500
ggcgattatc cctggtggt tcccgccaac ggttacttta ggttcgatag ttgggtcaac  1560
cagttctatt cactagcccc aatgggcacc ggtaacggca gacgccgggc tcagtag     1617

SEQ ID NO: 194          moltype = AA  length = 538
FEATURE                 Location/Qualifiers
source                  1..538
                        mol_type = protein
                        note = Norovirus
                        organism = unidentified
SEQUENCE: 194
MKMASNDAAP SNDGAAGLVP EGNNETLPLE PVAGAAIAAP VTGQNNIIDP WIITNFVQAP  60
NGEFTVSPRN SPGEILLNLE LGPDLNPYLA HLSRMYNGYA GGVEVQVLLA GNAFTAGKIL  120
FAAVPPNFPV EFLSPAQITM LPHLIVDVRT LEPIMIPLPD VRNTFFHYNN QPNSRMRLVA  180
MLYTPLRSNG SGDDVFTVSC RVLTRPTPDF EFTYLVPPSV ESKTKPFSLP ILTLSELTNS  240
RFPVPIDSLF TAQNNVLQVQ CQNGRCTLDG ELQGTTQLLP SGICAFRGRV TAETDHRDKW  300
HMQLQNLNGT TYDPTDDVPA PLGTPDFKGV VFGVASQRNV GNDAPGSTRA HEAVISTYSP  360
QFVPKLGSVN FRSNDNDFQL QPTKFTPVGI NDDGDHPFRQ WELPDYSGLL TLNMNLAPPV  420
APNFPGEQLL FFRSFVPCSG GYNQGIVDCL IPQEWIQHFY QESAPSQSDV ALIRYVNPDT  480
GRTLFEAKLH RSGYITVAHS GDYPLVVPAN GYFRFDSWVN QFYSLAPMGT GNGRRRAQ    538

SEQ ID NO: 195          moltype = DNA  length = 1617
FEATURE                 Location/Qualifiers
misc_feature            1..1617
                        note = Nucleic acid sequence of VP1 hCod GII.17 Kawa 2014
                         A0A077KVU6_R53I
source                  1..1617
                        mol_type = other DNA
                        organism = synthetic construct
SEQUENCE: 195
atgaaaatgg catctaacga cgcagccccc tcaaacgatg gcgctgctgg actcgtgccg  60
gaggggaata atgagacact tccactagag ccggttgcag gcgccgctat agctgcccca  120
gtgacagggc agaataatat tatagaccct tggattatca caaacttcgt gcaggcaccc  180
aacggcgagt ttacagtatc cccccggaac tccccaggtg agatactcct gaatcttgag  240
ctcggccctg acctcaatcc atatctggct catctgagcc gcatgtacaa tggttacgct  300
gggggggtcg aagtgcaggt cctcctggcc ggaaacgcct ttaccgctgg caaaattctg  360
tttgccgccg ttccaccaaa ctttccagtc gaattcctct ctcccgcgca aataaccatg  420
ctgccacatt tgatcgttga cgtgcggacc ctggagccaa taatgattcc cctgccggat  480
gtgcgtaaca cctttttcca ttataacaat cagccaaact ctcggatgag acttgttgct  540
atgctgtaca cccccctgcg gagcaacggc agtggcgatg atgtgtttac cgtgagttgc  600
agagtcctga cgcgcccaac cccggacttc gagttcacct acctggtgcc cccttctgtg  660
gaatctaaga ccaaaccgtt ttcactgcca atcttaactc tctccgaact gactaacagc  720
cggtttccag tacccataga ttctcttttt accgctcaaa acaacgtact ccaagtccag  780
tgccagaacg gccgctgtac gcttgatggt gagttgcagg ggacaacaca gctactcccc  840
agtggcatct gtgcattccg gggccgcgtg accgctgaga cagaccatcg tgacaaatgg  900
cacatgcaac tccaaaactt aaacgggacc acctacgacc caaccgacga cgtccctgct  960
ccgctaggga ctcctgactt taagggggtg gtgttcggag tggcctctca gcggaatgtt  1020
gggaatgacg cccccggctc tacccgagct cacgaggccg ttatctcaac atatagcccc  1080
caatttgtgc ccaagctcgg atccgttaat tttcgtagta acgacaacga cttccaactg  1140
caaccaacga agtttacgcc agtggggatt aatgatgatg gagaccatcc tttccgccaa  1200
tgggaactac cagattattc tgggctgctc accctcaata tgaacctcgc cccacccgtg  1260
gcccctaatt tccccggtga gcagctgctg ttttttcgga gctttgtgcc atgcagtggc  1320
ggatataatc aaggcatcgt agactgcttg attccccaag agtggataca acatttttac  1380
caggaaagtg cgccctccca gtccgatgtg gccctgatac ggtacgttaa ccccgatacc  1440
ggaagaacat tattcgaagc gaaattgcac agatcagggt acattaccgt tgcacattcc  1500
ggcgattatc cctggtggt tcccgccaac ggttacttta ggttcgatag ttgggtcaac  1560
cagttctatt cactagcccc aatgggcacc ggtaacggca gacgccgggc tcagtag     1617

SEQ ID NO: 196          moltype = AA  length = 538
FEATURE                 Location/Qualifiers
source                  1..538
                        mol_type = protein
                        note = Norovirus
                        organism = unidentified
SEQUENCE: 196
MKMASNDAAP SNDGAAGLVP EGNNETLPLE PVAGAAIAAP VTGQNNIIDP WIRTNFVQAP  60
NGEFTVSPRN SPGEILLNLE LGPDLNPYLL HLSRMYNGYA GGVEVQVLLA GNAFTAGKIL  120
FAAVPPNFPV EFLSPAQITM LPHLIVDVRT LEPIMIPLPD VRNTFFHYNN QPNSRMRLVA  180
MLYTPLRSNG SGDDVFTVSC RVLTRPTPDF EFTYLVPPSV ESKTKPFSLP ILTLSELTNS  240
RFPVPIDSLF TAQNNVLQVQ CQNGRCTLDG ELQGTTQLLP SGICAFRGRV TAETDHRDKW  300
```

-continued

```
HMQLQNLNGT TYDPTDDVPA PLGTPDFKGV VFGVASQRNV GNDAPGSTRA HEAVISTYSP  360
QFVPKLGSVN FRSNDNDFQL QPTKFTPVGI NDDGDHPFRQ WELPDYSGLL TLNMNLAPPV  420
APNFPGEQLL FFRSFVPCSG GYNQGIVDCL IPQEWIQHFY QESAPSQSDV ALIRYVNPDT  480
GRTLFEAKLH RSGYITVAHS GDYPLVVPAN GYFRFDSWVN QFYSLAPMGT GNGRRRAQ    538

SEQ ID NO: 197         moltype = DNA  length = 1617
FEATURE                Location/Qualifiers
misc_feature           1..1617
                       note = Nucleic acid sequence of VP1 hCod GII.17 Kawa 2014
                        A0A077KVU6_A90L
source                 1..1617
                       mol_type = other DNA
                       organism = synthetic construct
SEQUENCE: 197
atgaaaatgg catctaacga cgcagccccc tcaaacgatg gcgctgctgg actcgtgccg  60
gaggggaata atgagacact tccactagag ccggttgcag gcgccgctat agctgcccca  120
gtgacagggc agaataatat tatagaccct tggattcgga caaacttcgt gcaggcaccc  180
aacggcgagt ttacagtatc cccccggaac tccccaggtg agatactcct gaatcttgag  240
ctcggccctg acctcaatcc atatctgctg catctgagcc gcatgtacaa tggttacgct  300
ggggggtcg aagtgcaggt cctcctggcc ggaaacgcct ttaccgctgg caaaattctg  360
tttgccgccg ttccaccaaa ctttccagtc gaattcctct ctcccgcgca aataaccatg  420
ctgccacatt tgatcgttga cgtgcggacc ctggagccaa taatgattcc cctgccggat  480
gtgcgtaaca cctttttcca ttataacaat cagccaaact ctcggatgag acttgttgct  540
atgctgtaca cccccctgcg gagcaacggc agtggcgatg atgtgtttac cgtgagttgc  600
agagtcctga cgcgcccaac cccggacttc gagttcacct acctggtgcc cccttctgtg  660
gaatctaaga ccaaaccgtt ttcactgcca atcttaactc tctccgaact gactaacagc  720
cggtttccag tacccataga ttctcttttt accgctcaaa acaacgtact ccaagtccag  780
tgccagaacg gccgctgtac gcttgatggt gagttgcagg ggacaacaca gctactcccc  840
agtggcatct gtgcattccg gggccgcgtg accgctgaga cagaccatcg tgacaaatgg  900
cacatgcaac tccaaaactt aaacgggacc acctacgacc caaccgacga cgtccctgct  960
ccgctaggga ctcctgactt taagggggtg gtgttcggag tggcctctca gcggaatgtt  1020
gggaatgacg cccccggctc tacccgagct cacgaggccg ttatctcaac atatagcccc  1080
caatttgtgc ccaagctcgg atccgttaat tttcgtagta acgacaacga cttccaactg  1140
caaccaacga agtttacgcc agtggggatt aatgatgatg gagaccatcc tttccgccaa  1200
tgggaactac cagattattc tgggctgctc accctcaata tgaacctcgc cccacccgtg  1260
gcccctaatt tccccggtga gcagctgctg ttttttcgga gctttgtgcc atgcagtggc  1320
ggatataatc aaggcatcgt agactgcttg attccccaag agtggataca acatttttac  1380
caggaaagtg cgccctccca gtccgatgtg gccctgatac ggtacgttaa ccccgatacc  1440
ggaagaacat tattcgaagc gaaattgcac agatcagggt acattaccgt tgcacattcc  1500
ggcgattatc ccctggtggt tcccgccaac ggttacttta ggttcgatag ttgggtcaac  1560
cagttctatt cactagcccc aatgggcacc ggtaacggca gacgccgggc tcagtag     1617

SEQ ID NO: 198         moltype = AA  length = 538
FEATURE                Location/Qualifiers
source                 1..538
                       mol_type = protein
                       note = Norovirus
                       organism = unidentified
SEQUENCE: 198
MKMASNDAAP SNDGAAGLVP EGNNETLPLE PVAGAAIAVP VTGQNNIIDP WIITNFVQAP  60
NGEFTVSPRN SPGEILLNLE LGPDLNPYLA HLSRMYNGYA GGVEVQVLLA GNAFTAGKIL  120
FAAVPPNFPV EFLSPAQITM LPHLIVDVRT LEPIMIPLPD VRNTFFHYNN QPNSRMRLVA  180
MLYTPLRSNG SGDDVFTVSC RVLTRPTPDF EFTYLVPPSV ESKTKPFSLP ILTLSELTNS  240
RFPVPIDSLF TAQNNVLQVQ CQNGRCTLDG ELQGTTQLLP SGICAFRGRV TAETDHRDKW  300
HMQLQNLNGT TYDPTDDVPA PLGTPDFKGV VFGVASQRNV GNDAPGSTRA HEAVISTYSP  360
QFVPKLGSVN FRSNDNDFQL QPTKFTPVGI NDDGDHPFRQ WELPDYSGLL TLNMNLAPPV  420
APNFPGEQLL FFRSFVPCSG GYNQGIVDCL IPQEWIQHFY QESAPSQSDV ALIRYVNPDT  480
GRTLFEAKLH RSGYITVAHS GDYPLVVPAN GYFRFDSWVN QFYSLAPMGT GNGRRRAQ    538

SEQ ID NO: 199         moltype = DNA  length = 1617
FEATURE                Location/Qualifiers
misc_feature           1..1617
                       note = Nucleic acid sequence of VP1 hCod GII.17 Kawa 2014
                        A0A077KVU6_A39V+M53I
source                 1..1617
                       mol_type = other DNA
                       organism = synthetic construct
SEQUENCE: 199
atgaaaatgg catctaacga cgcagccccc tcaaacgatg gcgctgctgg actcgtgccg  60
gaggggaata atgagacact tccactagag ccggttgcag gcgccgctat agctgtgcca  120
gtgacagggc agaataatat tatagaccct tggattatca caaacttcgt gcaggcaccc  180
aacggcgagt ttacagtatc cccccggaac tccccaggtg agatactcct gaatcttgag  240
ctcggccctg acctcaatcc atatctggct catctgagcc gcatgtacaa tggttacgct  300
ggggggtcg aagtgcaggt cctcctggcc ggaaacgcct ttaccgctgg caaaattctg  360
tttgccgccg ttccaccaaa ctttccagtc gaattcctct ctcccgcgca aataaccatg  420
ctgccacatt tgatcgttga cgtgcggacc ctggagccaa taatgattcc cctgccggat  480
gtgcgtaaca cctttttcca ttataacaat cagccaaact ctcggatgag acttgttgct  540
atgctgtaca cccccctgcg gagcaacggc agtggcgatg atgtgtttac cgtgagttgc  600
agagtcctga cgcgcccaac cccggacttc gagttcacct acctggtgcc cccttctgtg  660
```

-continued

```
gaatctaaga ccaaaccgtt ttcactgcca atcttaactc tctccgaact gactaacagc  720
cggtttccag tacccataga ttctcttttt accgctcaaa acaacgtact ccaagtccag  780
tgccagaacg gccgctgtac gcttgatggt gagttgcagg ggacaacaca gctactcccc  840
agtggcatct gtgcattccg gggccgcgtg accgctgaga cagaccatcg tgacaaatgg  900
cacatgcaac tccaaaactt aaacgggacc acctacgacc caaccgacga cgtccctgct  960
ccgctaggga ctcctgactt taagggggtg gtgttcggag tggcctctca gcggaatgtt  1020
gggaatgacg cccccggctc tacccgagct cacgaggccg ttatctcaac atatagcccc  1080
caatttgtgc ccaagctcgg atccgttaat tttcgtagta acgacaacga cttccaactg  1140
caaccaacga agtttacgcc agtggggatt aatgatgatg gagaccatcc tttccgccaa  1200
tgggaactac cagattattc tgggctgctc accctcaata tgaacctcgc cccacccgtg  1260
gcccctaatt tccccggtga gcagctgctg ttttttcgga gctttgtgcc atgcagtggc  1320
ggatataatc aaggcatcgt agactgcttg attccccaag agtggataca acatttttac  1380
caggaaagtg cgccctccca gtccgatgtg gccctgatac ggtacgttaa ccccgatacc  1440
ggaagaacat tattcgaagc gaaattgcac agatcagggt acattaccgt tgcacattcc  1500
ggcgattatc ccctggtggt tcccgccaac ggttacttta ggttcgatag ttgggtcaac  1560
cagttctatt cactagcccc aatgggcacc ggtaacggca gacgccgggc tcagtag     1617
```

```
SEQ ID NO: 200          moltype = AA  length = 538
FEATURE                 Location/Qualifiers
source                  1..538
                        mol_type = protein
                        note = Norovirus
                        organism = unidentified
SEQUENCE: 200
MKMASNDAAP SNDGAAGLVP EGNNETLPLE PVAGAAIAAP VTGQNNIIDP WIRTNFVQAP  60
NGEFTVSPRN SPGEILLNLS LGPDLNPYLL HLSRMYNGYA GGVEVQVLLA GNAFTAGKIL  120
FAAVPPNFPV EFLSPAQITM LPHLIVDVRT LEPIMIPLPD VRNTFFHYNN QPNSRMRLVA  180
MLYTPLRSNG SGDDVFTVSC RVLTRPTPDF EFTYLVPPSV ESKTKPFSLP ILTLSELTNS  240
RFPVPIDSLF TAQNNVLQVQ CQNGRCTLDG ELQGTTQLLP SGICAFRGRV TAETDHRDKW  300
HMQLQNLNGT TYDPTDDVPA PLGTPDFKGV VFGVASQRNV GNDAPGSTRA HEAVISTYSP  360
QFVPKLGSVN FRSNDNDFQL QPTKFTPVGI NDDGDHPFRQ WELPDYSGLL TLNMNLAPPV  420
APNFPGEQLL FFRSFVPCSG GYNQGIVDCL IPQEWIQHFY QESAPSQSDV ALIRYVNPDT  480
GRTLFEAKLH RSGYITVAHS GDYPLVVPAN GYFRFDSWVN QFYSLAPMGT GNGRRRAQ    538
```

```
SEQ ID NO: 201          moltype = DNA  length = 1617
FEATURE                 Location/Qualifiers
misc_feature            1..1617
                        note = Nucleic acid sequence of VP1 hCod GII.17 Kawa 2014
                         A0A077KVU6_E80S plus sign A90L
source                  1..1617
                        mol_type = other DNA
                        organism = synthetic construct
SEQUENCE: 201
atgaaaatgg catctaacga cgcagccccc tcaaacgatg gcgctgctgg actcgtgccg  60
gaggggaata atgagacact tccactagag ccggttgcag gcgccgctat agctgcccca  120
gtgacagggc agaataatat tatagaccct tggattcgga caaacttcgt gcaggcaccc  180
aacggcgagt ttacagtatc cccccggaac tccccaggtg agatactcct gaatcttagc  240
ctcggccctg acctcaatcc atatctgctg catctgagcc gcatgtacaa tggttacgct  300
ggggggtcg aagtgcaggt cctcctggcc ggaaacgcct ttaccgctgg caaaattctg  360
tttgccgccg ttccaccaaa ctttccagtc gaattcctct ctcccgcgca aataaccatg  420
ctgccacatt tgatcgttga cgtgcggacc ctggagccaa taatgattcc cctgccggat  480
gtgcgtaaca cctttttcca ttataacaat cagccaaact ctcggatgag acttgttgct  540
atgctgtaca cccccctgcg gagcaacggc agtggcgatg atgtgtttac cgtgagttgc  600
agagtcctga cgcgcccaac cccggacttc gagttcacct acctggtgcc cccttctgtg  660
gaatctaaga ccaaaccgtt ttcactgcca atcttaactc tctccgaact gactaacagc  720
cggtttccag tacccataga ttctcttttt accgctcaaa acaacgtact ccaagtccag  780
tgccagaacg gccgctgtac gcttgatggt gagttgcagg ggacaacaca gctactcccc  840
agtggcatct gtgcattccg gggccgcgtg accgctgaga cagaccatcg tgacaaatgg  900
cacatgcaac tccaaaactt aaacgggacc acctacgacc caaccgacga cgtccctgct  960
ccgctaggga ctcctgactt taagggggtg gtgttcggag tggcctctca gcggaatgtt  1020
gggaatgacg cccccggctc tacccgagct cacgaggccg ttatctcaac atatagcccc  1080
caatttgtgc ccaagctcgg atccgttaat tttcgtagta acgacaacga cttccaactg  1140
caaccaacga agtttacgcc agtggggatt aatgatgatg gagaccatcc tttccgccaa  1200
tgggaactac cagattattc tgggctgctc accctcaata tgaacctcgc cccacccgtg  1260
gcccctaatt tccccggtga gcagctgctg ttttttcgga gctttgtgcc atgcagtggc  1320
ggatataatc aaggcatcgt agactgcttg attccccaag agtggataca acatttttac  1380
caggaaagtg cgccctccca gtccgatgtg gccctgatac ggtacgttaa ccccgatacc  1440
ggaagaacat tattcgaagc gaaattgcac agatcagggt acattaccgt tgcacattcc  1500
ggcgattatc ccctggtggt tcccgccaac ggttacttta ggttcgatag ttgggtcaac  1560
cagttctatt cactagcccc aatgggcacc ggtaacggca gacgccgggc tcagtag     1617
```

```
SEQ ID NO: 202          moltype = DNA  length = 59
FEATURE                 Location/Qualifiers
misc_feature            1..59
                        note = Primer GI.3Lil08(M57I).r
source                  1..59
                        mol_type = other DNA
                        organism = synthetic construct
SEQUENCE: 202
```

```
ctgaacgtaa tttgagatga tccaggggtc gatcatgttt acctgtcctg cggtggcgg   59

SEQ ID NO: 203          moltype = DNA  length = 59
FEATURE                 Location/Qualifiers
misc_feature            1..59
                        note = Primer GI.3Lil08(M57I).c
source                  1..59
                        mol_type = other DNA
                        organism = synthetic construct
SEQUENCE: 203
gtaaacatga tcgacccctg gatcatctca aattacgttc aggctccaca gggggagtt   59

SEQ ID NO: 204          moltype = DNA  length = 52
FEATURE                 Location/Qualifiers
misc_feature            1..52
                        note = Primer IF-(GI.7USA14)VP1.c
source                  1..52
                        mol_type = other DNA
                        organism = synthetic construct
SEQUENCE: 204
tcgtgcttcg gcaccagtac aatgatgatg gccagcaagg acgctccgag ta          52

SEQ ID NO: 205          moltype = DNA  length = 49
FEATURE                 Location/Qualifiers
misc_feature            1..49
                        note = Primer IF-(GI.7USA14)VP1.r
source                  1..49
                        mol_type = other DNA
                        organism = synthetic construct
SEQUENCE: 205
actaaagaaa ataggccttc acacccgcct cacgccgagt cgtcgcacg              49

SEQ ID NO: 206          moltype = DNA  length = 48
FEATURE                 Location/Qualifiers
misc_feature            1..48
                        note = Primer GI.7USA14_VP1(R84S).r
source                  1..48
                        mol_type = other DNA
                        organism = synthetic construct
SEQUENCE: 206
agtggggtcc taagctgagg tcaaacagaa tatcccctgg ggtgttat               48

SEQ ID NO: 207          moltype = DNA  length = 50
FEATURE                 Location/Qualifiers
misc_feature            1..50
                        note = Primer GI.7USA14_VP1(R84S).c
source                  1..50
                        mol_type = other DNA
                        organism = synthetic construct
SEQUENCE: 207
tattctgttt gacctcagct taggacccca cttgaacccc tttctgcttc             50

SEQ ID NO: 208          moltype = DNA  length = 51
FEATURE                 Location/Qualifiers
misc_feature            1..51
                        note = Primer GI.7USA14_VP1(M57I).r
source                  1..51
                        mol_type = other DNA
                        organism = synthetic construct
SEQUENCE: 208
aacgaaattg ttgattatcc acgggtcgat catattgact tggcctgcag t           51

SEQ ID NO: 209          moltype = DNA  length = 48
FEATURE                 Location/Qualifiers
misc_feature            1..48
                        note = Primer GI.7USA14_VP1(M57I).c
source                  1..48
                        mol_type = other DNA
                        organism = synthetic construct
SEQUENCE: 209
gatcgacccg tggataatca acaatttcgt tcaggcacca gaaggaga               48

SEQ ID NO: 210          moltype = DNA  length = 62
FEATURE                 Location/Qualifiers
misc_feature            1..62
                        note = Primer GII.2CGMH11(A39V).r
source                  1..62
                        mol_type = other DNA
                        organism = synthetic construct
```

```
SEQUENCE: 210
tttgtctgcc cggtcacagg cactgcgagg gcagcccctg caacaggctc caaggccatc  60
ac                                                                 62

SEQ ID NO: 211          moltype = DNA  length = 59
FEATURE                 Location/Qualifiers
misc_feature            1..59
                        note = Primer GII.2CGMH11(A39V).c
source                  1..59
                        mol_type = other DNA
                        organism = synthetic construct
SEQUENCE: 211
gttgcagggg ctgccctcgc agtgcctgtg accgggcaga caaatatcat cgatccttg   59

SEQ ID NO: 212          moltype = DNA  length = 59
FEATURE                 Location/Qualifiers
misc_feature            1..59
                        note = Primer GII.2CGMH11(R53I).r
source                  1..59
                        mol_type = other DNA
                        organism = synthetic construct
SEQUENCE: 212
cacgaaatta gcgataatcc aaggatcgat gatatttgtc tgcccggtca caggagctg   59

SEQ ID NO: 213          moltype = DNA  length = 59
FEATURE                 Location/Qualifiers
misc_feature            1..59
                        note = Primer GII.2CGMH11(R53I).c
source                  1..59
                        mol_type = other DNA
                        organism = synthetic construct
SEQUENCE: 213
ggcagacaaa tatcatcgat ccttggatta tcgctaattt cgtgcaagcc ccaaatggg   59

SEQ ID NO: 214          moltype = DNA  length = 53
FEATURE                 Location/Qualifiers
misc_feature            1..53
                        note = Primer IF-GII17Kaw14VP1.c
source                  1..53
                        mol_type = other DNA
                        organism = synthetic construct
SEQUENCE: 214
tcgtgcttcg gcaccagtac aatgaaaatg gcatctaacg acgcagcccc ctc         53

SEQ ID NO: 215          moltype = DNA  length = 56
FEATURE                 Location/Qualifiers
misc_feature            1..56
                        note = Primer IF-GII17Kaw14VP1.r
source                  1..56
                        mol_type = other DNA
                        organism = synthetic construct
SEQUENCE: 215
actaaagaaa ataggcctct actgagcccg gcgtctgccg ttaccggtgc ccattg      56

SEQ ID NO: 216          moltype = DNA  length = 59
FEATURE                 Location/Qualifiers
misc_feature            1..59
                        note = Primer GII.17Kaw14(A90L).r
source                  1..59
                        mol_type = other DNA
                        organism = synthetic construct
SEQUENCE: 216
gcggctcaga tgcagcagat atggattgag gtcagggccg agctcaagat tcaggagta   59

SEQ ID NO: 217          moltype = DNA  length = 51
FEATURE                 Location/Qualifiers
misc_feature            1..51
                        note = Primer GII.17Kaw14(A90L).c
source                  1..51
                        mol_type = other DNA
                        organism = synthetic construct
SEQUENCE: 217
cctgacctca atccatatct gctgcatctg agccgcatgt acaatggtta c           51

SEQ ID NO: 218          moltype = DNA  length = 59
FEATURE                 Location/Qualifiers
misc_feature            1..59
                        note = Primer GII.17Kaw14(A39V).r
source                  1..59
```

```
                         mol_type = other DNA
                         organism = synthetic construct
SEQUENCE: 218
attctgccct gtcactggca cagctatagc ggcgcctgca accggctcta gtggaagtg   59

SEQ ID NO: 219           moltype = DNA  length = 58
FEATURE                  Location/Qualifiers
misc_feature             1..58
                         note = Primer GII.17Kaw14(A39V).c
source                   1..58
                         mol_type = other DNA
                         organism = synthetic construct
SEQUENCE: 219
aggcgccgct atagctgtgc cagtgacagg gcagaataat attatagacc cttggatt    58

SEQ ID NO: 220           moltype = DNA  length = 59
FEATURE                  Location/Qualifiers
misc_feature             1..59
                         note = Primer GII.17Kaw14(R53I).r
source                   1..59
                         mol_type = other DNA
                         organism = synthetic construct
SEQUENCE: 220
acgaagtttg tgataatcca agggtctata atattattct gccctgtcac tggggcagc   59

SEQ ID NO: 221           moltype = DNA  length = 59
FEATURE                  Location/Qualifiers
misc_feature             1..59
                         note = Primer GII.17Kaw14(R53I).c
source                   1..59
                         mol_type = other DNA
                         organism = synthetic construct
SEQUENCE: 221
ggcagaataa tattatagac ccttggatta tcacaaactt cgtgcaggca cccaacggc   59

SEQ ID NO: 222           moltype = DNA  length = 50
FEATURE                  Location/Qualifiers
misc_feature             1..50
                         note = Primer GII.4Syd12(P80A).r
source                   1..50
                         mol_type = other DNA
                         organism = synthetic construct
SEQUENCE: 222
atcgggtccc aaggcggccg accacaggat ttctcctggc gcatttctcg              50

SEQ ID NO: 223           moltype = DNA  length = 50
FEATURE                  Location/Qualifiers
misc_feature             1..50
                         note = Primer GII.4Syd12(P80A).c
source                   1..50
                         mol_type = other DNA
                         organism = synthetic construct
SEQUENCE: 223
aatcctgtgg tcggccgcct tgggacccga tctgaacccc tatttgtcac              50

SEQ ID NO: 224           moltype = DNA  length = 50
FEATURE                  Location/Qualifiers
misc_feature             1..50
                         note = Primer GII.4Syd12(P80N).r
source                   1..50
                         mol_type = other DNA
                         organism = synthetic construct
SEQUENCE: 224
atcgggtccc aagttggccg accacaggat ttctcctggc gcatttctcg              50

SEQ ID NO: 225           moltype = DNA  length = 50
FEATURE                  Location/Qualifiers
misc_feature             1..50
                         note = Primer GII.4Syd12(P80N).c
source                   1..50
                         mol_type = other DNA
                         organism = synthetic construct
SEQUENCE: 225
aatcctgtgg tcggccaact tgggacccga tctgaacccc tatttgtcac              50

SEQ ID NO: 226           moltype = DNA  length = 50
FEATURE                  Location/Qualifiers
misc_feature             1..50
                         note = Primer GII.4Syd12(P80K).r
```

```
source                  1..50
                        mol_type = other DNA
                        organism = synthetic construct
SEQUENCE: 226
atcgggtccc aacttggccg accacaggat ttctcctggc gcatttctcg             50

SEQ ID NO: 227          moltype = DNA  length = 50
FEATURE                 Location/Qualifiers
misc_feature            1..50
                        note = Primer GII.4Syd12(P80K).c
source                  1..50
                        mol_type = other DNA
                        organism = synthetic construct
SEQUENCE: 227
aatcctgtgg tcggccaagt tgggacccga tctgaacccc tatttgtcac             50

SEQ ID NO: 228          moltype = DNA  length = 50
FEATURE                 Location/Qualifiers
misc_feature            1..50
                        note = Primer GII.4Syd12(P80H).r
source                  1..50
                        mol_type = other DNA
                        organism = synthetic construct
SEQUENCE: 228
atcgggtccc aagtgggccg accacaggat ttctcctggc gcatttctcg             50

SEQ ID NO: 229          moltype = DNA  length = 50
FEATURE                 Location/Qualifiers
misc_feature            1..50
                        note = Primer GII.4Syd12(P80H).c
source                  1..50
                        mol_type = other DNA
                        organism = synthetic construct
SEQUENCE: 229
aatcctgtgg tcggcccact tgggacccga tctgaacccc tatttgtcac             50

SEQ ID NO: 230          moltype = DNA  length = 54
FEATURE                 Location/Qualifiers
misc_feature            1..54
                        note = Primer GII.4Syd12(A39I).r
source                  1..54
                        mol_type = other DNA
                        organism = synthetic construct
SEQUENCE: 230
gaccggccac ggggattgct atggctgcgc ccaccacagg ctccagggcc atca         54

SEQ ID NO: 231          moltype = DNA  length = 54
FEATURE                 Location/Qualifiers
misc_feature            1..54
                        note = Primer GII.4Syd12(A39I).c
source                  1..54
                        mol_type = other DNA
                        organism = synthetic construct
SEQUENCE: 231
gggcgcagcc atagcaatcc ccgtggccgg tcagcagaat gtgattgacc cgtg         54

SEQ ID NO: 232          moltype = DNA  length = 54
FEATURE                 Location/Qualifiers
misc_feature            1..54
                        note = Primer GII.4Syd12(A39M).r
source                  1..54
                        mol_type = other DNA
                        organism = synthetic construct
SEQUENCE: 232
gaccggccac gggcattgct atggctgcgc ccaccacagg ctccagggcc atca         54

SEQ ID NO: 233          moltype = DNA  length = 54
FEATURE                 Location/Qualifiers
misc_feature            1..54
                        note = Primer GII.4Syd12(A39M).c
source                  1..54
                        mol_type = other DNA
                        organism = synthetic construct
SEQUENCE: 233
gggcgcagcc atagcaatgc ccgtggccgg tcagcagaat gtgattgacc cgtg         54

SEQ ID NO: 234          moltype = DNA  length = 54
FEATURE                 Location/Qualifiers
misc_feature            1..54
```

```
                        note = Primer GII.4Syd12(A39G).r
source                  1..54
                        mol_type = other DNA
                        organism = synthetic construct
SEQUENCE: 234
gaccggccac ggggcctgct atggctgcgc ccaccacagg ctccagggcc atca        54

SEQ ID NO: 235          moltype = DNA  length = 54
FEATURE                 Location/Qualifiers
misc_feature            1..54
                        note = Primer GII.4Syd12(A39G).c
source                  1..54
                        mol_type = other DNA
                        organism = synthetic construct
SEQUENCE: 235
gggcgcagcc atagcaggcc ccgtggccgg tcagcagaat gtgattgacc cgtg        54

SEQ ID NO: 236          moltype = DNA  length = 54
FEATURE                 Location/Qualifiers
misc_feature            1..54
                        note = Primer GII.4Syd12(A39S).r
source                  1..54
                        mol_type = other DNA
                        organism = synthetic construct
SEQUENCE: 236
gaccggccac ggggcttgct atggctgcgc ccaccacagg ctccagggcc atca        54

SEQ ID NO: 237          moltype = DNA  length = 54
FEATURE                 Location/Qualifiers
misc_feature            1..54
                        note = Primer GII.4Syd12(A39S).c
source                  1..54
                        mol_type = other DNA
                        organism = synthetic construct
SEQUENCE: 237
gggcgcagcc atagcaagcc ccgtggccgg tcagcagaat gtgattgacc cgtg        54

SEQ ID NO: 238          moltype = DNA  length = 54
FEATURE                 Location/Qualifiers
misc_feature            1..54
                        note = Primer GII.4Syd12(A39E).r
source                  1..54
                        mol_type = other DNA
                        organism = synthetic construct
SEQUENCE: 238
gaccggccac gggctctgct atggctgcgc ccaccacagg ctccagggcc atca        54

SEQ ID NO: 239          moltype = DNA  length = 49
FEATURE                 Location/Qualifiers
misc_feature            1..49
                        note = Primer GII.4Syd12(A39E).c
source                  1..49
                        mol_type = other DNA
                        organism = synthetic construct
SEQUENCE: 239
gggcgcagcc atagcagagc ccgtggccgg tcagcagaat gtgattgac              49

SEQ ID NO: 240          moltype = DNA  length = 54
FEATURE                 Location/Qualifiers
misc_feature            1..54
                        note = Primer GII.4Syd12(A39D).r
source                  1..54
                        mol_type = other DNA
                        organism = synthetic construct
SEQUENCE: 240
gaccggccac ggggtctgct atggctgcgc ccaccacagg ctccagggcc atca        54

SEQ ID NO: 241          moltype = DNA  length = 54
FEATURE                 Location/Qualifiers
misc_feature            1..54
                        note = Primer GII.4Syd12(A39D).c
source                  1..54
                        mol_type = other DNA
                        organism = synthetic construct
SEQUENCE: 241
gggcgcagcc atagcagacc ccgtggccgg tcagcagaat gtgattgacc cgtg        54

SEQ ID NO: 242          moltype = DNA  length = 54
FEATURE                 Location/Qualifiers
```

```
misc_feature          1..54
                      note = Primer GII.4Syd12(A39N).r
source                1..54
                      mol_type = other DNA
                      organism = synthetic construct
SEQUENCE: 242
accggccacg ggtttgcta tggctgcgcc caccacaggc tccagggcca tcac        54

SEQ ID NO: 243        moltype = DNA  length = 54
FEATURE               Location/Qualifiers
misc_feature          1..54
                      note = Primer GII.4Syd12(A39N).c
source                1..54
                      mol_type = other DNA
                      organism = synthetic construct
SEQUENCE: 243
gggcgcagcc atagcaaacc ccgtggccgg tcagcagaat gtgattgacc cgtg        54

SEQ ID NO: 244        moltype = DNA  length = 54
FEATURE               Location/Qualifiers
misc_feature          1..54
                      note = Primer GII.4Syd12(A39Q).r
source                1..54
                      mol_type = other DNA
                      organism = synthetic construct
SEQUENCE: 244
gaccggccac gggctgtgct atggctgcgc ccaccacagg ctccagggcc atca        54

SEQ ID NO: 245        moltype = DNA  length = 54
FEATURE               Location/Qualifiers
misc_feature          1..54
                      note = Primer GII.4Syd12(A39Q).c
source                1..54
                      mol_type = other DNA
                      organism = synthetic construct
SEQUENCE: 245
gggcgcagcc atagcacagc ccgtggccgg tcagcagaat gtgattgacc cgtg        54

SEQ ID NO: 246        moltype = DNA  length = 54
FEATURE               Location/Qualifiers
misc_feature          1..54
                      note = Primer GII.4Syd12(A39K).r
source                1..54
                      mol_type = other DNA
                      organism = synthetic construct
SEQUENCE: 246
gaccggccac gggctttgct atggctgcgc ccaccacagg ctccagggcc atca        54

SEQ ID NO: 247        moltype = DNA  length = 54
FEATURE               Location/Qualifiers
misc_feature          1..54
                      note = Primer GII.4Syd12(A39K).c
source                1..54
                      mol_type = other DNA
                      organism = synthetic construct
SEQUENCE: 247
gggcgcagcc atagcaaagc ccgtggccgg tcagcagaat gtgattgacc cgtg        54

SEQ ID NO: 248        moltype = DNA  length = 51
FEATURE               Location/Qualifiers
misc_feature          1..51
                      note = Primer GII.4Syd12(A39H).r
source                1..51
                      mol_type = other DNA
                      organism = synthetic construct
SEQUENCE: 248
gaccggccac ggggtgtgct atggctgcgc ccaccacagg ctccagggcc a           51

SEQ ID NO: 249        moltype = DNA  length = 54
FEATURE               Location/Qualifiers
misc_feature          1..54
                      note = Primer GII.4Syd12(A39H).c
source                1..54
                      mol_type = other DNA
                      organism = synthetic construct
SEQUENCE: 249
gggcgcagcc atagcacacc ccgtggccgg tcagcagaat gtgattgacc cgtg        54

SEQ ID NO: 250        moltype = DNA  length = 50
```

-continued

```
FEATURE                 Location/Qualifiers
misc_feature            1..50
                        note = Primer GI.7USA14_VP1(M57L).r
source                  1..50
                        mol_type = other DNA
                        organism = synthetic construct
SEQUENCE: 250
gaacgaaatt gttcagtatc cacgggtcga tcatattgac ttggcctgca             50

SEQ ID NO: 251          moltype = DNA  length = 48
FEATURE                 Location/Qualifiers
misc_feature            1..48
                        note = Primer GI.7USA14_VP1(M57L).c
source                  1..48
                        mol_type = other DNA
                        organism = synthetic construct
SEQUENCE: 251
gatcgacccg tggatactga acaatttcgt tcaggcacca gaaggaga               48

SEQ ID NO: 252          moltype = DNA  length = 52
FEATURE                 Location/Qualifiers
misc_feature            1..52
                        note = Primer GI.7USA14_VP1(M57G).r
source                  1..52
                        mol_type = other DNA
                        organism = synthetic construct
SEQUENCE: 252
gaacgaaatt gttgcctatc cacgggtcga tcatattgac ttggcctgca gt          52

SEQ ID NO: 253          moltype = DNA  length = 48
FEATURE                 Location/Qualifiers
misc_feature            1..48
                        note = Primer GI.7USA14_VP1(M57G).c
source                  1..48
                        mol_type = other DNA
                        organism = synthetic construct
SEQUENCE: 253
gatcgacccg tggataggca acaatttcgt tcaggcacca gaaggaga               48

SEQ ID NO: 254          moltype = DNA  length = 52
FEATURE                 Location/Qualifiers
misc_feature            1..52
                        note = Primer GI.7USA14_VP1(M57S).r
source                  1..52
                        mol_type = other DNA
                        organism = synthetic construct
SEQUENCE: 254
gaacgaaatt gttgcttatc cacgggtcga tcatattgac ttggcctgca gt          52

SEQ ID NO: 255          moltype = DNA  length = 48
FEATURE                 Location/Qualifiers
misc_feature            1..48
                        note = Primer GI.7USA14_VP1(M57S).c
source                  1..48
                        mol_type = other DNA
                        organism = synthetic construct
SEQUENCE: 255
gatcgacccg tggataagca acaatttcgt tcaggcacca gaaggaga               48

SEQ ID NO: 256          moltype = DNA  length = 52
FEATURE                 Location/Qualifiers
misc_feature            1..52
                        note = Primer GI.7USA14_VP1(M57T).r
source                  1..52
                        mol_type = other DNA
                        organism = synthetic construct
SEQUENCE: 256
gaacgaaatt gttggttatc cacgggtcga tcatattgac ttggcctgca gt          52

SEQ ID NO: 257          moltype = DNA  length = 48
FEATURE                 Location/Qualifiers
misc_feature            1..48
                        note = Primer GI.7USA14_VP1(M57T).c
source                  1..48
                        mol_type = other DNA
                        organism = synthetic construct
SEQUENCE: 257
gatcgacccg tggataacca acaatttcgt tcaggcacca gaaggaga               48
```

```
SEQ ID NO: 258          moltype = DNA  length = 52
FEATURE                 Location/Qualifiers
misc_feature            1..52
                        note = Primer GI.7USA14_VP1(M57N).r
source                  1..52
                        mol_type = other DNA
                        organism = synthetic construct
SEQUENCE: 258
gaacgaaatt gttgtttatc cacgggtcga tcatattgac ttggcctgca gt          52

SEQ ID NO: 259          moltype = DNA  length = 48
FEATURE                 Location/Qualifiers
misc_feature            1..48
                        note = Primer GI.7USA14_VP1(M57N).c
source                  1..48
                        mol_type = other DNA
                        organism = synthetic construct
SEQUENCE: 259
gatcgacccg tggataaaca acaatttcgt tcaggcacca gaaggaga               48

SEQ ID NO: 260          moltype = DNA  length = 52
FEATURE                 Location/Qualifiers
misc_feature            1..52
                        note = Primer GI.7USA14_VP1(M57Q).r
source                  1..52
                        mol_type = other DNA
                        organism = synthetic construct
SEQUENCE: 260
gaacgaaatt gttctgtatc cacgggtcga tcatattgac ttggcctgca gt          52

SEQ ID NO: 261          moltype = DNA  length = 48
FEATURE                 Location/Qualifiers
misc_feature            1..48
                        note = Primer GI.7USA14_VP1(M57Q).c
source                  1..48
                        mol_type = other DNA
                        organism = synthetic construct
SEQUENCE: 261
gatcgacccg tggatacaga acaatttcgt tcaggcacca gaaggaga               48

SEQ ID NO: 262          moltype = DNA  length = 52
FEATURE                 Location/Qualifiers
misc_feature            1..52
                        note = Primer GI.7USA14_VP1(M57K).r
source                  1..52
                        mol_type = other DNA
                        organism = synthetic construct
SEQUENCE: 262
gaacgaaatt gttctttatc cacgggtcga tcatattgac ttggcctgca gt          52

SEQ ID NO: 263          moltype = DNA  length = 48
FEATURE                 Location/Qualifiers
misc_feature            1..48
                        note = Primer GI.7USA14_VP1(M57K).c
source                  1..48
                        mol_type = other DNA
                        organism = synthetic construct
SEQUENCE: 263
gatcgacccg tggataaaga acaatttcgt tcaggcacca gaaggaga               48

SEQ ID NO: 264          moltype = DNA  length = 52
FEATURE                 Location/Qualifiers
misc_feature            1..52
                        note = Primer GI.7USA14_VP1(M57H).r
source                  1..52
                        mol_type = other DNA
                        organism = synthetic construct
SEQUENCE: 264
gaacgaaatt gttgtgtatc cacgggtcga tcatattgac ttggcctgca gt          52

SEQ ID NO: 265          moltype = DNA  length = 48
FEATURE                 Location/Qualifiers
misc_feature            1..48
                        note = Primer GI.7USA14_VP1(M57H).c
source                  1..48
                        mol_type = other DNA
                        organism = synthetic construct
SEQUENCE: 265
gatcgacccg tggatacaca acaatttcgt tcaggcacca gaaggaga               48
```

```
SEQ ID NO: 266          moltype = DNA  length = 54
FEATURE                 Location/Qualifiers
misc_feature            1..54
                        note = Primer GI.3Lil08(S94V).r
source                  1..54
                        mol_type = other DNA
                        organism = synthetic construct
SEQUENCE: 266
tctgagccaa gtgcaccaga aacggattca agtgtggtcc tagctgcagg tcaa        54

SEQ ID NO: 267          moltype = DNA  length = 54
FEATURE                 Location/Qualifiers
misc_feature            1..54
                        note = Primer GI.3Lil08(S94V).c
source                  1..54
                        mol_type = other DNA
                        organism = synthetic construct
SEQUENCE: 267
cttgaatccg tttctggtgc acttggctca gatgtataat ggatgggttg gaaa        54

SEQ ID NO: 268          moltype = DNA  length = 54
FEATURE                 Location/Qualifiers
misc_feature            1..54
                        note = Primer GI.3Lil08(S94I).r
source                  1..54
                        mol_type = other DNA
                        organism = synthetic construct
SEQUENCE: 268
tctgagccaa gtggatcaga aacggattca agtgtggtcc tagctgcagg tcaa        54

SEQ ID NO: 269          moltype = DNA  length = 54
FEATURE                 Location/Qualifiers
misc_feature            1..54
                        note = Primer GI.3Lil08(S94I).c
source                  1..54
                        mol_type = other DNA
                        organism = synthetic construct
SEQUENCE: 269
cttgaatccg tttctgatcc acttggctca gatgtataat ggatgggttg gaaa        54

SEQ ID NO: 270          moltype = DNA  length = 54
FEATURE                 Location/Qualifiers
misc_feature            1..54
                        note = Primer GI.3Lil08(S94M).r
source                  1..54
                        mol_type = other DNA
                        organism = synthetic construct
SEQUENCE: 270
tctgagccaa gtgcatcaga aacggattca agtgtggtcc tagctgcagg tcaa        54

SEQ ID NO: 271          moltype = DNA  length = 54
FEATURE                 Location/Qualifiers
misc_feature            1..54
                        note = Primer GI.3Lil08(S94M).c
source                  1..54
                        mol_type = other DNA
                        organism = synthetic construct
SEQUENCE: 271
cttgaatccg tttctgatgc acttggctca gatgtataat ggatgggttg gaaa        54

SEQ ID NO: 272          moltype = DNA  length = 54
FEATURE                 Location/Qualifiers
misc_feature            1..54
                        note = Primer GI.3Lil08(S94T).r
source                  1..54
                        mol_type = other DNA
                        organism = synthetic construct
SEQUENCE: 272
tctgagccaa gtgggtcaga aacggattca agtgtggtcc tagctgcagg tcaa        54

SEQ ID NO: 273          moltype = DNA  length = 54
FEATURE                 Location/Qualifiers
misc_feature            1..54
                        note = Primer GI.3Lil08(S94T).c
source                  1..54
                        mol_type = other DNA
                        organism = synthetic construct
SEQUENCE: 273
```

-continued

```
cttgaatccg tttctgaccc acttggctca gatgtataat ggatgggttg gaaa        54

SEQ ID NO: 274          moltype = DNA  length = 54
FEATURE                 Location/Qualifiers
misc_feature            1..54
                        note = Primer GI.3Lil08(S94E).r
source                  1..54
                        mol_type = other DNA
                        organism = synthetic construct
SEQUENCE: 274
tctgagccaa gtgctccaga aacggattca agtgtggtcc tagctgcagg tcaa        54

SEQ ID NO: 275          moltype = DNA  length = 54
FEATURE                 Location/Qualifiers
misc_feature            1..54
                        note = Primer GI.3Lil08(S94E).c
source                  1..54
                        mol_type = other DNA
                        organism = synthetic construct
SEQUENCE: 275
cttgaatccg tttctggagc acttggctca gatgtataat ggatgggttg gaaa        54

SEQ ID NO: 276          moltype = DNA  length = 54
FEATURE                 Location/Qualifiers
misc_feature            1..54
                        note = Primer GI.3Lil08(S94D).r
source                  1..54
                        mol_type = other DNA
                        organism = synthetic construct
SEQUENCE: 276
tctgagccaa gtggtccaga aacggattca agtgtggtcc tagctgcagg tcaa        54

SEQ ID NO: 277          moltype = DNA  length = 54
FEATURE                 Location/Qualifiers
misc_feature            1..54
                        note = Primer GI.3Lil08(S94D).c
source                  1..54
                        mol_type = other DNA
                        organism = synthetic construct
SEQUENCE: 277
cttgaatccg tttctggacc acttggctca gatgtataat ggatgggttg gaaa        54

SEQ ID NO: 278          moltype = DNA  length = 54
FEATURE                 Location/Qualifiers
misc_feature            1..54
                        note = Primer GI.3Lil08(S94N).r
source                  1..54
                        mol_type = other DNA
                        organism = synthetic construct
SEQUENCE: 278
tctgagccaa gtggttcaga aacggattca agtgtggtcc tagctgcagg tcaa        54

SEQ ID NO: 279          moltype = DNA  length = 54
FEATURE                 Location/Qualifiers
misc_feature            1..54
                        note = Primer GI.3Lil08(S94N).c
source                  1..54
                        mol_type = other DNA
                        organism = synthetic construct
SEQUENCE: 279
cttgaatccg tttctgaacc acttggctca gatgtataat ggatgggttg gaaa        54

SEQ ID NO: 280          moltype = DNA  length = 54
FEATURE                 Location/Qualifiers
misc_feature            1..54
                        note = Primer GI.3Lil08(S94Q).r
source                  1..54
                        mol_type = other DNA
                        organism = synthetic construct
SEQUENCE: 280
tctgagccaa gtgctgcaga aacggattca agtgtggtcc tagctgcagg tcaa        54

SEQ ID NO: 281          moltype = DNA  length = 54
FEATURE                 Location/Qualifiers
misc_feature            1..54
                        note = Primer GI.3Lil08(S94Q).c
source                  1..54
                        mol_type = other DNA
                        organism = synthetic construct
```

-continued

```
SEQUENCE: 281
cttgaatccg tttctgcagc acttggctca gatgtataat ggatgggttg gaaa        54

SEQ ID NO: 282          moltype = DNA  length = 54
FEATURE                 Location/Qualifiers
misc_feature            1..54
                        note = Primer GI.3Lil08(S94K).r
source                  1..54
                        mol_type = other DNA
                        organism = synthetic construct
SEQUENCE: 282
tctgagccaa gtgcttcaga aacggattca agtgtggtcc tagctgcagg tcaa        54

SEQ ID NO: 283          moltype = DNA  length = 54
FEATURE                 Location/Qualifiers
misc_feature            1..54
                        note = Primer GI.3Lil08(S94K).c
source                  1..54
                        mol_type = other DNA
                        organism = synthetic construct
SEQUENCE: 283
cttgaatccg tttctgaagc acttggctca gatgtataat ggatgggttg gaaa        54

SEQ ID NO: 284          moltype = DNA  length = 54
FEATURE                 Location/Qualifiers
misc_feature            1..54
                        note = Primer GI.3Lil08(S94H).r
source                  1..54
                        mol_type = other DNA
                        organism = synthetic construct
SEQUENCE: 284
tctgagccaa gtggtgcaga aacggattca agtgtggtcc tagctgcagg tcaa        54

SEQ ID NO: 285          moltype = DNA  length = 54
FEATURE                 Location/Qualifiers
misc_feature            1..54
                        note = Primer GI.3Lil08(S94H).c
source                  1..54
                        mol_type = other DNA
                        organism = synthetic construct
SEQUENCE: 285
cttgaatccg tttctgcacc acttggctca gatgtataat ggatgggttg gaaa        54

SEQ ID NO: 286          moltype = AA  length = 540
FEATURE                 Location/Qualifiers
VARIANT                 80
                        note = X may be Ala, Asn, Lys or His
source                  1..540
                        mol_type = protein
                        note = Norovirus
                        organism = unidentified
SEQUENCE: 286
MKMASSDANP SDGSAANLVP EVNNEVMALE PVVGAAIAAP VAGQQNVIDP WIRNNFVQAP  60
GGEFTVSPRN APGEILWSAX LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 287          moltype = DNA  length = 1623
FEATURE                 Location/Qualifiers
misc_feature            1..1623
                        note = Nucleic acid sequence of human codon optimized VP1
                         GII.4_Syd12_P80X
source                  1..1623
                        mol_type = other DNA
                        organism = synthetic construct
SEQUENCE: 287
atgaaaatgg cctcgagtga cgctaaccct agtgacggca gcgccgccaa tcttgtgcct  60
gaggttaata atgaggtgat ggccctggag cctgtggtgg gcgcagccat agcagcgccc  120
gtggccggtc agcagaatgt gattgacccg tggatacgca acaattttgt ccaagcccct  180
ggtggggagt tcaccgttag cccgagaaat gcgccaggag aaatcctgtg gtcggccvms  240
ttgggacccg atctgaaccc ctatttgtca catctcgctc ggatgtacaa cgggtatgcc  300
ggcggatttg aagtgcaggt gattctggct gggaacgcgt tcactgctgg caaagtgatc  360
tttgcagcgg tgcctcccaa cttccccact gaaggactgt ctccaagcca ggtcacaatg  420
tttccacaca tcgtggtgga cgtacggcag ctagagcctg tcctgattcc cctccctgat  480
```

-continued

```
gtacgcaata atttctacca ctacaatcaa tccaatgatc cgaccattaa actcatcgcg  540
atgttgtaca cccctctgcg cgctaacaat gctggagacg acgtattcac cgtgtcatgc  600
agagtgctca ccagaccttc accagacttt gactttatct tcttagtgcc ccccactgtt  660
gagagccgaa ccaagccctt tagtgtcccc gtactcacag tcgaggagat gacaaatagc  720
cgctttccaa tccccccttga gaaactgttc acaggacctt cctcggcatt cgtggttcag  780
ccacagaacg gacgctgcac aactgacggc gtgctgctcg gaaccaccca gcttagccct  840
gttaatatct gtacgtttag aggcgacgta actcacataa ctggctcacg gaactatacc  900
atgaatctgg catcacagaa ttggaatgac tacgacccaa ccgaagagat tcccgcacct  960
cttggaaccc ccgactttgt gggaaaaata cagggcgtcc tgacacaaac caccagaacc  1020
gatggctcca cacggggaca caaggcaacc gtctacactg gctctgccga ttttgccccg  1080
aaactgggta gagtgcagtt tgagaccgac actgaccggg actttgaagc caatcagaat  1140
actaagttca cacctgtagg agtgattcag gacgggggca ccactcaccg gaacgagccg  1200
caacaatggg tcctgccctc ttatagcggg aggaatactc ataatgtgca tttggctcct  1260
gcagtggctc ccacgtttcc cggggaacaa ctgctctttt ttcgttcaac catgcctgga  1320
tgctccggat atcccaatat ggatctcgat tgcctgctcc cacaggaatg ggtgcagtat  1380
ttttatcaag aggccgcacc agcccaatcc gacgtcgcac ttctgcggtt cgtgaatcca  1440
gacacaggcc gcgtgttgtt tgagtgcaaa ttgcacaaat caggatacgt tacagtggct  1500
catactggac agcatgacct ggtgatccca cccaacggat attttaggtt cgactcctgg  1560
gtgaatcagt tttatacatt agccccccatg ggaatggga ctggcagacg cagggctgtc  1620
tga                                                                1623

SEQ ID NO: 288          moltype = AA  length = 540
FEATURE                 Location/Qualifiers
VARIANT                 39
                        note = X may be Ile, Met, Gly, Ser, Glu, Asp, Asn, Gln, Lys
                         or His
source                  1..540
                        mol_type = protein
                        note = Norovirus
                        organism = unidentified
SEQUENCE: 288
MKMASSDANP SDGSAANLVP EVNNEVMALE PVVGAAIAXP VAGQQNVIDP WIRNNFVQAP  60
GGEFTVSPRN APGEILWSAS LGPDLNPYLS HLARMYNGYA GGFEVQVILA GNAFTAGKVI  120
FAAVPPNFPT EGLSPSQVTM FPHIVVDVRQ LEPVLIPLPD VRNNFYHYNQ SNDPTIKLIA  180
MLYTPLRANN AGDDVFTVSC RVLTRPSPDF DFIFLVPPTV ESRTKPFSVP VLTVEEMTNS  240
RFPIPLEKLF TGPSSAFVVQ PQNGRCTTDG VLLGTTQLSP VNICTFRGDV THITGSRNYT  300
MNLASQNWND YDPTEEIPAP LGTPDFVGKI QGVLTQTTRT DGSTRGHKAT VYTGSADFAP  360
KLGRVQFETD TDRDFEANQN TKFTPVGVIQ DGGTTHRNEP QQWVLPSYSG RNTHNVHLAP  420
AVAPTFPGEQ LLFFRSTMPG CSGYPNMDLD CLLPQEWVQY FYQEAAPAQS DVALLRFVNP  480
DTGRVLFECK LHKSGYVTVA HTGQHDLVIP PNGYFRFDSW VNQFYTLAPM GNGTGRRRAV  540

SEQ ID NO: 289          moltype = DNA  length = 1620
FEATURE                 Location/Qualifiers
misc_feature            1..1620
                        note = hCod optimize sequence of VP1 GII.4_Syd12_P80S+A39X
source                  1..1620
                        mol_type = other DNA
                        organism = synthetic construct
SEQUENCE: 289
atgaaaatgg cctcgagtga cgctaaccct agtgacggca gcgccgccaa tcttgtgcct  60
gaggttaata atgaggtgat ggccctggag cctgtggtgg gcgcagccat agcavdsgtg  120
gccggtcagc agaatgtgat tgacccgtgg atacgcaaca attttgtcca agcccctggt  180
ggggagttca ccgttagccc gagaaatgcg ccaggagaaa tcctgtggtc ggccagcttg  240
ggacccgatc tgaaccccta tttgtcacat ctcgctcgga tgtacaacgg gtatgccggc  300
ggatttgaag tgcaggtgat tctggctggg aacgcgttca ctgctggcaa agtgatcttt  360
gcagcggtgc ctcccaactt ccccactgaa ggactgtctc caagccaggt cacaatgttt  420
ccacacatcg tggtggacgt acggcagcta gagcctgtcc tgattcccct ccctgatgta  480
cgcaataatt tctaccacta caatcaatcc aatgatccga ccattaaact catcgcgatg  540
ttgtacaccc ctctgcgcgc taacaatgct ggagacgacg tattcaccgt gtcatgcaga  600
gtgctcacca gaccttcacc agactttgac tttatcttct tagtgccccc cactgttgag  660
agccgaacca agccctttag tgtccccgta ctcacagtcg aggagatgac aaatagccgc  720
tttccaatcc cccttgagaa actgttcaca ggaccttcct cggcattcgt ggttcagcca  780
cagaacggac gctgcacaac tgacggcgtg ctgctcggaa ccacccagct tagccctgtt  840
aatatctgta cgtttagagg cgacgtaact cacataactg gctcacggaa ctataccatg  900
aatctggcat cacagaattg gaatgactac gacccaaccg aagagattcc cgcacctctt  960
ggaacccccg actttgtggg aaaaatacag ggcgtcctga cacaaaccac cagaaccgat  1020
ggctccacac ggggacacaa ggcaaccgtc tacactggct ctgccgattt tgccccgaaa  1080
ctgggtagag tgcagtttga gaccgacact gaccgggact ttgaagccaa tcagaatact  1140
aagttcacac ctgtaggagt gattcaggac gggggcacca ctcaccggaa cgagccgcaa  1200
caatgggtcc tgccctctta tagcgggagg aatactcata atgtgcattt ggctcctgca  1260
gtggctccca cgtttcccgg ggaacaactg ctcttttttc gttcaaccat gcctggatgc  1320
tccggatatc ccaatatgga tctcgattgc ctgctcccac aggaatgggt gcagtatttt  1380
tatcaagagg ccgcaccagc ccaatccgac gtcgcacttc tgcggttcgt gaatccagac  1440
acaggccgcg tgttgtttga gtgcaaattg cacaaatcag gatacgttac agtggctcat  1500
actggacagc atgacctggt gatcccaccc aacggatatt ttaggttcga ctcctgggtg  1560
aatcagtttt atacattagc cccccatgggg aatgggactg gcagacgcag ggctgtctga  1620

SEQ ID NO: 290          moltype = AA  length = 538
FEATURE                 Location/Qualifiers
```

```
VARIANT                 57
                        note = X may be Leu, Gly, Ser, Thr, Asn, Gln, Lys or His
source                  1..538
                        mol_type = protein
                        note = Norovirus
                        organism = unidentified
SEQUENCE: 290
MMMASKDAPS NMDGTSGAGQ LVPEVNAAEP LPLEPVVGAA TAVATAGQVN MIDPWIXNNF  60
VQAPEGEFTI SPNNTPGDIL FDLRLGPHLN PFLLHLSQMY NGWVGNMRVR VMLAGNAFSA  120
GKIIICCVPP GFESQNISIG QATMFPHVIA DVRVLEPIEV PLDDVRNVLF HTNENRPTMR  180
LLCMLYTPLR AGGASSGTDP FVIAGRVLTC PAPDFNFLFL VPPSVEQKTR QLTIPNIPLN  240
NLANSRVPAM INKMTVSADQ NQVVQFQNGR CTLEGQLLGT TPVSANQVAR IRGKVFSTNS  300
GTGLNLTEVD GTPYHAFESP APLGFPDIGN CDWHVYAFKV NQNTGDPMYR LDITQGNSFA  360
PHLGSIEFSS ENHPSGDQLG TLTWISPLNN ASRVDPWKIP TYGSTLTEST NLAPPIFPPG  420
FGEAIVYFMS DFPIVSGNTA QIPCTLPQEF VSSFVEQQAP IRGEAALLHY VDPDTHRNLG  480
EFKLYPDGFI TCVPNTGGGP QNLPSNGVFV FSSWVSRYYQ LKPVGTTGPV RRLGVRRV    538

SEQ ID NO: 291          moltype = DNA  length = 1614
FEATURE                 Location/Qualifiers
misc_feature            1..1614
                        note = Human codon optimized VP1_GI.7/GA5043/USA/2014_M57x
source                  1..1614
                        mol_type = other DNA
                        organism = synthetic construct
variation               170
                        note = a, g, c or t
SEQUENCE: 291
atgatgatgg ccagcaagga cgctccgagt aacatggacg gcacttcggg cgcggggcag  60
ctggtgcccg aggtcaatgc cgcagaacca cttcctcttg agcccgtcgt tggcgccgcc  120
acagctgtcg caactgcagg ccaagtcaat atgatcgacc cgtggatavn saatttcgtt  180
caggcaccag aaggagaatt caccatctcc cccaataaca ccccagggga tattctgttt  240
gacctcaggt taggacccca cttgaacccc tttctgcttc atctctcaca aatgtataat  300
ggctgggtcg ggaatatgcg cgtgcgggtg atgctagccg gcaatgcttt ttctgcaggc  360
aagattatca tttgctgcgt tcctcctgga ttcgaatctc aaaatatcag cattggtcaa  420
gcaaccatgt ttccacatgt gatcgctgat gttcgcgtcc tggaacccat tgaagttcct  480
ctcgacgacg tgagaaatgt tctcttccac accaacgaga ataggccgac tatgagactt  540
ctgtgtatgc tctacacccc attaagagcc gggggagcat cctcaggtac tgacccattt  600
gtgattgccg ggcgggtgct cacatgcccg gctccagact ttaacttcct tttcttggtg  660
ccacccagtg ttgaacagaa aaccagacag ctcaccatcc caaatatccc attgaacaat  720
ctcgccaaca gcagggtgcc agcaatgata aacaaaatga cagtcagtgc tgaccagaac  780
caggtagtcc agtttcagaa cggcagatgc acgcttgagg gccaactgct tgggacgacc  840
ccagtctccg cgaaccaggt ggcccgaatc cggggtaaag tcttcagtac aaactccggc  900
actggcctta acctcacaga ggttgacggc actccctatc atgcttttga gtctccagcc  960
cctcttggct ttcccgatat aggcaactgt gactggcacg tttatgcgtt taaagtaaac  1020
cagaacaccg gcgatcctat gtataggttg gatataacac aaggtaattc attcgcccca  1080
cacttgggta gcatcgagtt cagttcagag aaccatccga gtggtgatca gctaggcaca  1140
ttgacgtgga tcagccctct gaataacgca tcaagagtgg atccctggaa gatccctacc  1200
tatgggtcca ctctgacaga gagcacaaat ttggctccgc ccattttccc acccggattc  1260
ggcgaggcca tagtgtactt tatgtctgac tttcctatcg tcagcgggaa tacagcccag  1320
attccttgca cactgccaca agaattcgtc tcatcctttg tagagcagca ggcacctatt  1380
cgaggtgagg ccgccctctt gcactacgtg gaccctgaca cccaccgcaa tcttggcgag  1440
tttaagctgt accctgacgg gtttattacc tgtgtaccca acaccggcgg cggcccacaa  1500
aatttgccca gcaatggcgt gtttgtcttt tcctcttggg tgtctcgata ctaccagctt  1560
aaacctgtcg gaactacggg ccccgtgcga cgactcggcg tgaggcgggt gtga        1614

SEQ ID NO: 292          moltype = AA  length = 543
FEATURE                 Location/Qualifiers
VARIANT                 94
                        note = X may be Val, Ile, Met, Thr, Glu, Asp, Asn, Gln, Lys
                         or His
source                  1..543
                        mol_type = protein
                        organism = unidentified
SEQUENCE: 292
MMMASKDAPT NMDGTSGAGQ LVPEVSTAEP ISMEPVAGAA TAAATAGQVN MIDPWIMSNY  60
VQAPQGEFTI SPNNTPGDIL FDLQLGPHLN PFLXHLAQMY NGWVGNMKVR VLLAGNAFTA  120
GKIIISCVPP GFAAQNVSIA QATMFPHVIA DVRVLEPIEV PLEDVRNVLF HNNDSTPTMR  180
LICMLYTPLR ASGSSSGTDP FVIAGRVLTC PSPDFNFLFL VPPNVEQKTK PFSVPNLPLN  240
VLSNSRVPSL IKSMMVSQDH GQMVQFQNGR VTLDGQLQGT TPTSASQLCK IRGTVYHATG  300
GQGLNLTEID GTPYHAFESP APIGFPDLGE CDWHINASPA NAFTDGSIIH RIDVAQDSTF  360
APHLGTIHYT NADYNANVGL ICSLEWLSPP SGGAPKVNPW AIPRYGSTLT EAAQLAPPIY  420
PPGFGEAIVF FMSDFPIANG SDGLSVPCTI PQEFVTHFVN EQAPTRGEAA LLHYVDPDTH  480
RNLGEFKLYP EGFMTCVPNS SGSGPQTLPI NGVFTFISWV SRFYQLKPVG TTGPVRRLGI  540
RRS                                                               543

SEQ ID NO: 293          moltype = DNA  length = 1632
FEATURE                 Location/Qualifiers
misc_feature            1..1632
                        note = hCod optimized VP1_GI.3_Lil08_S94x
```

-continued

```
source                1..1632
                      mol_type = other DNA
                      organism = synthetic construct
SEQUENCE: 293
atgatgatgg cttccaagga tgctcccaca aacatggatg gaacaagcgg cgcggggcaa  60
cttgtgccgg aggtgtccac ggcggaaccc atttccatgg aacctgtggc cggcgcagcc  120
actgctgccg ccaccgcagg acaggtaaac atgatcgacc cctggatcat gtcaaattac  180
gttcaggctc cacaggggga gtttaccata agcccaaaca acaccccggg tgacatcttg  240
tttgacctgc agctaggacc acacttgaat ccgtttctgv hscacttggc tcagatgtat  300
aatggatggg ttggaaacat gaaggtgcgc gtgctcctgg cgggcaatgc attcacagcc  360
gggaagatta ttatctcttg cgtgccacct ggatttgcag cccagaacgt gtctatcgca  420
caggcaacca tgtttccgca tgtcatcgca gatgtgcgcg tgctagagcc catcgaggtg  480
cccccttgagg acgtgcgcaa cgtcctattc cataacaatg atagcacccc caccatgcgc  540
ttgatatgta tgttatatac tcccctccgc gccagtgggt ccagctccgg gaccgatcct  600
tttgtgattg ctgggcgggt gttgacttgt cctagccctg acttcaactt ccttttctg  660
gtgcctccaa atgtagaaca gaaaacaaag ccattcagcg tgccaaacct gccccttaac  720
gtgctgtcga attcccgagt gccttccctt attaagtcca tgatggtatc tcaggatcac  780
ggtcaaatgg tgcagtttca gaacggccga gtgacgttag acgggcagct gcagggcaca  840
accccaacca gtgccagtca gctgtgtaag atcagaggca ccgtctacca cgcaactggc  900
ggacaggggc tgaatcttac tgagatcgat ggtacccccct accatgcatt cgagtcacct  960
gcacctattg gatttcccga tcttggggag tgtgattggc atatcaatgc ttcacctgcc  1020
aacgctttca cagacgggtc tattattcat cgcattgacg tagcacagga tagcacattt  1080
gccccgcacc tgggtaccat ccactatacg aacgcagatt acaacgcaaa cgtgggtctt  1140
atctgtagcc tagagtggct atctccgcca agcggtgggg cccctaaagt taacccatgg  1200
gctattcctc ggtacgggtc tacgctgact gaggccgctc agctggcacc ccccatatat  1260
ccaccaggat tcggggaagc cattgttttc tttatgtccg attttccgat agccaacggt  1320
tcagatggcc ttagtgtccc ttgcacgatt ccacaggaat ttgtgacaca cttcgtaaac  1380
gagcaggctc ctactcgggg cgaggctgcc ttgttgcatt acgtagaccc cgatacccat  1440
agaaacctgg gcgaattcaa actctaccct gaaggtttca tgacctgcgt acctaactcc  1500
tccggcagtg gccctcaaac cttgccgatc aacggcgtgt tcacgtttat cagctgggtt  1560
tcacggtttt accaactcaa gcccgtcgga acaactgggc cagttcggag gctcgggatc  1620
agacggagct ag                                                     1632
```

MODIFIED NOROVIRUS VP1 PROTEINS AND VLPS COMPRISING MODIFIED NOROVIRUS VP1 PROTEINS

CROSS REFERENCE TO RELATED APPLICATIONS

This application is a Continuation application of U.S. application Ser. No. 16/768,524 filed May 29, 2020, which is a National Stage of International Application No. PCT/CA2018/051530 filed Nov. 30, 2018, claiming priority based on U.S. Patent Application No. 62/593,006 filed Nov. 30, 2017 and U.S. Patent Application No. 62/712,744 filed Jul. 31, 2018, the entire contents of which are hereby incorporated by reference.

INCORPORATION BY REFERENCE OF SEQUENCE LISTING

The content of the electronically submitted sequence listing, file name: Q284770_Substitute_Sequence_Listing.xml; size: 528,965 bytes; and date of creation: Mar. 23, 2023, filed herewith, is incorporated herein by reference in its entirety.

FIELD OF INVENTION

The present invention relates to modified norovirus VP1 proteins, VLPs comprising modified norovirus VP1 proteins, and methods of producing the same.

BACKGROUND OF THE INVENTION

The global disease burden attributed to norovirus infection is high, being associated with an estimated 20% of all worldwide diarrheal cases and causing over 200,000 deaths annually. Noroviruses are the primary cause of foodborne disease outbreaks in North America and are the causative agent for the majority of healthcare-associated outbreaks amongst the elderly. Norovirus strains are also recognized as being the leading cause of pediatric gastrointestinal illness worldwide.

Noroviruses comprise one of a number of genera of the family Caliciviridae. The human norovirus genome is a single-stranded, positive-sense RNA molecule encoding three open reading frames (ORFs) and capped on its 5' end by a VPg protein. ORF1 encodes six non-structural viral proteins, including VPg, an RNA-dependent RNA polymerase, and a viral protease. ORF2 encodes the major structural capsid protein (VP1). ORF3 encodes a minor capsid protein (VP2).

VP1 is comprised of 2 domains: a shell (S) domain, and a protruding (P) domain. The S domain, for example of GI.1 strains, comprises the first 225 N-terminal amino acids and contains structural elements necessary for capsid assembly and the formation of the viral icosahedron. The P domain comprises the remainder of the VP1 protein and is further comprised of a P1 sub-domain and a P2 sub-domain. The P2 sub-domain is referred to as the hypervariable domain and is thought to play an important role in receptor binding and immune reactivity.

VP1 proteins form dimers via P domain-mediated protein interactions. Dimerization increases the stability of the virion capsid and results in formation of the protrusions extending from the base core of the norovirus particle formed by S domains. When expressed, norovirus VP1 proteins can automatically assemble to form 2 virion structures: a 180-mer capsid structure with T=3 icosahedral symmetry having a 38-40 nm diameter; and a 60-mer capsid structure with T=1 icosahedral symmetry having a 23 nm diameter.

VP2, the minor structural protein, has a molecular weight (MW) of approximately 21-24 kDa. Studies suggest that VP2 is highly basic and located inside the capsid. The function of VP2 is not yet fully understood but it is generally believed to play a role in capsid stability by protecting the virions from disassembly and degradation (Bertolotti-Ciarlet A., Crawford S. E., Hutson A. M., Estes M. K. 2003, J. Virol. 77:11603-11615). VP2 may also have a function during RNA genome packaging. The amount of VP2 minor structural protein in virions is relatively low with 1.5 to 8 copies incorporated into the mature virion. Bertolotti-Ciarlet et. al. (2003) report that in insect and mammalian cells, VLPs composed of VP1/VP2 are more resistant to protease cleavage than those with only VP1, and that expression of VP2 in cis, results in an increase in VP1 protein production. In addition, the presence of the 3'UTR downstream of the ORF2 gene increases the steady-state levels of NV ORF2 mRNA. The greatest increase in VP1 expression was observed when ORF2+ORF3+3'UTR, residing on the same construct and under regulation of one promoter, was expressed. Expression of VP2 in trans did not result in any increase in VP1 expression, indicating that the subgenomic organization of ORF2-ORF2-3'UTR was required for the observed increase in VP1 production.

Noroviruses are classified according to their phylogenetic clustering of the VP1 amino acid sequence. Seven genogroups have been classified to date (GI through GVII) with only genogroups GI, GII, and GIV known to infect humans. Of the 32 specific genotypes currently associated with human infections, GII.4 noroviruses have been responsible for the majority of recent norovirus outbreaks. New strains of GII.4 emerge every two to three years, evolving by a process driven by mutations in epitope determining regions of the hypervariable P2 domain of VP1. This process allows the norovirus to escape humoral immune responses acquired by previous exposure to earlier strains.

While faced with the difficulty of rapidly evolving and genetically diverse norovirus strains, the development of effective norovirus vaccines has been exacerbated by additional challenges. For instance, until recently, human norovirus could not be grown in cell culture and even now, robust cell culture systems for both VLPs and live attenuated noroviruses are lacking.

An additional challenge in vaccine development is that immunity to norovirus infection is strain and genotype specific with minimal cross-immunity conferred against other genogroups. Furthermore, immunity to a norovirus strain is not life-long and is estimated to persist from anywhere between six months and nine years.

Various approaches have been undertaken to develop a suitable vaccine against norovirus infection including the production of recombinant norovirus proteins in insect and plant expression systems.

Huo et al. (*Virus Research,* 2015, 204:1-5) demonstrated that an M27G mutant capsid protein, of norovirus VP1 VLPs produced in insect SF9 cells, resulted in the production of 38 nm and 21 nm VLPs, comprising proteins of 58 kDa and 55 kDa. The 55 kDa protein was a result of degradation or cleavage of the full-length P1 capsid protein as opposed to the translated product of an internal start codon. N-terminal deletion mutants comprising 26 or 38 deleted amino acid residues of the VP1 protein, resulted in the production of 21 nm VLPs. The 26 amino acid deletion mutants produced low numbers of 38 nm VLPs whereas 38 amino acid deletion mutants did not result in formation of 38 nm VLPs.

US 2013/0273105 teaches the production of norovirus formulations comprising antigenic peptides, proteins or VLPs derived from genogroup I (G1), genogroup II (GII), or consensus viral sequences. The norovirus antigens may include variants of the capsid proteins expressed in the VLPs.

US 2015/0023995 provides a vaccine formulation comprising VLPs produced in insect Sf9 cells, the VLPs comprising a composite amino acid sequence derived from at least two viral protein sequences. For Example, a composite GII.4 VP1 VLP, comprising a VP1 sequence from GII.4 Minerva 2006-a, and GII.4 Laurens 2006-b and GII.4 Houston 2002 norovirus strains, is described. Composite sequences derived from GII, GII.2 Snow Mountain and GII.3, as well as GI composite sequences derived from Norwalk GI.1, Southampton GI.1, and Chiba GI.1 are also described.

Mason et al. (*Proc Natl Acad Sci U.S.A.,* 1996, 93(11): 5335-40) teach the use of genetically engineered tobacco plants and potato tubers to express GI.1 norovirus VLPs from native VP1 protein. The plant produced norovirus VLPs are morphologically and physically similar to the 38 nm Norwalk VLPs produced in insect cells. Oral administration of purified tobacco-produced Norwalk VLPs from native capsid protein, or potato tubers expressing GI.1 capsid protein induced a humoral immune response in mice and humans (Tacket et al., *J. Infect. Dis.,* 2000, 182(1):302-5).

Huang et al. (*Biotechnol. Bioeng.,* 2009, 103(4):706-14) describe a geminivirus-derived DNA replicon vector for production of GI.1 norovirus VLP in plants. Co-delivery of bean yellow dwarf virus-derived vector and Rep/RepA-supplying vector in *Nicotiana benthamiana* resulted in rapid and robust protein production.

SUMMARY OF THE INVENTION

The present invention relates to modified norovirus proteins, virus like particles (VLPs) comprising modified norovirus proteins, and methods of producing norovirus proteins, and virus like particles (VLPs) comprising modified norovirus proteins.

It is an object of the invention to produce modified norovirus proteins, VLPs comprising modified norovirus proteins, and to produce VLPs comprising modified norovirus proteins in plants.

As described herein, there is provided a recombinant polynucleotide comprising, a nucleotide sequence encoding a modified norovirus VP1 protein, wherein the modified norovirus VP1 protein comprises one or more than one substitution, modification or mutation at:

- an amino acid selected from positions in sequence alignment with amino acids 43, 57, 84 and 94 of norovirus VP1 genotype GI.1,
- a deletion of a peptide fragment in sequence alignment with amino acids 39-46 of norovirus VP1 genotype GI.1,
- amino acids corresponding to positions 39-46 of norovirus VP1 genotype GI.1, are mutated to the sequence SSTAVATA, or
- a combination thereof, and the nucleotide sequence is not derived from a genotype GI.1 norovirus VP1.

Also provided is the recombinant polynucleotide as described above, wherein the nucleotide sequence is derived from a norovirus VP1 selected from a group consisting of genotypes GI.2, GI.3. GI.5, GI.7, GII.2, GII.3, GII.4, GII.6, GII.12 and GII.17. For example, which is not to be considered limiting, the nucleotide sequence may be derived from the group comprising of G1.2/Leuven/2003/BEL GI.3/S29/2008/Lilla Edet/Sweden, GI.5/Siklos-HUN5407/2013/HUN, GI.7/USA/2014/GA5043, GII.2/CGMH47/2011/TW; GII.3/Jingzhou/2013402/CHN, GII.4/Sydney/NSW0514/2012/AU, GII.6/Ohio/490/2012/USA, GII.12/H5206/2010/USA, and GII.17_Kawa_2014_A0A077KVU6.

The recombinant polynucleotide described above may comprise specific substitutions, modifications or mutations, independently selected from the following:

- a substitution, modification or mutation at the position in sequence alignment with amino acid 43 of VP1 genotype GI.1 to valine, isoleucine, leucine, methionine, threonine, aspartic acid, glutamic acid, asparagine, glutamine, lysine, or histidine;
- a substitution, modification or mutation at the position in sequence alignment with amino acid 57 of VP1 genotype GI.1 to isoleucine, leucine, valine, alanine, glycine, serine, threonine, asparagine, glutamine, lysine, or histidine;
- a substitution, modification or mutation at the position in sequence alignment with amino acid 84 of VP1 genotype GI.1 to serine, asparagine, cysteine, threonine, alanine, lysine or histidine; and
- a substitution, modification or mutation at the position in sequence alignment with amino acid 94 of VP1 genotype GI.1 to leucine, isoleucine, methionine, valine, threonine, aspartic acid, glutamic acid, asparagine, glutamine, lysine, or histidine.

Any of the recombinant polynucleotides described above may also be optimized for human codon usage, increased GC content, or a combination thereof.

A modified norovirus VP1 protein encoded by any one of the recombinant polynucleotides described above is also described herein. Furthermore, a VLP comprising the modified norovirus VP1 protein encoded by any one of the recombinant polynucleotides described above, is also disclosed. The VLP comprising the norovirus VP1 protein encoded by any one of the recombinant polynucleotides described above, may further comprise a norovirus VP2 protein.

A method for producing a modified norovirus VP1 in a plant, portion of a plant or plant cell is also provided herein. The modified norovirus VP1 may be encoded by any one of the recombinant polynucleotides described above. The method comprises introducing one or more than one of the recombinant polynucleotide described above into the plant, the portion of the plant or the plant cell, and incubating the plant, the portion of the plant or the plant cell under conditions that permit expression of the one or more than one modified norovirus VP1 protein. The method provided herein may further comprise a step of harvesting the plant, portion of the plant, or the plant cell. Additionally, the method may comprise a step of extracting, purifying, or both extracting and purifying the one or more than one modified norovirus VP1 protein from the plant, the portion of the plant or the plant cell. Furthermore, in the step of introducing, the method may further comprise introducing a second nucleic acid sequence encoding a norovirus VP2 protein into the plant, the portion of the plant, or the plant cell, and in the step of incubating, the conditions permit co-expression and co-production of both the one or more than one modified norovirus VP1 protein and the norovirus VP2 protein in the plant, portion of the plant or the plant cell.

Also described is a method for producing a norovirus virus like particle (VLP) in a plant, portion of a plant or plant cell, wherein the VLP comprises one or more than one of the modified norovirus VP1 proteins encoded by one or more of the recombinant polynucleotides described above. The method comprises introducing one or more than one of the recombinant polynucleotides described above into the plant, the portion of the plant or the plant cell, and incubating the plant, the portion of the plant or the plant cell under conditions that permit expression of the one or more than one modified norovirus VP1 protein, thereby producing the norovirus VLP. The method provided herein may further comprise a step of harvesting the plant, portion of the plant, or the plant cell. Additionally, the method may comprise a step of extracting, purifying, or both extracting and purifying the norovirus VLP from the plant, the portion of the plant or the plant cell. Furthermore, in the step of introducing, the method may further comprise introducing a second nucleic acid sequence encoding a norovirus VP2 protein into the plant, the portion of the plant, or the plant cell, and in the step of incubating, the conditions permit co-expression and co-production of both the modified norovirus VP1 protein and the norovirus VP2 protein in the plant, portion of the plant or the plant cell thereby producing the norovirus VLP. The norovirus VLP produced by the method described herein may have a diameter of about 15 nm to 50 nm. Alternatively, the VLP may have a diameter of about 23 nm (for T=1 icosahedral symmetry) or about 38 nm (for T=3 icosahedral symmetry).

A method of producing an antibody or antibody fragment is provided herein, wherein the method comprises administering one or more than one of the modified norovirus VP1 proteins encoded by one or more than one of the recombinant polynucleotide described above, or the norovirus VLP comprising one or more than one of the modified norovirus VP1 protein, to a subject or a host animal, thereby producing the antibody or the antibody fragment.

Also provided herein is a plant, portion of the plant, or plant cell comprising the recombinant polynucleotide described above, the modified norovirus VP1 encoded by one or more than one of the recombinant polynucleotide, or the norovirus VLP comprising one or more than one the modified norovirus VP1 protein.

A composition for inducing an immune response is also described herein. The composition comprises, an effective dose of one or more than one of the modified norovirus VP1 protein encoded by one or more than one of the recombinant polynucleotide described above, or the norovirus VLP comprising one or more than one of the modified norovirus VP1 protein, and a pharmaceutically acceptable carrier, adjuvant, vehicle or excipient.

The present disclosure also provides a vaccine for inducing an immune response, wherein the vaccine comprises an effective dose of one or more than one of the modified norovirus VP1 proteins encoded by one or more than one of the recombinant polynucleotide described above, or the VLP comprising one or more than one of the modified norovirus VP1 protein.

Multiple strains of Norovirus have been characterized, and norovirus strains may evolve over time. Therefore, the present disclosure is also directed to VP1 and VP2 proteins from norovirus that exhibit from about 30-100% or any amount therebetween, amino acid sequence identity, to the VP1 protein, the VP2 protein, or both the VP1 and the VP2 proteins, of any of the norovirus strains listed in FIGS. 2A and 2B, provided that the VP1 protein can be expressed in a plant, and that the VP1 protein induces immunity to norovirus in a subject, when the VP1 protein is administered to the subject. For example, norovirus strains include strains having 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100%, or any amount therebetween, amino acid sequence identity (sequence similarity; percent identity; percent similarity) to the VP1 protein, the VP2 protein, or both the VP1 and the VP2 proteins, with any of the strains listed in FIGS. 2A and 2B, provided that the VP1 protein can be expressed in a plant, and the VP1 protein induces immunity to norovirus in a subject, when the VP1 protein is administered to the subject.

An antibody or antibody fragment is provided herein, wherein the antibody or antibody fragment is prepared by administering one or more than one of the modified norovirus VP1 encoded by one or more than one of the recombinant polynucleotide described above, or the norovirus VLP comprising one or more than one of the modified norovirus VP1, to a subject or host animal.

Also described herein is a method of inducing immunity to a norovirus infection in a subject, wherein the method comprises administering one or more than one of the modified norovirus VP1 protein encoded by one or more than one of the recombinant polynucleotide described above, or the norovirus VLP comprising one or more than one of the modified norovirus VP1 protein. The one or more than one of the modified norovirus VP1 protein, or the norovirus VLP may be administered to the subject orally, intranasally, intramuscularly, intraperitoneally, intravenously subcutaneously, rectally, or intravaginally.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 2A shows Uniprot and NCBI references for several norovirus VP1 (upper panel) and VP2 (lower panel) proteins. FIG. 2B shows NCBI references for several norovirus VP1 (upper panel) and VP2 (lower panel) nucleic acid sequences.

#:4130, left panel), mut hCod GI.5/Siklos/HUN5407/2013/HUN_A94L VP1 (Construct #: 4131, middle panel), or mut hCod GI.5/Siklos/HUN5407/2013/HUN_Q84S+A94L VP1 (Construct #: 4132, right panel). 15,000× magnification; scale bar=200 nm.

FIG. 9G shows Coomassie-stained SDS-PAGE analysis of iodixanol density gradient fractions of crude protein extracts prepared from *N. benthamiana* leaves (upper panel), and transmission electron micrographs (TEM) of virus like particles (VLPs) purified from 31-35% iodixanol gradient fractions of crude protein extracts prepared from *N. benthamiana* leaves (lower panel), expressing: Left Panel: mut hCod GII.4/Sydney/NSW0514/2012/AU_R53I+P80S VP1 (Construct #4167); Right panel mut hCod GII.4/Sydney/NSW0514/2012/AU_A39V+R53I+P80S VP1 (Construct #4186; SEQ ID NO:191 (nucleotide); SEQ ID NO:190 (amino acid)); 15,000× magnification; scale bar=500 nm.

FIG. 12A shows the amino acid sequence of VP1 GI.1 United States Norwalk 1968 (SEQ ID NO:1); FIG. 12B shows the nucleic acid sequence of wild type VP1 GI.1 United States Norwalk 1968 (SEQ ID NO:2); FIG. 12C shows the nucleic acid sequence of hCod VP1 GI.1 United States Norwalk 1968 (SEQ ID NO:3).

FIG. 13A shows the amino acid sequence of VP1 G1.2 Leuven 2003 D2DEL3 (SEQ ID NO:4); FIG. 13B shows the nucleic acid sequence of hCod VP1 G1.2 Leuven 2003 D2DEL3 (SEQ ID NO:5).

FIG. 14A shows the amino acid sequence of VP1 GI.3 LillaEdet 2008 H2DG70 (SEQ ID NO:6); FIG. 14B shows the nucleic acid sequence of hCod GI.3 LillaEdet 2008 H2DG70 (SEQ ID NO:7).

FIG. 15A shows the amino acid sequence of VP1 GI.5 Siklos HUN5407 2013 HUN AHW99832 (SEQ ID NO:12). FIG. 15B shows the nucleic acid sequence of hCod VP1 GI.5 Siklos HUN5407 2013 HUN AHW99832 (SEQ ID NO:33).

FIG. 16A shows the amino acid sequence of GI.7/GA5043/USA/2014 VP1 (SEQ ID NO:101). FIG. 16B shows the nucleic acid sequence of GI.7/GA5043/USA/2014 VP1 (SEQ ID NO:175). FIG. 16C shows the amino acid sequence of VP1 GII.1 Ascension208 2010 USA AFA55174 (SEQ ID NO:13).

FIG. 17A shows the amino acid sequence of VP1 GII.2 CGMH47 2011 TW AGT39206 (SEQ ID NO:14). FIG. 17B shows the nucleic acid sequence of hCod VP1 GII.2 CGMH47 2011 TW AGT39206 (SEQ ID NO:40).

FIG. 18A shows the amino acid sequence of VP1 GII.3 Jingzhou 2013402 CHN AGX01095 (SEQ ID NO:15). FIG. 18B shows the nucleic acid sequence of hCod VP1 GII.3 Jingzhou 2013402 CHN AGX01095 (SEQ ID NO:45).

FIG. 19A shows the amino acid sequence of VP1 GII.4 Sydney NSW0514 2012 (SEQ ID NO:16). FIG. 19B shows the nucleic acid sequence of hCod VP1 GII.4 Sydney NSW0514 2012 (SEQ ID NO: 52). FIG. 19C shows the amino acid sequence of VP1 US96: GII.4 Dresden174 1997 DE AY741811 (SEQ ID NO:27). FIG. 19D shows the amino acid sequence of VP1 FH02: GII.4 FarmingtonHills 2002 US AY502023 (SEQ ID NO:28). FIG. 19E shows the amino acid sequence of VP1 Hnt04: GII.4 Hunter-NSW504D 2004 AU DQ078814 (SEQ ID NO:29). FIG. 19F shows the amino acid sequence of VP1 2006b: GII.4 Shellharbour-NSW696T 2006 AU EF684915 (SEQ ID NO:30). FIG. 19G shows the amino acid sequence of VP1NO09: GII.4 Orange-NSW001P 2008 AU GQ845367 (SEQ ID NO:31).

FIG. 20 shows the amino acid sequence of VP1 GII.5 Alberta 2013 CA ALT54485 (SEQ ID NO:17).

FIG. 21A shows the amino acid sequence of VP1 GII.6 Ohio 2012 M9T020 (SEQ ID NO:20). FIG. 21B shows the nucleic acid sequence of hCod-optimized VP1 GII.6 Ohio 2012 M9T020 (SEQ ID NO:21);

FIG. 22 shows the amino acid sequence of VP1 GII.7 Musa 2010 AII173774 (SEQ ID NO:18).

FIG. 23A shows the amino acid sequence of VP1 GII.12_HS206_2010 USA_AEI29586 (SEQ ID NO:19); FIG. 23B shows the nucleic acid sequence of hCod VP1 GII.12_HS206_2010_USA AEI29586 (SEQ ID NO:87).

FIG. 24A shows the amino acid sequence of VP1 GII.13 VA173 2010 H9AWU4 (SEQ ID NO:22). FIG. 24B shows the nucleic acid sequence of human codon-optimized VP1 GII.13 VA173 2010 H9AWU4 (SEQ ID NO:23).

FIG. 25 shows the amino acid sequence of VP1 GII.14 Saga 2008 JPN ADE28701 (SEQ ID NO:32).

FIG. 26A shows the amino acid sequence of VP1 GII.17 Kawa 2014 A0A077KVU6 (SEQ ID NO:24). FIG. 26B shows the nucleic acid sequence of human codon-optimized VP1 GII.17 Kawa 2014 A0A077KVU6 (SEQ ID NO:25).

FIG. 27 shows the amino acid sequence of VP1 GII.21 Sali 2011 USA AFC89665 (SEQ ID NO:26).

FIG. 28A shows the amino acid sequence of modified VP1 GI.3_ Lil08_Q84S (SEQ ID NO:98). FIG. 28B shows the nucleic acid sequence of VP1 GI.3_Lil08_Q84S (SEQ ID NO:167). FIG. 28C shows the amino acid sequence of VP1 GI.3 Lil08_S94L (SEQ ID NO:8). FIG. 28D shows the nucleic acid sequence of hCod VP1 GI.3 Lil108_S94L (SEQ ID NO:9). FIG. 28E shows the amino acid sequence of VP1 GI.3 Lil08_Q84S+S94L (SEQ ID NO:10). FIG. 28F shows the nucleic acid sequence of hCod VP1 GI.3 Lil08_Q84S+S94L (SEQ ID NO:11). FIG. 28G shows the amino acid sequence of VP1 GI.3 Lil08_A43V+S94L (SEQ ID NO:170). FIG. 28H shows the nucleic acid sequence of hCod VP1 GI.3 Lil08_A43V+S94L (SEQ ID NO:169). FIG. 28I shows the amino acid sequence of VP1 GI.3 Lil08_M57I+S94L (SEQ ID NO:172). FIG. 28J shows the nucleic acid sequence of hCod VP1 GI.3 Lil08_M57I+S94L (SEQ ID NO:171). FIG. 28K shows the amino acid sequence of VP1 GI.3 Lil08_A43V+M57I+S94L (SEQ ID NO:174). FIG. 28L shows the nucleic acid sequence of hCod VP1 GI.3 Lil08_A43V+M57I+S94L (SEQ ID NO:173). FIG. 28M shows the amino acid sequence of VP1_GI.3_Lil08_S94X (SEQ ID NO:292); wherein X is selected from V, I M, T, E, D, N, Q, K, or H. FIG. 28N shows the human codon optimized sequence of VP1_GI.3_Lil08_S94X (SEQ ID NO:293); wherein X is selected from a codon encoding V (e.g. XXX=GTG), I (e.g. XXX=ATC), M (e.g. XXX=ATG), T (e.g. XXX=ACC), E (e.g. XXX=GAG), D (e.g. XXX=GAC), N (e.g. XXX=AAC), Q (e.g. XXX=CAG), K (e.g. XXX=AAG), or H (e.g. XXX=CAC).

FIG. 29A shows the amino acid sequence of modified VP1 GI.5 Siklos Q84S (SEQ ID NO:34). FIG. 29B shows the nucleic acid sequence of modified VP1 GI.5 Siklos Q84S (SEQ ID NO:35). FIG. 29C shows the amino acid sequence of VP1 GI.5 Siklos A94L (SEQ ID NO:36). FIG. 29D shows the nucleic acid sequence of hCod VP1 GI.5 Siklos A94L (SEQ ID NO:37). FIG. 29E shows the amino acid sequence of VP1 GI.5 Siklos Q84S+A94L (SEQ ID NO:38). FIG. 29F shows the nucleic acid sequence of hCod VP1 GI.5 Siklos Q84S+A94L (SEQ ID NO:39). FIG. 29G shows the amino acid sequence of modified VP1 GI.7/GA5043/USA/2014_R84S (SEQ ID NO:177). FIG. 29H shows the nucleic acid sequence of modified VP1 hCod GI.7/GA5043/USA/2014_R84S (SEQ ID NO:176).

FIG. 29I shows the amino acid sequence of modified VP1 GI.7/GA5043/USA/2014_M57I (SEQ ID NO:179). FIG. 29J shows the nucleic acid sequence of modified VP1 hCod GI.7/GA5043/USA/2014_M57I (SEQ ID NO:178). FIG. 29K shows the amino acid sequence of modified VP1GI.7/GA5043/USA/2014_M57I+R84S (SEQ ID NO:181). FIG. 29L shows the nucleic acid sequence of modified VP1 hCod GI.7/GA5043/USA/2014_M57I+R84S (SEQ ID NO:180). FIG. 29M shows the amino acid sequence of VP1_GI.7/GA5043/USA/2014_M57X (SEQ ID NO:290); wherein X is selected from L, G, S, T, N, Q, K or H. FIG. 29N shows human codon optimized VP1_GI.7/GA5043/USA/2014_M57X (SEQ ID NO:291); wherein X is selected from a codon encoding L (e.g. XXX=CTG), G (e.g. XXX=GGC), S (e.g. XXX=AGC), T (e.g. XXX=ACC), N (e.g. XXX=AAC), Q (e.g. XXX=CAG), K (e.g. XXX=AAG), or H (e.g. XXX=CAC).

FIG. 30A shows the amino acid sequence of VP1 GII.2 CGMH47 E80S (SEQ ID NO:85). FIG. 30B shows the nucleic acid sequence of hCod VP1 GII.2 CGMH47 E80S (SEQ ID NO:86). FIG. 30C shows the amino acid sequence of VP1 GII.2 CGMH47 A90L (SEQ ID NO:41); FIG. 30D shows the nucleic acid sequence of hCod VP1 GII.2 CGMH47 A90L (SEQ ID NO:42). FIG. 30E shows the amino acid sequence of VP1_GII.2_CGMH47_E80S+A90L (SEQ ID NO:43). FIG. 30F shows the nucleic acid sequence of hCod VP1_GII.2_CGMH47_E80S+A90L (SEQ ID NO:44). FIG. 30G shows the amino acid sequence of VP1_GII.2_CGMH47_A39V+E80S+A90L (SEQ ID NO:182). FIG. 30H shows the nucleic acid sequence of hCod VP1_GII.2_CGMH47_A39V+E80S+A90L (SEQ ID NO:183). FIG. 30I shows the amino acid sequence of VP1_GII.2_CGMH47_R53I+E80S+A90L (SEQ ID NO:184). FIG. 30J shows the nucleic acid sequence of hCod VP1_GII.2_CGMH47_R53I+E80S+A90L (SEQ ID NO:185). FIG. 30K shows the amino acid sequence of VP1_GII.2_CGMH47_A39V+R53I+E80S+A90L (SEQ ID NO:186). FIG. 30L shows the nucleic acid sequence of hCod VP1_GII.2_CGMH47_A39V+R53I+E80S+A90L (SEQ ID NO:187).

FIG. 31A shows the amino acid sequence of VP1 GII.3_Jing_E80S (SEQ ID NO:46). FIG. 31B shows the nucleic acid sequence of hCod VP1 GII.3_Jing_E80S (SEQ ID NO:47). FIG. 31C the amino acid sequence of VP1 GII.3_Jing_A90L (SEQ ID NO:48). FIG. 31D shows the nucleic acid sequence of hCod VP1 GII.3_Jing_A90L (SEQ ID NO:49). FIG. 31E the amino acid sequence of VP1 GII.3_Jing_E80S+A90L (SEQ ID NO:50). FIG. 31F shows the nucleic acid sequence of hCod VP1 GII.3_Jing_E80S+A90L (SEQ ID NO:51).

FIG. 32A shows the amino acid sequence of VP1 GII.4 Syd12 A39V (SEQ ID NO:53). FIG. 32B shows the nucleic acid sequence of hCod VP1 GII.4_Syd12_A39V (SEQ ID NO:54). FIG. 32C shows the amino acid sequence of VP1 GII.4_Syd12_V47P (SEQ ID NO:55). FIG. 32D shows the nucleic acid sequence of hCod VP1 GII.4_Syd12_V47P (SEQ ID NO:56). FIG. 32E shows the amino acid sequence of VP1 GII.4_Syd12_R53I (SEQ ID NO:57). FIG. 32F shows the nucleic acid sequence of hCod VP1 GII.4_Syd12_R53I (SEQ ID NO:58). FIG. 32G shows the amino acid sequence of VP1; GII.4_Syd12_P80S (SEQ ID NO:59). FIG. 32H shows the nucleic acid sequence of hCod VP1 GII.4_Syd12_P80S (SEQ ID NO:60). FIG. 32I shows the amino acid sequence of VP1 GII.4_Syd12_S90L (SEQ ID NO:61). FIG. 32J shows the nucleic acid sequence of hCod VP1 GII.4_Syd12_S90L (SEQ ID NO:62). FIG. 32K shows the amino acid sequence of VP1GII.4_Syd12_Δ35-42 (SEQ ID NO:63). FIG. 32L shows the nucleic acid sequence of hCod VP1GII.4_Syd12_Δ35-42 (SEQ ID NO:64). FIG. 32M shows the amino acid sequence of VP1 GII.4_Syd12_SSTAVATA (SEQ ID NO:65). FIG. 32N shows the nucleic acid sequence of hCodVP1 GII.4_Syd12_SSTAVATA (SEQ ID NO:66). FIG. 32O shows the amino acid sequence of VP1GII.4_Syd12_P80S+A39V (SEQ ID NO:67). FIG. 32P shows the nucleic acid sequence of hCod VP1 GII.4_Syd12_P80S+A39V (SEQ ID NO:68). FIG. 32Q shows the amino acid sequence of VP1 GII.4_Syd12_P80S+V47P (SEQ ID NO:69). FIG. 32R shows the nucleic acid sequence of hCod VP1 GII.4_Syd12_P80S+V47P (SEQ ID NO:70). FIG. 32S shows the amino acid sequence of VP1GII.4_Syd12_P80S+R53I (SEQ ID NO:71). FIG. 32T shows the nucleic acid sequence of hCod VP1 GII.4_Syd12_P80S+R53I (SEQ ID NO:72). FIG. 32U shows the amino acid sequence of VP1 GII.4_Syd12_P80S+S90L (SEQ ID NO:73). FIG. 32V shows the nucleic acid sequence of hCod VP1 GII.4_Syd12_P80S+S90L (SEQ ID NO:74). FIG. 32W shows the amino acid sequence of VP1 GII.4_Syd12_P80S+Δ35-42 (SEQ ID NO:75). FIG. 32X shows the nucleic acid sequence of hCod VP1 GII.4_Syd12_P80S+Δ35-42 (SEQ ID NO:76). FIG. 32Y shows the amino acid sequence of VP1 GII.4_Syd12_P80S+SSTAVATA (SEQ ID NO:77). FIG. 32Z shows the nucleic acid sequence of hCod VP1 GII.4_Syd12_P80S+SSTAVATA (SEQ ID NO:78). FIG. 32AA shows the amino acid sequence of VP1 GII.4 Syd12 A39V+R53I (SEQ ID NO:188). FIG. 32BB shows the nucleic acid sequence of hCod VP1 GII.4_Syd12_A39V+R53I (SEQ ID NO:189). FIG. 32CC shows the amino acid sequence of VP1 GII.4 Syd12 A39V+R53I+P80S (SEQ ID NO:190). FIG. 32DD shows the nucleic acid sequence of hCod VP1 GII.4_Syd12_A39V+R53I+P80S (SEQ ID NO:191). FIG. 32EE shows the nucleic acid sequence of human codon optimized VP1 GII.4_Syd12_P80X (SEQ ID NO:287); wherein X is selected from a codon encoding A (e.g. XXX=GCC), N (e.g. XXX=AAC), K (e.g. XXX=AAG), or H (e.g. XXX=CAC). FIG. 32FF shows the amino acid sequence of VP1_GII.4_Syd12_P80X (SEQ ID NO:286); wherein X is selected from A, N, K, or H. FIG. 32GG shows the nucleic acid sequence of human codon optimize sequence of VP1 GII.4_Syd12_P80S+A39X (SEQ ID NO:289); wherein X is selected from a codon encoding I (e.g. XXX=ATC), M (e.g. XXX=ATG), G (e.g. XXX=GGC), S (e.g. XXX=AGC), E (e.g. XXX=GAG), D (e.g. XXX=GAC), N (e.g. XXX=AAC), Q (e.g. XXX=CAG), K (e.g. XXX=AAG), or H (e.g. XXX=CAC). FIG. 32HH show the amino acid sequence of VP1 GII.4_Syd12_P80S+A39X (SEQ ID NO:288); wherein X is selected from I, M, G, S, E, D, N, Q, K, or H.

FIG. 33A shows the amino acid sequence of VP1 GII.6_Ohio_E80S (SEQ ID NO:79). FIG. 33B shows the nucleic acid sequence of hCod VP1 GII.6_Ohio_E80S (SEQ ID NO:80). FIG. 33C shows the amino acid sequence of VP1 GII.6_Ohio_S90L (SEQ ID NO:81). FIG. 33D shows the nucleic acid sequence of hCod VP1 GII.6_Ohio_S90L (SEQ ID NO:82). FIG. 33E shows the amino acid sequence of VP1 GII.6_Ohio_E80S+S90L (SEQ ID NO:83). FIG. 33F shows the nucleic acid sequence of hCod VP1 GII.6_Ohio_E80S+S90L (SEQ ID NO:84).

FIG. 34A shows the amino acid sequence of VP1 GII.12_HS10_E80S (SEQ ID NO:88). FIG. 34B shows the nucleic acid sequence of hCod VP1 GII.12_HS10_E80S (SEQ ID NO:89). FIG. 34C shows the amino acid sequence of VP1 GII.12_HS10_A90L (SEQ ID NO:90). FIG. 34D shows the nucleic acid sequence of hCod VP1

GII.12_HS10_A90L (SEQ ID NO:91). FIG. 34E shows the amino acid sequence of VP1 GII.12_HS10_E80S+A90L (SEQ ID NO:92); FIG. 34F shows the nucleic acid sequence of hCod VP1 GII.12_HS10_E80S+A90L (SEQ ID NO:93). FIG. 34G shows the amino acid sequence of VP1 GII.17 Kawa 2014 A0A077KVU6_A39V (SEQ ID NO:192). FIG. 34H shows the nucleic acid sequence of VP1 hCod GII.17 Kawa 2014 A0A077KVU6_A39V (SEQ ID NO:193). FIG. 34I shows the amino acid sequence of VP1GII.17 Kawa 2014 A0A077KVU6_R53I (SEQ ID NO:194). FIG. 34J shows the nucleic acid sequence of VP1 hCod GII.17 Kawa 2014 A0A077KVU6 R53I (SEQ ID NO:195). FIG. 34K shows the amino acid sequence of VP1GII.17 Kawa 2014 A0A077KVU6_A90L (SEQ ID NO:196). FIG. 34L shows the nucleic acid sequence of VP1 hCod GII.17 Kawa 2014 A0A077KVU6_A90L (SEQ ID NO:197). FIG. 34M shows the amino acid sequence of VP1GII.17 Kawa 2014 A0A077KVU6_A39V+M53I (SEQ ID NO:198). FIG. 34N shows the nucleic acid sequence of VP1 hCod GII.17 Kawa 2014 A0A077KVU6_A39V+M53I (SEQ ID NO:199). FIG. 34O shows the amino acid sequence of VP1GII.17 Kawa 2014 A0A077KVU6_E80S+A90L (SEQ ID NO:200). FIG. 34P shows the nucleic acid sequence of VP1 hCod GII.17 Kawa 2014 A0A077KVU6_E80S+A90L (SEQ ID NO:201);

FIG. 35A shows the amino acid sequence of VP2_GI.1_Norwalk (SEQ ID NO:99). FIG. 35B shows the nucleic acid sequence of human codon optimized VP.2_GI1_Norwalk (SEQ ID NO:100).

FIG. 36A shows the amino acid sequence of VP2_GI.3_Lil08 (SEQ ID NO:94). FIG. 36B shows the nucleic acid sequence of human codon optimized VP2_GI.3_Lil08 (SEQ ID NO:95).

FIG. 37A shows the amino acid sequence of VP2_GII.6_HS10 (SEQ ID NO:96). FIG. 37B shows the nucleic acid sequence of human codon optimized VP2_GII6_HS10 (SEQ ID NO:97).

FIG. 38A shows the cloning vector 1190 from left to right T-DNA (SEQ ID NO:162). FIG. 38B shows the construct 2724 from 2×355 promoter to NOS terminator (SEQ ID NO:163). FIG. 38C shows the cloning vector 3677 from left to right T-DNA (SEQ ID NO:164). FIG. 38D shows the construct 4133 from 2×355 promoter to NOS terminator (SEQ ID NO:165). FIG. 38E shows the construct 4135 from 2×355 promoter to NOS terminator (SEQ ID NO:166).

GII.17_A39V+R53I).

DETAILED DESCRIPTION

Figure 1A:
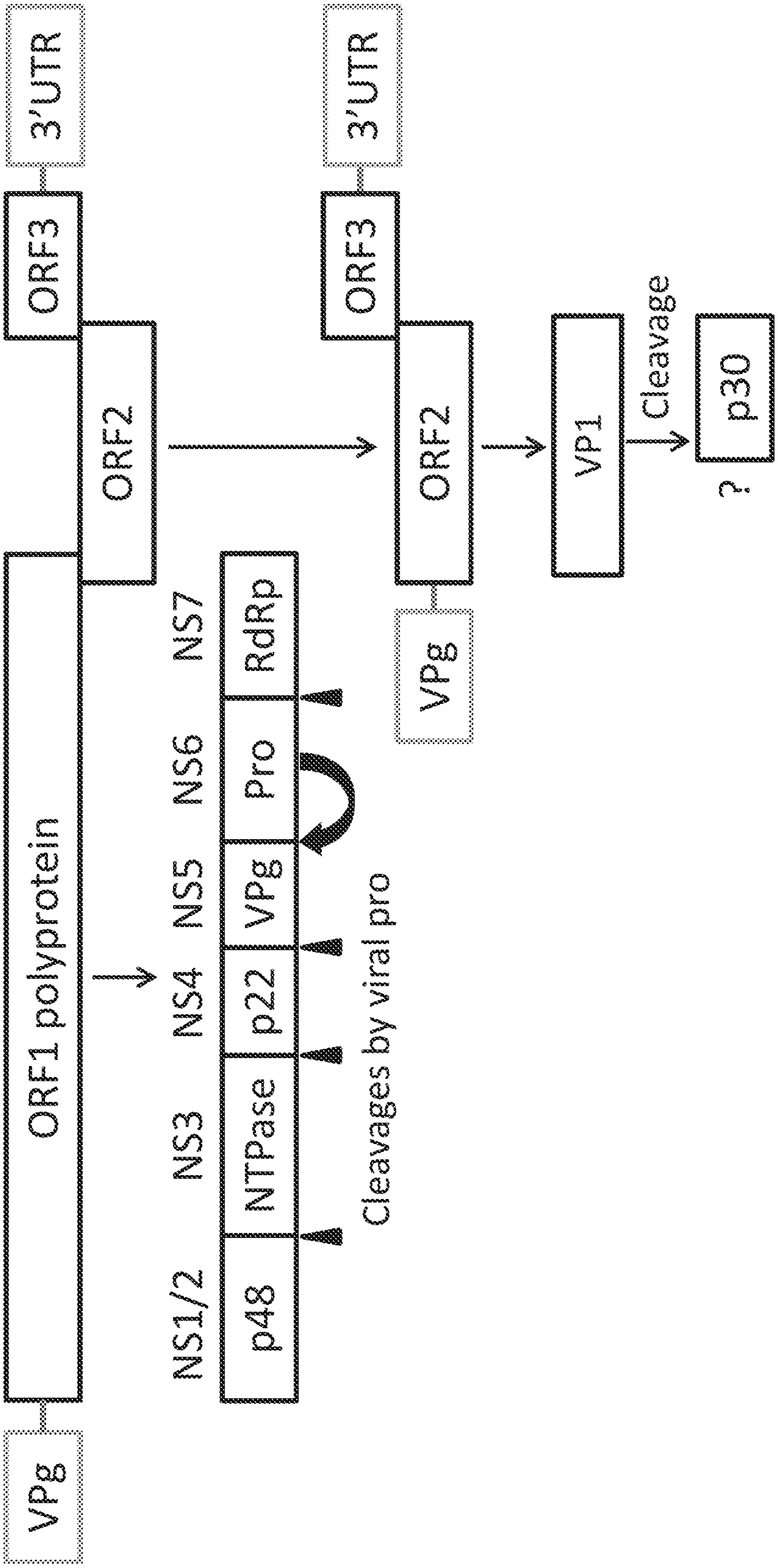
FIG. 1A shows a schematic representation of the linear structure of the norovirus genome and the polyprotein and proteins translated therefrom.

The following description is of a preferred embodiment.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments, consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The term "plant", "portion of a plant", "plant portion", "plant matter", "plant biomass", "plant material", plant extract", or "plant leaves", as used herein, may comprise an entire plant, tissue, cells, or any fraction thereof, intracellular plant components, extracellular plant components, liquid or solid extracts of plants, or a combination thereof, that are capable of providing the transcriptional, translational, and post-translational machinery for expression of one or more than one nucleic acids described herein, and/or from which an expressed protein or VLP may be extracted and purified. Plants may include, but are not limited to, agricultural crops including for example canola, *Brassica* spp., maize, *Nicotiana* spp., (tobacco) for example, *Nicotiana benthamiana, Nicotiana rustica, Nicotiana, tabacum, Nicotiana alata, Arabidopsis thaliana*, alfalfa, potato, sweet potato (*Ipomoea batatus*), ginseng, pea, oat, rice, soybean, wheat, barley, sunflower, cotton, corn, rye (*Secale cereale*), sorghum (*Sorghum bicolor, Sorghum vulgare*), safflower (*Carthamus tinctorius*).

The term "plant portion", as used herein, refers to any part of the plant including but not limited to leaves, stem, root, flowers, fruits, a plant cell obtained from leaves, stem, root, flowers, fruits, a plant extract obtained from leaves, stem, root, flowers, fruits, or a combination thereof. The term "plant extract", as used herein, refers to a plant-derived product that is obtained following treating a plant, a portion of a plant, a plant cell, or a combination thereof, physically (for example by freezing followed by extraction in a suitable buffer), mechanically (for example by grinding or homogenizing the plant or portion of the plant followed by extraction in a suitable buffer), enzymatically (for example using cell wall degrading enzymes), chemically (for example using one or more chelators or buffers), or a combination thereof. A plant extract may be further processed to remove undesired plant components for example cell wall debris. A plant extract may be obtained to assist in the recovery of one or more components from the plant, portion of the plant or plant cell, for example a protein (including protein complexes, protein surprastructures and/or VLPs), a nucleic acid, a lipid, a carbohydrate, or a combination thereof from the plant, portion of the plant, or plant cell. If the plant extract comprises proteins, then it may be referred to as a protein extract. A protein extract may be a crude plant extract, a partially purified plant or protein extract, or a purified product, that comprises one or more proteins, protein complexes, protein suprastructures, and/or VLPs, from the plant tissue. If desired a protein extract, or a plant extract, may be partially purified using techniques known to one of skill in the art, for example, the extract may be subjected to salt or pH precipitation, centrifugation, gradient density centrifugation, filtration, chromatography, for example, size exclusion chromatography, ion exchange chromatography, affinity chromatography, or a combination thereof. A protein extract may also be purified, using techniques that are known to one of skill in the art.

The term "nucleic acid segment" as used herein refers to a sequence of nucleic acids that encodes a protein of interest. In addition to the sequence of nucleic acids, the nucleic acid segment comprises a regulatory region and a terminator that are operatively linked to the sequence of nucleic acids. The regulatory region may for example comprise a promoter, and optionally, an enhancer element operatively linked to the promoter.

The term "nucleic acid complex" as used herein refers to a combination of two or more than two nucleic acid segments. The two or more than two nucleic acid segments may be present in a single nucleic acid, so that the nucleic acid complex comprises two, or more than two nucleic acid segments, with each nucleic acid segment under the control of a regulatory region and a terminator. Alternatively, the nucleic acid complex may comprise two or more separate nucleic acids, each of the nucleic acids comprising one or more than one nucleic acid segment, where each nucleic acid segment is under the control of a regulatory region and a terminator. For example a nucleic acid complex may comprise one nucleic acid that comprises two nucleic acid segments, a nucleic acid complex may comprise two nucleic acids, each nucleic acid comprising one nucleic acid segment, or a nucleic acid complex may comprise two or more than two nucleic acids, with each nucleic acid comprising one or more than one nucleic acid segment.

The term "vector" or "expression vector", as used herein, refers to a recombinant nucleic acid for transferring exogenous nucleic acid sequences into host cells (e.g. plant cells) and directing expression of the exogenous nucleic acid sequences in the host cells. "Expression cassette" refers to a nucleotide sequence comprising a nucleic acid of interest under the control of, and operably (or operatively) linked to, an appropriate promoter or other regulatory elements for transcription of the nucleic acid of interest in a host cell. As one of skill in the art would appreciate, the expression cassette may comprise a termination (terminator) sequence that is any sequence that is active in the plant host. For example the termination sequence may be derived from the RNA-2 genome segment of a bipartite RNA virus, e.g. a comovirus, the termination sequence may be a NOS terminator, or terminator sequence may be obtained from the 3'UTR of the alfalfa plastocyanin gene.

The constructs of the present disclosure may further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' untranslated regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1, 5-bisphosphate carboxylase gene (ssRUBISCO; U.S. Pat. No. 4,962,028; which is incorporated herein by reference), the promoter used in regulating plastocyanin expression.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a nucleotide sequence of interest, this may result in expression of the nucleotide sequence of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358). Examples, of potential inducible promoters include, but not limited to, tetracycline-inducible promoter (Gatz, C., 1997, Ann. Rev. Plant Physiol. Plant Mol. Biol. 48, 89-108), steroid inducible promoter (Aoyama, T. and Chua, N. H., 1997, Plant J. 2, 397-404) and ethanol-inducible promoter (Salter, M. G., et al, 1998, Plant Journal 16, 127-132; Caddick, M. X., et al, 1998, Nature Biotech. 16, 177-180) cytokinin inducible IB6 and CKI1 genes (Brandstatter, I. and Kieber, J. J., 1998, Plant Cell 10, 1009-1019; Kakimoto, T., 1996, Science 274, 982-985) and the auxin inducible element, DR5 (Ulmasov, T., et al., 1997, Plant Cell 9, 1963-1971).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812; which is incorporated herein by reference), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), the tobacco translational initiation factor 4A gene (Mandel et al, 1995 Plant Mol. Biol. 29: 995-1004); the Cassava Vein Mosaic Virus promoter, pCAS, (Verdaguer et al., 1996); the promoter of the small subunit of ribulose biphosphate carboxylase, pRbcS: (Outchkourov et al., 2003), the pUbi (for monocots and dicots).

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The expression constructs as described above may be present in a vector. The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

The term "native", "native protein" or "native domain", as used herein, refers to a protein or domain having a primary amino acid sequence identical to wildtype. Native proteins or domains may be encoded by nucleotide sequences having 100% sequence similarity to the wildtype sequence. A native amino acid sequence may also be encoded by a human codon (hCod) optimized nucleotide sequence or a nucleotide sequence comprising an increased GC content when compared to the wild type nucleotide sequence provided that the amino acid sequence encoded by the hCod-nucleotide sequence exhibits 100% sequence identity with the native amino acid sequence.

By a nucleotide sequence that is "human codon optimized" or a "hCod" nucleotide sequence, it is meant the selection of appropriate DNA nucleotides for the synthesis of an oligonucleotide sequence or fragment thereof that approaches the codon usage generally found within an oligonucleotide sequence of a human nucleotide sequence. By "increased GC content" it is meant the selection of appropriate DNA nucleotides for the synthesis of an oligonucleotide sequence or fragment thereof in order to approach codon usage that, when compared to the corresponding native oligonucleotide sequence, comprises an increase of GC content, for example, from about 1 to about 30%, or any amount therebetween, over the length of the coding portion of the oligonucleotide sequence. For example, from about 1, 2, 4, 6, 8, 10, 12, 14, 16, 18, 20, 22, 24, 26, 28, 30%, or any amount therebetween, over the length of the coding portion of the oligonucleotide sequence. As described below, a human codon optimized nucleotide sequence, or a nucleotide sequence comprising an increased GC content (when compared to the wild type nucleotide sequence) exhibits increased expression within a plant, portion of a plant, or a plant cell, when compared to expression of the non-human optimized (or lower GC content) nucleotide sequence.

Norovirus VP1 mutant proteins (also termed modified VP1 protein, or modified norovirus VP1 protein) and methods of producing norovirus VP1 mutant proteins in plants are described herein. Several of the modified norovirus VP1 proteins comprise specific substitutions, modifications or mutations in the S domain of non-GI.1 VP1s, to the corresponding amino acids that are found in GI.1 S domains. It has been observed that in certain norovirus genotypes, mutating specific amino acids to the corresponding amino acids found in GI.1 VP1s, results in similar or improved VP1 and/or VLP characteristics as compared to the wildtype (non-GI.1) VP1 and/or VLP. Examples of improved characteristics of the VP1 and/or VLP include:

- increased VP1 protein yield when expressed in plant cells as compared to the yield of wildtype VP1 of the same genotype that does not comprise the substitution(s), modification(s) or mutation(s);
- increased density of VLPs comprised of the modified VP1 proteins (for example as determined using density gradient separation, and optionally SDS-PAGE and/or Western analysis) as compared to the density of VLPs comprising wildtype VP1 of the same genotype that does not comprise the substitution(s), modification(s) or mutation(s);
- improved integrity, stability, or both integrity and stability, of VLPs that are comprised of the modified VP1 proteins as compared to the integrity, stability or both of VLPs comprising wildtype VP1 of the same genotype that does not comprise the substitution(s), modification(s) or mutation(s);
- increased VLP yield when expressed in plant cells as compared to the wildtype level of VLP production of the same genotype that does not comprise the substitution(s), modification(s) or mutation(s);
- improved accumulation of VLPs that are comprised of the modified VP1 proteins as compared to the accumulation of VLPs comprising wildtype VP1 of the same genotype that does not comprise the substitution(s), modification(s) or mutation(s);
- a greater proportion of VLPs that assemble into 38 nm VLPs as opposed to 23 nm VLPs as compared to the wildtype VP1 of the same genotype that does not comprise the substitution(s), modification(s) or mutation(s); and
- a combination thereof.

For example, the modified norovirus VP1 protein, and methods of producing the modified norovirus VP1 protein, may include a nucleotide sequence encoding a VP1 protein comprising an S domain substitution, mutation, or modification, at any one or more amino acids in sequence alignment with positions 43, 57, 84 and 94 of norovirus VP1 genotype GI.1 (SEQ ID NO:1; see FIG. 2C), or a deletion of a peptide fragment in sequence alignment with amino acids 39 to 46 of norovirus VP1 genotype GI.1 (SEQ ID NO:1), or a combination thereof. The sequence encoding the norovirus VP1 mutant protein may be optimized for human codon usage, for increased GC content, or a combination thereof.

Figure 2C:
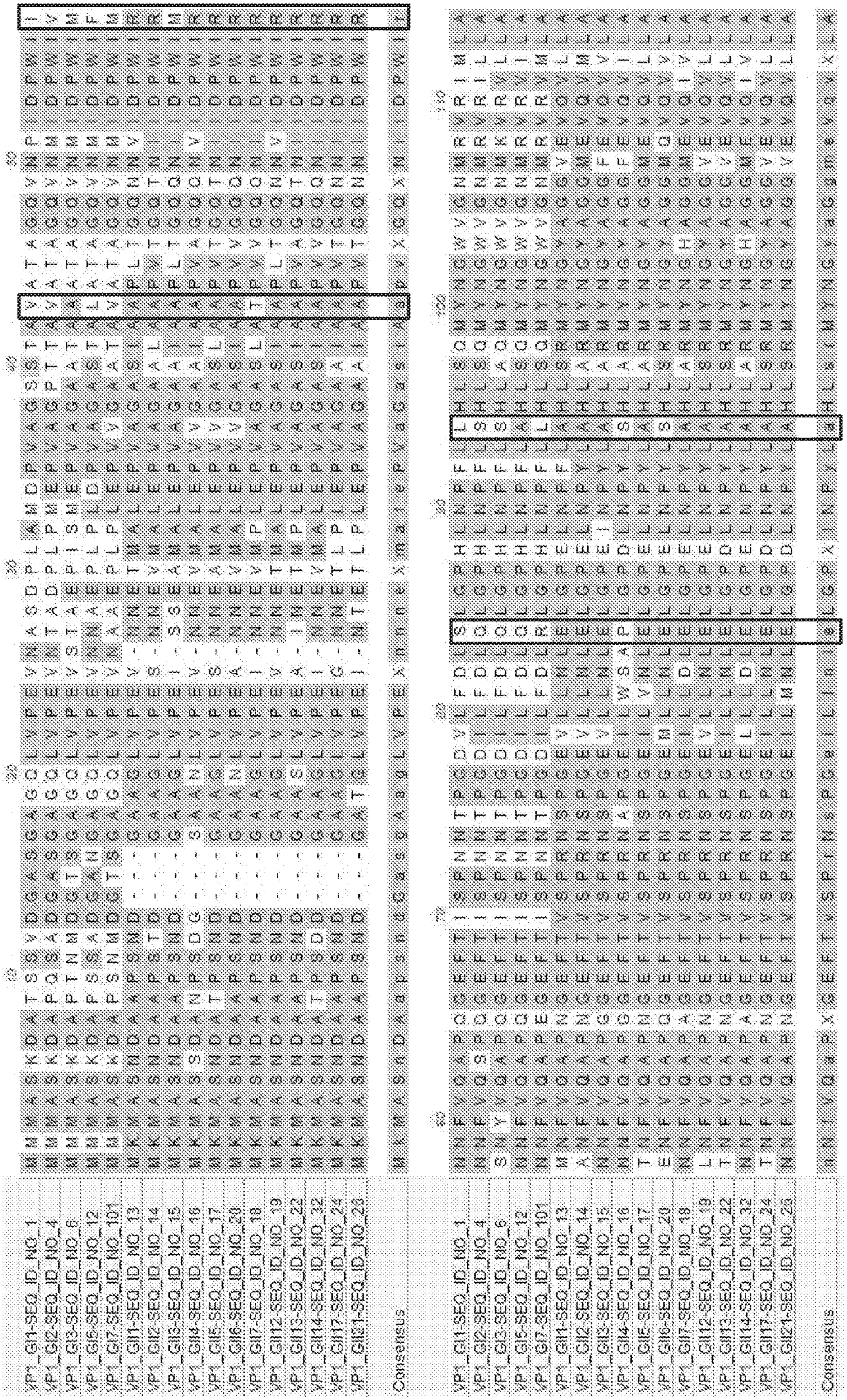
FIGS. 2C and 2D show an alignment of several S domains of norovirus VP1 proteins. The norovirus GI.1 sequence (SEQ ID NO:1) is used as a reference sequence to which the other norovirus VP1 sequences (GI.2, SEQ ID NO:4; GI.3, SEQ ID NO:6; GI.5, SEQ ID NO:12; GI.7 SEQ ID NO:101; GII.1. SEQ ID NO:13; GII.2. SEQ ID NO:14; GII.3, SEQ ID NO:15; GII.4, SEQ ID NO:16; GII.5, SEQ ID NO:17; GII.6, SEQ ID NO:20; GII.7, SEQ ID NO:18; GII.12, SEQ ID NO:19; GII.13, SEQ ID NO:22; GII.14, SEQ ID NO:32; GII.17, SEQ ID NO:24; and GII.21, SEQ ID NO:26) are aligned. The VP1 amino acid sequences for the "GII" family of VP1 proteins comprise a 3 amino acid deletion at amino acids 14-16, and a one amino acid deletion at position 26, this results in an alignment offset between the Gil VP1 sequences and the GI VP1 sequences by 4 amino acids.
Figure 2D:
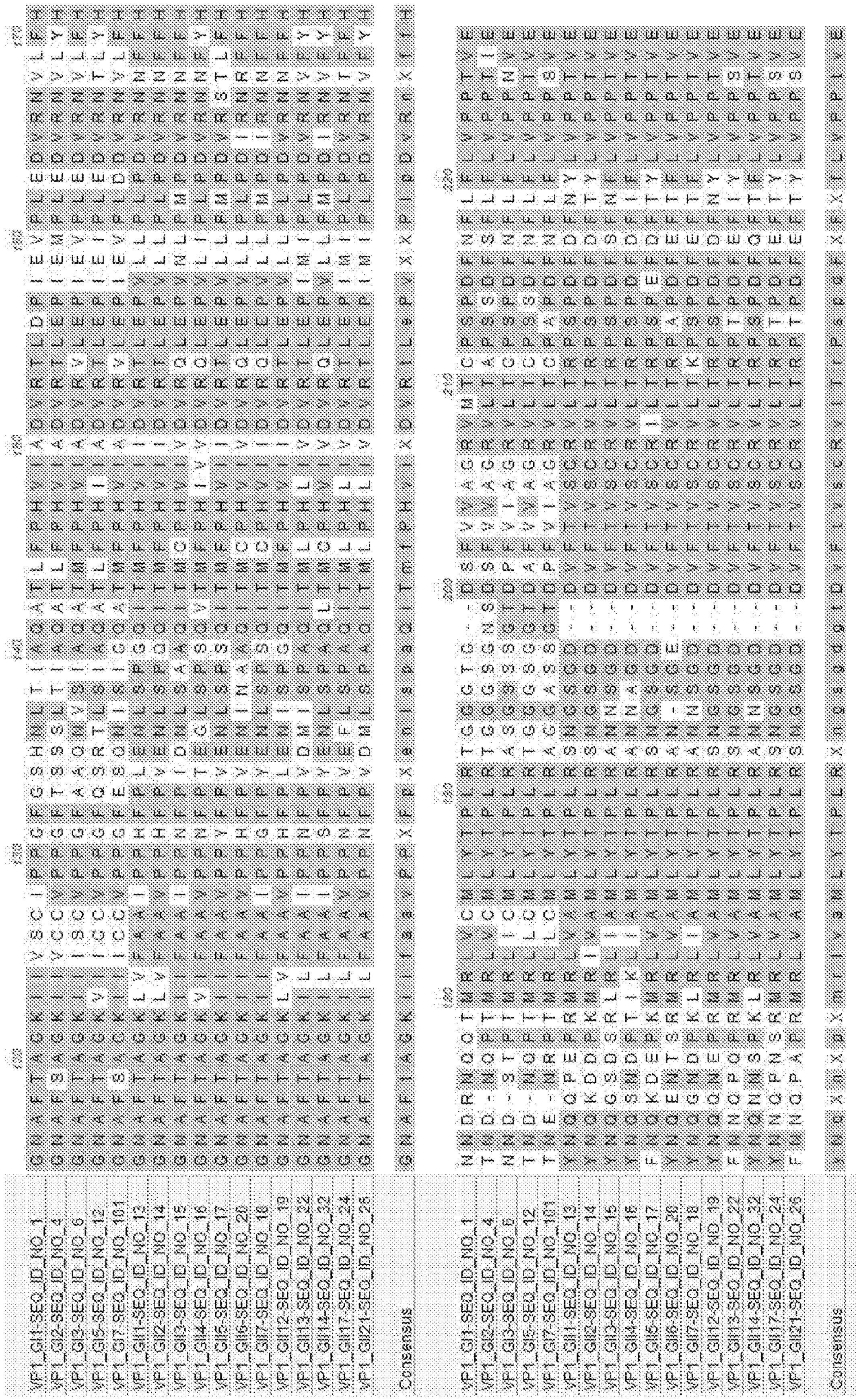

With reference to the sequences shown in FIG. 2C, the norovirus GI.1 sequence (SEQ ID NO:1) is used as a reference sequence against which the other norovirus VP1 sequences may be aligned. The VP1 amino acid sequences for the "GII" family of VP1 proteins comprise a 4 amino acid deletion relative to the GI.1 sequence, comprising a 3 amino acid deletion at positions 14-16, and a one amino acid deletion at position 26. As a result, the alignments between the GII VP1 sequences and the GI VP1 sequences are offset by 3 amino acids after amino acid 13, and 4 amino acids after position 26. For example, amino acid 84 of GI.1, aligns with amino acid 80 of GII.4 (see FIG. 2C). Reference to a substitution, modification or mutation at position 84 (GI.1) and 80 (GII.4) therefore refer to the same aligned amino acids:

| Strain | amino acid alignment | | | | |
|---|---|---|---|---|---|
| GI: | 39-46 | 43 | 57 | 84 | 94 |
| GII: | 35-42 | 39 | 53 | 80 | 90 |

Also provided herein are methods of increasing production of VLPs comprising modified norovirus VP1 proteins, in plants. For example, a method may involve introducing a nucleic acid encoding a norovirus VP1 mutant protein, as described herein, into the plant, portion of the plant, or plant cell. One or more than one norovirus mutant protein may be expressed in a plant, portion of the plant, or plant cell, in order to produce a VLP comprising one or more than one modified norovirus protein. Alternatively, the method may comprise providing a plant, portion of the plant, or plant cell that comprises the nucleic acid encoding the modified norovirus VP1 protein as described herein, and expressing the nucleic acid encoding the modified norovirus VP1 protein in order to produce a VLP comprising the one or more than one modified norovirus protein.

The methods of producing a VLP comprising a VP1 mutant protein may also comprise a step of co-expressing a nucleic acid sequence encoding a VP2 protein in the plant, portion of the plant, or plant cell.

The term "single construct" or "single constructs", as used herein, refers to nucleic acid vectors comprising a single nucleic acid sequence. The term "dual construct" or "dual constructs", as used herein, refers to a nucleic acid vector comprising two nucleic acid sequences.

By co-expression it is meant the introduction and expression of two or more nucleotide sequences, each of the two or more nucleotide sequences encoding a protein of interest, or a fragment of a protein of interest within a plant, portion of a plant or a plant cell. The two or more nucleotide sequences may be introduced into the plant, portion of the plant or the plant cell within one vector, so that each of the two or more nucleotide sequences is under the control of a separate regulatory region (e.g. comprising a dual construct). Alternatively, the two or more nucleotide sequences may be introduced into the plant, portion of the plant or the plant cell within separate vectors (e.g. comprising single constructs), and each vector comprising appropriate regulatory regions for the expression of the corresponding nucleic acid. For example, two nucleotide sequences, each on a separate vector and introduced into separate *Agrobacterium tumefaciens* hosts, may be co-expressed by mixing suspensions of each *A. tumefaciens* host in a desired volume (for example, an equal volume, or the ratios of each *A. tumefaciens* host may be altered) before vacuum infiltration. In this manner, co-infiltration of multiple *A. tumefaciens* suspensions permits co-expression of multiple transgenes.

The nucleic acid comprising encoding a norovirus VP1 mutant protein as described herein may further comprise sequences that enhance expression of the norovirus VP1 mutant protein in the plant, portion of the plant, or plant cell. Sequences that enhance expression may include, a CPMV enhancer element, or a plant-derived expression enhancer, in operative association with the nucleic acid encoding the norovirus VP1 mutant protein. The sequence encoding the VP1 mutant protein may also be optimized for human codon usage, increased GC content, or a combination thereof. Furthermore, a nucleic acid encoding VP2 may be co-expressed along with the sequence encoding the VP1 mutant protein. The co-expression of a nucleic acid encoding VP2 may lead to an increased yield, increased density, increased integrity, or combination thereof, of VLPs that comprise the one or more than one type of VP1 mutant protein.

The term "CPMV enhancer element", as used herein, refers to a nucleotide sequence encoding the 5'UTR regulating the Cowpea Mosaic Virus (CPMV) RNA2 polypeptide or a modified CPMV sequence as is known in the art. For example, a CPMV enhancer element or a CPMV expression enhancer, includes a nucleotide sequence as described in WO2015/14367; WO2015/103704; WO2007/135480; WO2009/087391; Sainsbury F., and Lomonossoff G. P., (2008, Plant Physiol. 148: pp. 1212-1218), each of which is incorporated herein by reference. A CPMV enhancer sequence can enhance expression of a downstream heterologous open reading frame (ORF) to which they are attached. The CPMV expression enhancer may include CPMV HT, CPMVX (where X=160, 155, 150, 114), for example CPMV 160, CPMVX+ (where X=160, 155, 150, 114), for example CPMV 160+, CPMV-HT+, CPMV HT+ [WT115], or CPMV HT+ [511] (WO2015/143567; WO2015/103704 which are incorporated herein by reference). The CPMV expression enhancer may be used within a plant expression system comprising a regulatory region that is operatively linked with the CPMV expression enhancer sequence and a nucleotide sequence of interest. The term "5'UTR" or "5' untranslated region" or "5' leader sequence" refers to regions of an mRNA that are not translated. The 5'UTR typically begins at the transcription start site and ends just before the translation initiation site or start codon of the coding region. The 5' UTR may modulate the stability and/or translation of an mRNA transcript.

The term "plant-derived expression enhancer", as used herein, refers to a nucleotide sequence obtained from a plant, the nucleotide sequence encoding a 5'UTR. Examples of a plant derived expression enhancer are described in U.S. Provisional Patent Application No. 62/643,053 (Filed Mar. 14, 2018; which is incorporated herein by reference) or in Diamos A. G. et. al. (2016, Front Plt Sci. 7:1-15; which is incorporated herein by reference). The plant-derived expression enhancer may be selected from nbMT78, nbATL75, nbDJ46, nbCHP79, nbEN42, atHSP69, atGRP62, atPK65, atRP46, nb30S72, nbGT61, nbPV55, nbPPI43, nbPM64 (SEQ ID NO:14), and nbH2A86 as described in U.S. 62/643,053). The plant derived expression enhancer may be used within a plant expression system comprising a regulatory region that is operatively linked with the plant-derived expression enhancer sequence and a nucleotide sequence of interest.

The term "5'UTR" or "5' untranslated region" or "5' leader sequence" refers to regions of an mRNA that are not translated. The 5'UTR typically begins at the transcription start site and ends just before the translation initiation site or start codon of the coding region. The 5' UTR may modulate the stability and/or translation of an mRNA transcript.

By "operatively linked" it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

When one or more than one type of the modified norovirus VP1 protein is expressed in the plant, portion of the plant or the plant cell, the one or more than one modified VP1 proteins auto-assemble into VLPs. The plant or portion of the plant may be harvested under suitable extraction and purification conditions to maintain the integrity of the VLP, and the VLP comprising the one or more than one type of VP1 mutant (modified) protein may be purified. The one or more than one VP1 mutant protein may also be co-expressed with nucleotide sequence encoding VP2, so that the VLP may comprise both modified VP1 protein and VP2 protein. The present disclosure also provides for the production of one or more than one type of VP1 mutant protein as described herein within a plant, portion of a plant, or plant cell, and the extraction and purification of the one or more than one type of VP1 mutant protein from the plant, the portion of the plant, or the plant cell to produce plant matter, a plant extract, or a protein extract, comprising the modified (mutant) VP1 protein.

Plant matter, a plant extract, or a protein extract comprising the norovirus VP1 mutant protein as described herein is also provided. The plant matter, plant extract, or protein extract may be used to induce immunity to norovirus infection in a subject. Alternatively, the VP1 mutant protein, or the VLP comprising the VP1 mutant protein (and optionally VP2), may be purified or partially purified, and the purified or partially purified preparation may be used to induce immunity to a norovirus infection in a subject.

The present disclosure also provides a composition comprising an effective dose of one or more than one type of modified norovirus VP1 protein, or VLPs comprising one or more than one modified norovirus VP1 protein, and optionally VP2, for inducing an immune response, and a pharmaceutically acceptable carrier, adjuvant, vehicle, or excipient.

Also provided herein are methods of inducing immunity to a norovirus infection in a subject comprising of administering one or more than one type of mutant (modified) norovirus VP1 protein or VLPs comprising one or more than one types of norovirus VP1 mutant proteins to a subject orally, intranasally, intramuscularly, intraperitoneally, intravenously, subcutaneously, rectally, or intravaginally.

The term "norovirus", as used herein, refers to a non-enveloped viral strain of the genus norovirus of the family Caliciviridae that is characterized as having a single-stranded, positive-sense RNA. The norovirus genome is 7,654 nucleotides in length. The ORF1 encodes a nonstructural polyprotein that is cleaved by viral 3C-like protease into 6 proteins, including an RNA-dependent RNA polymerase. ORF2 and ORF3 encode a major (VP1) and a minor (VP2) capsid protein, respectively (see FIG. 1A).

Norovirus strains as disclosed herein include any known norovirus strain, but also modifications to known norovirus strains that are known to develop on a regular basis over time. For example, norovirus strains may include (as described by their amino acids sequences), but are not limited to Hu/GI.1/United States/Norwalk/1968 (GI.1; SEQ ID NO:1; FIG. 12A), Hu/GI.2/Leuven/2003/BEL (GI.2; SEQ ID NO:4; FIG. 13A), Hu/GI.3/S29/2008/Lilla Edet/Sweden (GI.3; SEQ ID NO:6; FIG. 14A), Hu/GI.5/Siklos/Hun5407/2013/HUN (GI.5; SEQ ID NO:12; FIG. 15A), Hu/GI.7/USA/2014/GA5043 (GI.7; SEQ ID NO:101; FIG. 16A), Hu/GII.1/Ascension208/2010/USA (GII.1; SEQ ID NO:13; FIG. 16B), Hu/GII.2/CGMH47/2011/TW (GII.2; SEQ ID NO: 14; FIG. 17A), Hu/GII.3/Jingzhou/2013402/CHN (GII.3; SEQ ID NO: 15; FIG. 18A), Hu/GII.4/Sydney/NSW0514/2012/AU (GII.4; SEQ ID NO: 16; FIG. 19A), US96/GII.4/Dresden174/1997/DE_AY741811 (SEQ ID NO: 27; FIG. 19C), FH02/GII.4/FarmingtonHills/2002/US_AY502023 (SEQ ID NO: 28; FIG. 19D), Hnt04: GII.4/Hunter-NSW504D/2004/AU_DQ078814 (SEQ ID NO: 29; FIG. 19E), 2006b: GII.14/Shellharbour-NSW696T/2006/AU_EF684915 (SEQ ID NO: 30; FIG. 19F), NO09: GII.4/Orange-NSW001P/2008/AU_GQ845367 (SEQ ID NO: 31; FIG. 19G), Hu/GII.5/AlbertaEI390/2013/CA (GII.5; SEQ ID No:17; FIG. 20), Hu/GII.6/Ohio/490/2012/USA (GII.6; SEQ ID NO: 20; FIG. 21A), GII.7/Musa/2010/A1173774 (GII.7; SEQ ID NO:18; FIG. 22), Hu/GII.12/HS206/2010/USA (GII.2; SEQ ID NO: 19; FIG. 23A), GII.13/VA173/2010/H9AWU4 (GII.13; SEQ ID NO:22; FIG. 24A), GII.14_Saga_2008_JPN_ADE28701 native VP1 (GII.14; SEQ ID NO: 32; FIG. 25), Hu/GII.17/Kawasaki323/2014/JP (0117; SEQ ID NO: 24; FIG. 26A), and Hu/GII.21/Salisbury150/2011/USA (0121; SEQ ID NO:26; FIG. 27). Norovirus strains are known to readily mutate from year-to-year. Therefore, Norovirus strains also include strains having from about 30-100% or any amount therebetween, amino acid sequence identity, to the VP1 protein, the VP2 protein, or both the VP1 and the VP2 proteins, with any of the above norovirus strains of the strains listed above and in FIGS. 2A and 2B, provided that the VP1 protein can be expressed (i.e. produced) in a plant and that the VP1 protein induces immunity to norovirus in a subject, when the VP1 protein is administered to the subject. For example, norovirus strains also include strains having 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100%, or any amount therebetween, amino acid sequence identity (sequence similarity; percent identity; percent similarity) to the VP1 protein, the VP2 protein, or both the VP1 and the VP2 proteins, with any of the above norovirus strains of the strains listed above and in FIGS. 2A and 2B, provided that the that the VP1 protein can be expressed in a plant and that the VP1 protein induces immunity to norovirus in a subject, when the VP1 protein is administered to the subject. An amino acid sequence identity comparison between the S domain of VP1 proteins of several norovirus strains, which are not to be considered limiting, is shown in FIG. 2C.

The terms "percent similarity", "sequence similarity", "percent identity", or "sequence identity", when referring to a particular sequence, are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Natl. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example the BLASTN program (for nucleotide sequences) may use as defaults a wordlength (W) of 11, an expectation (E) of 10, M=5, N=−4 and a comparison of both strands. For amino acid sequences, the BLASTP program may use as defaults a word length of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

The term "VP1", as used herein, refers to the norovirus major capsid protein or polypeptide comprising an amino acid sequence similar to the protein or polypeptide encoded by ORF2 of one or more strains of norovirus as described herein. The major capsid protein folds into two principal domains, a shell (S) domain and a protruding (P) domain (see FIG. 1B). The VP1 protein forms a dimer (FIG. 1C) when incorporated into a virus like particle, or a VLP. The first portion of the N-terminal of VP1 comprise the S domain, with the remainder of the VP1 polypeptide comprising the P domain. For example, in GI.1, the first 225 amino acids of the N-terminal VP1 protein comprise the S domain. When folded, the VP1 assumes a conformation as depicted in FIG. 1B, comprising of a globular S domain (bottom of ribbon structure) and a P domain (top of ribbon structure).

Figure 1C:
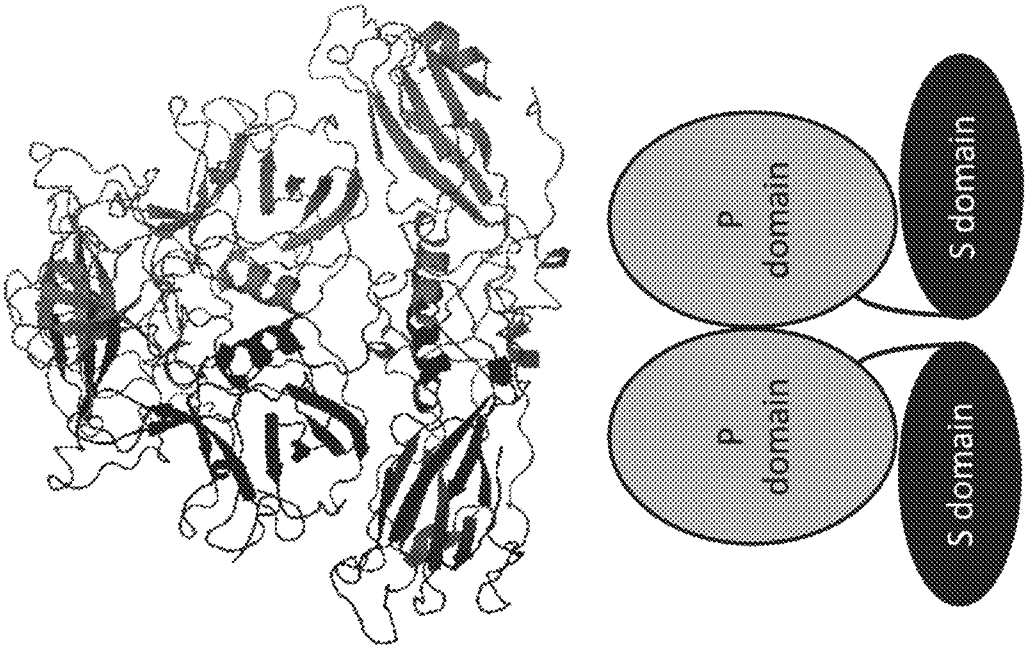
FIG. 1C shows a ribbon diagram representation of the 3-dimensional structure of a norovirus VP1 protein dimer comprising of two S domains (S), two P1 subdomains (P1), and two P2 subdomains (P2).
Figure 1B:
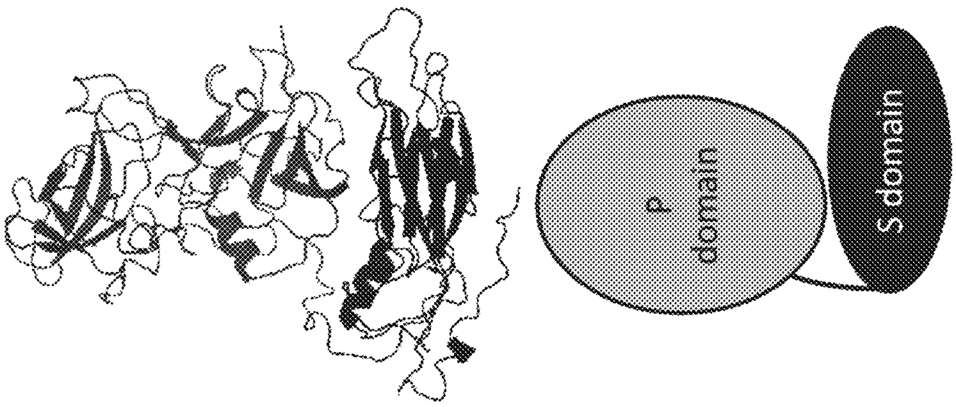
FIG. 1B shows a ribbon diagram representation of the 3-dimensional structure of the norovirus VP1 protein comprising a shell (S) domain, a P1 subdomain (P1), and a P2 subdomain (P2).

As shown in FIG. 1C, the VP1 protein dimerizes via P-domain interactions. These interactions stabilize the spontaneous assembly of norovirus capsid molecules.

Methods to produce norovirus VP1 proteins and modified norovirus VP1 proteins in a plant, portion of a plant or a plant cell are described herein that involve introducing the recombinant polynucleotide encoding the norovirus VP1 protein or modified VP1 protein, and incubating the plant, portion of the plant or the plant cell under conditions that permit expression of the norovirus VP1 protein or modified norovirus protein. However, it is also to be understood that norovirus VP1 proteins may be obtained from norovirus VLPs that comprise the VP1 protein, as described in Ausar et al. (Ausar S. F., Foubert T. R, Hudson M. H., Vedvick T. S., Middaugh C. R., 2006, J. Biol. Chem. 281:19478-19488). For example norovirus VLPs comprising norovirus proteins or modified norovirus proteins may dissociate at pH 8 and above, or at temperatures above 55° C., into their VP1 protein constituents, thereby yielding VP1 protein.

The term "virus like particle", "VLP", "virus like particles", or "VLPs", as used herein, refers to a norovirus virus like particle(s) that comprise one or more than one type of norovirus VP1 protein, one or more than one type of VP1 mutant protein, or a combination thereof, and that self-assemble into non-replicating, non-enveloped, non-infectious viral capsid structures lacking all parts of the norovirus genome. For example, the VLP may comprise one type of a modified VP1 protein as described herein, or the VLP may comprise two or more different modified VP1 proteins described herein. Furthermore the VLP may comprise a VP2 protein. VLPs comprising VP1 protein, VP1+VP2 protein, modified VP1 protein, or modified VP1 protein+VP2 protein are of the size from about 15 nm to 50 nm or any amount therebetween, for example 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nm, or any amount therebetween. For example, for T=1 icosahedral symmetry, VLPs may be about 23 nm, or for T=3 icosahedral symmetry, VLPs may be from about 38 to about 40 nm.

As shown in the electron micrographs of FIGS. 3B, 4B, 5C, 5E, 6C, 6E, 7C, 8B, 9B, 9C, 9D, 9G, 10B, 11C and 11D, plant produced VP1 proteins and modified VP1 proteins derived from several norovirus strains self-assemble into VLPs.

Norovirus VP1 Protein Production in Plants

The VP1 protein includes any VP1 protein comprising an amino acid sequence having from about 30 to about 100%, from about 40 to about 100%, from about 50 to about 100%, from about 60 to about 100%, from about 70 to about 100%, from about 80 to about 100%, from about 85 to about 100% from about 90 to about 100%, or from about 95 to about 100% from about 98 to about 100%, or any amount therebetween, sequence identity (which may be also termed sequence similarity) with a VP1 amino acid sequence from a norovirus GI.1 (SEQ ID NO:1; FIG. 12A), GI.2 (SEQ ID NO:4; FIG. 13A), GI.3 (SEQ ID NO:6; FIG. 14A), GI.5 (SEQ ID NO:12; FIG. 15A), Hu/GI.7/USA/2014/GA5043 (GI.7; SEQ ID NO:101; FIG. 16A), GII.1 (SEQ ID NO:13; FIG. 16B), GII.2 (SEQ ID NO:14; FIG. 17A), GII.3 (SEQ ID NO:15; FIG. 18A), GII.4/Sydney (SEQ ID NO:16; FIG. 19A), GII.14/Dresden (SEQ ID NO:27; FIG. 19C), GII.14/FarmingtonHills (SEQ ID NO:28; FIG. 19D), GII.4/Hunter (SEQ ID NO:29; FIG. 19E), GII.14/Shellharbour (SEQ ID NO:30; FIG. 19F), GII.14/Orange (SEQ ID NO:31; FIG. 19G), GII.5 (SEQ ID No:17; FIG. 20), GII.6 (SEQ ID NO:20; FIG. 21A), GII.7 (SEQ ID NO:18; FIG. 22), GII.12 (SEQ ID NO:19; FIG. 23A), GII.13 (SEQ ID NO:22; FIG. 24A), GII.14/Saga (SEQ ID NO:32; FIG. 25), GII.17 (SEQ ID NO:24; FIG. 26A), GII.21 (SEQ ID NO:26; FIG. 27), provided that the VP1 protein is expressed in a plant and it induces immunity to norovirus when administered to a subject.

The VP1 protein as described herein is modified and comprises an S domain substitution, modification or mutation, at any one or more amino acids in sequence alignment with positions 43, 57, 84 and 94 of norovirus VP1 genotype GI.1 (SEQ ID NO:1; see FIG. 2C), or a deletion of a peptide fragment in sequence alignment with amino acids 39 to 46 of norovirus VP1 genotype GI.1 (SEQ ID NO:1), or a combination thereof. The nucleotide sequence encoding the modified norovirus VP1 protein may be optimized for human codon usage, for increased GC content, or a combination thereof. The modified VP1 protein may be expressed in a plant, portion of a plant, or plant cell.

As shown in FIG. 2C, relative to the hypervariable P domain, the primary amino acid sequence of the norovirus VP1 S domain is well conserved. For example, the VP1 S domain sequences of the norovirus strains shown in FIG. 2C, have sequences ranging from 55.2-98.9% identity to the S domain of GI.1 VP1. For example, nucleic acid sequences described herein may exhibit from about 55 to about 99%, or any amount therebetween sequence identity to the S domain of GI.1 VP1, For example, nucleic acid sequences described herein may exhibit from about 55, 56, 58, 60, 62, 64, 66, 68, 70, 72, 74, 76, 78, 80, 82, 84, 86, 88, 90, 91, 92, 93, 94, 95, 96, 97, 98, 99% or any amount therebetween, sequence identity to the S domain of GI.1 VP1.

As previously shown in U.S. provisional application 62/475,660 (filed Mar. 23, 2017; which is incorporated herein by reference) and PCT/CA2018/050352 (filed Mar. 23, 2018, which is incorporated herein by reference), wild type (also termed native) norovirus VP1 protein may be produced in plants and VLPs comprising the VP1 protein produced. Vacuum infiltration of leaves (from *N. benthamiana*) with *Agrobacterium tumefaciens* comprising expression vectors encoding GI.1 VP1 as a single nucleic acid construct, GI.1 VP2 as a single nucleic acid construct, both GI.1 VP1 and VP2, with VP1 and VP2 nucleic acid sequences introduced in separate vectors ("VP1+VP2"; dual constructs), or on the same vector ("VP1/VP2" or "VP1/VP2/3'UTR"; single nucleic acid constructs) to permit co-expression of the VP1 and/or VP2 sequences and the leaves examined for VP1 and VP2 production. After 6 or 9 days post infiltration (6 DPI and 9 DPI, respectively), total crude protein extracts were prepared from leaf homogenates, separated by SDS-PAGE, and stained with Coomassie Brilliant Blue dye. Leaves infiltrated with expression vectors comprising nucleotide sequences that correspond to wildtype GI.1 ORF2, encoding the VP1 protein, produced low or non-detectable levels of GI.1 VP1 as determined using Coomassie stained gels. In contrast, leaves infiltrated with expression vectors comprising GI.1 VP1 nucleotide sequences that were codon optimized for human expression (hCod), or enriched for GC content when compared to the GC content of the wildtype VP1 nucleic acid sequence, produced increased amounts of GI.1 VP1 protein in Coomassie stained gels. Demonstrating that hCod GI.1 VP1 may be produced in plants when VP1 is expressed on its own.

Furthermore, as described in U.S. provisional application 62/475,660 and PCT/CA2018/050352 (filed Mar. 23, 2017; and Mar. 23, 2018, respectively, both of which are incorporated herein by reference), leaves infiltrated with vectors comprising either wildtype GI.1 VP1 and VP2 or human codon optimized GI.1 VP1 and VP2 produced low levels of GI.1 VP1 protein in Coomassie stained gels, suggesting that expression of VP1 is not enhanced by the presence of VP2 when co-expressed in cis on the same vector, using the same organization as found in the viral genome (using one promoter to control expression). However, when VP1 or human codon optimized VP1 was co-expressed in trans (on a separate construct) along with VP2 or hCod VP2 (hCod VP1+VP2), respectively, an increase in VP1 protein was observed. Each of the VP1 and VP2 nucleic acid segments comprised a regulatory region and a terminator, and the constructs were introduced into the plants as a nucleic acid complex, and this resulted in a corresponding increase in VP1 protein yield.

This observation is in contrast to that observed in insect and mammalian cells (Bertolotti-Ciarlet A., Crawford S. E., Hutson A. M., Estes M. K. 2003, J. Virol. 77:11603-11615), who reported that an increase in VP1 expression was only observed when VP1 and VP2 (or VP1+VP2+3'UTR) resided in cis, and were co-expressed using the same organization as that found in the viral genome, under the control of one promoter and terminator. No increase in VP1 expression was observed by Bertolotti-Ciarlet (2003) in insect or mammalian cells, when VP1 and VP2 were co-expressed in trans.

As described in more detail below, when the modified VP1 proteins, as described herein, are expressed in plants, it is preferred that the ORF3 sequence encoding VP2 is obtained from the same norovirus genotype and strain as that used to obtain the modified VP1 sequence. In the examples provided herein, and unless otherwise stated, the modified VP1 protein and the VP2 protein are obtained from the same norovirus genotype and strain, and the nucleotide sequences encoding the modified VP1 protein and the VP2 protein are co-expressed in the plant using separate expression systems, for example, on separate plasmids, or VP1 and VP2 may be expressed on the same vector but each of the sequences encoding VP1 and VP2 should be under the control of separate promoter and terminator sequences, so that they have a separate expression system.

Figure 3A:
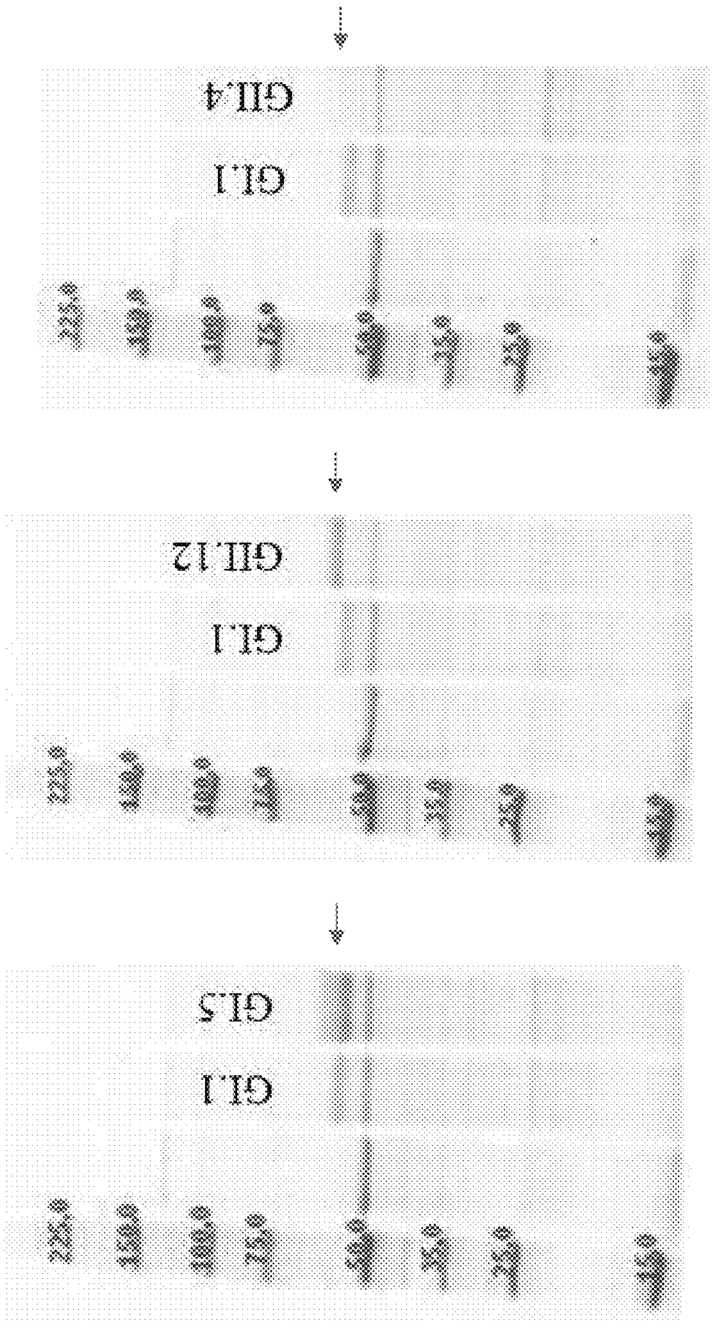
FIG. 3A shows a Coomassie-stained SDS-PAGE of crude protein extracts prepared from agroinfiltrated *Nicotiana benthamiana* leaves, 9 days post infiltration (DPI) with left panel: wild type (wt) human codon-optimized (hCod) GI.1/United States/Norwalk/1968 VP1 (Construct #: 2724; SEQ ID NO:3 (nucleotide); SEQ ID NO: 1 (amino acid)) and hCod GI.5 VP1 (Construct #: 3980; SEQ ID NO:33 (nucleotide); SEQ ID NO:12 (amino acid); center panel: wild type GI.1 and wt hCod GII.12/United States/HS206/2010 VP1 (Construct #: 3995; SEQ ID NO:87 (nucleotide); SEQ ID NO:19 (amino acid)); and right panel: wild type GI.1 and wt hCod GII.4/Sydney/NSW0514/2012 VP1 (Construct #: 3760; SEQ ID NO:52 (nucleotide); SEQ ID NO:16 (amino acid)). Arrow: VP1 norovirus protein. First lane in each of the panels crude protein extracts prepared from mock infiltrated *N. benthamiana* leaves.
Figure 3B:
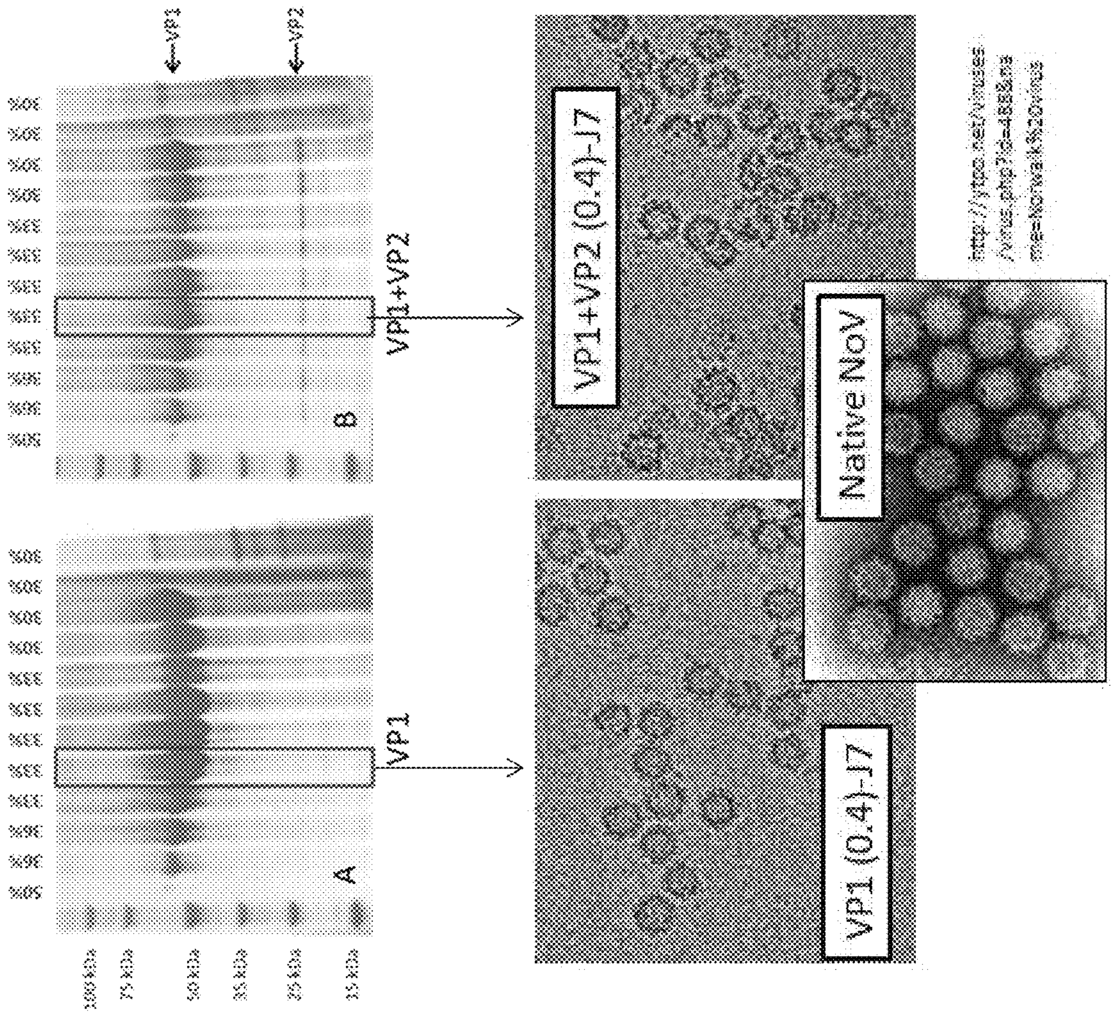
FIG. 3B upper panel shows norovirus protein expression and VLP assembly using Coomassie-stained SDS-PAGE analysis of fractions from an iodixanol density gradient separation of crude protein extracts prepared from *N. benthamiana* leaves expressing wt hCod VP1 GI.1/United States/Norwalk/1968 VP1 (construct #2724), or wt hCod VP1 (construct #2724) and co-expressed with wt hCod VP2 (construct #2725). Lower panel shows electron micrographs of norovirus VLPs purified from 33% iodixanol gradient fractions of VP1 or co-expression of VP1 and VP2 proteins. An electron micrograph of native norovirus VLP is shown for comparison.
Figure 3C:
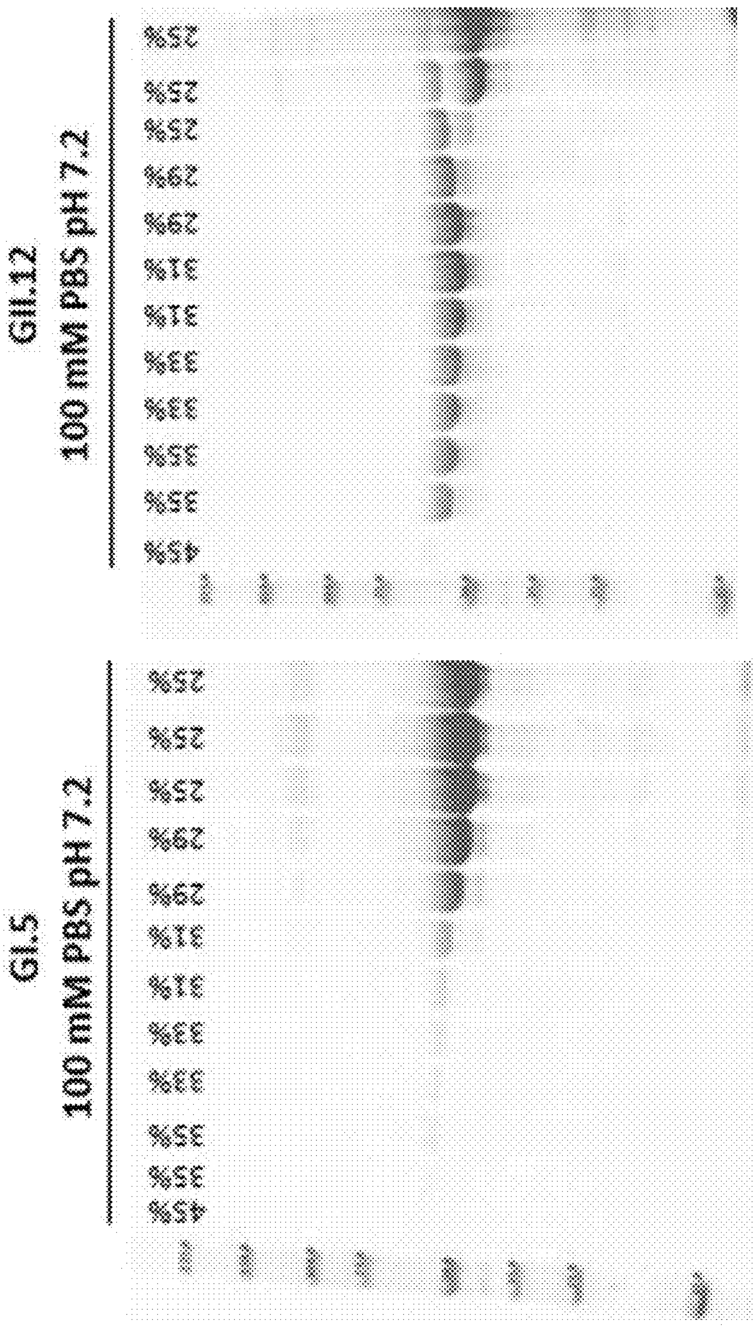
FIG. 3C shows a Coomassie-stained SDS-PAGE analysis of iodixanol density gradient fractions of crude protein extracts prepared from *N. benthamiana* leaves expressing left panel: wt hCod GI.5/Hungary/Siklos/HUN5407/2013 VP1 (Construct #: 3980; SEQ ID NO:33 (nucleotide); SEQ ID NO: 12 (amino acid)); right panel: GII.12/United States/HS206/2010 VP1 (Construct #: 3995; SEQ ID NO:87 (nucleotide); SEQ ID NO: 19 (amino acid).
Figure 4A:
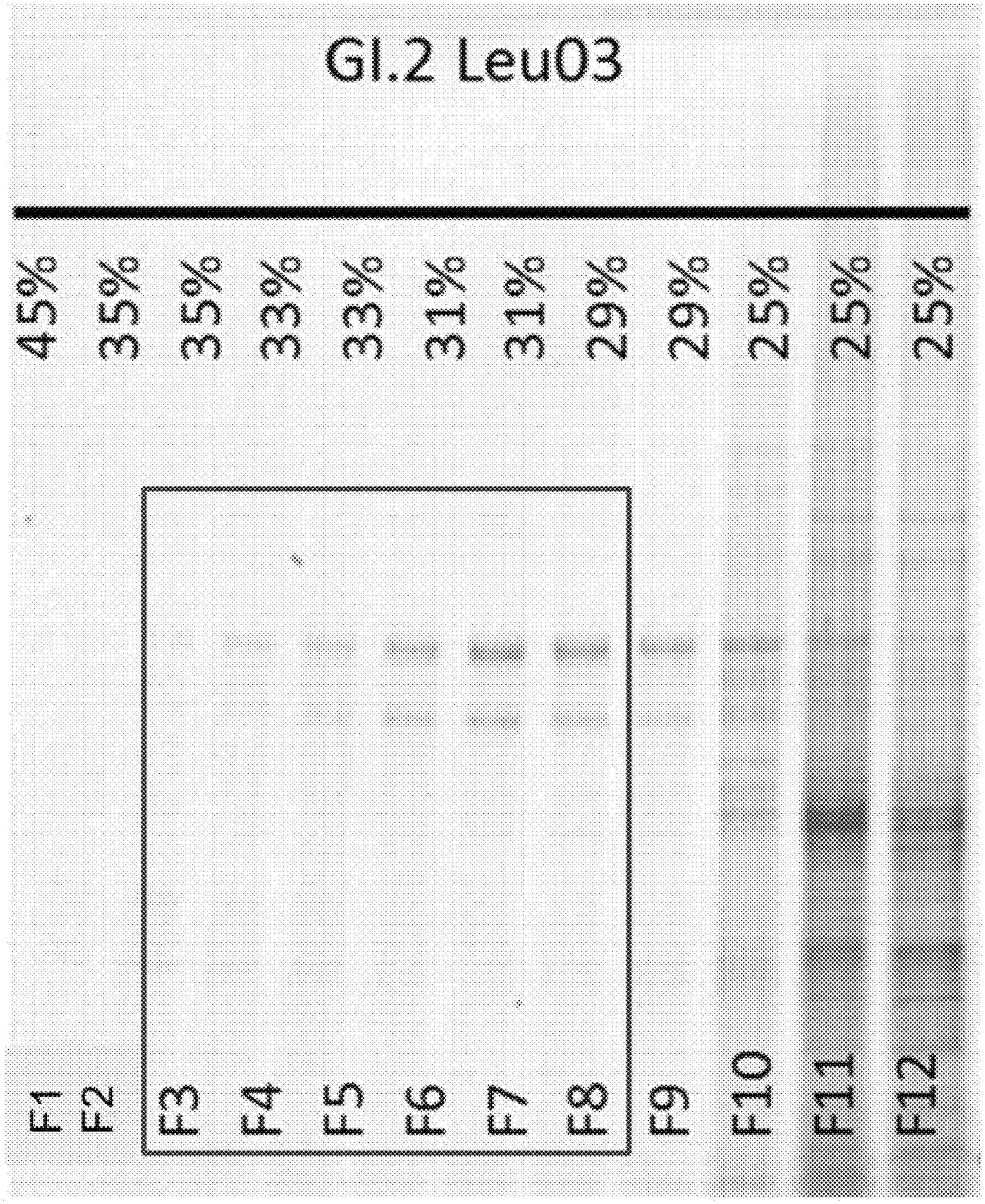
FIG. 4A shows a Coomassie-stained SDS-PAGE analysis of iodixanol density gradient fractions of crude protein extracts prepared from *N. benthamiana* leaves expressing wt hCod GI.2 VP1 (Construct #: 3300; SEQ ID NO:5 (nucleotide); SEQ ID NO:4 (amino acid)).
Figure 4B:
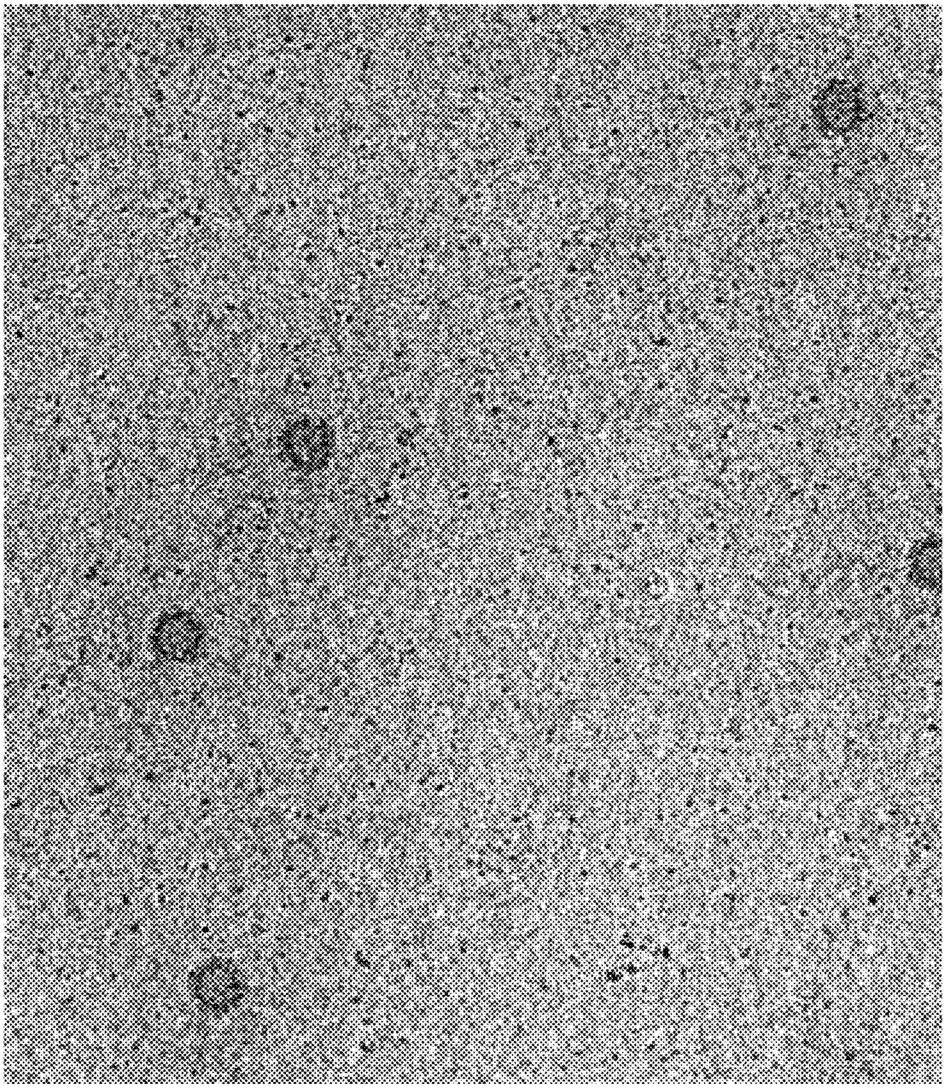
FIG. 4B shows electron micrographs of norovirus VLPs purified from 29-35% iodixanol gradient fractions of VP1.

The yield, or amount of extracted, norovirus VP1 protein and the production of VLPs comprising norovirus VP1 proteins in a plant, differs depending on the genotype of the norovirus VP1 being expressed. For example, as shown in FIG. 3A, the expression of wild type GI.1 VP1, GI.5 VP1, and GII.12 VP1 was robust with good protein yields (determined using SDS PAGE). Furthermore, high density wild type GI.1 VLPs, having well-formed capsids that are predominantly 38 nm in diameter were also produced (FIG. 3B), and high density VLPs were produced from plants expressing wild type GI.5 VLPs, GII.12 VLPs (FIG. 3C) and GI.2 VLPs, (FIG. 4A). In contrast, wild type GII.4 VP1 was poorly expressed in plants (FIG. 3A right hand panel), and low yields of VP1 protein, or non-detectable amounts of VP1 protein (using SDS-PAGE) were observed following expression other wild type VP1 proteins in plants, for example, GII.2 VP1, GII.3 VP1 and GII.6 VP1 (Table 5, Example 3).

Furthermore, expression of native VP1 proteins in plants may result in VLPs characterized as comprising a higher proportion of 23 nm VLPs rather than 38 nm VLPs. For example, expression of wild type GI.3 VP1 results in the production of a significant number of 23 nm VLPs (see FIG. 5C, left hand panel). A greater proportion of 23 nm VLPs also results in the VLPs characterized as being less dense following density gradient centrifugation (see FIG. 5B left hand panel).

The present disclosure provides nucleic acid sequences encoding modified norovirus VP1 proteins, wherein the modified norovirus VP1 comprises one or more than one substitution, modification or mutation at an amino acid selected from a group consisting of amino acids in sequence alignment with amino acids 43, 57, 84 and 94 of norovirus VP1 genotype GI.1 (SEQ ID NO:1) or a deletion of a peptide fragment in sequence alignment with amino acids 39 to 46 of norovirus genotype VP1 GI.1 (SEQ ID NO:1), or a combination thereof. Plant expressing nucleic acid sequences encoding the modified norovirus VP1 protein, and comprising one or more than one substitution, modification or mutation at an amino acid selected from a group consisting of amino acids in sequence alignment with amino acids 43, 57, 84 and 94 of norovirus VP1 genotype GI.1 or a deletion of a peptide fragment in sequence alignment with amino acids 39 to 46 of norovirus genotype VP1 GI.1, or a combination thereof, exhibit similar or improved VP1, and/or VLP characteristics as compared to the wildtype VP1 and/or VLP that does not comprise the one or more than one substitution, modification or mutation.

Examples of improved characteristics of the modified VP1 and/or VLP include,

- increased modified VP1 protein yield (determined for example using Coomassie stained SDS-PAGE and Western analysis) when expressed in plant cells as compared to the wildtype VP1 that does not comprise the one or more than one substitution, modification or mutation. For example, increased yields of modified VP1 protein may range from 1.5 to 50 fold, or any amount there between, over that of the corresponding wild type VP1 yield;

increased density of VLPs comprising the modified VP1 proteins, for example as determined using iodixanol density gradient separation of protein extracts as compared to density gradient separation of the wildtype VP1 that does not comprise the one or more than one substitution, modification or mutation. For example, VLPs comprising modified VP1 protein may be observed in the same or more dense fractions following density gradient centrifugation;

improved integrity of VLPs that are comprised of the modified VP1 proteins compared to the wildtype VP1 that does not comprise the one or more than one substitution, modification or mutation. For example, the number of disrupted, or partially assembled, VLPs may be determined using TEM;

increased VLP yield when expressed in plant cells as compared to the wildtype level of VLP production of the same genotype that does not comprise the substitution(s), modification(s) or mutation (s). VLP yield may be determined in washed samples obtained from VLP containing fractions following density gradient centrifugation using TEM. For example, increased yields of VLPs comprising modified VP1 protein may range from 1.5 to 20 fold, or any amount there between, over that of the corresponding yield of VLPs comprising wild type VP1 protein;

improved accumulation of VLPs that are comprised of the modified VP1 proteins as compared to the accumulation of VLPs comprising wildtype VP1 of the same genotype that does not comprise the substitution(s), modification(s) or mutation (s);

a greater proportion of VLPs that assemble into 38 nm VLPs as opposed to 23 nm VLPs, compared to VLPs comprising the wildtype VP1 that does not comprise the one or more than one substitution, modification or mutation (determined using TEM); and a combination of these improved characteristics.

Without wishing to be bound by theory, VLPs that are observed in higher density fractions following density gradient centrifugation, as compared to wildtype norovirus VLPs, indicates that the assembly of the VLPs comprising native VP1 may be less stable when expressed in, and extracted from, plants, than VLPs comprising the modified VP1 protein. The native VLP may therefore be more susceptible to malformed capsid particles and the generation of fragmentation products. As a result, the VLPs comprising modified VP1 protein that are characterized as having increased density may also exhibit greater structural integrity than VLPs produced using the corresponding wildtype VP1.

The nucleic acid sequences described herein may exhibit from about 50% to about 99% sequence similarity with any of the nucleic acid sequences encoding VP1 as identified above and as listed in FIGS. 2A-C, excluding GI. For example, nucleic acid sequences described herein may exhibit from about 50, 52, 54, 56, 58, 60, 62, 64, 66, 68, 70, 72, 74, 76, 78, 80, 82, 84, 86, 88, 90, 91, 92, 93, 94, 95, 96, 97, 98, 99% or any amount therebetween, sequence identity with any of the nucleic acid sequences encoding a norovirus VP1, for example from, Hu/GII.2/Leuven/2003/BEL (GI.2; SEQ ID NO:4; FIG. 12A), Hu/GI.3/S29/2008/Lilla Edet/Sweden (GI.3; SEQ ID NO:6; FIG. 14A), Hu/GI.5/Siklos/Hun5407/2013/HUN (GI.5; SEQ ID NO:12; FIG. 15A), Hu/GI.7/USA/2014/GA5043 (GI.7; SEQ ID NO:101; FIG. 16A), Hu/GII.1/Ascension208/2010/USA (GII.1; SEQ ID NO:13; FIG. 16B), Hu/GII.2/CGMH47/2011/TW (SEQ ID NO:14; FIG. 17A), Hu/GII.3/Jingzhou/2013402/CHN (GII.3; SEQ ID NO: 15; FIG. 18A), Hu/GII.4/Sydney/NSW0514/2012/AU (GII.4; SEQ ID NO: 16; FIG. 19A), US96/GII.4/Dresden174/1997/DE_AY741811 (SEQ ID NO: 27; FIG. 19C), FH02/GII.4/FarmingtonHills/2002/US_AY502023 (SEQ ID NO: 28; FIG. 19D), Hnt04: GII.4/Hunter-NSW504D/2004/AU_DQ078814 (SEQ ID NO: 29; FIG. 19E), 2006b: GII.4/Shellharbour-NSW696T/2006/AU_EF684915 (SEQ ID NO: 30; FIG. 19F), NO09: GII.4/Orange-NSW001P/2008/AU_GQ845367 (SEQ ID NO: 31; FIG. 19G), Hu/GII.5/AlbertaEI390/2013/CA (GII.5; SEQ ID No:17; FIG. 20), Hu/GII.6/Ohio/490/2012/USA (GII.6; SEQ ID NO: 20; FIG. 21A), GII.7/Musa/2010/A1173774 (GII7; SEQ ID NO:18; FIG. 22), Hu/GII.12/HS206/2010/USA (GII.12; SEQ ID NO: 19; FIG. 23A), GII.13/VA173/2010/H9AWU4 (SEQ ID NO:22; FIG. 24A), GII.14_Saga_2008_JPN_ADE28701 native VP1 (SEQ ID NO: 32; FIG. 25), Hu/GII.17/Kawasaki323/2014/JP (GII.117; SEQ ID NO: 24; FIG. 26A), Hu/GII.21/Salisbury150/2011/USA (GII.21; SEQ ID NO:26; FIG. 27), provided that the VP1 protein induces immunity to norovirus in a subject, when the VP1 protein is administered to the subject.

Similarly, the present invention includes amino acid sequences that exhibit from about 30% to about 99% or any amount therebetween, sequence similarity with any of the VP1 sequences for example, Hu/GI.2/Leuven/2003/BEL (GI.2; SEQ ID NO:4; FIG. 12A), Hu/GI.3/S29/2008/Lilla Edet/Sweden (GI.3; SEQ ID NO:6; FIG. 14A), Hu/GI.5/Siklos/Hun5407/2013/HUN (GI.5; SEQ ID NO:12; FIG. 15A), Hu/GI.7/USA/2014/GA5043 (GI.7; SEQ ID NO:101; FIG. 16A), Hu/GII.1/Ascension208/2010/USA (GII.1; SEQ ID NO:13; FIG. 16B), Hu/GII.2/CGM1147/2011/TW (SEQ ID NO:14; FIG. 17A), Hu/GII.3/Jingzhou/2013402/CHN (GII.3; SEQ ID NO: 15; FIG. 18A), Hu/GII.4/Sydney/NSW0514/2012/AU (GII.4; SEQ ID NO: 16; FIG. 19A), US96/GII.4/Dresden174/1997/DE_AY741811 (SEQ ID NO: 27; FIG. 19C), FH02/GII.4/FarmingtonHills/2002/US_AY502023 (SEQ ID NO: 28; FIG. 19D), Hnt04: GII.4/Hunter-NSW504D/2004/AU_DQ078814 (SEQ ID NO: 29; FIG. 19E), 2006b: GII.14/Shellharbour-NSW696T/2006/AU_EF684915 (SEQ ID NO: 30; FIG. 19F), NO09: GII.14/Orange-NSW001P/2008/AU_GQ845367 (SEQ ID NO: 31; FIG. 19G), Hu/GII.5/AlbertaEI390/2013/CA (GII.5; SEQ ID No:17; FIG. 20), Hu/GII.6/Ohio/490/2012/USA (GII.6; SEQ ID NO: 20; FIG. 21A), GII.7/Musa/2010/A1173774 (GII7; SEQ ID NO:18; FIG. 22), Hu/GII.12/HS206/2010/USA (GII.12; SEQ ID NO: 19; FIG. 23A), GII.13/VA173/2010/H9AWU4 (SEQ ID NO:22; FIG. 24A), GII.14_Saga_2008_JPN_ADE28701 native VP1 (SEQ ID NO: 32; FIG. 25), Hu/GII.17/Kawasaki323/2014/JP (GII.17; SEQ ID NO: 24; FIG. 26A), Hu/GII.21/Salisbury150/2011/USA (GII.21; SEQ ID NO:26; FIG. 27), provided that the VP1 protein induces immunity to norovirus when administered to a subject. For example, the amino acid sequences described herein may have from about 30, 32, 34, 36, 38. 40, 42, 44, 46, 48, 50, 52, 54, 56, 58, 60, 62, 64, 66, 68, 70, 72, 74, 76, 78, 80, 82, 84, 86, 88, 90, 91, 92, 93, 94, 95, 96, 97, 98, 99% or any amount therebetween, sequence similarity with any of the VP1 amino acid sequences defined above, provided that the VP1 protein induces immunity to norovirus when administered to a subject.

By "VP1 mutant protein", "mutant VP1 protein", "modified VP1 protein", "modified norovirus VP1 protein" and the like, it is meant, a norovirus VP1 protein comprising one or more than one substitution, mutation, or modification, at positions or amino acids in sequence alignment with amino acids 43, 57, 84 and 94 of norovirus VP1 genotype GI.1 (SEQ ID NO:1; see Table 1 below), or a deletion of a peptide fragment in sequence alignment with amino acids 39 to 46 of norovirus VP1 genotype GI.1 (SEQ ID NO:1), or a combination thereof. The terms "residue", "residue amino acid" and "amino acid" are used interchangeably, and typically refer to an amino acid at a specified position (location) within an amino acid sequence.

TABLE 1

Listing of Norovirus genotypes (strains) and equivalent amino acid locations of GI and GII strains.

| Position (GI.1 numbering) | 43 | 57 | 84 | 94 |
|---|---|---|---|---|
| Genotype | AA in equivalent position | | | |
| GI.1 | V43 | I57 | S84 | L94 |
| GI.2 | V43 | V57 | Q84 | S94 |
| GI.3 | A43 | M57 | Q84 | S94 |
| GI.5 | L43 | F57 | Q84 | A94 |
| GI.7 | V43 | M57 | R84 | L94 |
| GII.1 | A39 | R53 | E80 | A90 |
| GII.2 | A39 | R53 | E80 | A90 |
| GII.3 | A39 | M53 | E80 | A90 |
| GII.4 | A39 | R53 | P80 | S90 |
| GII.5 | A39 | R53 | E80 | A90 |
| GII.6 | A39 | R53 | E80 | S90 |
| GII.7 | T39 | R53 | E80 | A90 |
| GII.12 | A39 | R53 | E80 | A90 |
| GII.13 | A39 | R53 | E80 | A90 |
| GII.14 | A39 | R53 | E80 | A90 |
| GII.17 | A39 | R53 | E80 | A90 |
| GII.21 | A39 | R53 | E80 | A90 |

As used herein, the term "conserved substitution" or "conservative substitution" refers to the presence of an amino acid residue in the sequence of the GII.4 VP1 protein that is different from, but it is in the same class of amino acid as the described substitution. For example, a nonpolar amino acid may be used to replace a nonpolar amino acid, an aromatic amino acid to replace an aromatic amino acid, a polar-uncharged amino acid to replace a polar-uncharged amino acid, and/or a charged amino acid to replace a charged amino acid). In addition, conservative substitutions can encompass an amino acid having an interfacial hydropathy value of the same sign and generally of similar magnitude as the amino acid that is replacing the corresponding wild type amino acid.

As used herein, the term "nonpolar amino acid" refers to glycine (G, Gly), alanine (A, Ala), valine (V, Val), leucine (L, Leu), isoleucine (I, Ile), and proline (P, Pro); the term "aromatic residue" (or aromatic amino acid) refers to phenylalanine (F, Phe), tyrosine (Y, Tyr), and tryptophan (W, Trp); the term "polar uncharged amino acid" refers to serine (S, Ser), threonine (T, Thr), cysteine (C, Cys), methionine (M, Met), asparagine (N, Asn) and glutamine (Q, Gln); the term "charged amino acid" refers to the negatively charged amino acids aspartic acid (D, Asp) and glutamic acid (E, Glu), as well as the positively charged amino acids lysine (K, Lys), arginine (R, Arg), and histidine (H, His). Other classification of amino acids may be as follows: amino acids with hydrophobic side chain (aliphatic): Alanine (A, Ala), Isoleucine (I, Ile), Leucine (L, Leu), Methionine (M, Met) and Valine (V, Val); amino acids with hydrophobic side chain (aromatic): Phenylalanine (F, Phe), Tryptophan (W, Trp), Tyrosine (Y, Tyr); amino acids with polar neutral side chain: Asparagine (N, Asn), Cysteine (C, Cys), Glutamine (Q, Gln), Serine (S, Ser) and Threonine (T, Thr); amino acids with electrically charged side chains (acidic): Aspartic acid (D, Asp), Glutamic acid (E, Glu); amino acids with electrically charged side chains (basic): Arginine (R, Arg); Histidine (H, His); Lysine (K, Lys), Glycine G, Gly) and Proline (P, Pro).

Conservative amino acid substitutions are likely to have a similar effect on the activity of the resultant modified GII.4 VP1 protein as the original substitution or modification. Further information about conservative substitutions can be found, for example, in Ben Bassat et al. (J. Bacteriol, 169:751-757, 1987), O'Regan et al. (Gene, 77:237-251, 1989), Sahin-Toth et al. (Protein ScL, 3:240-247, 1994), Hochuli et al (Bio/Technology, 6:1321-1325, 1988).

The Blosum matrices are commonly used for determining the relatedness of polypeptide sequences (Henikoff et al., Proc. Natl. Acad. Sci. USA, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows examples of conservative amino acid substitutions: Table 2.

TABLE 2

Exemplary conservative amino acid substitutions.

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn; Gln, Tyr | Arg, Asn, Gln, Glu, Tyr |
| Ile | Leu; Val | Leu, Met, Val | Leu, Met, Phe, Val |
| Leu | Ile; Val | Ile, Met. Phe, Val | Ile, Met, Phe, Val |
| Lys | Arg; Gln; Glu | Arg, Asn, Gln, Glu | Arg, Asn, Gln, Glu, Ser |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |

TABLE 2-continued

| Exemplary conservative amino acid substitutions. | | | |
|---|---|---|---|
| Original Residue | Very Highly - Conserved Substitutions | Highly Conserved Substitutions (from the Blosum90 Matrix) | Conserved Substitutions (from the Blosum65 Matrix) |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

For the modifications described herein, the amino acids may be substituted using very high conserved substitutions, highly conserved substitutions or conserved substitutions as outlined in Table 2, as well as aromatic, polar, polar uncharged, polar neutral, or non-polar, negatively charged, positively charged, hydrophobic amino acids as described above.

As described herein, modified VP1 proteins comprising one or more than one substitutions of amino acids at amino acids 43, 57, 84 and 94 (in GI strains, equivalent to amino acids 39, 53, 80 and 90 in Gil strains), resulted in an improved characteristic of the modified VP1 protein, or VLP produced using the modified VP1 protein. It is to be understood that the improved characteristic is not limited to substituting the specific amino acid at the specified sites, as one of skill in the art would understand that amino acids with similar properties may be substituted for the amino acids at the identified positions. For example, the modification Q84S, comprises substituting glutamine at position 84 with serine, an amino acid characterized as having a polar neutral side chain. The glutamine at this position may also be substituted with an alternate amino acid characterized as having a polar neutral side chain, for example either asparagine, cysteine, or threonine, i.e. Q84X, where X=S, N, C or T. Similarly, E80S, comprising a substitution of glutamate at position 80 with serine, or P80S (a proline to serine substitution), in addition to substituting the native amino acid with serine, the amino acid at this position may also be substituted with an amino acid having a polar neutral side chain, for example asparagine, cysteine, or threonine, i.e. P80X, where X=S, N, C or T. Furthermore, as described herein additional P80X variants may be used to produce VP1, where X is selected from S, A, N, K or H. In the modifications S94L, S90L, A94L, or A90L, that comprise substituting serine or alanine with leucine (an amino acid characterized as having a hydrophobic side chain), the native amino acid may be substituted using an amino acid characterized as having a hydrophobic side chain, for example either isoleucine, methionine, valine, or in the case of S94X or 590X, an alanine, i.e. S94X (590X), where X=L, I, M, V or A, or A94X (A90X), where X=L, I, M or V. Furthermore, as described herein additional S94X variants may be used to produce VP1, where X is selected from V, I, M, T, E, D, N, Q, K, or H. The modification A39V that comprises substituting an alanine with valine (an amino acid characterized as having a hydrophobic side chain) at position 39, in addition to valine, native amino acid may also be substituted with an amino acid characterized as having a hydrophobic side chain, for example, isoleucine, leucine, or methionine i.e. A39X, where X=V, I, L or M. Furthermore, as described herein additional A39X variants may be used to produce VP1, where X is selected from I, M, G, S, E, D, N, Q, K, or H. The modification V47P comprising a substitution of valine with proline, may also comprise a substitution of valine with a glycine, i.e. V47X, where X=P or G. The modification R53I that comprises substituting an arginine with isoleucine (an amino acid characterized as having a hydrophobic side chain) at position 53, in addition to isoleucine, arginine may also be substituted with an amino acid characterized as having a hydrophobic side chain, for example, leucine, valine, alanine or methionine i.e. R53X, where X=I, L, V, A or M. The modification M57I that comprises substituting a methionine with isoleucine (an amino acid characterized as having a hydrophobic side chain) at position 57, in addition to isoleucine, methionine may also be substituted with an amino acid characterized as having a hydrophobic side chain, for example, leucine, valine, or alanine i.e. M57X, where X=I, L, V or A. Furthermore, as described herein additional M57X variants may be used to produce VP1, where X is selected from L, G, S, T, N, Q, K, or H.

Examples of VP1 mutant proteins (modified VP1 proteins) include, but are not limited to, the following.

GI.3_Q84S VP1 (GI.3_Q84X, where X=S, N, C or T VP1): wherein the glutamine corresponding to amino acid 84 of norovirus VP1 genotype GI.1 (SEQ ID NO:1) has been mutated, for example, to serine (GI.3_Q84S; SEQ ID NO:98, FIG. 28A), or a sequence that exhibits from about 80-100% or any amount therebetween, sequence similarity with the amino acid sequence of the GI.3_Q84S VP1 protein. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_Q84S VP1 protein (SEQ ID NO:98, FIG. 28A), provided that the substitution, modification or mutation at the position corresponding to amino acid 84 of norovirus VP1 genotype GI.1 remains an S, N, C or T, for example serine, and provided that the GI.3 Q84X VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6 amino acid; SEQ ID NO:7, nucleotide; FIGS. 14A, 14B).

GI.3_S94X VP1, where X=L, I, A, V, M, T, E, D, N, Q, K, or H, wherein the serine corresponding to amino acid 94 of norovirus VP1 genotype GI.1 (SEQ ID NO:1) has been mutated, for example, to leucine (GI.3_S94L; SEQ ID NO:8, FIG. 28C), valine, isoleucine, methionine, threonine, aspartic acid, glutamic acid, glutamine lysine or histidine (GI.3_S94X, where X=V, I, M, T, E, D, N, Q, K, or H; SEQ ID NO:292, FIG. 28M), or a sequence that exhibits from about 80-100% or any amount therebetween, sequence similarity with the amino acid sequence of the GI.3_S94X VP1 protein, where X=L, V, I, M, T, E, D, N, Q, K, or H. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_S94X VP1 protein, where X=L, V, I, M, T, E, D, N, Q, K, or H VP1 protein (SEQ ID NO:8, FIG. 28C, SEQ ID NO:292; FIG. 28M), provided that the substitution, modification or mutation at the position corresponding to amino acid 94 of norovirus VP1 genotype GI.1 remains an L, V, I, M, T, E, D, N, Q, K, or H, for example leucine, valine, isoleucine, methionine, threonine, aspartic acid, glutamic acid, glutamine lysine or histidine, and provided that the GI.3 S94X VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6 amino acid; SEQ ID NO:7, nucleotide; FIGS. 14A, 14B).

GI.3_A43X+S94x VP1, where X=V, L, I or M, and x=L, I, A, V, M, T, E, D, N, Q, K, or H, wherein the alanine and serine corresponding to amino acids 43 and 94, respectively, of norovirus VP1 genotype GI.1 (SEQ ID NO:1) have been substituted or mutated, for example but not limited to, to valine and leucine, respectively (GI.3_A43V+S94L; SEQ ID NO:170, FIG. 28G), or a sequence that exhibits from about 80-100% or any amount therebetween, sequence similarity with the amino acid sequence of the GI.3_A43V+S94L VP1 protein. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_A43V+S94L VP1 protein (SEQ ID NO:170, FIG. 28G), provided that the substitutions, modifications or mutations at the positions corresponding to amino acids 43 and 94 of norovirus VP1 genotype GI.1 remain a V, L, I or M, for example valine, and an L, I, A, V, M, T, E, D, N, Q, K, or H, for example leucine, respectively, and provided that the GI.3_A43X+S94x VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6, amino acid; SEQ ID NO:7, nucleotide; FIGS. 14A, 14B).

GI.3_M57X+S94x VP1, where X=I, V, A, L, G, S, T, N, Q, K, or H and x=L, I, A, V, M, T, E, D, N, Q, K, wherein the methionine and serine corresponding to amino acids 57 and 94, respectively, of norovirus VP1 genotype GI.1 (SEQ ID NO:1) have been mutated, for example, to isoleucine and leucine, respectively (GI.3_M57I+S94L; SEQ ID NO:172, FIG. 28I), or a sequence that exhibits from about 80-100% or any amount therebetween, sequence similarity with the amino acid sequence of the GI.3_M57I+S94L VP1 protein. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_M57I+S94L VP1 protein (SEQ ID NO:172, FIG. 28I), provided that the substitutions, modifications or mutations at the positions corresponding to amino acids 57 and 94 of norovirus VP1 genotype GI.1 remain an I, V, A, L, G, S, T, N, Q, K, or H, for example isoleucine, and an L, I, A, V, M, T, E, D, N, Q, K, for example leucine, respectively, and provided that the GI.3_M57X+S94x VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6, amino acid; SEQ ID NO:7, nucleotide; FIGS. 14A, 14B).

GI.3_Q84X+594x, VP1, where X=5, N, C or T, and x=L, I, A, V, M, T, E, D, N, Q, K, or H, wherein the glutamine and serine corresponding to amino acids 84 and 94, respectively, of norovirus VP1 genotype GI.1 (SEQ ID NO:1) have been mutated, for example, to serine and leucine, respectively (GI.3_Q84S+S94L; SEQ ID NO:10, FIG. 28E), or a sequence that exhibits from about 80-100% or any amount therebetween, sequence similarity with the amino acid sequence of the GI.3_Q84S+S94L VP1 protein. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_Q84S+S94L VP1 protein (SEQ ID NO:10, FIG. 28E), provided that the substitutions, modifications or mutations at the positions corresponding to amino acids 84 and 94 of norovirus VP1 genotype GI.1 remain an S, N, C or T, for example serine, and an L, I, A, V, M, T, E, D, N, Q, K, or H, for example leucine, respectively, and provided that the GI.3_Q84X+S94x VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6, amino acid; SEQ ID NO:7, nucleotide; FIGS. 14A, 14B).

GI.3_A43X+M57z+S94x VP1, where X=V, L, I or M, z=I, V, A, L, G, S, T, N, Q, K, or H, and x=L, I, A, V, M, T, E, D, N, Q, K, or H, wherein the alanine, methionine and serine corresponding to amino acids 43, 57 and 94, respectively, of norovirus VP1 genotype GI.1 (SEQ ID NO:1) have been mutated, for example, to valine, isoleucine and leucine, respectively (GI.3_A43V+M57I+S94L; SEQ ID NO:174, FIG. 28K), or a sequence that exhibits from about 80-100% or any amount therebetween, sequence similarity with the amino acid sequence of the GI.3_A43V+M57I+S94L VP1 protein. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_A43V+M57I+S94L VP1 protein (SEQ ID NO:174, FIG. 28K), provided that the substitutions, modifications or mutations at the positions corresponding to amino acids 43, 57 and 94 of norovirus VP1 genotype GI.1 remain a V, L, I or M, for example valine, a I, V, A, L, G, S, T, N, Q, K, or H, for example isoleucine, and L, I, A, V, M, T, E, D, N, Q, K, or H, for example leucine, respectively, and provided that the GI.3_A43X+M57z+S94x VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6, amino acid; SEQ ID NO:7, nucleotide; FIGS. 14A, 14B).

GI.5_Q84S VP1 (GI.5_Q84X, where X=S, N, C or T, VP1): wherein the glutamine corresponding to amino acid 84 of norovirus VP1 genotype GI.1 (SEQ ID NO:1) has been mutated, for example, to serine (GI.5_Q84S; SEQ ID NO:34, FIG. 29A), or a sequence that exhibits from about 80-100% or any amount therebetween, sequence similarity with the amino acid sequence of the GI.5_Q84S VP1 protein. For example, the GI.5 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.5_Q84S VP1 protein (SEQ ID NO:34, FIG. 29A), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GI.5 VP1 may be obtained from any GI.5 strain, for example, but not limited to GI.5/Siklos/HUN5407/2013/HUN (SEQ ID NO:12, amino acid; FIG. 15A).

GI.5_A94L VP1 (GI.5_A94X, where X=L, I, M or V, VP1): wherein the alanine corresponding to amino acid 94 of norovirus VP1 genotype GI.1 (SEQ ID NO:1) has been mutated, for example, to leucine (GI.5_A94L; SEQ ID NO:36, FIG. 29C), or a sequence that exhibits from about 80-100% or any amount therebetween, sequence similarity with the amino acid sequence of the GI.5_A94L VP1 protein. For example, the GI.5 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.5_A94L VP1 protein (SEQ ID NO:36, FIG. 29C), provided that the substitution, modification or mutation at the position corresponding to amino acid 94 of norovirus VP1 genotype GI.1 remains an L, I, M or V, for example leucine, and provided that the VP1 protein induces immunity to norovirus when administered to a subject. The sequence encoding the GI.5 VP1 may be obtained from any GI.5 strain, for example, but not limited to GI.5/Siklos/HUN5407/2013/HUN (SEQ ID NO:12, amino acid; FIG. 15A).

GI.5_Q84S+A94L VP1 (GI.5_Q84X, where X=S, N, C or T+A94X, where X=L, I, M or V, VP1): wherein the glutamine and alanine corresponding to amino acids 84 and 94, respectively of norovirus VP1 genotype GI.1 (SEQ ID NO:1) have been mutated, for example, to serine and leucine, respectively (GI.5_Q84S+A94L; SEQ ID NO:38, FIG. 29E), or a sequence that exhibits from about 80-100% or any amount therebetween, sequence similarity with the amino acid sequence of the GI.5_Q84S+A94L VP1 protein. For example, the GI.5 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.5_Q84S+A94L VP1 protein (SEQ ID NO:38, FIG. 29E), provided that the substitutions, modifications or mutations at the positions corresponding to amino acids 84 and 94 of norovirus VP1 genotype GI.1 remain an S, N, C or T, for example serine and an L, I, M or V, for example leucine, respectively, and provided that the VP1 protein induces immunity to norovirus when administered to a subject. The sequence encoding the GI.5 VP1 may be obtained from any GI.5 strain, for example, but not limited to GI.5/Siklos/HUN5407/2013/HUN (SEQ ID NO:12, amino acid; FIG. 15A).

GI.7_M57X VP1, where X=I, V, A, L, G, S, T, N, Q, K, or H, wherein the methionine corresponding to amino acid 57 of norovirus VP1 genotype GI.1 (SEQ ID NO:1) has been mutated, for example, to isoleucine (GI.7_M57I; SEQ ID NO:179, FIG. 29I), valine, alanine, leucine, glycine, serine, threonine, asparagine, glutamine, lysine or histidine (GI.7_M57X VP1, where X=I, V, A, L, G, S, T, N, Q, K, or H; SEQ ID NO: 290; FIG. 29M), or a sequence that exhibits from about 80-100% or any amount therebetween, sequence similarity with the amino acid sequence of the GI.7_M57X VP1 protein, where X=I, V, A, L, G, S, T, N, Q, K, or H. For example, the GI.7 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.7_M57X VP1 protein, where X=I, V, A, L, G, S, T, N, Q, K, or H; (SEQ ID NO:179, FIG. 29I; SEQ ID NO:290; FIG. 29M), provided that the substitution, modification or mutation at the position corresponding to amino acid 57 of norovirus VP1 genotype GI.1 remains an I, V, A, L, G, S, T, N, Q, K, or H, for example isoleucine, valine, alanine, leucine, glycine, serine, threonine, asparagine, glutamine, lysine or histidine, and provided that the GI.7_M57X VP1 protein induces immunity to norovirus when administered to a subject. The sequence encoding the GI.7 VP1 may be obtained from any GI.7 strain, for example, but not limited to GI.7/GA5043/USA/2014 (SEQ ID NO:101, amino acid; FIG. 16A).

GI.7_R84S VP1 (GI.7_R84X, where X=S, N, C, or T, VP1): wherein the arginine corresponding to amino acid 84 of norovirus VP1 genotype GI.1 (SEQ ID NO:1) has been mutated, for example, to serine (GI.7_R84S; SEQ ID NO:177, FIG. 29G), or a sequence that exhibits from about 80-100% or any amount therebetween, sequence similarity with the amino acid sequence of the GI.7_R84S VP1 protein. For example, the GI.7 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.7_R84S VP1 protein (SEQ ID NO:177, FIG. 29G), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GI.7 VP1 may be obtained from any GI.7 strain, for example, but not limited to GI.7/GA5043/USA/2014 (SEQ ID NO:101, amino acid; FIG. 16A).

GI.7_M57X+R84x VP1, where X=L, I, A, V, M, T, E, D, N, Q, K, or H, and x=S, N, C, or T, wherein the methionine and arginine, corresponding to amino acids 57 and 84, respectively of norovirus VP1 genotype GI.1 (SEQ ID NO:1) have been mutated, for example, to isoleucine and serine, respectively (GI.7_M57I+R84S; SEQ ID NO:181, FIG. 29K), or a sequence that exhibits from about 80-100% or any amount therebetween, sequence similarity with the amino acid sequence of the GI.7_M57I+R84S VP1 protein. For example, the GI.7 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.7_M57I+R84S VP1 protein (SEQ ID NO:181, FIG. 29K), provided that the substitutions, modifications or mutations at the positions corresponding to amino acids 57 and 84 of norovirus VP1 genotype GI.1 remain an L, I, A, V, M, T, E, D, N, Q, K, or H, for example isoleucine, and an S, N, C or T, for example serine, respectively, and provided that the GI.7_M57X+R84x VP1 protein induces immunity to norovirus when administered to a subject. The sequence encoding the GI.7 VP1 may be obtained from any GI.7 strain, for example, but not limited to GI.7/GA5043/USA/2014 (SEQ ID NO:101, amino acid; FIG. 16A).

GII.2_E80S VP1 (GII.2_E80X, where X=S, N, C or T, VP1): wherein the glutamic acid corresponding to amino acid 84 of norovirus VP1 genotype GI.1 (SEQ ID NO:1) has been mutated, for example, to serine (GII.2_E80S; SEQ ID NO:85, FIG. 30A), or a sequence that exhibits from about 80-100% or any amount therebetween, sequence similarity with the amino acid sequence of the GII.2_E80S VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2_E80S VP1 protein (SEQ ID NO:85, FIG. 30A), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.2_A90L VP1 (GII.2_A90X, where X=L, I, M or V, VP1): wherein alanine corresponding to amino acid 94 of norovirus VP1 genotype GI.1 (SEQ ID NO:1) has been mutated, for example, to leucine (GII.2_A90L; SEQ ID NO:41, FIG. 30C), or a sequence that exhibits from about 80-100% or any amount therebetween, sequence similarity with the amino acid sequence of the mut GII.2_A90L VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2_A90L VP1 protein (SEQ ID NO:41, FIG. 30C), provided that the substitution, modification or mutation at the position corresponding to amino acid 94 of norovirus VP1 genotype GI.1 remains an L, I, M or V for example leucine, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.2_E80S+A90L VP1 (GII.2_E80X, where X=S, N, C or T+A90X, where X=L, I, M or V, VP1): wherein the glutamic acid and alanine corresponding to amino acids 84 and 94, respectively of norovirus VP1 genotype GI.1 (SEQ ID NO:1) have been mutated, for example, to serine and leucine, respectively (GII.2_E80S+A90L; SEQ ID NO:43, FIG. 30E), or a sequence that exhibits from about 80-100% or any amount therebetween, sequence similarity with the amino acid sequence of the mut GII.2_E80S+A90L VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2_E80S+A90L VP1 protein (SEQ ID NO:43, FIG. 30E), provided that the substitutions, modifications or mutations at the positions corresponding to amino acids 84 and 94 of norovirus VP1 genotype GI.1 remain an S, N, C or T, for example serine, and an L, I, M or V, for example leucine, respectively, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.2_A39V+E80S+A90L VP1 (GII.2_A39X, where X=V, L. I or M+E80X, where X=S, N, C or T+A90X, where X=L, I, M or V, VP1): wherein the alanine, glutamic acid and alanine corresponding to amino acids 43, 84 and 94, respectively of norovirus VP1 genotype GI.1 (SEQ ID NO:1) have been mutated, for example, to valine, serine and leucine, respectively (GII.2_A39V+E80S+A90L; SEQ ID NO:182, FIG. 30G), or a sequence that exhibits from about 80-100% or any amount therebetween, sequence similarity with the amino acid sequence of the GII.2_A39V+E80S+A90L VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2_A39V+E80S+A90L VP1 protein (SEQ ID NO:182, FIG. 30G), provided that the substitutions, modifications or mutations at the positions corresponding to amino acids 43, 84 and 94 of norovirus VP1 genotype GI.1 remain a V, I, L or M, for example valine, an S, N, C or T, for example serine, and an L, I, M or V, for example leucine, respectively, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.2 R53I+E80S+A90L VP1 (GII.2_R53X, where X=I, L, M, V or A+E80X, where X=S, N, C or T+A90X, where X=L, I, M or V, VP1): wherein the arginine, glutamic acid and alanine corresponding to amino acids 57, 84 and 94, respectively of norovirus VP1 genotype GI.1 (SEQ ID NO:1) have been mutated, for example, to isoleucine, serine and leucine, respectively (GII.2_M53I+E80S+A90L; SEQ ID NO:184, FIG. 30I), or a sequence that exhibits from about 80-100% or any amount therebetween, sequence similarity with the amino acid sequence of the GII.2_M53I+E80S+A90L VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2_M53I+E80S+A90L VP1 protein (SEQ ID NO:184, FIG. 30I), provided that the substitutions, modifications or mutations at the positions corresponding to amino acids 57, 84 and 94 of norovirus VP1 genotype GI.1 remain an I, L, M or A, for example isoleucine, an S, N, C or T, for example serine, and an L, I, M or V, for example leucine, respectively, and provided that the VP1 protein induces immunity to norovirus when administered to a subject.

The sequence encoding the GII.2 VP1 may be obtained from any GII.2 strain, for example, but not limited to Hu/GII.2/CGMH47/2011/TW (SEQ ID NO:14, amino acid; FIG. 17A).

GII.2 A39V+R53I+E80S+A90L VP1 (GII.2_A39X, where X=V, I, L or, M+R53X, where X=I, L, M, A or V+E80X, where X=S, N, C or T+A90X, where X=L, I, M or V, VP1): wherein the glutamic acid and alanine corresponding to amino acids 43, 57, 84 and 94, respectively of norovirus VP1 genotype GI.1 (SEQ ID NO:1) have been mutated, for example, to valine, isoleucine, serine and leucine, respectively (GII.2_A39V+R53I+E80S+A90L; SEQ ID NO:186, FIG. 30K), or a sequence that exhibits from about 80-100% or any amount therebetween, sequence similarity with the amino acid sequence of the GII.2_A39V+R53I+E80S+A90L VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2_A39V+R53I+E80S+A90L VP1 protein (SEQ ID NO:186, FIG. 30K), provided that the substitutions, modifications or mutations at the positions corresponding to amino acids 43, 57, 84 and 94 of norovirus VP1 genotype GI.1 remain an V, I, L or M, for example valine, an I, L, M, A or V, for example isoleucine, an S, N, C or T, for example serine, and an L, I, M or V, for example leucine, respectively, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.3_E80S VP1 (GII.3_E80X, where X=S, N, C or T, VP1): wherein the glutamic acid corresponding to amino acid 84 of norovirus VP1 genotype GI.1 (SEQ ID NO:1) has been mutated, for example, to serine (GII.3_E80S; SEQ ID NO:46, FIG. 31A), or a sequence that exhibits from about 80-100% or any amount therebetween, sequence similarity with the amino acid sequence of the mut GII.3_E80S VP1 protein. For example, the GII.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.3_E80S VP1 protein (SEQ ID NO:46, FIG. 31A), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GII.3 VP1 may be obtained from any GII.3 strain, for example, but not limited to GII.3/Jingzhou/2013402/CHN (SEQ ID NO:15, amino acid; FIG. 18A).

GII.3_A90L VP1 (GII.3_A90X, where X=L, I, M or V, VP1): wherein the alanine corresponding to amino acid 94 of norovirus VP1 genotype GI.1 (SEQ ID NO:1) has been mutated, for example, to leucine (GII.3_A90L; SEQ ID NO:48, FIG. 31C), or a sequence that exhibits from about 80-100% or any amount therebetween, sequence similarity with the amino acid sequence of the GII.3_A90L VP1 protein. For example, the GII.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.3_A90L VP1 protein (SEQ ID NO:48, FIG. 31C), provided that the substitution, modification or mutation at the position corresponding to amino acid 94 of norovirus VP1 genotype GI.1 remains an L, I, M or V, for example leucine, and provided that the VP1 protein induces immunity to norovirus when administered to a subject. The sequence encoding the GII.3 VP1 may be obtained from any GII.3 strain, for example, but not limited to GII.3/Jingzhou/2013402/CHN (SEQ ID NO:15, amino acid; FIG. 18A).

GII.3_E80S+A90L VP1 (GII.3_E80X, where X=S, N, C or T+A90X, where X=L, I, M or V, VP1): wherein the glutamic acid and alanine corresponding to amino acids 84 and 94, respectively of norovirus VP1 genotype GI.1 (SEQ ID NO:1) have been mutated, for example, to serine and leucine, respectively (GII.3_E80S+A90L; SEQ ID NO:50, FIG. 31E), or a sequence that exhibits from about 80-100% or any amount therebetween, sequence similarity with the amino acid sequence of the GII.3_E80S+A90L VP1 protein. For example, the GII.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.3_E80S+A90L VP1 protein (SEQ ID NO:50, FIG. 31E), provided that the substitutions, modifications or mutations at the positions corresponding to amino acids 84 and 94 of norovirus VP1 genotype GI.1 remain an S, N, C or T, for example serine, and an L, I, M or V, for example leucine, respectively, and provided that the VP1 protein induces immunity to norovirus when administered to a subject. The sequence encoding the GII.3 VP1 may be obtained from any GII.3 strain, for example, but not limited to GII.3/Jingzhou/2013402/CHN (SEQ ID NO:15, amino acid; FIG. 18A).

GII.4_A39X VP1, where X=V, I, L, M, G, S, E, D, N, Q, K, or H, wherein the alanine corresponding to amino acid 43 of norovirus VP1 genotype GI.1 (SEQ ID NO:1) has been mutated, for example, to valine (GII.4_A39V; SEQ ID NO:53, FIG. 32A), isoleucine, leucine, methionine, glycine, serine, aspartic acid, glutamic acid, asparagine, glutamine, lysine, histidine, or a sequence that exhibits from about 80-100% or any amount therebetween, sequence similarity with the amino acid sequence of the GII.4_A39X VP1, where X=V, I, L, M, G, S, E, D, N, Q, K, or H, VP1 protein. For example which is not to be considered limiting, the GII.4 VP1 protein may have from about 0, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V VP1 protein (SEQ ID NO:53, FIG. 32A), provided that the substitution, modification or mutation at the position corresponding to amino acid 43 of norovirus VP1 genotype GI.1 remains a V, I, L, M, G, S, E, D, N, Q, K, or H, for example valine, isoleucine, leucine, methionine, glycine, serine, aspartic acid, glutamic acid, asparagine, glutamine, lysine, or histidine, and provided that the GII.4_A39X VP1 protein induces immunity to norovirus when administered to a subject. The sequence encoding the GII.4 VP1 may be obtained from any GII.4 strain, for example, but not limited to GII.14/Sydney/NSW0514/2012/AU (SEQ ID NO:16, amino acid; SEQ ID NO:52, nucleotide; FIGS. 19A and 19B).

GII.4_V47P VP1 (GII.4_V47X, where X=P or G, VP1): wherein the valine corresponding to amino acid 51 of norovirus VP1 genotype GI.1 (SEQ ID NO:1) has been mutated, for example, to proline (GII.4_V47P; SEQ ID NO:55, FIG. 32C), or a sequence that exhibits from about 80-100% or any amount therebetween, sequence similarity with the amino acid sequence of the GII.4_V47P VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_V47P VP1 protein (SEQ ID NO:55, FIG. 32C), provided that the substitution, modification or mutation at the position corresponding to amino acid 51 of norovirus VP1 genotype GI.1 remains a P or G, for example proline, and provided that the VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_R53I VP1 (GII.4_R53I, where X=I, L, V, A or M, VP1): wherein the arginine corresponding to amino acid 57 of norovirus VP1 genotype GI.1 (SEQ ID NO:1) has been mutated, for example, to isoleucine (GII.14_R53I; SEQ ID NO:57, FIG. 32E), or a sequence that exhibits from about 80-100% or any amount therebetween, sequence similarity with the amino acid sequence of the GII.4_R53I VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_R53I VP1 protein (SEQ ID NO:57, FIG. 32E), provided that the substitution, modification or mutation at the position corresponding to amino acid 57 of norovirus VP1 genotype GI.1 remains an I, L, V, A or M, for example isoleucine, and provided that the VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_P80X VP1, where X=S, N, C, T, A, K, or H, wherein the proline corresponding to amino acid 84 of norovirus VP1 genotype GI.1 (SEQ ID NO:1) has been mutated, for example, to serine (GII.4_P80S; SEQ ID NO:59, FIG. 32G), asparagine, cysteine, threonine, alanine, lysine, histidine, or a sequence that exhibits from about 80-100% or any amount therebetween, sequence similarity with the amino acid sequence of the GII.4_P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S VP1 protein (SEQ ID NO:59, FIG. 32G), provided that the substitution, modification or mutation at the position corresponding to amino acid 84 of norovirus VP1 genotype GI.1 remains an S, N, C, T, A, K, or H, for example serine, asparagine, cysteine, threonine, alanine, lysine, or histidine, and provided that the GII.4_P80X VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_S90L VP1 (GII.4_S90X, where X=L, I, M, A or V, VP1): wherein the serine corresponding to amino acid 94 of norovirus VP1 genotype GI.1 (SEQ ID NO:1) has been mutated, for example, to leucine (GII.4_S90L; SEQ ID NO:61, FIG. 32I), or a sequence that exhibits from about 80-100% or any amount therebetween, sequence similarity with the amino acid sequence of the GII.4_S90L VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_S90L VP1 protein (SEQ ID NO:61, FIG. 32I), provided that the substitution, modification or mutation at the position corresponding to amino acid 94 of norovirus VP1 genotype GI.1 remains an L, I, M, A or V, for example leucine, and provided that the VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_Δ35-42 VP1: wherein the amino acids corresponding to positions 39-46 of norovirus VP1 genotype GI.1 (SEQ ID NO:1) have been deleted (GII.4_Δ35-42; SEQ ID NO:63, FIG. 32K), or a sequence that exhibits from about 80-100% or any amount therebetween, sequence similarity with the amino acid sequence of the GII.4_Δ35-42 VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_Δ35-42 VP1 protein (SEQ ID NO:63, FIG. 32K), provided that the amino acids corresponding to positions 39-46 of norovirus VP1 genotype GI.1 (SEQ ID NO:1) remain deleted, and that the VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_SSTAVATA VP1: wherein the amino acids corresponding to positions 39-46 of norovirus VP1 genotype GI.1 (SEQ ID NO:1) have been mutated to the peptide sequence SSTAVATA (SEQ ID NO:168; GII.4_SSTAVATA; SEQ ID NO:65, FIG. 32M), or a sequence that exhibits from about 80-100% or any amount therebetween, sequence similarity with the amino acid sequence of the mut GII.4_SSTAVATA VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_SSTAVATA VP1 protein (SEQ ID NO:65, FIG. 32M), provided that the positions corresponding to amino acids 39-46 of norovirus VP1 genotype GI.1 remain the peptide sequence SSTAVATA, and provided that the VP1 protein induces immunity to norovirus when administered to a subject.

The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_A39X+R53x VP1, where X=V, I, L, M, G, S, E, D, N, Q, K, or H, and x=I, L, M, A or V, wherein the alanine and arginine corresponding to amino acids 43 and 57, respectively, of norovirus VP1 genotype GI.1 (SEQ ID NO:1) have been mutated, for example, to valine, isoleucine, leucine, methionine, glycine, serine, aspartic acid, glutamic acid, asparagine, glutamine, lysine or histidine and isoleucine, respectively (e.g. GII.4_A39V+R53I; SEQ ID NO:188, FIG. 32AA), or a sequence that exhibits from about 80-100% or any amount therebetween, sequence similarity with the amino acid sequence of the GII.4_A39V+R53I VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V+R53I VP1 protein (SEQ ID NO:188, FIG. 32AA), provided that the substitutions, modifications or mutations at the positions corresponding to amino acids 43 and 57 of norovirus VP1 genotype GI.1 remain a V, I, L, M, G, S, E, D, N, Q, K, or H, for example valine, isoleucine, leucine, methionine, glycine, serine, aspartic acid, glutamic acid, asparagine, glutamine, lysine or histidine, and an I, L, M, V or A, for example isoleucine, respectively, and provided that the GII.4_A39X+R53x VP1 protein induces immunity to norovirus when administered to a subject. The sequence encoding the GII.4 VP1 may be obtained from any GII.4 strain, for example, but not limited to GII.14/Sydney/NSW0514/2012/AU (SEQ ID NO:16, amino acid; SEQ ID NO:52, nucleotide; FIGS. 19A and 19B).

GII.4_A39X+P80x VP1, where X=V, I, L, M, G, S, E, D, N, Q, K, or H, and x=S, N, C, T, A, K, or H, VP1): wherein the alanine and proline corresponding to amino acids 43 and 84, respectively, of norovirus VP1 genotype GI.1 (SEQ ID NO:1) have been substituted or mutated, for example but not limited to, to valine, isoleucine, leucine, methionine, glycine, serine, aspartic acid, glutamic acid, asparagine, glutamine, lysine, or histidine, and serine, asparagine, cysteine, threonine, alanine, lysine, or histidine, respectively (e.g. GII.4_A39V+P80S; SEQ ID NO:67, FIG. 32O), or a sequence that exhibits from about 80-100% or any amount therebetween, sequence similarity with the amino acid sequence of the GII.4_A39X+P80x VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V+P80S VP1 protein (SEQ ID NO:67, FIG. 32O), provided that the substitutions, modifications or mutations at the positions corresponding to amino acids 43 and 84 of norovirus VP1 genotype GI.1 remain a V, I, L, M, G, S, E, D, N, Q, K, or H, for example valine, isoleucine, leucine, methionine, glycine, serine, aspartic acid, glutamic acid, asparagine, glutamine, lysine, or histidine, and an S, N, C, T, A, K, or H, for example serine, asparagine, cysteine, threonine, alanine, lysine, or histidine, respectively, and provided that the GII.4_A39X+P80x VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_V47P+P80S VP1 (GII.4_V47X, where X=P or G+P80x, where x=S, N, C, T, A, K, or H VP1): wherein the valine and proline corresponding to amino acids 51 and 84, respectively, of norovirus VP1 genotype GI.1 (SEQ ID NO:1) have been substituted or mutated, for example, to proline and serine, asparagine, cysteine, threonine, alanine, lysine, or histidine, respectively (e.g. GII.4_V47P+P80S; SEQ ID NO:69, FIG. 32Q), or a sequence that exhibits from about 80-100% or any amount therebetween, sequence similarity with the amino acid sequence of the GII.4_V47P+P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_V47P+P80S VP1 protein (SEQ ID NO:69, FIG. 32Q), provided that the substitutions, modifications or mutations at the positions corresponding to amino acids 51 and 84 of norovirus VP1 genotype GI.1 remain a P or G, for example proline, and an S, N, C, T, A, K, or H, for example serine, asparagine, cysteine, threonine, alanine, lysine, or histidine, respectively, and provided that the GII.4_V47X+P80x VP1 protein induces immunity to norovirus when administered to a subject. The sequence encoding the GII.4 VP1 may be obtained from any GII.4 strain, for example, but not limited to GII.4/Sydney/NSW0514/2012/(SEQ ID NO:16, amino acid; SEQ ID NO:52, nucleotide; FIGS. 19A and 19B).

GII.4_R53I+P80S VP1 (GII.4_R53X, where X=I, L, V, A or M+P80x, where x=S, N, C, T, A, K, or H, VP1): wherein the arginine and proline corresponding to amino acids 57 and 84, of norovirus VP1 genotype GI.1 (SEQ ID NO:1) have been mutated, for example, to an isoleucine and a serine, asparagine, cysteine, threonine, alanine, lysine, or histidine, respectively (e.g. GII.4_R53I+P80S; SEQ ID NO:71, FIG. 32S), or a sequence that exhibits from about 80-100% or any amount therebetween, sequence similarity with the amino acid sequence of the GII.4_R53I+P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_R53I+P80S VP1 protein (SEQ ID NO:71, FIG. 32S), provided that the substitution, modification or mutation at the position corresponding to amino acids 57 and 84 of norovirus VP1 genotype GI.1 remain an I, L, V, A or M, for example isoleucine, and an S, N, C, T, A, K, or H, for example serine, asparagine, cysteine, threonine, alanine, lysine, histidine, respectively, and provided that the GII.4_R53X+P80x VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_P80S+S90L VP1 (GII.4_P80X, where X=S, N, C, T, A, K, or H+S90x, where x=L, I, M, A or V, VP1): wherein the proline and serine corresponding to amino acids 84 and 94, respectively, of norovirus VP1 genotype GI.1 (SEQ ID NO:1) have been mutated, for example, to serine, asparagine, cysteine, threonine, alanine, lysine, or histidine, and leucine, respectively (e.g. GII.4_P80S+S90L; SEQ ID NO:73, FIG. 32U), or a sequence that exhibits from about 80-100% or any amount therebetween, sequence similarity with the amino acid sequence of the GII.4_P80S+S90L VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S+S90L VP1 protein (SEQ ID NO:73, FIG. 32U), provided that the substitutions, modifications or mutations at the positions corresponding to amino acids 84 and 94 of norovirus VP1 genotype GI.1 remain an S, N, C, T, A, K, or H, for example serine, asparagine, cysteine, threonine, alanine, lysine, or histidine and an L, I, M, A or V, for example leucine, respectively, and provided that the GII.4_P80X+S90x VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_A39X+R53x+P80z VP1, where X=V, I, L, M, G, S, E, D, N, Q, K, or H, where x=I, L, M, A or V, and z=S, N, C, T, A, K, or H, wherein the alanine and arginine corresponding to amino acids 43, 57 and 84, respectively, of norovirus VP1 genotype GI.1 (SEQ ID NO:1) have been substituted or mutated, for example, at position 39, to valine, isoleucine, leucine, methionine, glycine, serine, aspartic acid, glutamic acid, asparagine, glutamine, lysine, or histidine, at portion 53 to isoleucine, and at position 80 to serine, asparagine, cysteine, threonine, alanine, lysine, or histidine, respectively (e.g. GII.4_A39V+R53I+P80S; SEQ ID NO:190, FIG. 32CC), or a sequence that exhibits from about 80-100% or any amount therebetween, sequence similarity with the amino acid sequence of the GII.4_ A39V+R53I+P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V+R53I+P80S VP1 protein (SEQ ID NO:190, FIG. 32CC), provided that the substitutions, modifications or mutations at the positions corresponding to amino acids 43, 57 and 84 of norovirus VP1 genotype GI.1 remain a V, I, L, M, G, S, E, D, N, Q, K, or H, for example valine, isoleucine, leucine, methionine, glycine, serine, aspartic acid, glutamic acid, asparagine, glutamine, lysine, or histidine, an I, L, M, V or A, for example isoleucine, and an S, N, C, T, A, K, or H, for example serine, asparagine, cysteine, threonine, alanine, lysine, or histidine, respectively, and provided that the GII.4_A39X+R53x+P80z VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_P80S+Δ35-42 VP1 (GII.4_P80X, where X=S, N, C, T, A, K, or H, +Δ35-42, VP1): wherein the proline corresponding to position 84 of norovirus VP1 genotype GI.1 (SEQ ID NO:1) has been mutated, for example, to serine, asparagine, cysteine, threonine, alanine, lysine, or histidine, and the amino acids corresponding to positions 39-46 of norovirus VP1 genotype GI.1 have been deleted (GII.4_P80S+Δ35-42; SEQ ID NO:75, FIG. 32W), or a sequence that exhibits from about 80-100% or any amount therebetween, sequence similarity with the amino acid sequence of the GII.4_P80S+Δ35-42 VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S+Δ35-42 VP1 protein (SEQ ID NO:75, FIG. 32W), provided that the substitution, modification or mutation at the position corresponding to amino acid 84 of norovirus genotype GI.1 remains an S, N, C, T, A, K, or H, for example serine, asparagine, cysteine, threonine, alanine, lysine, or histidine, and the amino acids corresponding to positions 39-46 of norovirus VP1 genotype GI.1 remain deleted, and that the GII.4_P80X+Δ35-42 VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_P80S+SSTAVATA VP1 (GII.4_P80X, where X=S, N, C, T, A, K, or H+SSTAVATA, VP1): wherein the proline corresponding to position 84 of norovirus VP1 genotype GI.1 (SEQ ID NO:1) has been mutated, for example, to serine, asparagine, cysteine, threonine, alanine, lysine, or histidine, and the amino acids corresponding to positions 39-46 of norovirus VP1 genotype GI.1 have been mutated to the peptide sequence SSTAVATA (SEQ ID NO:168; GII.4_P80S+SSTAVATA; SEQ ID NO:77, FIG. 32Y), or a sequence that exhibits from about 80-100% or any amount therebetween, sequence similarity with the amino acid sequence of the mut GII.4_P80S+SSTAVATA VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4 P80S+SSTAVATA VP1 protein (SEQ ID NO:77, FIG. 32Y), provided that the position corresponding to amino acid 84 or norovirus VP1 genotype GI.1 remains an S, N, C, T, A, K, or H, for example serine, asparagine, cysteine, threonine, alanine, lysine, or histidine, and the positions corresponding to amino acids 39-46 of norovirus VP1 genotype GI.1 remain the peptide sequence SSTAVATA, and that the GII.4_P80X+SSTAVATA VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.6_E80S VP1 (GII.6_E80X, where X=S, N, C or T, VP1): wherein the glutamic acid corresponding to amino acid 84 of norovirus VP1 genotype GI.1 (SEQ ID NO:1) has been mutated, for example, to serine (GII.6_E80S; SEQ ID NO:79, FIG. 33A), or a sequence that exhibits from about 80-100% or any amount therebetween, sequence similarity with the amino acid sequence of the GII.6_E80S VP1 protein. For example, the GII.6 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.6_E80S VP1 protein (SEQ ID NO:79, FIG. 33A), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GII.6 VP1 may be obtained from any GII.6 strain, for example, but not limited to GII.6/Ohio/490/2012/USA (SEQ ID NO:20, amino acid; SEQ ID NO:21, nucleotide; FIGS. 21A and 21B).

GII.6_S90L VP1 (GII.6_590X, where X=L, I, M, A or V, VP1): wherein the serine corresponding to amino acid 94 of norovirus VP1 genotype GI.1 (SEQ ID NO:1) has been mutated, for example, to leucine (GII.6_S90L; SEQ ID NO:81, FIG. 33C), or a sequence that exhibits from about 80-100% or any amount therebetween, sequence similarity with the amino acid sequence of the GII.6_S90L VP1 protein. For example, the GII.6 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.6_S90L VP1 protein (SEQ ID NO:81, FIG. 33C), provided that the substitution, modification or mutation at the position corresponding to amino acid 94 of norovirus VP1 genotype GI.1 remains an L, I, M or V, for example leucine, and provided that the VP1 protein induces immunity to norovirus when administered to a subject. The sequence encoding the GII.6 VP1 may be obtained from any GII.6 strain, for example, but not limited to GII.6/Ohio/490/2012/USA (SEQ ID NO:20, amino acid; SEQ ID NO:21, nucleotide; FIGS. 21A and 21B).

GII.6_E80S+S90L VP1 (GII.6_E80X, where X=S, N, C or T+S90X, where X=L, I, M, A or V, VP1): wherein the glutamic acid and serine corresponding to amino acids 84 and 94, respectively of norovirus VP1 genotype GI.1 (SEQ ID NO:1) have been mutated, for example, to serine and leucine, respectively (GII.6_E80S+S90L; SEQ ID NO:83, FIG. 33E), or a sequence that exhibits from about 80-100% or any amount therebetween, sequence similarity with the amino acid sequence of the GII.6_E80S+S90L VP1 protein. For example, the GII.6 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.6_E80S+S90L VP1 protein (SEQ ID NO:83, FIG. 33E), provided that the substitutions, modifications or mutations at the positions corresponding to amino acids 84 and 94 of norovirus VP1 genotype GI.1 remain an S, N, C or T, for example serine, and an L, I, M, A or V, for example leucine, respectively, and provided that the VP1 protein induces immunity to norovirus when administered to a subject. The sequence encoding the GII.6 VP1 may be obtained from any GII.6 strain, for example, but not limited to GII.6/Ohio/490/2012/USA (SEQ ID NO:20, amino acid; SEQ ID NO:21, nucleotide; FIGS. 21A and 21B).

GII.12_E80S VP1 (GII.12_E80X, where X=S, N, C or T, VP1): wherein the glutamic acid corresponding to amino acid 84 of norovirus VP1 genotype GI.1 (SEQ ID NO:1) has been mutated, for example, to serine (GII.12_E80S; SEQ ID NO:88, FIG. 34A), or a sequence that exhibits from about 80-100% or any amount therebetween, sequence similarity with the amino acid sequence of the GII.12_E80S VP1 protein. For example, the GII.12 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.12_E80S VP1 protein (SEQ ID NO:88, FIG. 34A), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GII.12 VP1 may be obtained from any GII.12 strain, for example, but not limited to GII.12/HS206/2010/USA (SEQ ID NO:19, amino acid; FIG. 23A).

GII.12_A90L VP1 (GII.12_A90X, where X=L, I, M or V, VP1): wherein the alanine corresponding to amino acid 94 of norovirus VP1 genotype GI.1 (SEQ ID NO:1) has been mutated, for example, to leucine (GII.12_A90L; SEQ ID NO:90, FIG. 34C), or a sequence that exhibits from about 80-100% or any amount therebetween, sequence similarity with the amino acid sequence of the GII.12_A90L VP1 protein. For example, the GII.12 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.12_A90L VP1 protein (SEQ ID NO:90, FIG. 34C), provided that the substitution, modification or mutation at the position corresponding to amino acid 94 of norovirus VP1 genotype GI.1 remains an L, I, M or V, for example leucine, and provided that the VP1 protein induces immunity to norovirus when administered to a subject. The sequence encoding the GII.12 VP1 may be obtained from any GII.12 strain, for example, but not limited to GII.12/HS206/2010/USA (SEQ ID NO:19, amino acid; FIG. 23A).

GII.12_E80S+A90L VP1 (GII.12_E80X, where X=S, N, C or T+A90X, where X=L, I, M or V, VP1): wherein the glutamic acid and alanine corresponding to amino acids 84 and 94, respectively, of norovirus VP1 genotype GI.1 (SEQ ID NO:1) have been mutated, for example, to serine and leucine, respectively (GII.12_E80S+A90L; SEQ ID NO:92, FIG. 34E), or a sequence that exhibits from about 80-100% or any amount therebetween, sequence similarity with the amino acid sequence of the GII.12_E80S+A90L VP1 protein. For example, the GII.12 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.12_E80S+A90L VP1 protein (SEQ ID NO:92, FIG. 34E), provided that the substitutions, modifications or mutations at the positions corresponding to amino acids 84 and 94 of norovirus VP1 genotype GI.1 remain an S, N, C or T, for example serine, and an L, I. M or V, for example leucine, respectively, and provided that the VP1 protein induces immunity to norovirus when administered to a subject. The sequence encoding the GII.12 VP1 may be obtained from any GII.12 strain, for example, but not limited to GII.12/HS206/2010/USA (SEQ ID NO:19, amino acid; FIG. 23A).

GII.17_A39V VP1 (GII.17_A39X, where X=V, I, L or M, VP1): wherein the alanine corresponding to amino acid 43 of norovirus VP1 genotype GI.1 (SEQ ID NO:1) has been mutated, for example, to valine (GII.17_A39V; SEQ ID NO:192, FIG. 34G), or a sequence that exhibits from about 80-100% or any amount therebetween, sequence similarity with the amino acid sequence of the GII.17_A39V VP1 protein. For example, the GII.17 VP1 protein may have from about 0, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.17_A39V VP1 protein (SEQ ID NO:192, FIG. 34G), provided that the substitution, modification or mutation at the position corresponding to amino acid 43 of norovirus VP1 genotype GI.1 remains a V, I, L or M, for example valine, and provided that the VP1 protein induces immunity to norovirus when administered to a subject. The sequence encoding the GII.17 VP1 may be obtained from any GII.17 strain, for example, but not limited to Hu/GII.17/Kawasaki323/2014/JP (SEQ ID NO:24, amino acid; SEQ ID NO:25, nucleotide; FIGS. 26A and 26B).

GII.17_R53I VP1 (GII.17_R53I, where X=I, L, V, A or M, VP1): wherein the arginine corresponding to amino acid 57 of norovirus VP1 genotype GI.1 (SEQ ID NO:1) has been mutated, for example, to isoleucine (GII.17_R53I; SEQ ID NO:194, FIG. 34I), or a sequence that exhibits from about 80-100% or any amount therebetween, sequence similarity with the amino acid sequence of the GII.17_R53I VP1 protein. For example, the GII.17 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.17_R53I VP1 protein (SEQ ID NO:194, FIG. 34I), provided that the substitution, modification or mutation at the position corresponding to amino acid 57 of norovirus VP1 genotype GI.1 remains an I, L, V, A or M, for example isoleucine, and provided that the VP1 protein induces immunity to norovirus when administered to a subject. The sequence encoding the GII.17 VP1 may be obtained from any GII.17 strain, for example, but not limited to Hu/GII.17/Kawasaki323/2014/JP (SEQ ID NO:24, amino acid; SEQ ID NO:25, nucleotide; FIGS. 26A and 26B).

GII.17_A90L VP1 (GII.4_A90X, where X=L, I, M or V, VP1): wherein the serine corresponding to amino acid 94 of norovirus VP1 genotype GI.1 (SEQ ID NO:1) has been mutated, for example, to leucine (GII.17_A90L; SEQ ID NO:196, FIG. 34K), or a sequence that exhibits from about 80-100% or any amount therebetween, sequence similarity with the amino acid sequence of the GII.17_A90L VP1 protein. For example, the GII.17 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.17_A90L VP1 protein (SEQ ID NO:196, FIG. 34K), provided that the substitution, modification or mutation at the position corresponding to amino acid 94 of norovirus VP1 genotype GI.1 remains an L, I, M or V, for example leucine, and provided that the VP1 protein induces immunity to norovirus when administered to a subject. The sequence encoding the GII.17 VP1 may be obtained from any GII.17 strain, for example, but not limited to Hu/GII.17/Kawasaki323/2014/JP (SEQ ID NO:24, amino acid; SEQ ID NO:25, nucleotide; FIGS. 26A and 26B).

GII.17_A39V+R53I VP1 (GII.17_A39X, where X=V, I, L or M+R53X, where X=I, L, M, A or V, VP1): wherein the alanine and arginine corresponding to amino acids 43 and 57, respectively, of norovirus VP1 genotype GI.1 (SEQ ID NO:1) have been mutated, for example, to valine and isoleucine, respectively (GII.17_A39V+R53I; SEQ ID NO:198, FIG. 34M), or a sequence that exhibits from about 80-100% or any amount therebetween, sequence similarity with the amino acid sequence of the GII.17_A39V+R53I VP1 protein. For example, the GII.17 VP1 protein may have from about 0, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.17_A39V+R53I VP1 protein (SEQ ID NO:198, FIG. 34M), provided that the substitutions, modifications or mutations at the positions corresponding to amino acid 43 and 57 of norovirus VP1 genotype GI.1 remain a V, I, L or M, for example valine, and an I, L, M, V or A, for example isoleucine, respectively, and provided that the VP1 protein induces immunity to norovirus when administered to a subject. The sequence encoding the GII.17 VP1 may be obtained from any GII.17 strain, for example, but not limited to Hu/GII.17/Kawasaki323/2014/JP (SEQ ID NO:24, amino acid; SEQ ID NO:25, nucleotide; FIGS. 26A and 26B).

GII.17_E80S+A90L VP1 (GII.4_E80X, where X=S, N, C or T+A90X, where X=L, I, M or V, VP1): wherein the glutamic acid and alanine corresponding to amino acids 84 and 94, respectively, of norovirus VP1 genotype GI.1 (SEQ ID NO:1) have been mutated, for example, to serine and leucine, respectively (GII.17_E80S+A90L; SEQ ID NO:200, FIG. 34O), or a sequence that exhibits from about 80-100% or any amount therebetween, sequence similarity with the amino acid sequence of the GII.17_E80S+A90L VP1 protein. For example, the GII.17 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.17_E80S+A90L VP1 protein (SEQ ID NO:200, FIG. 34O), provided that the substitutions, modifications or mutations at the positions corresponding to amino acids 84 and 94 of norovirus VP1 genotype GI.1 remain an S, N, C or T, for example serine, and an L, I, M or V, for example leucine, respectively, and provided that the VP1 protein induces immunity to norovirus when administered to a subject. The sequence encoding the GII.17 VP1 may be obtained from any GII.17 strain, for example, but not limited to Hu/GII.17/Kawasaki323/2014/JP (SEQ ID NO:24, amino acid; SEQ ID NO:25, nucleotide; FIGS. 26A and 26B).

VLP Yield

Figure 5A:
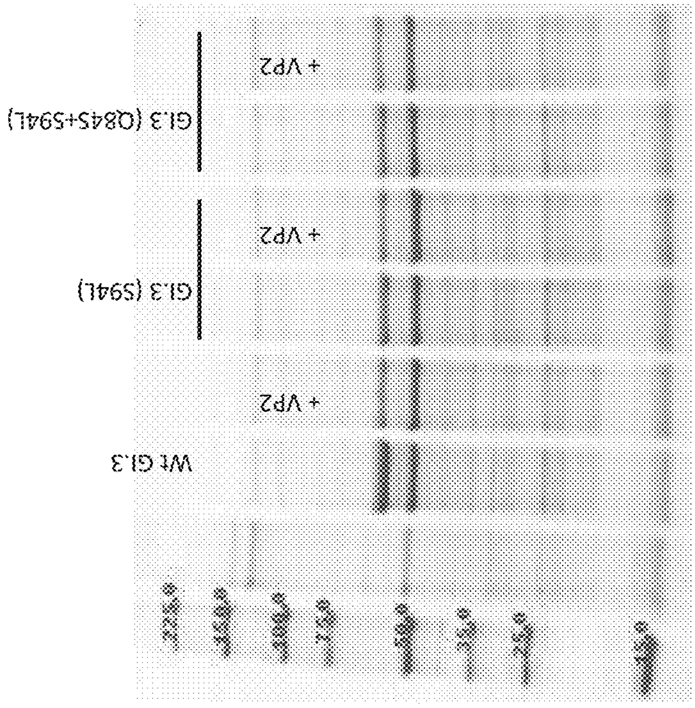
FIG. 5A shows a Coomassie-stained SDS-PAGE of crude protein extracts prepared from agroinfiltrated *N. benthamiana* leaves, 9 days post infiltration (DPI) with wt hCod GI.3/S29/2008/Lila Edet/Sweden VP1 (Construct #: 3979; SEQ ID NO:7 (nucleotide); SEQ ID NO:6 (amino acid)), mut hCod GI.3/S29/2008/Lila Edet/Sweden_S94L VP1 (Construct #: 4141; SEQ ID NO:9 (nucleotide); SEQ ID NO:8 (amino acid)), or mut hCod GI.3/S29/2008/Lila Edet/Sweden_Q84S+S94L VP1 (Construct #: 4142; SEQ ID NO:11 (nucleotide); SEQ ID NO:10 (amino acid)), with and without wt hCod GI.3/S29/2008/Lila Edet/Sweden VP2 (Construct #: 3303; SEQ ID NO:95 (nucleotide); SEQ ID NO:94 (amino acid)). First lane: crude protein extracts prepared from mock infiltrated *N. benthamiana* leaves.
Figure 5B:
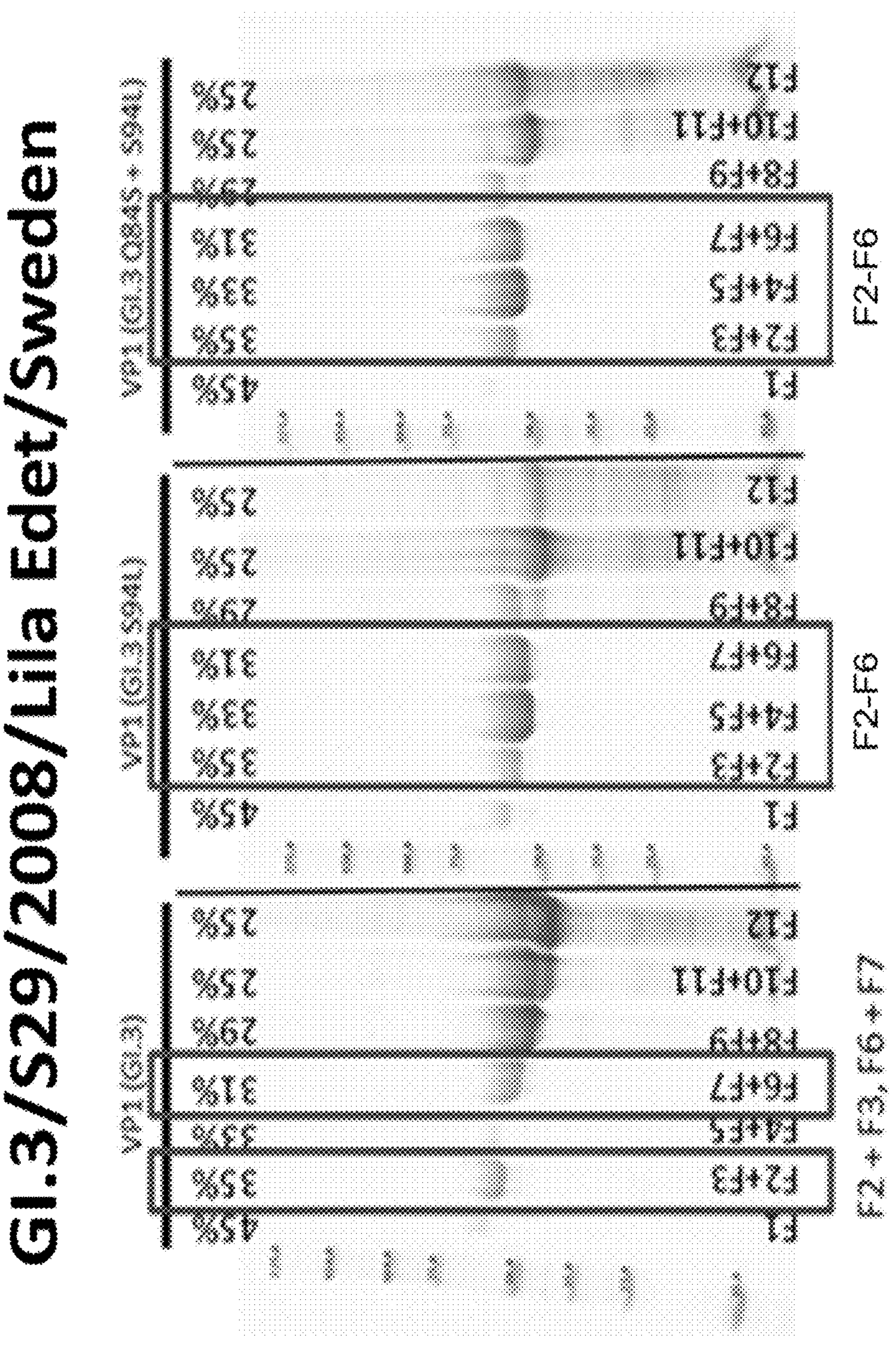
FIG. 5B shows a Coomassie-stained SDS-PAGE analysis of iodixanol density gradient fractions of crude protein extracts prepared from *N. benthamiana* leaves expressing wt hCod GI.3/S29/2008/Lila Edet/Sweden VP1 (Construct #: 3979, left panel), mut hCod GI.3/S29/2008/Lila Edet/Sweden VP1_S94L (Construct #: 4141, middle panel), or mut hCod GI.3/S29/2008/Lila Edet/Sweden VP1_Q84S+S94L (Construct #:4142, right panel).

An example of an improved characteristic of VP1 may be observed comparing the yields of VLPs comprising GI.3 VP1 protein is shown with reference to FIG. 5B (see Example 3). Expression of modified norovirus VP1 proteins GI.3_S94X, where X=L, V, I, M, T, E, D, N, Q, K, or H (see FIG. 5F), GI.3_M57I+S94L (see FIG. 5D), and GI.3_Q84S+S94L (see FIG. 5B) in plants resulted in similar or higher VLPs yields as compared to the yield of wildtype GI.3 VP1. Furthermore, expression of modified norovirus VP1 proteins GI.7_M57X, where X=I, L, G, S, T, N, Q, K, or H (see FIG. 6F) in plants resulted in similar or higher VLPs yields as compared to the yield of wildtype GI.7 VP1.

An analogous improved characteristic of increased VLP yield is shown with reference to FIGS. 9A-9E, and 9H. VLPs comprising norovirus modified VP1 proteins GII.4_R53I (FIG. 9D), GII.4_P80X, where X=S, A, N, K, or H (FIGS. 9B and 9H), GII.4_P80S+R53I (FIG. 9D), GII.4_P80S+A39X, where X=V, I, M, T, E, D, N, Q, K, or H (FIGS. 9C and 9I), GII.4_P80S+S90L (FIG. 9B), GII.4_P80S+Δ35-42 (FIG. 9C), GII.4_P80S+SSTAVATA (FIG. 9F), and GII.4_A39V+R53I P80S (FIG. 9G), exhibited enhanced VLP yield in plants, while GII.4_A39V and GII.4_V47P exhibited a slight increase in protein yield, as compared to VLPs comprising wildtype GII.4 VP1.

Figure 10A:
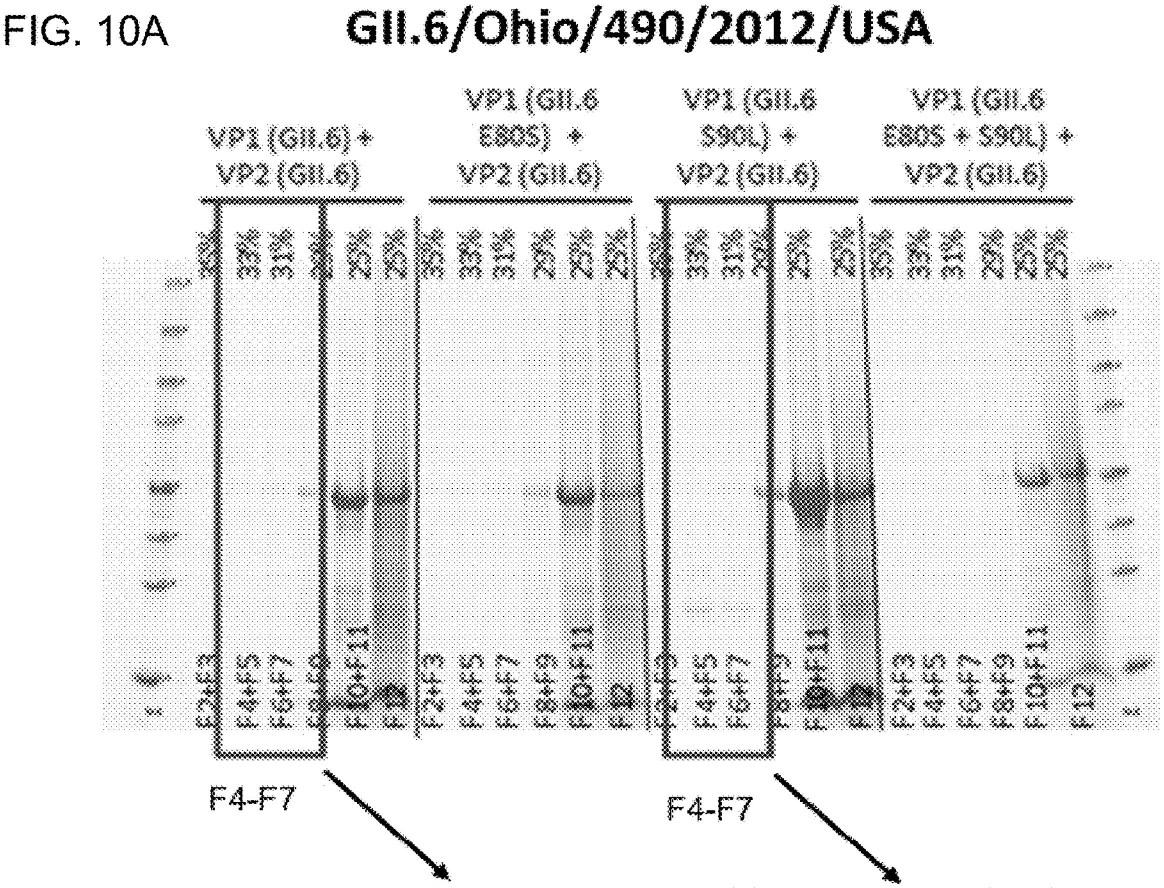
FIG. 10A shows a Coomassie-stained SDS-PAGE analysis of iodixanol density gradient fractions of crude protein extracts prepared from *N. benthamiana* leaves expressing wt hCod GII.6/Ohio/490/2012/USA VP1 (Construct #: 3993; SEQ ID NO:21 (nucleotide); SEQ ID NO: 20 (amino acid)) and wt hCod GII.6/HS245/2010/USA VP2 (Construct #: 3307; SEQ ID NO:97 (nucleotide); SEQ ID NO:96 (amino acid)), mut hCod GII.6/Ohio/490/2012/USA_E80S VP1 (Construct #: 4149; SEQ ID NO:80 (nucleotide); SEQ ID NO:79 (amino acid)) and wt hCod GII.6/HS245/2010/USA VP2 (Construct #: 3307), mut hCod GII.6/Ohio/490/2012/USA_S90L VP1 (Construct #: 4150; SEQ ID NO:82 (nucleotide); SEQ ID NO:81 (amino acid))) and wt hCod GII.6/HS245/2010/USA VP2 (Construct #3307), or mut hCod GII.6/Ohio/490/2012/USA_E80S+S90L VP1 (Construct #: 4151; SEQ ID NO:84 (nucleotide); SEQ ID NO:83 (amino acid)) and wt hCod GII.6/HS245/2010/USA VP2 (Construct #: 3307).
Figure 10B:
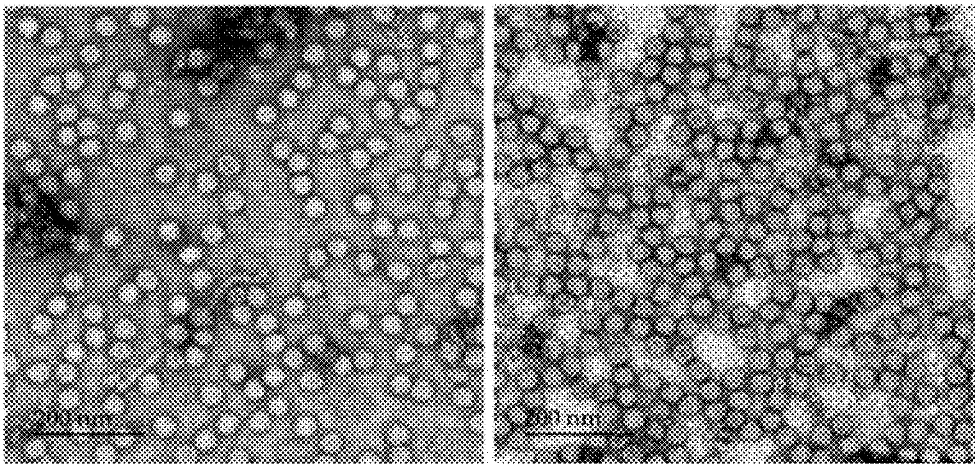
FIG. 10B shows transmission electron micrographs (TEM) of virus like particles (VLPs) purified from 31-35% iodixanol gradient fractions of crude protein extracts prepared from *N. benthamiana* leaves expressing wt hCod GII.6/Ohio/490/2012/USA VP1 (Construct #: 3993) and wt hCod GII.6/HS245/2010/USA VP2 (Construct #: 3307), mut hCod GII.6/Ohio/490/2012/USA_S90L VP1 (Construct #: 4150) and wt hCod GII.6/HS245/2010/USA VP2 (Construct #: 3307). 15,000× magnification; scale bar=200 nm.

Increased VLP yield, compared to wild type was also observed in plant extracts expressing GII.6_S90L VP1 (FIGS. 10A and 10B).

Figure 8A:
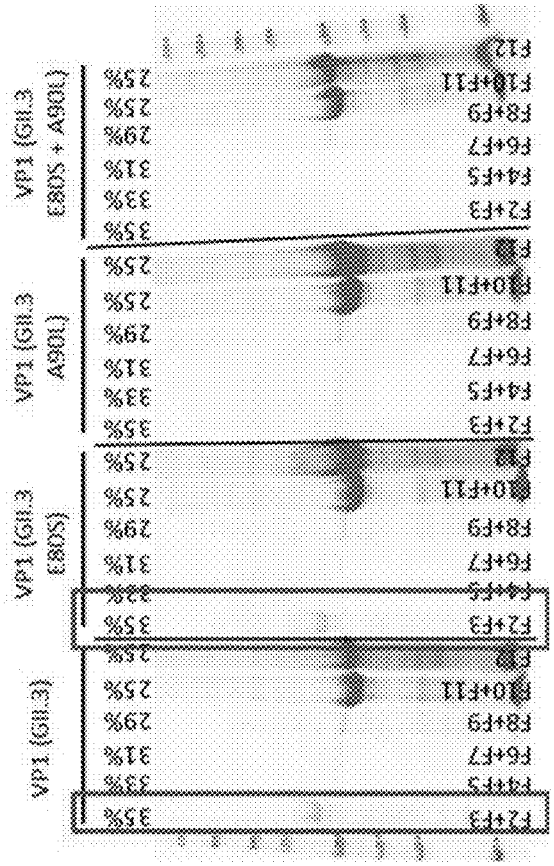
FIG. 8A shows a Coomassie-stained SDS-PAGE analysis of iodixanol density gradient fractions of crude protein extracts prepared from *N. benthamiana* leaves expressing, from left to right, wt hCod GII.3/Jingzhou/2013402/CHN VP1 (Construct #: 3983; SEQ ID NO:45 (nucleotide); SEQ ID NO: 15 (amino acid; first panel)), mut hCod GII.3/Jingzhou/2013402/CHN_E80S VP1 (Construct #: 4146; SEQ ID NO:47 (nucleotide); SEQ ID NO:46 (amino acid; second panel)), mut hCod GII.3/Jingzhou/2013402/CHN_A90L VP1 (Construct #: 4147; SEQ ID NO:49 (nucleotide); SEQ ID NO:48 (amino acid; third panel)), or mut hCod GII.3/Jingzhou/2013402/CHN_E80S+A90L VP1 (Construct #: 4148, SEQ ID NO:51 (nucleotide); SEQ ID NO:50 (amino acid; fourth panel)).

VLPs comprising modified VP1 protein with a substitution of an amino acid at position 84 (GI strains) or position 80 (GII strains, corresponding to, or in alignment with, position 84 of GI.1 VP1) exhibited the same (GI.3_Q84S; GI.5_Q84S, also see FIG. 6B; GII.3_E80S, also see FIG. 8A), or an increased (GI.7_R84S; GI.7_M57I+R84S; also see FIG. 6D; GII.4_P80S also see FIGS. 9B-9F; GII.12_E80S) VLP yield when compared to the yield of VLPs comprising the corresponding wild type (native) VP1 protein.

Figure 5C:
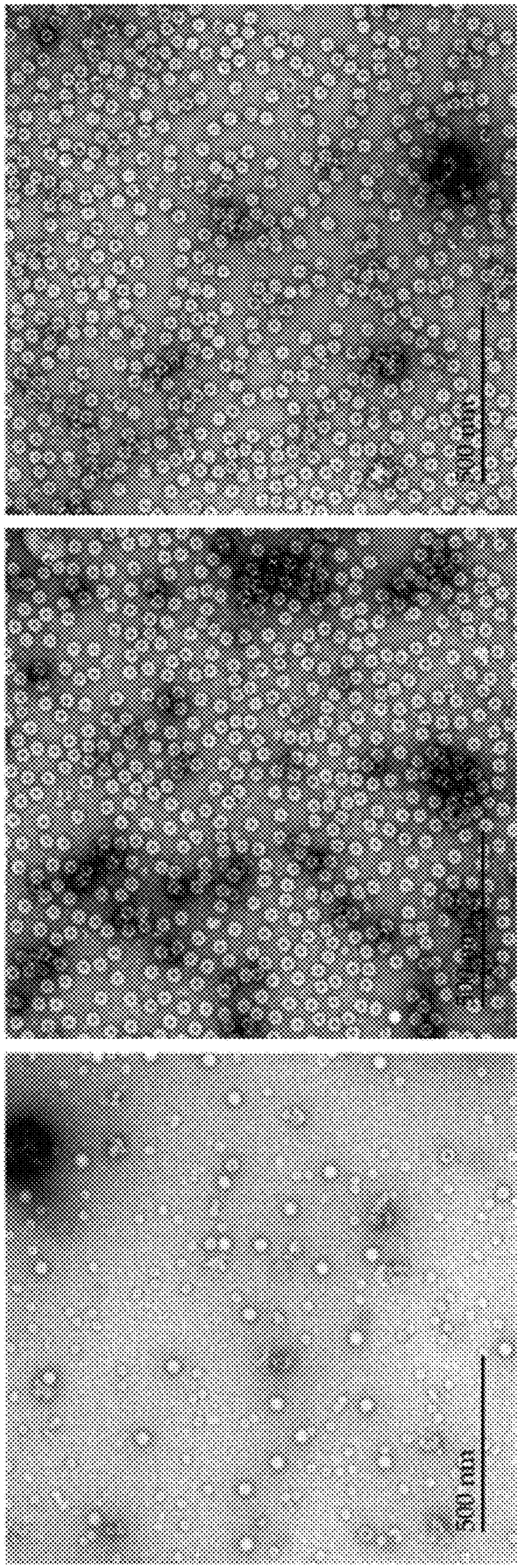
FIG. 5C shows transmission electron micrographs (TEM) of virus like particles (VLPs) purified from 31-35% iodixanol gradient fractions of crude protein extracts prepared from *N. benthamiana* leaves expressing wt hCod GI.3/S29/2008/Lila Edet/Sweden VP1 (Construct #: 3979, left panel; fractions F2+F3, F6+F7 of FIG. 5B), mut hCod GI.3/S29/2008/Lila Edet/Sweden VP1_S94L (Construct #: 4141, middle panel; fractions F2-F6 of FIG. 5B), or mut hCod GI.3/S29/2008/Lila Edet/Sweden VP1_Q84S+S94L (Construct #: 4142, right panel; fractions F2-F6 of FIG. 5B). 15,000× magnification; scale bar=500 nm.
Figure 5D:
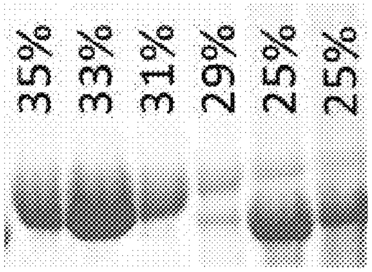
FIG. 5D shows a Coomassie-stained SDS-PAGE of crude protein extracts prepared from agroinfiltrated *N. benthamiana* leaves, 9 days post infiltration (DPI) with mut hCod GI.3/S29/2008/Lila Edet/Sweden_M57I+S94L VP1 (Construct #:4180; SEQ ID NO:171 (nucleotide); SEQ ID NO:172 (amino acid)).
Figure 5E:
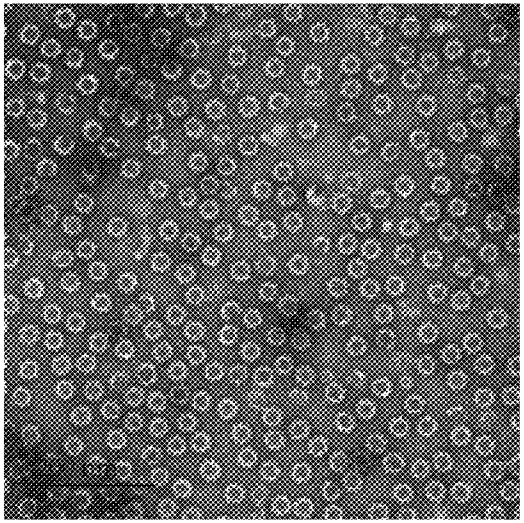
FIG. 5E shows transmission electron micrographs (TEM) of virus like particles (VLPs) purified from 31-35% iodixanol gradient fractions of crude protein extracts prepared from *N. benthamiana* leaves expressing mut hCod GI.3/S29/2008/Lila Edet/Sweden_M57I+S94L VP1 (Construct #: 4180); 15,000× magnification; scale bar=500 nm.
Figure 5F:
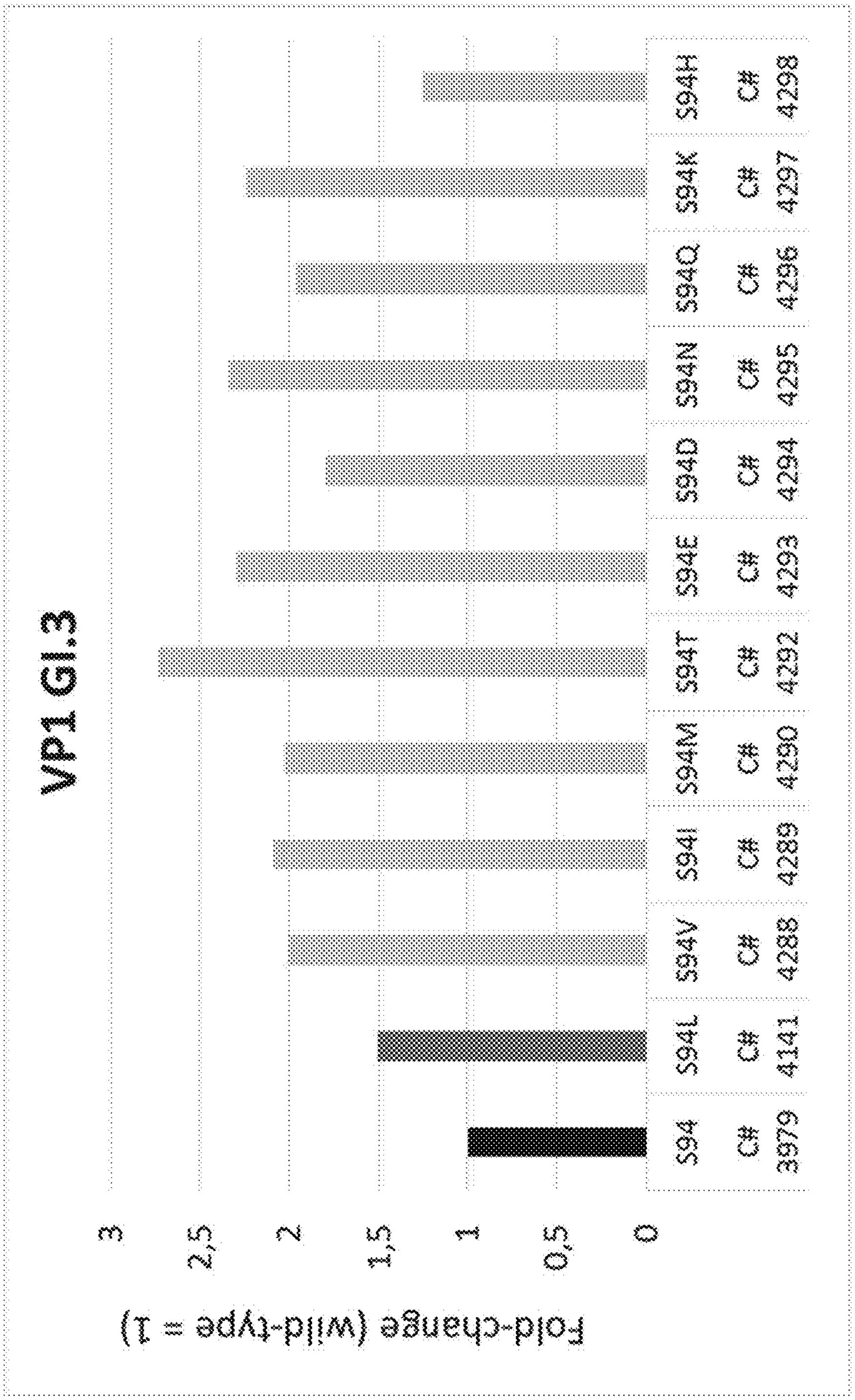
FIG. 5F shows the relative yield of VLPs comprising non-native VP1 GI.3 with substitutions at amino acid position 94, compared to the VLP yield of wild-type GI.3 (GI.3 S94; set as "Fold Change" of 1): C #: construct number.

VLPs comprising modified VP1 protein with a substitution of an amino acid at position 94 (GI strains) or at position 90 (GII strains, corresponding to, or in alignment with, position 94 of GI.1 VP1) exhibited the same or an increase in VLP yield when compared to the yield of VLPs comprising the corresponding wild type, or native, VP1 protein, for all modified VP1 proteins that were examined (GI.3_S94X, where X=L, V, I, M, T, E, D, N, Q, K, or H (FIGS. 5B and 5F); GI.5_A94L (see FIG. 6B); GII.2_A90L (see FIG. 7B); GII.4_S90L (see FIG. 9B); GII.6_S90L (see FIG. 10A); GII.12_A90L (see FIG. 11B); and GII.17_A90L (see FIG. 11D).

Similarly, VLPs comprising modified VP1 protein with a substitution of an amino acid at positions 84 and 94 (GI strains) or positions 80 and 90 (GII strains, corresponding to, or in alignment with, position 84 and 94 of GI.1 VP1) exhibited an increase in VLP yield when compared to the yield of VLPs comprising the corresponding wild type, or native, VP1 protein, for all modified VP1 proteins that were examined (GI.3_Q84S+S94L, also see FIG. 5B; GI.5_Q84S+A94L, also see FIG. 6B; GII.2_E80S+A90L, also see FIGS. 7B and 7C; GII.4_P80S+S90L, also see FIG. 9B; and GII.2_E80S+A90L, also see FIG. 11B).

Figure 9A:
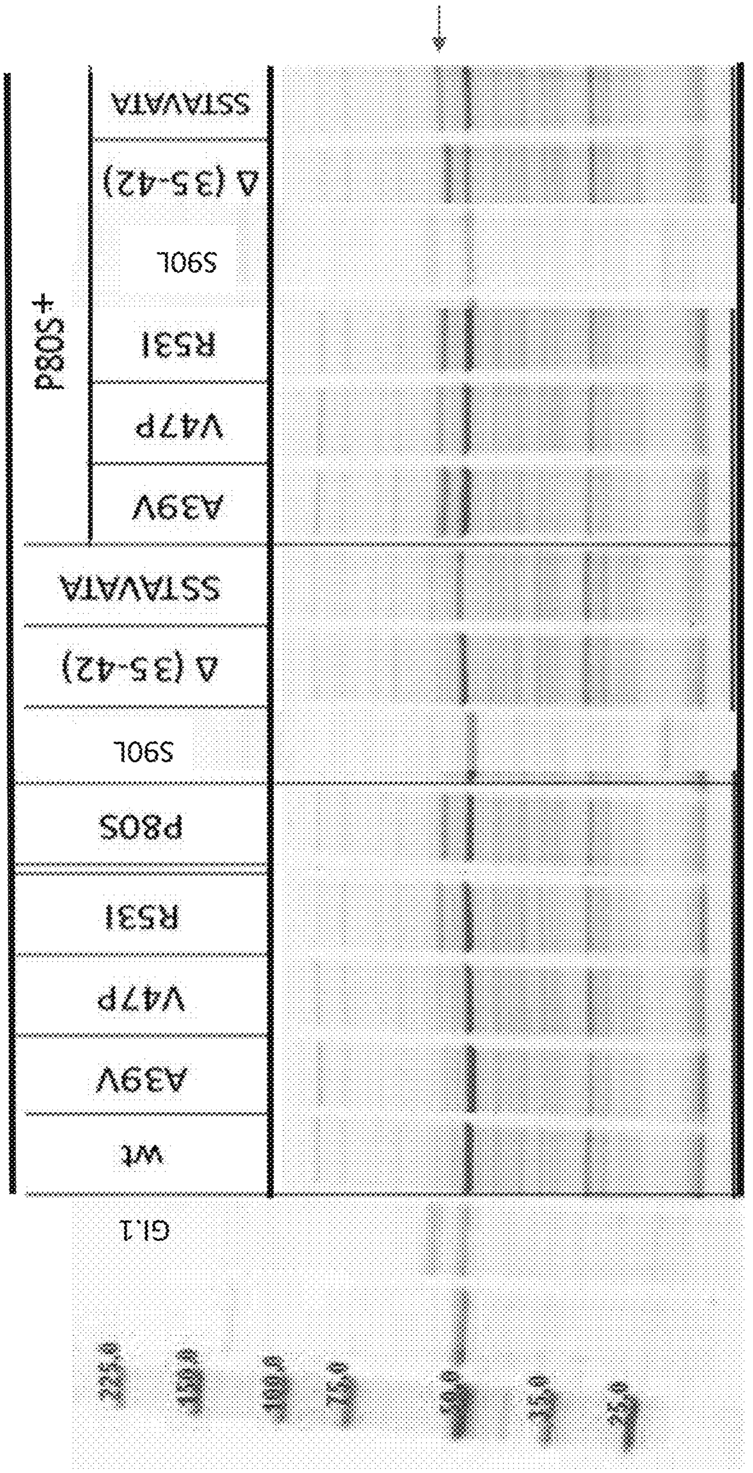
FIG. 9A shows a Coomassie-stained SDS-PAGE of crude protein extracts prepared from agroinfiltrated *N. benthamiana* leaves, 9 days post infiltration (DPI) with wt GI.1/United States/Norwalk/1968 VP1 (Construct #: 2724; SEQ ID NO:3 (nucleotide); SEQ ID NO:1 (amino acid)), wt hCod GII.4/Sydney/NSW0514/2012/AU VP1 (Construct #: 3760; SEQ ID NO:52 (nucleotide); SEQ ID NO:16 (amino acid)), mut hCod GII.4/Sydney/NSW0514/2012/AU_A39V VP1 (Construct #: 4155; SEQ ID NO:54 (nucleotide); SEQ ID NO:53 (amino acid)), mut hCod GII.14/Sydney/NSW0514/2012/AU_V47P VP1 (Construct #: 4156; SEQ ID NO:56 (nucleotide); SEQ ID NO:55 (amino acid)), mut hCod GII.14/Sydney/NSW0514/2012/AU_R53I VP1 (Construct #: 4157; SEQ ID NO:58 (nucleotide); SEQ ID NO:57 (amino acid)), mut hCod GII.14/Sydney/NSW0514/2012/AU_P80S VP1 (Construct #: 4133; SEQ ID NO:60 (nucleotide); SEQ ID NO:59 (amino acid)), mut hCod GII.14/Sydney/NSW0514/2012/AU_S90L VP1 (Construct #: 4134; SEQ ID NO:62 (nucleotide); SEQ ID NO:61 (amino acid)), mut hCod GII.14/Sydney/NSW0514/2012/AU_Δ35-42 VP1 (Construct #: 4158; SEQ ID NO:64 (nucleotide); SEQ ID NO:63 (amino acid)), mut hCod GII.14/Sydney/NSW0514/2012/AU_SSTAVATA VP1 (Construct #: 4159; SEQ ID NO:66 (nucleotide); SEQ ID NO:65 (amino acid)), mut hCod GII.14/Sydney/NSW0514/2012/AU_P80S+A39V (Construct #: 4165; SEQ ID NO:68 (nucleotide); SEQ ID NO:67 (amino acid)), mut hCod GII.14/Sydney/NSW0514/2012/AU_P80S+V47P VP1 (Construct #: 4166; SEQ ID NO:70 (nucleotide); SEQ ID NO:69 (amino acid)), mut hCod GII.14/Sydney/NSW0514/2012/AU_P80S+R53I VP1 (Construct #: 4167; SEQ ID NO:72 (nucleotide); SEQ ID NO:71 (amino acid)), mut hCod GII.14/Sydney/NSW0514/2012/AU_P80S+S90L VP1 (Construct #: 4135; SEQ ID NO:74 (nucleotide); SEQ ID NO:73 (amino acid)), mut hCod GII.14/Sydney/NSW0514/2012/AU_P80S+Δ35-42 VP1 (Construct #: 4168; SEQ ID NO:76 (nucleotide); SEQ ID NO:75 (amino acid)), or mut hCod GII.14/Sydney/NSW0514/2012/AU_P80S+SSTAVATA VP1 (Construct #: 4169; SEQ ID NO:78 (nucleotide); SEQ ID NO:77 (amino acid)). Arrow: VP1 norovirus protein; First lane=crude protein extracts prepared from mock infiltrated *N. benthamiana* leaves.

Additional modifications were also observed to increase VLP yield. These modifications include GI.3_M57I+594L (FIG. 5D), GI.7_M57I (FIG. 6D), GI.7_M57I+R84S (FIG. 6D), GII.2_A39V+E80S+A90L (FIG. 7C), GII.2_R53I+E80S+A90L (FIG. 7C), GII.4_R53I (FIG. 9D), GII.4_A39V+P80X, where X=S, A, N, K, or H (FIGS. 9C and 9I); GII.4_R53I+P80S (FIG. 9D); GII.4_V47P+P80S (FIG. 9E); GII.4_Δ35-42+P80S (FIG. 9C), and GII.4_A39V+R53I+P80S (FIG. 9G).

Size, Density, Stability and Quality of VLPs

As shown in FIG. 5B, mutant norovirus VP1 proteins GI.3_S94L and GI.3_Q84S+S94L, exhibited the improved characteristic of VLPs having greater densities (determined by Coomassie stained SDS PAGE of iodixanol density gradient fractions of protein extracts), so that the VLPs are observed in fraction 1 (F1) and peaking in fractions F2-F6 as compared to wildtype norovirus GI.3 VP1. These results indicate that the assembly of native GI.3 VLPs may be less stable than GI.3_S94L VLPs and the native GI.3 VLP may be more susceptible to malformed capsid particles and the generation of fragmentation products. As a result, the VLPs comprising GI.3_S94L VP1, GI.3_M57I+S94L and GI.3_Q84S+S94L VP1 exhibit greater structural integrity than wildtype GI.3 VP1. It is also observed that VLPs comprising GI.3_S94L VP1, GI.3_M57I+S94L and GI.3_Q84S+S94L VP1 comprise a greater relative proportion of 38 nm diameter VLPs vs. 23 nm diameter VLPs than wildtype (FIGS. 5C and 5E) as determined using transmission electron micrography (TEM).

Figure 6A:
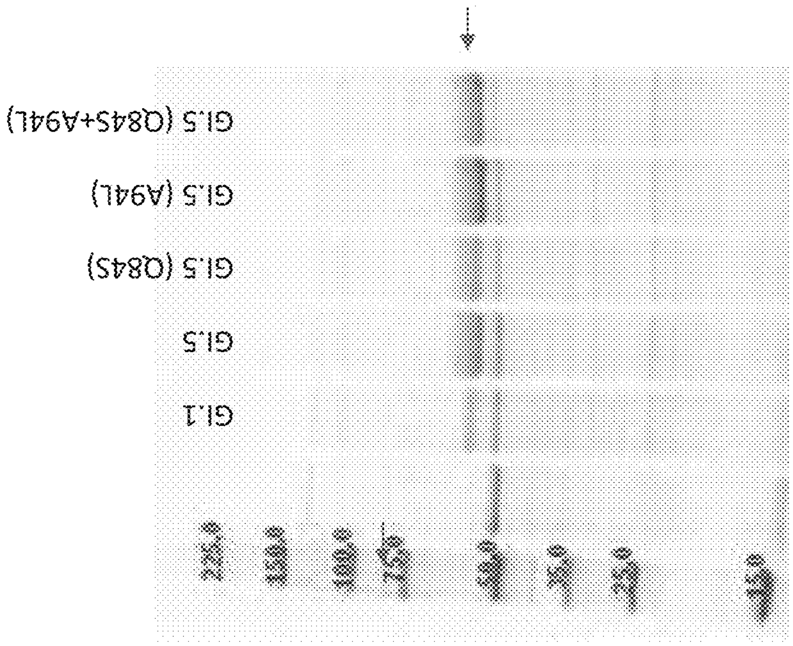
FIG. 6A shows a Coomassie-stained SDS-PAGE of crude protein extracts prepared from agroinfiltrated *N. benthamiana* leaves, 9 days post infiltration (DPI) with wt hCod GI.1/United States/Norwalk/1968 VP1 (Construct #:2724; SEQ ID NO:3 (nucleotide); SEQ ID NO:1 (amino acid)), wt hCod GI.5/Siklos/HUN5407/2013/HUN VP1 (Construct #: 3980; SEQ ID NO:33 (nucleotide); SEQ ID NO:12 (amino acid)), mut hCod GI.5/Siklos/HUN5407/2013/HUN_Q84S VP1 (Construct #: 4130; SEQ ID NO:35 (nucleotide); SEQ ID NO:34 (amino acid)), mut hCod GI.5/Siklos/HUN5407/2013/HUN_A94L VP1 (Construct #: 4131; SEQ ID NO:37 (nucleotide); SEQ ID NO:36 (amino acid)) or mut hCod GI.5/Siklos/HUN5407/2013/HUN_Q84S+A94L VP1 (Construct #: 4132; SEQ ID NO:39 (nucleotide); SEQ ID NO:38 (amino acid)). Arrow: VP1 norovirus protein; First lane=crude protein extracts prepared from mock infiltrated *N. benthamiana* leaves.
Figure 6B:
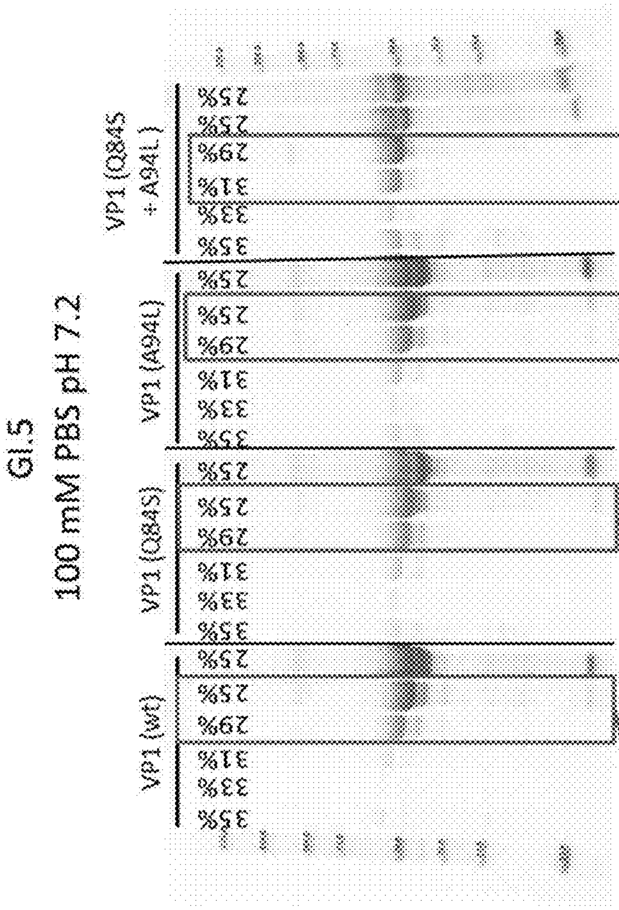
FIG. 6B shows a Coomassie-stained SDS-PAGE analysis of iodixanol density gradient fractions of crude protein extracts prepared from *N. benthamiana* leaves expressing, from left to right, wt hCod GI.5/Siklos/HUN5407/2013/HUN VP1 (Construct #3980), mut hCod GI.5/Siklos/HUN5407/2013/HUN_Q84S VP1 (Construct #: 4130, left panel), mut hCod GI.5/Siklos/HUN5407/2013/HUN_A94L VP1 (Construct #: 4131, middle panel), or mut HCod GI.5/Siklos/HUN5407/2013/HUN_Q84S+A94L VP1 (Construct #: 4132, right panel).
Figure 6C:
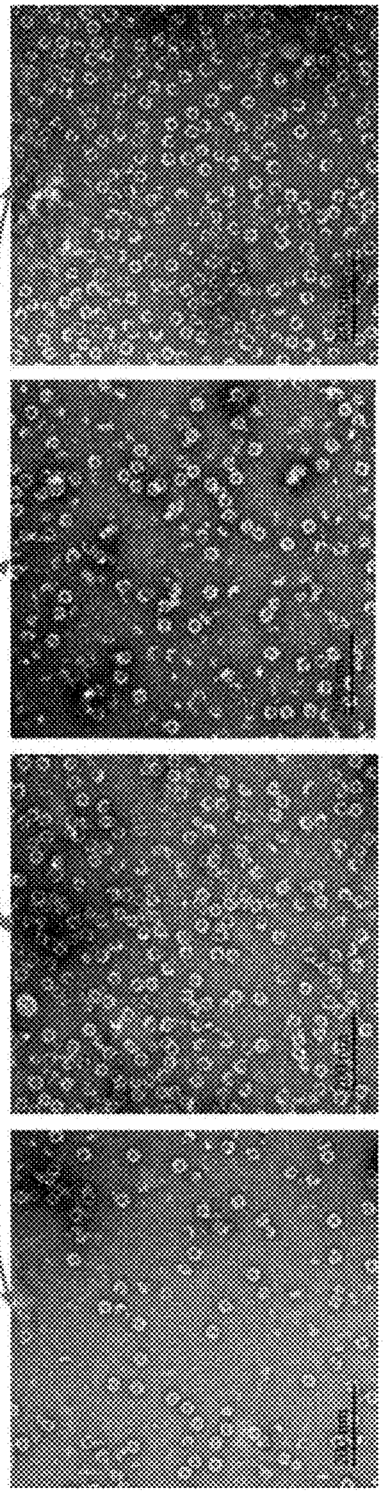
FIG. 6C shows transmission electron micrographs (TEM) of virus like particles (VLPs) purified from 31-35% iodixanol gradient fractions of crude protein extracts prepared from *N. benthamiana* leaves expressing, from left to right, wt hCod GI.5/Siklos/HUN5407/2013/HUN VP1 (Construct #3980), wt hCod GI.5/Siklos/HUN5407/2013/HUN_Q84S VP1 (Construct

VLPs comprising of GI.5_Q84S VP1, GI.5_A94L VP1, or GI.5_Q84S+A94L VP1 proteins exhibited an increase in yield, and GI.5_Q84S+A94L VP1 also exhibited greater density, stability and structural integrity (in a manner similar to that described above for VLPs produced using modified GI.3 VP1), as compared to wildtype norovirus GI.5 VP1 (FIG. 6B). As shown in FIG. 6C, the resulting VLPs had fewer damaged VLP particles, and a greater relative proportion of 38 nm diameter particles vs 23 nm diameter VLPs, as compared to wildtype.

Figure 6D:
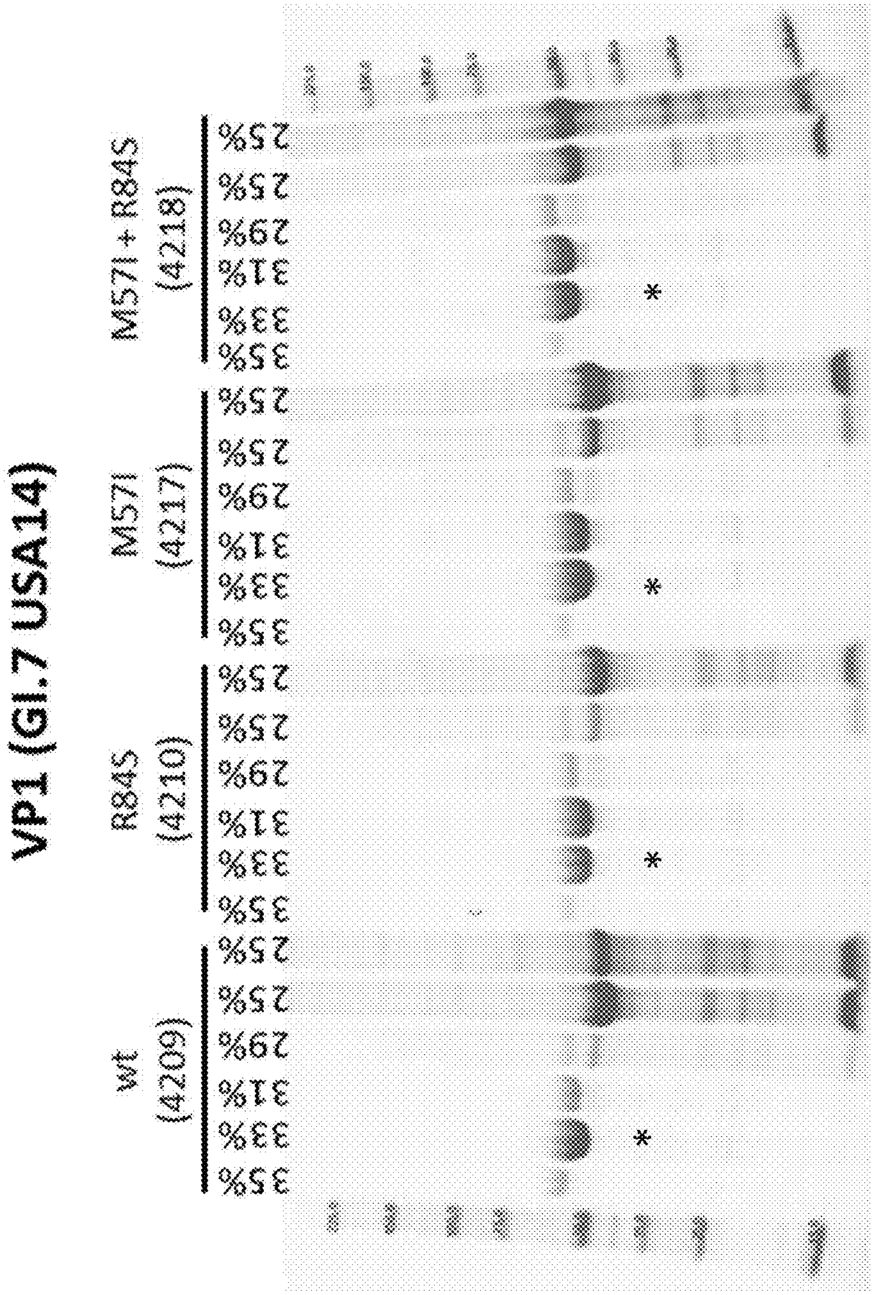
FIG. 6D shows a Coomassie-stained SDS-PAGE analysis of iodixanol density gradient fractions of crude protein extracts prepared from *N. benthamiana* leaves expressing, from left to right, wt hCod GI.7/GA5043/USA/2014 VP1 (Construct #4209; SEQ ID NO:101 (nucleotide); SEQ ID NO:204 (amino acid)), mut hCod GI.7/GA5043/USA/2014_R84S (Construct #4210; SEQ ID NO:176 (nucleotide); SEQ ID NO:177 (amino acid)), mut hCod GI.7/GA5043/USA/2014_M57I (Construct 4217; SEQ ID NO:178 (nucleotide); SEQ ID NO:179 (amino acid)), mut hCod GI.7/GA5043/USA/2014_M57I+R84S Construct #4218; SEQ ID NO:180 (nucleotide); SEQ ID NO:181 (amino acid)). * samples obtained for TEM analysis (see FIG. 6E).
Figure 6E:
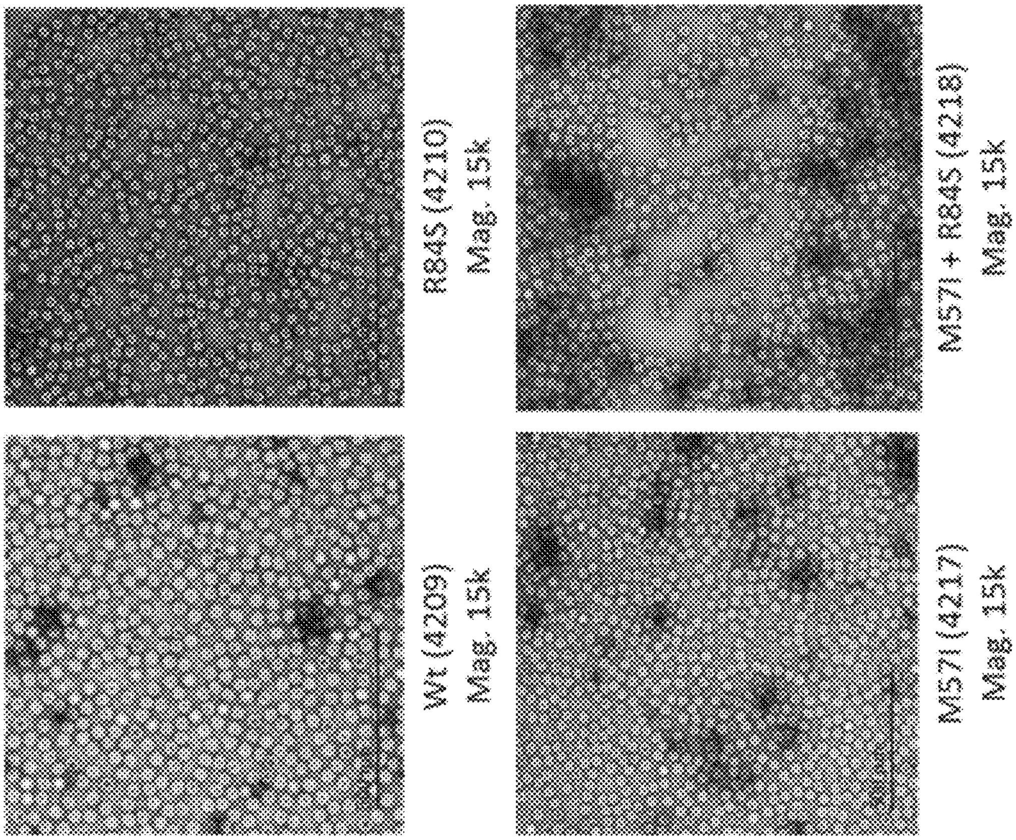
FIG. 6E shows transmission electron micrographs (TEM) of virus like particles (VLPs) purified from 31-35% iodixanol gradient fractions of crude protein extracts prepared from *N. benthamiana* leaves expressing, Top left: wt hCod GI.7/GA5043/USA/2014 VP1 (Construct #4209), Top right: mut hCod GI.7/GA5043/USA/2014_R84S (Construct #4210); Bottom left: mut hCod GI.7/GA5043/USA/2014_M57I (Construct 4217); Bottom Right mut hCod GI.7/GA5043/USA/2014_M57I+R84S Contract #4218). 15,000× magnification; scale bar=500 nm.

VLPs comprising of GI.7_R84S, GI.7_M57I, GI.7_M57I+R84S VP1 proteins were also observed to exhibit the same or greater density as compared to wildtype norovirus GI.7 VP1 (FIG. 6D). As shown in FIG. 6E, the modified VLPs had fewer damaged VLP particles, and a greater relative proportion of 38 nm diameter particles vs 23 nm diameter VLPs, as compared to wildtype.

Figure 7A:
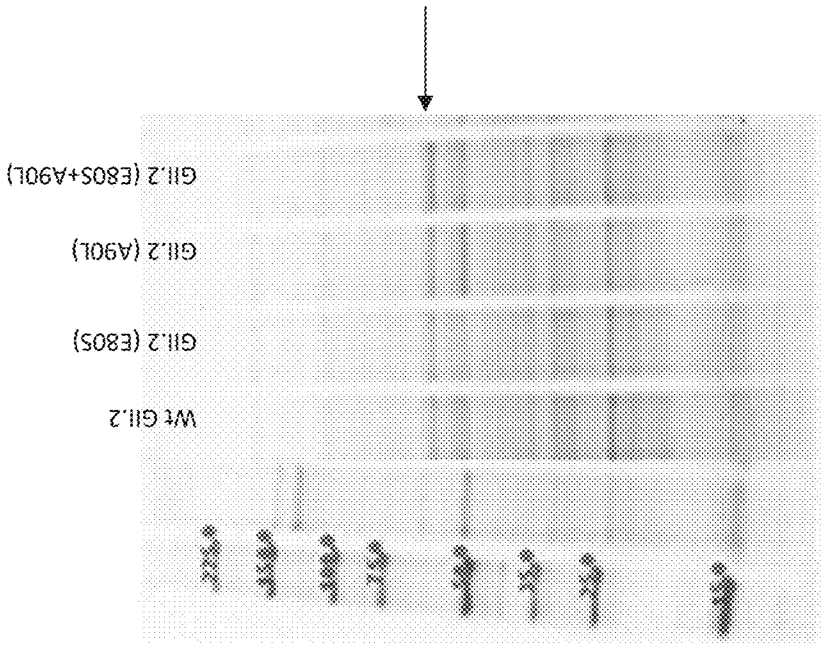
FIG. 7A shows a Coomassie-stained SDS-PAGE of crude protein extracts prepared from agroinfiltrated *N. benthamiana* leaves, 9 days post infiltration (DPI) with wt hCod GII.2/CGMH47/2011/TW VP1 (Construct #: 3982; SEQ ID NO:40 (nucleotide); SEQ ID NO:14 (amino acid)), mut hCod GII.2/CGMH47/2011/TW_E80S VP1 (Construct #: 4143; SEQ ID NO:86 (nucleotide); SEQ ID NO:85 (amino acid)), mut hCod GII.2/CGMH47/2011/TW_A90L VP1 (Construct #: 4144; SEQ ID NO:42 (nucleotide); SEQ ID NO:41 (amino acid)) or mut hCod GII.2/CGMH47/2011/TW_E80S+A90L VP1 (Construct #: 4145; SEQ ID NO:44 (nucleotide); SEQ ID NO:43 (amino acid)). Arrow: VP1 norovirus protein; First lane=crude protein extracts prepared from mock infiltrated *N. benthamiana* leaves.
Figure 7B:
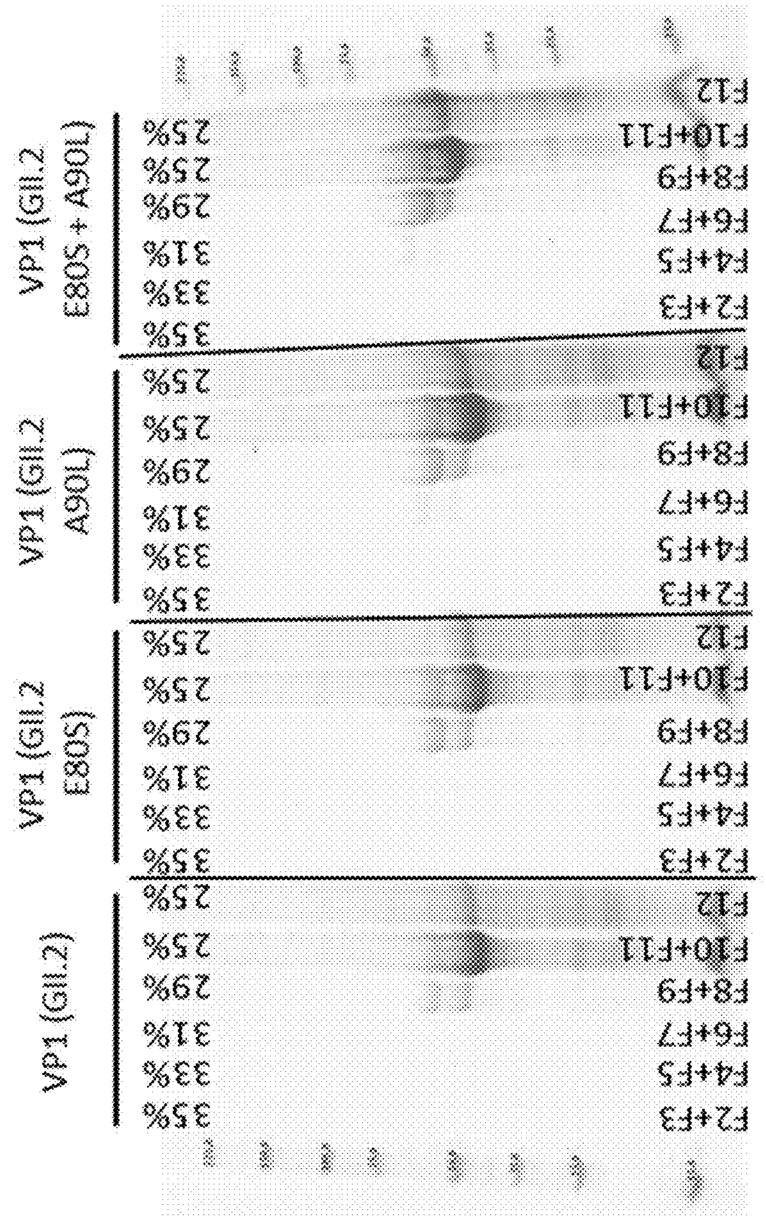
FIG. 7B shows a Coomassie-stained SDS-PAGE analysis of iodixanol density gradient fractions of crude protein extracts prepared from *N. benthamiana* leaves expressing, from left to right, wt hCod GII.2/CGMH47/2011/TW VP1 (Construct #3982), mut hCod GII.2/CGMH47/2011/TW_E80S VP1 (Construct #4143), mut hCod GII.2/CGMH47/2011/TW_A90L (Construct #: 4144), or mut hCod GII.2/CGMH47/2011/TW_E80S+A90L VP1 (Construct #: 4145).
Figure 7C:
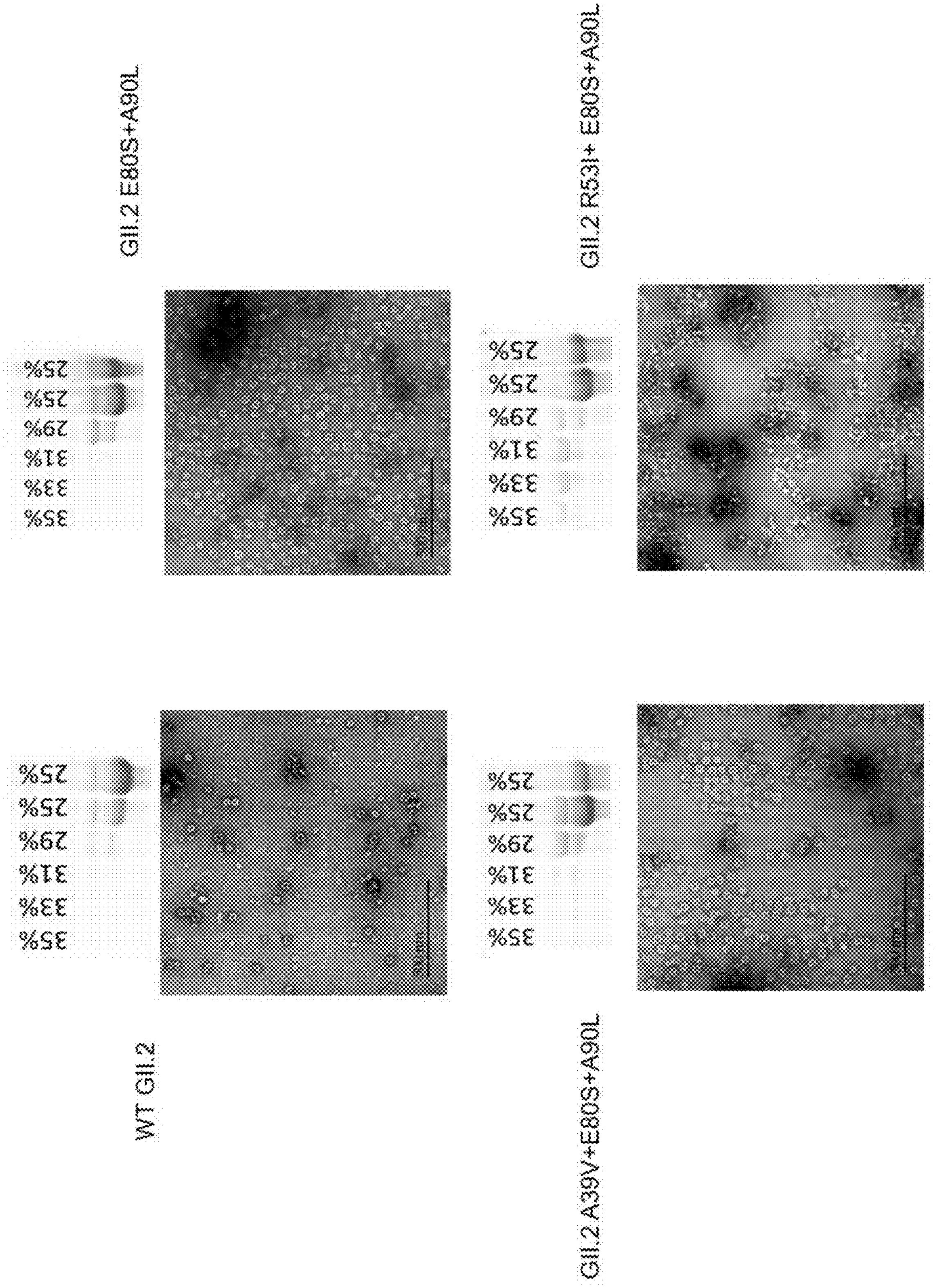
FIG. 7C shows Coomassie-stained SDS-PAGE analysis of iodixanol density gradient fractions of crude protein extracts prepared from *N. benthamiana* leaves (upper part of each panel), and transmission electron micrographs (TEM) of virus like particles (VLPs) purified from 29-35% iodixanol gradient fractions of crude protein extracts prepared from *N. benthamiana* leaves (lower part of each panel), expressing: Top Left Panel: wt hCod GII.2/CGMH47/2011/TW VP1 (Construct #3982), Top Right panel mut hCod GII.2/CGMH47/2011/TW_E80S+A90L VP1 (Construct #4145); Bottom Left Panel: mut hCod GII.2/CGMH47/2011/TW_A39V+E80S+A90L VP1 (Construct #4182; SEQ ID NO:183 (nucleotide); SEQ ID NO:182 (amino acid)); Bottom Right Panel: mut hCod GII.2/CGMH47/2011/TW_M53I+E80S+A90L VP1 (Construct #4183 SEQ ID NO:185 (nucleotide); SEQ ID NO:184 (amino acid)); 15,000× magnification; scale bar=500 nm.

VLPs comprising of GII.2_E80S+A90L, GII.2_A39V+E80S+A90L VP1 proteins exhibited greater density, stability and structural integrity (in a manner similar to that described above) as compared to wildtype norovirus GII.2 VP1 (FIG. 7C). As shown in FIG. 7C, the modified VLPs had fewer damaged VLP particles, and a greater relative proportion of 38 nm diameter particles vs 23 nm diameter VLPs, as compared to wildtype.

Figure 8B:
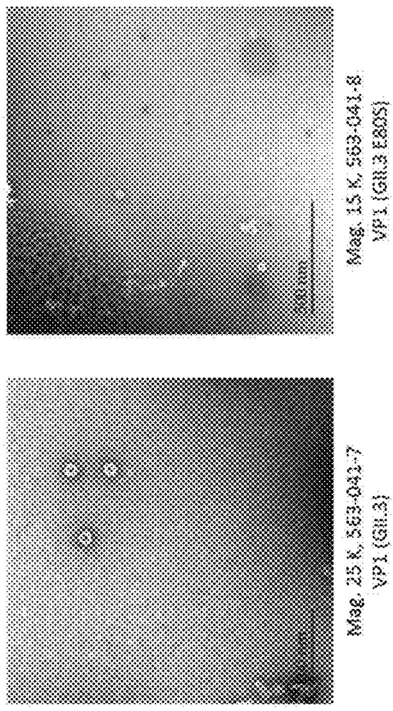
FIG. 8B shows transmission electron micrographs (TEM) of virus like particles (VLPs) purified from 31-35% iodixanol gradient fractions of crude protein extracts prepared from *N. benthamiana* leaves expressing wt hCod GII.3/Jingzhou/2013402/CHN VP1 (Construct #3983, first panel), or mut hCod GII.3/Jingzhou/2013402/CHN_E80S VP1 (Construct #: 4146, second panel). 15,000× magnification; scale bar=500 nm.

Expression of GII.3_E80S in plants, resulted in VLPs of 38 nm diameter particles (FIG. 8B). However, yields of VP1 protein (determined via SDS-PAGE) remained low.

Figure 9B:
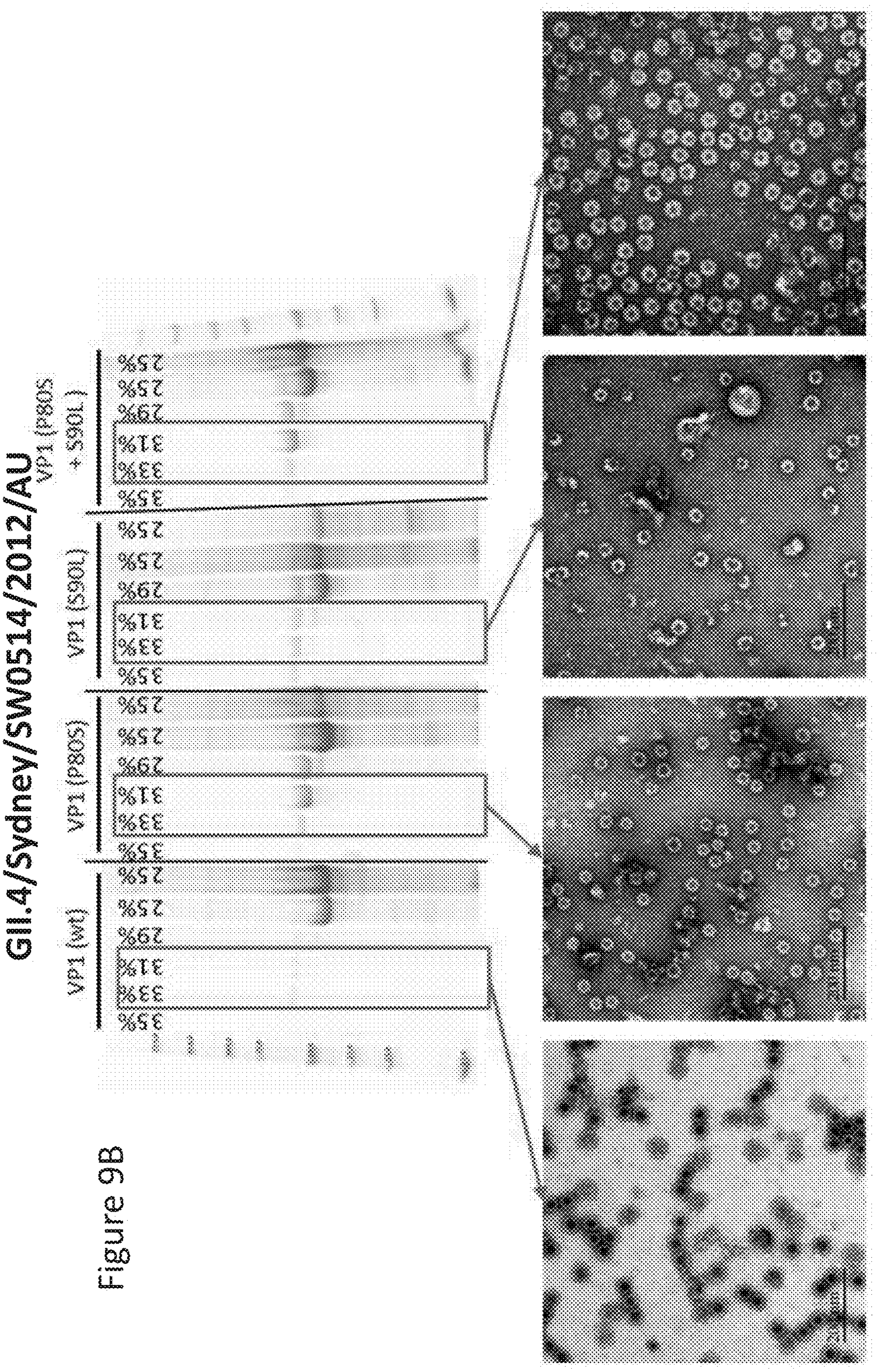
FIG. 9B shows a Coomassie-stained SDS-PAGE analysis (upper panel) and transmission electron micrographs (TEM; lower panel; 15,000× magnification; scale bar=200 nm) of virus like particles (VLPs) purified from iodixanol density gradient fractions of crude protein extracts prepared from *N. benthamiana* leaves expressing wt hCod GII.14/Sydney/NSW0514/2012/AU VP1 (Construct #: 3760), mut hCod GII.14/Sydney/NSW0514/2012/AU_P80S VP1 (Construct #: 4133), mut hCod GII.14/Sydney/NSW0514/2012/AU_S90L VP1 (Construct #: 4134), GII.4/Sydney/NSW0514/2012/AU_P80S+S90L VP1 (Construct #: 4135).
Figure 9C:
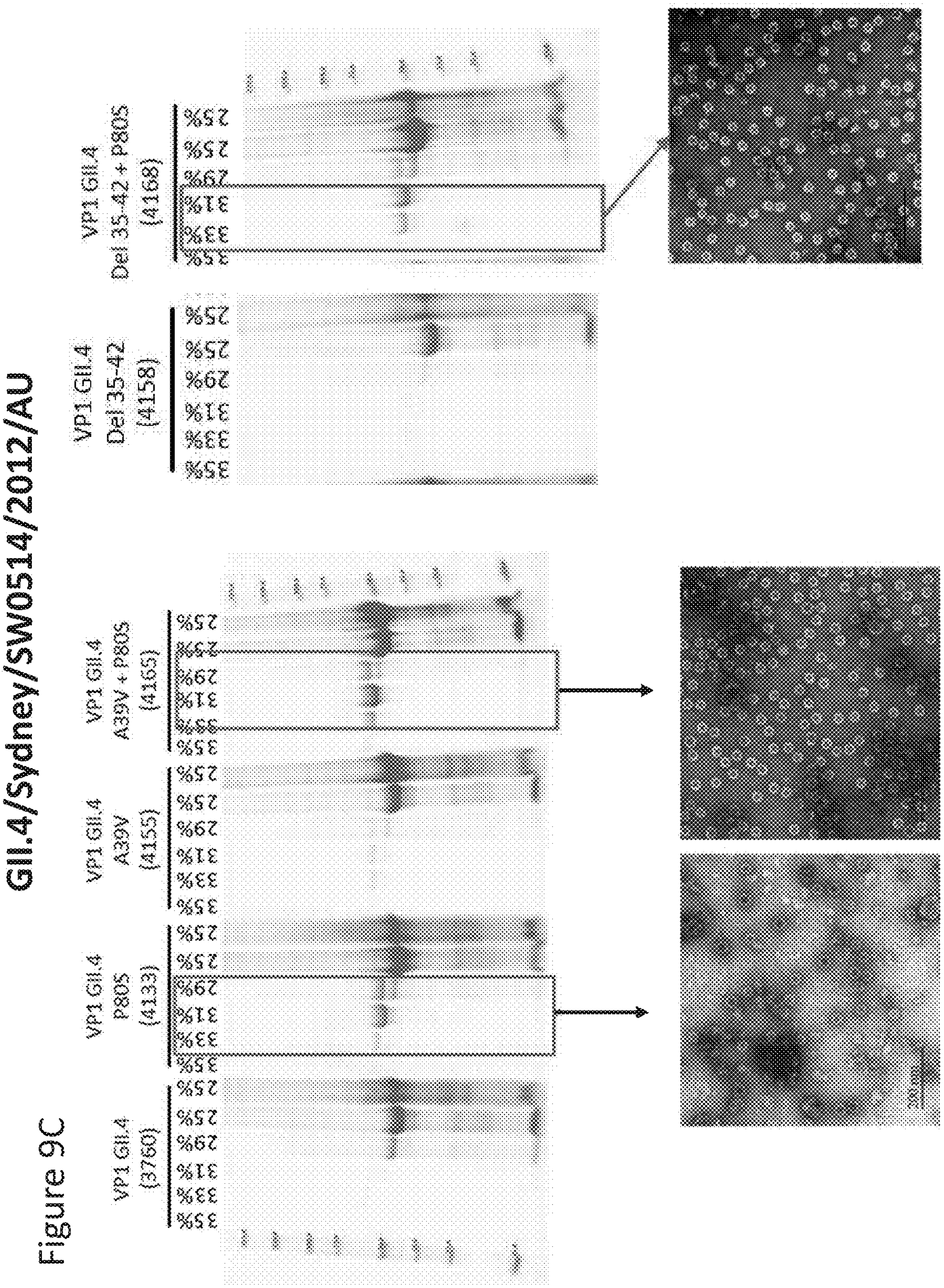
FIG. 9C shows a Coomassie-stained SDS-PAGE analysis (upper panel) and transmission electron micrographs (TEM; lower panel; 15,000× magnification; scale bar=200 nm) of virus like particles (VLPs) purified from iodixanol density gradient fractions of crude protein extracts prepared from *N. benthamiana* leaves expressing wt hCod GII.4/Sydney/NSW0514/2012/AU VP1 (Construct #: 3760), mut hCod GII.4/Sydney/NSW0514/2012/AU_P80S VP1 (Construct #: 4133), mut hCod GII.4/Sydney/NSW0514/2012/AU_A39V VP1 (Construct #: 4155), mut hCod GII.4/Sydney/NSW0514/2012/AU_P80S+A39V (Construct #: 4165), mut hCod GII.4/Sydney/NSW0514/2012/AU_Δ35-42 VP1 (Construct #: 4158), mut hCod GII.4/Sydney/NSW0514/2012/AU_P80S+Δ35-42 VP1 (Construct #: 4168).
Figure 9D:
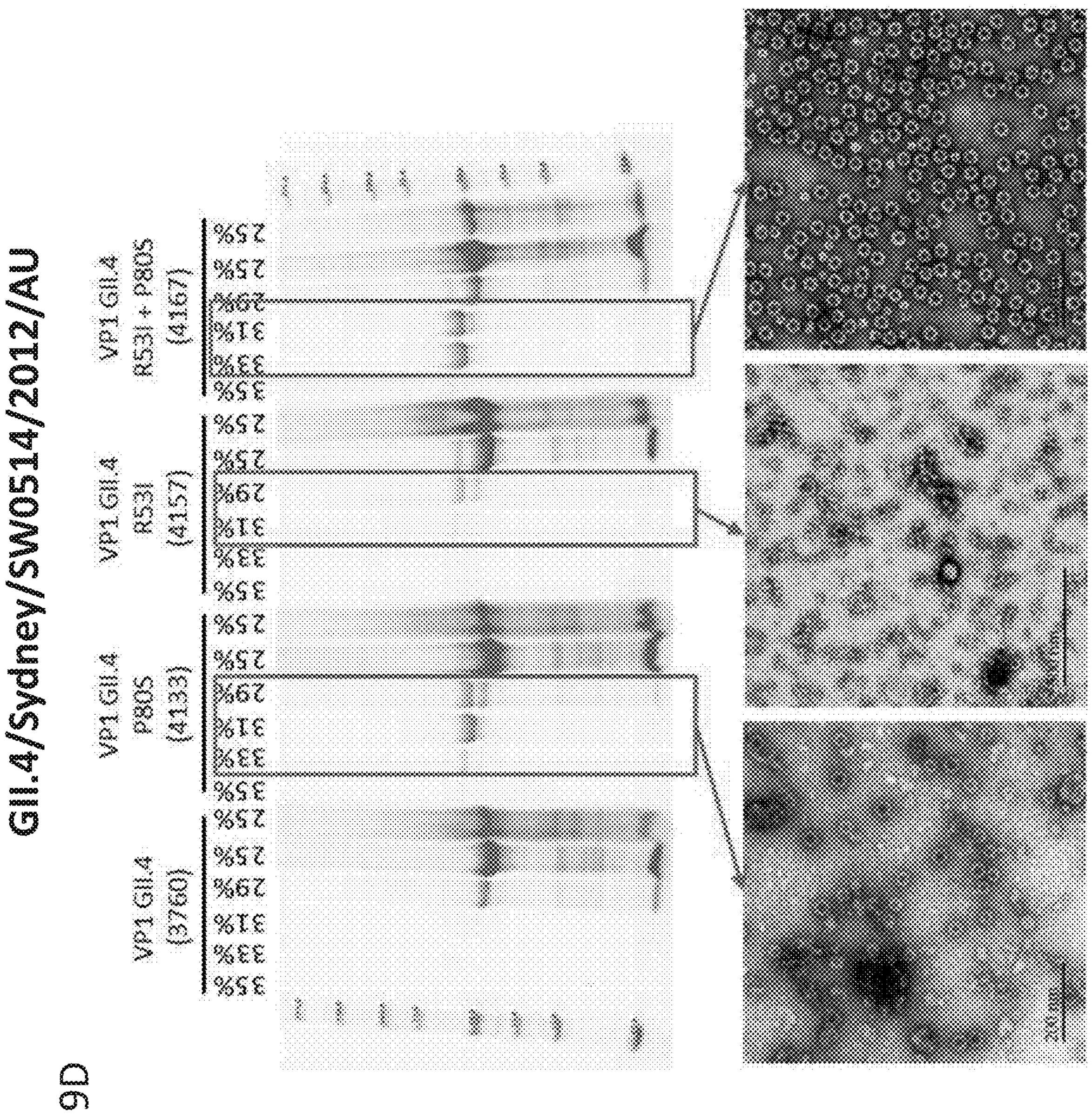
FIG. 9D shows a Coomassie-stained SDS-PAGE analysis (upper panel) and transmission electron micrographs (TEM; lower panel; 15,000× magnification; scale bar=200 nm) of virus like particles (VLPs) purified from iodixanol density gradient fractions of crude protein extracts prepared from *N. benthamiana* leaves expressing wt hCod GII.4/Sydney/NSW0514/2012/AU VP1 (Construct #: 3760), mut hCod GII.4/Sydney/NSW0514/2012/AU_P80S VP1 (Construct #: 4133), mut hCod GII.4/Sydney/NSW0514/2012/AU_R53I VP1 (Construct #: 4157), mut hCod GII.4/Sydney/NSW0514/2012/AU_R53I+P80S VP1 (Construct #: 4167).
Figure 9E:
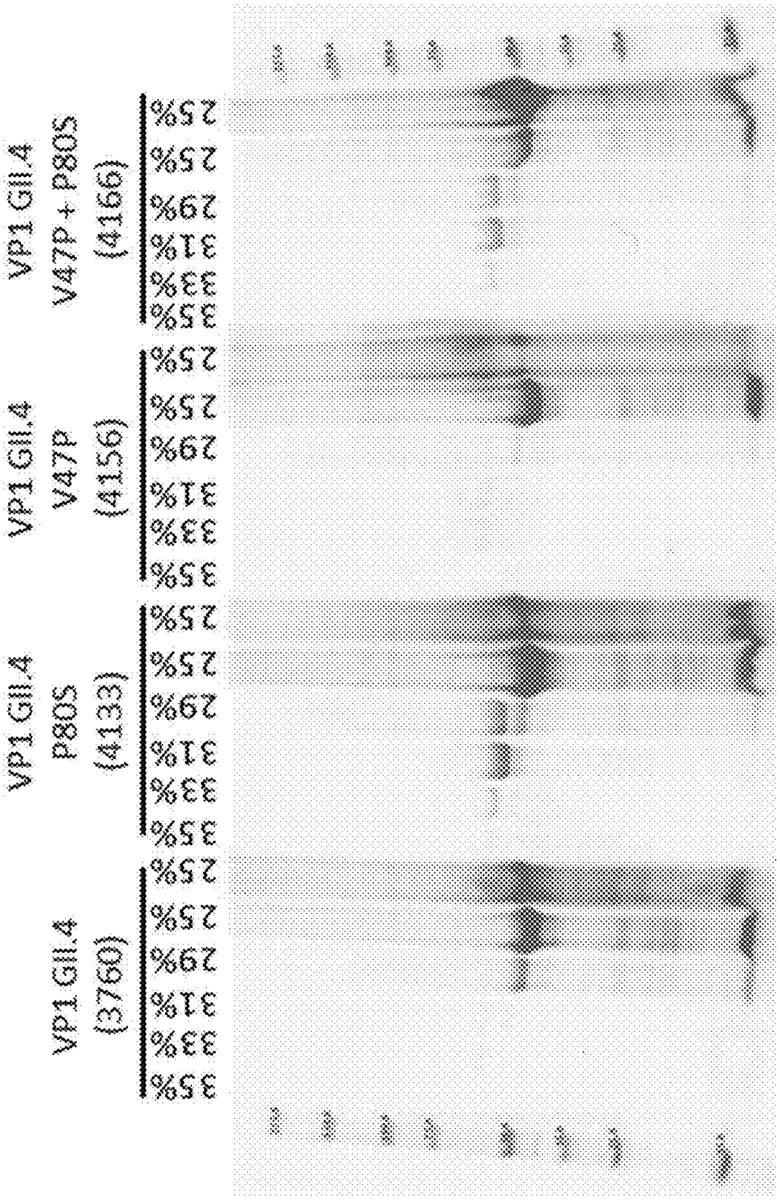
FIG. 9E shows a Coomassie-stained SDS-PAGE analysis of virus like particles (VLPs) purified from iodixanol density gradient fractions of crude protein extracts prepared from *N. benthamiana* leaves expressing wt hCod GII.4/Sydney/NSW0514/2012/AU VP1 (Construct #: 3760), mut hCod GII.4/Sydney/NSW0514/2012/AU_P80S VP1 (Construct #: 4133), mut hCod GII.4/Sydney/NSW0514/2012/AU_V47P VP1 (Construct #: 4156, mut hCod GII.4/Sydney/NSW0514/2012/AU_P80S+V47P VP1 (Construct #: 4166).
Figure 9F:
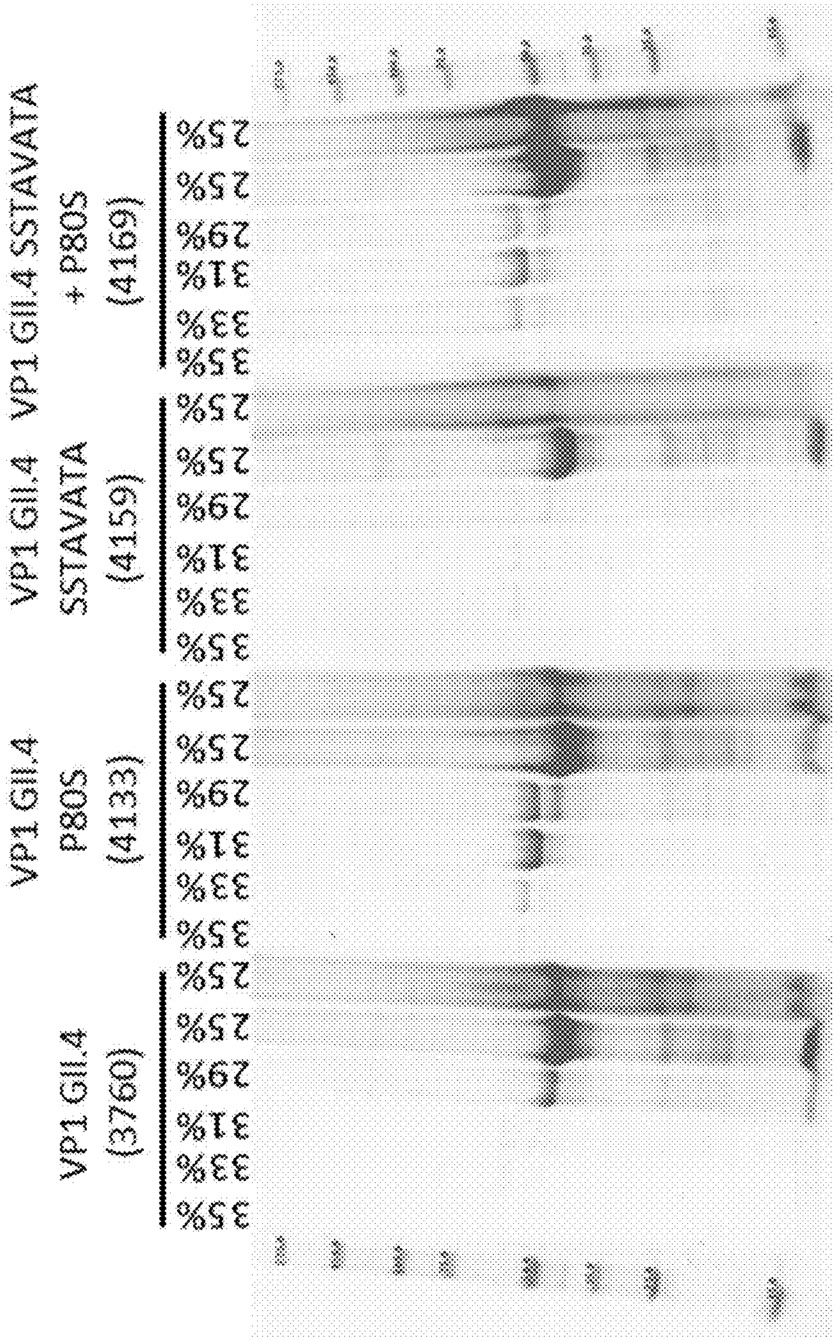
FIG. 9F shows a Coomassie-stained SDS-PAGE analysis of virus like particles (VLPs) purified from iodixanol density gradient fractions of crude protein extracts prepared from *N. benthamiana* leaves expressing wt hCod GII.4/Sydney/NSW0514/2012/AU VP1 (Construct #: 3760), mut hCod GII.4/Sydney/NSW0514/2012/AU_P80S VP1 (Construct #: 4133), mut hCod GII.4/Sydney/NSW0514/2012/AU_SSTAVATA VP1 (Construct #: 4159), mut hCod GII.4/Sydney/NSW0514/2012/AU_SSTAVATA+P80S VP1 (Construct #: 4169).

As shown in FIGS. 9B, 9C, 9D and 9G, modified VP1 proteins, GII.4_A39V, GII.4_V47P, GII.4_R53I, GII.4_P80S, GII.4_S90L, GII.4_A39V+P80S, GII.4_R53I+P80S, GII.4_P80S+S90L, GII.4_P80S+Δ35-42 and GII.4_A39V+R53I+P80S all exhibited VLPs having greater densities, stability, and structural integrity than VLPs comprising wildtype GII.4 VP1 protein. Further, the VLPs comprising GII.4_A39V+P80S, GII.4_R53I+P80S, GII.4_P80S+S90L, GII.4_P80S+Δ35-42, and GII.4_A39V+R53I+P80S all had improved viral capsid integrity and fewer damaged particles as seen by TEM (FIGS. 9B, 9C, 9D and 9E). VLPs comprising GII.4_A39V+P80S and GII.4_P80S+Δ35-42 were also observed to have a greater proportion of 38 nm diameter particles vs 23 nm diameter particles as compared to wildtype GII.4 VLPs (FIGS. 9B and 9C). VLPs were also produced from GII.4_V47P; GII.4_V47P+P80S, GII.4_SSTAVATA; GII.4_P80S+SSTAVATA (FIGS. 9E and 9F).

As shown in FIGS. 10A and 10B, expression of modified norovirus VP1 protein GII.6_S90L produced 38 nm diameter VLPs, determined using transmission electron micrography (TEM).

VLPs comprising GII.12_E80S, GII.12_A90L and GII.12_E80S+A90L, also exhibited the improved characteristic of having a greater density of 38 nm diameter VLPs than VLPs comprising wildtype GII.12 VP1 (FIG. 11C) as determined using transmission electron micrography (TEM).

VLPs comprising GII.17_A39V, GII.17_A90L, and GII.17_R53I, also exhibited the improved characteristic of having a greater density of 38 nm diameter VLPs than VLPs comprising wildtype GII.17 VP1 (FIG. 11D) as determined using transmission electron micrography (TEM).

Induction of Immunity Against Norovirus Infection

An "immune response" generally refers to a response of the adaptive immune system of a subject. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity may be of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-norovirus antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al, 1973. Virus neutralization titers may be quantified in a number of ways, including: enumeration of lysis plaques (plaque assay) following crystal violent fixation/coloration of cells; microscopic observation of cell lysis in in vitro culture; and 2) ELISA and spectrophotometric detection of norovirus.

The term "epitope" or "epitopes", as used herein, refers to a structural part of an antigen to which an antibody specifically binds.

Figure 3D:
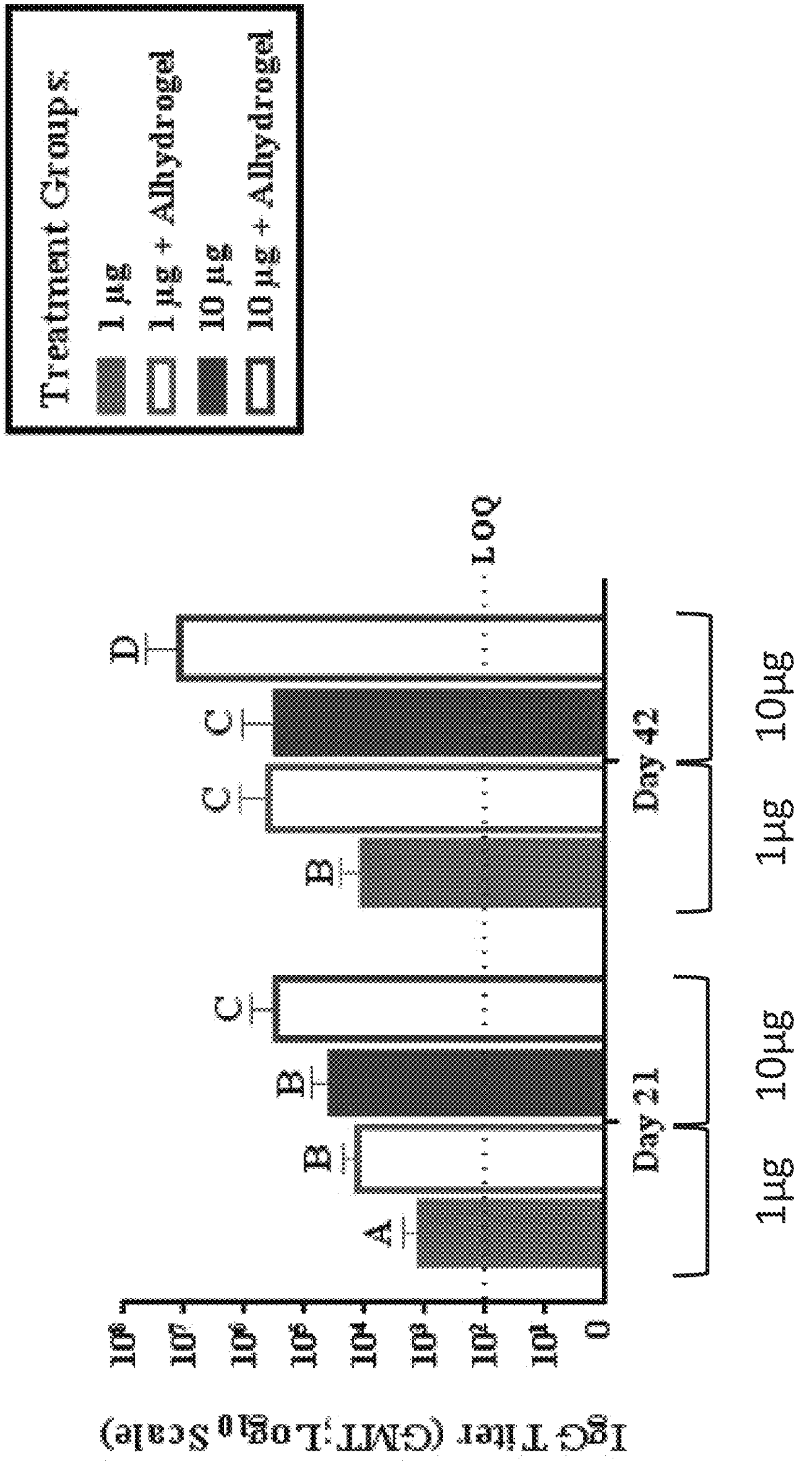
FIG. 3D shows GI.1 VLP-specific total IgG titers measured in serum samples from animals after IM immunization with one dose (Day 21) and two doses (Day 42) of 1 μg or 10 μg of each formulation. Total IgG titers were measured by ELISA using GI.1 VLP-coated plates (LOQ=100). Total IgG titers per treatment group (n=8 animals/group) are represented by geometric mean titer (GMT) with a 95% confidence interval. Same letter (A, B, C, D): no significant difference detected between treatment groups ($p>0.05$).

Immune response to plant produced wild type Norovirus native GI.1 (SEQ ID NO:1) VLP administration were performed using BALB/c mice (Example 4). Plant-produced modified VP1 proteins, or VLPs comprising modified VP1 proteins, for example, produced using GI.3_Q84S (construct 4140; SEQ ID NO:167), GI.3_S94L (construct 4141; SEQ ID NO:9), GI.3_A43V+S94L (construct 4179; SEQ ID NO:169), GI.3_M57I+S94L (construct 4180; SEQ ID NO:171), GI.3_P84S+S94L (construct 4142; SEQ ID NO:11), GI.3_A43V+M57I+S94L (construct 4181; SEQ ID NO:173), GI.5_Q84S (construct 4130; SEQ ID NO:35), GI.5_A94L (construct 4131; SEQ ID NO:37), GI.5_Q84S+A94L (construct 4132; SEQ ID NO:39), GI.7_R84S (construct 4210; SEQ ID NO:176), GI.7_M57I (construct 4217; SEQ ID NO:178), GI.7_M57I+R84S (construct 4218; SEQ ID NO:180), GII.2_E80S (construct 4143; SEQ ID NO:86), GII.2_A90L (construct 4144; SEQ ID NO:42), GII.2_Q80S+A90L (construct 4145; SEQ ID NO:44), GII.2_A39V+Q80S+A90L (construct 4182; SEQ ID NO:183), GII.2_R53I+Q80S+A90L (construct 4183; SEQ ID NO:185), GII.2_A39V+R53I+Q80S+A90L (construct 4184; SEQ ID NO:187), GII.3_E80S_(construct 4146; SEQ ID NO:47), GII.3_A90L (construct 4147; SEQ ID NO:49), GII.3_E80S+A90L (construct 4148; SEQ ID NO:51), GII.4_A39V (construct 4155; SEQ ID NO:54), GII.4_V47P (construct 4156; SEQ ID NO:56), GII.4_R53I (construct 4157; SEQ ID NO:58), GII.4_P80S (construct 4133; SEQ ID NO:60), GII.4_S90L (construct 4134; SEQ ID NO:62), GII.4_Δ35-42 (construct 4158; SEQ ID NO:64), GII.4_SSTAVATA (construct 4159; SEQ ID NO:66). GII.4_A39V+R53I (construct 4185; SEQ ID NO:189), GII.4_A39V+P80S (construct 4165; SEQ ID NO:68), GII.4_V47P+P80S (construct 4166; SEQ ID NO:70), GII.4_R53I+P80S (construct 4167; SEQ ID NO:72), GII.4_P80S+S90L (construct 4135; SEQ ID NO:74), GII.4_Δ35-42+P80S (construct 4168; SEQ ID NO:76), GII.4_P80S+SSTAVATA (construct 4169; SEQ ID NO:78), GII.4_A39V+R53I+P80S (construct 4186; SEQ ID NO:191), GII.6_E80S (construct 4149; SEQ ID NO:80), GII.6_S90L (construct 4150; SEQ ID NO:82), GII.6_E80S+S90L (construct 4151; SEQ ID NO:84), GII.12_E80S (construct 4136; SEQ ID NO:89), GII.12_A90L (construct 4137; SEQ ID NO:91), GII.12_E80S+A90L (construct 4138; SEQ ID NO:93), GII.17_A39V (construct 4234; SEQ ID NO:193), GII.17_R53I (construct 4235; SEQ ID NO:195), GII.17_A90L (construct 4232; SEQ ID NO:197), GII.17_A39V+R53I (construct 4236; SEQ ID NO:199), GII.17_E80S+A90L (construct 4233; SEQ ID NO:201), or a combination thereof, may also administered to mice. Serum samples from blood collected from animals were analyzed by ELISA for GI.1 VLP-specific total IgG and IgA antibodies using GI.1 VLP-coated plates. With reference to FIG. 3D, mice immunized with plant norovirus native VP1 VLPs from GI.1 genotype exhibit GI.1 VLP-specific IgG antibody titers in sera for each treatment group. The IgG titer levels induced by each treatment were statistically higher than the titers quantified for the placebo group ($p<0.05$). IgG titer level increased in a dose-dependent manner (significant difference detected between the 1 μg and 10 μg treatments formulated with or without Alhydrogel; $p<0.05$). A significant increase of IgG titer level was also detected for each treatment group between Days 21 and 42 ($p<0.05$). These results collectively demonstrate the ability of plant produced Norovirus native VP1 VLPs to elicit a robust immune response in mice.

Therefore, there is provided herein a method of producing an antibody or antibody fragment comprising, administering a modified norovirus VP1 protein, or a norovirus VLP comprising one or more than one modified VP1 protein to a subject, or a host animal, thereby producing the antibody or the antibody fragment. The modified norovirus VP1 protein (either a GI VP1 protein or Gil VP1 protein), comprising one or more than one substitution, modification or mutation at: an amino acid residue selected from positions in sequence alignment with amino acids 43, 57, 84 and 94 of norovirus VP1 genotype GI.1 (SEQ ID NO:1); a deletion of a peptide fragment in sequence alignment with amino acids 39 to 46 of norovirus VP1 genotype GI.1 (SEQ ID NO:1); amino acids corresponding to amino acid residues 39-46 of norovirus VP1 genotype GI.1 are mutated to the sequence SSTAVATA, or a combination thereof, and the nucleotide sequence is not derived from a genotype GI.1 norovirus VP1. The VLP may further comprise a norovirus VP2 protein.

There is also provided a composition for inducing an immune response comprising, an effective dose of the VLP comprising the modified norovirus VP1 protein, and a pharmaceutically acceptable carrier, adjuvant, vehicle or excipient.

Plant Expression

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, *Fundamentals of Gene Transfer in Plants*. In *Plant Metabolism,* 2d Ed. DT. Dennis, DH Turpin, DD Lefebrvre, DB Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991*, Gene* 100: 247-250), Scheid et al. (1991*, Mol. Gen. Genet.* 228: 104-112), Guerche et al. (1987*, Plant Science* 52: 111-116), Neuhause et al. (1987*, Theor. Appl Genet.* 75: 30-36), Klein et al. (2987*, Nature* 327: 70-73); Freeman et al. (1984*, Plant Cell Physiol.* 29: 1353), Howell et al. (1980*, Science* 208: 1265), Horsch et al. (1985*, Science* 227: 1229-1231), DeBlock et al. (1989*, Plant Physiology* 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002*, J Virol Meth,* 105:343-348), EP 290395; WO 8706614; U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient expression methods may be used to express the constructs of the present invention (see D'Aoust et al., 2009*, Methods in molecular biology*, Vol 483, pages 41-50; Liu and Lomonossoff, 2002*, Journal of Virological Methods,* 105:343-348; which is incorporated herein by reference). Alternatively, a vacuum-based transient expression method, as described by Kapila et al. (1997*, Plant Sci.* 122, 101-108; which is incorporated herein by reference), or WO 00/063400, WO 00/037663 (which are incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage of t-DNA inside the nucleus is transient.

Also considered part of this invention are transgenic plants, plant cells or seeds containing the gene construct of the present invention that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy RRD ed) Oxford, BIOS Scientific Publishers, pp 121-148). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al. (Cell Culture and Somatic Cell Genetics of Plants, Vol I, II and III, Laboratory Procedures and Their Applications, Academic Press, 1984), and Weissbach and Weissbach (Methods for Plant Molecular Biology, Academic Press, 1989). The method of obtaining transformed and regenerated plants is not critical to the present invention.

If plants, plant portions or plant cells are to be transformed or co-transformed by two or more nucleic acid constructs, the nucleic acid construct may be introduced into the *Agrobacterium* in a single transfection event so that the nucleic acids are pooled, and the bacterial cells transfected. Alternatively, the constructs may be introduced serially. In this case, a first construct is introduced into the *Agrobacterium* as described, the cells are grown under selective conditions (e.g. in the presence of an antibiotic) where only the singly transformed bacteria can grow. Following this first selection step, a second nucleic acid construct is introduced into the *Agrobacterium* as described, and the cells are grown under doubly-selective conditions, where only the doubly-transformed bacteria can grow. The doubly-transformed bacteria may then be used to transform a plant, plant portion or plant cell as described herein, or may be subjected to a further transformation step to accommodate a third nucleic acid construct.

Alternatively, if plants, plant portions, or plant cells are to be transformed or co-transformed by two or more nucleic acid constructs, the nucleic acid construct may be introduced into the plant by co-infiltrating a mixture of *Agrobacterium* cells with the plant, plant portion, or plant cell, each *Agrobacterium* cell may comprise one or more constructs to be introduced within the plant. In order to vary the relative expression levels within the plant, plant portion or plant cell, of a nucleotide sequence of interest within a construct, during the step of infiltration, the concentration of the various Agrobacteria populations comprising the desired constructs may be varied.

Therefore, there is provided herein, a plant, a portion of a plant, a plant cell, or a plant extract, comprising, one or more than one modified norovirus VP1 protein, or a norovirus VLP comprising one or more than one modified VP1 protein. The one or more than one modified norovirus VP1 protein comprising one or more than one substitution, modification or mutation at a position selected from amino acid residues in sequence alignment with amino acids 43, 57, 84 and 94 of norovirus VP1 genotype GI.1 (SEQ ID NO:1); a deletion of a peptide fragment in sequence alignment with amino acids 39 to 46 of norovirus VP1 genotype GI.1 (SEQ ID NO:1); or a combination thereof, and the nucleotide sequence is not derived from a genotype GI.1 norovirus VP1. The VLP may further comprise a norovirus VP2 protein.

Also provided herein is a plant, portion of a plant, a plant cell, or a plant extract comprising, a polynucleotide sequence encoding one or more than one modified norovirus VP1 protein. The one or more than one modified norovirus VP1 protein comprising one or more than one substitution, modification or mutation at a position selected from amino acid residues in sequence alignment with amino acids 43, 57, 84 and 94 of norovirus VP1 genotype GI.1 (SEQ ID NO:1); a deletion of a peptide fragment in sequence alignment with amino acids 39 to 46 of norovirus VP1 genotype GI.1 (SEQ ID NO:1); or a combination thereof, and the nucleotide sequence is not derived from a genotype GI.1 norovirus VP1.

A list of the Norovirus strains and constructs is provided in Table 3.

TABLE 3

Norovirus strains and constructs.

| Trivial Name | Norovirus Strain | SEQ ID NO: | SEQ FIG. # | Const # | Const. FIG. # |
|---|---|---|---|---|---|
| VP1 GI.1 | | | | | |
| Wt GI.1 (aa) | Hu/GI.1/United States/Norwalk/1968 | 1 | 12A | — | |
| Wt GI.1 (na) | Hu/GI.1/United States/Norwalk/1968 | 2 | 12B | — | |
| Wt GI.1 hCod (na) | Hu/GI.1/United States/Norwalk/1968 | 3 | 12C | 2724 | 39A |
| VP1 GI.2 | | | | | |
| Wt GI.2 (aa) | Hu/G1.2/Leuven/2003/BEL | 4 | 13A | — | |
| Wt GI.2 hCod (na) | Hu/G1.2/Leuven/2003/BEL | 5 | 13B | 3300 | 39B |
| VP1 GI.3 | | | | | |
| Wt GI.3 (aa) | Hu/GI.3/S29/2008/Lilla Edet/Sweden | 6 | 14A | — | |
| Wt GI.3 hCod (na) | Hu/GI.3/S29/2008/Lilla Edet/Sweden | 7 | 14B | 3979 | 39C |
| Mut GI.3_Q84S (aa) | Hu/GI.3/S29/2008/Lilla Edet/Sweden | 98 | 28A | | |
| Mut GI.3_Q84S hCod (na) | Hu/GI.3/S29/2008/Lilla Edet/Sweden | 167 | 28B | 4140 | 40A |
| Mut GI.3_S94L (aa) | Hu/GI.3/S29/2008/Lilla Edet/Sweden | 8 | 28C | — | |
| Mut GI.3_S94L hCod (na) | Hu/GI.3/S29/2008/Lilla Edet/Sweden | 9 | 28D | 4141 | 40B |
| Mut GI.3_S94V (aa) | Hu/GI.3/S29/2008/Lilla Edet/Sweden | 292 | 28M | — | |
| Mut GI.3_S94V hCod (na) | Hu/GI.3/S29/2008/Lilla Edet/Sweden | 293 | 28N | 4288 | 52 |
| Mut GI.3_S94I (aa) | Hu/GI.3/S29/2008/Lilla Edet/Sweden | 292 | 28M | — | |
| Mut GI.3_S94I hCod (na) | Hu/GI.3/S29/2008/Lilla Edet/Sweden | 293 | 28N | 4289 | 52 |
| Mut GI.3_S94M (aa) | Hu/GI.3/S29/2008/Lilla Edet/Sweden | 292 | 28M | — | |
| Mut GI.3_S94M hCod (na) | Hu/GI.3/S29/2008/Lilla Edet/Sweden | 293 | 28N | 4290 | 52 |
| Mut GI.3_S94T (aa) | Hu/GI.3/S29/2008/Lilla Edet/Sweden | 292 | 28M | — | |
| Mut GI.3_S94T hCod (na) | Hu/GI.3/S29/2008/Lilla Edet/Sweden | 293 | 28N | 4292 | 52 |
| Mut GI.3_S94E (aa) | Hu/GI.3/S29/2008/Lilla Edet/Sweden | 292 | 28M | — | |
| Mut GI.3_S94E hCod (na) | Hu/GI.3/S29/2008/Lilla Edet/Sweden | 293 | 28N | 4293 | 52 |
| Mut GI.3_S94D (aa) | Hu/GI.3/S29/2008/Lilla Edet/Sweden | 292 | 28M | — | |
| Mut GI.3_S94D hCod (na) | Hu/GI.3/S29/2008/Lilla Edet/Sweden | 293 | 28N | 4294 | 52 |
| Mut GI.3_S94N (aa) | Hu/GI.3/S29/2008/Lilla Edet/Sweden | 292 | 28M | — | |
| Mut GI.3_S94N hCod (na) | Hu/GI.3/S29/2008/Lilla Edet/Sweden | 293 | 28N | 4295 | 52 |
| Mut GI.3_S94Q (aa) | Hu/GI.3/S29/2008/Lilla Edet/Sweden | 292 | 28M | — | |
| Mut GI.3_S94Q hCod (na) | Hu/GI.3/S29/2008/Lilla Edet/Sweden | 293 | 28N | 4296 | 52 |
| Mut GI.3_S94K (aa) | Hu/GI.3/S29/2008/Lilla Edet/Sweden | 292 | 28M | — | |
| Mut GI.3_S94K hCod (na) | Hu/GI.3/S29/2008/Lilla Edet/Sweden | 293 | 28N | 4297 | 52 |
| Mut GI.3_S94H (aa) | Hu/GI.3/S29/2008/Lilla Edet/Sweden | 292 | 28M | — | |
| Mut GI.3_S94H hCod (na) | Hu/GI.3/S29/2008/Lilla Edet/Sweden | 293 | 28N | 4298 | 52 |
| Mut GI.3_A43V + S94L (na) | Hu/GI.3/S29/2008/Lilla Edet/Sweden | 169 | 28H | 4179 | 40D |
| Mut GI.3_A43V + S94L (aa) | Hu/GI.3/S29/2008/Lilla Edet/Sweden | 170 | 28G | — | |
| Mut GI.3_M57I + S94L (na) | Hu/GI.3/S29/2008/Lilla Edet/Sweden | 171 | 28J | 4180 | 40E |
| Mut GI.3_M57I + S94L (aa) | Hu/GI.3/S29/2008/Lilla Edet/Sweden | 172 | 28I | — | |
| Mut GI.3_A43V + M57I + S94L (na) | Hu/GI.3/S29/2008/Lilla Edet/Sweden | 173 | 28L | 4181 | 40F |
| Mut GI.3_A43V + M57I + S94L (aa) | Hu/GI.3/S29/2008/Lilla Edet/Sweden | 174 | 28K | — | |
| Mut GI.3_Q84S + S94L (aa) | Hu/GI.3/S29/2008/Lilla Edet/Sweden | 10 | 28E | — | |
| Mut GI.3_Q84S + S94L hCod (na) | Hu/GI.3/S29/2008/Lilla Edet/Sweden | 11 | 28F | 4142 | 40C |
| VP1 Gi.5 | | | | | |
| Wt GI.5 (aa) | Hu/GI.5/Siklos/HUN5407/2013/HUN | 12 | 15A | — | |
| Wt GI.5 hCod (na) | Hu/GI.5/Siklos/HUN5407/2013/HUN | 33 | 15B | 3980 | 41A |
| Mut GI.5_Q84S (aa) | Hu/GI.5/Siklos/HUN5407/2013/HUN | 34 | 29A | — | |
| Mut GI.5_Q84S (na) | Hu/GI.5/Siklos/HUN5407/2013/HUN | 35 | 29B | 4130 | 41B |
| Mut GI.5_A94L (aa) | Hu/GI.5/Siklos/HUN5407/2013/HUN | 36 | 29C | — | |
| Mut GI.5_A94L hCod (na) | Hu/GI.5/Siklos/HUN5407/2013/HUN | 37 | 29D | 4131 | 41C |

TABLE 3-continued

| Norovirus strains and constructs. | | | | |
|---|---|---|---|---|
| Mut GI.5_Q84S + A94L (aa) | Hu/GI.5/Siklos/HUN5407/2013/HUN | 38 | 29E | — |
| Mut GI.5_Q84S + A94L hCod (na) | Hu/GI.5/Siklos/HUN5407/2013/HUN | 39 | 29F | 4132 41D |
| VP1 GI.7 | | | | |
| Wt GI.7 (na) | Hu/GI.7/USA/2014/GA5043 | 175 | 16B | — |
| Wt GI.7 (aa) | Hu/GI.7/USA/2014/GA5043 | 101 | 16A | — |
| Mut GI.7_R84S (na) | Hu/GI.7/USA/2014/GA5043 | 176 | 29H | 4210 41E |
| Mut GI.7_R84S (aa) | Hu/GI.7/USA/2014/GA5043 | 177 | 29G | — |
| Mut GI.7_M57I (na) | Hu/GI.7/USA/2014/GA5043 | 178 | 29J | 4217 41F |
| Mut GI.7_M57I (aa) | Hu/GI.7/USA/2014/GA5043 | 179 | 29I | — |
| Mut GI.7_M57L (na) | Hu/GI.7/USA/2014/GA5043 | 291 | 29N | 4266 51 |
| Mut GI.7_M57L (aa) | Hu/GI.7/USA/2014/GA5043 | 290 | 29M | — |
| Mut GI.7_M57G (na) | Hu/GI.7/USA/2014/GA5043 | 291 | 29N | 4268 51 |
| Mut GI.7_M57G (aa) | Hu/GI.7/USA/2014/GA5043 | 290 | 29M | — |
| Mut GI.7_M57S (na) | Hu/GI.7/USA/2014/GA5043 | 291 | 29N | 4269 51 |
| Mut GI.7_M57S (aa) | Hu/GI.7/USA/2014/GA5043 | 290 | 29M | — |
| Mut GI.7_M57T (na) | Hu/GI.7/USA/2014/GA5043 | 291 | 29N | 4270 51 |
| Mut GI.7_M57T (aa) | Hu/GI.7/USA/2014/GA5043 | 290 | 29M | — |
| Mut GI.7_M57N (na) | Hu/GI.7/USA/2014/GA5043 | 291 | 29N | 4273 51 |
| Mut GI.7_M57N (aa) | Hu/GI.7/USA/2014/GA5043 | 290 | 29M | — |
| Mut GI.7_M57Q (na) | Hu/GI.7/USA/2014/GA5043 | 291 | 29N | 4274 51 |
| Mut GI.7_M57Q (aa) | Hu/GI.7/USA/2014/GA5043 | 290 | 29M | — |
| Mut GI.7_M57K (na) | Hu/GI.7/USA/2014/GA5043 | 291 | 29N | 4275 51 |
| Mut GI.7_M57K (aa) | Hu/GI.7/USA/2014/GA5043 | 290 | 29M | — |
| Mut GI.7_M57H (na) | Hu/GI.7/USA/2014/GA5043 | 291 | 29N | 4276 51 |
| Mut GI.7_M57H (aa) | Hu/GI.7/USA/2014/GA5043 | 290 | 29M | — |
| Mut GI.7_M57I + R84S (na) | Hu/GI.7/USA/2014/GA5043 | 180 | 29L | 4218 41G |
| Mut GI.7_M57I + R84S (aa) | Hu/GI.7/USA/2014/GA5043 | 181 | 29K | |
| VP1 GII.1 | | | | |
| Wt GII.1 (aa) | GII.1_Ascension208/2010/USA_AFA55174 | 13 | 16C | — |
| VP1 GII.2 | | | | |
| Wt GII.2 (aa) | Hu/GII.2/CGMH47/2011/TW | 14 | 17A | — |
| Wt GII.2 hCod (na) | Hu/GII.2/CGMH47/2011/TW | 40 | 17B | 3982 42A |
| Mut GII.2_E80S (aa) | Hu/GII.2/CGMH47/2011/TW | 85 | 30A | — |
| Mut GII.2_E80S (aa) | Hu/GII.2/CGMH47/2011/TW | 86 | 30B | 4143 42B |
| Mut GII.2_A90L (aa) | Hu/GII.2/CGMH47/2011/TW | 41 | 30C | — |
| Mut GII.2_A90L hCod (na) | Hu/GII.2/CGMH47/2011/TW | 42 | 30D | 4144 42C |
| Mut GII.2_E80S + A90L (aa) | Hu/GII.2/CGMH47/2011/TW | 43 | 30E | — |
| Mut GII.2_E80S + A90L hCod (na) | Hu/GII.2/CGMH47/2011/TW | 44 | 30F | 4145 42D |
| Mut GII.2_A39V + E80S + A90L (aa) | Hu/GII.2/CGMH47/2011/TW | 182 | 30G | — |
| Mut GII.2_A39V + E80S + A90L hCod (na) | Hu/GII.2/CGMH47/2011/TW | 183 | 30H | 4182 42E |
| Mut GII.2_R53I + E80S + A90L (aa) | Hu/GII.2/CGMH47/2011/TW | 184 | 30I | — |
| Mut GII.2_R53I + E80S + A90L hCod (na) | Hu/GII.2/CGMH47/2011/TW | 185 | 30J | 4183 42F |
| Mut GII.2_A39V + R53I + E80S + A90L (aa) | Hu/GII.2/CGMH47/2011/TW | 186 | 30K | — |
| Mut GII.2_A39V + R53I + E80S + A90L hCod (na) | Hu/GII.2/CGMH47/2011/TW | 187 | 30L | 4184 42G |
| VP1 GII.3 | | | | |
| Wt GII.3 (aa) | Hu/GII.3/Jingzhou/2013402/CHN | 15 | 18A | — |
| Wt GII.3 hCod (na) | Hu/GII.3/Jingzhou/2013402/CHN | 45 | 18B | 3983 43A |
| Mut GII.3_E80S (aa) | Hu/GII.3/Jingzhou/2013402/CHN | 46 | 31A | — |
| Mut GII.3_E80S hCod (na) | Hu/GII.3/Jingzhou/2013402/CHN | 47 | 31B | 4146 43B |
| Mut GII.3_A90L (aa) | Hu/GII.3/Jingzhou/2013402/CHN | 48 | 31C | — |
| Mut GII.3_A90L hCod (na) | Hu/GII.3/Jingzhou/2013402/CHN | 49 | 31D | 4147 43C |
| Mut GII.3_E80S + A90L (aa) | Hu/GII.3/Jingzhou/2013402/CHN | 50 | 31E | — |
| Mut GII.3_E80S + A90L hCod (na) | Hu/GII.3/Jingzhou/2013402/CHN | 51 | 31F | 4148 43D |
| VP1 GII.4 | | | | |
| Wt GII.4 (aa) | Hu/GII.4/Sydney/NSW0514/2012/AU | 16 | 19A | — |
| Wt GII.4 hCod ( na ) | Hu/GII.4/Sydney/NSW0514/2012/AU | 52 | 19B | 3760 44A |
| Mut GII.4_A39V (aa) | Hu/GII.4/Sydney/NSW0514/2012/AU | 53 | 32A | — |
| Mut GII.4_A39V hCod (na) | Hu/GII.4/Sydney/NSW0514/2012/AU | 54 | 32B | 4155 44B |
| Mut GII.4_V47P (aa) | Hu/GII.4/Sydney/NSW0514/2012/AU | 55 | 32C | — |
| Mut GII.4_V47P hCod (na) | Hu/GII.4/Sydney/NSW0514/2012/AU | 56 | 32D | 4156 44C |
| Mut GII.4_R53I (aa) | Hu/GII.4/Sydney/NSW0514/2012/AU | 57 | 32E | — |
| Mut GII.4_R53I hCod (na) | Hu/GII.4/Sydney/NSW0514/2012/AU | 58 | 32F | 4157 44D |
| Mut GII.4_P80S (aa) | Hu/GII.4/Sydney/NSW0514/2012/AU | 59 | 32G | — |
| Mut GII.4_P80S hCod (na) | Hu/GII.4/Sydney/NSW0514/2012/AU | 60 | 32H | 4133 44E |
| Mut GII.4_P80A (aa) | Hu/GII.4/Sydney/NSW0514/2012/AU | 287 | 32FF | — |
| Mut GII.4_P80A hCod (na) | Hu/GII.4/Sydney/NSW0514/2012/AU | 286 | 32EE | 4281 50A |
| Mut GII.4_P80N (aa) | Hu/GII.4/Sydney/NSW0514/2012/AU | 287 | 32FF | — |
| Mut GII.4_P80N hCod (na) | Hu/GII.4/Sydney/NSW0514/2012/AU | 286 | 32EE | 4285 50A |
| Mut GII.4_P80K (aa) | Hu/GII.4/Sydney/NSW0514/2012/AU | 287 | 32FF | — |
| Mut GII.4_P80K hCod (na) | Hu/GII.4/Sydney/NSW0514/2012/AU | 286 | 32EE | 4286 50A |
| Mut GII.4_P80H (aa) | Hu/GII.4/Sydney/NSW0514/2012/AU | 287 | 32FF | — |
| Mut GII.4_P80H hCod (na) | Hu/GII.4/Sydney/NSW0514/2012/AU | 286 | 32EE | 4287 50A |
| Mut GII.4_S90L (aa) | Hu/GII.4/Sydney/NSW0514/2012/AU | 61 | 32I | — |

TABLE 3-continued

Norovirus strains and constructs.

| | | | | | |
|---|---|---|---|---|---|
| Mut GII.4_S90L hCod (na) | Hu/GII.4/Sydney/NSW0514/2012/AU | 62 | 32J | 4134 | 44F |
| Mut GII.4_Δ35-42 (aa) | Hu/GII.4/Sydney/NSW0514/2012/AU | 63 | 32K | — | |
| Mut GII.4_Δ35-42 hCod (na) | Hu/GII.4/Sydney/NSW0514/2012/AU | 64 | 32L | 4158 | 44G |
| Mut GII.4_SSTAVATA (aa) | Hu/GII.4/Sydney/NSW0514/2012/AU | 65 | 32M | — | |
| Mut GII.4_SSTAVATA hCod (na) | Hu/GII.4/Sydney/NSW0514/2012/AU | 66 | 32N | 4159 | 44H |
| Mut GII.4_A39V + R53I (aa) | Hu/GII.4/Sydney/NSW0514/2012/AU | 188 | 32AA | — | |
| Mut GII.4_A39V + R53I hCod (na) | Hu/GII.4/Sydney/NSW0514/2012/AU | 189 | 32BB | 4185 | 44O |
| Mut GII.4_A39V + P80S (aa) | Hu/GII.4/Sydney/NSW0514/2012/AU | 67 | 32O | — | |
| Mut GII.4_A39V + P80S hCod (na) | Hu/GII.4/Sydney/NSW0514/2012/AU | 68 | 32P | 4165 | 44I |
| Mut GII.4_A39I + P80S (aa) | Hu/GII.4/Sydney/NSW0514/2012/AU | 288 | 32HH | — | |
| Mut GII.4_A39I + P80S hCod (na) | Hu/GII.4/Sydney/NSW0514/2012/AU | 289 | 32GG | 4256 | 50B |
| Mut GII.4_A39M + P80S (aa) | Hu/GII.4/Sydney/NSW0514/2012/AU | 288 | 32HH | — | |
| Mut GII.4_A39M + P80S hCod (na) | Hu/GII.4/Sydney/NSW0514/2012/AU | 289 | 32GG | 4257 | 50B |
| Mut GII.4_A39G + P80S (aa) | Hu/GII.4/Sydney/NSW0514/2012/AU | 288 | 32HH | — | |
| Mut GII.4_A39G + P80S hCod (na) | Hu/GII.4/Sydney/NSW0514/2012/AU | 289 | 32GG | 4258 | 50B |
| Mut GII.4_A39S + P80S (aa) | Hu/GII.4/Sydney/NSW0514/2012/AU | 288 | 32HH | — | |
| Mut GII.4_A39S + P80S hCod (na) | Hu/GII.4/Sydney/NSW0514/2012/AU | 289 | 32GG | 4259 | 50B |
| Mut GII.4_A39E + P80S (aa) | Hu/GII.4/Sydney/NSW0514/2012/AU | 288 | 32HH | — | |
| Mut GII.4_A39E + P80S hCod (na) | Hu/GII.4/Sydney/NSW0514/2012/AU | 289 | 32GG | 4260 | 50B |
| Mut GII.4_A39D + P80S (aa) | Hu/GII.4/Sydney/NSW0514/2012/AU | 288 | 32HH | — | |
| Mut GII.4_A39D + P80S hCod (na) | Hu/GII.4/Sydney/NSW0514/2012/AU | 289 | 32GG | 4261 | 50B |
| Mut GII.4_A39N + P80S (aa) | Hu/GII.4/Sydney/NSW0514/2012/AU | 288 | 32HH | — | |
| Mut GII.4_A39N + P80S hCod (na) | Hu/GII.4/Sydney/NSW0514/2012/AU | 289 | 32GG | 4262 | 50B |
| Mut GII.4_A39Q + P80S (aa) | Hu/GII.4/Sydney/NSW0514/2012/AU | 288 | 32HH | — | |
| Mut GII.4_A39Q + P80S hCod (na) | Hu/GII.4/Sydney/NSW0514/2012/AU | 289 | 32GG | 4263 | 50B |
| Mut GII.4_A39K + P80S (aa) | Hu/GII.4/Sydney/NSW0514/2012/AU | 288 | 32HH | — | |
| Mut GII.4_A39K + P80S hCod (na) | Hu/GII.4/Sydney/NSW0514/2012/AU | 289 | 32GG | 4264 | 50B |
| Mut GII.4_A39H + P80S (aa) | Hu/GII.4/Sydney/NSW0514/2012/AU | 288 | 32HH | — | |
| Mut GII.4_A39H + P80S hCod (na) | Hu/GII.4/Sydney/NSW0514/2012/AU | 289 | 32GG | 4265 | 50B |
| Mut GII.4_V47P + P80S (aa) | Hu/GII.4/Sydney/NSW0514/2012/AU | 69 | 32Q | — | |
| Mut GII.4_V47P + P80S hCod (na) | Hu/GII.4/Sydney/NSW0514/2012/AU | 70 | 32R | 4166 | 44J |
| Mut GII.4_R53I + P80S (aa) | Hu/GII.4/Sydney/NSW0514/2012/AU | 71 | 32S | — | |
| Mut GII.4_R53I + P80S hCod (na) | Hu/GII.4/Sydney/NSW0514/2012/AU | 72 | 32T | 4167 | 44K |
| Mut GII.4_P80S + S90L (aa) | Hu/GII.4/Sydney/NSW0514/2012/AU | 73 | 32U | — | |
| Mut GII.4_P80S + S90L hCod (na) | Hu/GII.4/Sydney/NSW0514/2012/AU | 74 | 32V | 4135 | 44L |
| Mut GII.4_P80S + Δ35-42 (aa) | Hu/GII.4/Sydney/NSW0514/2012/AU | 75 | 32W | — | |
| Mut GII.4_P80S + Δ35-42 hCod (na) | Hu/GII.4/Sydney/NSW0514/2012/AU | 76 | 32X | 4168 | 44M |
| Mut GII.4_P80S + SSTAVATA (aa) | Hu/GII.4/Sydney/NSW0514/2012/AU | 77 | 32Y | — | |
| Mut GII.4_P80S + SSTAVATA hCod (na) | Hu/GII.4/Sydney/NSW0514/2012/AU | 78 | 32Z | 4169 | 44N |
| Mut GII.4_A39V + R53I + P80S(aa) | Hu/GII.4/Sydney/NSW0514/2012/AU | 190 | 32CC | — | |
| Mut GII.4_A39V + R53I + P80ShCod (na) | Hu/GII.4/Sydney/NSW0514/2012/AU | 191 | 32DD | 4186 | 44P |
| Wt GII.4 (aa) | US96/GII.4/Dresden174/1997/DE_AY741811 | 27 | 19C | — | |
| Wt GII.4 (aa) | FH02/GII.4/FarmingtonHills/2002/US_AY502023 | 28 | 19D | — | |
| Wt GII.4 (aa) | Hnt04: GII.4/Hunter-NSW504D/2004/AU_DQ078814 | 29 | 19E | — | |
| Wt GII.4 (aa) | 2006b: GII.4/Shellharbour-NSW696T/2006/AU_EF684915 | 30 | 19F | — | |
| Wt GII.4 (aa) | NO09/GII.4/Orange-NSW001P/2008/AU_GQ845367 | 31 | 19G | — | |
| VP1 GII.5 | | | | | |
| Wt GII.5 (aa) | GII.5_Alberta/2013/CA_ALT54485 | 17 | 20 | — | |
| VP1 GII.6 | | | | | |
| Wt GII.6 (aa) | Hu/GII.6/Ohio/490/2012/USA | 20 | 21A | — | |
| Wt GII.6 hCod (na) | Hu/GII.6/Ohio/490/2012/USA | 21 | 21B | 3993 | 45A |
| Mut GII.6_E80S (aa) | Hu/GII.6/Ohio/490/2012/USA | 79 | 33A | — | |
| Mut GII.6_E80S hCod (na) | Hu/GII.6/Ohio/490/2012/USA | 80 | 33B | 4149 | 45B |
| Mut GII.6_S90L (aa) | Hu/GII.6/Ohio/490/2012/USA | 81 | 33C | — | |
| Mut GII.6_S90L hCod (na) | Hu/GII.6/Ohio/490/2012/USA | 82 | 33D | 4150 | 45C |
| Mut GII.6_E80S + S90L (aa) | Hu/GII.6/Ohio/490/2012/USA | 83 | 33E | — | |
| Mut GII.6_E80S + S90L hCod (na) | Hu/GII.6/Ohio/490/2012/USA | 84 | 33F | 4151 | 45D |
| VP1 GII.7 | | | | | |
| Wt GII.7 (aa) | GII.7_Musa_2010_AII73774 | 8 | 22 | — | |
| VP1 GII.12 | | | | | |
| Wt GII.12 (aa) | GII.12_HS206_2010_USA_AEI29586 | 19 | 23A | — | |
| Wt GII.12 hCod (na) | GII.12_HS206_2010_USA_AEI29586 | 87 | 23B | 3995 | 46A |
| Mut GII.12_E80S (aa) | GII.12_HS206_2010_USA_AEI29586 | 88 | 34A | — | |
| Mut GII.12_E80S hCod (na) | GII.12_HS206_2010_USA_AEI29586 | 89 | 34B | 4136 | 46B |
| Mut GII.12_A90L (aa) | GII.12_HS206_2010_USA_AEI29586 | 90 | 34C | — | |
| Mut GII.12_A90L hCod (na) | GII.12_HS206_2010_USA_AEI29586 | 91 | 34D | 4137 | 46C |

TABLE 3-continued

Norovirus strains and constructs.

| | | | | | |
|---|---|---|---|---|---|
| Mut GII.12_E80S + A90L (aa) | GII.12_HS206_2010_USA_AEI29586 | 92 | 34E | — | |
| Mut GII.12_E80S + A90L hCod (na) | GII.12_HS206_2010_USA_AEI29586 | 93 | 34F | 4138 | 46D |
| VP1 GII.13 | | | | | |
| Wt GII.13 (aa) | GII.13_VA173_2010_H9AWU4 | 22 | 24A | — | |
| Wt GII.13 hCod (na) | GII.13_VA173_2010_H9AWU4 | 23 | 24B | — | |
| VP1 GII.14 | | | | | |
| Wt GII.14 (aa) | GII.14_Saga/2008/JPN/_ADE28701 | 32 | 25 | — | |
| VP1 GII.17 | | | | | |
| Wt GII.17 (aa) | GII.17_Kawa_2014_A0A077KVU6 | 24 | 26A | — | |
| Wt GII.17 hCod (na) | GII.17_Kawa_2014_A0A077KVU6 | 25 | 26B | — | |
| Mut GII.17_A39V (aa) | GII.17_Kawa_2014_A0A077KVU6 | 192 | 34G | — | |
| Mut GII.17_A39V hCod (na) | GII.17_Kawa_2014_A0A077KVU6 | 193 | 34H | 4234 | 46E |
| Mut GII.17_R53I (aa) | GII.17_Kawa_2014_A0A077KVU6 | 194 | 34I | — | |
| Mut GII.17_R53I hCod (na) | GII.17_Kawa_2014_A0A077KVU6 | 195 | 34J | 4235 | 46F |
| Mut GII.17_A90L (aa) | GII.17_Kawa_2014_A0A077KVU6 | 196 | 34K | — | |
| Mut GII.17_A90L hCod (na) | GII.17_Kawa_2014_A0A077KVU6 | 197 | 34L | 4232 | 46G |
| Mut GII.17_A39V + R53I (aa) | GII.17_Kawa_2014_A0A077KVU6 | 198 | 34M | — | |
| Mut GII.17_A39V + R53I hCod (na) | GII.17_Kawa_2014_A0A077KVU6 | 199 | 34N | 4236 | 46H |
| Mut GII.17_E80S + A90L (aa) | GII.17_Kawa_2014_A0A077KVU6 | 200 | 34O | — | |
| Mut GII.17_E80S + A90L hCod (na) | GII.17_Kawa_2014_A0A077KVU6 | 201 | 34P | 4233 | 46I |
| VP1 GII.21 | | | | | |
| Wt GII.21 (aa) | GII.21_Sali_2011_USA_AFC89665 | 26 | 27 | — | |
| VP2 | | | | | |
| Wt GI.1 (aa) | Hu/GI.1/United States/Norwalk/1968 | 99 | 35A | — | |
| Wt GI.1 hCod (na) | Hu/GI.1/United States/Norwalk/1968 | 100 | 35B | 2725 | 47A |
| Wt GI.3 (aa) | GI.3/S29/2008/Lila Edet/Sweden | 94 | 36A | — | |
| Wt GI.3 hCod (na) | GI.3/S29/2008/Lila Edet/Sweden | 95 | 36B | 3303 | 47B |
| Wt GII.6 (aa) | GII.6 HS245/2010/USA | 96 | 37A | — | |
| Wt GII.6 hCod (na) | GII.6 HS245/2010/USA | 97 | 37B | 3307 | 47C |

| Construct | SEQ ID NO: | SEQ FIG. # | Const # | Const. FIG. # |
|---|---|---|---|---|
| Cloning vector 1190 from left to right T-DNA | 162 | 38A | 1190 | 48 |
| Construct 2724 from 2X35S promoter to NOS terminator | 163 | 38B | 2724 | |
| Cloning vector 3677 from left to right T-DNA | 164 | 38C | 3677 | 49 |
| Construct 4133 from 2X35S promoter to NOS terminator | 165 | 38D | 4133 | |
| Construct 4135 from 2X35S promoter to NOS terminator | 166 | 38E | 4135 | |

The present invention will be further illustrated in the following examples.

Example 1: Norovirus VP1 Constructs

The candidate sequences for VP1 and VP2 are available in Genbank (see FIGS. 2A and 2B). Non-limiting examples of these sequences are:

- Hu/GI.2/Leuven/2003/BEL (GI.2; SEQ ID NO:4; FIG. 13A);
- Hu/GI.3/S29/2008/Lilla Edet/Sweden (GI.3; SEQ ID NO:6; FIG. 14A);
- Hu/GI.5/Siklos/Hun5407/2013/HUN (GI.5; SEQ ID NO:12; FIG. 15A);
- Hu/GI.7/USA/2014/GA5043 (GI.7, SEQ ID NO:101, FIG. 16A)
- Hu/GII.1/Ascension208/2010/USA SEQ ID NO:13; FIG. 16C);
- Hu/GII.2/CGMH47/2011/TW (GII.2; SEQ ID NO:14; FIG. 17A);
- Hu/GII.3/Jingzhou/2013402/CHN (GII.3; SEQ ID NO:15; FIG. 18A);
- Hu/GII.4/Sydney/NSW0514/2012/AU (GII.4; SEQ ID NO:16; FIG. 19A);
- US96/GII.4/Dresden174/1997/DE_AY741811 (GII.4; SEQ ID NO:27; FIG. 19C);
- FH02/GII.4/FarmingtonHills/2002/US_AY502023 (GII.4; SEQ ID NO:28; FIG. 19D);
- Hnt04: GII.4/Hunter-NSW504D/2004/AU_DQ078814 (GII.4; SEQ ID NO:29; FIG. 19E);
- 2006b: GII.14/Shellharbour-NSW696T/2006/AU_EF684915 (GII.14; SEQ ID NO:30; FIG. 19F);
- NO09: GII.4/Orange-NSW001P/2008/AU_GQ845367 (GII.4; SEQ ID NO:31; FIG. 19G);
- GII.14_Saga_2008_JPN_ADE28701 native VP1 (0114; SEQ ID NO:32; FIG. 25);
- Hu/GII.5/AlbertaEI390/2013/CA (GII.5; SEQ ID No:17; FIG. 20);
- Hu/GII.6/Ohio/490/2012/USA (GII.6; SEQ ID NO: 20; FIG. 21A);
- GII.7/Musa/2010/A1173774 (GII.7; SEQ ID NO:18; FIG. 22);
- Hu/GII.12/HS206/2010/USA (GII.2; SEQ ID NO:19; FIG. 23A);

GII.13/VA173/2010/H9AWU4 (GII.13; SEQ ID NO:22; FIG. 24A);

Hu/GII.17/Kawasaki323/2014/JP (GII.17; SEQ ID NO:24; FIG. 26A);

Hu/GII.21/Salisbury150/2011/USA (GII.21; SEQ ID NO:26; FIG. 27).

The primers listed in Table 4 were used to prepare the constructs described below.

TABLE 4 primers used to prepare constructs defined herein.

| Primer | Sequence | SEQ ID NO |
|---|---|---|
| IF-NOV(US68)VP1(ORF1)(hCod).c | TCGTGCTTCGGCACCAGTACAATGATGATGGCTAGT AAAGATGCGACCT | 102 |
| IF-NOV(US68)VP1(ORF1)(hCod).r | ACTAAAGAAAATAGGCCTTTATCTCCGCAGACCGAG GCGTCCGCGGGCAGAA | 103 |
| IF-GI3Lil08VP1.c | TCGTGCTTCGGCACCAGTACAATGATGATGGCTTCC AAGGATGCTCCCA | 104 |
| IF-GI3Lil08VP1.r | ACTAAAGAAAATAGGCCTCTAGCTCCGTCTGATCCC GAGCCTCCGAACT | 105 |
| VP1_GI.3Lil08(S94L).r | CTGAGCCAAGTGGAGCAGAAACGGATTCAAGTGTGG TCCTAGCTGCAGGTCAAACAAGA | 106 |
| VP1_GI.3Lil08(S94L).c | AGGACCACACTTGAATCCGTTTCTGCTCCACTTGGC TCAGATGTATAATGGATGGG | 107 |
| VP1_GI.3Lil08(Q84S).r | GTGTGGTCCTAGGCTCAGGTCAAACAAGATGTCACC CGGGGTGTTGTTTGGGCTTAT | 108 |
| VP1_GI.3Lil08(Q84S).c | GGTGACATCTTGTTTGACCTGAGCCTAGGACCACAC TTGAATCCGTTT | 109 |
| IF-GI3Lil08VP2.c | TCGTGCTTCGGCACCAGTACAATGGCTCAGGCAATC TTCGGCGCAATC | 110 |
| IF-GI3Lil08VP2.r | ACTAAAGAAAATAGGCCTTCACTTCCTCATGTTTGC GAACAGGGGAAGC | 111 |
| IF-(160)GI.5_Sik113_VP1.c | TCGTGCTTCGGCACCAGTACAATGATGATGGCCTCC AAAGACGCTCCT | 112 |
| IF-GI.5_Sik113_VP1.r | ACTAAAGAAAATAGGCCTTCAGCGCCGCACGCCAAG GCGCCCCCGGGCAGATG | 113 |
| GI.5(hCod)(Q84S).r | GATGAGGGCCTAAGCTCAGGTCGAACAGAATATCCC CTGGTGTGTTGTTAG | 114 |
| GI.5(hCod)(Q84S).c | TATTCTGTTCGACCTGAGCTTAGGCCCTCATCTCAA CCCCTTCTTGGCCCA | 115 |
| GI.5(hCod)(A94L).r | ATCTGGCTCAGGTGGAGCAAGAAGGGGTTGAGATGA GGGCCTAACTGCAG | 116 |
| GI.5(hCod)(A94L).c | TCTCAACCCCTTCTTGCTCCACCTGAGCCAGATGTA CAATGGCTGGGTGGG | 117 |
| IF-(160)GII.2_CGMH11_VP1.c | TCGTGCTTCGGCACCAGTACAATGAAGATGGCATCC AACGACGCCGCACCCAGC | 118 |
| IF-GII.2_CGMH11_VP1.r | ACTAAAGAAAATAGGCCTTTACTGGATCCGTCGGCG ACCGTTCCCTGTGCCCA | 119 |
| VP1_GII.2CGMH11(E80S).r | TTCTGGTCCCAGGCTGAGATTGAGGAGCACTTCCCC AGGGCTATTTCTAGGGCTGACCG | 120 |
| VP1_GII.2CGMH11(E80S).c | GGAAGTGCTCCTCAATCTCAGCCTGGGACCAGAACT TAATCCGTACCT | 121 |
| VP1_GII.2CGMH11(A90L).r | TCCGGGCCAGGTGGAGCAGGTACGGATTAAGTTCTG GTCCCAGCTCGAGATTGAGGAGC | 122 |
| VP1_GII.2CGMH11(A90L).c | GGGACCAGAACTTAATCCGTACCTGCTCCACCTGGC CCGGATGTACAATGGATATGCAG | 123 |
| IF-(160)GII.3_Jing13_VP1.c | TCGTGCTTCGGCACCAGTACAATGAAAATGGCTTCC AACGATGCAGCACCCT | 124 |

TABLE 4-continued

| primers used to prepare constructs defined herein. | | |
|---|---|---|
| Primer | Sequence | SEQ ID NO |
| IF-GII.3_Jing13_VP1.r | ACTAAAGAAAATAGGCCTTTACTGGATCCGCCGTCT GCCATTGCCTGTAC | 125 |
| VP1_GII.3Jing13(E80S).r | ATTTCAGGGCCCAGGCTCAAATTCAAGAGAACCTCC CCGGGGGAGTTTCGAGGAGAGAC | 126 |
| VP1_GII.3Jing13(E80S).c | GGAGGTTCTCTTGAATTTGAGCCTGGGCCCTGAAAT TAATCCTTATCT | 127 |
| VP1_GII.3Jing13(A90L).r | ATTCGGGCTAGATGGAGCAGATAAGGATTAATTTCA GGGCCCAGTTCCAAATTCAAGAG | 128 |
| VP1_GII.3Jing13(A90L).c | GGGCCCTGAAATTAATCCTTATCTGCTCCATCTAGC CCGAATGTACAACGGCTACG | 129 |
| IF-GII.4Syd12VP1.c | TCGTGCTTCGGCACCAGTACAATGAAAATGGCCTCG AGTGACGCTAACC | 130 |
| IF-GII.4Syd12VP1.r | ACTAAAGAAAATAGGCCTTCAGACAGCCCTGCGTCT GCCAGTCCCATT | 131 |
| VP1_GII.4Syd12(A39V).r | GACCGGCCACGGGGACTGCTATGGCTGCGCCCACCA CAGGCTCCAGGGCCATCA | 132 |
| VP1_GII.4Syd12(A39V).c | GGGCGCAGCCATAGCAGTCCCCGTGGCCGGTCAGCA GAATGTGATTGACCCGTG | 133 |
| VP1_GII.4Syd12(V47P).r | CGTATCCACGGGTCAATGGGATTCTGCTGACCGGCC ACGGGCGCTGCTATG | 134 |
| VP1_GII.4Syd12(V47P).c | GGCCGGTCAGCAGAATCCCATTGACCCGTGGATACG CAACAATTTTGTCCAAG | 135 |
| VP1_GII.4Syd12(R531).r | TGGACAAAATTGTTGATTATCCACGGGTCAATCACA TTCTGCTGACCG | 136 |
| VP1_GII.4Syd12(R53I).c | GATTGACCCGTGGATAATCAACAATTTTGTCCAAGC CCCTGGTGGGGAGT | 137 |
| GII.4(P80S).r | GATCGGGTCCCAAGCTGGCCGACCACAGGATTTCTC CTGGCGCATTTCTC | 138 |
| GII.4(P80S).c | AATCCTGTGGTCGGCCAGCTTGGGACCCGATCTGAA CCCCTATTTGTCAC | 139 |
| GII.4(S90L).r | ATCCGAGCGAGATGCAGCAAATAGGGGTTCAGATCG GGTCCCAATGGGGCCGACCA | 140 |
| GII.4(S90L).c | TCTGAACCCCTATTTGCTGCATCTCGCTCGGATGTA CAACGGGTATGC | 141 |
| VP1_GII.4Syd12(Del(35-42)).r | CACATTCTGCTGACCGCCCACCACAGGCTCCAGGGC CATCACCTCATTAT | 142 |
| VP1_GII.4Syd12(Del(35-42)).c | GGAGCCTGTGGTGGGCGGTCAGCAGAATGTGATTGA CCCGTGGATACG | 143 |
| VP1_GII.4Syd12(SSTAVATA).r | CTGACCGGCTGTAGCGACGGCGGTGGAGCTGCCCAC CACAGGCTCCAGGGCCATCACCTC | 144 |
| VP1_GII.4Syd12(SSTAVATA).c | TGTGGTGGGCAGCTCCACCGCCGTCGCTACAGCCGG TCAGCAGAATGTGATTGACCCGTG | 145 |
| IF-GII.6Ohi12VP1.c | TCGTGCTTCGGCACCAGTACAATGAAGATGGCAAGC AACGACGCAGCTC | 146 |
| IF-GII.6Ohi12VP1.r | ACTAAAGAAAATAGGCCTTCACTGATCCCGGCGTCG CCCCTGGCCTGTCCCCAT | 147 |
| IF-GII.6HS10VP2.c | TCGTGCTTCGGCACCAGTACAATGGCCTCCGCATTT CTAGCTGGATTGGCC | 148 |
| IF-GII.6HS10VP2.r | ACTAAAGAAAATAGGCCTCTAAACTTGTGATTCTCC CCGTCGCCTGGGGTGTG | 149 |

TABLE 4-continued primers used to prepare constructs defined herein.

| Primer | Sequence | SEQ ID NO |
|---|---|---|
| VP1_GII.6Ohi12(E80S).r | AGTTCAGGGCCGAGGCTCAGATTGAGCAGCATCTCG CCCGGGGAGTTCCGGGGGGAGAC | 150 |
| VP1_GII.6Ohi12(E80S).c | CGAGATGCTGCTCAATCTGAGCCTCGGCCCTGAACT AAACCCTTATCT | 151 |
| VP1_GII.6Ohi12(S90L).r | ATCCGTGAAAGGTGGAGCAGATAAGGGTTTAGTTCA GGGCCGAGTTCCAGATTGAGCAG | 152 |
| VP1_GII.60hi12(S90L).c | CCCTGAACTAAACCCTTATCTGCTCCACCTTTCACG GATGTACAATGGCTACGCAGGAG | 153 |
| IF-(160)GII.12_HS10_VP1.c | TCGTGCTTCGGCACCAGTACAATGAAGATGGCGTCT AATGATGCTGCTCCTT | 154 |
| IF-GII.12_HS10 VP1.r | ACTAAAGAAAATAGGCCTTTACTGCACACGCCTCCT CCCATTTCCTGTTCCCAT | 155 |
| GII.12(E80S).r | AGTTCTGGTCCTAAGCTCAAATTCAATAACACTTCG CCGGGGGAGTTT | 156 |
| GII.12(E80S). | AGTGTTATTGAATTTGAGCTTAGGACCAGAACTCAA CCCCTATCTGGCA | 157 |
| GII.12(A90L).r | ATCCGAGACAGATGGAGCAGATAGGGGTTGAGTTCT GGTCCTAATTCCAA | 158 |
| GII.12(A90L).c | ACTCAACCCCTATCTGCTCCATCTGTCTCGGATGTA CAACGGCTATGCGGGCGGAGT | 159 |
| IF-NOV(US68)VP2(ORF3)(hCod).c | TCGTGCTTCGGCACCAGTACAATGGCTCAGGCCATT ATTGGCGCCAT | 160 |
| IF-NOV(US68)VP2(ORF3)(hCod).r | ACTAAAGAAAATAGGCCTTCAGCGGCGGTTGTTAGC GAACAGAGGAAGTC | 161 |
| GI.3Lil08(M571).r | CTGAACGTAATTTGAGATGATCCAGGGGTCGATCAT GTTTACCTGTCCTGCGGTGGCGG | 202 |
| GI.3Lil08(M57I).c | GTAAACATGATCGACCCCTGGATCATCTCAAATTAC GTTCAGGCTCCACAGGGGGAGTT | 203 |
| IF-(GI.7USA14)VP1.c | TCGTGCTTCGGCACCAGTACAATGATGATGGCCAGC AAGGACGCTCCGAGTA | 204 |
| IF-(GI.7USA14)VP1.r | ACTAAAGAAAATAGGCCTTCACACCCGCCTCACGCC GAGTCGTCGCACG | 205 |
| GI.7USA14_VP1(R84S).r | AGTGGGGTCCTAAGCTGAGGTCAAACAGAATATCCC CTGGGGTGTTAT | 206 |
| GI.7USA14_VP1(R84S).c | TATTCTGTTTGACCTCAGCTTAGGACCCCACTTGAA CCCCTTTCTGCTTC | 207 |
| GI.7USA14_VP1(M571).r | AACGAAATTGTTGATTATCCACGGGTCGATCATATT GACTTGGCCTGCAGT | 208 |
| GI.7USA14_VP1(M571).c | GATCGACCCGTGGATAATCAACAATTTCGTTCAGGC ACCAGAAGGAGA | 209 |
| GII.2CGMH11(A39V).r | TTTGTCTGCCCGGTCACAGGCACTGCGAGGGCAGCC CCTGCAACAGGCTCCAAGGCCATCAC | 210 |
| GII.2CGMH11(A39V).c | GTTGCAGGGGCTGCCCTCGCAGTGCCTGTGACCGGG CAGACAAATATCATCGATCCTTG | 211 |
| GII.2CGMH11(R531).r | CACGAAATTAGCGATAATCCAAGGATCGATGATATT TGTCTGCCCGGTCACAGGAGCTG | 212 |
| GII.2CGMH11(R531).c | GGCAGACAAATATCATCGATCCTTGGATTATCGCTA ATTTCGTGCAAGCCCCAAATGGG | 213 |
| IF-GII17Kaw14VP1.c | TCGTGCTTCGGCACCAGTACAATGAAAATGGCATCT AACGACGCAGCCCCCTC | 214 |

TABLE 4-continued primers used to prepare constructs defined herein.

| Primer | Sequence | SEQ ID NO |
|---|---|---|
| IF-GII17Kaw14VP1.r | ACTAAAGAAAATAGGCCTCTACTGAGCCCGGCGTCT GCCGTTACCGGTGCCCATTG | 215 |
| GII.17Kaw14(A90L).r | GCGGCTCAGATGCAGCAGATATGGATTGAGGTCAGG GCCGAGCTCAAGATTCAGGAGTA | 216 |
| GII.17Kaw14(A90L).c | CCTGACCTCAATCCATATCTGCTGCATCTGAGCCGC ATGTACAATGGTTAC | 217 |
| GII.17Kaw14(A39V).r | ATTCTGCCCTGTCACTGGCACAGCTATAGCGGCGCC TGCAACCGGCTCTAGTGGAAGTG | 218 |
| GII.17Kaw14(A39V).c | AGGCGCCGCTATAGCTGTGCCAGTGACAGGGCAGAA TAATATTATAGACCCTTGGATT | 219 |
| GII.17Kaw14(R531).r | ACGAAGTTTGTGATAATCCAAGGGTCTATAATATTA TTCTGCCCTGTCACTGGGGCAGC | 220 |
| GII.17Kaw14(R531).c | GGCAGAATAATATTATAGACCCTTGGATTATCACAA ACTTCGTGCAGGCACCCAACGGC | 221 |
| GII.4Syd12(P80A).r | ATCGGGTCCCAAGGCGGCCGACCACAGGATTTCTCC TGGCGCATTTCTCG | 222 |
| GII.4Syd12(P80A).c | AATCCTGTGGTCGGCCGCCTTGGGACCCGATCTGAA CCCCTATTTGTCAC | 223 |
| GII.4Syd12(P80N).r | ATCGGGTCCCAAGTTGGCCGACCACAGGATTTCTCC TGGCGCATTTCTCG | 224 |
| GII.4Syd12(P80N).c | AATCCTGTGGTCGGCCAACTTGGGACCCGATCTGAA CCCCTATTTGTCAC | 225 |
| GII.4Syd12(P80K).r | ATCGGGTCCCAACTTGGCCGACCACAGGATTTCTCC TGGCGCATTTCTCG | 226 |
| GII.4Syd12(P80K).c | AATCCTGTGGTCGGCCAAGTTGGGACCCGATCTGAA CCCCTATTTGTCAC | 227 |
| GII.4Syd12(P80H).r | ATCGGGTCCCAAGTGGGCCGACCACAGGATTTCTCC TGGCGCATTTCTCG | 228 |
| GII.4Syd12(P80H).c | AATCCTGTGGTCGGCCCACTTGGGACCCGATCTGAA CCCCTATTTGTCAC | 229 |
| GII.4Syd12(A391).r | GACCGGCCACGGGGATTGCTATGGCTGCGCCCACCA CAGGCTCCAGGGCCATCA | 230 |
| GII.4Syd12(A391).c | GGGCGCAGCCATAGCAATCCCCGTGGCCGGTCAGCA GAATGTGATTGACCCGTG | 231 |
| GII.4Syd12(A39M).r | GACCGGCCACGGGCATTGCTATGGCTGCGCCCACCA CAGGCTCCAGGGCCATCA | 232 |
| GII.4Syd12(A39M).c | GGGCGCAGCCATAGCAATGCCCGTGGCCGGTCAGCA GAATGTGATTGACCCGTG | 233 |
| GII.4Syd12(A39G).r | GACCGGCCACGGGGCCTGCTATGGCTGCGCCCACCA CAGGCTCCAGGGCCATCA | 234 |
| GII.4Syd12(A39G).c | GGGCGCAGCCATAGCAGGCCCCGTGGCCGGTCAGCA GAATGTGATTGACCCGTG | 235 |
| GII.4Syd12(A39S).r | GACCGGCCACGGGGCTTGCTATGGCTGCGCCCACCA CAGGCTCCAGGGCCATCA | 236 |
| GII.4Syd12(A39S).c | GGGCGCAGCCATAGCAAGCCCCGTGGCCGGTCAGCA GAATGTGATTGACCCGTG | 237 |
| GII.4Syd12(A39E).r | GACCGGCCACGGGCTCTGCTATGGCTGCGCCCACCA CAGGCTCCAGGGCCATCA | 238 |
| GII.4Syd12(A39E).c | GGGCGCAGCCATAGCAGAGCCCGTGGCCGGTCAGCA GAATGTGATTGAC | 239 |

TABLE 4-continued primers used to prepare constructs defined herein.

| Primer | Sequence | SEQ ID NO |
|---|---|---|
| GII.4Syd12(A39D).r | GACCGGCCACGGGGTCTGCTATGGCTGCGCCCACCA CAGGCTCCAGGGCCATCA | 240 |
| GII.4Syd12(A39D).c | GGGCGCAGCCATAGCAGACCCCGTGGCCGGTCAGCA GAATGTGATTGACCCGTG | 241 |
| GII.4Syd12(A39N).r | ACCGGCCACGGGGTTTGCTATGGCTGCGCCCACCAC AGGCTCCAGGGCCATCAC | 242 |
| GII.4Syd12(A39N).c | GGGCGCAGCCATAGCAAACCCCGTGGCCGGTCAGCA GAATGTGATTGACCCGTG | 243 |
| GII.4Syd12(A39Q).r | GACCGGCCACGGGCTGTGCTATGGCTGCGCCCACCA CAGGCTCCAGGGCCATCA | 244 |
| GII.4Syd12(A39Q).c | GGGCGCAGCCATAGCACAGCCCGTGGCCGGTCAGCA GAATGTGATTGACCCGTG | 245 |
| GII.4Syd12(A39K).r | GACCGGCCACGGGCTTTGCTATGGCTGCGCCCACCA CAGGCTCCAGGGCCATCA | 246 |
| GII.4Syd12(A39K).c | GGGCGCAGCCATAGCAAAGCCCGTGGCCGGTCAGCA GAATGTGATTGACCCGTG | 247 |
| GII.4Syd12(A39H).r | GACCGGCCACGGGGTGTGCTATGGCTGCGCCCACCA CAGGCTCCAGGGCCA | 248 |
| GII.4Syd12(A39H).c | GGGCGCAGCCATAGCACACCCCGTGGCCGGTCAGCA GAATGTGATTGACCCGTG | 249 |
| GI.7USA14(M57L).r | GAACGAAATTGTTCAGTATCCACGGGTCGATCATAT TGACTTGGCCTGCA | 250 |
| GI.7USA14(M57L).c | GATCGACCCGTGGATACTGAACAATTTCGTTCAGGC ACCAGAAGGAGA | 251 |
| GI.7USA14(M57G).r | GAACGAAATTGTTGCCTATCCACGGGTCGATCATAT TGACTTGGCCTGCAGT | 252 |
| GI.7USA14(M57G).c | GATCGACCCGTGGATAGGCAACAATTTCGTTCAGGC ACCAGAAGGAGA | 253 |
| GI.7USA14(M57S).r | GAACGAAATTGTTGCTTATCCACGGGTCGATCATAT TGACTTGGCCTGCAGT | 254 |
| GI.7USA14(M57S).c | GATCGACCCGTGGATAAGCAACAATTTCGTTCAGGC ACCAGAAGGAGA | 255 |
| GI.7USA14(M57T).r | GAACGAAATTGTTGGTTATCCACGGGTCGATCATAT TGACTTGGCCTGCAGT | 256 |
| GI.7USA14(M57T).c | GATCGACCCGTGGATAACCAACAATTTCGTTCAGGC ACCAGAAGGAGA | 257 |
| GI.7USA14(M57N).r | GAACGAAATTGTTGTTTATCCACGGGTCGATCATAT TGACTTGGCCTGCAGT | 258 |
| GI.7USA14(M57N).c | GATCGACCCGTGGATAAACAACAATTTCGTTCAGGC ACCAGAAGGAGA | 259 |
| GI.7USA14(M57Q).r | GAACGAAATTGTTCTGTATCCACGGGTCGATCATAT TGACTTGGCCTGCAGT | 260 |
| GI.7USA14(M57Q).c | GATCGACCCGTGGATACAGAACAATTTCGTTCAGGC ACCAGAAGGAGA | 261 |
| GI.7USA14(M57K).r | GAACGAAATTGTTCTTTATCCACGGGTCGATCATAT TGACTTGGCCTGCAGT | 262 |
| GI.7USA14(M57K).c | GATCGACCCGTGGATAAAGAACAATTTCGTTCAGGC ACCAGAAGGAGA | 263 |
| GI.7USA14(M57H).r | GAACGAAATTGTTGTGTATCCACGGGTCGATCATAT TGACTTGGCCTGCAGT | 264 |

TABLE 4-continued primers used to prepare constructs defined herein.

| Primer | Sequence | SEQ ID NO |
|---|---|---|
| GI.7USA14(M57H).c | GATCGACCCGTGGATACACAACAATTTCGTTCAGGC ACCAGAAGGAGA | 265 |
| GI.3Lil08(S94V).r | TCTGAGCCAAGTGCACCAGAAACGGATTCAAGTGTG GTCCTAGCTGCAGGTCAA | 266 |
| GI.3Lil08(S94V).c | CTTGAATCCGTTTCTGGTGCACTTGGCTCAGATGTA TAATGGATGGGTTGGAAA | 267 |
| GI.3Lil08(S941).r | TCTGAGCCAAGTGGATCAGAAACGGATTCAAGTGTG GTCCTAGCTGCAGGTCAA | 268 |
| GI.3Lil08(S941).c | CTTGAATCCGTTTCTGATCCACTTGGCTCAGATGTA TAATGGATGGGTTGGAAA | 269 |
| GI.3Lil08(S94M).r | TCTGAGCCAAGTGCATCAGAAACGGATTCAAGTGTG GTCCTAGCTGCAGGTCAA | 270 |
| GI.3Lil08(S94M).c | CTTGAATCCGTTTCTGATGCACTTGGCTCAGATGTA TAATGGATGGGTTGGAAA | 271 |
| GI.3Lil08(S94T).r | TCTGAGCCAAGTGGGTCAGAAACGGATTCAAGTGTG GTCCTAGCTGCAGGTCAA | 272 |
| GI.3Lil08(S94T).c | CTTGAATCCGTTTCTGACCCACTTGGCTCAGATGTA TAATGGATGGGTTGGAAA | 273 |
| GI.3Lil08(S94E).r | TCTGAGCCAAGTGCTCCAGAAACGGATTCAAGTGTG GTCCTAGCTGCAGGTCAA | 274 |
| GI.3Lil08(S94E).c | CTTGAATCCGTTTCTGGAGCACTTGGCTCAGATGTA TAATGGATGGGTTGGAAA | 275 |
| GI.3Lil08(S94D).r | TCTGAGCCAAGTGGTCCAGAAACGGATTCAAGTGTG GTCCTAGCTGCAGGTCAA | 276 |
| GI.3Lil08(S94D).c | CTTGAATCCGTTTCTGGACCACTTGGCTCAGATGTA TAATGGATGGGTTGGAAA | 277 |
| GI.3Lil08(S94N).r | TCTGAGCCAAGTGGTTCAGAAACGGATTCAAGTGTG GTCCTAGCTGCAGGTCAA | 278 |
| GI.3Lil08(S94N).c | CTTGAATCCGTTTCTGAACCACTTGGCTCAGATGTA TAATGGATGGGTTGGAAA | 279 |
| GI.3Lil08(S94Q).r | TCTGAGCCAAGTGCTGCAGAAACGGATTCAAGTGTG GTCCTAGCTGCAGGTCAA | 280 |
| GI.3Lil08(S94Q).c | CTTGAATCCGTTTCTGCAGCACTTGGCTCAGATGTA TAATGGATGGGTTGGAAA | 281 |
| GI.3Lil08(S94K).r | TCTGAGCCAAGTGCTTCAGAAACGGATTCAAGTGTG GTCCTAGCTGCAGGTCAA | 282 |
| GI.3Lil08(S94K).c | CTTGAATCCGTTTCTGAAGCACTTGGCTCAGATGTA TAATGGATGGGTTGGAAA | 283 |
| GI.3Lil08(S94H).r | TCTGAGCCAAGTGGTGCAGAAACGGATTCAAGTGTG GTCCTAGCTGCAGGTCAA | 284 |
| GI.3Lil08(S94H).c | CTTGAATCCGTTTCTGCACCACTTGGCTCAGATGTA TAATGGATGGGTTGGAAA | 285 |

WT GI.1 Norovirus VP1: A2×35S/CPMV 160/wt VP1 GI.1/NOS (Construct Number 2724)

Figure 39A:
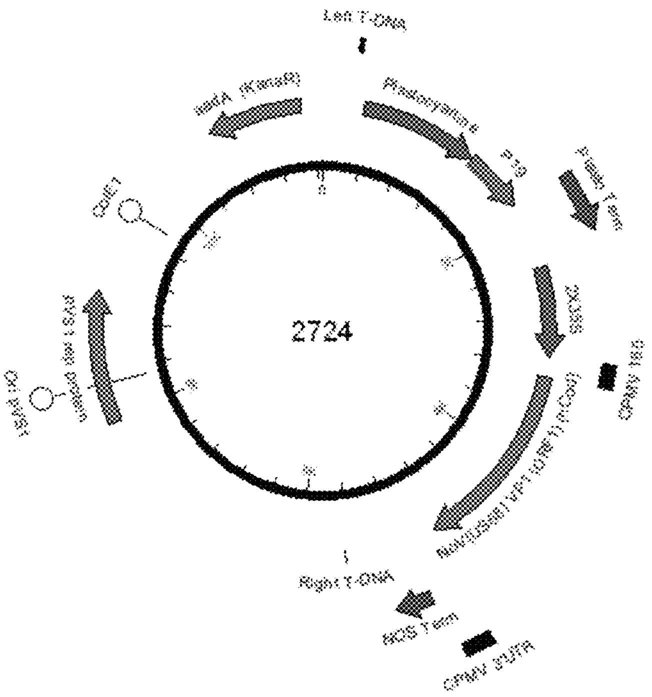
FIG. 39A shows a schematic representation of construct 2724 (VP1 Wt GI.1 hCod).
Figure 39B:
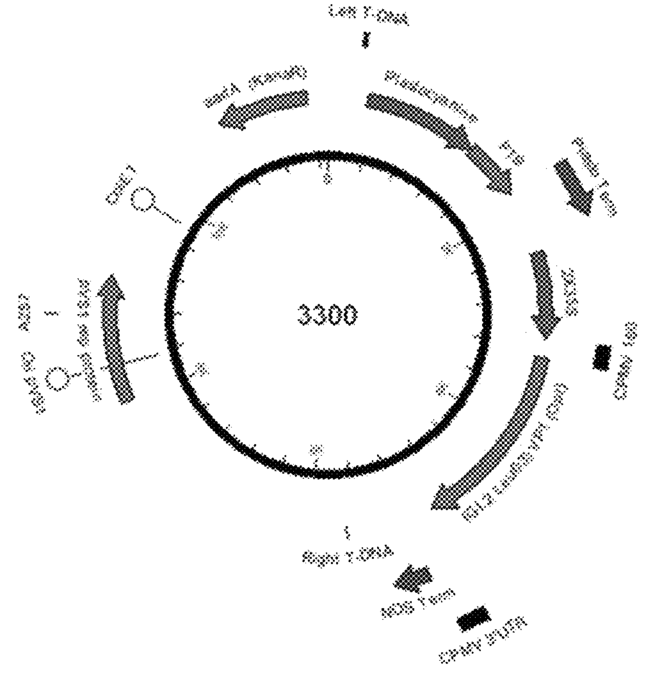
FIG. 39B shows a schematic representation of construct 3300 (VP1 Wt GI.2 hCod).
Figure 39C:
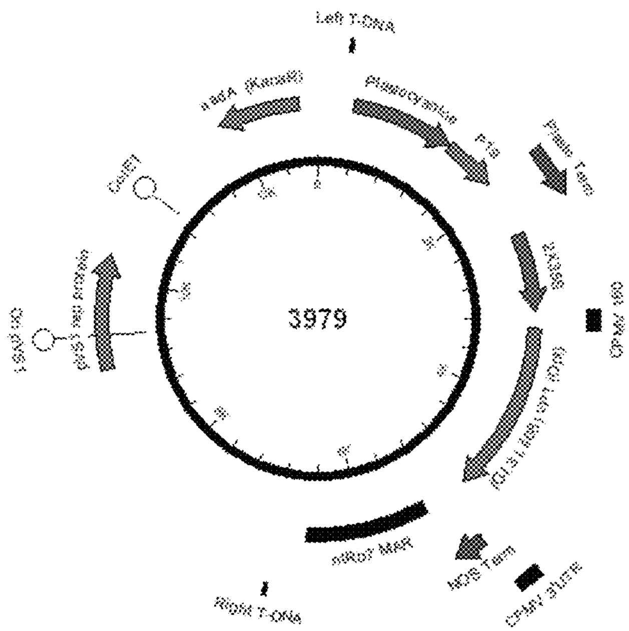
FIG. 39C shows a schematic representation of construct 3979 (VP1 Wt GI.3 hCod).
Figure 40A:
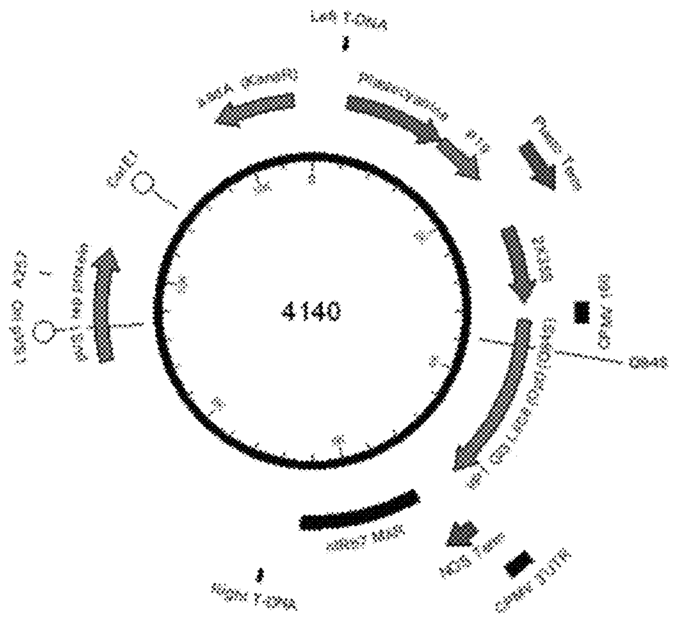
FIG. 40A shows a schematic representation of construct 4140 (VP1 GI.3_Q84S hCod).
Figure 40B:
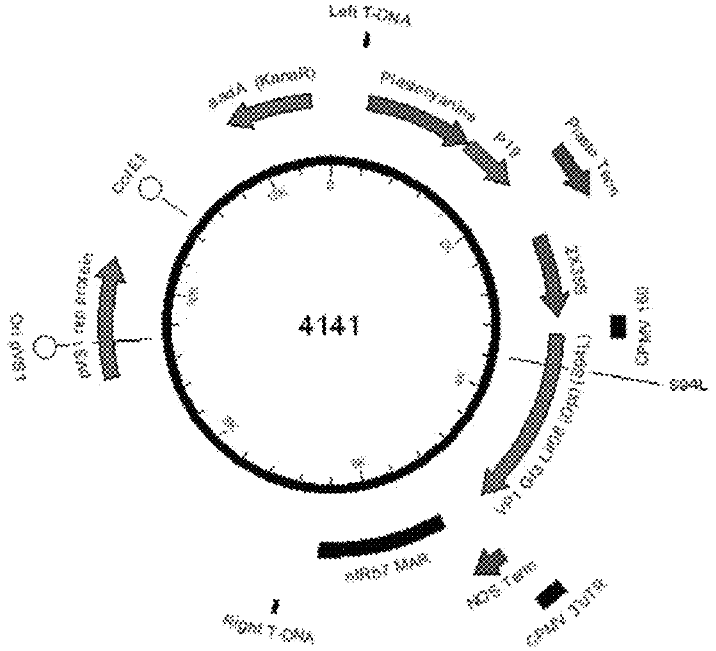
FIG. 40B shows a schematic representation of construct 4141 (VP1 GI.3_S94L hCod).
Figure 40C:
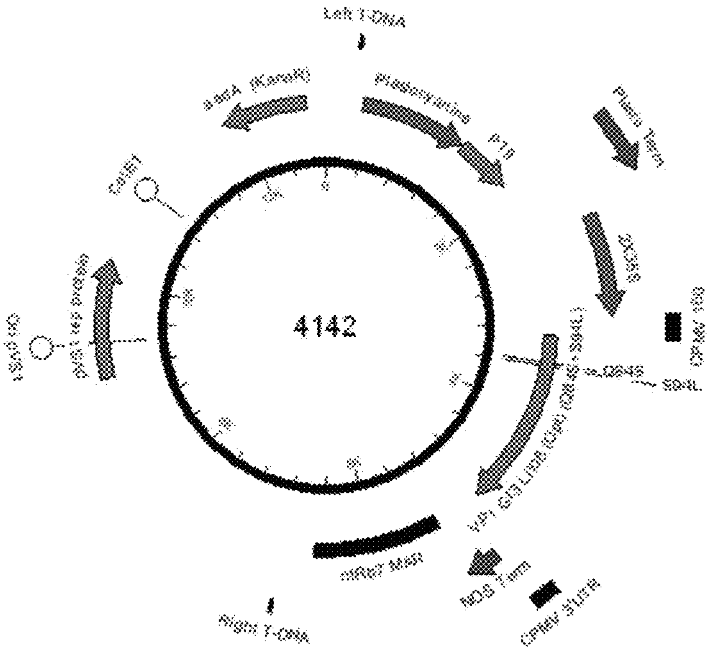
FIG. 40C shows a schematic representation of construct 4142 (VP1 GI.3_P84S+S94L hCod).
Figure 40D:
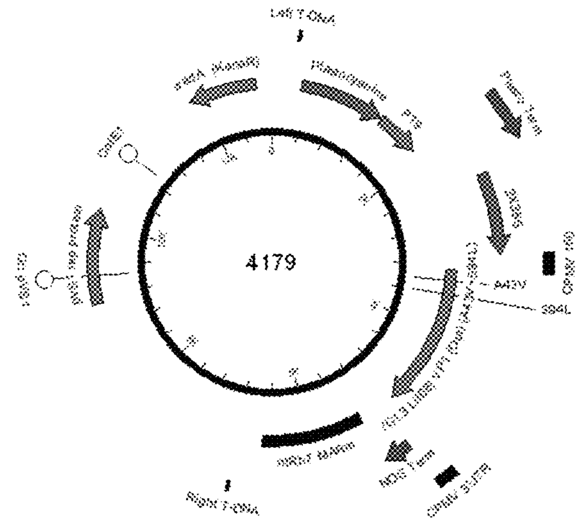
FIG. 40D shows a schematic representation of construct 4179 (VP1 GI.3_A43V+S94L hCod).
Figure 40E:
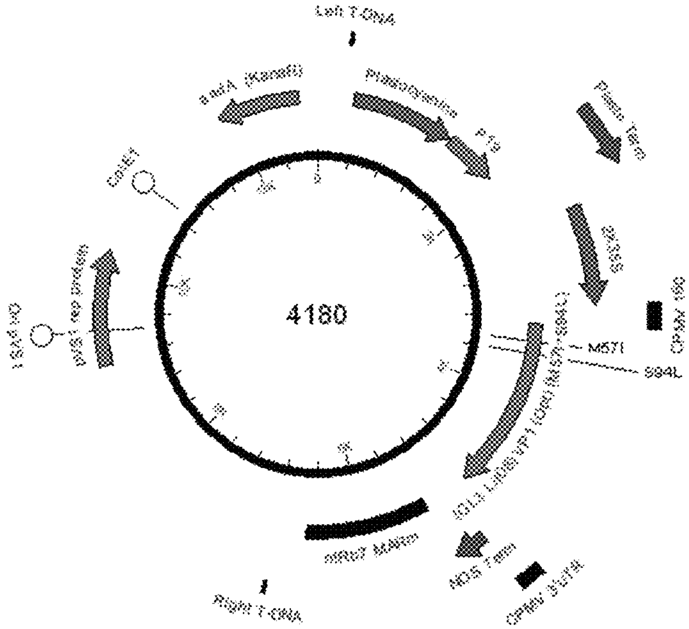
FIG. 40E shows a schematic representation of construct 4180 (VP1 GI.3_M57I+S94L hCod).
Figure 40F:
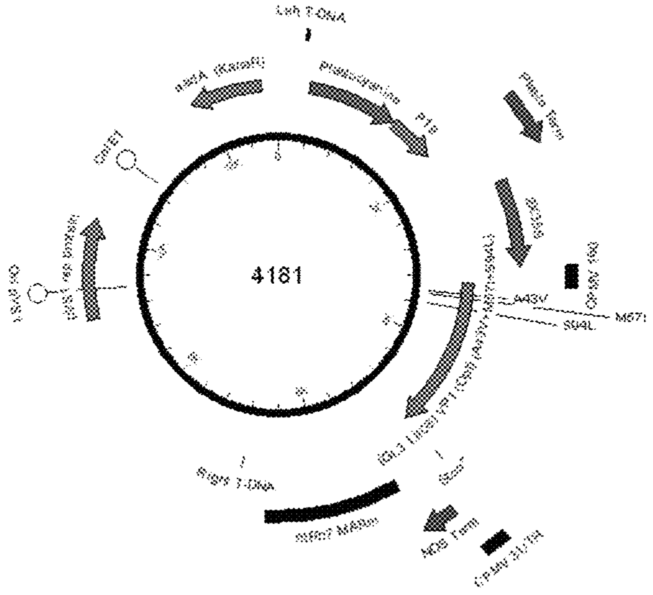
FIG. 40F shows a schematic representation of construct 4181 (VP1 GI.3_A43V+M57I+S94L hCod).
Figure 41A:
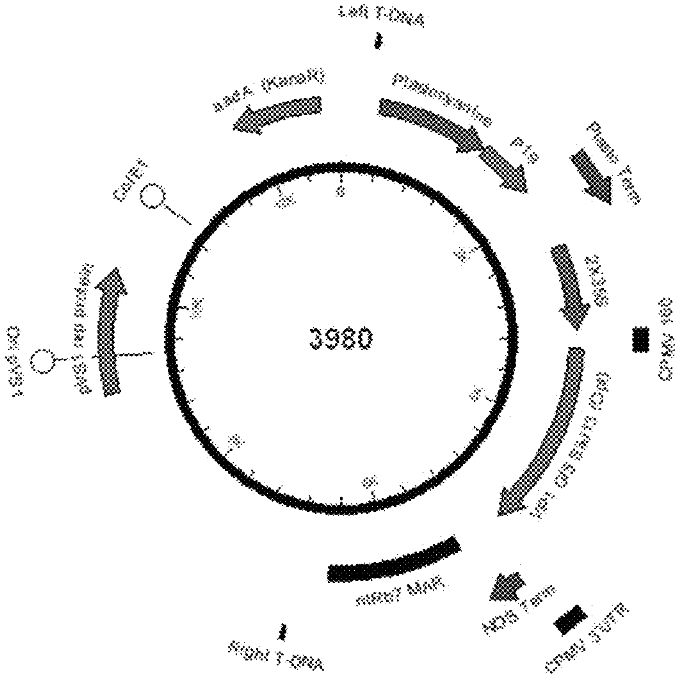
FIG. 41A shows a schematic representation of construct 3980 (VP1 Wt GI.5 hCod (Wt GI.5 hCod).
Figure 41B:
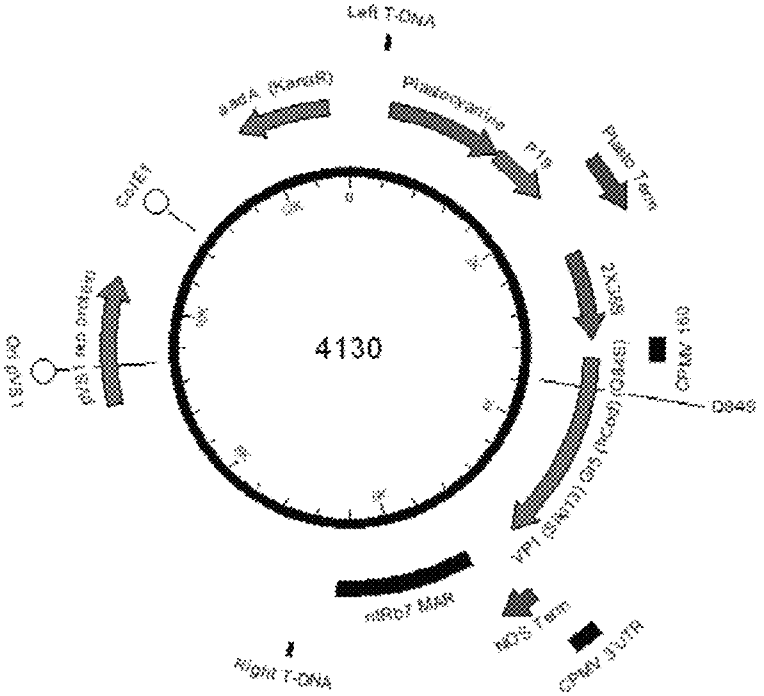
FIG. 41B shows a schematic representation of construct 4130 (VP1 GI.5_Q84S).
Figure 41C:
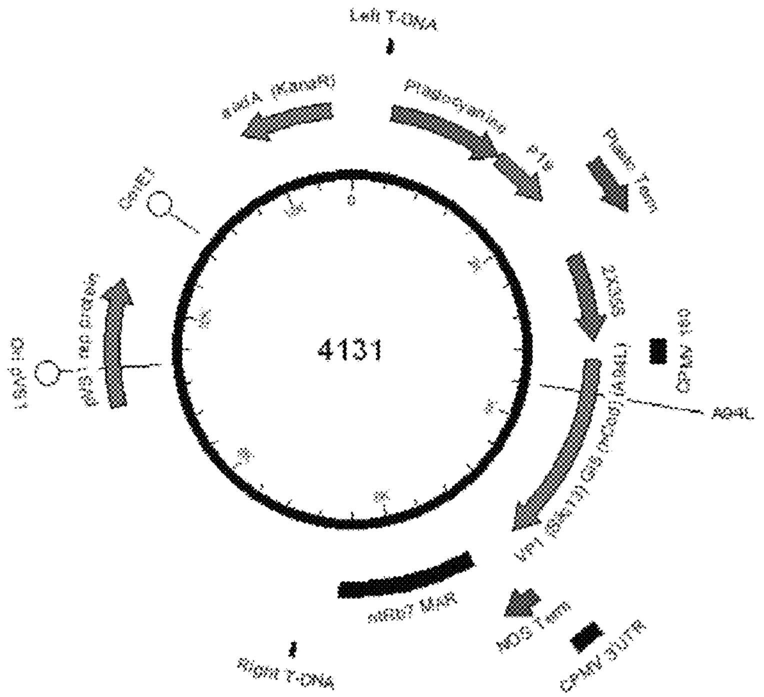
FIG. 41C shows a schematic representation of construct 4131 (VP1 GI.5_A94L hCod).
Figure 41D:
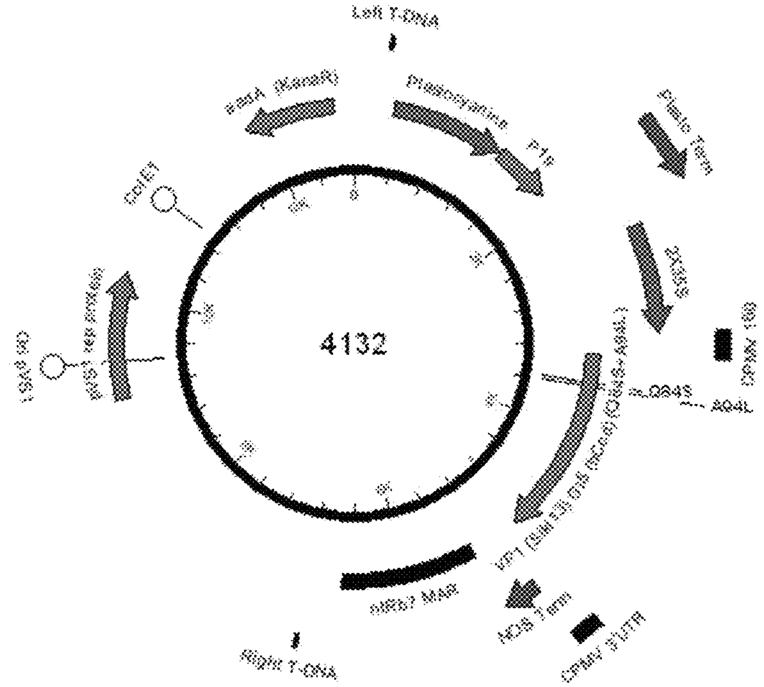
FIG. 41D shows a schematic representation of construct 4132 (VP1 GI.5_Q84S+A94L hCod).
Figure 41E:
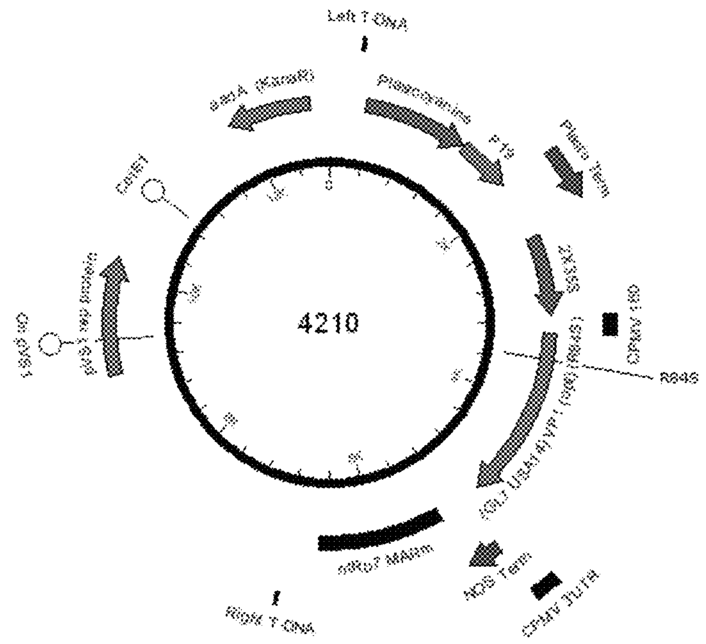
FIG. 41E shows a schematic representation of construct 4210 (VP1 GI.7_R84S hCod).
Figure 41F:
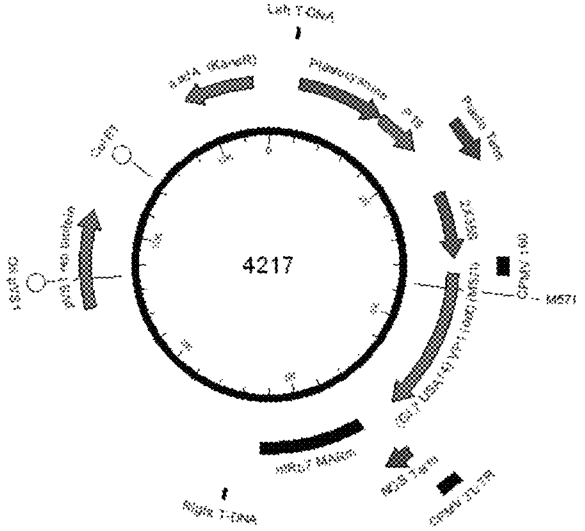
FIG. 41F shows a schematic representation of construct 4217 (VP1 GI.7_M57I hCod).
Figure 41G:
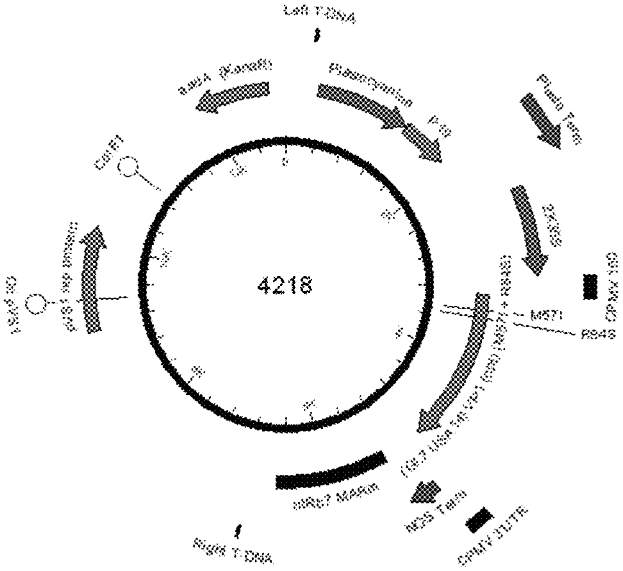
FIG. 41G shows a schematic representation of construct 4218 (VP1 GI.7_M57I+R84S hCod).
Figure 42A:
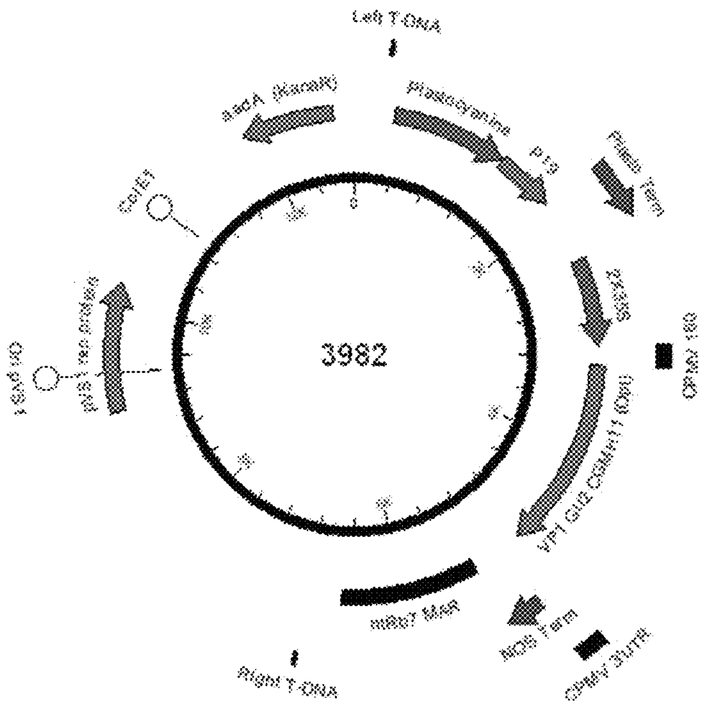
FIG. 42A shows a schematic representation of construct 3982 (Wt VP1 GII.2 hCod).
Figure 42B:
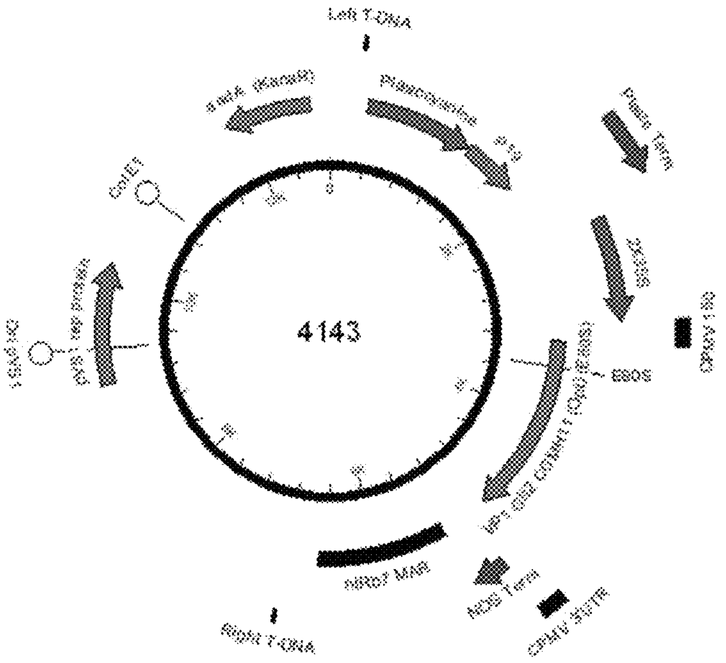
FIG. 42B shows a schematic representation of construct 4143 (VP1 GII.2_E80S).
Figure 42C:
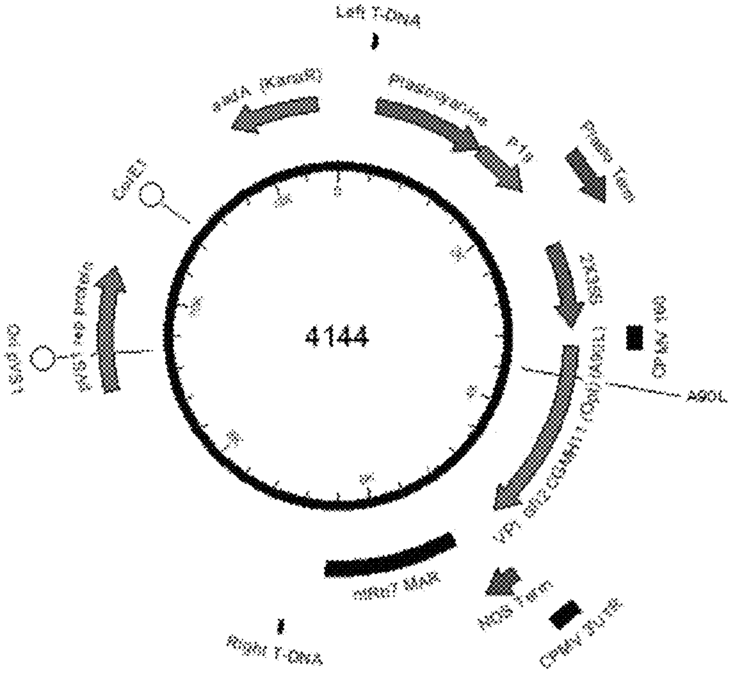
FIG. 42C shows a schematic representation of construct 4144 (VP1 GII.2_A90L hCod).
Figure 42D:
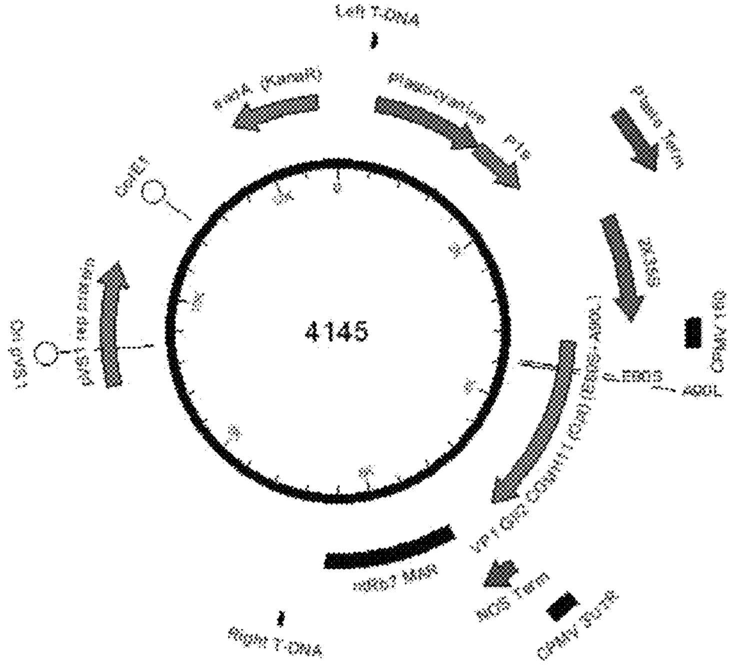
FIG. 42D shows a schematic representation of construct 4145 (VP1 GII.2_E80S+A90L hCod).
Figure 42E:
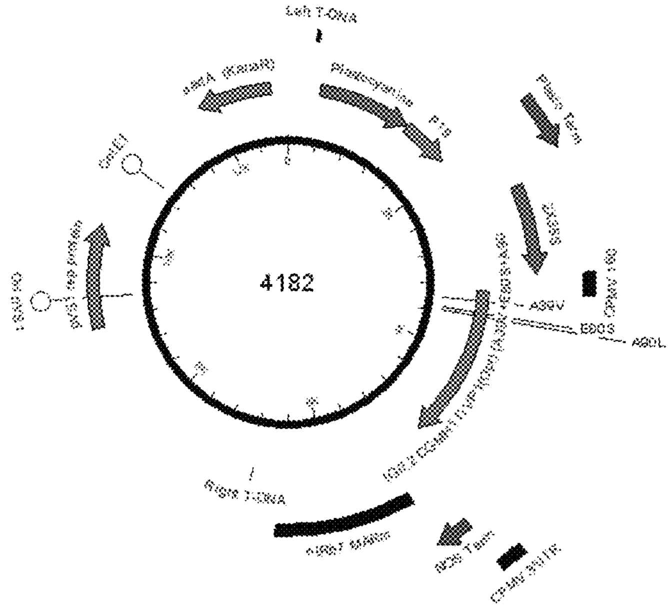
FIG. 42E shows a schematic representation of construct 4182 (VP1 GII.2_A39V+E80S+A90L hCod).
Figure 42F:
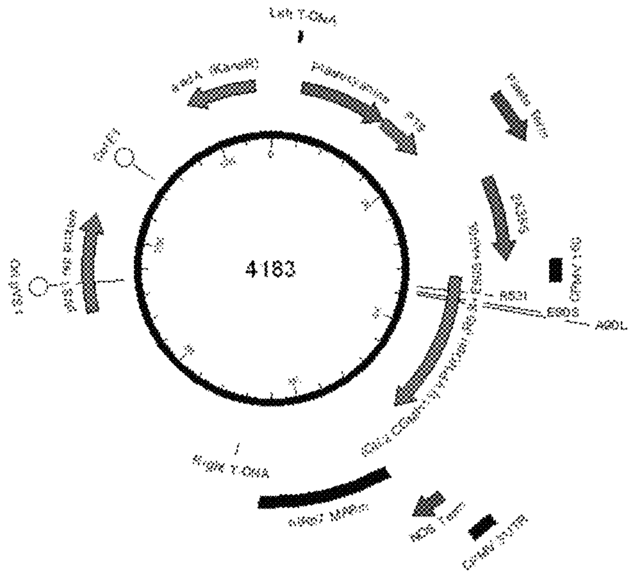
FIG. 42F shows a schematic representation of construct 4183 (VP1 GII.2_R53I+E80S+A90L hCod).
Figure 42G:
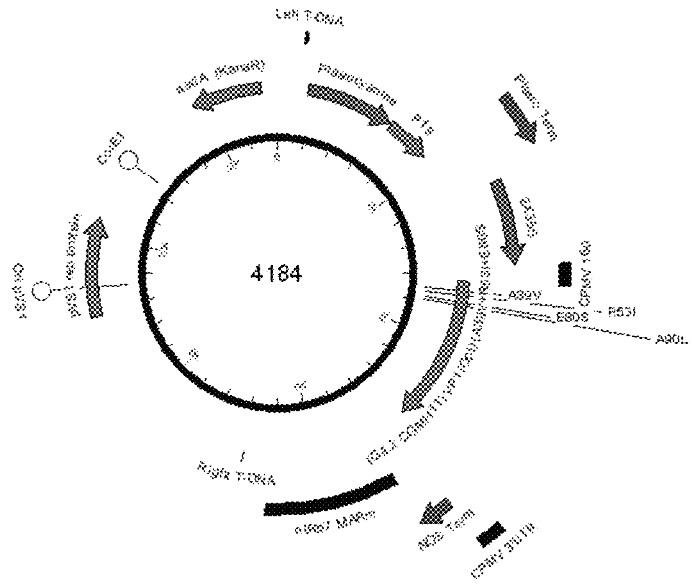
FIG. 42G shows a schematic representation of construct 4184 (VP1 GII.2_A39V+R53I+E80S+A90L hCod).
Figure 43A:
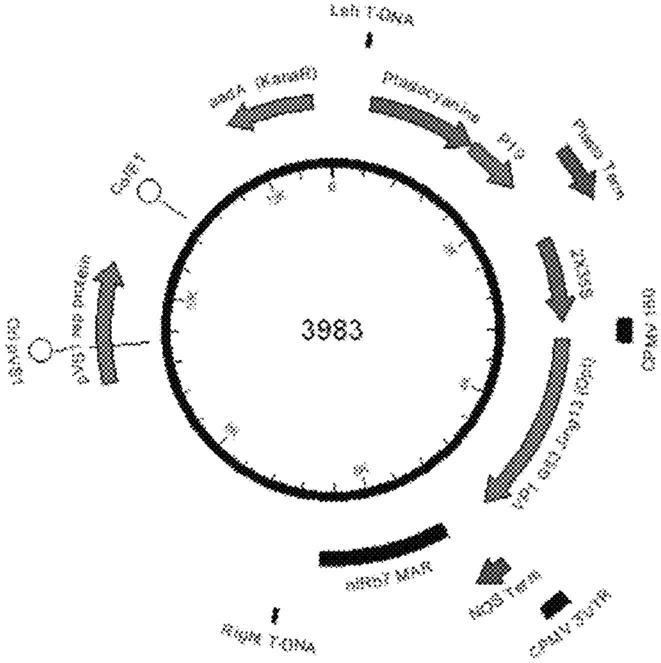
FIG. 43A shows a schematic representation of construct 3983 (Wt VP1 GII.3 hCod).
Figure 43B:
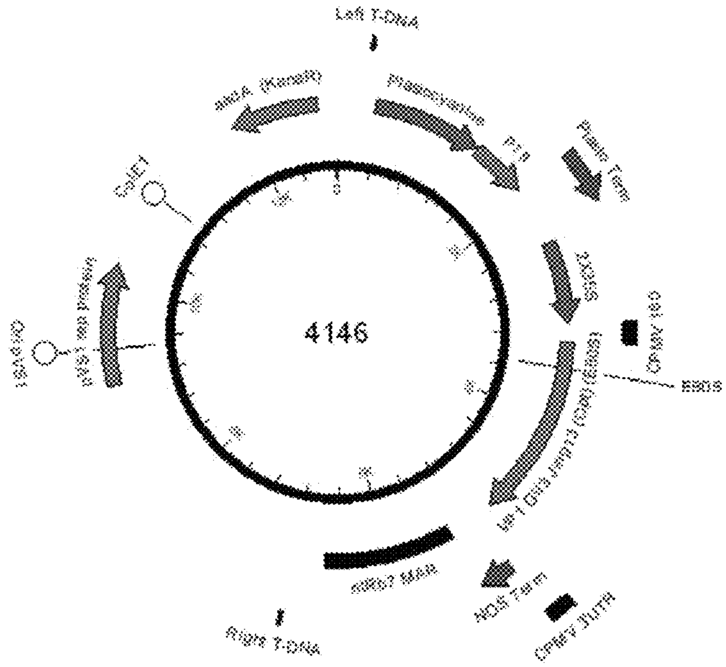
FIG. 43B shows a schematic representation of construct 4146 (VP1 GII.3_E80S hCod).
Figure 43C:
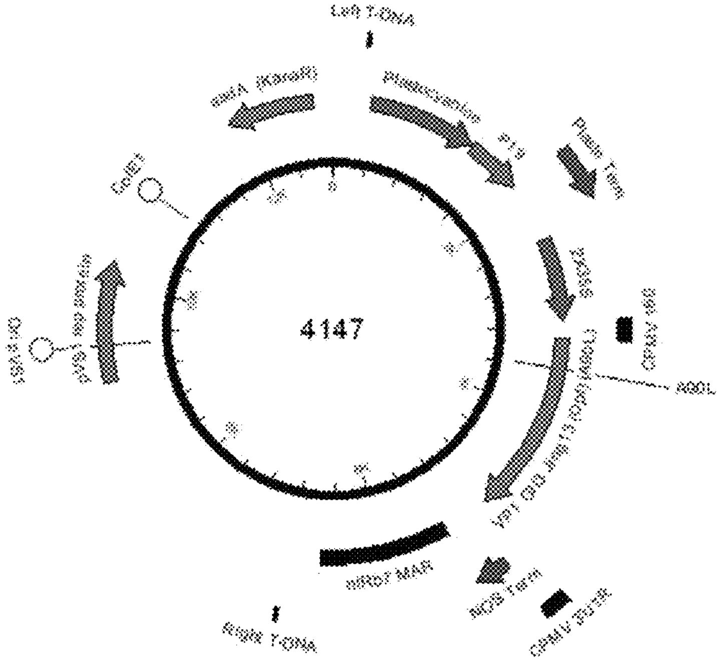
FIG. 43C shows a schematic representation of construct 4147 (VP1 GII.3_A90L hCod).
Figure 43D:
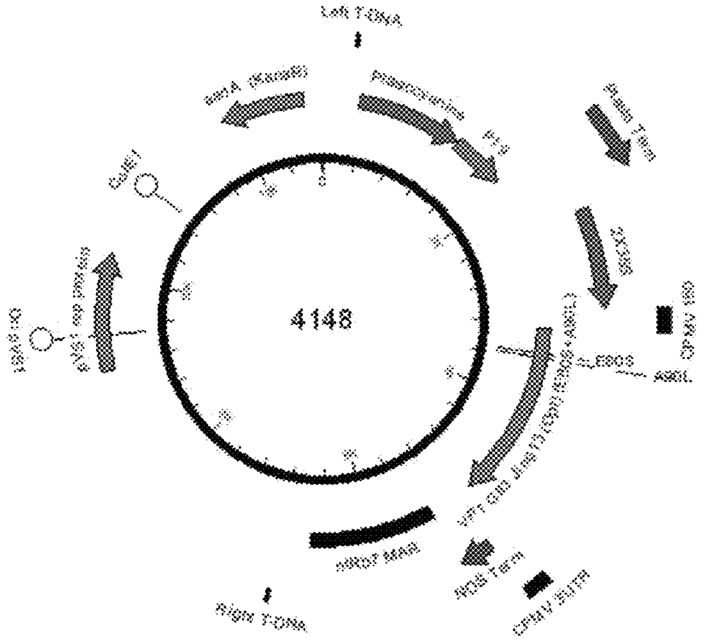
FIG. 43D shows a schematic representation of construct 4148 (VP1 GII.3_E80S+A90L).
Figure 48:
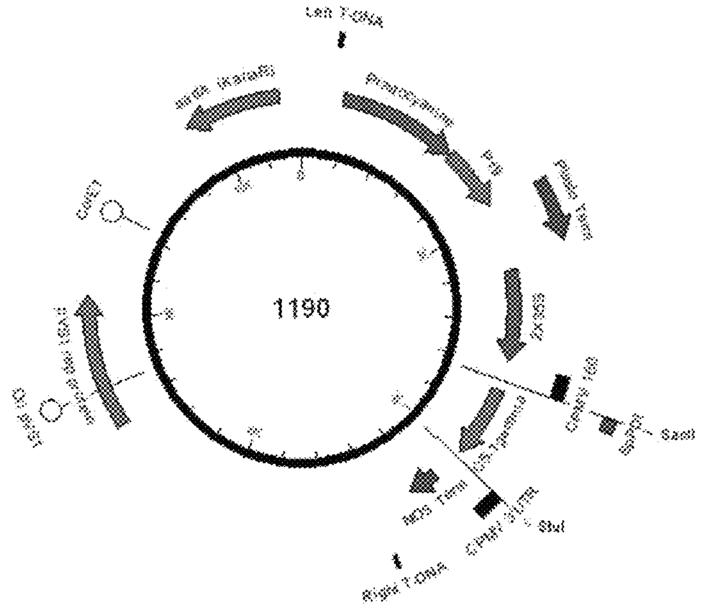
FIG. 48 shows a schematic representation of construct 1190 (Cloning vector 1190).

A human codon-optimized sequence encoding VP1 from Norovirus strain GI.1/Norwalk/1968/US was cloned into 2×35S/CPMV 160/NOS expression system using the following PCR-based method. A fragment containing the GI.1 VP1 coding sequence was amplified using primers IF-NoV (US68)VP1(ORF2)(hCod).c (SEQ ID NO:102) and IF-NoV (US68)VP1(ORF2)(hCod).r (SEQ ID NO:103), using human codon-optimized GI.1 VP1 gene sequence (SEQ ID NO:3) as template. For sequence optimization, GI.1/Norwalk/1968/US VP1 protein sequence (Genbank accession number NP_056821) was backtranslated and optimized for human codon usage, GC content and mRNA structure. The PCR product was cloned in 2×35S/CPMV 160/NOS expression system using In-Fusion cloning system (Clontech, Mountain View, CA). Construct number 1190 (SEQ ID NO:162; FIGS. 38A and 48) was digested with SacII and StuI restriction enzyme and the linearized plasmid was used for the In-Fusion assembly reaction. Construct number 1190 is an acceptor plasmid intended for "In Fusion" cloning of genes of interest in a 2×35S/CPMV 160/NOS-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO:162. The resulting construct was given number 2724 (FIG. 38B; SEQ ID NO: 163). The amino acid sequence of native VP1 from Norovirus strain GI.1/Norwalk/1968/US is presented in SEQ ID NO: 1. A representation of plasmid 2724 is presented in FIG. 39A.

2×35S/CPMV 160/GII.4_P80S (hCod)/NOS+MAR (Construct Number 4133)

Figure 44A:
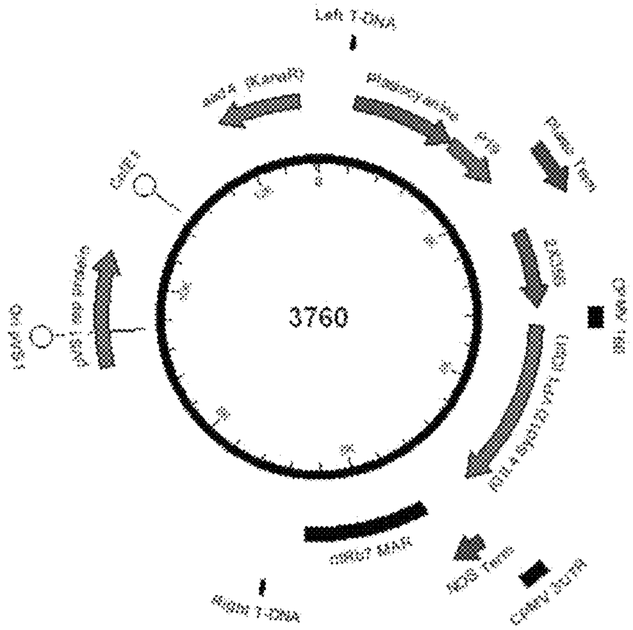
FIG. 44A shows a schematic representation of construct 3760 (Wt VP1 GII.4 hCod).
Figure 44B:
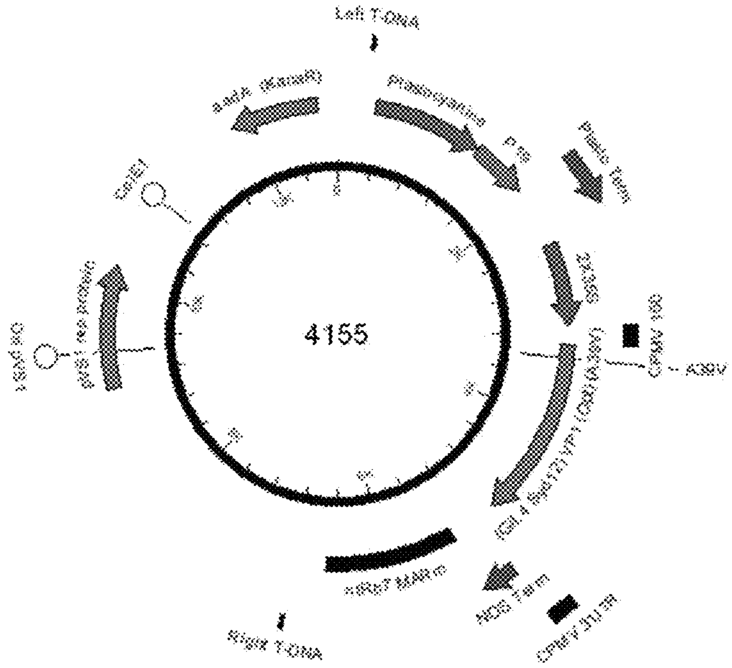
FIG. 44B shows a schematic representation of construct 4155 (VP1 GII.4_A39V hCod).
Figure 44C:
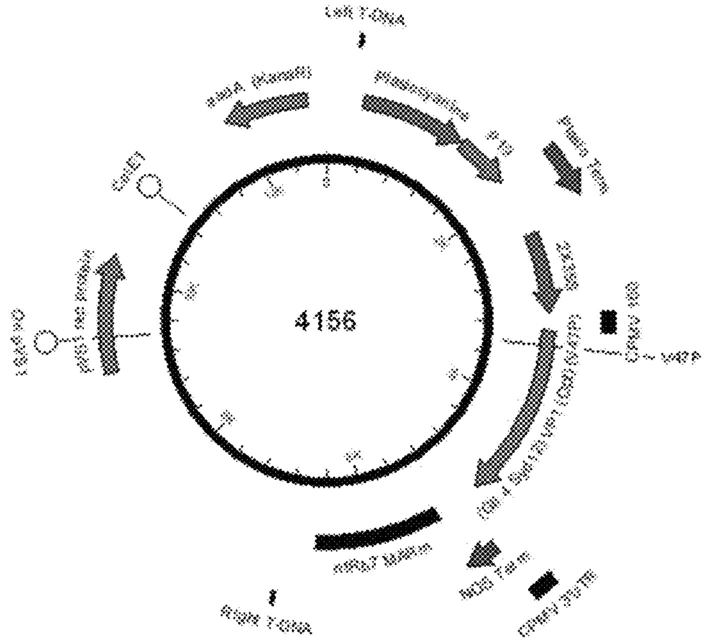
FIG. 44C shows a schematic representation of construct 4156 (VP1 GII.4_V47P hCod).
Figure 44D:
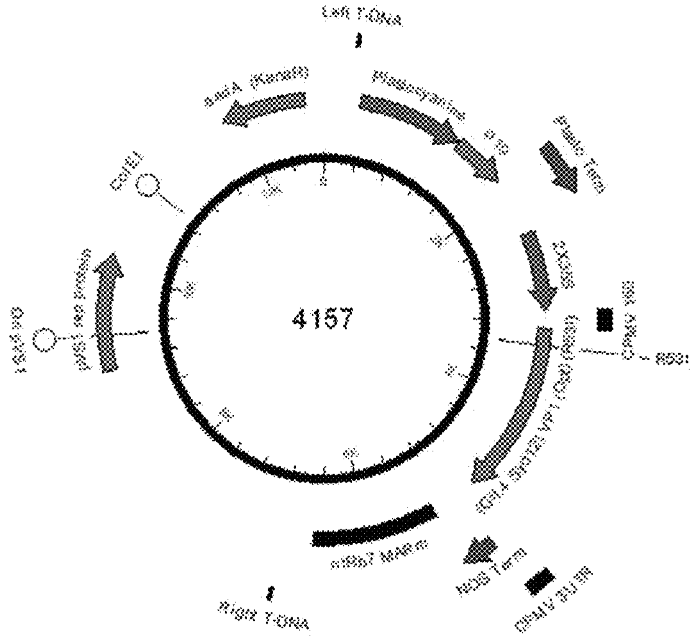
FIG. 44D shows a schematic representation of construct 4157 (VP1 GII.4_R53I hCod).
Figure 44E:
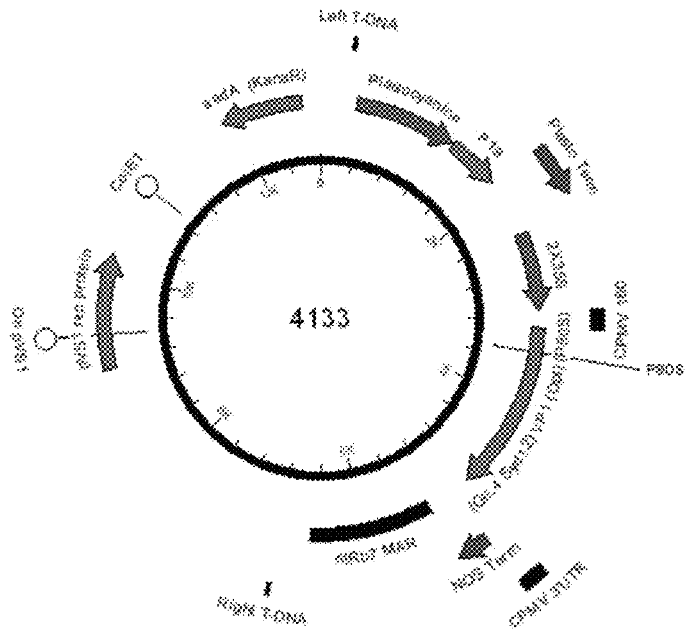
FIG. 44E shows a schematic representation of construct 4133 (VP1 GII.4_P80S hCod).
Figure 44F:
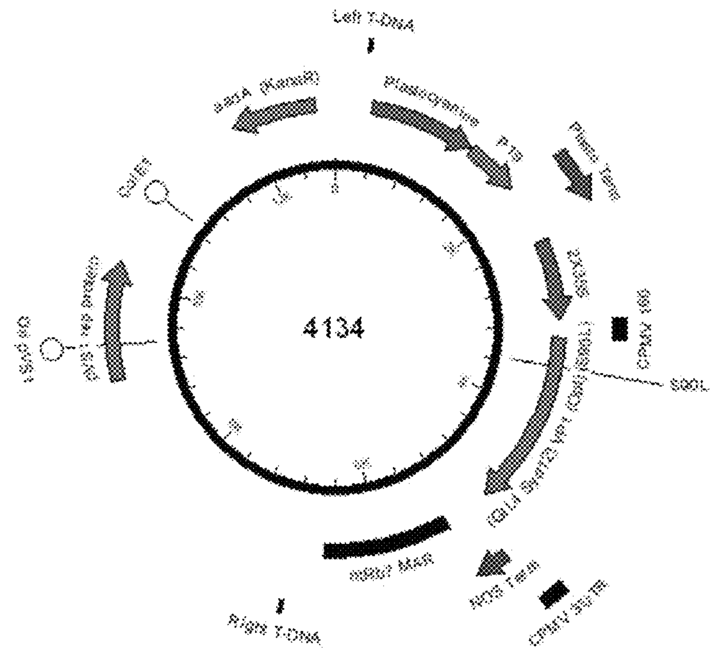
FIG. 44F shows a schematic representation of construct 4134 (VP1 GII.4_S90L hCod).
Figure 44G:
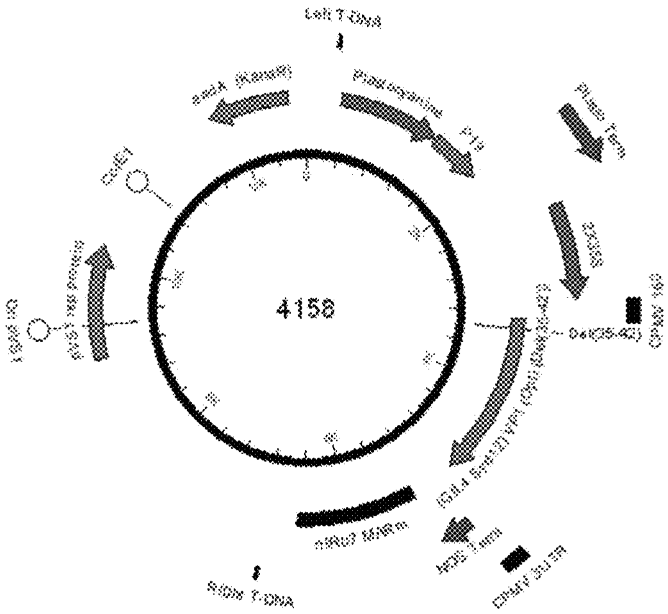
FIG. 44G shows a schematic representation of construct 4158 (VP1 GII.4_Δ35-42 hCod).
Figure 44H:
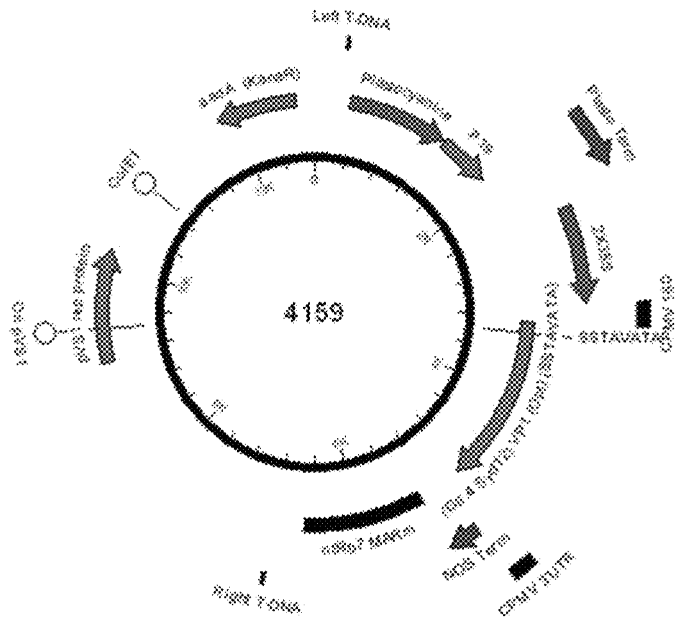
FIG. 44H shows a schematic representation of construct 4159 (VP1 GII.4_SSTAVATA hCod).
Figure 44I:
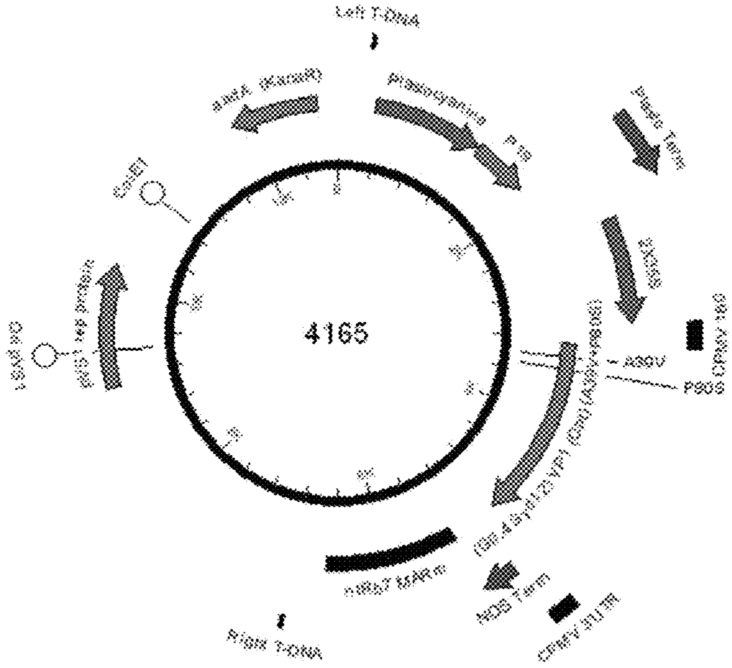
FIG. 44I shows a schematic representation of construct 4165 (VP1 GII.4_A39V+P80S hCod).
Figure 44J:
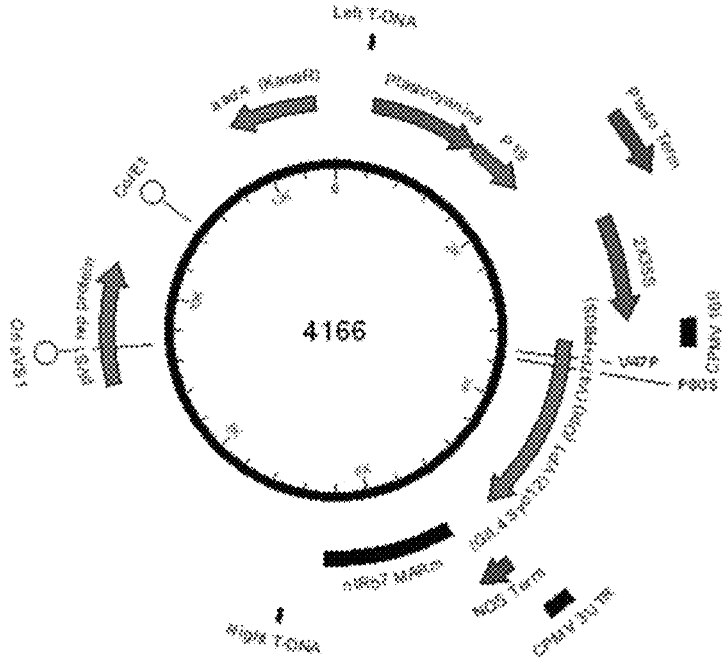
FIG. 44J shows a schematic representation of construct 4166 (VP1 GII.4_V47P+P80S hCod).
Figure 44K:
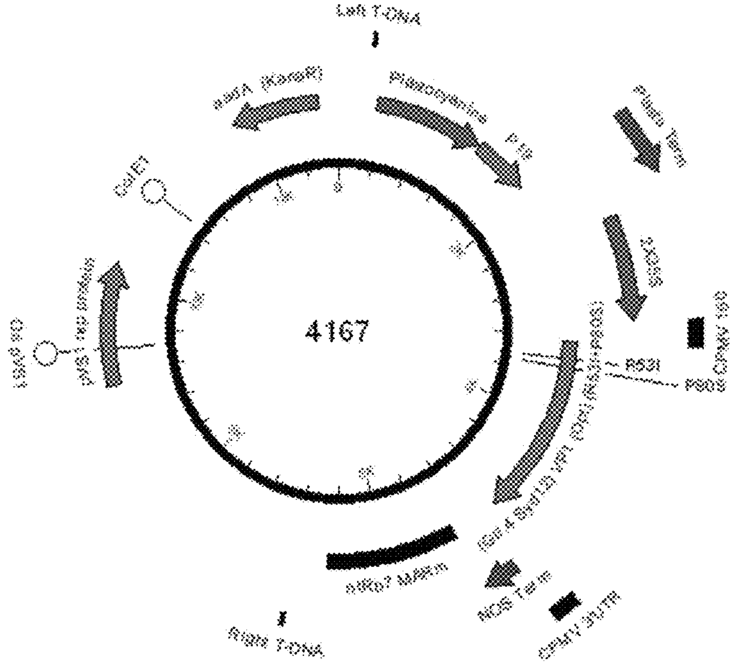
FIG. 44K shows a schematic representation of construct 4167 (VP1 GII.4_R53I+P80S hCod).
Figure 49:
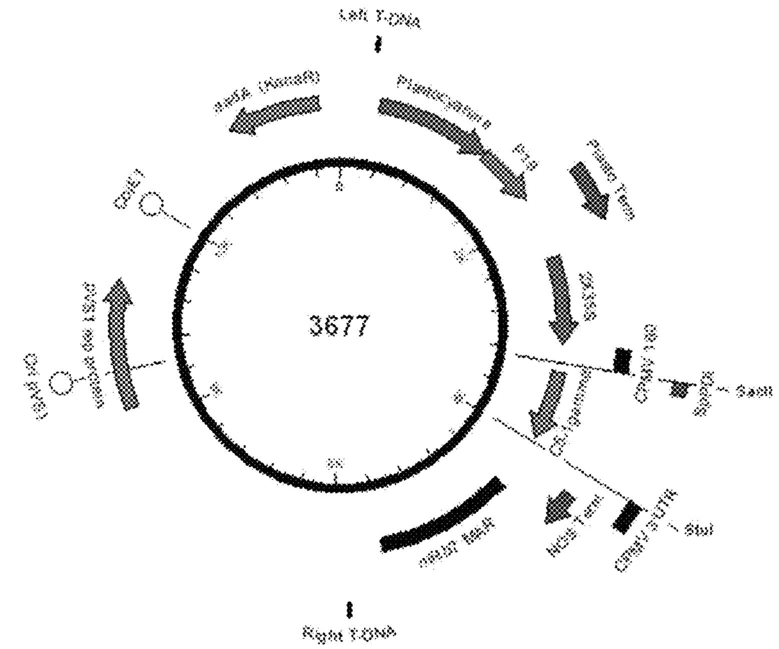
FIG. 49 shows a schematic representation of construct 3677 (Cloning vector 3677).
Figure 50A:
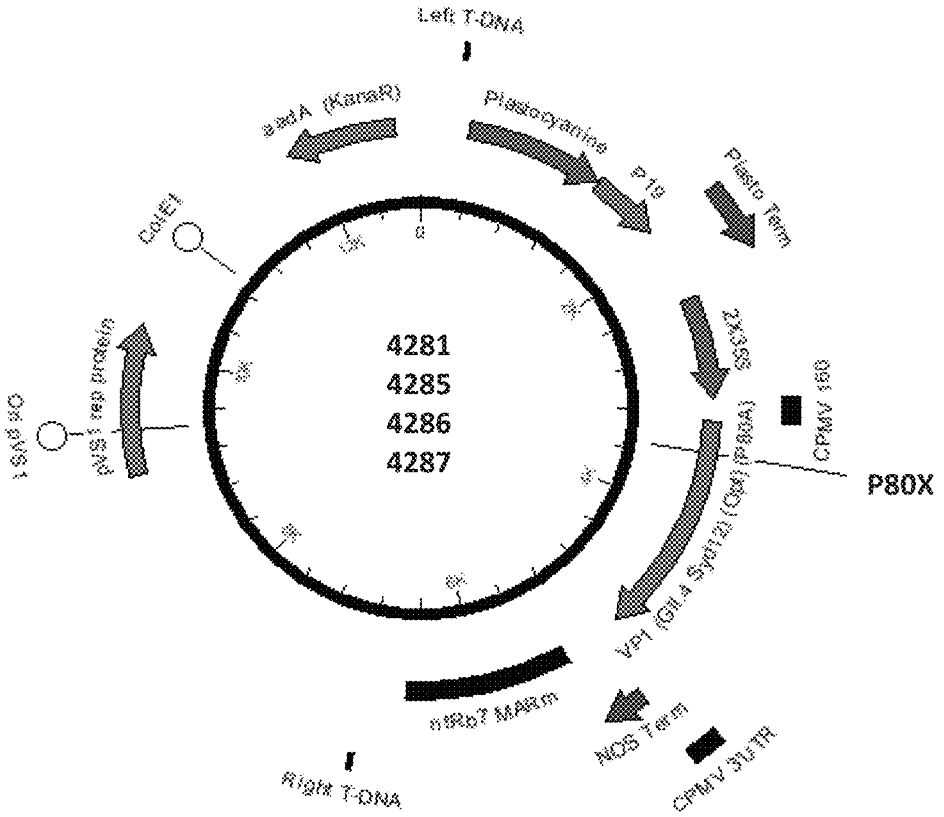
FIG. 50A shows a schematic representation of GII.4 P80X constructs (cloning vectors), wherein X is selected from: A (construct 4281); N (construct 4285); K (construct 4286); or H (construct 4287).
Figure 50B:
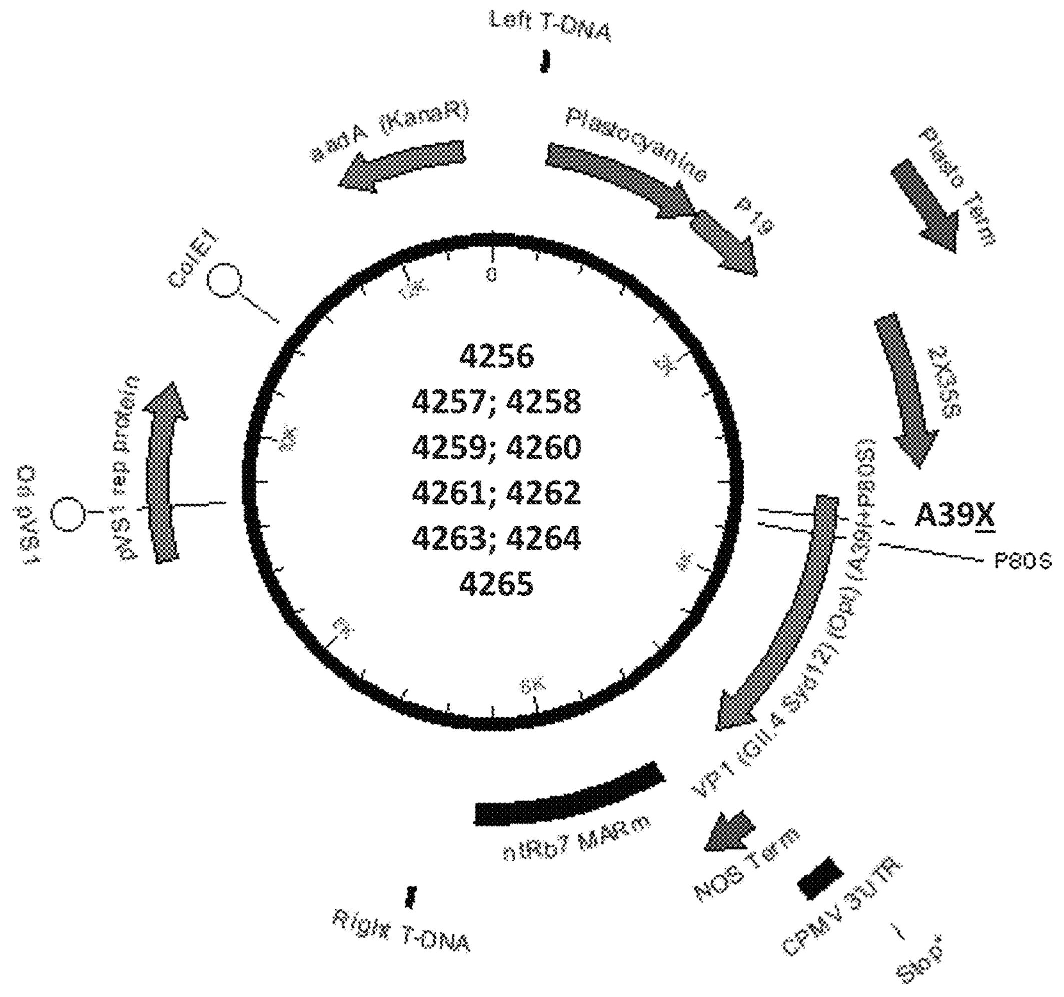
FIG. 50B shows a schematic representation of GII.4 P80s+A39X constructs (cloning vectors), wherein X is selected from I (construct 4256); M (construct 4257); G (construct 4258); S (construct 4259); E (construct 4260); D (construct 4261); N (construct 4262); Q (construct 4263); construct K (4264); or H (construct 4265).
Figure 51:
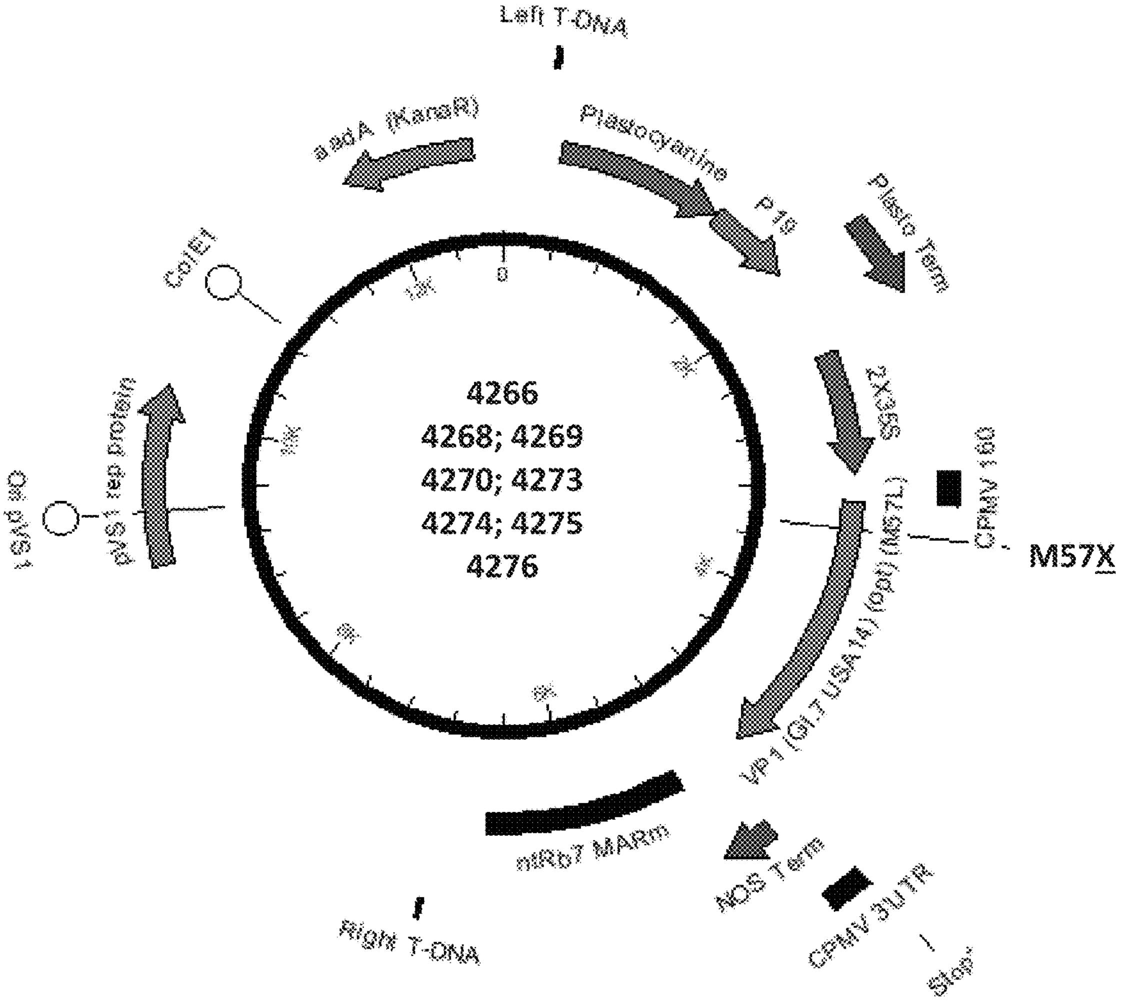
FIG. 51 shows a schematic representation of GI.7 M57X constructs (cloning vectors), wherein X is selected from: L (construct 4266); G (construct 4268); S (construct 4269); T (construct 4270; N (construct 4273); Q (construct 4274); K (construct 4275); or H (construct 4276).
Figure 52:
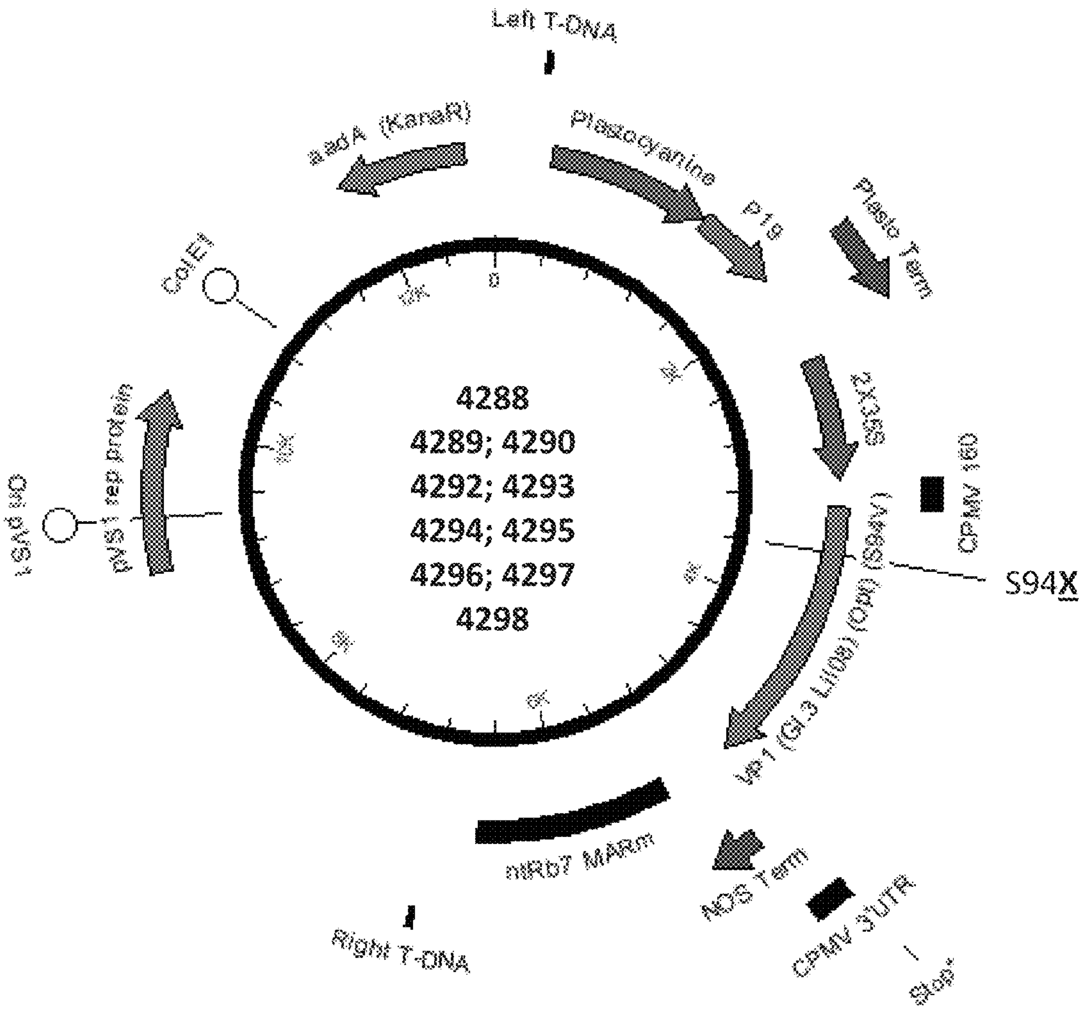
FIG. 52 shows a schematic representation of GI.3 S94X constructs (cloning vectors), wherein X is selected from: V (construct 4288); I (construct 4289); M (construct 4290); T (construct 4292); E (construct 4293); D (construct 4294); N (construct 4295); Q (construct 4296); K (construct 4297); or H (construct 4298).

A human codon-optimized sequence encoding VP1 from GII.4/Sydney/NSW0514/2012/AU comprising the P80S substitution in the S domain was cloned into 2×35S/CPMV 160/NOS+MAR expression system using the following PCR-based method. In a first round of PCR, a fragment containing the S domain with the mutated P80S amino acid was amplified using primers IF-GII.4Syd12VP1.c (SEQ ID NO:130) and GII.4(P80S).r (SEQ ID NO:138), using human codon-optimized GII.4 VP1 gene sequence (SEQ ID NO:52) as template. A second fragment containing the P80S substitution with the remaining of the S and P domain was amplified using GII.4(P80S).c (SEQ ID NO:139) and IF-GII.4Syd12VP1.r (SEQ ID NO:131), using human codon-optimized GII.4 VP1 gene sequence (SEQ ID NO:52) as template. For sequence optimization, GII.4/Sydney/NSW0514/2012/AU VP1 protein sequence (Genbank accession number AFV08795) was backtranslated and optimized for human codon usage, GC content and mRNA structure. The PCR products from both amplifications were then mixed and used as template for a second round of amplification using IF-GII.4Syd12VP1.c (SEQ ID NO:130) and IF-01.4Syd12VP1.r (SEQ ID NO:131) as primers. The final PCR product was cloned in 2×35S/CPMV 160/NOS+MAR expression system using In-Fusion cloning system (Clontech, Mountain View, CA). Construct number 3677 (SEQ ID NO:164; FIGS. 38C and 49) was digested with SacII and StuI restriction enzyme and the linearized plasmid was used for the In-Fusion assembly reaction. Construct number 3677 is an acceptor plasmid intended for "In Fusion" cloning of genes of interest in a 2×35S/CPMV 160/NOS+MAR-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO:164. The resulting construct was given number 4133 (FIG. 38D; SEQ ID NO:165). The amino acid sequence of mutated GII.4_P80S is presented in SEQ ID NO:59. A representation of plasmid 4133 is presented in FIG. 44E.

2×35S/CPMV 160/GII.4_P80S+S90L (hCod)/NOS+MAR (Construct Number 4135)

Figure 44L:
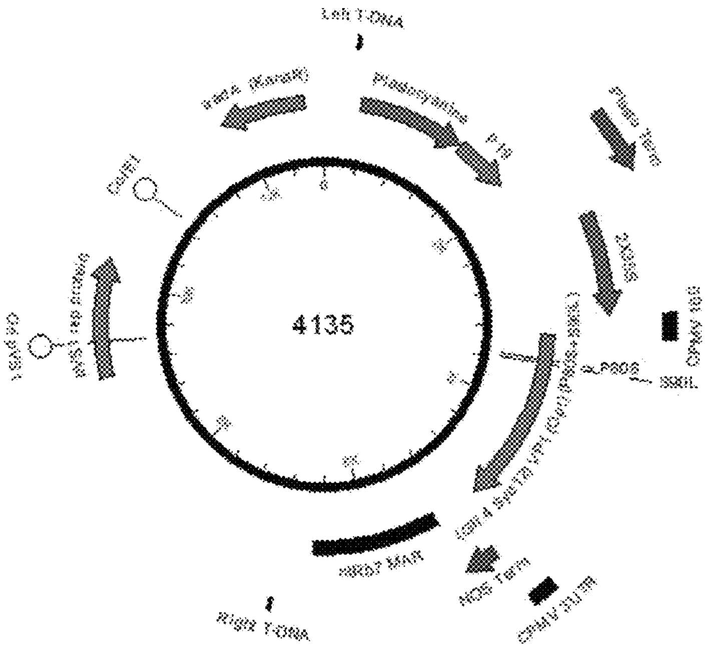
FIG. 44L shows a schematic representation of construct 4135 (VP1 GII.4_P80S+S90L hCod).
Figure 44M:
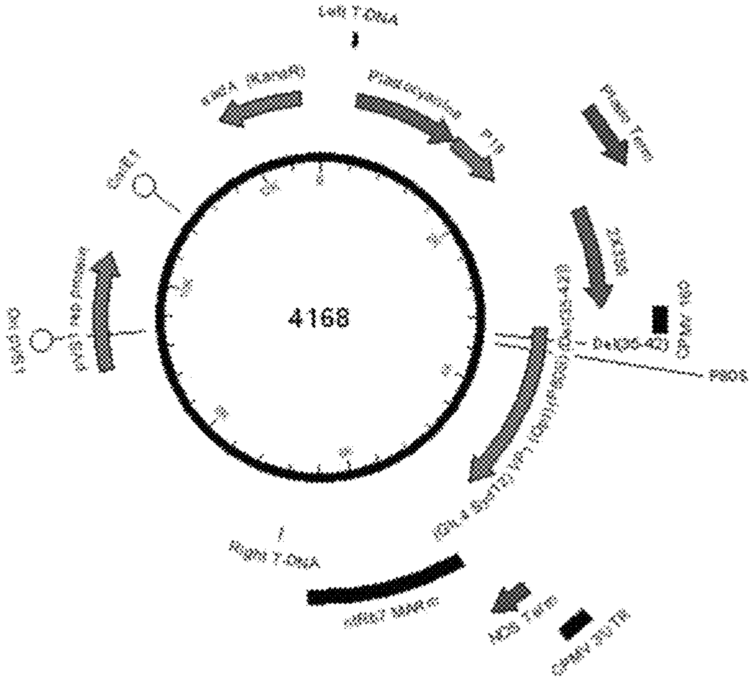
FIG. 44M shows a schematic representation of construct 4168 (GII.4_ P80S+Δ35-42 hCod).
Figure 44N:
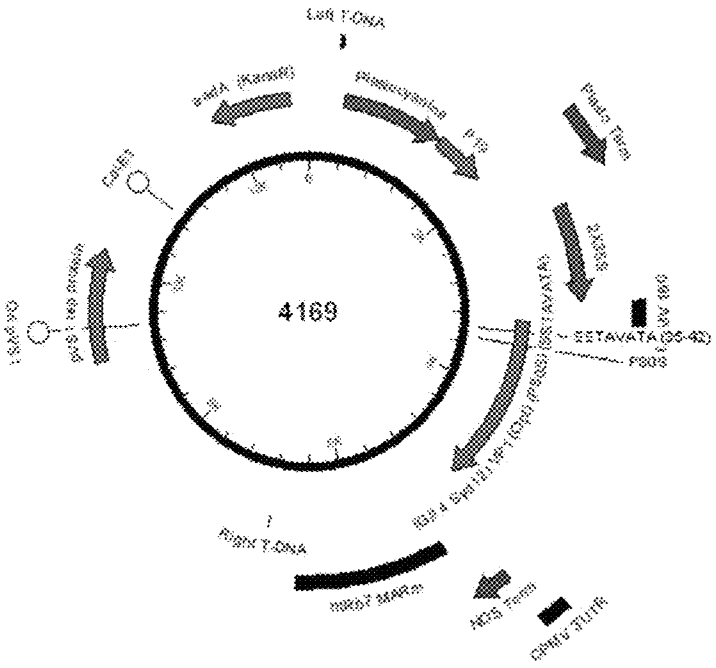
FIG. 44N shows a schematic representation of construct 4169 (VP1 GII.4_P80S+SSTAVATA hCod).
Figure 44O:
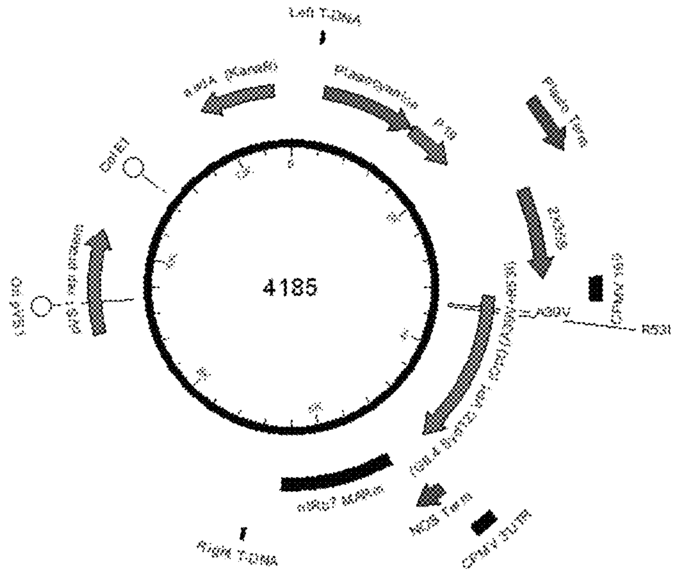
FIG. 44O shows a schematic representation of construct 4185 (VP1 GII.4_A39V+R53I hCod).
Figure 44P:
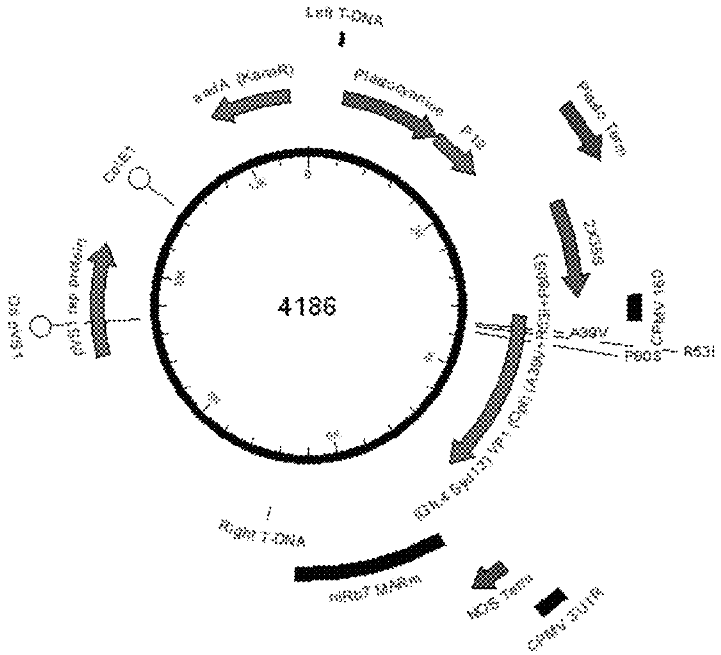
FIG. 44P shows a schematic representation of construct 4186 (VP1 GII.4_A39V+R53I+P80S hCod).
Figure 45A:
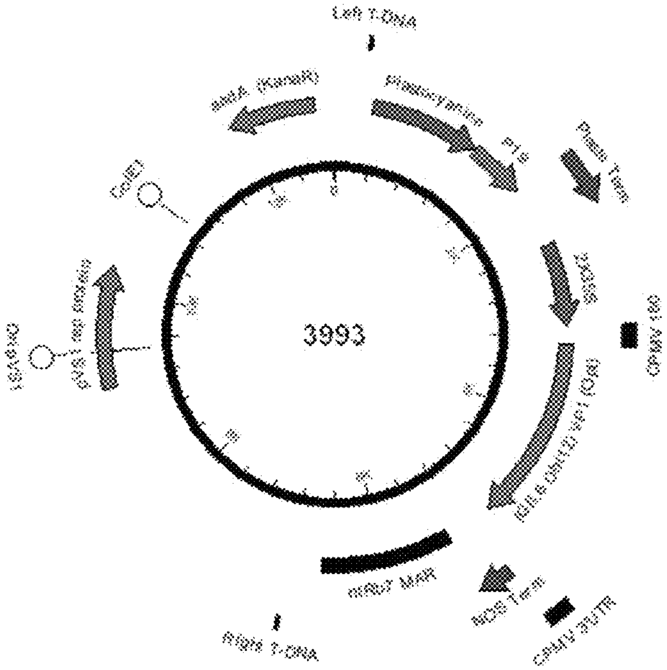
FIG. 45A shows a schematic representation of construct 3993 (Wt VP1 GII.6 hCod).
Figure 45B:
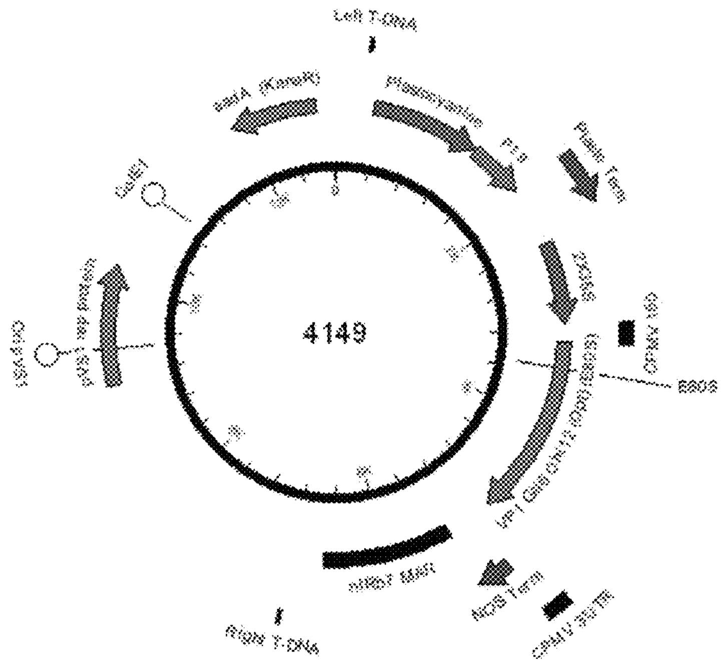
FIG. 45B shows a schematic representation of construct 4149 (VP1 GII.6_E80S hCod).
Figure 45C:
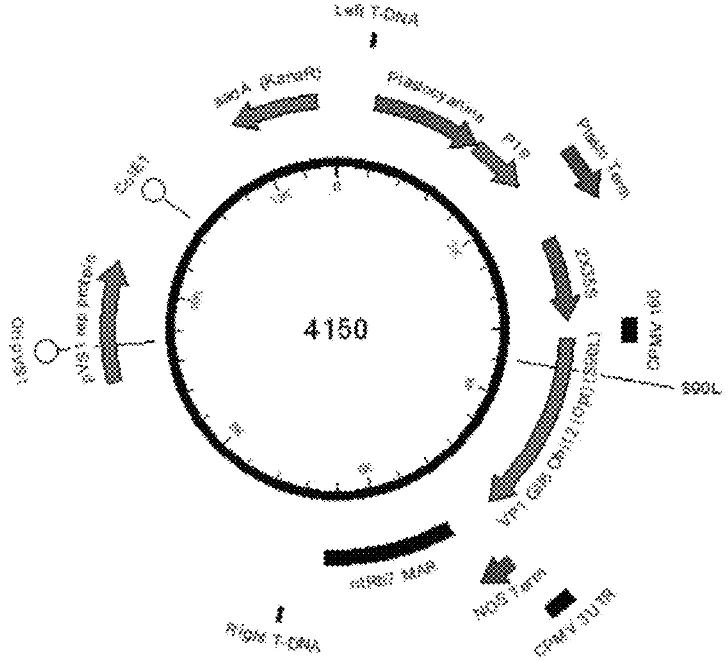
FIG. 45C shows a schematic representation of construct 4150 (VP1 GII.6_S90L hCod).
Figure 45D:
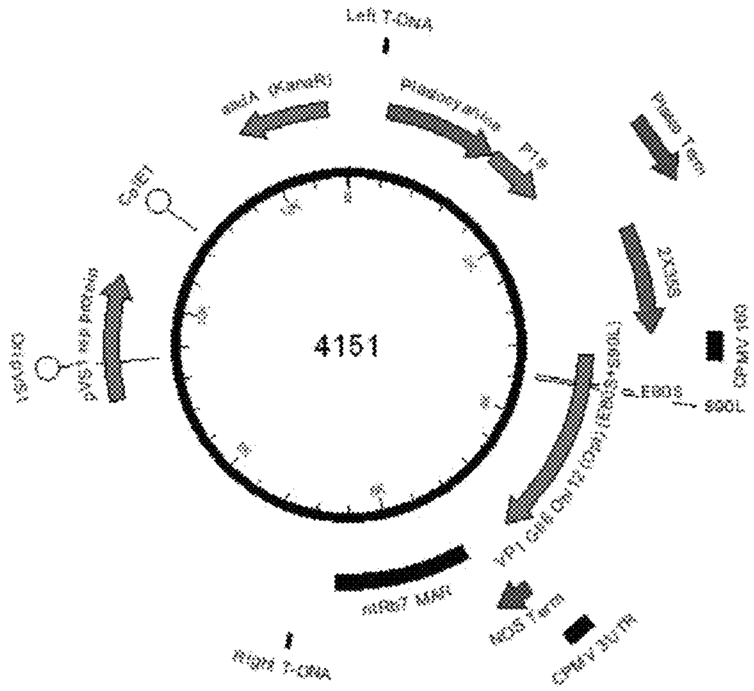
FIG. 45D shows a schematic representation of construct 4151 (VP1 GII.6_E80S+S90L).
Figure 46A:
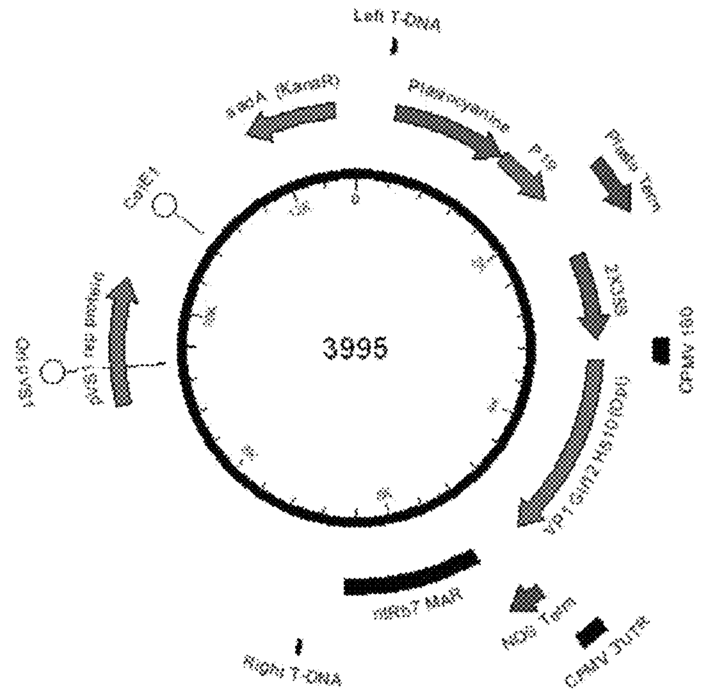
FIG. 46A shows a schematic representation of construct 3995 (Wt VP1 GII.12 hCod).
Figure 46B:
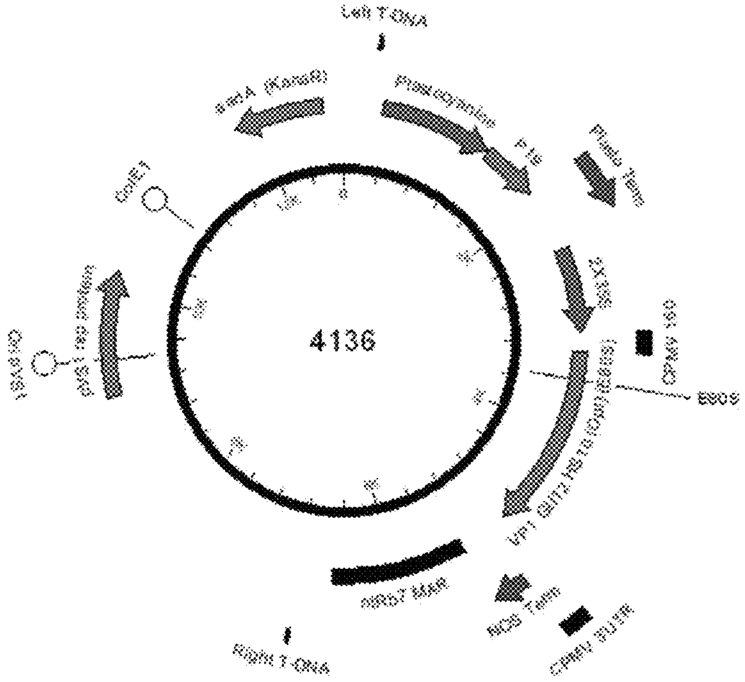
FIG. 46B shows a schematic representation of construct 4136 (VP1 GII.12_E80S hCod.
Figure 46C:
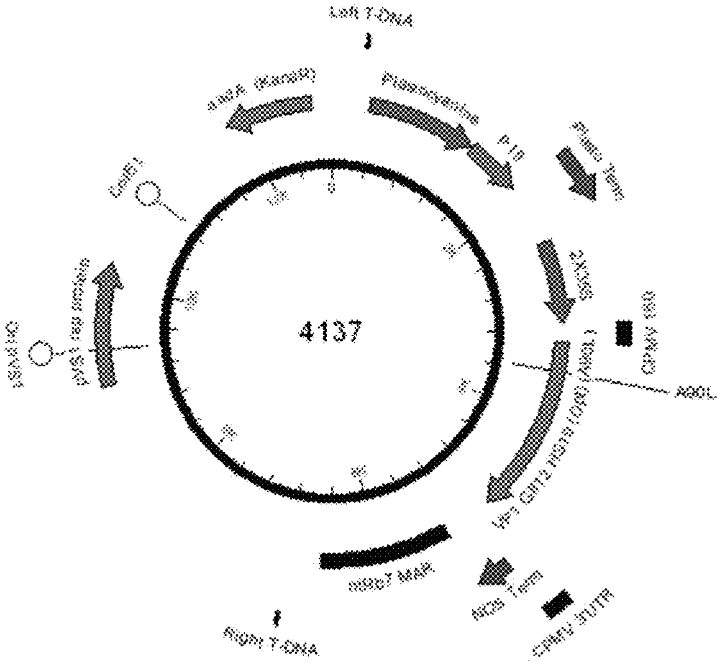
FIG. 46C shows a schematic representation of construct 4137 (VP1 GII.12_A90L hCod).
Figure 46D:
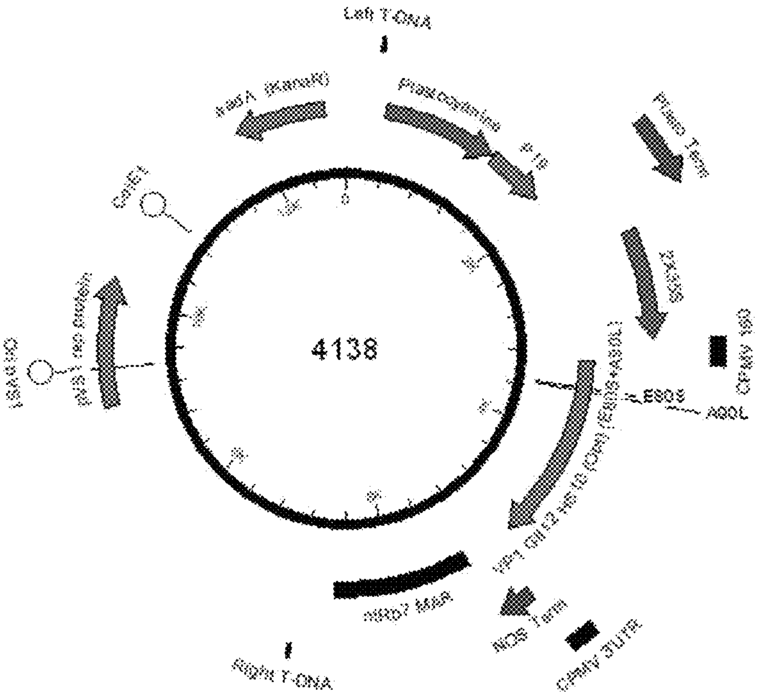
FIG. 46D shows a schematic representation of construct 4138 (VP1 GII.12_E80S+A90L).
Figure 46E:
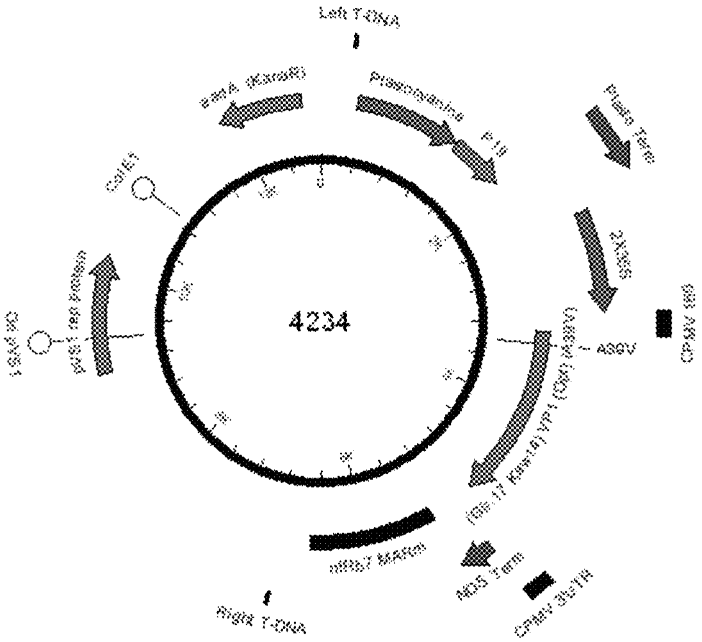
FIG. 46E shows a schematic representation of construct 4234 (VP1 GII.17_A39V).
Figure 46F:
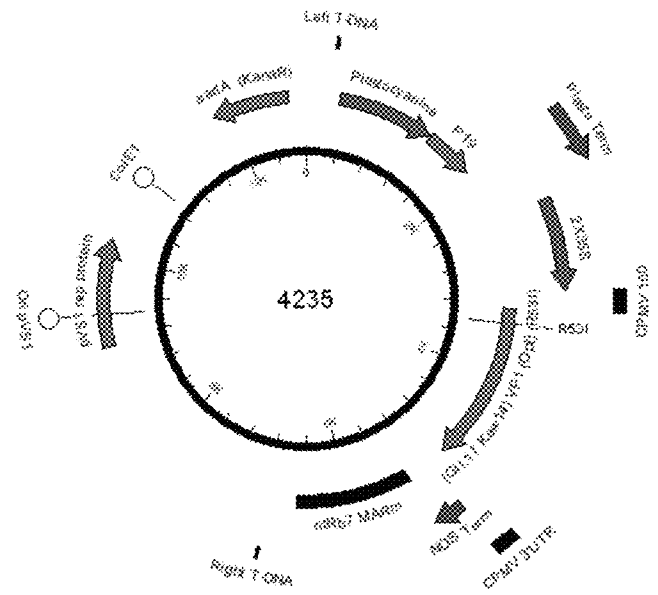
FIG. 46F shows a schematic representation of construct 4235 (VP1 GII.17_R53I).
Figure 46G:
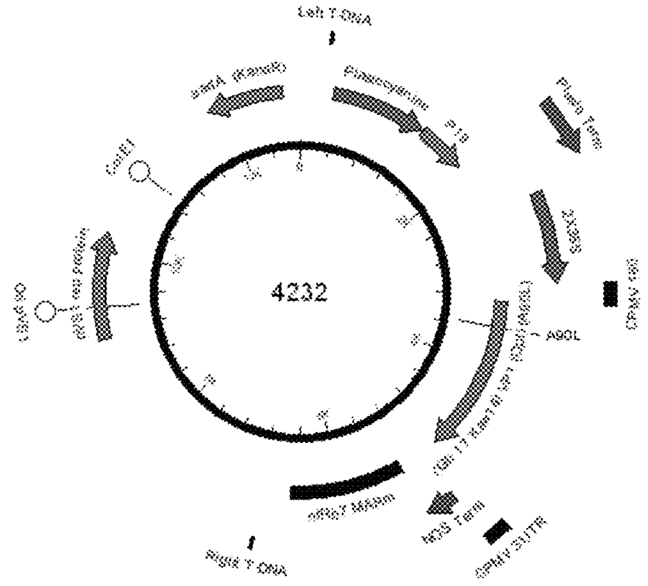
FIG. 46G shows a schematic representation of construct 4232 (VP1 GII.17_A90L).
Figure 46H:
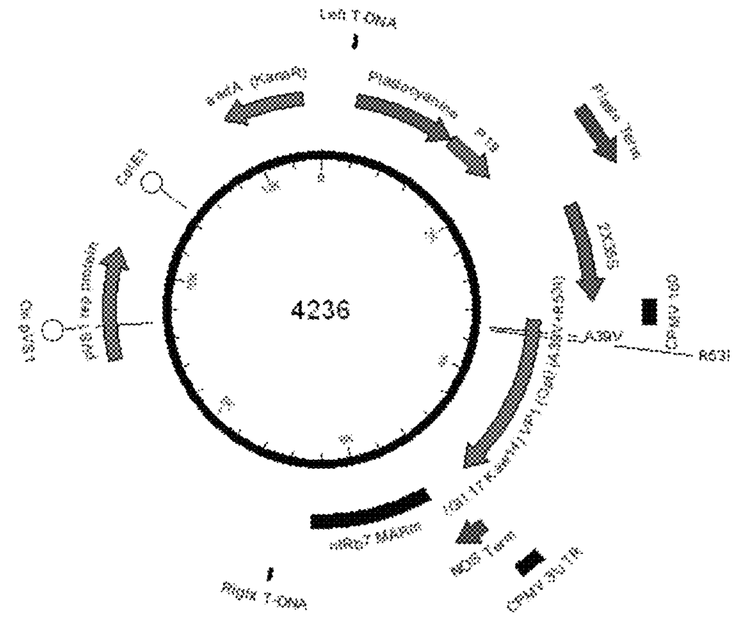
FIG. 46H shows a schematic representation of construct 4236 (VP1
Figure 46I:
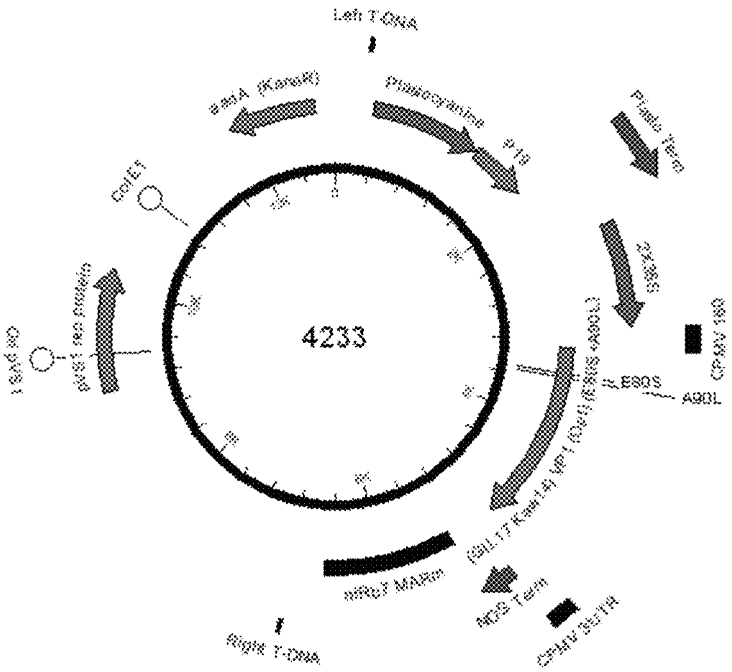
FIG. 46I shows a schematic representation of construct 4233 (VP1 GII.17_E80S+A90L).
Figure 47A:
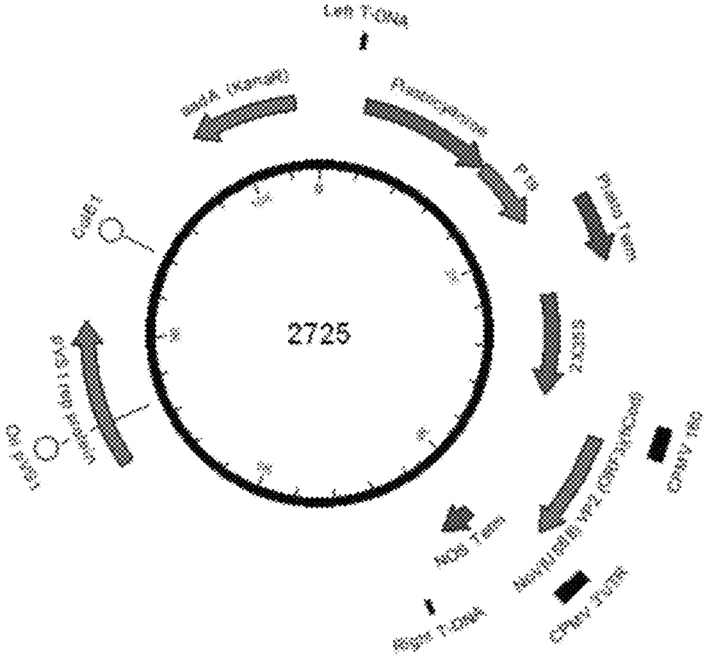
FIG. 47A shows a schematic representation of construct 2725 (Wt VP2 GI.1).
Figure 47B:
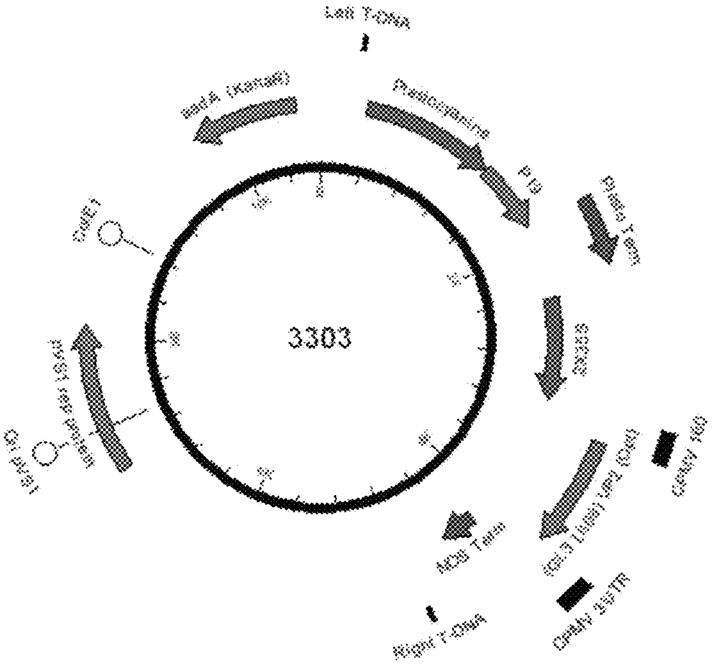
FIG. 47B shows a schematic representation of construct 3303 (Wt VP2 GI.3 hCod).
Figure 47C:
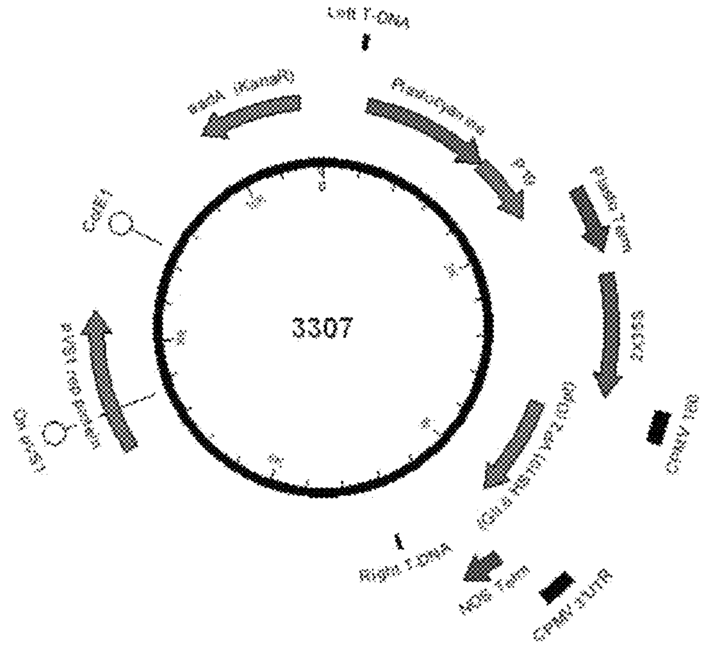
FIG. 47C shows a schematic representation of construct 3307 (Wt VP2 GII.6).

A human codon-optimized sequence encoding VP1 from GII.4/Sydney/NSW0514/2012/AU comprising the P80S and the S90L substitutions in the S domain was cloned into 2×35S/CPMV 160/NOS+MAR expression system using the following PCR-based method. In a first round of PCR, a fragment containing the S domain with the mutated P80S and S90L amino acids was amplified using primers IF-GII.4Syd12VP1.c (SEQ ID NO:130) and GII.4(S90L).r (SEQ ID NO:140), using human codon-optimized GII.4_P80S VP1 gene sequence (SEQ ID NO:60) as template. A second fragment containing the S90L substitution with the remaining of the S and P domain was amplified using GII.4(S90L).c (SEQ ID NO:141) and IF-GII.4Syd12VP1.r (SEQ ID NO:131), using human codon-optimized GII.4_P80S VP1 gene sequence (SEQ ID NO:60) as template. For sequence optimization, GII.4/Sydney/NSW0514/2012/AU VP1 protein sequence (Genbank accession number AFV08795) was backtranslated and optimized for human codon usage, GC content and mRNA structure. The PCR products from both amplifications were then mixed and used as template for a second round of amplification using IF-GII.4Syd12VP1.c (SEQ ID NO:130) and IF-GII.4Syd12VP1.r (SEQ ID NO:131) as primers. The final PCR product was cloned in 2×35S/CPMV 160/NOS+MAR expression system using In-Fusion cloning system (Clontech, Mountain View, CA). Construct number 3677 (SEQ ID NO:164; FIGS. 38C and 49) was digested with SacII and StuI restriction enzyme and the linearized plasmid was used for the In-Fusion assembly reaction. Construct number 3677 is an acceptor plasmid intended for "In Fusion" cloning of genes of interest in a 2×35S/CPMV 160/NOS+MAR-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO:164. The resulting construct was given number 4135 (SEQ ID NO:166). The amino acid sequence of mutated GII.4_P80S+S90L is presented in SEQ ID NO:73. A representation of plasmid 4135 is presented in FIG. 44L.

A summary of the wildtype and mutated VP1 and VP2 proteins, primers, templates and products is provided in Tables 3 and 4. The VP1 proteins with single, double, triple, and quadruple modifications, substitutions, or mutations were constructed using the same methods as described above, with reference to construct #4133 for single modification and #4135 for the double, triple, and quadruple modifications. VP2 proteins are assembled using essentially the same method as that described for construct #2724.

Example 2: Methods

*Agrobacterium tumefaciens* Transfection

*Agrobacterium tumefaciens* strain AGL1 was transfected by electroporation with the native norovirus VP1, native norovirus VP2, or norovirus VP1 mutant protein expression vectors using the methods described by D'Aoust et al., 2008 (*Plant Biotech. J.* 6:930-40). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

*N. benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions Agrobacteria transfected with each native norovirus VP1, native norovirus VP2, or norovirus VP1 mutant expression vector were grown in a YEB medium supplemented with 10 mM 2-(N-morpholino)ethanesulfonic acid (MES), 20 μM acetosyringone, 50 μg/ml kanamycin and 25 μg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 6 or 9 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 2 volumes of cold 100 mM phosphate buffer pH 7.2+150 mM NaCl, 0.4 μg/ml Metabisulfite and 1 mM phenylmethanesulfonyl fluoride. After homogenization, the slurries were centrifuged at 10,000 g for 10 min at 4° C. and these clarified crude extracts (supernatant) kept for analyses.

The total protein content of clarified crude extracts was determined by the Bradford assay (Bio-Rad, Hercules, California) using bovine serum albumin as the reference standard. Proteins were separated by SDS-PAGE under reducing conditions using Criterion™ TGX Stain-Free™ precast gels (Bio-Rad Laboratories, Hercules, CA). Proteins were visualized by staining the gels with Coomassie Brilliant Blue. Alternatively, proteins were visualized with Gel Doc™ EZ imaging system (Bio-Rad Laboratories, Hercules, CA) and electrotransferred onto polyvinylene difluoride (PVDF) membranes (Roche Diagnostics Corporation, Indianapolis, Indiana) for immunodetection. Prior to immunoblotting, the membranes were blocked with 5% skim milk and 0.1% Tween-20 in Tris-buffered saline (TBS-T) for 16-18 h at 4° C.

Protein Analysis and Immunoblotting

Immunoblotting was performed with a first incubation with a primary mAb 242P antibody specific to VP1 from GI and GII genotypes, diluted 1/500 in 2% skim milk in TBS-Tween 20 0.1%. Peroxydase-conjugated goat anti-mouse (Jackson Immunoresearch, cat #115-035-146) diluted 1/10000 was used as secondary antibody for chemiluminescence detection, diluted in 2% skim milk in TBS-Tween 20 0.1% Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

Analysis of VLP Formation/Iodixanol Gradients

Proteins were extracted from frozen biomass by mechanical extraction in a blender with 2 volumes of extraction buffer (100 mM phosphate buffer pH 7.2+150 mM NaCl). The slurry was filtered through a large pore nylon filter to remove large debris and centrifuged 5000 g for 5 min at 4° C. The supernatant was collected and centrifuged again at 5000 g for 30 min (4° C.) to remove additional debris. The supernatant is then loaded on a discontinuous iodixanol density gradient. Analytical density gradient centrifugation was performed as follows: 38 ml tubes containing discontinuous iodixanol density gradient in acetate buffer (1 ml at 45%, 2 ml at 35%, 2 ml at 33%, 2 ml at 31%, 2 ml at 29% and 5 ml at 25% of iodixanol) were prepared and overlaid with 25 ml of the extracts containing the virus-like particles. The gradients were centrifuged at 175 000 g for 4 hours (4° C.). After centrifugation, 1 ml fractions were collected from the bottom to the top and fractions were analyzed by SDS-PAGE combined with protein staining or Western blot.

Electron Microscopy

Following centrifugation of partially clarified plant extracts on discontinuous iodixanol density gradients, as described above, fractions (1 ml/fraction) containing the samples are pooled, mixed with 100 mM PBS pH 7.2+150 mM NaCl buffer to completely fill the tube and centrifuged 120 minutes at 100000 g. The pellets were re-suspended in 300-1000 μl of buffer depending of the VP1 quantity.

Carbon-coated copper grids with a 200 nm mesh size are made hydrophilic by placing the carbon side face up on a Whatman paper in a petri dish and incubated overnight at 4° C. 20 μl of pooled fractions from density gradient centrifugation to be observed by transmission electron microscopy (TEM) are deposited on a Parafilm and grids were floated with the carbon side facing down and incubated at room temperature for 5 minutes. Grids are then washed 4 times on 20 μl water droplet and the excess water from the last wash is drained by touching a Whatman paper with the side of the grid. Grids are then incubated 1 minute on a 20 μl droplet of 2% uranyl acetate in water. Grids are allowed to dry 5 minutes on a Whatman paper. Observation was performed under transmission electron microscopy at magnifications ranging from 10,000× to 150,000×.

Example 3: VP1 Protein and VLP Production in Plants

*N. benthamiana* leaves were, vacuum infiltrated, as described in Example 2, with *Agrobacterium tumefaciens* comprising expression vectors encoding wildtype norovirus VP1s or mutant norovirus VP1 constructs to permit expression of the VP1 sequences, and the leaves examined for VP1 protein and/or VLP production. After 9 days post infiltration (DPI), total crude protein extracts were prepared from leaf homogenates were separated by SDS-PAGE, and stained with Coomassie (VP1 production), or separated using discontinuous iodixanol density gradients as described in Example 2, above (VLP production). Fractions from the density gradients were examined using Coomassie-stained SDS-PAGE. Norovirus VP1 proteins appear at an approximate 55-60 kDa band. The occurrence of the VP1 protein within a fraction of the density gradients is indicative of the fraction(s) to which the VLPs equilibrate during density gradient centrifugation. The yield of VLPs obtained from peak fractions after density gradient centrifugation was also determined.

The yield, or amount of extracted, wild type norovirus VP1 protein from plants differs depending on the genotype of the norovirus VP1 being expressed. Wild type GI.1 VP1, GI.5 VP1, and GII.12 VP1 exhibit readily detectable protein yields as determined using SDS PAGE (FIG. 3A). In contrast, wild type GII.4 VP1 was poorly expressed in plants (FIG. 3A right hand panel), and low yields of VP1 protein, or non-detectable amounts of VP1 protein (using SDS-PAGE) were also observed following expression, for example, wild type GII.2 VP1, GII.3 VP1 and GII.6 VP1 (Table 5).

TABLE 5

VP1 yields (determined in crude extracts) of several wildtype (native) norovirus strains produced in plants.

| Genotype | Strain | Native Max yields |
|---|---|---|
| GI.1 | GI.1/US/68 | +++++ |
| GI.3 | S29/2008/Lilla Edet/Sweeden | +++ |
| GII.2 | CGMH47/2011/TW | ++ |
| GII.3 | Jingzhou/2013402/CHN | − |
| GII.6 | Ohio/490/2012/USA | +/− |

GI.3 VLPs and VLPs Comprising Modified GI.3 VP1 Proteins

Norovirus GI.3 VP1 constructs having a glutamine to serine substitution at position 84 (Q84S) resulted in similar yield than the wildtype GI.3 VP1, while norovirus GI.3 VP1 constructs having a serine to leucine substitution at position 94 (S94L), or combination of substitutions including the S94L substitution, exhibited a greater yield of VLP comprising the VP1 protein, of a 1.9 to 3.8 fold increase (S94L), a 4.2 fold increase (A43V+S94L), a 1.8 fold increase (Q84S+S94L), and a 10.2 fold increase (A34V+M57I+Q84S+S94L) as compared to VLPs comprising wild type GI.3 VP1. Furthermore, constructs having a serine to leucine, valine, isoleucine, methionine, threonine, glutamic acid, aspartic acid, asparagine, glutamine, lysine, or histidine substitution at position 94 (GI.3_S94X, where X=L, V, I, M, T, E, D, N, Q, K, or H), exhibited a greater yield, from about 1.2 to about 2.75 fold, compared to VLPs comprising the wild type GI.3 VP1 protein (FIG. 5F).

As shown in FIGS. 5B and 5D, expression of norovirus GI.3 constructs having, a serine to leucine substitution at position 94 (S94L), or a combination including a glutamine to serine substitution at position 84 (Q84S) and a serine to leucine substitution at position 94 (Q84S+S94L), or methionine to isoleucine substitution at position 57 (M57I+S94L), resulted in a shift of VLPs into higher density fractions (F2-F6; 31-35% iodixanol), as compared to VLPs comprising wildtype GI.3 VP1, which predominantly separated into lower density fractions (F8-F11; 25-29% iodixanol).

VLPs comprised of modified GI.3 VP1 proteins having a S94L substitution, a combination of Q84S+S94L, or a combination of M57I+S94L, had fewer damaged viral particles and a greater proportion of 38 nm particles, over 23 nm particles, when compared to wildtype GI.3 VLPs (FIGS. 5C and 5E).

GI.5 VLPs and VLPs Comprising Modified GI.5 VP1 Proteins

Norovirus GI.5 VP1 constructs having a serine to proline substitution at position 84 (Q84S), an alanine to leucine substitution at position 94 (A94L), or a combination of these substitutions (Q84S+A94L), exhibited a similar yield of VP1 protein in plant extracts when compared to the yield of wild type GI.5 VP1 protein expressed in plants (FIG. 6A). After gradient purification, centrifugation and resuspension, Norovirus GI.5 construct having an alanine to leucine substitution at position 94 (A94L) exhibited a greater yield, 1.5 fold increase, when compared to the wildtype GI.5 VP1.

As shown in FIG. 6B, a GI.5 VP1 construct having a glutamine to serine substitution at position 84 in combination with an alanine to leucine substitution at position 94 (Q84S+A94L), resulted in VP1 proteins that exhibited a shift to higher density iodixianol fractions (29-31%) as compared to wildtype GI.5 VP1 (predominantly found in 25-29% iodixanol fractions). The VLP preparations also comprised fewer damaged viral particles when compared to wildtype GI.5 VLPs (FIG. 6C).

GI.7 VLPs and VLPs Comprising Modified GI.7 VP1 Proteins

Figure 6F:
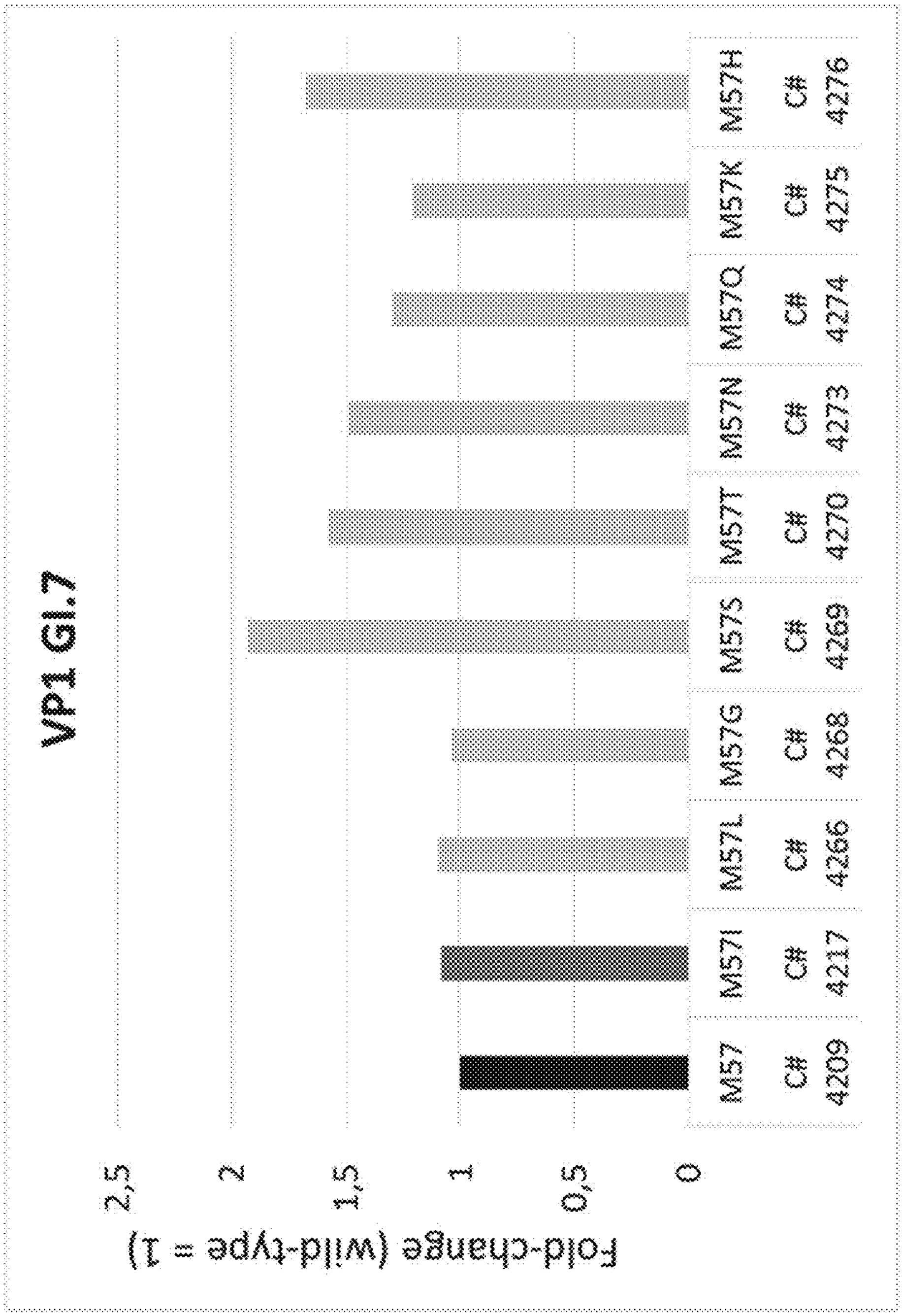
FIG. 6F shows the relative yield of VLPs comprising non-native VP1 GI.7 with substitutions at amino acid position 57, compared to the VLP yield of wild-type GI.7 (GI.7 M57; set as "Fold Change" of 1): C #: construct number.

Norovirus GI.7 VP1 constructs having an arginine to serine substitution at position 84 (R84S), a methionine to isoleucine substitution at position 57 (M57I), or a combination of these substitutions (M57I+R84S), exhibited an increased yield of VP1 protein after gradient purification, centrifugation and resuspension, when compared to the wildtype GI.7 VP1. Furthermore, GI.7 constructs having a methionine to isoleucine, leucine, glycine, serine, threonine, asparagine, glutamine, lysine, or histidine substitution at position 57 (GI.7_M57X, where X=I, L, G, S, T, N, Q, K, or H), exhibited a greater yield, from about 1.1 to about 1.95 fold, VLPs comprising the wild type GI.7 VP1 protein (FIG. 6F).

As shown in FIG. 6D, a GI.7 VP1 construct having the M57I, R84S or M57I+R84S substitutions resulted in VP1 proteins that exhibited a shift to higher density iodixianol fractions (31-35%) as compared to wildtype GI.7 VP1. The GI.7 VLP preparations having the M57I, R84S or M57I+R84S substitutions also comprised the same or fewer damaged viral particles when compared to wildtype GI.7 VLPs (FIG. 6E).

GII.2 VLPs and VLPs Comprising Modified GIL 2 VP1 Proteins

Expression of modified norovirus VP1 proteins GII.2_A90L and GII.2_E80S+A90L in plants resulted in higher VP1 protein yield as compared to the yield of wildtype GII.2 VP1 (see FIG. 7A).

Norovirus GII.2 VP1 constructs having a glutamate to serine substitution at position 84 and an alanine to leucine substitution at position 90 (E84S+A90L), an alanine to valine substitution at position 39, a glutamate to serine substitution at position 84, and an alanine to leucine substitution at position 90 (A39S+E84S+A90L), an arginine to isoleucine substitution at position 53, a glutamate to serine substitution at position 84, and an alanine to leucine substitution at position 90 (R53I+E84S+A90L), an alanine to valine substitution at position 39, an arginine to isoleucine substitution at position 53, a glutamate to serine substitution at position 84, and an alanine to leucine substitution at position 90 (A39V+R53I+E84S+A90L), all exhibited an increased yield of VP1 protein after gradient purification, centrifugation and resuspension, when compared to the wildtype GII.2 VP1.

Expression of a GII.2 VP1 constructs having a glutamic acid to serine substitution at position 80 (E80S), an alanine to leucine substitution at position 90 (A90L), or a glutamic acid to serine substitution at position 80 and an alanine to leucine substitution at positions 80 and 90 (E80S+A90L) resulted in similar production of VLPs as that of the wildtype GII.2 (FIG. 7B). The GII.2 VLP preparations having the E80S+A90L, or A39V+E80S+A90L substitution s also comprised the same or fewer damaged viral particles when compared to wildtype GII.2 VLPs (FIG. 7C).

GII.3 VLPs and VLPs Comprising Modified GIL 3 VP1 Proteins

Norovirus GII.3 VP1 constructs having a replacement of glutamic acid with serine at position 80 (E80S) exhibited a similar yield of VP1 protein in plant extracts, when compared to the yield of wild type GII.3 VP1 protein expressed in plants. The yields of VLPs comprising either wild type of modified VP1 protein were generally low.

Expression of a GII.3 VP1 constructs having a glutamic acid to serine substitution at position 80 (E80S) resulted in similar production of VLPs that resided in similar density iodixanol fractions (35%) as that of the wildtype GII.3 (FIG. 8B).

GII.4 VLPs and VLPs Comprising Modified GII.4 VP1 Proteins

Figure 9H:
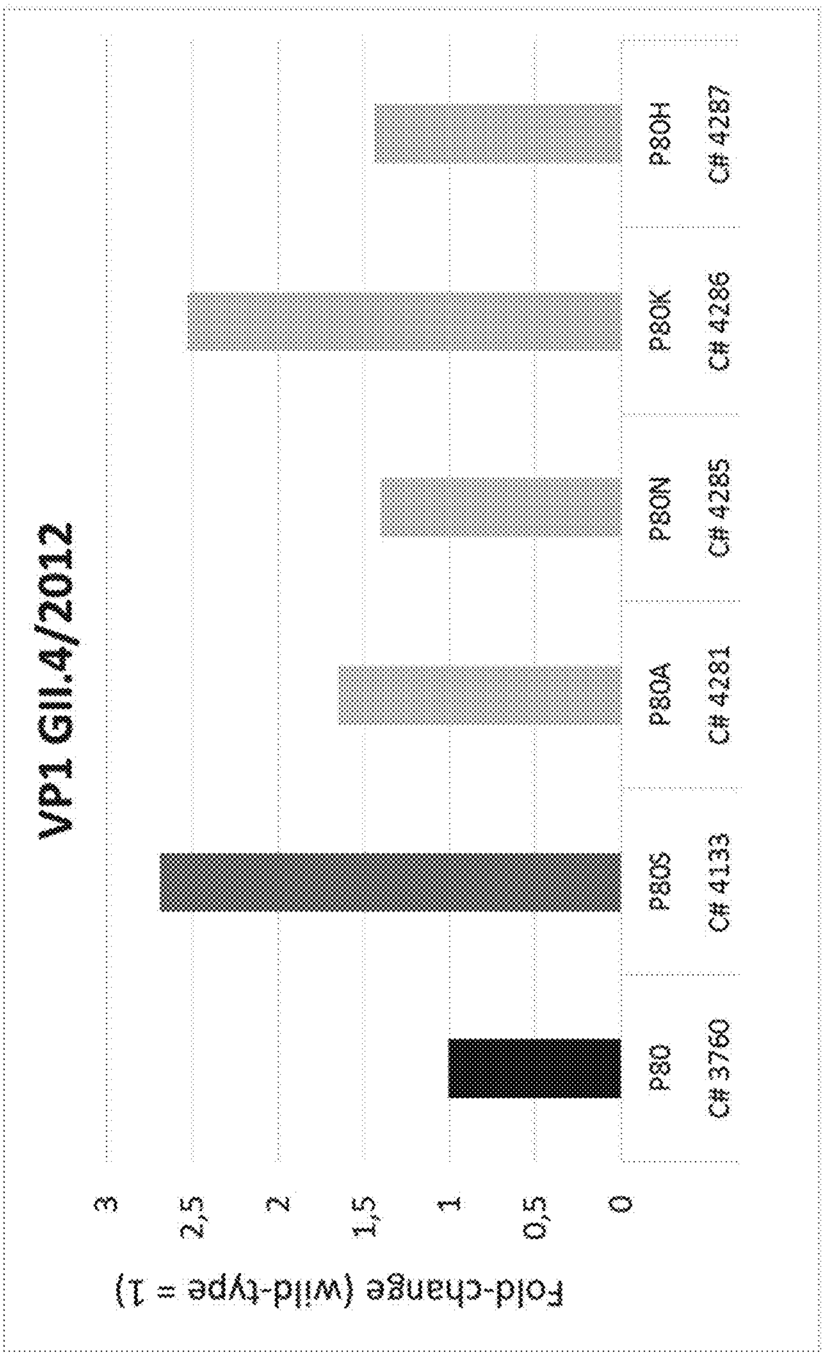
FIG. 9H shows the relative yield of VLPs comprising non-native VP1 GII.4/2012 with substitutions at amino acid position 80, compared to the VLP yield of wild-type (native) GII.4/2012 (GII.14/2012 P80 set as "Fold Change" of 1; C #: construct number.
Figure 9I:
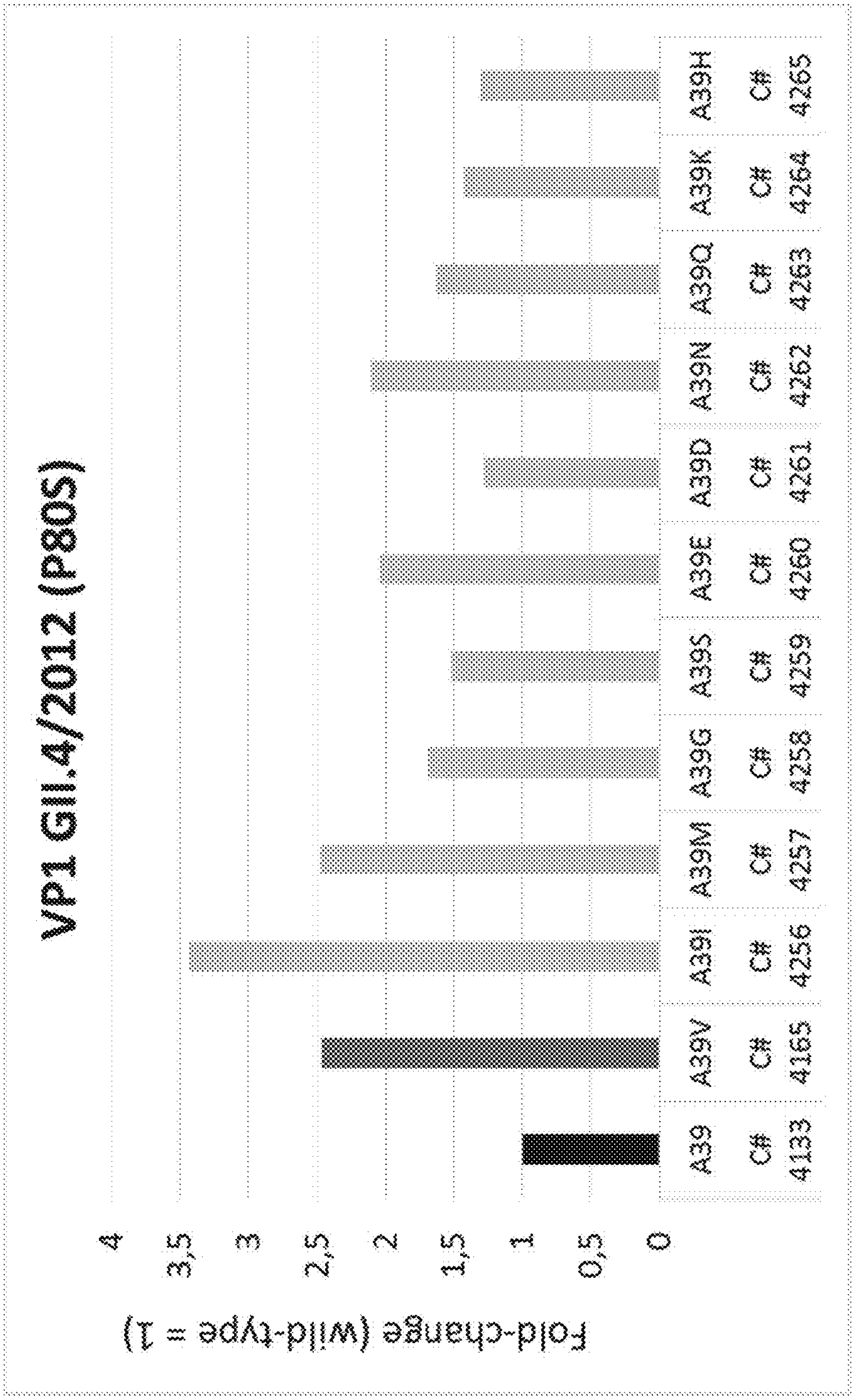
FIG. 9I shows the relative yield of VLPs comprising VP1 GII.4/2012 (P80S) with an additional substitution at amino acid position 39, compared to the VLP yield of GII.14/2012 (P80S) comprising A39. GII.4/2012 (P80S) A39 set as "Fold Change" of 1; C #: construct number.

With reference to FIGS. 9A, 9H and 9I, norovirus GII.4 VP1 constructs having: an arginine to isoleucine substitution at position 53 (R53I); a proline to serine, alanine, asparagine, lysine, or histidine substitution at position 80 (P80X, where X=5, A, N, K, or H); a serine to leucine substitution at position 90 (S90L); an alanine to valine, isoleucine, methionine, threonine, aspartic acid, glutamic acid, asparagine, glutamine, lysine, or histidine substitution at position 39 (A39X, where X=V, I, M, T, E, D, N, Q, K, or H) in combination with a proline to serine substitution at position 80 (A39V+P80S); an arginine to isoleucine substitution at position 53 in combination with a proline to serine substitution at position 80 (R53I+P80S); a serine to leucine substitution at position 90 in combination with a proline to serine substitution at position 80 (P80S+S90L); and a deletion of positions 35 to 42 (Δ35-42) in combination with a proline to serine substitution at position 80 (Δ35-42+P80S), resulted in higher VP1 protein yields following extraction for plants, as compared to VP1 yields using wildtype GI.4.

For each of the tested modified GII.4 VP1 proteins, the VLP yield, comprising the various modified GII.4 VP1 proteins, was greater than that of VLPs comprising wild type GII.4 VP1 protein. A ten-fold increase in VLP yield was observed in VLPs comprising GII.4_A39V VP1; from about a 1.4 to about a 2.7 fold increase in VLP yield was observed in VLPs comprising GII.4_P80X, where X=5, A, N, K, H, an over 8-fold increase in VLP yield was observed in VLPs comprising either GII.4_S90L VP1, or GII.4_Δ35-42+P80S VP1; a 14-fold increase in VLP yield was observed in VLPs comprising GII.4_P80S+P90L VP1; from about 1.3 to about 3.4 fold increase in VLP yield was observed in VLPs comprising GII.4_A39X+P80S VP1, where X=V, I, M, T, E, D, N, Q, K, or H, GII.4_R53I+P80S (21 fold increase), or GII.4_A39V+P80S+A90L VP1 (38.5 fold increase); a five-fold increase in VLP yield was observed in VLPs comprising GII.4_A39V+R53I VP1; a four-fold increase in VLP yield was observed in VLPs comprising GII.4_V47P+P80S VP1; and a 1.5-fold increase in VLP yield was observed in VLPs comprising GII.4_R53I VP1.

Results of VLPs comprising modified GII.4 proteins are shown in FIGS. 9B-9D and 9G. Constructs comprising GII.4 VP1 having: a proline to serine substitution at position 80 (P80S; FIG. 9B, 9C, 9D); a serine to leucine substitution at position 90 (S90L; FIG. 9B); an alanine to valine substitution at position 39 in combination with a proline to serine substitution at position 80 (A39V+P80S; FIG. 9C); an arginine to isoleucine substitution at position 53 in combination with a proline to serine substitution at position 80 (R53I+P80S; FIG. 9D); a proline to serine substitution at position 80 in combination with a serine to leucine substitution at position 90 (P80S+S90L; FIG. 9B); a proline to serine substitution at position 80 in combination with a deletion of positions 35-42 (P80S+Δ35-42; FIG. 9C), and an alanine to valine substitution at position 39, in combination with a proline to serine substitution at position 80 and a serine to leucine substitution at position 90 (GII.4_A39V+P80S+A90L; FIG. 9G), resulted in the production of VLPs that reside in higher density iodixanol fractions (29-33%).

VLPs comprising GII.4 VP1 proteins having: a P80S substitution in combination with an S90L substitution (P80S+S90L; FIG. 9B); an A39V substitution in combination with a P80S substitution (A39V+P80S; FIG. 9C); a P80S substitution in combination with a deletion of positions 35-42 (Δ35-42+P80S; FIG. 9C); an R53I substitution in combination with a P80S substitution (R53I+P80S; FIG. 9D); and an alanine to valine substitution at position 39, in combination with a proline to serine substitution at position 80 and a serine to leucine substitution at position 90 (GII.4_A39V+P80S+A90L; FIG. 9G), had fewer damaged viral particles and/or a greater ratio of 38 nm particles:23 nm particles, as compared to wildtype GII.4 VLPs.

GII.6 VLPs and VLPs Comprising Modified GIL 6 VP1 Proteins

Increased VLP yield of over 2.2 fold, compared to wild type, (determined following gradient purification, centrifugation and resuspension) was also observed in plant extracts expressing GII.6_S90L VP1.

GII.12 VLPs and VLPs Comprising Modified GII.12 VP1 Proteins

Figure 11A:
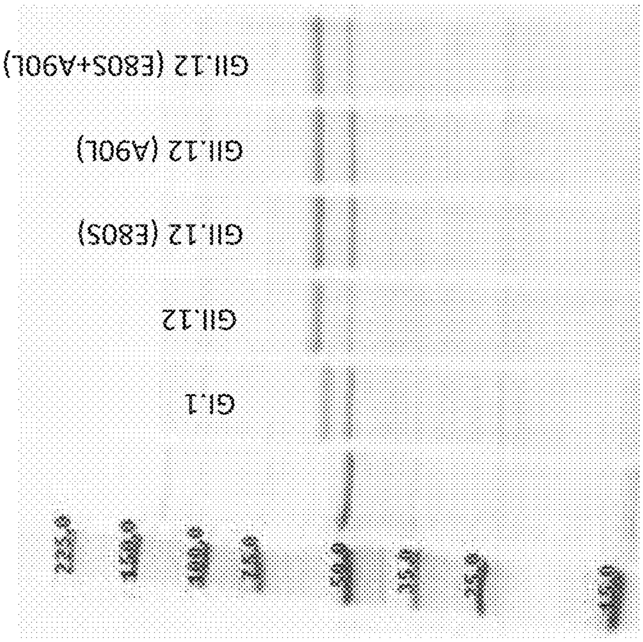
FIG. 11A shows a Coomassie-stained SDS-PAGE of crude protein extracts prepared from agroinfiltrated *N. benthamiana* leaves, 9 days post infiltration (DPI) with wt hCod GI.1/United States/Norwalk/1968 VP1 (Construct #: 2724; SEQ ID NO:3 (nucleotide); SEQ ID NO: 1 (amino acid)), wt hCod GII.12/HS206/2010/USA VP1 (Construct #: 3995; SEQ ID NO:87 (nucleotide); SEQ ID NO:19 (amino acid)), mut hCod GII.12/H5206/2010/USA_E80S VP1 (Construct #: 4136; SEQ ID NO:89 (nucleotide); SEQ ID NO:88 (amino acid)), mut hCod GII.12/HS206/2010/USA_A90L VP1 (Construct #: 4137; SEQ ID NO:91 (nucleotide); SEQ ID NO:90 (amino acid)), or mut hCod GII.12/HS206/2010/USA_E80S+A90L VP1 (Construct #: 4138; SEQ ID NO:93 (nucleotide); SEQ ID NO:92 (amino acid)). First lane=crude protein extracts prepared from mock infiltrated *N. benthamiana* leaves.
Figure 11B:
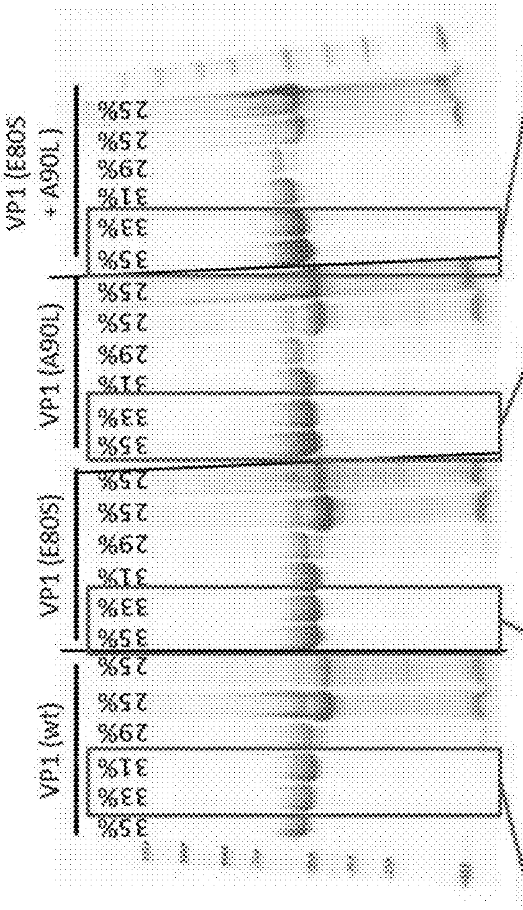
FIG. 11B shows a Coomassie-stained SDS-PAGE analysis of iodixanol density gradient fractions of crude protein extracts prepared from *N. benthamiana* leaves expressing wt GII.12/H5206/2010/USA VP1 (Construct #: 3995), GII.12/H5206/2010/USA_E80S VP1 (Construct #: 4136), GII.12/HS206/2010/USA_A90L VP1 (Construct #: 4137), or GII.12/HS206/2010/USA_E80S+A90L VP1 (Construct #: 4138).
Figure 11C:
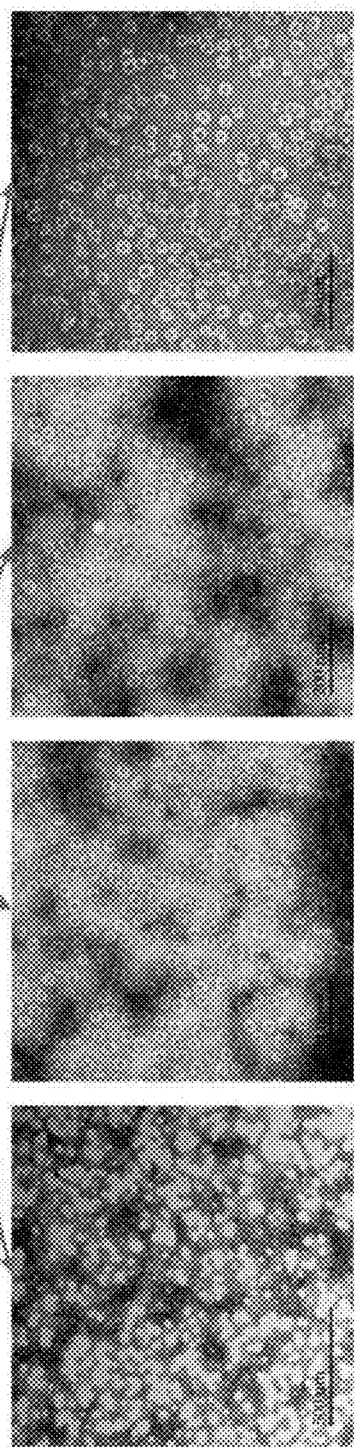
FIG. 11C shows transmission electron micrographs (TEM) of virus like particles (VLPs) purified from 31-35% iodixanol gradient fractions of crude protein extracts prepared from *N. benthamiana* leaves expressing wt GII.12/H5206/2010/USA VP1 (Construct #: 3995, first panel GII.12/HS206/2010/USA_P80S VP1 (Construct #: 4136, second panel), GII.12/HS206/2010/USA_S90L VP1 (Construct #: 4137, third panel), or GII.12/H5206/2010/USA_P80S+S90L VP1 (Construct #: 4138, fourth panel) .15,000× magnification; scale bar=500 nm.
Figure 11D:
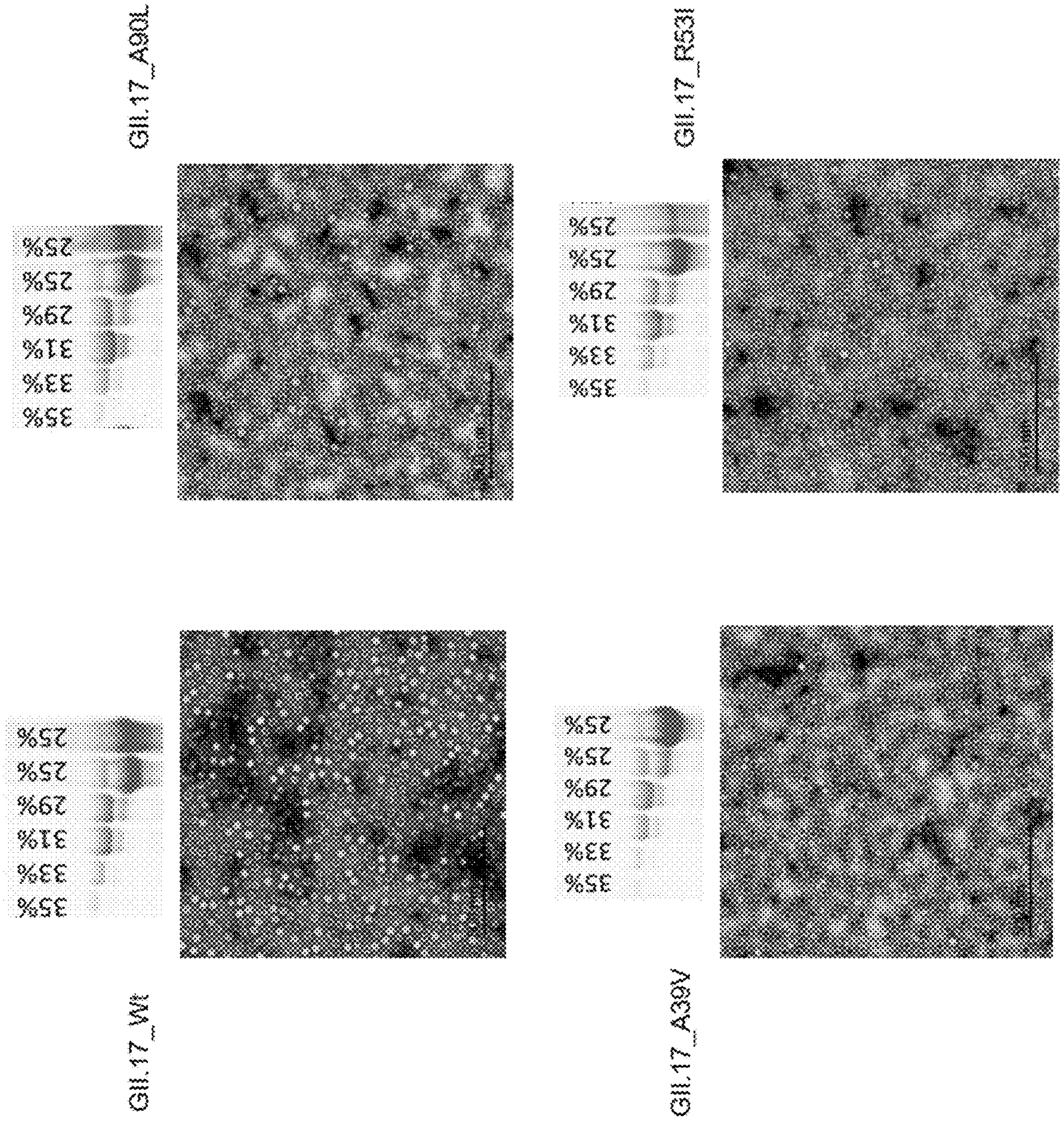
FIG. 11D shows Coomassie-stained SDS-PAGE analysis of iodixanol density gradient fractions of crude protein extracts prepared from *N. benthamiana* leaves (upper part of each panel), and transmission electron micrographs (TEM) of virus like particles (VLPs) purified from 31-35% iodixanol gradient fractions of crude protein extracts prepared from *N. benthamiana* leaves (lower part of each panel), expressing: Top Left Panel: wt hCod GII.17 Kawa 2014 A0A077KVU6VP1 (Construct #3998; SEQ ID NO:25 (nucleotide); SEQ ID NO:24 (amino acid)), Top Right panel mut hCod GII.17 Kawa 2014 A0A077KVU6_A90L VP1 (Construct #4232; SEQ ID NO:197 (nucleotide); SEQ ID NO:196 (amino acid)); Bottom Left Panel: mut hCod GII.17 Kawa 2014 A0A077KVU6_A39V VP1 (Construct #4234; SEQ ID NO:193 (nucleotide); SEQ ID NO:192 (amino acid)); Bottom Right Panel: mut hCod GII.17 Kawa 2014 A0A077KVU6_R53I VP1 (Construct #4235; SEQ ID NO:195 (nucleotide); SEQ ID NO:194 (amino acid)); 15,000× magnification; scale bar=500 nm.

The yield of modified GII.12, for example, GII.12 comprising a glutamic to serine substitution at position 80 (E80S), an arginine to leucine substitution at position 90 (A90L), or a combination of these substitutions (E80S+A90L) resulted in an increase of about 1.2-1.4 fold compared to wild type, (determined following gradient purification, centrifugation and resuspension; FIG. 11A).

GII.12 constructs having: a glutamic acid to serine substitution at position 80 (E80S); an alanine to leucine substitution at position 90 (A90L); and a combination thereof (E80S+A90L), resulted in the expression of GII.12 VP1 protein that resided in higher density iodixanol fractions (33-35%) as compared to wildtype GII.12 VP1 (31-33%).

GII.17 VLPs and VLPs Comprising Modified GII.17 VP1 Proteins

The yield of modified GII.17, for example, GII.17 comprising an alanine to valine substitution at position 39 (A39V), a arginine to isoleucine substitution at position 53 (R53I), or an alanine to leucine substitution at position 90 (A90L) resulted in an increase of about 1.1-3.4 fold compared to wild type, (determined following gradient purification, centrifugation and resuspension).

GII.17 constructs having: an alanine to valine substitution at position 39 (A39V), a arginine to isoleucine substitution at position 53 (R53I), or an alanine to leucine substitution at position 90 (A90L), resulted in the expression of GII.17 VP1 protein that resided in higher density iodixanol fractions (33-35%) as compared to wildtype GII.12 VP1 (31-33%).

Collectively, the above described results demonstrate that protein components from the high density iodixanol gradient fractions demonstrate that Norovirus VP1 proteins, and modified Norovirus VP1 proteins, were found to self-assemble into VLPs in plants. The isolated VLPs comprised of mutant VP1 proteins exhibited a structural conformation similar to that of wildtype norovirus virion particles.

Example 4: Immune Response Using VP1

Studies on the immune response to Norovirus native GI.1 (SEQ ID NO:1) VLP administration were performed with 6-8 week old female BALB/c mice (Charles River Laboratories). Thirty seven mice were randomly divided into four groups of eight animals for Norovirus VLP vaccine and a group of five animals for placebo. All groups were injected using intramuscular immunization. All groups were immunized in a two-dose regimen, the boost immunization being administered 3 weeks following the first immunization.

For intramuscular administration in hind legs, two groups (eight animals) of unanaesthetized mice were immunized with the plant-made VLP native VP1 from Norovirus GI.1 genotype vaccine (1 or 10 μg). Placebo group (five animals) was immunized using the same route and regimen as the candidate vaccine using vaccine buffer (PBS at pH 6.0).

To measure the potential benefit of adjuvant, two groups of animals (8 animals) were immunized by intramuscular administration in hind legs on unanaesthetized mice with 1 or 10 plant-made VLP Norovirus vaccine plus one volume Alhydrogel 2% (alum, Cedarlane Laboratories Ltd., Burlington, Ontario, Canada). All groups were immunized according to a prime-boost regimen with the boost immunization performed 3 weeks following the first immunization.

Mice were evaluated through clinical observations during the in-life period as followed: daily monitoring for mortality and clinical signs, weekly detailed examinations, injection site observations and body weight measurements. All animals were under observation and sacrificed on Day 42 for gross examination. Blood was collected from all animals prior to dosing on Day 0, on Days 21 and 42 (21 days after each immunization). Samples were processed to isolate the serum for specific antibody response analyses.

Serum samples from blood collected on Days 21 and 42 from all animals were analyzed individually by ELISA for GI.1 VLP-specific total IgG and IgA antibodies using GI.1 VLP-coated plates. Pre-immune serum samples (Day 0—prior dosing) collected from all animals were pooled by treatment group and each pool was analyzed to insure that they were negative (or below the cut-off value of the analytical test).

Descriptive statistics were performed using GraphPad Prism software (Version 6.05; GraphPad Software, La Jolla, CA, USA). Antibody titers measured for each group were reported as geometric mean titer (GMT) with 95% confidence intervals (CI). Half of the value of the limit of detection was attributed to antibody titers below the limit of detection of the method specific to the tested antibodies. Therefore, in this study, an animal was considered to be a positive responder if its GMT value for a determined condition was equal or above the limit of detection of the method (LOQ=100). Statistical comparisons between IgG titers of treatment groups were performed using one-way ANOVA followed by a Tukey's test on log 10-transformed data. A comparison between the placebo group and each treatment group was also performed using oneway ANOVA followed by a post hoc Dunnett's test on log 10-transformed data.

The GI.1 VLP-specific total IgG titers that were measured in serum samples from all animals after IM immunization with one dose (Day 21) and two doses (Day 42) of 1 μg or 10 μg of each formulation. Total IgG titers were measured by ELISA using GI.1 VLP-coated plates (LOQ=100). The results are present in FIG. 3D. Total IgG titers per treatment group (n=8 animals/group) are represented by geometric mean titer (GMT) with a 95% confidence interval. Statistical comparisons between IgG titers of treatment groups were performed using one-way ANOVA followed by a Tukey's test on log 10-transformed data. A comparison between the placebo group and each treatment group was also performed using one-way ANOVA followed by a post-hoc Dunnett's test on log 10-transformed data. Significant differences were annotated as letters in FIG. 3D (the same letter indicates that no significant difference was detected between treatment groups; $p>0.05$).

In a similar manner plant-produced modified VP1 proteins, as described herein, including for example: produced using GI.3_Q84S (construct 4140; SEQ ID NO:167), GI.3_S94L (construct 4141; SEQ ID NO:9), GI.3_A43V+S94L (construct 4179; SEQ ID NO:169), GI.3_M57I+S94L (construct 4180; SEQ ID NO:171), GI.3_P84S+S94L (construct 4142; SEQ ID NO:11), GI.3_A43V+M57I+S94L (construct 4181; SEQ ID NO:173), GI.5_Q84S (construct 4130; SEQ ID NO:35), GI.5_A94L (construct 4131; SEQ ID NO:37), GI.5_Q84S+A94L (construct 4132; SEQ ID NO:39), GI.7_R84S (construct 4210; SEQ ID NO:176), GI.7_M57I (construct 4217; SEQ ID NO:178), GI.7_M57I+R84S (construct 4218; SEQ ID NO:180), GII.2_E80S (construct 4143; SEQ ID NO:86), GII.2_A90L (construct 4144; SEQ ID NO:42), GII.2_E80S+A90L (construct 4145; SEQ ID NO:44), GII.2_A39V+E80S+A90L (construct 4182; SEQ ID NO:183), GII.2_R53I+E80S+A90L (construct 4183; SEQ ID NO:185), GII.2_A39V+R53I+E80S+A90L (construct 4184; SEQ ID NO:187), GII.3_E80S_(construct 4146; SEQ ID NO:47), GII.3_A90L (construct 4147; SEQ ID NO:49), GII.3_E80S+A90L (construct 4148; SEQ ID NO:51), GII.4_A39V (construct 4155; SEQ ID NO:54), GII.4_V47P (construct 4156; SEQ ID NO:56), GII.4_R53I (construct 4157; SEQ ID NO:58), GII.4_P80S (construct 4133; SEQ ID NO:60), GII.4_S90L (construct 4134; SEQ ID NO:62), GII.4_Δ35-42 (construct 4158; SEQ ID NO:64), GII.4_SSTAVATA (construct 4159; SEQ ID NO:66). GII.4_A39V+R53I (construct 4185; SEQ ID NO:189), GII.4_A39V+P80S (construct 4165; SEQ ID NO:68), GII.4_V47P+P80S (construct 4166; SEQ ID NO:70), GII.4_R53I+P80S (construct 4167; SEQ ID NO:72), GII.4_P80S+S90L (construct 4135; SEQ ID NO:74), GII.4_Δ35-42+P80S (construct 4168; SEQ ID NO:76), GII.4_P80S+SSTAVATA (construct 4169; SEQ ID NO:78), GII.4_A39V+R53I+P80S (construct 4186; SEQ ID NO:191), GII.6_E80S (construct 4149; SEQ ID NO:80), GII.6_S90L (construct 4150; SEQ ID NO:82), GII.6_E80S+S90L (construct 4151; SEQ ID NO:84), GII.12_E80S (construct 4136; SEQ ID NO:89), GII.12_A90L (construct 4137; SEQ ID NO:91), GII.12_E80S+A90L (construct 4138; SEQ ID NO:93), GII.17_A39V (construct 4234; SEQ ID NO:193), GII.17_R53I (construct 4235; SEQ ID NO:195), GII.17_A90L (construct 4232; SEQ ID NO:197), GII.17_A39V+R53I (construct 4236; SEQ ID NO:199), GII.17_E80S+A90L (construct 4233; SEQ ID NO:201), or a combination thereof may be administered to mice following the same protocol as described in this example.

Mouse Immune Response to Norovirus Native VP1 VLPs

As demonstrated in FIG. 3D, mice immunized with plant-made Norovirus native VP1 VLPs from GI.1 genotype had shown GI.1 VLP-specific IgG antibody titers in sera and were detected for each treatment group on Days 21 and 42. IgG titer levels that were induced by each treatment on Days 21 and 42 were statistically higher than the titers quantified for the placebo group ($p<0.05$). On each day, IgG titer level increased in a dose-dependent manner as demonstrated by the significant differences detected between the 1 μg and 10 μg treatments formulated with Alhydrogel or not ($p<0.05$) and the addition of Alhydrogel to the NoV VLP vaccine enhanced significantly the induced immune response at doses of 1 μg and 10 μg ($p<0.05$). A significant increase of IgG titer level was also detected for each treatment group between Days 21 and 42 ($p<0.05$). These results collectively demonstrate the ability of plant produced Norovirus native VP1 VLPs to elicit a robust immune response in mice.

Similar results may also be observed with the administration of VLPs comprising modified VP1 proteins, including for example: produced using GI.3_Q84S (construct 4140; SEQ ID NO:167), GI.3_S94L (construct 4141; SEQ ID NO:9), GI.3_A43V+S94L (construct 4179; SEQ ID NO:169), GI.3_M57I+S94L (construct 4180; SEQ ID NO:171), GI.3_P84S+S94L (construct 4142; SEQ ID NO:11), GI.3_A43V+M57I+S94L (construct 4181; SEQ ID NO:173), GI.5_Q84S (construct 4130; SEQ ID NO:35), GI.5_A94L (construct 4131; SEQ ID NO:37), GI.5_Q84S+A94L (construct 4132; SEQ ID NO:39), GI.7_R84S (construct 4210; SEQ ID NO:176), GI.7_M57I (construct 4217; SEQ ID NO:178), GI.7_M57I+R84S (construct 4218; SEQ ID NO:180), GII.2_E80S (construct 4143; SEQ ID NO:86), GII.2_A90L (construct 4144; SEQ ID NO:42), GII.2_E80S+A90L (construct 4145; SEQ ID NO:44), GII.2_A39V+E80S+A90L (construct 4182; SEQ ID NO:183), GII.2_R53I+E80S+A90L (construct 4183; SEQ ID NO:185), GII.2_A39V+R53I+E80S+A90L (construct 4184; SEQ ID NO:187), GII.3_E80S_(construct 4146; SEQ ID NO:47), GII.3_A90L (construct 4147; SEQ ID NO:49), GII.3_E80S+A90L (construct 4148; SEQ ID NO:51), GII.4_A39V (construct 4155; SEQ ID NO:54), GII.4_V47P (construct 4156; SEQ ID NO:56), GII.4_R53I (construct 4157; SEQ ID NO:58), GII.4_P80S (construct 4133; SEQ ID NO:60), GII.4_S90L (construct 4134; SEQ ID NO:62), GII.4_Δ35-42 (construct 4158; SEQ ID NO:64), GII.4_SSTAVATA (construct 4159; SEQ ID NO:66). GII.4_A39V+R53I (construct 4185; SEQ ID NO:189), GII.4_A39V+P80S (construct 4165; SEQ ID NO:68), GII.4_V47P+P80S (construct 4166; SEQ ID NO:70), GII.4_R53I+P80S (construct 4167; SEQ ID NO:72), GII.4_P80S+S90L (construct 4135; SEQ ID NO:74), GII.4_Δ35-42+P80S (construct 4168; SEQ ID NO:76), GII.4_P80S+SSTAVATA (construct 4169; SEQ ID NO:78), GII.4_A39V+R53I+P80S (construct 4186; SEQ ID NO:191), GII.6_E80S (construct 4149; SEQ ID NO:80), GII.6_S90L (construct 4150; SEQ ID NO:82), GII.6_E80S+S90L (construct 4151; SEQ ID NO:84), GII.12_E80S (construct 4136; SEQ ID NO:89), GII.2_A90L (construct 4137; SEQ ID NO:91), GII.12_E80S+A90L (construct 4138; SEQ ID NO:93), GII.17_A39V (construct 4234; SEQ ID NO:193), GII.17_R53I (construct 4235; SEQ ID NO:195), GII.17_A90L (construct 4232; SEQ ID NO:197), GII.17_A39V+R53I (construct 4236; SEQ ID NO:199), GII.17_E80S+A90L (construct 4233; SEQ ID NO:201), or a combination thereof, following the same protocol as described in this example.

All citations are hereby incorporated by reference.

The present invention has been described with regard to one or more embodiments. However, it will be apparent to persons skilled in the art that a number of variations and modifications can be made to the described subject matter. The scope of the claims should not be limited by the preferred embodiments set forth in the examples, but should be given the broadest interpretation consistent with the description as a whole.

The invention claimed is:

1. A norovirus VP1 protein comprising one or more than one amino acid substitution at a position in sequence alignment with amino acids 43, 57, 84 and 94 of reference sequence SEQ ID NO: 1, wherein the amino acid substitution at the position in sequence alignment with amino acid 43 is to isoleucine, methionine, aspartic acid, glutamic acid, asparagine, glutamine, lysine, or histidine;

the amino acid substitution at the position in sequence alignment with amino acid 57 is to leucine, alanine, glycine, serine, asparagine, glutamine, or histidine;

the amino acid substitution at the position in sequence alignment with amino acid 84 is to asparagine, cysteine, threonine, alanine, or lysine;

the amino acid substitution at the position in sequence alignment with amino acid 94 is to leucine, isoleucine, methionine, valine, threonine, asparagine, lysine, or histidine; and the wild type norovirus VP1 protein is not a GI.1 genotype.

2. The norovirus VP1 protein of claim 1, wherein the norovirus VP1 is selected from a group consisting of genotypes GI.3, GI.5, GI.7, GII.2, GII.3, GII.4, GII.6, GII.12 and GII.17.

3. The norovirus VP1 protein of claim 1, wherein the one or more than one substitution at the position in sequence alignment with amino acid 43 is to valine;

wherein the one or more than one substitution at the position in sequence alignment with amino acid 57 is to isoleucine;

wherein the one or more than one substitution at the position in sequence alignment with amino acid 84 is to serine; or wherein the one or more than one substitution at the position in sequence alignment with amino acid 94 is to leucine.

4. A recombinant polynucleotide encoding the norovirus VP1 protein of claim 1.

5. A virus-like particle (VLP) comprising the norovirus VP1 of claim 1.

6. The VLP of claim 5, further comprising a norovirus VP2 protein.

7. A method of producing a norovirus VP1 protein, or a VLP comprising the norovirus VP1 protein, in a plant, portion of a plant or a plant cell, the method comprising:

introducing the recombinant polynucleotide of claim 4; and incubating the plant, portion of the plant or the plant cell under conditions that permit expression of the norovirus VP1 protein.

8. The method of claim 7, wherein the method further comprises a step of harvesting the plant, portion of the plant, or the plant cell.

9. The method of claim 7, wherein in the step of introducing, a second polynucleotide encoding a norovirus VP2 protein is introduced into the plant, the portion of the plant or the plant cell, and in the step of incubating, the conditions permit co-expression and co-production of both the norovirus VP1 protein and the norovirus VP2 protein in the plant, portion of the plant, or the plant cell.

10. The method of claim 8, wherein the method further comprises a step of:

extracting, purifying, or both extracting and purifying the norovirus VP 1 protein, or extracting, purifying, or both extracting and purifying the virus-like particle (VLP) from the plant, the portion of the plant or the plant cell, wherein the VLP comprises the norovirus VP1 protein.

11. A norovirus virus like particle (VLP) produced by the method of claim 7.

12. A method of producing an antibody or antibody fragment comprising, administering the norovirus VP1 protein of claim 1 to a subject, or a host animal, thereby producing the antibody or the antibody fragment.

13. A method of producing an antibody or an antibody fragment comprising, administering the VLP of claim 5 to a subject, or a host animal, thereby producing the antibody or the antibody fragment.

14. A plant, portion of the plant, or plant cell comprising the norovirus VP1 protein of claim 1.

15. A plant, portion of the plant, or plant cell comprising the VLP of claim 5.

16. A plant, portion of the plant, or plant cell comprising the recombinant polynucleotide of claim 4.

17. A composition for inducing an immune response comprising, an effective dose of the norovirus VP1 protein of claim 1, and a pharmaceutically acceptable carrier, adjuvant, vehicle or excipient.

18. A composition for inducing an immune response comprising, an effective dose of the VLP of claim 6, and a pharmaceutically acceptable carrier, adjuvant, vehicle or excipient.

19. A vaccine comprising an effective dose of the norovirus VP1 protein of claim 1, for inducing an immune response.

20. An antibody or antibody fragment prepared by administering the norovirus VP1 protein of claim 1 to a subject, or host animal.

21. An antibody or antibody fragment prepared by administering the VLP claim 5 to a subject, or host animal.

22. A method for inducing immunity to a norovirus infection in a subject, the method comprising administering the VLP of claim 5 to the subject.

23. The method of claim 22, wherein the VLP is administered to the subject orally intranasally, intramuscularly, intraperitoneally, intravenously, subcutaneously, rectally, or intravaginally.

24. A vaccine comprising an effective dose of the VLP of claim 5, for inducing an immune response.

25. A method of producing a norovirus VP1 protein, the method comprising:

(i) providing a norovirus VP1 protein, wherein the norovirus VP1 protein is not a GI.1 genotype;

(ii) making one or more than one amino acid substitution in the amino acid sequence of the norovirus VP1 protein, selected from:

an amino acid substitution at a position in sequence alignment with amino acid 43 of reference sequence SEQ ID NO: 1 to valine, isoleucine, leucine, methionine, threonine, aspartic acid, glutamic acid, asparagine, glutamine, lysine, or histidine;

an amino acid substitution at a position in sequence alignment with amino acid 57 of reference sequence SEQ ID NO:1 to isoleucine, leucine, valine, alanine, glycine, serine, threonine, asparagine, glutamine, lysine, or histidine;

an amino acid substitution at a position in sequence alignment with amino acid 84 of reference sequence SEQ ID NO:1 to serine, asparagine, cysteine, threonine, alanine, lysine or histidine; and an amino acid substitution at a position in sequence alignment with amino acid 94 of reference sequence SEQ ID NO: 1 to leucine, isoleucine, methionine, valine, threonine, aspartic acid, glutamic acid, asparagine, glutamine, lysine, or histidine.

* * * * *